(12) United States Patent
Campbell et al.

(10) Patent No.: US 12,172,983 B2
(45) Date of Patent: *Dec. 24, 2024

(54) EGFR INHIBITORS

(71) Applicant: Blueprint Medicines Corporation, Cambridge, MA (US)

(72) Inventors: John Emmerson Campbell, Cambridge, MA (US); Thomas A. Dineen, Cambridge, MA (US); Natasja Brooijmans, Cambridge, MA (US); Jason D. Brubaker, Cambridge, MA (US); Meredith Suzanne Eno, Cambridge, MA (US); Joseph L. Kim, Cambridge, MA (US); Aysegül Özen, Cambridge, MA (US); Emanuele Perola, Cambridge, MA (US); Brett D. Williams, Cambridge, MA (US); Douglas Wilson, Cambridge, MA (US); Kevin J. Wilson, Cambridge, MA (US); Christopher De Savi, Cambridge, MA (US)

(73) Assignee: Blueprint Medicines Corporation, Cambridge, MA (US)

( * ) Notice: Subject to any disclaimer, the term of this patent is extended or adjusted under 35 U.S.C. 154(b) by 511 days.

This patent is subject to a terminal disclaimer.

(21) Appl. No.: 17/514,457

(22) Filed: Oct. 29, 2021

(65) Prior Publication Data

US 2023/0056541 A1  Feb. 23, 2023

Related U.S. Application Data

(63) Continuation of application No. PCT/US2020/066629, filed on Dec. 22, 2020.

(60) Provisional application No. 62/953,030, filed on Dec. 23, 2019.

(51) Int. Cl.

| C07D 401/14  | (2006.01) |
| A61K 31/506  | (2006.01) |
| C07D 471/04  | (2006.01) |
| C07D 471/08  | (2006.01) |
| C07D 491/048 | (2006.01) |
| C07D 491/107 | (2006.01) |
| C07D 491/113 | (2006.01) |
| C07D 498/08  | (2006.01) |
| C07D 519/00  | (2006.01) |

(52) U.S. Cl.
CPC ........ *C07D 401/14* (2013.01); *C07D 471/04* (2013.01); *C07D 471/08* (2013.01); *C07D 491/048* (2013.01); *C07D 491/107* (2013.01); *C07D 491/113* (2013.01); *C07D 498/08* (2013.01); *C07D 519/00* (2013.01); *C07B 2200/05* (2013.01); *C07B 2200/07* (2013.01)

(58) Field of Classification Search
CPC .. C07D 401/14; C07D 403/14; A61K 31/506; A61K 31/5025; A61K 31/53; A61P 35/00
USPC ........ 544/324, 236, 182; 514/256, 275, 248, 514/242
See application file for complete search history.

(56) References Cited

U.S. PATENT DOCUMENTS

| 11,718,602 B2 * | 8/2023 | Brooijmans ......... C07D 471/08 |
| | | 514/210.21 |
| 2013/0225528 A1 | 8/2013 | Wang et al. |

FOREIGN PATENT DOCUMENTS

| CN | 112409331 A | 2/2021 |
| WO | 2010/129053 A2 | 11/2010 |
| WO | 2014/074675 A1 | 5/2014 |
| WO | 2014/081718 A1 | 5/2014 |
| WO | 2014/210354 A1 | 12/2014 |
| WO | 2017/161028 A1 | 9/2017 |
| WO | 2018/175746 A1 | 9/2018 |
| WO | 2020/073945 A1 | 4/2020 |
| WO | 2021/146370 A1 | 7/2021 |

OTHER PUBLICATIONS

Chan et al., Discovery of a Noncovalent, Mutant-Selective Epidermal Growth Factor Receptor Inhibitor. J Med Chem. Oct. 13, 2016;59(19):9080-9093.
Gunther et al., Lung Cancer: EGFR Inhibitors with Low Nanomolar Activity against a Therapy-Resistant L858R/T790M/C797S Mutant. Angew Chem Int Ed Engl. Aug. 26, 2016;55(36):10890-4.

(Continued)

*Primary Examiner* — Charanjit Aulakh
(74) *Attorney, Agent, or Firm* — McCarter & English, LLP; Steven G. Davis; Xin Zhang

(57) ABSTRACT

The present disclosure provides a compound represented by structural formula (I): or a pharmaceutically acceptable salt thereof useful for treating a cancer.

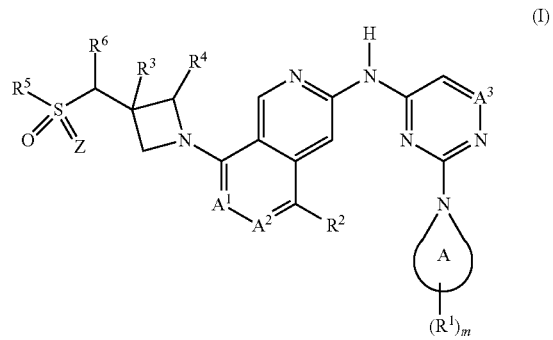

21 Claims, No Drawings

(56) References Cited

OTHER PUBLICATIONS

Hanan et al., Discovery of selective and noncovalent diaminopyrimidine-based inhibitors of epidermal growth factor receptor containing the T790M resistance mutation. J Med Chem. Dec. 11, 2014;57(23):10176-91.
Lei et al., Discovery of novel 9-heterocyclyl substituted 9H-purines as L858R/T790M/C797S mutant EGFR tyrosine kinase inhibitors. Eur J Med Chem. Jan. 15, 2020;186:111888, 16 pages.
International Search Report and Written Opinion for Application No. PCT/US2020/066629, dated Feb. 19, 2021, 10 pages.

* cited by examiner

EGFR INHIBITORS

CROSS-REFERENCE TO RELATED APPLICATIONS

This application is a continuation application of International Patent Application No. PCT/US2020/066629, filed Dec. 22, 2020, which claims priority from U.S. Provisional Application No. 62/953,030, filed Dec. 23, 2019. The entire contents of the aforementioned application are incorporated herein by reference.

BACKGROUND

EGFR (Epidermal Growth Factor Receptor) is a member of the erbB receptor family, which includes transmembrane protein tyrosine kinase receptors. By binding to its ligand, such as epidermal growth factor (EGF), EGFR can form a homodimer on the cell membrane or form a heterodimer with other receptors in the family, such as erbB2, erbB3, or erbB4. The formation of these dimers can cause the phosphorylation of key tyrosine residues in EGFR cells, thereby activating a number of downstream signaling pathways in cells. These intracellular signaling pathways play an important role in cell proliferation, survival and anti-apoptosis. Disorders of EGFR signal transduction pathways, including increased expression of ligands and receptors, EGFR gene amplification and alterations such as mutations, deletions and the like, can promote malignant transformation of cells and play an important role in tumor cell proliferation, invasion, metastasis and angiogenesis. For example, alterations such as mutations and deletions in the EGFR gene are found in non-small lung cancer (NSCLC) tumors. The two most frequent EGFR alternations found in NSCLC tumors are short in-frame deletions in exon 19 (del19) and L858R, a single missense mutation in exon 21 (*Cancer Discovery* 2016 6(6) 601). These two alterations cause ligand-independent EGFR activation and are referred to as primary or activating mutations in EGFR mutant NSCLC (EGFR M+). Clinical experience shows an objective response rate (ORR) of approximately 60-85% in EGFR M+NSCLC patients treated first line (1L) with EGFR tyrosine kinase inhibitors (TKIs) erlotinib, gefitinib, afatinib and osimertinib (*Lancet Oncol.* 2010 Vol. 11, 121; *Lancet Oncol.* 2016 Vol. 17, 577; N. Engl. J. Med. 2017 Nov. 18 Doi:10.1056/NEJMoa1713137; *Lancet Oncol.* 2011 Vol. 12, 735), thus demonstrating that EGFR mutant NSCLC tumors depend on oncogenic EGFR activity for survival and proliferation and establishing del19 and L858R mutated EGFR as oncogenic drivers of disease and thus, validating drug targets and biomarkers for the treatment of NSCLC.

However, after an average of 10-12 months of treatment with first generation (erlotinib and gefitinib) and second generation (afatinib) EGFR TKIs, resistance to these small molecule inhibitors has been observed in almost all NSCLC patients (Lancet Oncol. 2010 February; 11(2):121-8; *Lancet Oncol.* 2016 May; 17(5):577-89; *Lancet Oncol.* 2011 August; 12(8):735-42). The most prominent resistance mechanism to first and second generation EGFR TKIs is due to the secondary mutation in EGFR of T790M, occurs in 50% to 70% of patients progressing on 1st and 2nd generation EGFR inhibitors. (Blakely, 2012; Kobayashi, 2005). This secondary mutation reduces the affinity of the drug with the target, thereby producing drug resistance, and resulting in tumor recurrence or disease progression.

In view of the prevelance of this mutation in drug resistance produced in therapy targeting EGFR of lung cancer, a number of companies have attempted to develop new small molecule EGFR inhibitors for treating these patients with drug-resistant lung cancer by inhibiting the resistant mutant EGFR-T790M. For example, osimertinib (Tagrisso®), a third generation EGFR TKI, has been developed to treat NSCLC patients if the cancer cells are positive for the primary EGFR mutations del19 or L858R with or without the T790M mutation in the gene coding for EGFR.

Although the third generation EGFR TKI, osimertinib, has shown efficacy on NSCLC patients, unfortunately, resistance mediated by an exon 20 C797 mutation in EGFR usually develops within approximately 10 months (*European Journal of Medicinal Chemistry* 2017 Vol. 142: 32-47) and accounts for the majority of osimertinib resistance cases (*Cancer Letters* 2016 Vol. 385: 51-54). The EGFR del19/L858R T790M C797S cis mutant kinase variant typically emerges in second line (2L) patients following treatment with osimertinib and is often referred to as "triple mutant" EGFR and it can no longer be inhibited by first, second, or third generation EGFR inhibitors.

No approved EGFR TKI can inhibit the triple mutant variant. Therefore, there is a need to develop new EGFR inhibitors, which can inhibit with high selectivity EGFR mutants with the triple mutant, del19/L858R T790M C797S, while at the same time have no or low activity to wild-type EGFR. In addition to treating a mutant form of EGFR for which there is no current therapy, such selective EGFR inhibitors are likely to be more suitable as therapeutic agents, particularly for the treatment of cancer, due to reduction of toxicologies (diarrhea, skin rash) associated with wild-type EGFR inhibition.

SUMMARY

The applicant has discovered novel compounds which are effective inhibitors of certain mutant forms of EGFR (see Synthetic Examples 1-43). In particular, it has been demonstrated that the compounds of the present disclosure effectively inhibit certain mutant forms of EGFR. Compounds of the disclosure (also referred to herein as the "disclosed compounds") or pharmaceutically acceptable salts thereof effectively inhibit EGFR with one or more alterations, including L858R and/or exon 19 deletion mutation, T790M mutation, and/or C797S mutation. Compounds of the disclosure or pharmaceutically acceptable salts thereof effectively inhibit EGFR with L858R and/or exon 19 deletion mutation, T790M mutation, and C797S mutation (hereinafter "EGFR with LRTMCS mutations" or "triple mutant EGFR") (see Biological Example 1) and can be used treat various cancers, for example, lung cancer (see Biological Example 2). Importantly, the disclosed compounds are selective EGFR inhibitors, i.e., the disclosed compounds have no or low activity against wild-type EGFR and the kinome. Advantages associated with such selectivity may include facilitating efficacious dosing and reducing EGFR-mediated on-target toxicities. Some of the disclosed compounds exhibit good penetration of the brain and blood brain barrier (e.g., a PGP efflux ratio of less than 5). As such, the compounds of the disclosure or pharmaceutically acceptable salts thereof are expected to be effective for the treatment of metastatic cancer, including brain metastesis, including leptomeningeal disease and other systemic metastesis. Some of the disclosed compounds also have the advantage of having high microsomal stability. Compounds of the disclosure also may have favorable toxicity profiles related to other non-kinase targets.

In one aspect, the present disclosure provides a compound represented by the following structural Formula (I):

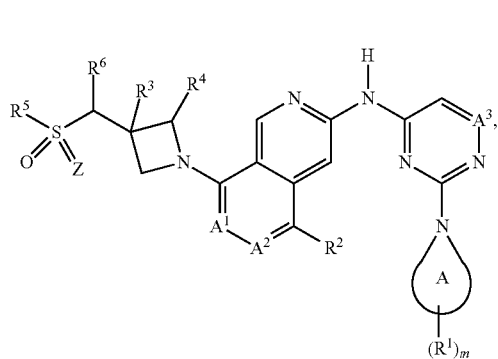

or a pharmaceutically acceptable salt thereof, the definition of each variable is provided below.

In another aspect, the present disclosure provides a pharmaceutical composition comprising a pharmaceutically acceptable carrier or diluent and one or more of the compounds disclosed herein, or a pharmaceutically acceptable salt thereof (a "pharmaceutical composition of the disclosure").

The present disclosure provides a method of treating a subject with cancer, comprising administering to the subject an effective amount of a compound of the disclosure (e.g., a compound of Formula (I)) or a pharmaceutically acceptable salt thereof or a pharmaceutical composition of the disclosure. In one embodiment, the cancer is non-small cell lung cancer. In another embodiment, the subject cancer has metastasized to the brain. In another embodiment, the subject has brain metastasis from non-small cell lung cancer.

In one embodiment, the cancer to be treated has epidermal growth factor receptor (EGFR) L858R mutation and/or exon 19 deletion mutation and T790M mutation. In another embodiment, the cancer to be treated may further has epidermal growth factor receptor (EGFR) L858R mutation and/or exon 19 deletion mutation and the T790M mutation and the C797S mutation. In another embodiment, the cancer to be treated in either of the foregoing embodiments is lung cancer, e.g., non-small cell lung cancer. In a specific embodiment, the cancer is non-small cell lung cancer with brain metastasis.

The treatment method disclosed herein further comprises administering to the subject an effective amount of afatinib, osimertinib, erlotinib, or gefitinib.

The present disclosure also provides a method of inhibiting epidermal growth factor receptor (EGFR) in a subject in need thereof, comprising administering to the subject an effective amount of a compound of the disclosure (e.g., a compound of Formula (I)) or a pharmaceutically acceptable salt thereof or a pharmaceutical composition of the disclosure.

The present disclosure also provides the use of an effective amount of a compound of the disclosure (e.g., a compound of Formula (I)), or a pharmaceutically acceptable salt thereof, or a pharmaceutical composition of the disclosure, for the preparation of a medicament for the treatment of cancers.

In another aspect, provided herein a compound of Formula (I), or a pharmaceutically acceptable salt thereof, or a pharmaceutical composition of the disclosure for use in treating cancers.

DETAILED DESCRIPTION

Definitions

The term "halo" as used herein means halogen and includes chloro, fluoro, bromo and iodo.

The term "alkyl" used alone or as part of a larger moiety, such as "alkoxy" or "haloalkyl" and the like, means saturated aliphatic straight-chain or branched monovalent hydrocarbon radical. Unless otherwise specified, an alkyl group typically has 1-4 carbon atoms, i.e. $(C_1-C_4)$alkyl. As used herein, a "$(C_1-C_4)$alkyl" group means a radical having from 1 to 4 carbon atoms in a linear or branched arrangement. Examples include methyl, ethyl, n-propyl, iso-propyl, and the like.

The term "alkenyl" means an alkyl group in which one or more carbon/carbon single bond is replaced by a double bond.

The term "alkoxy" means an alkyl radical attached through an oxygen linking atom, represented by —O-alkyl. For example, "$(C_1-C_4)$alkoxy" includes methoxy, ethoxy, propoxy, and butoxy.

The term "aminoalkyl" means an alkyl group substituted —$NH_2$.

The terms "haloalkyl" and "haloalkoxy" means alkyl or alkoxy, as the case may be, substituted with one or more halogen atoms.

The term "cycloalkyl" refers to a monocyclic saturated hydrocarbon ring system. Unless otherwise specified, cycloalkyl has from 3-6 carbon atoms. For example, a $C_3-C_6$ cycloalkyl includes cyclopropyl, cyclobutyl, cyclopentyl and cyclohexyl. Unless otherwise described, a "cycloalkyl" has from three to six carbon atoms.

The term "heterocyclyl" or "heterocyclic" refers to a radical of a 4- to 12-membered non-aromatic ring system having ring carbon atoms and 1 to 4 ring heteroatoms, wherein each heteroatom is independently selected from nitrogen, quaternary nitrogen, oxidized nitrogen (e.g., NO), oxygen, and sulfur, including sulfoxide and sulfone ("4-12 membered heterocyclyl"). In some embodiments, a heterocyclyl group is a 4-10 membered non-aromatic ring system having ring carbon atoms and 1-4 ring heteroatoms, wherein each heteroatom is independently selected from nitrogen, oxygen, and sulfur ("4-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a bicyclic system ("bicyclic heterocyclyl") or tricyclic system ("tricyclic heterocyclyl"); polycyclic ring systems include fused, bridged, or spiro ring systems). Exemplary monocyclic heterocyclyl groups include azetidinyl, oxetanyl, thietanyl, tetrahydrofuranyl, pyrrolidinyl, piperidinyl, tetrahydropyranyl, piperazinyl, morpholinyl, azepanyl, oxepanyl, thiepanyl, tetrahydropyridinyl, and the like. Heterocyclyl polycyclic ring systems can include heteroatoms in one or more rings in the polycyclic ring system. Substituents (e.g., $R^1$) may be present on one or more rings in the polycyclic ring system.

A bridged bicyclic system has two non-aromatic rings containing from 7-12 ring atoms (heterocyclyl or cycloalkyl) and which share three or more atoms, with the two bridgehead atoms separated by a bridge containing at least one atom. "Bridged heterocyclyl" includes bicyclic or polycyclic hydrocarbon or aza-bridged hydrocarbon groups; examples include 2-azabicyclo[2.2.1]heptanyl, 3-azabicyclo[3.2.1]octanyl, 6-oxa-2-azabicyclo[3.2.1]octanyl, 6-oxa-3-azabicyclo[3.2.1]octanyl, and 8-oxa-3-azabicyclo[3.2.1]octanyl.

A fused bicyclic system has two non-aromatic rings (heterocyclyl or cycloalkyl) containing from 7-12 ring atoms and which share two adjacent ring atoms. Examples of fused bicyclic systems include hexahydro-1H-furo[3,4-b]pyrrolyl, and hexahydro-1H-furo[3,4-c]pyrrolyl.

A spiro bicyclic system has two non-aromatic rings containing (heterocyclyl or cycloalkyl) from 7-12 ring atoms and which share one ring atom. Examples of spiro bicyclic systems include 1-oxa-7-azaspiro[3.5]nonan-7-yl, 1,4-dioxa-8-azaspiro[4.5]decan-8-yl, and 1,4-dioxa-9-azaspiro[5.5]undecan-9-yl.

Compounds of the Present Disclosure

Disclosed herein are embodiments of compounds having a general structure of Formula (I). These compounds are selective inhibitors of LRTM and LRTMCS EGFR. In contrast to other EGFR inhibitors such as osimertinib which binds EGFR irreversibly, the compounds of the disclosure are non-covalent inhibitors.

In a first embodiment, the present disclosure provides a compound represented by the following structural formula (I):

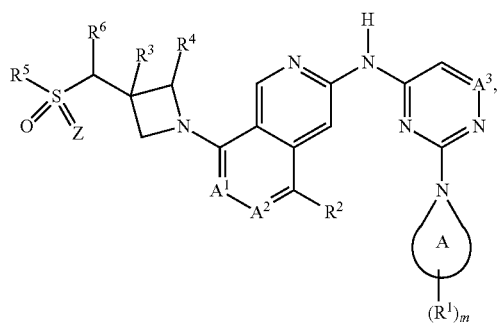

or a pharmaceutically acceptable salt thereof, wherein:
Z is O or NH;
each $A^1$, $A^2$, and $A^3$ is independently N or CR; wherein each R is independently H, halogen, or $CH_3$;
Ring A is 4-10 membered heterocyclyl;
each $R^1$ is independently halogen, CN, OH, $NR_aR_b$, $C_1$-$C_4$ alkyl, $C_1$-$C_4$ alkoxy, $C_3$-$C_6$ cycloalkyl or —O—$C_3$-$C_6$ cycloalkyl, wherein the alkyl, alkoxy or cycloalkyl represented by $R^1$ or in the group represented by $R^1$ is optionally substituted with 1 to 3 groups selected from deuterium, halogen, OH, $NR_aR_b$, $C_1$-$C_2$ alkyl, and $C_1$-$C_2$ alkoxy;
m is 0, 1, 2, 3, 4, 5, or 6;
$R^2$ is H, halogen, $C_1$-$C_4$ alkyl, $C_1$-$C_4$ alkoxy, or $C_3$-$C_6$ cycloalkyl, wherein the alkyl, alkoxy or cycloalkyl represented by $R^2$ is optionally substituted with 1 to 3 groups selected from halogen and OH;
$R^3$ is H or methyl;
$R^4$ is H or methyl;
$R^5$ is H, $C_1$-$C_4$ alkyl, $C_3$-$C_6$ cycloalkyl or 4-6 membered monocyclic heterocyclyl, wherein the alkyl, cycloalkyl or heterocyclyl represented by $R^5$ is optionally substituted with 1 to 3 three groups selected from halogen, CN, OH, $NR_aR_b$, $C_1$-$C_2$ alkyl, and $C_1$-$C_2$ alkoxy;
$R^6$ is H or $C_1$-$C_4$ alkyl optionally substituted with 1 to 3 three groups selected from halogen, CN, OH, $NR_aR_b$, and $C_1$-$C_2$ alkoxy; and
each $R_a$ and $R_b$ is independently H or $C_1$-$C_4$ alkyl.

In an alterative first embodiment, the present disclosure provides a compound represented by the following structural formula (I):

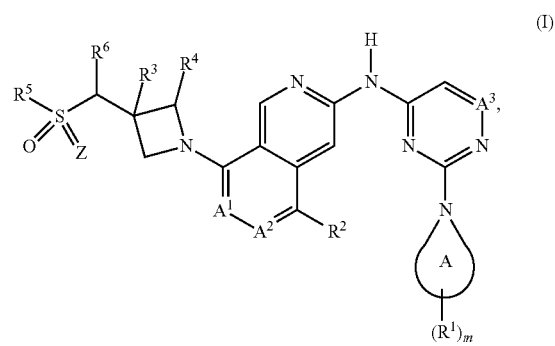

or a pharmaceutically acceptable salt thereof, wherein:
Z is O or NH;
each $A^1$, $A^2$, and $A^3$ is independently N or CR; wherein each R is independently H, halogen, or $CH_3$;
Ring A is 4-10 membered heterocyclyl;
each $R^1$ is independently halogen, CN, OH, $NR_aR_b$, $C_1$-$C_4$ alkyl, $C_1$-$C_4$ alkoxy, $C_3$-$C_6$ cycloalkyl or —O—$C_3$-$C_6$ cycloalkyl, wherein the alkyl, alkoxy or cycloalkyl represented by $R^1$ or in the group represented by $R^1$ is optionally substituted with 1 to 3 groups selected from deuterium, halogen, OH, $NR_aR_b$, $C_1$-$C_2$ alkyl, and $C_1$-$C_2$ alkoxy;
m is 0, 1, 2, 3, 4, 5, or 6;
$R^2$ is H, halogen, $C_1$-$C_4$ alkyl, $C_1$-$C_4$ alkoxy, or $C_3$-$C_6$ cycloalkyl, wherein the alkyl, alkoxy or cycloalkyl represented by $R^2$ is optionally substituted with 1 to 3 groups selected from halogen, $OR_a$, and $NR_aR_b$;
$R^3$ is H or methyl;
$R^4$ is H or methyl;
$R^5$ is H, $C_1$-$C_4$ alkyl, $C_3$-$C_6$ cycloalkyl or 4-6 membered monocyclic heterocyclyl, wherein the alkyl, cycloalkyl or heterocyclyl represented by $R^5$ is optionally substituted with 1 to 3 three groups selected from halogen, CN, OH, $NR_aR_b$, $C_1$-$C_2$ alkyl, and $C_1$-$C_2$ alkoxy;
$R^6$ is H or $C_1$-$C_4$ alkyl optionally substituted with 1 to 3 three groups selected from halogen, CN, OH, $NR_aR_b$, and $C_1$-$C_2$ alkoxy; and
each $R_a$ and $R_b$ is independently H or $C_1$-$C_4$ alkyl.

In a second embodiment, the present disclosure provides a compound represented by structural formula (II-A), (II-B), (II-D), or (II-E):

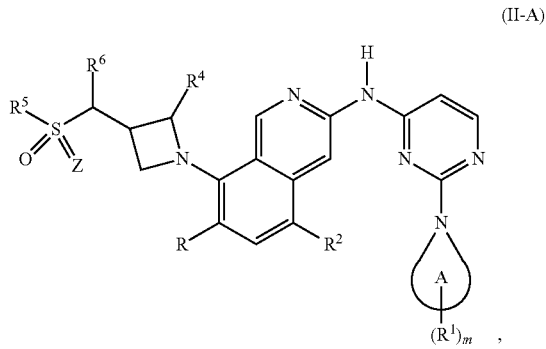

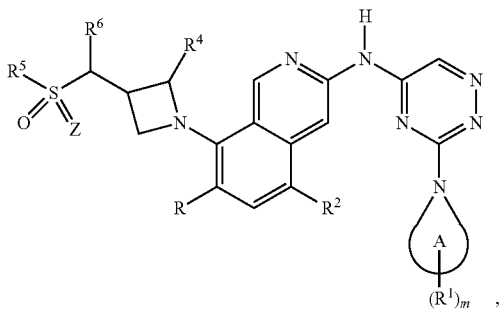

(II-B)

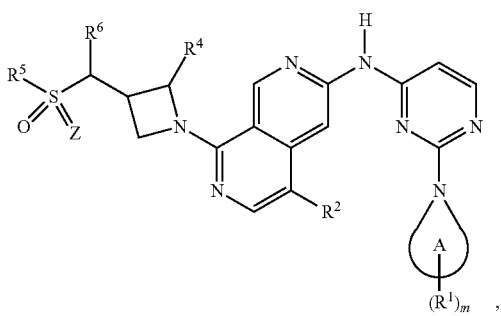

(II-C)

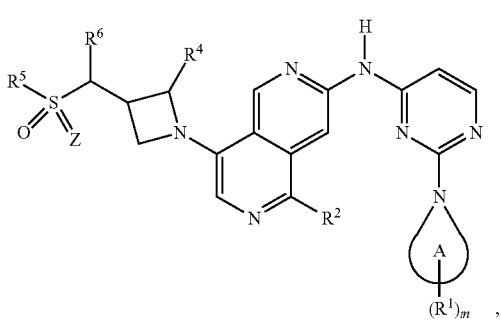

(II-D)

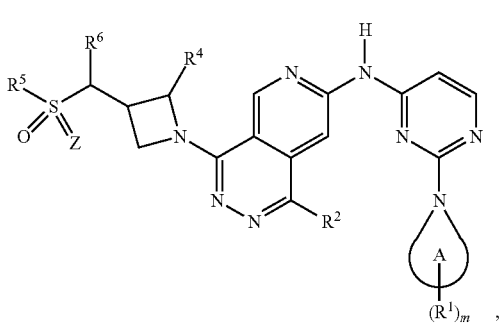

(II-E)

or a pharmaceutically acceptable salt thereof, wherein the variables are as defined in the first embodiment.

In a third embodiment, the present disclosure provides a compound represented by structural formula (II-A):

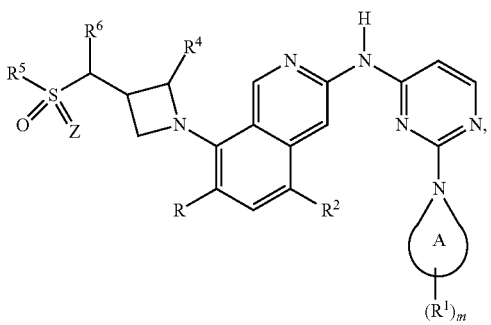

(II-A)

or a pharmaceutically acceptable salt thereof, wherein the variables are as defined in the first embodiment.

In a fourth embodiment, the present disclosure provides a compound according to structural formula (I), (II-A), (II-B), (II-C), (II-D), or (II-E), or a pharmaceutically acceptable salt thereof, wherein Z is O, wherein the remainder of the variables are as defined in the first embodiment.

In a fifth embodiment, the present disclosure provides a compound according to structural formula (I), (II-A), (II-B), (II-C), (II-D), or (II-E), or a pharmaceutically acceptable salt thereof, wherein $R^2$ is H, fluorine, $C_1$-$C_4$ alkyl, $C_1$-$C_4$ alkoxy, or $C_3$-$C_6$ cycloalkyl, wherein the alkyl, alkoxy, or cycloalkyl represented by $R^2$ is optionally substituted with 1 to 3 groups selected from halogen and OH, wherein the remainder of the variables are as defined in the first or fourth embodiment. In an alternative fifth embodiment, $R^2$ is H, fluorine, $C_1$-$C_4$ alkyl, $C_1$-$C_4$ alkoxy, or $C_3$-$C_6$ cycloalkyl, wherein the alkyl, alkoxy or cycloalkyl represented by $R^2$ is optionally substituted with 1 to 3 groups selected from halogen, OH, and $NH_2$, wherein the remainder of the variables are as defined in the first or fourth embodiment.

In a sixth embodiment, the present disclosure provides a compound according to structural formula (I), (II-A), (II-B), (II-C), (II-D), or (II-E), or a pharmaceutically acceptable salt thereof, wherein $R^6$ is H, methyl, ethyl, $C_1$-$C_2$ haloalkyl, or $C_1$-$C_2$ aminoalkyl, wherein the remainder of the variables are as defined in the first, fourth, or fifth embodiment.

In a seventh embodiment, the present disclosure provides a compound according to structural formula (I), (II-A), (II-B), (II-C), (II-D), or (II-E), or a pharmaceutically acceptable salt thereof, wherein $R^5$ H; is $C_1$-$C_4$ alkyl optionally substituted with 1 to 3 three groups selected from halogen, CN, and $NR_aR_b$; $C_3$-$C_6$ cycloalkyl; or 4-6 membered monocyclic heterocyclyl optionally substituted with $C_1$-$C_4$ alkyl; wherein $R_a$ and $R_b$ are each independently selected from H, methyl and ethyl; and wherein the remainder of the variables are as defined in the first, fourth, fifth, or sixth embodiment.

In an eighth embodiment, the present disclosure provides a compound according to structural formula (I), (II-A), (II-B), (II-C), (II-D), or (II-E), or a pharmaceutically acceptable salt thereof, wherein Ring A is 4-7 membered monocyclic heterocyclyl optionally substituted with 1-6 $R^1$, wherein the remainder of the variables are as defined in the first, fourth, fifth, sixth, or seventh embodiment.

In a ninth embodiment, the present disclosure provides a compound according to structural formula (I), (II-A), (II-B), (II-C), (II-D), or (II-E), or a pharmaceutically acceptable salt thereof, wherein Ring A is 7-12 membered bicyclic heterocyclyl optionally substituted with 1-6 $R^1$, wherein the remainder of the variables are as defined in the first, fourth, fifth, sixth or seventh embodiment.

In a tenth embodiment, the present disclosure provides a compound according to structural formula (I), (II-A), (II-B), (II-C), (II-D), or (II-E), or a pharmaceutically acceptable salt thereof, wherein m is 1, 2, 3, 4, or 5; each $R^1$ is independently halogen, CN, OH, $NR_aR_b$, $C_1$-$C_4$ alkyl, $C_1$-$C_4$ alkoxy, —O—$C_3$-$C_6$ cycloalkyl, wherein the alkyl, alkoxy, or cycloalkyl represented by $R^1$ or in the group represented by $R^1$ is optionally substituted with 1 to 3 groups selected from deuterium, halogen, OH, $NR_aR_b$, $C_1$-$C_2$ alkyl, and $C_1$-$C_2$ alkoxy; and wherein the remainder of the variables are as defined in the first, fourth, fifth, sixth, seventh, eighth, or ninth embodiment.

In an eleventh embodiment, the present disclosure provides a compound according to structural formula (I), (II-A), (II-B), (II-C), (II-D), or (II-E), or a pharmaceutically acceptable salt thereof, wherein $R^2$ is H, F, methyl, ethyl, isopropyl, $CH(CH_3)CH_2F$, $CH(CH_3)CH_2OH$, $CF_3$, $OCH_3$, $OCH_2CH_3$, or cyclopropyl, wherein the remainder of the variables are as defined in the first, fourth, fifth, sixth, seventh, eighth, ninth, or tenth embodiment. In an alternative eleventh embodiment, the present disclosure provides a compound according to structural formula (I), (II-A), (II-B), (II-C), (II-D), or (II-E), or a pharmaceutically acceptable salt thereof, wherein $R^2$ is H, F, methyl, ethyl, isopropyl, $CH(CH_3)CH_2F$, $CH(CH_3)CH_2OH$, $CF_3$, $OCH_3$, $OCH_2CH_3$, $C(CH_3)_2NH_2$, or cyclopropyl, wherein the remainder of the variables are as defined in the first, fourth, fifth (or alternative fifth), sixth, seventh, eighth, ninth, or tenth embodiment.

In a twelfth embodiment, the present disclosure provides a compound according to structural formula (I), (II-A), (II-B), (II-C), (II-D), or (II-E), or a pharmaceutically acceptable salt thereof, wherein $R^6$ is H, $CH_3$, or $CH_2NH_2$, wherein the remainder of the variables are as defined in the first, fourth, fifth, sixth, seventh, eighth, ninth, tenth, or eleventh embodiment.

In a thirteenth embodiment, the present disclosure provides a compound according to structural formula (I), (II-A), (II-B), (II-C), (II-D), or (II-E), or a pharmaceutically acceptable salt thereof, wherein Ring A is optionally substituted with 1-6 $R^1$, and Ring A is pyrrolidinyl, piperidinyl, morpholinyl, piperazinyl, azepanyl, 2-azabicyclo[2.2.1]heptanyl, 3-azabicyclo[3.2.1]octanyl, 6-oxa-2-azabicyclo[3.2.1]octanyl, 6-oxa-3-azabicyclo[3.2.1]octanyl, 8-oxa-3-azabicyclo[3.2.1]octanyl, hexahydro-1H-furo[3,4-b]pyrrolyl, hexahydro-1H-furo[3,4-c]pyrrolyl, hexahydro-1H-furo[3,4-c]pyrrolyl, 1-oxa-7-azaspiro[3.5]nonan-7-yl, 1,4-dioxa-8-azaspiro[4.5]decan-8-yl or 1,4-dioxa-9-azaspiro[5.5]undecan-9-yl, wherein the remainder of the variables are as defined in the first, fourth, fifth, sixth, seventh, tenth, eleventh, or twelfth embodiment.

In a fourteenth embodiment, the present disclosure provides a compound according to structural formula (I), (II-A), (II-B), (II-C), (II-D), or (II-E), or a pharmaceutically acceptable salt thereof, wherein at least one $R^1$ is OH, $C_1$-$C_4$ alkoxy, or —O—$C_3$-$C_6$ cycloalkyl, wherein the alkoxy or cycloalkyl represented by $R^1$ or in the group represented by $R^1$ is optionally substituted with 1 to 3 groups selected from deuterium, halogen, OH, $NR_aR_b$, $C_1$-$C_2$ alkyl, and $C_1$-$C_2$ alkoxy, wherein the remainder of the variables are as defined in the first, fourth, fifth, sixth, seventh, eighth, ninth, tenth, eleventh, twelfth, or thirteenth embodiment.

In a fifteenth embodiment, the present disclosure provides a compound according to structural formula (I), (II-A), (II-B), (II-C), (II-D), or (II-E), or a pharmaceutically acceptable salt thereof, wherein each $R^1$ is independently F, CN, OH, $NH_2$, $CH_3$, $CH_2CH_3$, $CHF_2$, $CH(OH)CH_3$, $CH_2OH$, $CH_2NH_2$, $CH_2CH_2NH_2$, $OCH_3$, $OCD_3$, $OCH_2CH_2OH$, $OCH_2CH(OH)CH_3$, $OCH_2C(OH)(CH_3)_2$, $OCH_2CH_2OCH_3$, $OCH_2CH_2NH_2$, $OCH_2CH_2NHCH_3$, $OCH_2CH_2N(CH_3)_2$, —O-cyclopropyl, $NHCH_3$, $N(CH_3)_2$, and wherein the remainder of the variables are as defined in the first, fourth, fifth, sixth, seventh, eighth, ninth, tenth, eleventh, twelfth, thirteenth, or fourteenth embodiment. In one specific embodiment, each $R^1$ is independently F, OH, Me, Et, OMe, $OCD_3$, or $OCH_2CH_2OH$. In another specific embodiment, each $R^1$ is independently F, OH, Me, or $OCD_3$.

In a sixteenth embodiment, the present disclosure provides a compound according to structural formula (I), (II-A), (II-B), (II-C), (II-D), or (II-E), or a pharmaceutically acceptable salt thereof, wherein

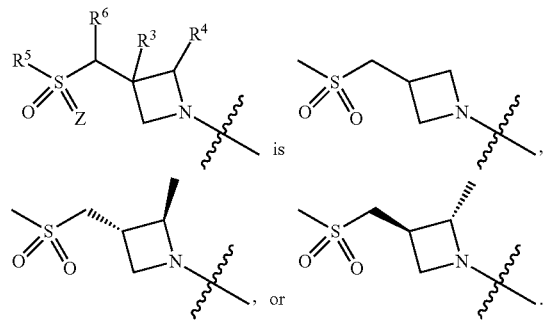

wherein the remainder of the variables are as defined in the first, fourth, fifth, sixth, seventh, eighth, ninth, tenth, eleventh, twelfth, thirteenth, fourteenth, or fifteenth embodiment. In one specific embodiment,

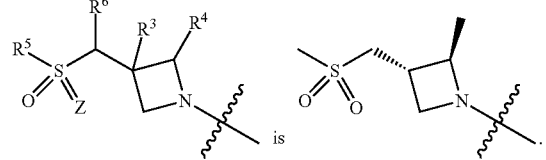

In a seventeenth embodiment, the present disclosure provides a compound according to structural formula (I), (II-A), (II-B), (II-C), (II-D), or (II-E), or a pharmaceutically acceptable salt thereof, wherein $R^2$ is H or isopropyl, wherein the remainder of the variables are as defined in the first, fourth, fifth, sixth, seventh, eighth, ninth, tenth, eleventh, twelfth, thirteenth, fourteenth, fifteenth, or sixteenth embodiment.

In an eighteenth embodiment, the present disclosure provides a compound according to structural formula (I), (II-A), (II-B), (II-C), (II-D), or (II-E), or a pharmaceutically acceptable salt thereof, wherein Ring A is piperidinyl optionally substituted with 1-6 $R^1$, wherein $R^2$ is H or isopropyl, wherein the remainder of the variables are as defined in the first, fourth, fifth, sixth, seventh, eighth, ninth, tenth, eleventh, twelfth, thirteenth, fourteenth, fifteenth, sixteenth, or seventeenth embodiment.

In one embodiment, a compound of the present disclosure is any one of the compounds disclosed in the examples and Table 1, or a pharmaceutically acceptable salt thereof.

The term "pharmaceutically-acceptable salt" refers to a pharmaceutical salt that is, within the scope of sound medical judgment, suitable for use in contact with the tissues of humans and lower animals without undue toxicity, irritation, and allergic response, and is commensurate with a reasonable benefit/risk ratio. Pharmaceutically-acceptable salts are well known in the art. For example, S. M. Berge et al. describes pharmacologically acceptable salts in *J. Pharm. Sci.*, 1977, 66, 1-19.

Included in the present teachings are pharmaceutically acceptable salts of the compounds disclosed herein. Compounds having basic groups can form pharmaceutically acceptable salts with pharmaceutically acceptable acid(s). Suitable pharmaceutically acceptable acid addition salts of the compounds described herein include salts of inorganic acids (such as hydrochloric, hydrobromic, phosphoric, metaphosphoric, nitric, and sulfuric acids) and of organic acids (such as acetic, benzenesulfonic, benzoic, ethanesulfonic, methanesulfonic, and succinic acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

Compounds having one or more chiral centers can exist in various stereoisomeric forms, i.e., each chiral center can have an R or S configuration, or can be a mixture of both. Stereoisomers are compounds that differ only in their spatial arrangement. Stereoisomers include all diastereomeric and enantiomeric forms of a compound. Enantiomers are stereoisomers that are mirror images of each other. Diastereomers are stereoisomers having two or more chiral centers that are not identifcal and are not mirror images of each other.

When the stereochemical configuration at a chiral center in a compound having one or more chiral centers is depicted by its chemical name (e.g., where the configuration is indicated in the chemical name by "R" or "S") or structure (e.g., the configuration is indicated by "wedge" bonds), the enrichment of the indicated configuration relative to the opposite configuration is greater than 50%, 60%, 70%, 80%, 90%, 99% or 99.9% (except when the designation "rac" or "racemate accompanies the structure or name, as explained in the following two paragraphs). "Enrichment of the indicated configuration relative to the opposite configuration" is a mole percent and is determined by dividing the number of compounds with the indicated stereochemical configuration at the chiral center(s) by the total number of all of the compounds with the same or opposite stereochemical configuration in a mixture.

When the stereochemical configuration at a chiral center in a compound is depicted by chemical name (e.g., where the configuration is indicated in the name by "R" or "S") or structure (e.g., the configuration is indicated by "wedge" bonds) and the designation "rac" or "racemate" accompanies the structure or is designated in the chemical name, a racemic mixture is intended.

When two stereoisomers are depicted by their chemical names or structures, and the chemical names or structures are connected by an "and", a mixture of the two stereoisomers is intended.

When two stereoisomers are depicted by their chemical names or structures, and the names or structures are connected by an "or", one or the other of the two stereoisomers is intended, but not both.

When a disclosed compound having a chiral center is depicted by a structure without showing a configuration at that chiral center, the structure is meant to encompass the compound with the S configuration at that chiral center, the compound with the R configuration at that chiral center, or the compound with a mixture of the R and S configuration at that chiral center. When a disclosed compound having a chiral center is depicted by its chemical name without indicating a configuration at that chiral center with "S" or "R", the name is meant to encompass the compound with the S configuration at that chiral center, the compound with the R configuration at that chiral center or the compound with a mixture of the R and S configuration at that chiral center.

A racemic mixture means a mixture of 50% of one enantiomer and 50% of its corresponding enantiomer. The present teachings encompass all enantiomerically-pure, enantiomerically-enriched, diastereomerically pure, diastereomerically enriched, and racemic mixtures, and diastereomeric mixtures of the compounds disclosed herein.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

"Peak 1" in the Experimental section refers to an intended reaction product compound obtained from a chromatography separation/purification that elutes earlier than a second intended reaction product compound from the same preceding reaction. The second intended product compound is referred to as "peak 2".

When a disclosed compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that, unless otherwise indicated, one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

In the compounds of the disclosure, any position specifically designated as "D" or "deuterium" is understood to have deuterium enrichment at 50, 80, 90, 95, 98 or 99%. "Deuterium enrichment" is a mole percent and is determined by dividing the number of compounds with deuterium at the indicated position by the total number of all of the compounds. When a position is designated as "H" or "hydrogen", the position has hydrogen at its natural abundance. When a position is silent as to whether hydrogen or deuterium is present, the position has hydrogen at its natural abundance. One specific alternative embodiment is directed to a compound of the disclosure having deuterium enrichment of at least 5, 10, 25, 50, 80, 90, 95, 98 or 99% at one or more positions not specifically designated as "D" or "deuterium".

As used herein, many moieties (e.g., alkyl, alkoxy, cycloalkyl or heterocyclyl) are referred to as being either "substituted" or "optionally substituted". When a moiety is modified by one of these terms, unless otherwise noted, it denotes that any portion of the moiety that is known to one skilled in the art as being available for substitution can be substituted, which includes one or more substituents. Where if more than one substituent is present, then each substituent may be independently selected. Such means for substitution are well-known in the art and/or taught by the instant disclosure. The optional substituents can be any substituents that are suitable to attach to the moiety.

Compounds of the disclosure are selective EGFR inhibitors. As used herein, the term "selective EGFR inhibitor" means a compound which selectively inhibits certain mutant EGFR kinases over wild-type EGFR and the kinome. Said another way, a selective EGFR inhibitor has no or low activity against wild-type EGFR and the kinome. A selective EGFR inhibitor's inhibitory activity against certain mutant EGFR kinases is more potent in terms of $IC_{50}$ value (i.e., the $IC_{50}$ value is subnanomolar) when compared with its inhibitory activity against wild-type EGFR and many other kinases. Potency can be measured using known biochemical assays.

Some compounds of the disclosure have the advantage of good penetration of the brain. The ability of a particular compound to cross the BBB and penetrate the brain can be assessed using a variety of known methods or combinations of such methods. One in vitro method that is frequently used to predict a compound's in vivo brain penetration is P-gp efflux ratio. P-glycoprotein (P-gp) is expressed at the blood-brain barrier (BBB) and restricts the penetration of its substrates into the central nervous system (CNS). Compounds that are found to be good P-gp substrates in vitro (i.e., have a high efflux ratio) are predicted to have poor in vivo brain penetration. In order to measure the P-gp efflux ratio, Madin-Darby canine kidney cells overexpressing P-gp (MDCK-MDR1 cells) the apparent apical to basolateral permeability (Papp[A-B]) and the apparent basolateral to apical permeability (Papp[B-A]) for compounds is determined. The P-gp efflux ratio is a measure of the ratio of Papp[B-A]/Papp[A-B]. In some embodiments, a compound of the disclosure has a P-gp efflux ratio of less than 2, less than 3, less than 4, less than 5.

Some compounds of the disclosure have the advantage of good metabolic stability. One indicator of good metabolic stability is high microsomal stability. Hepatic metabolism is a predominant route of elimination for small molecule drugs. The clearance of compounds by hepatic metabolism can be assessed in vitro using human liver microsomes (HLMs) or human hepatocytes. Compounds are incubated with HLMs plus appropriate co-factors or human hepatocytes and compound depletion is measured to determine an in vitro intrinsic clearance (Clint). The Clint is scaled to total body clearance (CL), and a hepatic extraction ratio (ER) is determined by dividing CL to standard human hepatic blood flow. Compounds that have a low hepatic extraction ratio are considered to have good metabolic stability. In some embodiments, a compound of the disclosure has a calculated ER of <0.3, <0.4, <0.5, <0.6.

Pharmaceutical Compositions

Pharmaceutical compositions of the disclosure (also referred to herein as the "disclosed pharmaceutical compositions") comprise one or more pharmaceutically acceptable carrier(s) or diluent(s) and a compound of the disclosure (e.g., a compound of Formula (I)), or a pharmaceutically acceptable salt thereof.

"Pharmaceutically acceptable carrier" and "pharmaceutically acceptable diluent" refer to a substance that aids the formulation and/or administration of an active agent to and/or absorption by a subject and can be included in the pharmaceutical compositions of the disclosure without causing a significant adverse toxicological effect on the subject. Non-limiting examples of pharmaceutically acceptable carriers and/or diluents include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, hydroxymethycellulose, fatty acid esters, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds or pharmaceutically acceptable salts thereof.

The pharmaceutical compositions of the disclosure optionally include one or more pharmaceutically acceptable carriers and/or diluents therefor, such as lactose, starch, cellulose and dextrose. Other excipients, such as flavoring agents, sweeteners, and preservatives, such as methyl, ethyl, propyl and butyl parabens, can also be included. More complete listings of suitable excipients can be found in the Handbook of Pharmaceutical Excipients ($5^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Methods of Treatment

The present disclosure provides a method of inhibiting certain mutant forms of epidermal growth factor receptor (EGFR) in a subject in need thereof, comprising administering to the subject an effective amount of a compound disclosed herein, a pharmaceutically acceptable salt thereof or a pharmaceutical composition disclosed herein. Mutant forms of EGFR include for example, EGFR with LRTMCS mutation (the exon 19 deletion (del19) or exon 21 (L858R) substitution mutation, T790M mutation, and C797S mutation). Subjects "in need of inhibiting EGFR" are those having a disease for which a beneficial therapeutic effect can be achieved by inhibiting at least one mutant EGFR, e.g., a slowing in disease progression, alleviation of one or more symptoms associated with the disease or increasing the longevity of the subject in view of the disease.

In some embodiments, the disclosure provides a method of treating a disease/condition/or cancer associated with or modulated by mutant EGFR, wherein the inhibition of the mutant EGFR is of therapeutic benefit, including but not limited to the treatment of cancer in a subject in need thereof. The method comprises administering to the subject an effective amount of a compound disclosed herein, a pharmaceutically acceptable salt thereof, or pharmaceutical composition disclosed herein.

In another embodiment, the disclosure provides a method of treating a subject with cancer, comprising administering to the subject an effective amount of a compound disclosed herein, a pharmaceutically acceptable salt thereof, or a pharmaceutical composition disclosed herein. Cancers to be treated according to the disclosed methods include lung cancer, colon cancer, urothelial cancer, breast cancer, prostate cancer, brain cancers, ovarian cancer, gastric cancer, pancreatic cancer, head and neck cancer, bladder cancer, and mesothelioma, including metastasis (in particular brain metastasis) of all cancers listed. Typically, the cancer is characterized by at one or more EGFR mutations described herein. In a specific embodiment, the cancer has progressed on or after EGFR tyrosine kinase inhibitor (TKI) Therapy. In a specific embodiment, the disease has progressed on or after first line osimertinib.

In a specific embodiment, the cancer to be treated is lung cancer. In a more specific embodiment, the cancer is non-small cell lung cancer (NSCLC). In some embodiments, the lung cancer is locally advanced or metastatic NSCLC, NSCLC adenocarcinoma, NSCLC with squamous histology and NSCLC with non-squamous histology. In another embodiment, the lung cancer is NSCLC adenocarcinoma. In another specific embodiment, the lung cancer (or non-small cell lung cancer) has metastasized to the brain.

In another embodiment, the disease/condition/or cancer associated with or modulated by mutant EGFR that is characterized by an EGFR genotype selected from genotypes 1-17 according the Table below (del18=Exon 18 deletion, specifically, e.g., del E709_T710 insD; del19=Exon 19 deletion, specifically, e.g., delE746_A750 (most common), delE746_S752insV, del747A750insP, delL747_P753insS, and delS752_1759; ex20ins—Exon 20 insertion, specifically, e.g., D761-E762insX, A763-Y764insX, Y764-V765insX, V765-M766insX, A767-S768insX, S768-D769insX, V769-D770insX, N771-P772insX, P772-H773insX, H773-V774insX, and V774-C775insX):

| | EGFR Genotype |
|---|---|
| 1 | EGFR del19 |
| 2 | EGFR del19 T790M |
| 3 | EGFR del19 C797S |
| 4 | EGFR del19 C797X (C797G or C797N) |
| 5 | EGFR del19 T790M C797S |
| 6 | EGFR del19 T790M C797S Q791P |
| 7 | EGFR del19 T790M (C797G or C797N) |
| 8 | EGFR del19 L792X (L792F, L792H or L792Y) |
| 9 | EGFR del19 T790M L792X (L792F, L792H, or L792Y) |
| 10 | EGFR del19 G796R (G796S) |
| 11 | EGFR del19 T790M G796R (G796S) C797S L792X (L792F, L792H or L792Y) |
| 12 | EGFR del19 L792R (L792V or L792P) |
| 13 | EGFR del19 L718Q (L718V) |
| 14 | EGFR del19 T790M L718Q (L718V) L792X (L792F, L792H or L792Y) |
| 15 | EGFR del19 T790M G796R (G796S) |
| 16 | EGFR del19 T790M L792R (L792V or L792P) |
| 17 | EGFR del19 T790M L718Q (L718V) |
| 18 | EGFR del19 T790M C797S L718Q (L718V) |
| 19 | EGFR del19 G724S |
| 20 | EGFR del19 T790M G724S |
| 21 | EGFR del19 S768I (SV768IL) |
| 22 | EGFR del19 T790M S768I (SV768IL) |
| 23 | EGFR del19 T790M C797S/G L792X (L792F, L792H, L792R, or L792Y) |
| 24 | EGFR del 19 V834L |
| 25 | EGFR del 19 T790M V834L |
| 27 | EGFR del19 T790M L792X (L792F, L792H, L792R, or L792Y) |
| 28 | EGFR del19 C797S L718Q (L718V) |
| 29 | EGFR del19 L718Q (L718V) A750P |
| 30 | EGFR del19 T790M L718Q (L718V) A750P L792V G796R |
| 31 | EGFR L858R |
| 32 | EGFR L858R T790M |
| 33 | EGFR L858R C797S |
| 34 | EGFR L858R C797X (797G or C797N) |
| 35 | EGFR L858R T790M C797S |
| 36 | EGFR L858R T790M C797S Q791P |
| 37 | EGFR L858R T790M C797X (C797G or C797N) |
| 38 | EGFR L858R L792X (L792F, L792H or L792Y) |
| 39 | EGFR L858R T790M L792X (L792F, L792H or L792Y) |
| 40 | EGFR L858R G796R (G796S) |
| 41 | EGFR L858R T790M G796R (G796S) C797S L792X (L792F, L792H or L792Y) |
| 42 | EGFR L858R L792R (L792V or L792P) |
| 43 | EGFR L858R L718Q (L718V) |
| 44 | EGFR L858R T790M G796R (G796S) |
| 45 | EGFR L858R T790M L792R (L792V or L792P) |
| 46 | EGFR L858R T790M L718Q (L718V) |
| 47 | EGFR L858R T790M C797S L718Q (L718V) |
| 48 | EGFR L858R T790M L718Q (L718V) L792X (L792F, L792H or L792Y) |
| 49 | EGFR L858R G724S |
| 50 | EGFR L858R T790M G724S |
| 51 | EGFR L858R S768I (SV768IL) |
| 52 | EGFR L858R T790M S768I (SV768IL) |
| 53 | EGFR L858R T790M C797S/G L792X (L792F, L792H, L792R, or L792Y) |
| 54 | EGFR L858R V834L |
| 55 | EGFR L858R T790M V834L |
| 57 | EGFR L858R T790M L792X (L792F, L792H, L792R, or L792Y) |
| 58 | EGFR L858R C797S L718Q (L718V) |
| 59 | EGFR L858R L718Q (L718V) A750P |
| 60 | EGFR L858R T790M L718Q (L718V) A750P L792V G796R |
| 61 | EGFR L861Q |
| 62 | EGFR L861Q T790M |
| 63 | EGFR L861Q T790M C797S/G/N |
| 64 | EGFR L861Q C797S/G/N |
| 65 | EGFR del18 |
| 66 | EGFR G719X (G719A, G719S, G719C, G719R, G719D, or G719V) |
| 67 | EGFR E709X (E709K, E709H, or E709A) |
| 68 | EGFR E709X (E709K, E709H, or E709A) (G719A, G719S, G719C, G719D, G719R, or G719V) |
| 69 | EGFR G719X (G719A, G719S, G719C, G719D, G719R, or G719V) S768I |
| 70 | EGFR ex20ins |
| 71 | EGFR ex20ins L718Q |
| 72 | EGFR ex20ins T790M |
| 73 | EGFR ex20ins C797S |
| 74 | EGFR S768I |
| 75 | EGFR T790M |
| 76 | EGFR T790M C797S/G L792X (L792F, L792H, L792R, or L792Y) |

In another embodiment, the disease/condition/or cancer (e.g., NSCLC) being treated with a disclosed compound, a pharmaceutically acceptable salt or a pharmaceutical composition disclosed herein is characterized by EGFR comprising EGFR del19.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR del19 T790M.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR del19 C797S.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR del19 C797X (C797G or C797N).

In another embodiment, the disease/condition/or cancer (e.g., NSCLC) being treated with a disclosed compound, a pharmaceutically acceptable salt or a pharmaceutical composition disclosed herein is characterized by EGFR comprising EGFR del19 T790M C797S.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR del19 T790M (C797G or C797N).

In another embodiment, the disease/condition/or cancer (e.g., NSCLC) being treated with a disclosed compound, a pharmaceutically acceptable salt, or a pharmaceutical composition is characterized by EGFR comprising EGFR del19 L792X (L792F, L792H or L792Y).

In another embodiment, the disease/condition/or cancer (e.g., NSCLC) being treated with a disclosed compound, a pharmaceutically acceptable salt thereof, or pharmaceutical composition disclosed herein is characterized by EGFR comprising EGFR del19 T790M L792X (L792F, L792H, or L792Y).

In another embodiment, the disease/condition/or cancer (e.g., NSCLC) being treated with a disclosed compound, a pharmaceutically acceptable salt thereof, or pharmaceutical composition disclosed herein is characterized by EGFR comprising EGFR del19 G796R (G796S).

In another embodiment, the disease/condition/or cancer (e.g., NSCLC) being treated with a disclosed compound, a pharmaceutically acceptable salt thereof, or pharmaceutical composition disclosed herein is characterized by EGFR comprising EGFR del19 L792R (L792V or L792P).

In another embodiment, the disease/condition/or cancer (e.g., NSCLC) being treated with a disclosed compound, a pharmaceutically acceptable salt thereof, or pharmaceutical composition disclosed herein is characterized by EGFR comprising EGFR del19 L718Q (L718V).

In another embodiment, the disease/condition/or cancer (e.g., NSCLC) being treated with a disclosed compound, a pharmaceutically acceptable salt thereof, or pharmaceutical composition described herein is characterized by EGFR comprising EGFR del19 T790M G796R (G796S).

In another embodiment, the disease/condition/or cancer (e.g., NSCLC) being treated with a disclosed compound, a pharmaceutically acceptable salt thereof, or pharmaceutical composition described herein is characterized by EGFR comprising EGFR del19 T790M L792R (L792V or L792P).

In another embodiment, the disease/condition/or cancer (e.g., NSCLC) being treated with a disclosed compound, a pharmaceutically acceptable salt thereof or pharmaceutical composition described herein is characterized by EGFR comprising EGFR del19 T790M L718Q (L718V).

In another embodiment, the disease/condition/or cancer (e.g., NSCLC) being treated with a disclosed compound, a pharmaceutically acceptable salt thereof or a pharmaceutical composition disclosed herein is characterized by EGFR comprising EGFR L858R.

In another embodiment, the disease/condition/or cancer (e.g., NSCLC) being treated with a disclosed compound, a pharmaceutically acceptable salt thereof or a pharmaceutical composition disclosed herein is characterized by EGFR comprising EGFR L858R T790M.

In another embodiment, the disease/condition/or cancer (e.g., NSCLC) being treated with a disclosed compound, a pharmaceutically acceptable salt thereof or a pharmaceutical composition disclosed herein is characterized by EGFR comprising EGFR L858R C797S.

In another embodiment, the disease/condition/or cancer (e.g., NSCLC) being treated with a disclosed compound, a pharmaceutically acceptable salt thereof or a pharmaceutical composition disclosed herein is characterized by EGFR comprising EGFR L858R C797X (797G or C797N).

In another embodiment, the disease/condition/or cancer (e.g., NSCLC) being treated with a disclosed compound, a pharmaceutically acceptable salt thereof or a pharmaceutical composition disclosed herein is characterized by EGFR comprising EGFR L858R T790M C797S.

In another embodiment, the disease/condition/or cancer (e.g., NSCLC) being treated with a disclosed compound, a pharmaceutically acceptable salt thereof or a pharmaceutical composition disclosed herein is characterized by EGFR comprising EGFR L858R T790M C797X (797G or C797N).

In another embodiment, the disease/condition/or cancer (e.g., NSCLC) being treated with a disclosed compound, a pharmaceutically acceptable salt thereof or a pharmaceutical composition disclosed herein is characterized by EGFR comprising EGFR L858R L792X (L792F, L792H or L792Y).

In another embodiment, the disease/condition/or cancer (e.g., NSCLC) being treated with a disclosed compound, a pharmaceutically acceptable salt thereof or a pharmaceutical composition disclosed herein is characterized by EGFR comprising EGFR L858R L790M L792X (L792F, L792H or L792Y).

In another embodiment, the disease/condition/or cancer (e.g., NSCLC) being treated with a disclosed compound, a pharmaceutically acceptable salt thereof or pharmaceutical composition disclosed herein is characterized by EGFR comprising EGFR L858R G796R (G796S).

In another embodiment, the disease/condition/or cancer (e.g., NSCLC) being treated with a disclosed compound, a pharmaceutically acceptable salt thereof or pharmaceutical composition disclosed herein is characterized by EGFR comprising EGFR L858R L792R (L792V or L792P).

In another embodiment, the disease/condition/or cancer (e.g., NSCLC) being treated with a disclosed compound, a pharmaceutically acceptable salt thereof or pharmaceutical composition disclosed herein is characterized by EGFR comprising EGFR L858R L718Q (L718V).

In another embodiment, the disease/condition/or cancer (e.g., NSCLC) being treated with a disclosed compound, a pharmaceutically acceptable salt thereof or pharmaceutical composition disclosed herein is characterized by EGFR comprising EGFR L858R T790M G796R (G796S).

In another embodiment, the disease/condition/or cancer (e.g., NSCLC) being treated with a disclosed compound, a pharmaceutically acceptable salt thereof or pharmaceutical composition disclosed herein is characterized by EGFR comprising EGFR L858R T790M L792R (L792V or L792P).

In another embodiment, the disease/condition/or cancer (e.g., NSCLC) being treated with a disclosed compound, a pharmaceutically acceptable salt thereof or pharmaceutical composition disclosed herein is characterized by EGFR comprising EGFR L858R T790M L718Q (L718V).

In another embodiment, the disease/condition/or cancer (e.g., NSCLC) being treated with a disclosed compound, a pharmaceutically acceptable salt or a pharmaceutical composition disclosed herein is characterized by EGFR comprising EGFR del18.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR G719X (G719A, G719S, G719C, G719R, G719D, or G719V).

In another embodiment, the disease/condition/or cancer (e.g., NSCLC) being treated with a disclosed compound, a pharmaceutically acceptable salt or a pharmaceutical composition disclosed herein is characterized by EGFR comprising EGFR E709X (E709K, E709H, or E709A).

In another embodiment, the disease/condition/or cancer (e.g., NSCLC) being treated with a disclosed compound, a pharmaceutically acceptable salt or a pharmaceutical composition disclosed herein is characterized by EGFR comprising EGFR E709X (E709K, E709H, or E709A) (G719A, G719S, G719C, G719D, G719R, or G719V).

In another embodiment, the disease/condition/or cancer (e.g., NSCLC) being treated with a disclosed compound, a pharmaceutically acceptable salt or a pharmaceutical composition disclosed herein is characterized by EGFR comprising EGFR G719X (G719A, G719S, G719C, G719D, G719R, or G719V) S768I.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR ex20ins.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR ex20ins L718Q.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR ex20ins T790M.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR ex20ins C797S.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR S768I.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR T790M.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR T790M C797S/G L792X (L792F, L792H, L792R, or L792Y).

In another embodiment, the disease/condition/or cancer (e.g., NSCLC) being treated with a disclosed compound, a pharmaceutically acceptable salt or a pharmaceutical composition disclosed herein is characterized by an EGFR genotype selected from genotypes 1-17.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to osimertinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to afatinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to dacomitinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to gefitinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to erlotinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to osimertinib and afatinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to osimertinib and dacomitinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to osimertinib and gefitinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to osimertinib and erlotinib.

Another embodiment is the treatment a subject with metastatic NSCLC with tumors harboring activating Exon 19 Deletion or L858R EGFR mutations as well as a resistance mutation disclosed herein as detected by an approved molecular testing methodology. Another embodiment is a disclosed compound used in combination with a $1^{st}$ or $3^{rd}$ generation TKI indicated for the treatment of subject with metastatic NSCLC with tumors harboring T790M and C797S mutations as detected by an approved test, and whose disease has progressed on or after at least 2 prior EGFR TKI therapies.

Another embodiment is a disclosed compound for the treatment of subjects with metastatic NSCLC whose disease with on-target EGFR resistance has progressed on or after any EGFR TKI. In a specific embodiment, the disclosed compound is used in combination with a $1^{st}$ or $3^{rd}$ generation TKI indicated for the treatment of subject with metastatic NSCLC.

Another embodiment is a disclosed compound for the treatment of subjects with metastatic EGFR C797S mutation-positive NSCLC as detected by an approved molecular test, whose disease has progressed on or after first-line osimertinib. In a specific embodiment, the disclosed compound is used in combination with a $1^{st}$ or $3^{rd}$ generation TKI indicated for the treatment of subject with metastatic NSCLC.

In a particular embodiment, the deletions, mutations, and insertions disclosed herein are detected by an FDA-approved test.

A person of ordinary skill in the art can readily determine the certain EGFR alterations a subject possesses in a cell, cancer, gene, or gene product, e.g., whether a subject has one or more of the mutations or deletions described herein using a detection method selected from those known in the art such as hybridization-based methods, amplification-based methods, microarray analysis, flow cytometry analysis, DNA sequencing, next-generation sequencing (NGS), primer extension, PCR, in situ hybridization, fluorescent in situ hybridization, dot blot, and Southern blot.

To detect one or more EGFR deletions and/or mutations, a primary tumor sample, circulating tumor DNA (ctDNA), circulating tumor cells (CTC), and/or circulating exosomes may be collected from a subject. The samples are processed, the nucleic acids are isolated using techniques known in the art, then the nucleic acids are sequenced using methods known in the art. Sequences are then mapped to individual exons, and measures of transcriptional expression (such as RPKM, or reads per kilobase per million reads mapped), are quantified. Raw sequences and exon array data are available from sources such as TCGA, ICGC, and the NCBI Gene Expression Omnibus (GEO). For a given sample, individual exon coordinates are annotated with gene identifier information, and exons belonging to kinase domains are flagged. The exon levels are then z-score normalized across all tumors samples.

The compounds of the disclosure, pharmaceutically acceptable salts thereof or pharmaceutical compositions disclosed herein may be used for treating to a subject who has become refractory to treatment with one or more other EGFR inhibitors. "Refractory" means that the subject's cancer previously responded to drugs but later responds poorly or not at all. In some embodiments, the subject has become refractory to one or more first generation EGFR inhibitors such as erlotinib, gefitinib, icotinib or lapatinib. In some embodiments, the subject has been become refractory to treatment with one or more second generation EGFR inhibitors such as afatinib, dacomitinib, poziotinib, or neratinib. In some embodiments the subject has become refractory to treatment with one or more first generation inhibitors and one or more second generation inhibitors. In some embodiments, the subject has become refractory to treatment with one or more third generation inhibitors such as osimertinib, nazartinib, or avitinib. In one embodiment, the subject has become refractory to treatment with one or more first generation EGFR inhibitors and one or more third generation EGFR inhibitors. In some embodiments, the subject has become refractory to treatment with one or more second generation EGFR inhibitors and one or more third generation EGFR inhibitors. In some embodiments, the subject has become refractory to treatment with one or more first generation inhibitors, and one or more third generation EGFR inhibitors.

Combinations

The compounds of the disclosure, pharmaceutically acceptable salts thereof, or pharmaceutical compositions disclosed herein can be used in combination with one or more additional pharmacologically active substances. For example, the disclosure includes methods of treating a condition/disease/or cancer comprising administering to a subject in need thereof a compound of the disclosure or a pharmaceutically acceptable salt or a pharmaceutical composition disclosed herein thereof in combination with an EGFR (or EGFR mutant) inhibitor, such as afatinib, osimertinib, lapatinib, erlotinib, dacomitinib, poziotinib, neratinib, gefitinib JBJ-04-125-02, alflutinib (AST 2818), almonertinib (HS10296), BBT-176, BI-4020, CH7233163, gilitertinib, JND-3229, lazertinib, nazartinib (EGF 816), PCC-0208027, rezivertinib (BPI-7711), TQB3804, zorifertinib (AZ-3759), or DZD9008; an EGFR antibody such as cetuximab, panitumumab, necitumumab, HLX07, JMT101; or a bispecific EGFR and MET antibody (e.g., amivantamab ((JNJ-61186372, JNJ-372)). For the treatment of cancer e.g., NSCLC using a compound of the disclosure or pharmaceutically acceptable salt thereof or pharmaceutical composition disclosed herein in combination with a first line therapy, for example a first, second, or third generation EGFR inhibitor (i.e., as an initial treatment before the cancer has become refractory) may forestall or delay the cancer from becoming refractory. Typically, the cancer is characterized by one of the EGFR genotypes described herein.

Alternatively, a compound of the disclosure, a pharmaceutically acceptable salt thereof or a pharmaceutical composition disclosed herein can be administered in combination with other anti-cancer agents that are not EGFR inhibitors e.g., in combination with MEK, including mutant MEK inhibitors (trametinib, cobimtetinib, binimetinib, selumetinib, refametinib); c-MET, including mutant c-Met inhibitors (savolitinib, cabozantinib, foretinib, glumetinib, tepotinib) and MET antibodies (emibetuzumab, telisotuzumab vedotin (ABBV 339)); mitotic kinase inhibitors (CDK4/6 inhibitors such as palbociclib, ribociclib, abemacicilb, GIT38); anti-angiogenic agents e.g., bevacizumab, nintedanib; apoptosis inducers such as Bcl-2 inhibitors e.g, venetoclax, obatoclax, navitoclax, palcitoclax (APG-1252), and Mc1-1 inhibitors e.g., AZD-5991, AMG-176, S-64315; mTOR inhibitors e.g, rapamycin, temsirolimus, everolimus, ridoforolimus; RET inhibitors, like pralsetinib and selpercatinib, and PI3K inhibitors dactolisib (BEZ235), pictilisib (GDC-0941, LY294002, idelalisib (CAL-101); JAK inhibitors (e.g., AZD4205, itacitinib), Aurora A inhibitors (e.g., alisertib); BCR/ABL and/or Src family tyrosine kinase inhibitors (e.g., dasatinib); VEGF inhibitors (e.g., MP0250; ramucirumab); multi-kinase protein inhibitors (e.g., anlotinib, midostaurin); PARP inhibitors (e.g., niraparib); platinum therapies (e.g., cisplatin (CDDP), carboplatin (CBDCA), or nedaplatin (CDGP)); PD-L1 inhibitors (e.g., durvalumab (MEDI 4736)); HER2/neu receptor inhibitors (e.g., trastuzumab); anti-HER2 or anti-HER3 antibody-drug conjugates (e.g., patritumab deruxtecan (U3-1402), trastuzumab emtansine); or immunogene therapy (e.g., oncoprex).

A "subject" is a human in need of treatment.

Methods of Administration and Dosage Forms

The precise amount of compound administered to provide an "effective amount" to the subject will depend on the mode of administration, the type, and severity of the cancer, and on the characteristics of the subject, such as general health, age, sex, body weight, and tolerance to drugs. The skilled artisan will be able to determine appropriate dosages depending on these and other factors. When administered in combination with other therapeutic agents, e.g., when administered in combination with an anti-cancer agent, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound of Formula (I) being used by following, for example, dosages reported in the literature and recommended in the *Physician's Desk Reference* (57th Ed., 2003).

"Treating" or "treatment" refers to obtaining a desired pharmacological and/or physiological effect. The effect can be therapeutic, which includes achieving, partially or substantially, one or more of the following results: partially or substantially reducing the extent of the disease, condition or cancer; ameliorating or improving a clinical symptom or indicator associated with the disease, condition or cancer; delaying, inhibiting or decreasing the likelihood of the progression of the disease, condition or cancer; or decreasing the likelihood of recurrence of the disease, condition or cancer.

The term "effective amount" means an amount when administered to the subject which results in beneficial or desired results, including clinical results, e.g., inhibits, suppresses or reduces the symptoms of the condition being treated in the subject as compared to a control. For example, a therapeutically effective amount can be given in unit dosage form (e.g., 0.1 mg to about 50 g per day, alternatively from 1 mg to about 5 grams per day; and in another alternatively from 10 mg to 1 gram per day).

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa.

In addition, a compound of the disclosure, a pharmaceutically acceptable salt thereof or a pharmaceutical composition of the disclosure can be co-administered with other therapeutic agents. As used herein, the terms "co-administration", "administered in combination with", and their grammatical equivalents, are meant to encompass administration of two or more therapeutic agents to a single subject, and are intended to include treatment regimens in which the agents are administered by the same or different route of administration or at the same or different times. In some embodiments the one or more compounds of the disclosure, a pharmaceutically acceptable salt thereof or a pharmaceutical composition of the disclosure will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, the compounds described herein and the other agent(s) are admixed in the composition.

The particular mode of administration and the dosage regimen will be selected by the attending clinician, taking into account the particulars of the case (e.g. the subject, the disease, the disease state involved, the particular treatment). Treatment can involve daily or multi-daily or less than daily (such as weekly or monthly etc.) doses over a period of a few days to months, or even years. However, a person of ordinary skill in the art would immediately recognize appropriate and/or equivalent doses looking at dosages of approved compositions for treating a disease using the disclosed EGFR inhibitors for guidance.

The compounds of the disclosure or a pharmaceutically acceptable salt thereof can be administered to a patient in a variety of forms depending on the selected route of administration, as will be understood by those skilled in the art. The compounds of the present teachings may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

The pharmaceutical composition of the disclosure is formulated to be compatible with its intended route of administration. In an embodiment, the composition is formulated in accordance with routine procedures as a pharmaceutical composition adapted for intravenous, subcutaneous, intramuscular, oral, intranasal, or topical administration to human beings. In preferred embodiments, the pharmaceutical composition is formulated for intravenous administration.

Typically, for oral therapeutic administration, a compound of the disclosure or a pharmaceutically acceptable salt thereof may be incorporated with excipient and used in the form of ingestible tablets, buccal tablets, troches, capsules, elixirs, suspensions, syrups, wafers, and the like.

Typically for parenteral administration, solutions of a compound of the disclosure can generally or a pharmaceutically acceptable salt thereof be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound of the disclosure for the extemporaneous preparation of sterile injectable solutions or dispersions are appropriate.

The following examples are intended to be illustrative and are not intended to be limiting in any way to the scope of the disclosure.

EXEMPLIFICATION

Examples

Preparation of Exemplary Compounds
Definitions
  TsOH 4-methylbenzenesulfonic acid
  TEA triethylamine
  THF tetrahydrofuran
  MSCl methanesulfonyl chloride
  DCM dichloromethane
  NH4Cl ammonium chloride
  MgSO4 magnesium sulfate
  NaN3 sodium azide
  DMF dimethyl formamide
  EA ethyl acetate
  Na2SO4 sodium sulfate
  MeOH methanol
  N2 nitrogen
  H2 hydrogen
  LiAlH4 lithium aluminum hydride
  NaHCO3 sodium bicarbonate
  CbzCl benzyl carbonochloridate
  PE petroleum ether
  DAST N-ethyl-N-(trifluoro-sulfanyl)ethanamine
  HCl hydrochloride
  ACN acetontirile
  DIPEA diisopropylethylamine
  DMSO dimethylsulfoxide
  DMA dimethylacetamide h hs
HPLC high performance liquid chromatography
min minutes
C Celsius
$IC_{50}$ inhibitory concentration 50%
IPA isopropyl alcohol
MTBE methyl tert-butyl ether
rt room temperature
TFA trifluoroacetic acid Methods for preparing compounds of the invention can be carried out in suitable solvents which can be readily selected by one of skill in the art of organic synthesis. Suitable solvents can be substantially non-reactive with the starting materials (reactants), intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 5th ed., John Wiley & Sons: New Jersey, (2014), which is incorporated herein by reference in its entirety.

Reactions can be monitored according to any suitable method known in the art. For example, product formation can be monitored by spectroscopic means, such as nuclear magnetic resonance (NMR) spectroscopy (e.g., $^1H$ or $^{13}C$), infrared (IR) spectroscopy, spectrophotometry (e.g., UV-visible), mass spectrometry (MS), or by chromatographic methods such as high performance liquid chromatography (HPLC) or thin layer chromatography (TLC). Analytical instruments and methods for compound characterization:

LC-MS: The liquid chromatography-mass spectrometry (LC-MS) data (sample analyzed for purity and identity) were obtained with an Agilent model-1260 LC system using an Agilent model 6120 mass spectrometer utilizing ES-API ionization fitted with an Agilent Poroshel 120 (EC-C18, 2.7 um particle size, 3.0×50 mm dimensions) reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 4 minutes was utilized. The flow rate was constant at 1 mL/min.

Alternatively, the liquid chromatography-mass spectrometry (LC-MS) data (sample analyzed for purity and identity) were obtained with a Shimadzu LCMS system using an Shimadzu LCMS mass spectrometer utilizing ESI ionization fitted with an Agilent (Poroshel HPH-C18 2.7 um particle size, 3.0×50 mm dimensions) reverse-phase column at 22.4 degrees Celsius. The mobile phase consisted of a mixture of solvent 5 mM $NH_4HCO_3$ (or 0.05% TFA) in water and acetonitrile. A constant gradient from 90% aqueous/10% organic to 5% aqueous/95% organic mobile phase over the course of 2 minutes was utilized. The flow rate was constant at 1.5 mL/min.

Prep LC-MS: Preparative HPLC was performed on a Shimadzu Discovery VP® Preparative system fitted with a Luna 5 u C18(2) 100 A, AXIA packed, 250×21.2 mm reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 25 minutes was utilized. The flow rate was constant at 20 mL/min. Reactions carried out in a microwave were done so in a Biotage Initiator microwave unit.

Alternatively, the preparative HPLC was performed on a Waters Preparative system fitted with Column: XBridge Shield RP18 OBD Column, 30*150 mm, 5um; The mobile phase consisted of a mixture of solvent Water (10 mmol/L $NH_4HCO_{3+0.05}$% $NH3·H2O$) and acetonitrile. A constant gradient from 95% aqueous/5% organic to 5% aqueous/95% organic mobile phase over the course of 11 minutes was utilized. The flow rate was constant at 60 mL/min. Reactions carried out in a microwave were done so in a Biotage Initiator microwave unit.

Silica gel chromatography: Silica gel chromatography was performed on a Teledyne Isco CombiFlash® Rf unit, a Biotage® Isolera Four unit, or a Biotage® Isolera Prime unit.

Proton NMR: $^1H$ NMR spectra were obtained with a Varian 400 MHz Unity Inova 400 MHz NMR instrument (acquisition time=3.5 seconds with a 1 second delay; 16 to 64 scans) or a Avance 400 MHz Unity Inova 400 MHz NMR instrument (acquisition time=3.99 seconds with a 1 second delay; 4 to 64 scans) or a Avance 300 MHz Unity Inova 300 MHz NMR instrument (acquisition time=5.45 seconds with a 1 second delay; 4 to 64 scans). Unless otherwise indicated, all protons were reported in DMSO-d6 solvent as parts-per million (ppm) with respect to residual DMSO (2.50 ppm).

SFC: Waters Preparative system.

Chiral-HPLC was performed on an Agilent 1260 Preparative system.

One of ordinary skill in the art will recognize that modifications of the gradient, column length, and flow rate are possible and that some conditions may be more suitable for compound characterization than others, depending on the chemical species being analyzed.

Generic Synthesis Schemes:

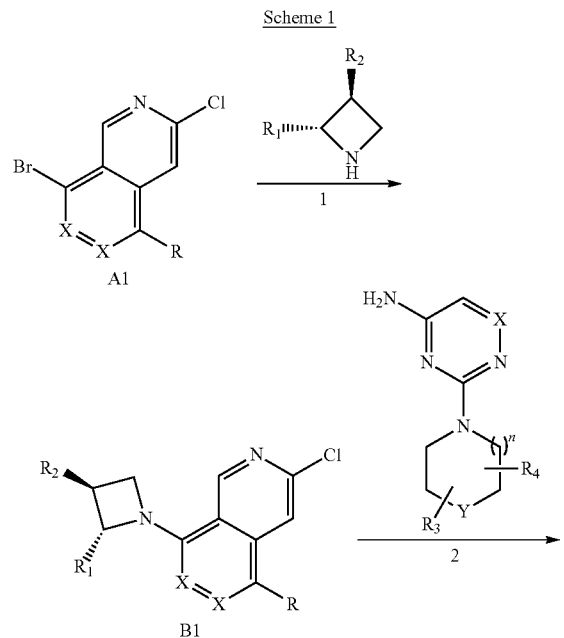

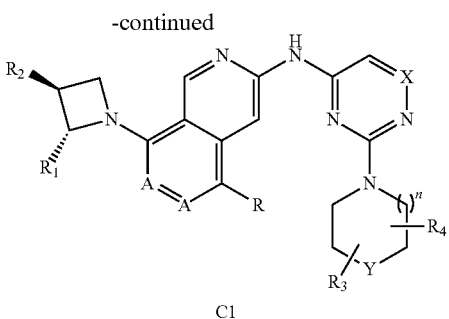

In certain embodiments optionally substituted bicyclic heteroaromatic, A1, where X=C or N, R=H, halo, optionally substituted alkyl, or —O-alkyl is reacted with an optionally substituted azetidine, 1, where R1=H, alkyl and R2=optionally substituted methyl sulfone or sulfinimide using standard Buchwald coupling conditions to form optionally substituted condensation products, B1. The resulting species is further homologated with an optionally substituted pyrimidine or triazine where Y=C, N, O; n=0, 1, 2; and R3 and R4 are either or both H, halo, optionally substituted alklyl, O-alkyl, or N-Alkyl via a second Buchwald coupling to afford final products, C1.

Synthetic Examples

Example A1: Synthesis of 3-(ethylsulfonylmethyl)azetidine Trifluoroacetic Acid Salt

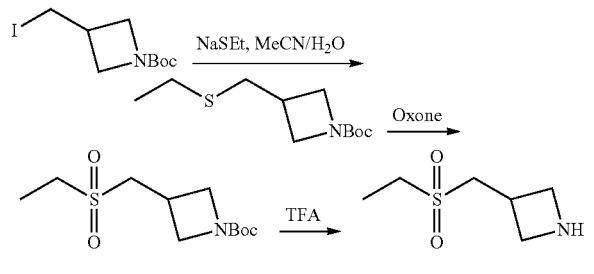

Step I: Synthesis of tert-butyl 3-(ethylthiomethyl)azetidine-1-carboxylate

Tert-butyl 3-(iodomethyl)azetidine-1-carboxylate (2 g, 6.73 mmol, 1 equiv.) and (ethylsulfanyl)sodium (1.12 g, 13.4 mmol, 2 equiv.) was dissolved in mixture solvent (CH$_3$CN/H$_2$O=3:1, 20 mL). The resulting solution was stirred at 60° C. for 18 h. The resulting solution was concentrated under vacuum. The residue was purified by chromatography with DCM/MeOH (30/1). This resulted in 1.4 g (90%) of the title compound as an off-white solid.
Analytical Data: LC-MS: (ES, m/z)=176 [M+1−56].

Step 2: Synthesis of tert-butyl 3-(ethylsulfonylmethyl)azetidine-1-carboxylate Tert-butyl 3-[(ethylsulfanyl)methyl]azetidine-1-carboxylate (1.4 g, 6.05 mmol, 1 equiv.) was dissolved in mixture solvent (THF:EtOH=1:1, 10 mL), and then added pentapotassium sulfuric acid diperoxymonosulfate hydrogen sulfate (Oxone, 11.1 g, 18.1 mmol, 3 equiv.) in 0.5 mL of water. The resulting solution was stirred at 0° C. for 10 min, and then stirred at rt for 2 h. The resulting solution was concentrated under vacuum and purified by chromatography with DCM/MeOH (20:1) to afford 1.3 g (81%) of the title compound as white solid.
Analytical Data: LC-MS: (ES, m/z)=286 [M+23].

Step 3: Synthesis of 3-(ethylsulfonylmethyl)azetidine Trifluoroacetic Acid Salt Trifluoroacetic acid (3.36 g, 29.5 mmol) was added to a solution of tert-butyl 3-[(ethanesulfonyl)methyl]azetidine-1-carboxylate (1.3 g, 4.93 mmol) in DCM (8 mL). The resulting solution was stirred at rt for 3 h. The resulting solution was concentrated under vacuum and the residue was washed with methyl tertiary butyl ether to afford 800 mg of the title compound as a white solid. Analytical Data: LC-MS: (ES, m/z)=164 [M+1].

Example A2: Synthesis of 3-(isopropylsulfonylmethyl)azetidine

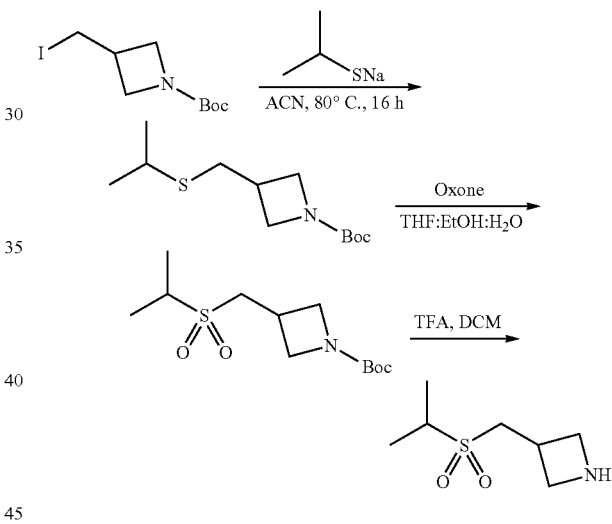

Step I: Synthesis of tert-butyl 3-(isopropylthiomethyl)azetidine-1-carboxylate Tert-butyl 3-(iodomethyl)azetidine-1-carboxylate (200 mg, 673 μmol, 1 equiv.) and (propan-2-ylsulfanyl)sodium (66.0 mg, 673 μmol, 1 equiv.) was dissolved in ACN (3 mL). The resulting solution was stirred at 80° C. for 16 h. The resulting solution was extracted with DCM, and then the organic layers combined, dried over anhydrous sodium sulfate and concentrated under vacuum. The resulted in 150 mg (90%) of the title compound.

Step 2: Synthesis of tert-butyl 3-(isopropylsulfonylmethyl)azetidine-1-carboxylate Tert-butyl 3-[(propan-2-ylsulfanyl)methyl]azetidine-1-carboxylate (140 mg, 570 μmol, 1 equiv.) and pentapotassium sulfuric acid diperoxymonosulfate hydrogen sulfate (525 mg, 855 μmol, 1.50 equiv.) was dissolved in mixed solution (THF:EtOH:H$_2$O=1:1:1; 1 mL). The resulting solution was stirred at room temperature for 2 h. The resulting solution was added sodium sulfite solution to end the reaction, then extracted with EA. The organic layers was combined and concentrated under vacuum. This is resulted in 130 mg (82%) of the title compound as an off-white.
Analytical Data: LC-MS: (ES, m/z)=300 [M+23].

Step 3: Synthesis of 3-(isopropylsulfonylmethyl)azetidine Trifluoroacetic Acid Salt Into a 8-mL tube was placed tert-butyl 3-[(propane-2-sulfonyl)methyl]azetidine-1-carboxylate (120 mg, 432 μmol) in DCM (4 mL)/TFA (1 mL). The resulting solution was stirred at rt for 2 h. The resulting solution was concentrated under vacuum. This resulted in 70 mg of the title compound as a white solid.
Analytical Data: LC-MS: (ES, m/z)=178 [M+1].

Example A3: Synthesis of 3-((trifluoromethylsulfonyl)methyl)azetidine

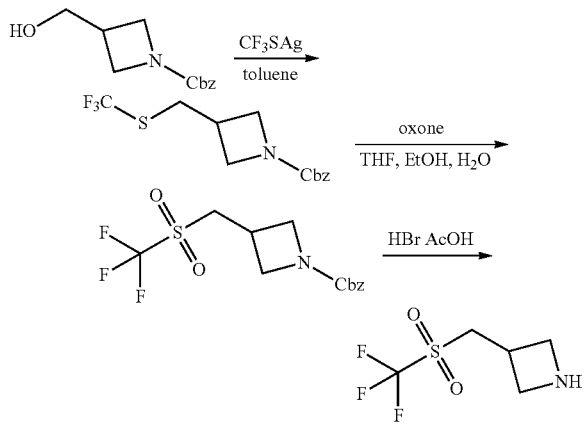

Step 1: Synthesis of benzyl 3-((trifluoromethylthio)methyl)azetidine-1-carboxylate The mixture of benzyl 3-(hydroxymethyl)azetidine-1-carboxylate (100 mg, 0.450 mmol, 1 equiv.), AgSCF₃ (420 mg, 1.8 mmol, 4.00 equiv.) and nBu₄NI (1725 mg, 5.4 mmol, 12 equiv.) in toluene (8 mL) was stirred for 12 h at 80° C. The solids were filtered out. The resulting mixture was concentrated. The residue was applied onto a silica gel column with EA/PE (3:1). This resulted in 50 mg (36.4%) of the title compound as a light-yellow solid.
Analytical Data: LC-MS: (ES, m/z=306 [M+1].

Step 2: Synthesis of benzyl 3-((trifluoromethyl-sulfonyl)methyl)azetidine-1-carboxylate Oxone (330.5 mg, 1.97 mmol, 3 equiv.) was added the solution of benzyl 3-[[(trifluoromethyl)sulfanyl]methyl]azetidine-1-carboxylate (200 mg, 0.66 mmol, 1 equiv.) in THF (1 mL)/EtOH (1 mL)/H₂O (1 mL). The resulting solution was stirred for 2 h at 60° C. The reaction was then quenched by the addition of 1 mL of Na₂S₂O₃ and extracted with 3×5 mL of EA. The residue was applied onto a silica gel column with EA/PE (3:1). This resulted in 120 mg (54.5%) of the title compound as light-yellow oil.
Analytical Data: LC-MS: (ES, m/z)=338 [M+1].

Step 3: Synthesis of 3-((trifluoromethylsulfonyl)methyl)azetidine Hydrobromide

Benzyl 3-(trifluoromethanesulfonylmethyl)azetidine-1-carboxylate (50 mg, 0.148 mmol, 1 equiv.) was added to ethanecarboperoxoyl bromide (30% in AcOH, 1 mL). The resulting solution was stirred for 3 h at rt. The resulting mixture was concentrated and resulted in 20 mg (66.4%) of 3-(trifluoromethanesulfonylmethyl)azetidine hydrobromide as a light-yellow solid. The crude product was used directly for next step without further purification.
Analytical Data: LC-MS: (ES, m/z): =204 [M+1].

Example A4: Synthesis of (2R,3S)-2-methyl-3-(methylsulfonylmethyl)azetidine

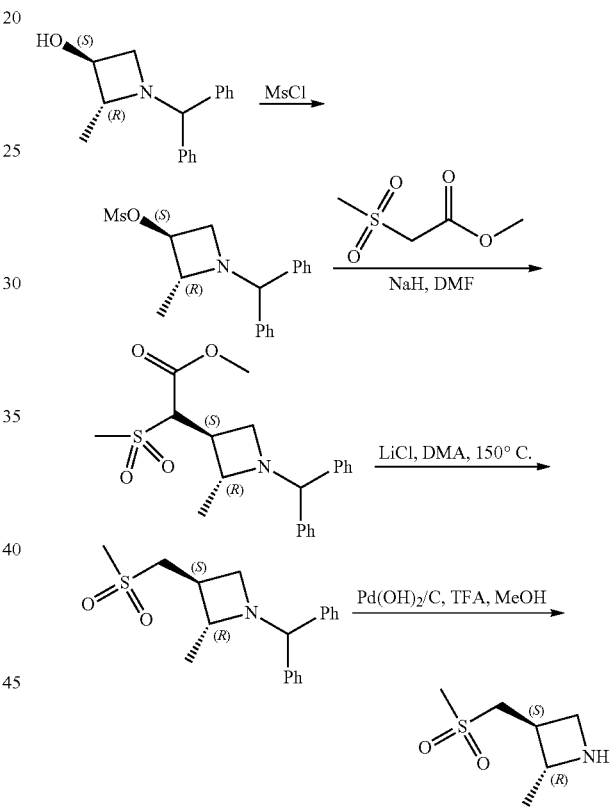

Step 1: Synthesis of (2R,3S)-1-benzhydryl-2-methylazetidin-3-yl Methanesulfonate (2R,3S)-1-benzhydryl-2-methylazetidin-3-ol (Pharmablock, 20 g, 78.9 mmol) was dissolved in 300 mL DCM and TEA (9.55 g, 94.6 mmol) was added and the reaction mixture cooled in an ice bath. Mesyl chloride (9.93 g, 86.7 mmol) was added dropwise and allowed to stir, warming slowly to rt and stirred overnight. The mixture was diluted with DCM and washed with water and the organic phase dried over sodium sulfate, filtered and evaporated to give 26 g (98%) of the title compound as a viscous yellow oil.
Analytical Data: LC-MS: (ES, m/z)=332 [M+1].

Step 2: Synthesis of (S)-methyl 2-((2R,3S)-1-benz-hydryl-2-methylazetidin-3-yl)-2-(methylsulfonyl) acetate (2R,3S)-1-benzhydryl-2-methylazetidin-3-yl methanesulfonate (26 g, 78.4 mmol) and methyl 2-(methylsulfonyl)acetate (15.3 g, 101 mmol) were dissolved in 260 mL DMF and then NaH (3.75 g of 60% dispersion in mineral oil, 6.63 mmol) was added and stirred for ~15 minutes, until hydrogen evolution had ceased. The reaction mixture was heated to 80° C. overnight. The reaction was cooled and then diluted with ~200 mL water and extracted with EA and combined organics washed with water, brine and dried over sodium sulfate, filtered and evaporated to give the crude product. The residue was purified by chromatography (0 to 7% MeOH/DCM). Pure fractions combined and evaporated to give 24 g (80%) of the title compound as a pale-yellow foam.

Step 3: Synthesis of (2R,3S)-1-benzhydryl-2-methyl-3-(methylsulfonylmethyl)azetidine (S)-methyl-2-((2R,3S)-1-benzhydryl-2-methylazetidin-3-yl)-2-(methylsulfonyl)acetate (24 g, 61.9 mmol) was dissolved in 240 mL DMA and lithium chloride (20.9 g, 495 mmol) was added and the flask put into a preheated block that was kept at 150° C. LC/MS indicated the starting material was consumed after 1.5 h. Cooled to room temperature and dilute with water, extracted with EA and the combined organics washed with water, brine and dried over sodium sulfate. Filtered and evaporated to give the crude product and further purified by chromatography (0 to 5% MeOH/DCM). Pure fractions were combined and evaporated to give 19 g (93%) of the title compound as a pale-yellow foam.

Analytical Data: LC-MS: (ES, m/z)=330 [M+1].

Step 4: Synthesis of (2R,3S)-2-methyl-3-(methylsulfonylmethyl)azetidine

To a solution of (2R,3S)-1-(diphenylmethyl)-3-(methanesulfonylmethyl)-2-methylazetidine (1 9 g, 57.3 mmol) in MeOH (270 mL) was added TFA (9 mL) and Pd(OH)$_2$ (5.7 g), the reaction was stirred overnight at rt under H$_2$ atmosphere. The reaction mixture was filtered and evaporated to give the crude title compound (17 g) as a light-brown oil.

Analytical Data: LC-MS: (ES, m/z)=164 [M+1].

Example A5: Synthesis of 3-methyl-3-(methylsulfonylmethyl)azetidine

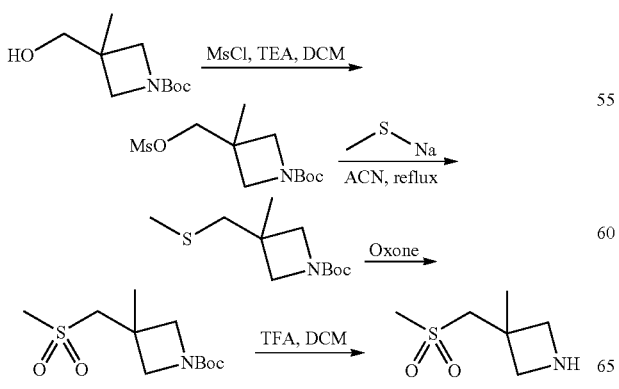

Step I: Synthesis of tert-butyl 3-methyl-3-((methylsulfonyloxy)methyl)azetidine-1-carboxylate Methanesulfonyl chloride (255 mg, 2.23 mmol) was added dropwise to TEA (301 mg, 2.98 mmol) and tert-butyl 3-(hydroxymethyl)-3-methylazetidine-1-carboxylate (300 mg, 1.49 mmol) in DCM at 0° C. The mixture was stirred at rt for 4 h. The mixture was diluted with DCM, washed with brine. The organic layer was dried and concentrated under vacuum to get 350 mg (95%) of the title compound as a colorless oil.

Analytical Data: LC-MS: (ES, m/z)=224 [M+1-56].

Step 2: Synthesis of tert-butyl 3-methyl-3-(methylsulfonylmethyl)azetidine-1-carboxylate Sodium methylsulfanide (175 mg, 2.50 mmol) was added to tert-butyl 3-[(methanesulfonyloxy)methyl]-3-methylazetidine-1-carboxylate (350 mg, 1.25 mmol) in ACN (30 mL) at rt. The resulting mixture was heated to reflux for 16 h. The mixture was diluted with DCM, washed with brine. The organic layer was concentrated under vacuum. The residue was purified by a silica gel column with PE:EA=1:1. This resulted in 250 mg (75%) of the title compound as a white solid.

Analytical Data: LC-MS: (ES, m/z)=176 [M+1−56].

Step 3: Synthesis of tert-butyl 3-methyl-3-(methylsulfonylmethyl)azetidine-1-carboxylate Oxone (362 mg, 2.16 mmol) was added to tert-butyl 3-methyl-3-[(methylsulfanyl)methyl]azetidine-1-carboxylate (250 mg, 1.08 mmol) in THF/H$_2$O/EtOH(5/5/5 mL) at rt. The resulting mixture was stirred at rt for 16 h. The mixture was extracted with EA, washed with brine. The organic layer was dried, concentrated under vacuum. The residue was purified by a silica gel column with DCM:MeOH=20:1. This is resulted in 200 mg (88%) of the title compound as a colorless.

Analytical Data: LC-MS: (ES, m/z)=208 [M+1−56].

Step 4: Synthesis of 3-methyl-3-(methylsulfonylmethyl)azetidine

TFA (5 mL) was added to tert-butyl 3-(methanesulfonylmethyl)-3-methylazetidine-1-carboxylate (150 mg, 569 μmol) in DCM (15 mL) at rt. The mixture was stirred at rt for 1 h. The mixture was concentrated under vacuum to afford 100 mg of the title compound as a colorless oil.

Analytical Data: LC-MS: (ES, m/z)=164 [M+1].

Example A6: Synthesis of N-((azetidin-3-ylmethyl)(methyl)(oxo)-16-sulfaneylidene)benzamide

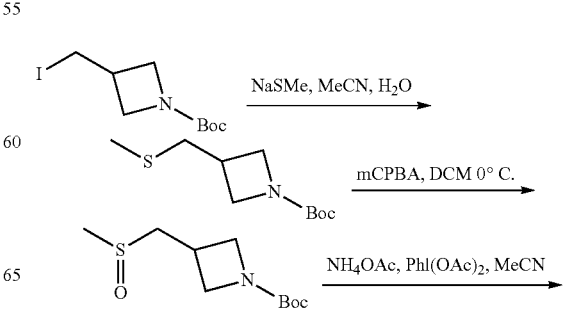

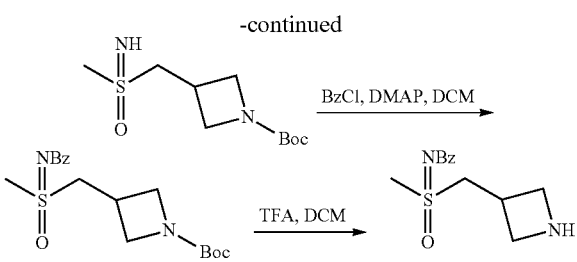

Step 1: Synthesis of Tert-butyl 3-(methylthiomethyl)azetidine-1-carboxylate

A mixture of tert-butyl 3-(iodomethyl)azetidine-1-carboxylate (5.05 g, 17 mmol, 1 equiv.) and NaSMe (3.56 g, 25.5 mmol, 1.50 equiv.) in MeCN (30 mL) and H₂O (10 mL) was heated to 60° C. for 18 h. After cooling down to rt, the mixture was concentrated, the residue was diluted with EA. The organic solution was washed with water, dried over Na₂SO₄. This solution was concentrated to afford the title compound (3.69 g, quant.) as a light-yellow oil.

Step 2: Synthesis of tert-butyl 3-(methylsulfinylmethyl)azetidine-1-carboxylate A solution of tert-butyl 3-[(methylsulfanyl)methyl]azetidine-1-carboxylate (3.69 g, 17 mmol, 1 equiv.) in DCM (50 mL) was added mCPBA (2.92 g, 17 mmol, 1 equiv.) portionwise at 0° C. The reaction was carried on at 0° C. for 2 h before quenching by adding sat. NaHCO₃ (200 mL). The mixture was extracted with DCM. The organic layer was combined and concentrated, the residue was purified by silica gel column chromatography (DCM/MeOH=15:1) to afford the title compound (2.7 g, 68.2%) as a light-yellow syrup.

Step 3: Synthesis of tert-butyl 3-(S-methylsulfonimidoylmethyl)azetidine-1-carboxylate A mixture of tert-butyl 3-(methanesulfinylmethyl)azetidine-1-carboxylate (2.68 g, 11.5 mmol, 1 equiv.), Ammonium acetate (4.41 g, 57.4 mmol, 5.00 equiv.) and PhI(OAc)₂ (5.53 mg, 17.2 mmol, 1.50 equiv.) in MeCN (60 mL) was stirred at 35° C. for 18 h. The mixture was filtered and the filtrate was concentrated. The residue was purified by silica gel column chromatography (DCM/MeOH=15:1) to afford the title compound (1.5 g, 52.63%) as a light-yellow syrup.
Analytical Data: LC-MS: (ES, m/z)=249 [M+1].

Step 4: Synthesis of tert-butyl 3-((N-benzoyl-S-methylsulfonimidoyl)methyl)azetidine-1-carboxylate A mixture of tert-butyl 3-{[imino(methyl)-oxo-λ⁶-sulfanyl]methyl}azetidine-1-carboxylate (372 mg, 1.50 mmol, 1 equiv.) and DMAP (366 mg, 3 mmol, 2 equiv.) in DCM (6 mL) was added BzCl (281 mg, 2 mmol, 1.33 equiv.) at 0° C. The reaction was carried on at rt for 3 h and concentrated. The residue was purified by silica gel column chromatography (DCM/MeOH=20:1) to afford the title compound (440 mg, 83.3%) as a yellow syrup.
Analytical Data: LC-MS: (ES, m/z)=375 [M+23].

Step 5: Synthesis of N-((azetidin-3-ylmethyl)(methyl)(oxo)-16-sulfaneylidene)benzamide Tert-butyl 3-((N-benzoyl-S-methylsulfonimidoyl)methyl)azetidine-1-carboxylate (440 mg, 1.25 mmol, 1 equiv.) in TFA (1 mL) and DCM (3 mL) was stirred at rt for 4 h. The mixture was concentrated to afford the title compound (315 mg, quant.) trifluoroacetic acid salt as a yellow syrup.

Example A7: Synthesis of (2R,3S)-3-(ethylsulfonylmethyl)-2-methylazetidine

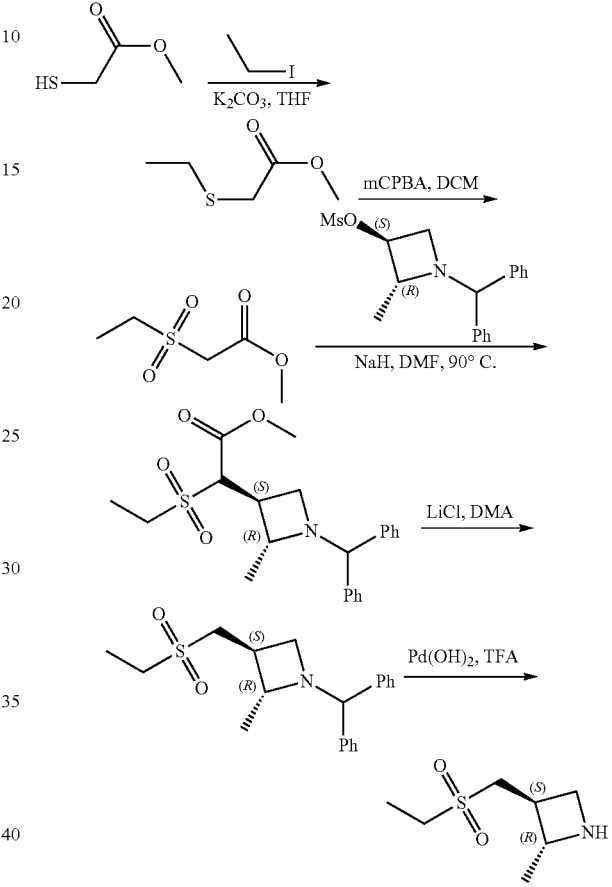

Step 1: Synthesis of methyl 2-(ethylthio)acetate

The solution of methyl 2-sulfanylacetate (20 g, 188 mmol), iodoethane (87.9 g, 564 mmol) and K₂CO₃ (39.5 g, 282 mmol) in THF (300 mL) was reflux for 5 h. Water was added and the reaction mixture was extracted with EA. The organic layer was concentrated under vacuum to give the title compound (20 g) as a light-yellow oil.
Analytical Data: LC-MS: (ES, m/z)=157 [M+23].

Step 2: Synthesis of methyl 2-(ethylsulfonyl)acetate m-CPBA (76.7 g, 446 mmol) was added to a solution of methyl 2-(ethylsulfanyl)acetate (20 g, 149 mmol) in DCM (500 mL) at 0° C. and the reaction was stirred at rt overnight. The reaction mixture was washed with water and concentrated under vacuum. The residue was applied onto a silica gel column with EA/PE (1:3) to give the title compound (13.5 g) as a light-yellow oil.

Step 3: Synthesis of methyl 2-((2R,3S)-1-benzhydryl-2-methylazetidin-3-yl)-2-(ethylsulfonyl)acetate (2R,3S)-1-benzhydryl-2-methylazetidin-3-yl methanesulfonate (Step 1, Example A4 13 g 39.2 mmol) and methyl 2-(ethanesulfonyl)acetate were dissolved in 130 mL DMF, and then NaH (1.12 g of 60% dispersion in mineral oil, 47.0 mmol) was added and stirred for ~15 minutes, until hydrogen evolution had ceased. The reaction mixture was heated to 80° C. overnight. The reaction was cooled and then diluted with water and extracted with EA and combined organics washed with water, brine and dried over sodium sulfate. Filter and evaporate to give the crude product. The crude product was purified by chromatography (0 to 7% MeOH/DCM to give 8 g of the title compound as a pale-yellow foam.

Analytical Data: LC-MS: (ES, m/z)=402 [M+1].

Step 4: Synthesis of (2R,3S)-1-benzhydryl-3-(ethylsulfonylmethyl)-2-methylazetidine To a solution of methyl 2-[(2R,3S)-1-(diphenylmethyl)-2-methylazetidin-3-yl]-2-(ethanesulfonyl)acetate (8 g, 19.9 mmol) in DMA (150 mL) was added chlorolithium (6.74 g, 159 mmol) and heated to 150° C. for 1.5 h. Cool to rt and dilute with 150 mL water and extract (×3) with EA and the combined organics washed with water (×3), brine and dried over sodium sulfate. Filter and evaporate to give the crude product, which was purified by chromatography (0 to 5% MeOH/DCM) to give 6 g of the title compound as a pale-yellow foam.

Analytical Data: LC-MS: (ES, m/z)=344 [M+1].

Step 5: Synthesis of (2R,3S)-3-(ethylsulfonylmethyl)-2-methylazetidine

To a solution of methyl 2-[(2R,3S)-1-(diphenylmethyl)-2-methylazetidin-3-yl]-2-(ethanesulfonyl)acetate (6 g, 14.9 mmol) in MeOH (270 mL)/TFA (30 mL) was stirred at rt overnight under H₂ atmosphere. The reaction was filter and concentrated under vacuum to give the title compound 3.8 g (trifluoroacetic acid salt) as light-brown oil.

Analytical Data: LC-MS: (ES, m/z)=178 [M+1].

Example A8: Synthesis of rac-N-(methyl(((trans)-2-methylazetidin-3-yl)methyl)(oxo)-16-sulfaneylidene) benzamide

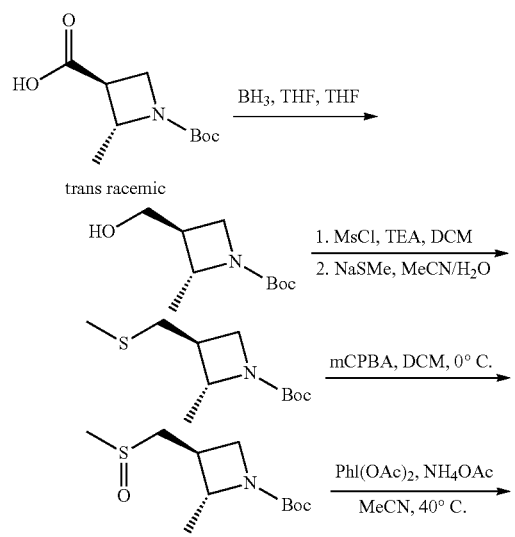

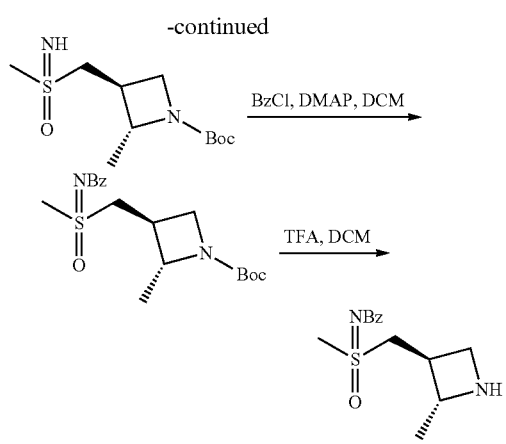

Step 1: Synthesis of rac-tert-butyl (trans)-3-(hydroxymethyl)-2-methylazetidine-1-carboxylate A solution of rac-(trans)-1-[(tert-butoxy)carbonyl]-2-methylazetidine-3-carboxylic acid (1.50 g, 7 mmol, 1 equiv.) in THF (20 mL) was added BH₃ (21.0 mL, 21.0 mmol, 3 equiv., 1M in THF) at 0° C. The reaction was carried on at rt for 18 h before quenching with 1N HCl (10 mL). The mixture was neutralized with 10% Na₂CO₃. The mixture was extracted with EA (30 mL*3). The organic layer was combined and concentrated. The residue was purified by silica gel column chromatography (DCM/EA=1:1) to afford the title compound (1.2 g, 85.7%) as a colourless syrup.

Analytical Data: 1H-NMR (300 MHz, CD₃Cl) δ ppm 4.09-3.99 (m, 1H), 3.91 (t, 1H, J=8.5 Hz), 3.76 (dd, 2H, J=6.5, 5.2 Hz), 3.60 (dd, 1H, J=8.6, 6.0 Hz), 2.33-2.21 (m, 1H), 1.54 (t, 1H, J=5.3 Hz), 1.46 (s, 9H), 1.41 (d, 3H, J=6.3 Hz)

Step 2: Synthesis of rac-(trans)-tert-butyl 2-methyl-3-(methylthiomethyl)azetidine-1-carboxylate A solution of rac-tert-butyl (trans)-3-(hydroxymethyl)-2-methylazetidine-1-carboxylate (1.20 g, 6 mmol, 1 equiv.) in DCM (35 mL) was added TEA (1.21 g, 12.0 mmol, 2 equiv.), followed by MsCl (889 mg, 7.80 mmol, 1.3 equiv.) at 0° C. The reaction was carried on at 0° C. for 1 h before quenching with sat. NaHCO₃ (50 mL). The mixture was extracted with DCM (30 mL*3). The organic layer was combined and concentrated. The residue was dissolved in MeCN (12 mL) and H₂O (3 mL). NaSMe (840 mg, 12.0 mmol, 2 equiv.) was added. The reaction was carried on at 60° C. for 18 h. After cooling down to rt, EA (100 mL) was added. The mixture was washed with water (50 mL) and concentrated. The residue was purified by silica gel column chromatography (PE/EA=4:1) to afford the title compound (1.38 g, quant.) as a yellow oil.

Analytical Data: 1H-NMR (300 MHz, CD₃Cl) δ ppm 3.96 (dd, 2H, J=9.8, 7.0 Hz), 3.51 (dd, 1H, J=8.7, 6.1 Hz), 2.69 (d, 2H, J=7.8 Hz), 2.34-2.23 (m, 1H), 2.12 (s, 3H), 1.46 (s, 9H), 1.42 (d, 3H, J=6.2 Hz)

Step 3: Synthesis of rac-(trans)-tert-butyl 2-methyl-3-(methylsulfinylmethyl)azetidine-1-carboxylate A solution of rac-tert-butyl (trans)-2-methyl-3-[(methylsulfanyl)methyl]azetidine-1-carboxylate (1.38 g, 6 mmol, 1 equiv.) in DCM (30 mL) was added mCPBA (1.08 g, 6.30 mmol, 1.05 equiv.) portionwise at 0° C. for 2 h before quenching with sat. NaHCO$_3$ (50 mL). The mixture was extracted with DCM (30 mL*3). The organic layer was combined and concentrated. The residue was purified by silica gel column chromatography (DCM/MeOH=15:1) to afford the title compound (1.2 g, 81.1%) as a light-yellow oil.

Analytical Data: 1H-NMR (300 MHz, CD$_3$Cl) δ ppm 4.15-4.02 (m, 2H), 3.66 (td, 1H, J=9.0, 6.2 Hz), 3.11-2.79 (m, 2H), 2.74-2.65 (m, 1H), 2.61 (d, 3H, J=3.9 Hz), 1.51-1.40 (m, 12H)

Step 4: Synthesis of rac-(2R,3S)-tert-butyl 2-methyl-3-(S-methylsulfonimidoylmethyl)azetidine-1-carboxylate A mixture of rac-tert-butyl (trans)-3-(methanesulfinylmethyl)-2-methylazetidine-1-carboxylate (1.23 g, 5 mmol, 1 equiv.), PhI(OAc)$_2$ (2.41 g, 7.50 mmol, 1.5 equiv.) and ammonium acetate (2.31 g, 30.0 mmol, 6 equiv.) in ACN (30 mL) was stirred at 35° C. for 18 h. After cooling down to rt, the mixture was concentrated. The residue was purified by silica gel column chromatography (DCM/MeOH=15:1) to afford the title compound (600 mg, 45.8%) as a light-yellow syrup.

Analytical Data: LC-MS: (ES, m/z)=263 [M+1].

Step 5: Synthesis of rac-tert-butyl (trans)-3-((N-benzoyl-S-methylsulfonimidoyl)methyl)-2-methylazetidine-1-carboxylate A mixture of rac-tert-butyl (trans)-3-{[imino(methyl)oxo-λ$^6$-sulfanyl]methyl}-2-methylazetidine-1-carboxylate (393 mg, 1.5 mmol, 1 equiv.) and DMAP (292 mg, 2.40 mmol, 1.6 equiv.) in DCM (5 mL) was added benzoyl chloride (274 mg, 1.95 mmol, 1.3 equiv.) at 0° C. The reaction was carried on at 0° C. for 2 h before quenching with sat. NaHCO$_3$ (20 mL). The mixture was extracted with DCM (20 mL*3). The organic layer was combined and concentrated. The residue was purified by silica gel column chromatography (DCM/EA=1:1) to afford the title compound (400 mg, 72.9%) as a colourless syrup.

Analytical Data: LC-MS: (ES, m/z)=367 [M+1].

Step 5: Synthesis of rac-N-(methyl(((trans)-2-methylazetidin-3-yl)methyl)(oxo)-16-sulfaneylidene)benzamide A solution of rac-(trans)-tert-butyl 3-((N-benzoyl-S-methylsulfonimidoyl)methyl)-2-methylazetidine-1-carboxylate (732 mg, 2 mmol, 1 equiv.) in TFA (2 mL) and DCM (6 mL) was stirred at rt. for 3 h. The mixture was concentrated to afford the title compound (370 mg, 69.6%) as a colorless syrup.

Analytical Data: LC-MS: (ES, m/z)=267 [M+1].

Example B1: Synthesis of (3S,4R)-1-(4-aminopyrimidin-2-yl)-3-fluoro-3-methylpiperidin-4-ol and (3R,4S)-1-(4-aminopyrimidin-2-yl)-3-fluoro-3-methylpiperidin-4-ol and (3R,4R)-1-(4-aminopyrimidin-2-yl)-3-fluoro-3-methylpiperidin-4-ol and (3S,4S)-1-(4-aminopyrimidin-2-yl)-3-fluoro-3-methylpiperidin-4-ol

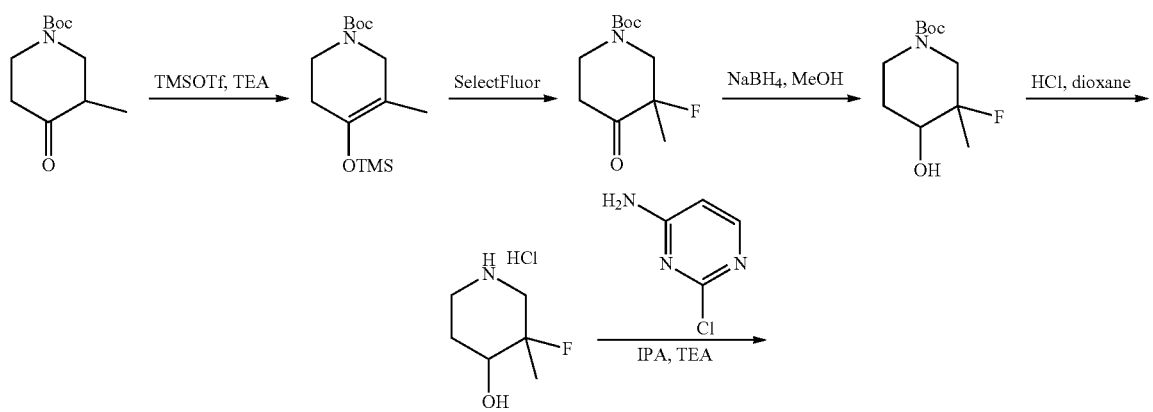

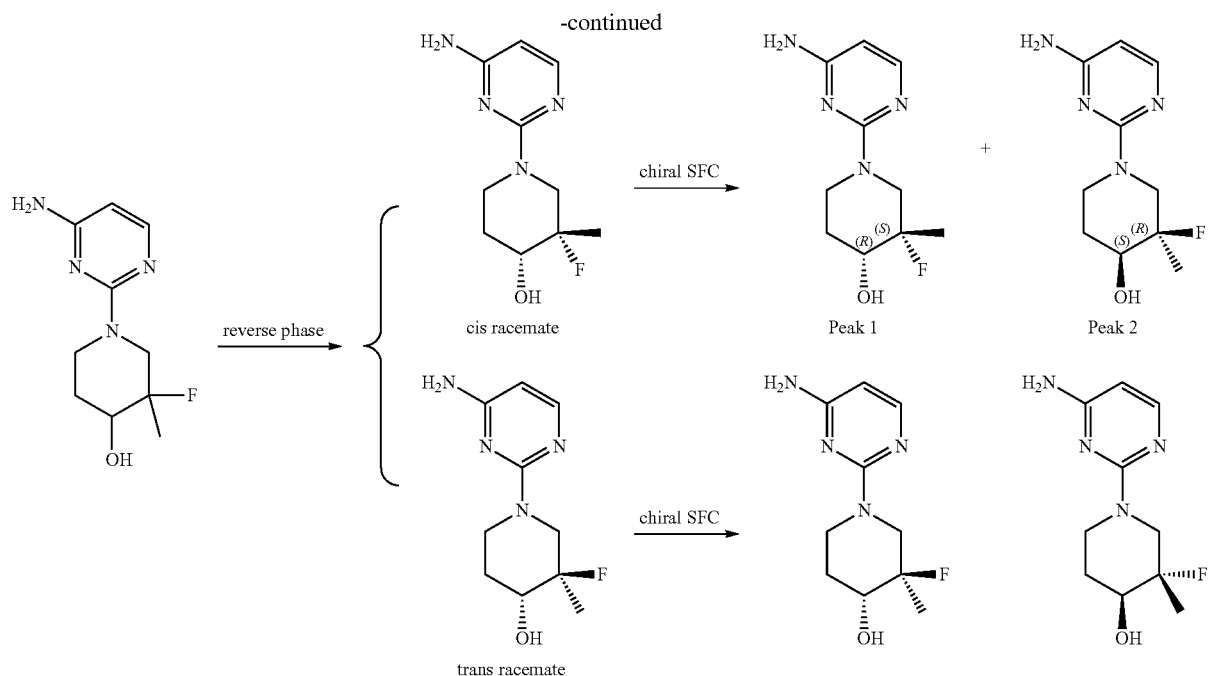

Step 1: Synthesis of tert-butyl 3-methyl-4-(trimethylsilyloxy)-5,6-dihydropyridine-1(2H)-carboxylate Trimethylsilyl trifluoromethanesulfonate (12.50 g, 56.25 mmol, 1.20 equiv.) was added drop wise to a pre-cooled solution of tert-butyl3-methyl-4-oxopiperidine-1-carboxylate (10 g, 46.88 mmol, 1 equiv.) and TEA (11.38 g, 112.5 mmol, 2.40 equiv.) in toluene (100 mL) at 0° C. The resulting mixture was stirred for 4 h at 0° C. The solution was quenched with water (50 mL) and extracted twice with EA. The organic layers were combined, washed with brine, dried over anhydrous sodium sulfate and concentrated in vacuum to afford the title compound the title compound (10.5 g, 78.5%) as yellow oil.

Analytical Data: 1H-NMR (400 MHz, 6d-DMSO) δ ppm 3.68-3.66 (m, 2H), 3.43 (t, 2H, J=5.8 Hz), 2.05 (tq, 2H, J=6.0, 2.0 Hz), 1.53-1.47 (m, 3H), 1.41 (s, 9H), 0.15 (s, 9H).

Step 2: Synthesis of tert-butyl 3-fluoro-3-methyl-4-oxopiperidine-1-carboxylate A mixture of tert-butyl 5-methyl-4-[(trimethylsilyl)oxy]-1,2,3,6-tetrahydropyridine-1-carboxylate (10 g, 35.0 mmol, 1 equiv.) and SelectFluor (13.6 g, 38.5 mmol, 1.10 equiv.) in acetonitrile (100 mL) and stirred for 1 h at 0° C. The solution was diluted with water (100 mL) and extracted with EA. The organic layers were washed with brine, dried over anhydrous sodium sulfate, filtered and concentrated in vacuum. This resulted in 8 g (98.8%) of the title compound as light-yellow oil.

Step 3: Synthesis of tert-butyl 3-fluoro-4-hydroxy-3-methylpiperidine-1-carboxylate The mixture of tert-butyl 3-fluoro-3-methyl-4-oxopiperidine-1-carboxylate (7 g, 30.2 mmol, 1 equiv.) and NaBH$_4$ (1.37 g, 36.2 mmol, 1.12 equiv.) in methanol (70 mL) was stirred for 3 h at rt. The solution was extracted with EA. The organic layers were washed with brine, dried over anhydrous sodium sulfate, filtered and concentrated in vacuum. This resulted in the crude compound 7 g (99.4%) of the title compound light-yellow oil.

Step 4: Synthesis of 3-fluoro-3-methylpiperidin-4-ol Hydrochloride

To a reaction vessel was added tert-butyl 3-fluoro-4-hydroxy-3-methylpiperidine-1-carboxylate (7 g, 30.0 mmol), DCM (70 mL) and hydrochloric (4 M in dioxane, 50 mL). The resulting mixture was stirred at rt for 3 h. The reaction precipitate was collected by filtration to afford the title compound the title compound (4.5 g) as a white solid.

Step 5: Synthesis of 1-(4-aminopyrimidin-2-yl)-3-fluoro-3-methylpiperidin-4-ol The mixture of 2-chloropyrimidin-4-amine (2.7 g, 20.8 mmol, 1 equiv.), 3-fluoro-3-methylpiperidin-4-ol hydrochloride (3.86 g, 22.8 mmol, 1.10 equiv.) and TEA (6.30 g, 62.4 mmol, 3 equiv.) in isopropyl alcohol (45 mL) stirred for 5 h at 130° C. in a sealed vial. The reaction mixture was cooled to rt. The solids were filtered out. The filtrate was concentrated under vacuum to give the crude compound the title compound (6 g) as a yellow oil.

The crude product 1-(4-aminopyrimidin-2-yl)-3-fluoro-3-methylpiperidin-4-ol was purified by HP-FLASH with the following conditions (Column: XBridge Prep OBD C18 Column 30×150 mm 5 um; Mobile Phase A: Water (3 MMOL/L NH$_4$HCO$_3$), Mobile Phase B: ACN; Flow rate: 100 mL/min; Gradient: 10% B to 30% B in 35 min; 254/220 nm; Rt: 21.12 min). The fractions containing the desired compound were evaporated to dryness to afford cis racemate (1.3 g, 26.1%) as a white solid and trans racemate (500 mg, 10.0%) as a white solid.

The cis racemate (3S,4R)-1-(4-aminopyrimidin-2-yl)-3-fluoro-3-methylpiperidin-4-ol was separated by Prep-Chiral-SFC-HPLC with the following conditions (Column: Phenomenex Lux 5 u Cellulose-3, 5*25 cm, 5 um; Mobile Phase A: CO$_2$: 50, Mobile Phase B: MEOH (0.1% DEA): 50; Flow rate: 170 mL/min; 220 nm). The fractions containing the desired compound were evaporated to dryness to afford (3 S,4R)-1-(4-aminopyrimidin-2-yl)-3-fluoro-3-methylpiperidin-4-ol (Stereochemistry assigned by xray crystallography of Compound 55; 500 mg, peak 1) as a white solid and (3R,4S)-1-(4-aminopyrimidin-2-yl)-3-fluoro-3-methylpiperidin-4-ol (500 mg, peak 2) as a white solid.

Analytical Data: LC-MS: (ES, m/z)=227 [M+1]; 1H-NMR (400 MHz, 6d-DMSO) δ ppm 7.71 (d, 1H, J=5.6 Hz), 6.37 (s, 2H), 5.69 (d, 1H, J=5.6 Hz), 4.93 (d, 1H, J=6.5 Hz), 4.66 (ddd, 1H, J=14.1, 9.1, 2.2 Hz), 4.60-4.50 (m, 1H), 3.44 (ddt, 1H, J=24.8, 11.0, 5.6 Hz), 3.02-2.78 (m, 2H), 1.69-1.53 (m, 2H), 1.31 (d, 3H, J=21.2 Hz).

The trans racemate was separated by Prep-Chiral-SFC with the following conditions (Column: CHIRALPAK AD-H-TC001 SFC, 2*25 cm, 5 um; Mobile Phase A: CO$_2$: 70, Mobile Phase B: MeOH-Preparative: 30; Flow rate: 40 mL/min; 220 nm) The fractions containing the desired compound were evaporated to dryness to afford (3R,4R)-1-(4-aminopyrimidin-2-yl)-3-fluoro-3-methylpiperidin-4-ol or (3S,4S)-1-(4-aminopyrimidin-2-yl)-3-fluoro-3-methylpiperidin-4-ol (180 mg) as a white solid (peak 1) and (3S,4S)-1-(4-aminopyrimidin-2-yl)-3-fluoro-3-methylpiperidin-4-ol or (3R,4R)-1-(4-aminopyrimidin-2-yl)-3-fluoro-3-methylpiperidin-4-ol (190 mg) as a white solid (peak 2).

Analytical Data: LC-MS: (ES, m/z)=227 [M+1]; 1H-NMR (300 MHz, 6d-DMSO) δ ppm 7.72 (d, 1H J=5.7 Hz), 6.40 (s, 2H), 5.70 (d, 1H, J=5.6 Hz), 5.24 (d, 1H, J=4.5 Hz), 3.83-3.56 (m, 5H), 1.78 (ddt, 1H, J=12.9, 10.0, 4.7 Hz), 1.48-1.36 (m, 1H), 1.24 (d, 3H, J=22.5 Hz).

Example B2: Synthesis of (S)-2-(5,5-difluoro-1-oxa-7-azaspiro[3.5]nonan-7-yl)pyrimidin-4-amine and (R)-2-(5,5-difluoro-1-oxa-7-azaspiro[3.5]nonan-7-yl)pyrimidin-4-amine

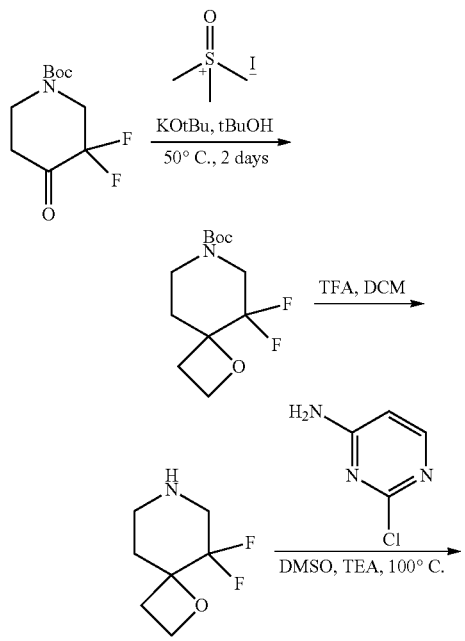

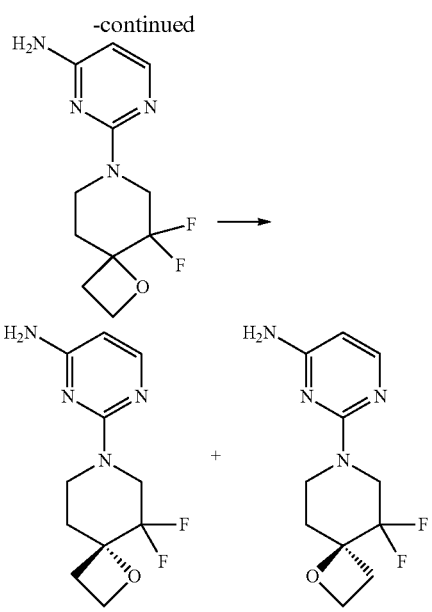

Step 1: Synthesis of tert-butyl 5,5-difluoro-1-oxa-7-azaspiro[3.5]nonane-7-carboxylate Tert-butyl 3,3-difluoro-4-oxopiperidine-1-carboxylate (2 g, 8.50 mmol, 1 equiv.), trimethylsulfoxonium iodide (5.61 g, 25.5 mmo, 3 equiv.) and t-BuOK (2.85 g, 25.5 mmol, 3 equiv.) was dissolved/suspended in t-BuOH. The mixture was stirred at 50° C. for 2 days. The reaction mixture was added water and extracted with EA. The organic layers and concentrated under vacuum. This resulted in 2 g (89%) of the title compound.

Step 2: Synthesis of 5,5-difluoro-1-oxa-7-azaspiro[3.5]nonane

TFA (3 mL) was added to tert-butyl 5,5-difluoro-1-oxa-7-azaspiro[3.5]nonane-7-carboxylate (2 g, 7.59 mmol) in DCM (10 mL). The reaction was stirred at rt for 2 h. The mixture was concentrated under vacuum to afford the title compound 2.1 g as the trifluoroacetic acid salt. The crude product was used directly for next step.

Analytical Data: LC-MS: (ES, m/z)=164 [M+1].

Step 3: Synthesis of (S)-2-(5,5-difluoro-1-oxa-7-azaspiro[3.5]nonan-7-yl)pyrimidin-4-amine and (R)-2-(5,5-difluoro-1-oxa-7-azaspiro[3.5]nonan-7-yl)pyrimidin-4-amine TEA (12.3 g, 122 mmol, 2 equiv.) was added to 5,5-difluoro-1-oxa-7-azaspiro[3.5]nonane (10 g, 61.2 mmol, 1 equiv.) and 2-chloropyrimidin-4-amine (8.41 g, 61.2 mmol, equiv.) in DMSO (100 mL). The reaction was stirred at 100° C. for 2 h. The mixture was added water and extracted with EA. The organic layers and washed with brine, dried and concentrated. The residue was purified by FLASH (5% MeOH in DCM) to give the title compound (2.1 g).

2.1 g of the product was separated by Prep-SFC-HPLC with the following conditions (Column: Column: CHIRAL-ART Amylose-SA, 2*25 cm, 5 um; Mobile Phase A: CO$_2$, Mobile Phase B: EtOH; Flow rate: 40 mL/min; Gradient: 35% B; 254 nm, fractions containing the desired compound were evaporated to dryness to afford 800 mg of peak 1:

(S)-2-(5,5-difluoro-1-oxa-7-azaspiro[3.5]nonan-7-yl)pyrimidin-4-amine or (R)-2-(5,5-difluoro-1-oxa-7-azaspiro[3.5]nonan-7-yl)pyrimidin-4-amine and peak 2:805 mg of (R)-2-(5,5-difluoro-1-oxa-7-azaspiro[3.5]nonan-7-yl)pyrimidin-4-amine or (S)-2-(5,5-difluoro-1-oxa-7-azaspiro[3.5]nonan-7-yl)pyrimidin-4-amine.

peak 1: (S)-2-(5,5-difluoro-1-oxa-7-azaspiro[3.5]nonan-7-yl)pyrimidin-4-amine or (R)-2-(5,5-difluoro-1-oxa-7-azaspiro[3.5]nonan-7-yl)pyrimidin-4-amine Analytical Data: LC-MS: (ES, m/z)=257 [M+1]; 1H-NMR (300 MHz, 6d-DMSO) δ ppm 7.74 (d, 1H, J=5.6 Hz), 6.52 (s, 2H), 5.77 (d, 1H, J=5.7 Hz), 4.46 (t, 2H, J=7.8 Hz), 4.23 (td, 1H, J=14.1, 7.2 Hz), 3.93-3.74 (m, 2H), 3.53 (ddd, 1H, J=13.2, 8.9, 3.5 Hz), 2.74 (dt, 1H, J=11.4, 7.5 Hz), 2.50-2.39 (m, 1H), 2.10-1.97 (m, 1H), 1.90 (ddt, 1H, J=13.4, 8.9, 4.3 Hz).

peak 2: (R)-2-(5,5-difluoro-1-oxa-7-azaspiro[3.5]nonan-7-yl)pyrimidin-4-amine or (S)-2-(5,5-difluoro-1-oxa-7-azaspiro[3.5]nonan-7-yl)pyrimidin-4-amine Analytical Data: LC-MS: (ES, m/z)=257 [M+1]; 1H-NMR (300 MHz, 6d-DMSO) δ ppm 7.75 (d, 1H, J=5.7 Hz), 6.52 (s, 2H), 5.77 (d, 1H, J=5.6 Hz), 4.46 (t, 2H, J=7.8 Hz), 4.23 (td, 1H, J=14.2, 7.2 Hz), 3.93-3.74 (m, 2H), 3.53 (ddd, 1H, J=13.1, 8.8, 3.5 Hz), 2.74 (dt, 1H, J=11.4, 7.5 Hz), 2.50-2.41 (m, 1H), 2.10-1.97 (m, 1H), 1.91 (ddt, 1H, J=13.4, 8.8, 4.3 Hz).

Example B3: Synthesis of 2-(4-methylpiperazin-1-yl)pyrimidin-4-amine

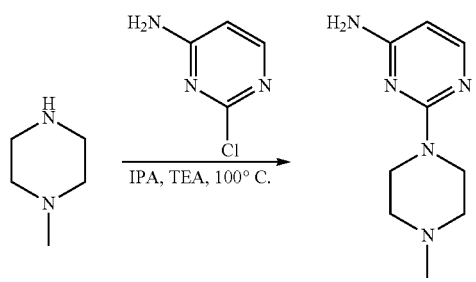

The mixture of 2-chloropyrimidin-4-amine (300 mg, 2.31 mmol, 1 equiv.), 1-methylpiperazine (231 mg, 2.31 mmol, 1 equiv.) and TEA (466 mg, 4.62 mmol, 2 equiv.) in IPA (3 mL) was heated to 100° C. for 1.5 h. LCMS showed the reaction was complete. The mixture was diluted with water and extracted with EA. The organic phase was dried, concentrated and purified by FLASH (DCM:MeOH=5%). This is resulted in the title compound, 270 mg (60%) as yellow solid.

Analytical Data: LC-MS: (ES, m/z)=194 [M+1].

Example B4: Synthesis of 2-(4-methoxypiperidin-1-yl)pyrimidin-4-amine

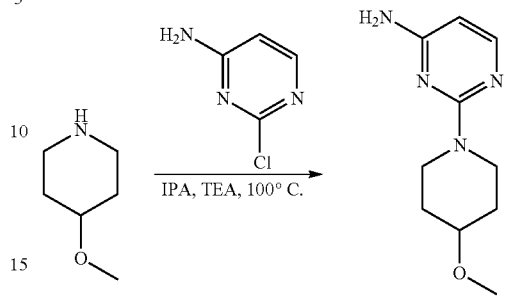

The mixture of 4-methoxypiperidine (1.15 g, 10 mmol, 1.0 equiv.), 2-chloropyrimidin-4-amine (1.3 g, 10 mmol, 1.0 equiv.) and TEA (2.0 g, 20 mmol, 2.0 equiv.) in IPA (15 mL) was stirred overnight at 100° C. The mixture was concentrated and residue was purified by Combi Flash (5% MeOH in DCM) to afford the title compound, 1.12 g (53%) as pale-yellow solid.

Analytical Data: LC-MS: (ES, m/z)=209 [M+1].

Example B5: Synthesis of 2-morpholinopyrimidin-4-amine

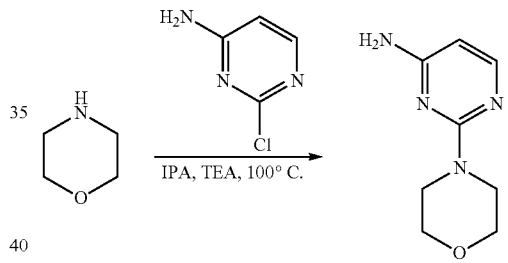

The mixture of 2-chloropyrimidin-4-amine (296 mg, 2.3 mmol, 1 equiv), morpholine (200 mg, 2.3 mmol, 1 equiv.) and TEA (460 mg, 4.6 mmol, 2.0 equiv.) in IPA (5 mL) was stirred for 5 h at 100° C. The mixture was cooled to rt and concentrated. The reside was purified by Prep-TLC to afford the title compound, 360 mg (87%) as yellow solid.

Analytical Data: LC-MS: (ES, m/z)=181 [M+1].

Example B6: Synthesis of rac-2-(1-oxa-7-azaspiro[3.5]nonan-7-yl)pyrimidin-4-amine

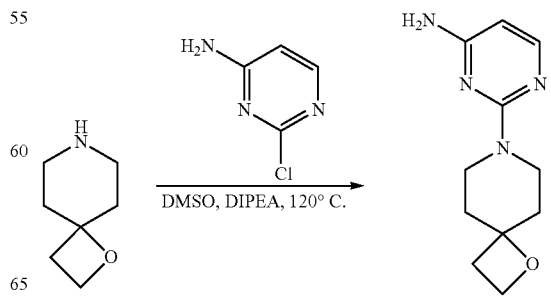

The mixture of 1-oxa-7-azaspiro[3.5]nonane (1.27 g, 10 mmol, 1 equiv.), DIPEA (2.6 g, 20 mmol, 2 equiv.) and 2-chloropyrimidin-4-amine (1.29 g, 10 mmol, 10.00 equiv.) in DMSO (12 mL) was stirred overnight at 120° C. The mixture of cooled to rt and diluted with water. The suspension was extracted with EA. The organic layers was washed with brine, dried and concentrated. The residue was purified by Prep-TLC to afford the title compound, 1.3 g (59%) as pale-yellow solid.

Analytical Data: LC-MS: (ES, m/z)=221 [M+1].

Example B7: Synthesis of 2-((3aR,6aS)-tetrahydro-1H-furo[3,4-c]pyrrol-5(3H)-yl)pyrimidin-4-amine

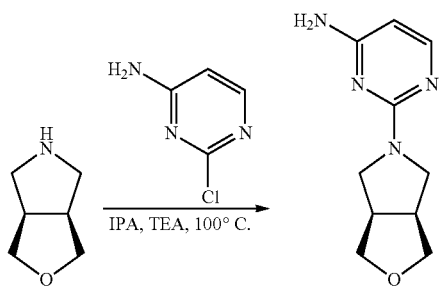 [SMILES: C1NC[C@H]2COC[C@@H]12 ; Nc1ccnc(Cl)n1 ; Nc1ccnc(N2C[C@H]3COC[C@H]3C2)n1]

To a solution of commercially available (3aR,6aS)-hexahydro-1H-furo[3,4-c]pyrrole (841 mg, 6.49 mmol, 1 equiv.) in IPA were added commercially available hexahydro-1H-furo[3,4-c]pyrrole (970 mg, 8.57 mmol, 1.32 equiv.) and TEA (1.30 g, 12.9 mmol, 2 equiv.) and heated to 100° C. and stirred overnight. LCMS showed the reaction was complete. The mixture was added water and extracted with EA. The organic phase was concentrated and purified by FLASH (5% MeOH in DCM). This is obtained the title compound, 500 mg (37%) as pale-yellow solid.

Analytical Data: LC-MS: (ES, m/z)=207 [M+1].

Example B8: Synthesis of 2-((3R,4S)-3,4-difluoropyrrolidin-1-yl)pyrimidin-4-amine

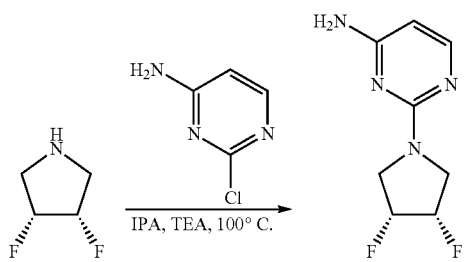 [SMILES: F[C@@H]1CNC[C@@H]1F ; Nc1ccnc(Cl)n1 ; Nc1ccnc(N2C[C@@H](F)[C@@H](F)C2)n1]

In a 20 mL sealed tube, 2-chloropyrimidin-4-amine (600 mg, 4.63 mmol, 1 equiv.), (3R,4S)-3,4-difluoropyrrolidine (495 mg, 4.63 mmol, 1 equiv.), TEA (1.39 g, 13.8 mmol, 3 equiv.) in IPA (10 mL) were added under nitrogen and warmed to 100° C. for 12 h. The reaction mixture was filtered, evaporated to afford the title compound, 800 mg (86%) as a yellow solid.

Analytical Data: LC-MS: (ES, m/z)=201 [M+1].

Example B9: Synthesis of 1-(4-aminopyrimidin-2-yl)-4-methylpiperidin-4-ol

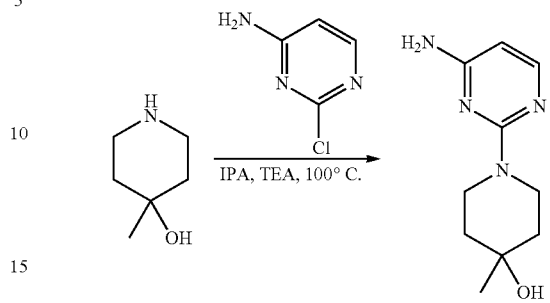

The mixture of 4-methylpiperidin-4-ol (230 mg, 2 mmol, 1 equiv.), 2-chloropyrimidin-4-amine (258 mg, 2 mmol, 1 equiv.) and TEA (300 mg, 3 mmol, 1.5 equiv.) in IPA (5 mL) was stirred overnight at rt. The solvent was removed under vacuum. The residue was purified by Prep-TLC (6% MeOH in DCM) to afford the title compound, 210 mg (50%).

Analytical Data: LC-MS: (ES, m/z)=209 [M+1].

Example B10: Synthesis of (3S,4R)-1-(4-aminopyrimidin-2-yl)-4-methoxypiperidin-3-ol and (3R,4S)-1-(4-aminopyrimidin-2-yl)-4-methoxypiperidin-3-ol

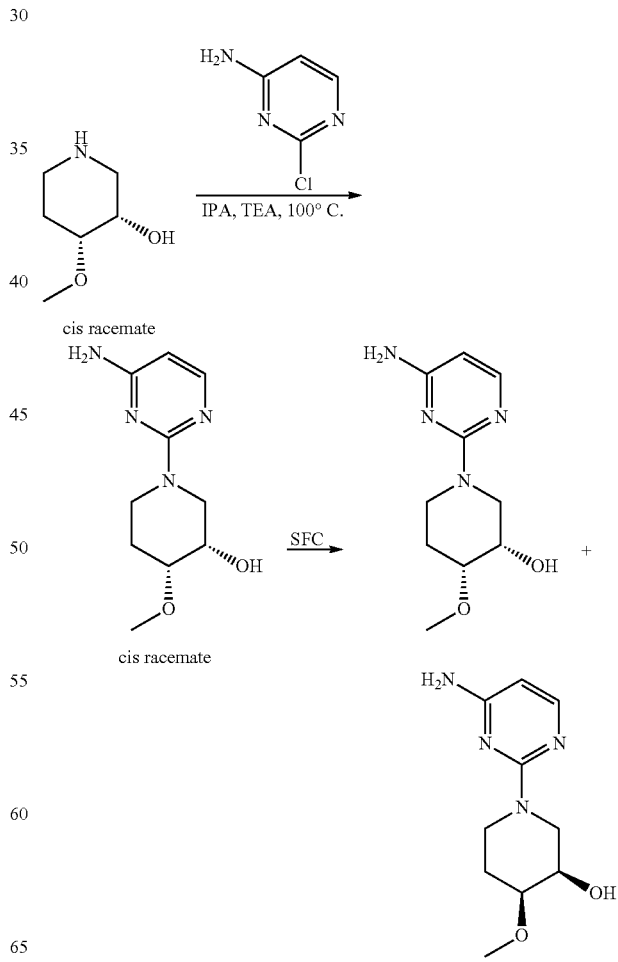

Step 1: Synthesis of cis-1-(4-aminopyrimidin-2-yl)-4-methoxypiperidin-3-ol

The mixture of cis-4-methoxypiperidin-3-ol (1.7 g, 13 mmol, 1 equiv.), 2-chloropyrimidin-4-amine (1.7 g, 13 mmol, 1 equiv.) and TEA (2.6 g, 26 mmol, 2.0 equiv.) in IPA (15 mL) was stirred overnight at 100° C. The mixture was concentrated and the residue was purified by FLASH (5% MeOH in DCM) to afford the title compound, 2.4 g (82.7%) as yellow solid.

Analytical Data: LC-MS: (ES, m/z)=225 [M+1].

Step 2: Synthesis of (3S,4R)-1-(4-aminopyrimidin-2-yl)-4-methoxypiperidin-3-ol and (3R,4S)-1-(4-aminopyrimidin-2-yl)-4-methoxypiperidin-3-ol 2.4 of cis-1-(4-aminopyrimidin-2-yl)-4-methoxypiperidin-3-ol 2.4 g was separated by Chiral-SFC by following conditions: Column name, CHIRALPAK IA (4.6*150 mm, 5 um); solvent, CO$_2$/10% MEOH (0.1% DEA); Flow rate, 4 mL/min; The fractions containing the desired compound were evaporated to dryness to afford peak 1: (3S,4R)-1-(4-aminopyrimidin-2-yl)-4-methoxypiperidin-3-ol or (3R,4S)-1-(4-aminopyrimidin-2-yl)-4-methoxypiperidin-3-ol (900 mg) and peak 2: (3R,4S)-1-(4-aminopyrimidin-2-yl)-4-methoxypiperidin-3-ol or (3 S,4R)-1-(4-aminopyrimidin-2-yl)-4-methoxypiperidin-3-ol (890 mg).

Example B11: Synthesis of (4R,5S)-1-(4-aminopyrimidin-2-yl)-5-fluoro-3,3-dimethylpiperidin-4-ol and (4S,5R)-1-(4-aminopyrimidin-2-yl)-5-fluoro-3,3-dimethylpiperidin-4-ol

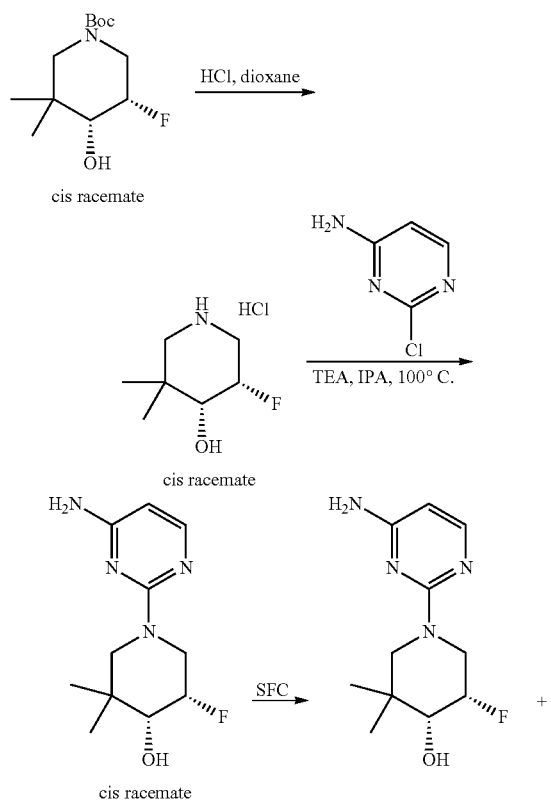

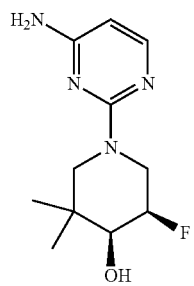

Step 1: Synthesis of cis-5-fluoro-3,3-dimethylpiperidin-4-ol

Cis-tert-butyl 5-fluoro-4-hydroxy-3,3-dimethylpiperidine-1-carboxylate (4.7 g, 19.0 mmol) was added to a solution of HCl in 1,4-dioxane (30 mL), the resulting mixture was stirred at rt for 16 h. The solvent was removed under reduced pressure to afford the title compound as the hydrochloride salt, 3.6 gas a white solid.

Step 2: Synthesis of cis-1-(4-aminopyrimidin-2-yl)-5-fluoro-3,3-dimethylpiperidin-4-ol TEA (3.83 g, 38.0 mmol) was added to a mixture of cis-5-fluoro-3,3-dimethylpiperidin-4-ol (3.6 g, 19.0 mmol) and 2-chloropyrimidin-4-amine (2.46 g, 19.0 mmol) in iPrOH (10 mL), the resulting mixture was stirred at 100° C. for 3 h. The solid was filtered out, the filtrate was concentrated under reduced pressure. The crude product was purified by preparative HPLC: Column: XBridge Prep OBD C18 Column 30×150 mm 5 um; Mobile Phase A: Water (10 mmol/L NH$_4$HCO$_3$+0.1% NH$_3$·H$_2$O), Mobile Phase B: ACN; Flow rate: 60 mL/min; Gradient: 5% B to 32% B in 8 min; 254/220 nm; Rt: 6.92 min; Fractions containing the desired compound were evaporated to dryness to afford the title compound (1.8 g, 39.4%) as a white solid.

Analytical Data: LC-MS: (ES, m/z)=241 [M+1].

Step 3: Synthesis of (4R,5S)-1-(4-aminopyrimidin-2-yl)-5-fluoro-3,3-dimethylpiperidin-4-ol and (4S,5R)-1-(4-aminopyrimidin-2-yl)-5-fluoro-3,3-dimethylpiperidin-4-ol The 1.8 g of cis racemate was separated by preparative chiral-HPLC onColumn: EnantioPak-A1-5(02), 5*25 cm, 5 um; Mobile Phase A: CO$_2$:60, Mobile Phase B: EtOH 0.1% DEA; Flow rate: 2 mL/min; 220 nm. The fractions containing the desired compound were evaporated to dryness to afford peak 1: (4R,5S)-1-(4-aminopyrimidin-2-yl)-5-fluoro-3,3-dimethylpiperidin-4-ol or (4S,5R)-1-(4-aminopyrimidin-2-yl)-5-fluoro-3,3-dimethylpiperidin-4-ol (776 mg, 43.3%) as a white solid, and peak 2: (4S,5R)-1-(4-aminopyrimidin-2-yl)-5-fluoro-3,3-dimethylpiperidin-4-ol or (4R,5S)-1-(4-aminopyrimidin-2-yl)-5-fluoro-3,3-dimethylpiperidin-4-ol (700 mg, 39.1%) as a white solid.

(4R,5S)-1-(4-aminopyrimidin-2-yl)-5-fluoro-3,3-dimethylpiperidin-4-ol or (4S,5R)-1-(4-aminopyrimidin-2-yl)-5-fluoro-3,3-dimethylpiperidin-4-ol Analytical Data: LC-MS: (ES, m/z)=241 [M+1]; 1H-NMR (300 MHz, 6d-DMSO) δ ppm 7.69 (d, 1H, J=5.7 Hz), 6.36 (s, 2H), 5.67 (d, 1H, J=5.6 Hz), 5.00 (d, 1H, J=5.4

Hz), 4.75-4.47 (m, 1H), 4.09-3.93 (m, 1H), 3.86-3.67 (m, 1H), 3.62 (d, 1H, J=12.9 Hz), 3.37 (ddd, 1H, J=22.0, 5.5, 2.9 Hz), 3.31-3.18 (m, 1H), 0.95-0.78 (m, 6H).

Example B12: Synthesis of (3S,4R)-1-(4-aminopyrimidin-2-yl)-3-fluoro-4-methylpiperidin-4-ol and (3R,4S)-1-(4-aminopyrimidin-2-yl)-3-fluoro-4-methylpiperidin-4-ol

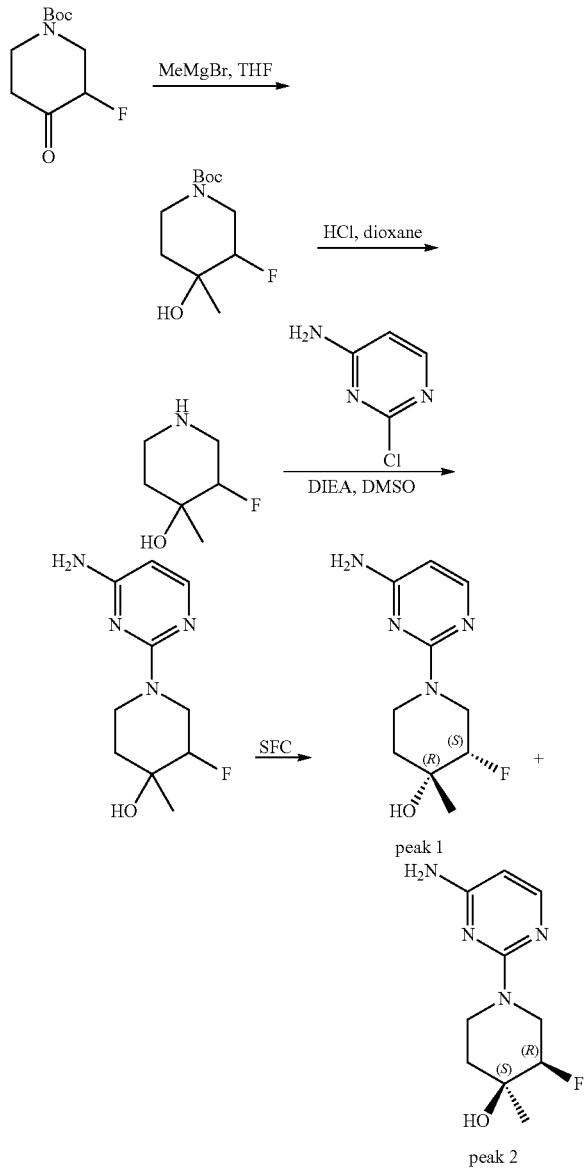

Step 1: Synthesis of rac-cis-tert-butyl 3-fluoro-4-hydroxy-4-methylpiperidine-1-carboxylate MeMgBr (9.2 mL, 27.6 mmol) was added to a solution of tert-butyl 3-fluoro-4-oxopiperidine-1-carboxylate (5 g, 2.3 mmol) in THF (50 mL) at −78° C. The mixture was stirred overnight at rt. The reaction mixture was carefully diluted with sat. NH₄Cl (aq), then extracted with EA and washed with brine. The organic layer was dried over Na₂SO₄, filtered, evaporated to afford the title compound 4.8 g (crude) as a yellow solid.

Analytical Data:LC-MS: (ES, m/z)=178 [M+1−56].

Step 2: Synthesis of rac-cis-3-fluoro-4-methylpiperidin-4-ol

Tert-butyl 3-fluoro-4-hydroxy-4-methylpiperidine-1-carboxylate (4.8 g, 20 mmol) in HCl/dioxane (50 mL) was stirred at rt for 4 h. The reaction mixture was evaporated to afford 3-fluoro-4-methylpiperidin-4-ol 3 g (crude) as a yellow solid. The crude product was used directly for next step.

Analytical Data: LC-MS: (ES, m/z)=134 [M+1].

Step 3: Synthesis of rac-cis-1-(4-aminopyrimidin-2-yl)-3-fluoro-4-methylpiperidin-4-ol The mixture of 2-chloropyrimidin-4-amine (1.5 g, 11.5 mmol), 3-fluoro-4-methylpiperidin-4-ol (3 g, crude) and DIPEA (11.9 g, 92.3 mmol) in DMSO (40 mL) was stirred overnight at 120° C. The reaction mixture was diluted with water, extracted with EA and washed with brine. The organic layer was dried over Na₂SO₄, filtered, evaporated, purified by column chromatography (PE:EA=1:1) to afford the title compound (1.3 g) as a light-yellow solid.

Analytical Data:LC-MS: (ES, m/z)=227 [M+1].

Step 4: Synthesis of (3S,4R)-1-(4-aminopyrimidin-2-yl)-3-fluoro-4-methylpiperidin-4-ol and (3R,4S)-1-(4-aminopyrimidin-2-yl)-3-fluoro-4-methylpiperidin-4-ol Rac-cis 1-(4-aminopyrimidin-2-yl)-3-fluoro-4-methylpiperidin-4-ol was separated by preparative SFC with following conditions: Column: CHIRAL Cellulose-SJ (4.6*150 mm, 5 um); Mobile Phase: CO₂/MeOH (0.1% DEA); Flow Rate: 4 g/min); to afford peak 1: (3S,4R)-1-(4-aminopyrimidin-2-yl)-3-fluoro-4-methylpiperidin-4-ol (450 mg, Stereochemistry assigned by xray crystallography of Compound 117) as a white solid and peak 2: (3R,4S)-1-(4-aminopyrimidin-2-yl)-3-fluoro-4-methylpiperidin-4-ol (470 mg) as a white solid.

peak 1: (3S, 4R)-1-(4-aminopyrimidin-2-yl)-3-fluoro-4-methylpiperidin-4-ol

Analytical Data: 1H-NMR (300 MHz, 6d-DMSO) δ ppm 7.73 (d, 1H J=5.6 Hz), 6.40 (s, 2H), 5.72 (d, 1H, J=5.6 Hz), 4.71 (s, 1H), 4.39-3.92 (m, 3H), 3.38 (dddd, 2H, J=40.5, 13.6, 10.3, 4.6 Hz), 1.62 (q, 1H, J=6.2 Hz), 1.42 (td, 1H, J=13.6, 12.0, 4.3 Hz), 1.20 (s, 3H).

peak 2: (3R, 4S)-1-(4-aminopyrimidin-2-yl)-3-fluoro-4-methylpiperidin-4-ol

Analytical Data: 1H-NMR (300 MHz, 6d-DMSO) δ ppm 7.73 (d, 1H, J=5.6 Hz), 6.40 (s, 2H), 5.72 (d, 1H, J=5.6 Hz), 4.71 (s, 1H), 4.36-4.07 (m, 2H), 4.07-3.95 (m, 1H), 3.44 (ddd, 1H, J=13.2, 9.4, 4.8 Hz), 3.31 (ddd, 1H, J=13.4, 8.3, 3.2 Hz), 1.61 (ddt, 1H, J=14.1, 7.2, 3.9 Hz), 1.41 (ddd, 1H, J=13.9, 10.3, 4.4 Hz), 1.20 (s, 3H).

Example B13: Synthesis of (S)-1-(4-aminopyrimidin-2-yl)-3,3-difluoro-4-methylpiperidin-4-ol and (R)-1-(4-aminopyrimidin-2-yl)-3,3-difluoro-4-methylpiperidin-4-ol

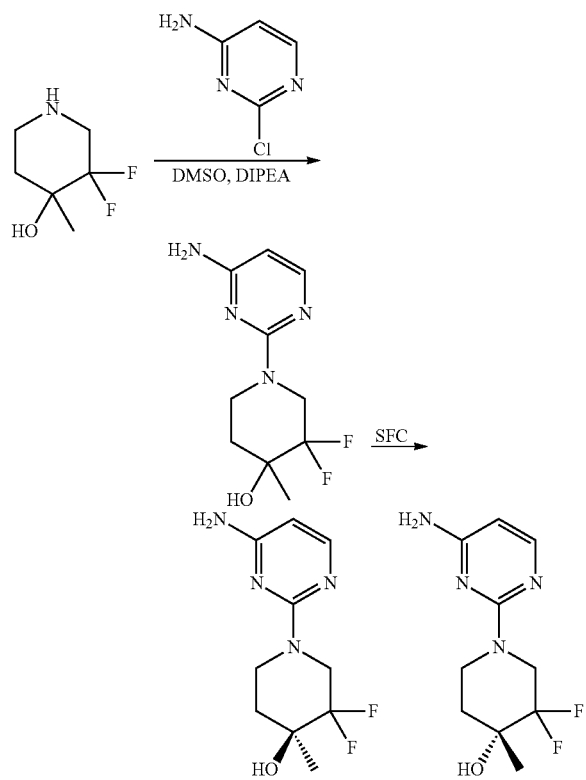

Step 1: Synthesis of 1-(4-aminopyrimidin-2-yl)-3,3-difluoro-4-methylpiperidin-4-ol The mixture of 3,3-difluoro-4-methylpiperidin-4-ol (300 mg, 2.0 mmol), 2-chloropyrimidin-4-amine (260 mg, 2.0 mmol) and TEA (300 mg, 3.0 mmol) in DMSO (2 mL) was stirred overnight at 120° C. Water was added and the mixture was extracted with EA. The organic phase was washed with brine, dried and purified by FLASH (5% MeOH in DCM) to give 320 mg (65%) of the title compound as white solid.
Analytical Data: LC-MS: (ES, m/z)=245 [M+1].

Step 2: Synthesis of (S)-1-(4-aminopyrimidin-2-yl)-3,3-difluoro-4-methylpiperidin-4-ol and (R)-1-(4-aminopyrimidin-2-yl)-3,3-difluoro-4-methylpiperidin-4-ol 320 mg of 1-(4-aminopyrimidin-2-yl)-3,3-difluoro-4-methylpiperidin-4-ol was separated by Prep-chiral-SFC with following conditions: Column name: CHIRALPAK AD-3 3*100 m m, 3 um; Co-Solvent: MeOH (0.1% DEA); Gradient (B %): 10% to 50% in 4.0 min, hold 2.0 min at 50%; Back Pressure (psi): 1500.000; Flow: 2 mL/min; to give 145 mg of peak 1: (S)-1-(4-aminopyrimidin-2-yl)-3,3-difluoro-4-methylpiperidin-4-ol or (R)-1-(4-aminopyrimidin-2-yl)-3,3-difluoro-4-methylpiperidin-4-ol and peak 2: 150 mg of (R)-1-(4-aminopyrimidin-2-yl)-3,3-difluoro-4-methylpiperidin-4-ol or (S)-1-(4-aminopyrimidin-2-yl)-3,3-difluoro-4-methylpiperidin-4-ol. Both are pale-yellow solid.
Analytical Data: 1H-NMR (300 MHz, 6d-DMSO) δ ppm 7.74 (d, 1H, J=5.6 Hz), 6.45 (s, 2H), 5.74 (d, 1H, J=5.7 Hz), 5.41 (s, 1H), 4.58 (dt, 1H, J=13.4, 9.4 Hz), 4.29 (d, 1H, J=13.3 Hz), 3.59-3.38 (m, 1H), 3.23 (ddd, 1H, J=13.8, 9.6, 4.7 Hz), 1.62 (q, 2H, J=5.8, 4.8 Hz), 1.22 (d, 3H, J=1.6 Hz)

Example B14: Synthesis of rac-(trans)-1-(4-aminopyrimidin-2-yl)-4-fluoropiperidin-3-ol

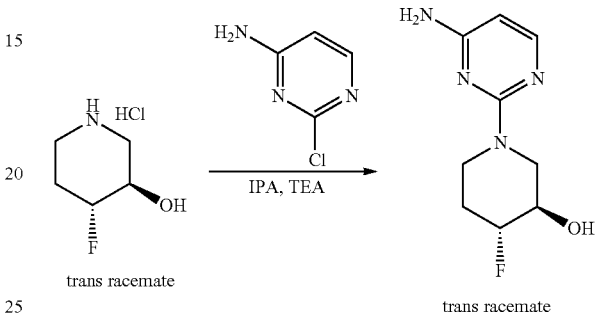

To a solution of 2-chloropyrimidin-4-amine (216 mg, 1.67 mmol) in IPA were added rac-(3R,4R)-4-fluoropiperidin-3-ol hydrochloride (200 mg, 1.67 mmol) and TEA (337 mg, 3.34 mmol) and heated to 100° C. and stirred overnight. LCMS showed the reaction was complete. The mixture was added water and extracted with EA. The organic phase was concentrated and purified by FLASH. This is obtained the title compound, 180 mg (65%) as yellow solid.
Analytical Data: LC-MS: (ES, m/z)=213 [M+1].

Example B15: Synthesis of rac-(1R,5S,8s)-3-(4-aminopyrimidin-2-yl)-3-azabicyclo[3.2.1]octan-8-ol

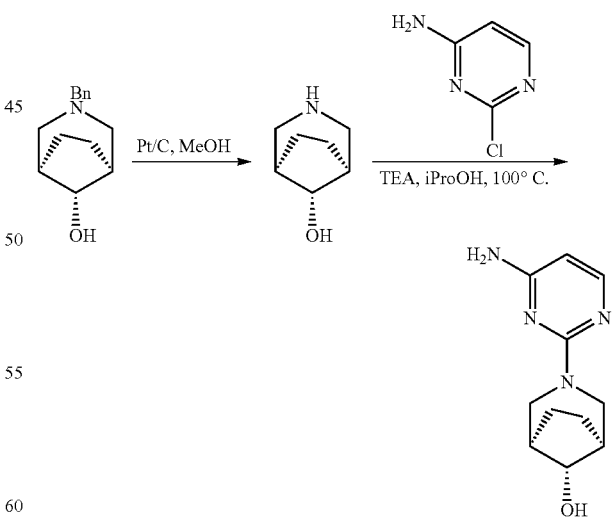

Step 1: Synthesis of (1R,5S,8s)-3-azabicyclo[3.2.1]octan-8-ol

A mixture of commercially available rac-(1R,5S,8S)-3-benzyl-3-azabicyclo[3.2.1]octan-8-ol (200 mg, 920 μmol), Pd/C (97.9 mg, 920 μmol) in MeOH (3 mL) was stirred at rt for 3 h. The solid was filtered out and the filtrate was concentrated to afford the title compound (110 mg) as a yellow solid.

Analytical Data: LC-MS: (ES, m/z)=128 [M+1].

Step 2: Synthesis of rac-(1R,5S,8s)-3-(4-aminopyrimidin-2-yl)-3-azabicyclo[3.2.1]octan-8-ol A mixture of rac-(1R,5S,8S)-3-azabicyclo[3.2.1]octan-8-ol (100 mg, 786 μmol), 2-chloropyrimidin-4-amine (101 mg, 786 μmol), TEA (237 mg, 2.35 mmol) in IPA (3 mL) was stirred at 100° C. for 16 h. The reaction mixture was concentrated and purified by preparative TLC (10% MeOH in DCM) to afford crude product 110 mg (64%) as a yellow solid.

Analytical Data: LC-MS: (ES, m/z)=221 [M+1].

Example B16: Synthesis of rac-1-(1-(4-aminopyrimidin-2-yl)-3-fluoropyrrolidin-3-yl)ethanol

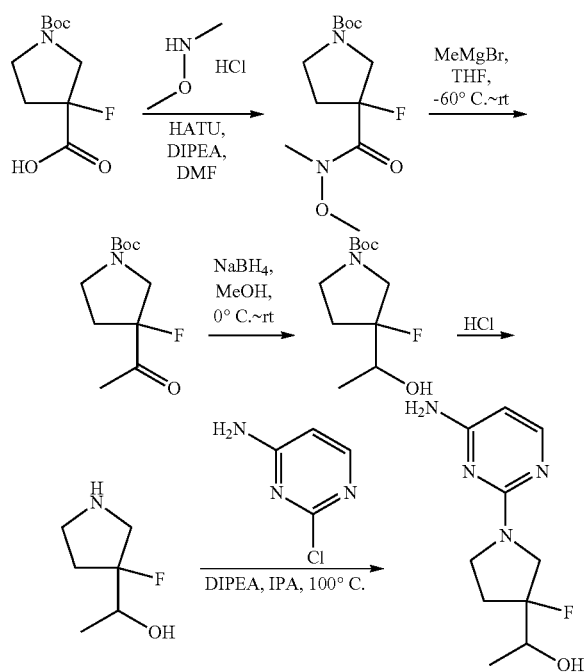

Step 1: Synthesis of rac-tert-butyl 3-fluoro-3-(methoxy(methyl)carbamoyl)pyrrolidine-1-carboxylate To a solution of rac-1-[(tert-butoxy)carbonyl]-3-fluoropyrrolidine-3-carboxylicacid (1 g, 4.28 mmol), methoxy(methyl)amine (339 mg, 5.56 mmol), HATU (3.25 g, 8.56 mmol) and DIPEA (1.65 g, 12.8 mmol) in DMF (30 mL) was stirred at rt for 16 h. The reaction mixture was extracted with EA and the organic layers combined and dried over anhydrous sodium sulfate and concentrated under vacuum. The residue was applied onto a silica gel column with EA/PE (1:6) to give the title compound, 900 mg (76%) as a light-yellow oil.

Analytical Data: LC-MS: (ES, m/z)=221 [M+1−56].

Step 2: Synthesis of rac-tert-butyl 3-acetyl-3-fluoropyrrolidine-1-carboxylate

To a solution of rac-tert-butyl 3-fluoro-3-[methoxy(methyl)carbamoyl]pyrrolidine-1-carboxylate (900 mg, 3.25 mmol) in THF (20 mL) was added bromo(methyl)magnesium (7.7 mL, 2.5 M, 16.2 mmol) at −60° C. under N$_2$. The reaction was warmed slowly to rt and stirred overnight. The reaction was quenched with aq NH$_4$Cl (10 mL), and extracted with EA and the organic layers combined and dried over anhydrous sodium sulfate and concentrated under vacuum to give the title compound 780 mg (crude) as a light-yellow oil.

Step 3: Synthesis of rac-tert-butyl 3-fluoro-3-(1-hydroxyethyl)pyrrolidine-1-carboxylate To a solution of rac-tert-butyl 3-acetyl-3-fluoropyrrolidine-1-carboxylate (780 mg, 3.37 mmol) in MeOH (10 mL) was added NaBH$_4$ (191 mg, 5.05 mmol) at 0° C. and stirred at rt for 1.5 h. The reaction was concentrated under vacuum and extracted with EA and the organic layers combined and dried over anhydrous sodium sulfate and concentrated under vacuum to give product 700 mg as light-yellow oil.

Step 4: Synthesis of rac-1-(3-fluoropyrrolidin-3-yl)ethanol

To a solution of rac-tert-butyl 3-fluoro-3-(1-hydroxyethyl)pyrrolidine-1-carboxylate (700 mg, 3 mmol) in DCM (5 mL) was added HCl/dioxane (3 mL) and stirred at rt for 2 h. The reaction was concentrated under vacuum to give product 500 mg as a light-yellow solid.

Step 5: Synthesis of rac-1-(1-(4-aminopyrimidin-2-yl)-3-fluoropyrrolidin-3-yl)ethanol The solution of rac-1-(3-fluoropyrrolidin-3-yl)ethan-1-ol (550 mg, 4.13 mmol), 2-chloropyrimidin-4-amine (535 mg, 4.13 mmol) and TEA (1.24 g, 12.3 mmol) in IPA (6 mL) was heated to 100° C. and stirred overnight. The reaction was concentrated under vacuum and purified by TLC (DCM:MeOH=15:1) to give product 800 mg as a light-yellow solid.

Analytical Data: LC-MS: (ES, m/z)=227 [M+1].

Example B17: Synthesis of rac-2-(4-aminopyrimidin-2-yl)-2-aza-bicyclo[2.2.1]heptan-5-ol

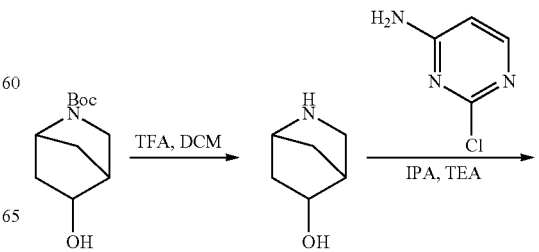

Step 1: Synthesis of rac-2-aza-bicyclo[2.2.1]heptan-5-ol

To a solution of rac-tert-butyl 5-hydroxy-2-azabicyclo[2.2.1]heptane-2-carboxylate (500 mg, 2.34 mmol) in DCM (8 mL) were added TFA (226 mg, 2.34 mmol) and the mixture was stirred at rt for 1 h LCMS showed the reaction was complete and solution was concentrated to give 450 mg of product that was used for the next step directly.

Analytical Data: LC-MS: (ES, m/z)=114 [M+1].

Step 2: Synthesis of rac-2-(4-aminopyrimidin-2-yl)-2-aza-bicyclo[2.2.1]heptan-5-ol

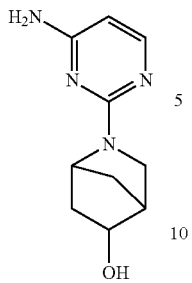

The mixture of 2-chloropyrimidin-4-amine (200 mg, 1.54 mmol), rac-2-azabicyclo[2.2.1]heptan-5-ol (174 mg, crude) and TEA (311 mg, 3.08 mmol) in IPA (5 mL) was stirred overnight at 110° C. LCMS showed the reaction was complete. The mixture was added water and extracted with EA. The organic phase was concentrated and purified by FLASH. This afforded the title compound, 180 mg as yellow solid.

Analytical Data: LC-MS: (ES, m/z)=207 [M+1].

Example B18: Synthesis of rac-cis-1-(4-aminopyrimidin-2-yl)-4-fluoropiperidin-3-ol

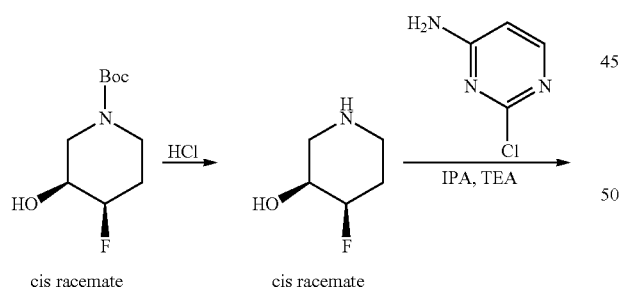

Step 1: Synthesis of cis-4-fluoropiperidin-3-ol

Tert-butyl (cis)-4-fluoro-3-hydroxypiperidine-1-carboxylate (300 mg) was dissolved into dioxane (1 mL). HCl in dioxane (4M, 2 mL) was added and stirred for 1 h. The reaction mixture was concentrated to afford the title compound a white solid (140 mg).

Analytical Data: LC-MS: (ES, m/z)=120 [M+1].

Step 2: Synthesis of cis-1-(4-aminopyrimidin-2-yl)-4-fluoropiperidin-3-ol

The mixture of 2-chloropyrimidin-4-amine (129 mg), cis-4-fluoropiperidin-3-ol (118 mg), DIPEA (384 mg) in DMSO was stirred at 120° C. for 12 h. Water was added and the mixture was extracted with EA and purified by pre-TLC to (5% MeOH in DCM) afford the title compound (95 mg) as yellow solid.

Analytical Data: LC-MS: (ES, m/z)=213 [M+1].

Example B19: Synthesis of 2-(1,4-dioxa-8-azaspiro[4.5]decan-8-yl)pyrimidin-4-amine

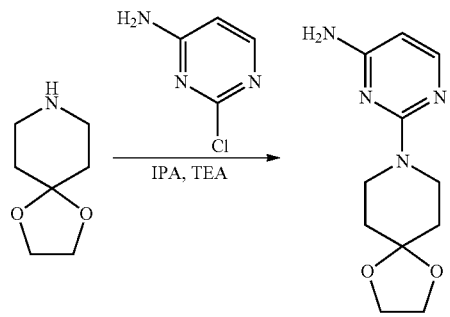 [SMILES: C1CC2(CCN1)OCCO2 ; Nc1ccnc(Cl)n1 ; Nc1ccnc(N2CCC3(CC2)OCCO3)n1]

To a solution of 2-chloropyrimidin-4-amine (1 g, 7.71 mmol) in IPA (12 mL) were added 1,4-dioxa-8-azaspiro[4.5]decane (1.10 g, 7.71 mmol) and TEA (1.55 g, 15.4 mmol) and heated to 100° C. and stirred overnight. The mixture was added water and extracted with EA. The organic layer was concentrated and purified by FLASH (5% MeOH in DCM). It obtained the title compound, 1.5 g (82.8%) as a yellow solid.

Analytical Data: LC-MS: (ES, m/z)=237 [M+1].

Example B20: Synthesis of rac-tert-butyl 4-(4-aminopyrimidin-2-yl)-2-(difluoromethyl)piperazine-1-carboxylate

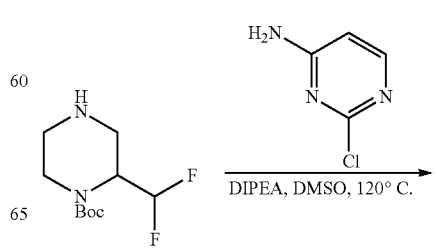

-continued

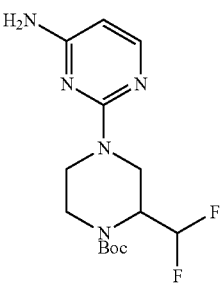

The mixture of rac-tert-butyl 2-(difluoromethyl)piperazine-1-carboxylate (200 mg, 846 umol), 2-chloropyrimidin-4-amine (109 mg, 846 umol) and DIEA (326 mg, 2.53 umol) in DMSO (5 mL) was stirred at 120° C. for 3 h. The reaction mixture was diluted with water and extracted with EA. The organic layer was dried and purified by column chromatography (DCM:MeOH=20:1) to afford the title compound, (200 mg, 72%) as a yellow solid.

Analytical Data: LC-MS: (ES, m/z)=330 [M+1].

Example B21: Synthesis of (3R,4R)-1-(4-aminopyrimidin-2-yl)-3-methylpiperidin-4-ol and (3S,4S)-1-(4-aminopyrimidin-2-yl)-3-methylpiperidin-4-ol To a solution of rac-trans-3-methylpiperidin-4-ol (800 mg, 6.94 mmol) in IPA (10 mL) was added 2-chloropyrimidin-4-amine (1.34 g, 10.4 mmol) and TEA (2.1 g, 20.8 mmol). The mixture was stirred at 100° C. for 8 h. The reaction mixture was cooled to rt and concentrated under vacuum. The crude product was purified by flash with the following conditions: DCM:MEOH=10:1. This resulted in 1.2 g (83.3%) of the title compound as a white solid.

Rac-trans-1-(4-aminopyrimidin-2-yl)-3-methylpiperidin-4-ol (1.2 g, 5.76 mmol) were further separated by Chiral-Prep-HPLC with the following conditions: Column: CHIRALPAK AD-H-TC001 SFC, 2*25 cm, 5 um; Mobile Phase A: $CO_2$, Mobile Phase B: MEOH (2 mM $NH_3$-MEOH); Flow rate: 40 mL/min; Gradient: 25% B; 220 nm to afford peak 1: 500 mg (3R,4R)-1-(4-aminopyrimidin-2-yl)-3-methylpiperidin-4-ol or (3S,4S)-1-(4-aminopyrimidin-2-yl)-3-methylpiperidin-4-ol and peak 2: 460 mg (3S,4S)-1-(4-aminopyrimidin-2-yl)-3-methylpiperidin-4-ol or (3R,4R)-1-(4-aminopyrimidin-2-yl)-3-methylpiperidin-4-ol as a white solid.

Analytical Data: LC-MS: (ES, m/z)=209 [M+1].

Example B22: Synthesis of rac-(cis)-1-(4-aminopyrimidin-2-yl)-3-fluoro-3,4-dimethylpiperidin-4-ol and rac-(trans)-1-(4-aminopyrimidin-2-yl)-3-fluoro-3,4-dimethylpiperidin-4-ol

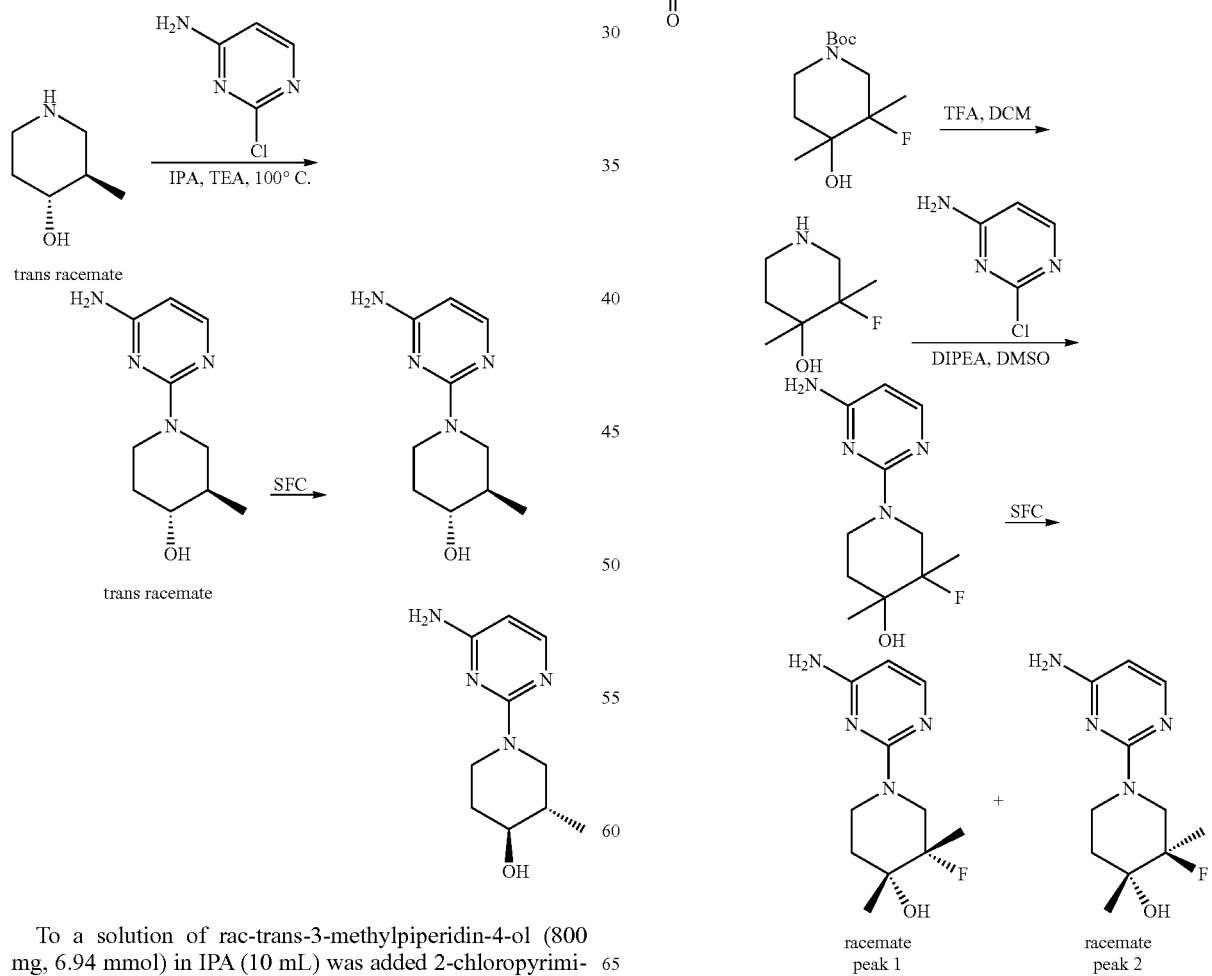

Step 1: Synthesis of tert-butyl 3-fluoro-4-hydroxy-3,4-dimethylpiperidine-1-carboxylate LiMe (27 mL, 43.2 mmol) was added into a mixture of rac-tert-butyl 3-fluoro-3-methyl-4-oxopiperidine-1-carboxylate (5 g, 21.6 mmol, from step 2 of Example B1) in THF at 0° C. The reaction was stirred at 0° C. for 1 h. The reaction was quenched by H₂O and extracted by EA. The organic layer was evaporated in vacuum to afford a colorless oil (6 g, 24.2 mmol) and used to next step directly.

Step 2: Synthesis of 3-fluoro-3,4-dimethylpiperidin-4-ol

Rac-tert-butyl 3-fluoro-4-hydroxy-3,4-dimethylpiperidine-1-carboxylate (6 g, 24.2 mmol) was placed in DCM/TFA (50 mL/15 mL). The mixture was stirred at rt for 1 h. The solvent was removed by evaporation to give 6 g of crude product.

Step 3: Synthesis of rac-(3S,4R)-1-(4-aminopyrimidin-2-yl)-3-fluoro-3,4-dimethylpiperidin-4-ol and rac-(3R,4R)-1-(4-aminopyrimidin-2-yl)-3-fluoro-3,4-dimethylpiperidin-4-ol DIPEA (7.85 g, 60.9 mmol) was added into 3-fluoro-3,4-dimethylpiperidin-4-ol (3 g, crude) and 2-chloropyrimidin-4-amine (2.62 g, 20.3 mmol) in DMSO (20 mL). The mixture was stirred at 100° C. for 16 h. Water was added and the suspension was extracted with EA. The organic phase was concentrated and the residue was purified by FLASH (50% EA in PE) to afford the title compound as a light-yellow solid (1.5 g).

1-(4-aminopyrimidin-2-yl)-3-fluoro-3,4-dimethylpiperidin-4-ol (1.5 g, 6.24 mmol) was separated by SFC HPLC: Column: CHIRALPAK IC-3, 3*100 mm 3 um; Mobile Phase A: Mobile Phase B: MeOH (0.1% DEA); Flow rate: 2 mL/min; Gradient: 10% B; 220 nm; To afford peak 1: rac-cis-1-(4-aminopyrimidin-2-yl)-3-fluoro-3,4-dimethylpiperidin-4-ol (identified as cis by 2D NMR, 400 mg) as a white solid and peak 2: rac-trans-1-(4-aminopyrimidin-2-yl)-3-fluoro-3,4-dimethylpiperidin-4-ol (identified as trans by 2D NMR, 300 mg) as a white solid.

Analytical Data: LC-MS: (ES, m/z)=241 [M+1].

Example B23: Synthesis of rac-(cis)-1-(4-aminopyrimidin-2-yl)-3-ethyl-3-fluoropiperidin-4-ol and rac-(trans)-1-(4-aminopyrimidin-2-yl)-3-ethyl-3-fluoropiperidin-4-ol

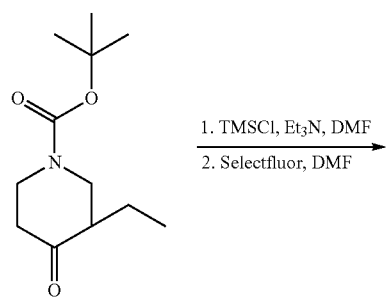
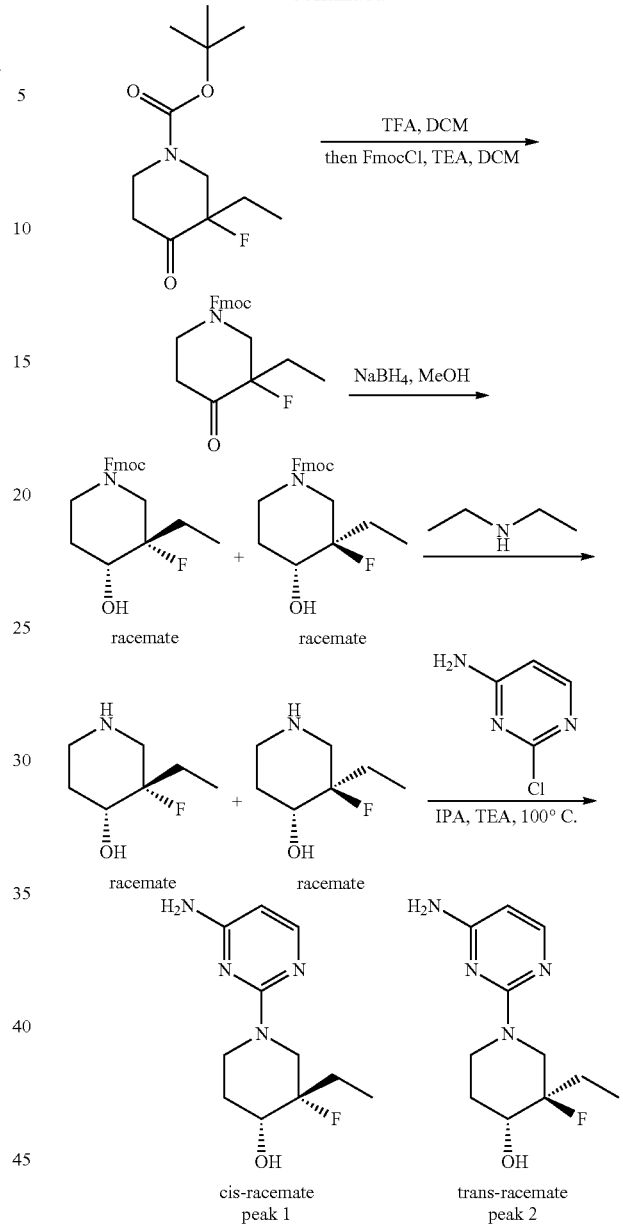

Step 1: Synthesis of rac-tert-butyl 3-ethyl-3-fluoro-4-oxopiperidine-1-carboxylate A solution of tert-butyl 3-ethyl-4-oxopiperidine-1-carboxylate (7.95 g, 35 mmol, 1 equiv.) in DMF (35 mL) was added TEA (7.07 g, 70.0 mmol, 2 equiv.), followed by TMSCl (5.67 g, 52.5 mmol, 1.50 equiv.) at rt. The reaction was carried on at 120° C. for 18 h before quenching with sat. NaHCO₃. The mixture was extracted with MTBE. The organic layer was combined and concentrated. The residue was dissolved in DMF (70 mL), Selectfluor (12.3 g, 35 mmol, 1 equiv) was added at 0° C. The mixture was stirred for 2 h at rt and then quenched with brine. The mixture was extracted with EA. The organic layer was combined and concentrated to afford a mixture of tert-butyl 3-ethyl-3-fluoro-4-oxopiperidine-1-carboxylate, tert-butyl 3-ethyl-5- fluoro-4-oxopiperidine-1-carboxylate and tert-butyl 3-ethyl-4-oxopiperidine-1-carboxylate as yellow oil (6.5 g).

Step 2: Synthesis of rac-(9H-fluoren-9-yl)methyl 3-ethyl-3-fluoro-4-oxopiperidine-1-carboxylate A solution of tert-butyl 3-ethyl-3-fluoro-4-oxopiperidine-1-carboxylate (6.5 g, 26.4 mmol, 1 equiv.) in TFA (20 mL) and DCM (60 mL) was stirred at rt for 2 h. The mixture was concentrated and re-dissolved in DCM (120 mL), TEA (13.3 g, 132 mmol, 5.00 equiv.) was added, followed by (9H-fluoren-9-yl)methyl carbonochloridate (10.2 g, 39.5 mmol, 1.50 equiv.). The reaction was carried on at rt for 2 h. Sat. NaHCO₃ was added. The mixture was extracted with DCM. The organic layer was combined and concentrated. The residue was purified by silica gel column chromatography (DCM/EA=30:1) to afford the title compound (3.7 g, 30.53% over 2 steps) as a colorless syrup.
Analytical Data: LC-MS: (ES, m/z)=390 [M+23].

Step 3: Synthesis of rac-cis-(9H-fluoren-9-yl)methyl 3-ethyl-3-fluoro-4-hydroxypiperidine-1-carboxylate and rac-trans-(9H-fluoren-9-yl)methyl 3-ethyl-3-fluoro-4-hydroxypiperidine-1-carboxylate Into a 25-mL round-bottom flask, was placed 9H-fluoren-9-ylmethyl 3-ethyl-3-fluoro-4-oxopiperidine-1-carboxylate (500 mg, 1.361 mmol, 1 equiv.), methanol (10 mL), NaBH₄ (102.97 mg, 2.722 mmol, 2 equiv.). The resulting solution was stirred for 1 h at 0° C. The reaction was then quenched by the addition of 1 mL of water. The resulting mixture was concentrated. The residue was applied onto silica gel column with EA/PE (1:1). This resulted in 200 mg of peak 1: rac-cis-(9H-fluoren-9-yl)methyl 3-ethyl-3-fluoro-4-hydroxypiperidine-1-carboxylate (identified as cis by 2D NMR) and 100 mg of peak 2: rac-trans-(9H-fluoren-9-yl)methyl 3-ethyl-3-fluoro-4-hydroxypiperidine-1-carboxylate (identified as trans by 2D NMR).
Analytical Data: LC-MS: (ES, m/z)=370 [M+1].

Step 4: Synthesis of rac-cis-3-ethyl-3-fluoropiperidin-4-ol and rac-trans-3-ethyl-3-fluoropiperidin-4-ol Diethyl amine (3 mL) was added to the solution of rac-cis-(9H-fluoren-9-yl)methyl 3-ethyl-3-fluoro-4-hydroxypiperidine-1-carboxylate (200.0 mg, 0.54 mmol) in methanol (15 mL). The resulting solution was stirred for 2 h at 0° C. The resulting mixture was concentrated. This resulted in 60 mg (75%) of the title compound as light-yellow oil.
Analytical Data: LC-MS: (ES, m/z)=148 [M+1].

Step 5: Synthesis of rac-cis-1-(4-aminopyrimidin-2-yl)-3-ethyl-3-fluoropiperidin-4-ol and rac-trans-1-(4-aminopyrimidin-2-yl)-3-ethyl-3-fluoropiperidin-4-ol The mixture of rac-cis-3-ethyl-3-fluoropiperidin-4-ol (1 g, 6.794 mmol, 1 equiv.), 2-chloropyrimidin-4-amine (0.88 g, 6.794 mmol, 1 equiv.) and TEA (2.06 g, 20.38 mmol, 3 equiv.) IPA (10.00 mL) was stirred for 12 h at 100° C. The resulting mixture was concentrated. The residue was applied onto a silica gel column with DCM/MeOH (5:1). This resulted in 1 g (61.3%) of rac-cis-1-(4-aminopyrimidin-2-yl)-3-ethyl-3-fluoropiperidin-4-ol as light-yellow solid.
Analytical Data: LC-MS: (ES, m/z)=241 [M+1]; 1H-NMR (400 MHz, 6d-DMSO) δ ppm 7.72 (d, 1H, J=5.6 Hz), 6.35 (s, 2H), 5.69 (d, 1H, J=5.6 Hz), 4.88 (d, 1H, J=6.5 Hz), 4.62 (ddd, 1H, J=14.0, 9.0, 1.9 Hz), 4.52-4.40 (m, 1H), 3.63-3.42 (m, 1H), 3.08-2.86 (m, 2H), 1.84 (ddt, 1H, J=15.1, 9.4, 7.5 Hz), 1.75-1.49 (m, 3H), 0.92 (t, 3H, J=7.6 Hz)

The mixture of rac-trans-3-ethyl-3-fluoropiperidin-4-ol (900 mg, 6.114 mmol, 1 equiv.), 2-chloropyrimidin-4-amine (792.12 mg, 6.114 mmol, 1 equiv.) and TEA (1856.15 mg, 18.343 mmol, 3 equiv.) in IPA (10.00 mL) was stirred for 12 h at 100° C. The resulting mixture was concentrated. The residue was applied onto a silica gel column with DCM/MeOHl (5:1). This resulted in 500 mg (34.03%) of rac-trans-1-(4-aminopyrimidin-2-yl)-3-ethyl-3-fluoropiperidin-4-ol as light-yellow solid.
Analytical Data: LC-MS: (ES, m/z)=241 [M+1].

Example B24: Synthesis of (3R,4S)-1-(4-aminopyrimidin-2-yl)-3-methylpiperidin-4-ol and (3S,4R)-1-(4-aminopyrimidin-2-yl)-3-methylpiperidin-4-ol

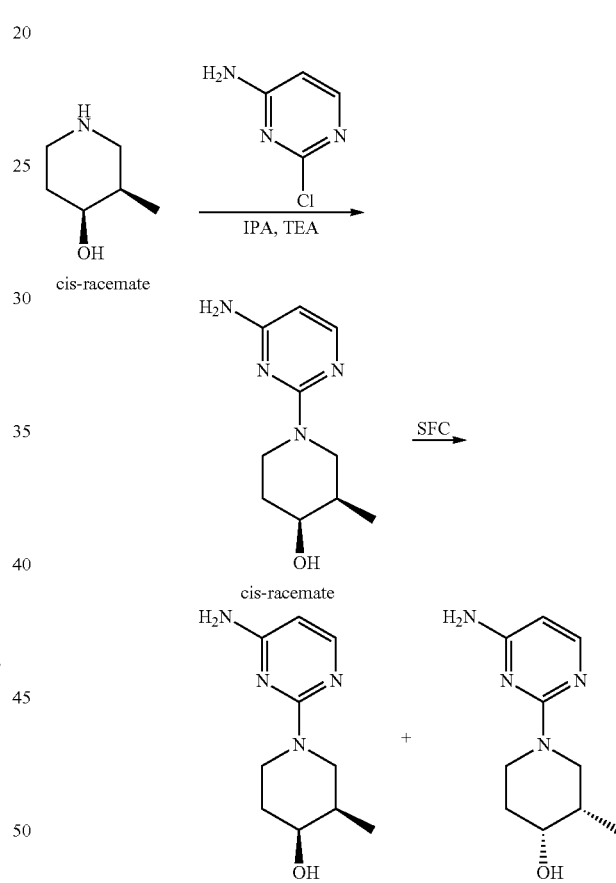

The mixture of 2-chloropyrimidin-4-amine (700 mg, 5.42 mmol), rac-(3R,4S)-3-methylpiperidin-4-ol (900 mg, 5.42 mmol) and TEA (1.7 g, 16.8 mmol) in IPA (10 mL) was stirred for 2 h at 100° C. The mixture was concentrated and the residue was purified by Prep-TLC with DCM/MeOH (20:1). This resulted in 700 mg (56%) of rac-(3R,4S)-1-(4-aminopyrimidin-2-yl)-3-methylpiperidin-4-ol as a yellow solid. The rac-(3R,4S)-1-(4-aminopyrimidin-2-yl)-3-methylpiperidin-4-ol was purified by Prep-HPLC with the following conditions Column: CHIRALPAK ID-3, 4.6*100 mm, 3 um; Mobile Phase A: Mobile Phase B: IPA (0.1% DEA; Flow rate: 4 mL/min; Gradient: 10% B; 220 nm; fractions containing the desired compound were evaporated to dryness to afford peak 1: (3R,4S)-1-(4-aminopyrimidin- 2-yl)-3-methylpiperidin-4-ol or (3S,4R)-1-(4-aminopyrimidin-2-yl)-3-methylpiperidin-4-ol as a yellow solid (200 mg, 33%) and peak 2: (3S,4R)-1-(4-aminopyrimidin-2-yl)-3-methylpiperidin-4-ol or (3R,4S)-1-(4-aminopyrimidin-2-yl)-3-methylpiperidin-4-ol as a light-yellow solid (200 mg, 33%).

Analytical Data: LC-MS: (ES, m/z)=209 [M+1].

Example B25: Synthesis of 2-(1,4-dioxa-9-azaspiro[5.5]undecan-9-yl)pyrimidin-4-amine

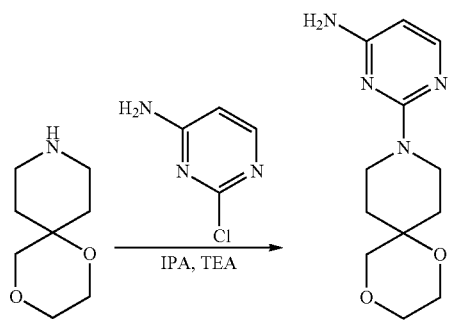 [SMILES: C1CC2(CCN1)COCCO2 ; Nc1ccnc(Cl)n1 ; Nc1ccnc(N2CCC3(CC2)COCCO3)n1]

The mixture of 2-chloropyrimidin-4-amine (80 mg, 617 umol), 1,4-dioxa-9-azaspiro[5.5]undecane (97.0 mg, 617 umol) and TEA (186 mg, 1.85 mmol) in IPA (2 mL) was stirred at 100° C. for 3 h. The reaction mixture was diluted with water, extracted with EA and washed with brine. The organic layer was dried, evaporated and purified by Prep-TLC (DCM:MeOH=20:1) to afford the title compound (85 mg, 55%) as a yellow solid.

Analytical Data: LC-MS: (ES, m/z)=251 [M+1].

Example B26: Synthesis of (3S,4R,5R)-1-(4-aminopyrimidin-2-yl)-3,5-difluoro-3-methylpiperidin-4-ol and (3R,4S,5S)-1-(4-aminopyrimidin-2-yl)-3,5-difluoro-3-methylpiperidin-4-ol and (3S,4S,5S)-1-(4-aminopyrimidin-2-yl)-3,5-difluoro-3-methylpiperidin-4-ol and (3R,4R,5R)-1-(4-aminopyrimidin-2-yl)-3,5-difluoro-3-methylpiperidin-4-ol

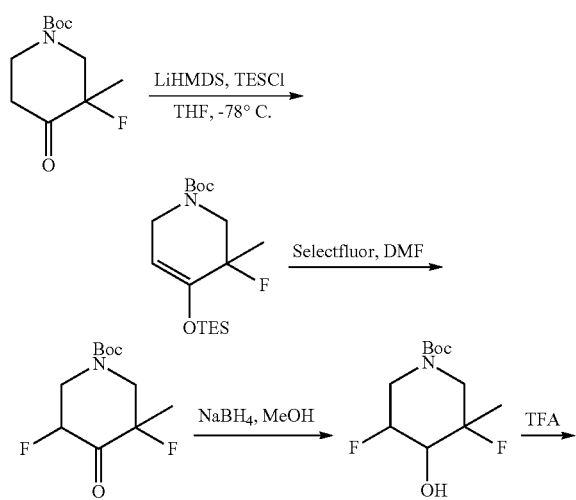

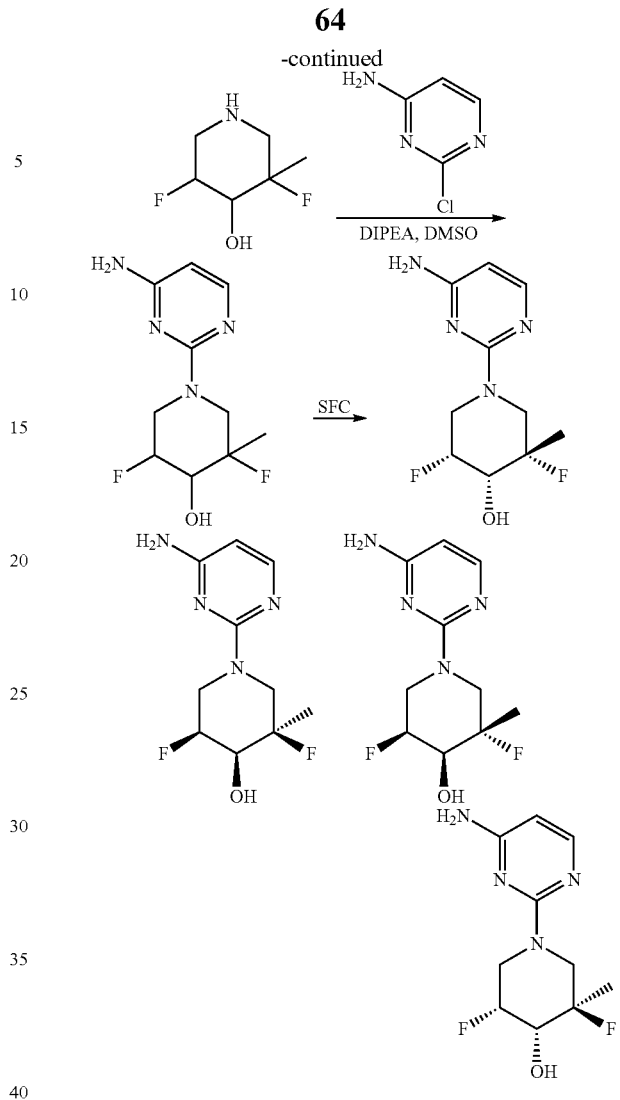

Step 1: Synthesis of rac-tert-butyl 5-fluoro-5-methyl-4-(triethylsilyloxy)-5,6-dihydropyridine-1(2H)-carboxylate To a solution of rac-tert-butyl 3-fluoro-3-methyl-4-oxopiperidine-1-carboxylate (4.7 g, 20.3 mmol) in THF (30 mL) was added LiHDMS (30.4 mL, 30.4 mmol) at −70° C. and stirred at −30° C.~−20° C. for 1 h. And then TESCl (6.11 g, 40.6 mmol) was added and stirred at rt for 2 h. The reaction was quenched with water and extracted with EA. The organic layer was dried and concentrated. The residue was purified on silica column with 10% EtOAc in PE to afford the title compound (6.2 g, 88%) as a colorless oil.

Step 2: Synthesis of rac-tert-butyl 3,5-difluoro-3-methyl-4-oxopiperidine-1-carboxylate To a solution of rac-tert-butyl 3-fluoro-3-methyl-4-[(triethylsilyl)oxy]-1,2,3,6-tetrahydropyridine-1-carboxylate (6.2 g, 17.9 mmol) in DMF (30 mL) was added SelectFluor (12.6 g, 35.8 mmol) at 10° C. The mixture was stirred at rt. for 2 h. The reaction was quenched with water, extracted with EA. The organic layer was dried and concentrated. The residue was purified on silica gel column with 30% EtOAc in PE to afford the title compound (3 g, 67%) as a light-yellow oil.

Step 3: Synthesis of rac-tert-butyl 3,5-difluoro-4-hydroxy-3-methylpiperidine-1-carboxylate To a solution of rac-tert-butyl 3,5-difluoro-3-methyl-4-oxopiperidine-1-carboxylate (3.5 g, 14.0 mmol) in MeOH was added NaBH$_4$ (1.06 g, 28 mmol) at ice-cream bath. The mixture was stirred at rt for 3 h. The mixture was diluted with water, extracted with EA and washed with brine. The mixture was dried over anhydrous sodium sulfate and concentrated under vacuum. This resulted in 2.9 g (82.6%) of the title compound as a colorless oil.

Analytical Data: LC-MS: (ES, m/z)=196 [M+1−56].

Step 4: Synthesis of rac-3,5-difluoro-3-methylpiperidin-4-ol

Rac-tert-butyl 3,5-difluoro-4-hydroxy-3-methylpiperidine-1-carboxylate (1.6 g, 6.36 mmol) was added to the mixture of DCM (20 mL) and TFA (5 mL). The resulting mixture was stirred at rt for 2 h. The mixture was concentrated under vacuum to afford the title compound as the salt (1.6 g).

Analytical Data: LC-MS: (ES, m/z)=152 [M+1].

Step 5: Synthesis of (3S,4R,5R)-1-(4-aminopyrimidin-2-yl)-3,5-difluoro-3-methylpiperidin-4-ol and (3R,4S,5S)-1-(4-aminopyrimidin-2-yl)-3,5-difluoro-3-methylpiperidin-4-ol and (3S,4S,5S)-1-(4-aminopyrimidin-2-yl)-3,5-difluoro-3-methylpiperidin-4-ol and (3R,4R,5R)-1-(4-aminopyrimidin-2-yl)-3,5-difluoro-3-methylpiperidin-4-ol Into three 40-mL sealed tubes, was placed 3,5-difluoro-3-methylpiperidin-4-ol (900 mg, 5.95 mmol) in DMSO (10 mL), 2-chloropyrimidin-4-amine (1.6 g, crude, TFA salt) and DIEA (3.07 g, 23.8 mmol). The resulting solution was stirred for 24 h at 120° C. The reaction mixture was cooled to rt and diluted with water and extracted with EA and concentrated under vacuum. The residue was purified by Prep-HPLC with Column: XBridge Prep OBD C18 Column, 30×150 mm Sum; Mobile Phase A: Water (10 mmol/L NH$_4$HCO$_3$+0.1% NH3·H2O), Mobile Phase B: ACN; Flow rate: 60 mL/min; Gradient: 7 B to 20 B in 7 min; 254; 220 nm. This resulted in 380 mg of (3S,4R,5R)-1-(4-aminopyrimidin-2-yl)-3,5-difluoro-3-methylpiperidin-4-ol and (3R,4S,5S)-1-(4-aminopyrimidin-2-yl)-3,5-difluoro-3-methylpiperidin-4-ol and 350 mg (3S,4S,5S)-1-(4-aminopyrimidin-2-yl)-3,5-difluoro-3-methylpiperidin-4-ol and (3R,4R,5R)-1-(4-aminopyrimidin-2-yl)-3,5-difluoro-3-methylpiperidin-4-ol as a white solid. Isomers were further separated by SFC to give 150 mg peak 1: (3S,4R,5R)-1-(4-aminopyrimidin-2-yl)-3,5-difluoro-3-methylpiperidin-4-ol or (3R,4S,5S)-1-(4-aminopyrimidin-2-yl)-3,5-difluoro-3-methylpiperidin-4-ol and 150 mg peak 2: (3R,4S,5S)-1-(4-aminopyrimidin-2-yl)-3,5-difluoro-3-methylpiperidin-4-ol or (3S,4R,5R)-1-(4-aminopyrimidin-2-yl)-3,5-difluoro-3-methylpiperidin-4-ol. The second mixture was further separated by SFC to give 140 mg peak 1: (3S,4S,5S)-1-(4-aminopyrimidin-2-yl)-3,5-difluoro-3-methylpiperidin-4-ol or (3R,4R,5R)-1-(4-aminopyrimidin-2-yl)-3,5-difluoro-3-methylpiperidin-4-ol and 140 mg peak 2: (3R,4R,5R)-1-(4-aminopyrimidin-2-yl)-3,5-difluoro-3-methylpiperidin-4-ol or (3S,4S,5S)-1-(4-aminopyrimidin-2-yl)-3,5-difluoro-3-methylpiperidin-4-ol Analytical Data: LC-MS: (ES, m/z)= 245 [M+1].

Example B27: Synthesis of rac-2-(6-fluoro-1,4-dioxa-8-azaspiro[4.5]decan-8-yl)pyrimidin-4-amine

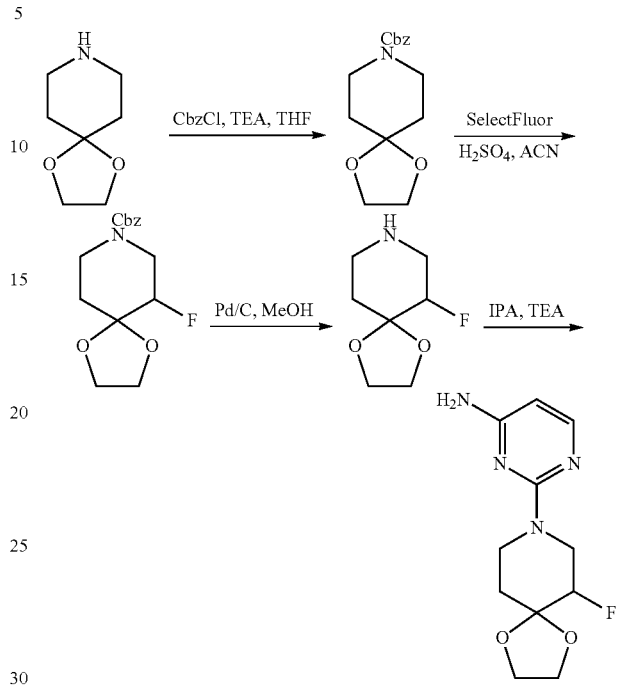

Step 1: Synthesis of Benzyl 1,4-dioxa-8-azaspiro[4.5]decane-8-carboxylate

To a solution of 1,4-dioxa-8-azaspiro[4.5]decane (500 mg, 3.49 mmol), TEA (386 mg, 3.83 mmol) in THF (10 mL), benzyl carbonochloridate (386 mg, 3.83 mmol) was added at 0° C. and stirred at rt for 3 h. The reaction mixture was diluted with water and extracted with EA and saturated brine. The organic layer was dried over Na$_2$SO$_4$, filtered, evaporated and purified by column chromatography (PE: EA=1:1) to afford benzyl the title compound (800 mg) as a yellow oil.

Analytical Data: LC-MS: (ES, m/z)=278 [M+1].

Step 2: Synthesis of rac-benzyl 6-fluoro-1,4-dioxa-8-azaspiro[4.5]decane-8-carboxylate H$_2$SO$_4$ (14.1 mg, 144 umol) was added to the mixture of benzyl 1,4-dioxa-8-azaspiro[4.5]decane-8-carboxylate (800 mg, 2.88 mmol) and SelectFluor (2.04 g, 5.76 mmol) in ACN (10 mL) at rt and stirred at 50° C. for 1 h, ethylene glycol (886 mg, 14.3 mmol) was added and stirred for 2 h. The reaction mixture was diluted with water and extracted with EA and washed with brine. The organic layer was dried over Na$_2$SO$_4$, filtered, evaporated and purified by column chromatography (PE:EA=1:1) to afford the title compound (620 mg) as a yellow oil.

Analytical Data: LC-MS: (ES, m/z)=296 [M+1].

Step 3: Synthesis of rac-6-fluoro-1,4-dioxa-8-azaspiro[4.5]decane

The mixture of rac-benzyl 6-fluoro-1,4-dioxa-8-azaspiro[4.5]decane-8-carboxylate (600 mg, 2.03 mmol) and Pd/C (239 mg, 2.03 mmol) in MeOH (20 mL) was stirred at rt for 2 h under hydrogen atmosphere. The reaction mixture was filtered, evaporated to afford the title compound (340 mg) as a brown oil.

Analytical Data: LC-MS: (ES, m/z)=162 [M+1].

Step 4: Synthesis of rac-2-(6-fluoro-1,4-dioxa-8-azaspiro[4.5]decan-8-yl)pyrimidin-4-amine The mixture of 2-chloropyrimidin-4-amine (180 mg, 1.38 mmol), rac-6-fluoro-1,4-dioxa-8-azaspiro[4.5]decane (333 mg, 2.07 mmol) and TEA (418 mg, 4.14 mmol) in IPA (5 mL) was stirred for 4 h at 100° C. The reaction mixture was diluted with water, extracted with EA and washed with brine. The organic layer was dried over Na₂SO₄, filtered, evaporated and purified by column chromatography (DCM:MeOH=30:1) to afford the title compound (200 mg) as a yellow solid.

Analytical Data:LC-MS: (ES, m/z)=255 [M+1].

Example B28: Synthesis of (3S,4S)-1-(4-aminopyrimidin-2-yl)-4-methoxypiperidin-3-ol and (3R,4R)-1-(4-aminopyrimidin-2-yl)-4-methoxypiperidin-3-ol

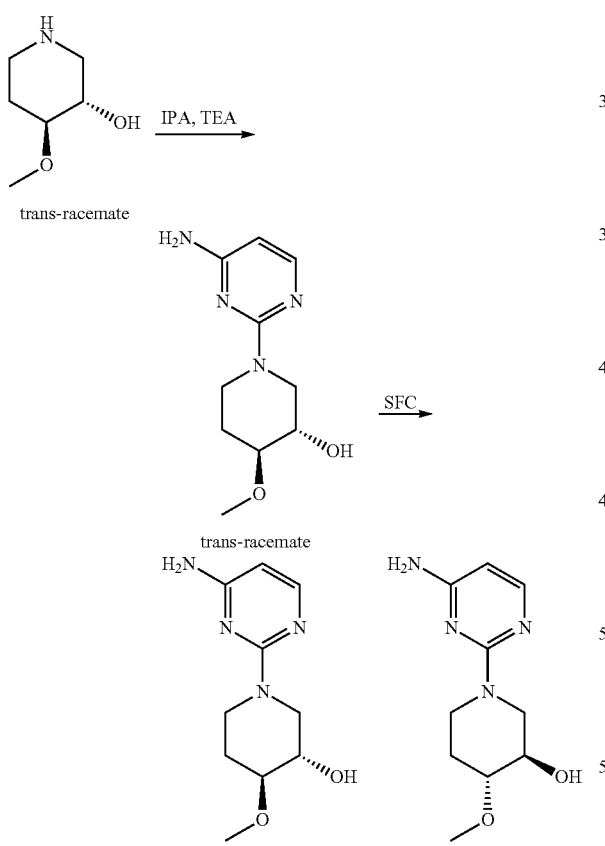

2-chloropyrimidin-4-amine (987 mg, 7.62 mmol) was added to trans-(3S,4S)-4-methoxypiperidin-3-ol (1.0 g, 7.62 mmol) and TEA (2.30 g, 22.8 mmol) in IPA (20 mL) at rt. The mixture was stirred at 100° C. for 16 h. The mixture was concentrated under vacuum and the residue was purified by a silica gel column with DCM: MeOH=20:1. The result in 1.2 g trans-(3S,4S)-1-(4-aminopyrimidin-2-yl)-4-methoxypiperidin-3-ol as a colorless oil. Trans-(3S,4S)-1-(4-aminopyrimidin-2-yl)-4-methoxypiperidin-3-ol (1.2 g, 5.35 mmol) was purified by Chiral-SFC with following conditions: Column: CHIRALPAK IC, 2*25 cm, 5 um; Mobile Phase A: CO₂, Mobile Phase B: EtOH (8 mmol/L NH₃.MeOH)-HPLC; Flow rate: 40 mL/min; Gradient: 25% B; 254 nm. The result in 450 mg peak 1: (3S,4S)-1-(4-aminopyrimidin-2-yl)-4-methoxypiperidin-3-ol or (3R,4R)-1-(4-aminopyrimidin-2-yl)-4-methoxypiperidin-3-ol as a white solid and 460 mg peak 2: (3R,4R)-1-(4-aminopyrimidin-2-yl)-4-methoxypiperidin-3-ol or (3S,4S)-1-(4-aminopyrimidin-2-yl)-4-methoxypiperidin-3-ol as a white solid.

Analytical Data: LC-MS: (ES, m/z)=225 [M+1].

Example B29: Synthesis of 2-(azetidin-3-ylmethylsulfonyl)-N,N-dimethylethanamine

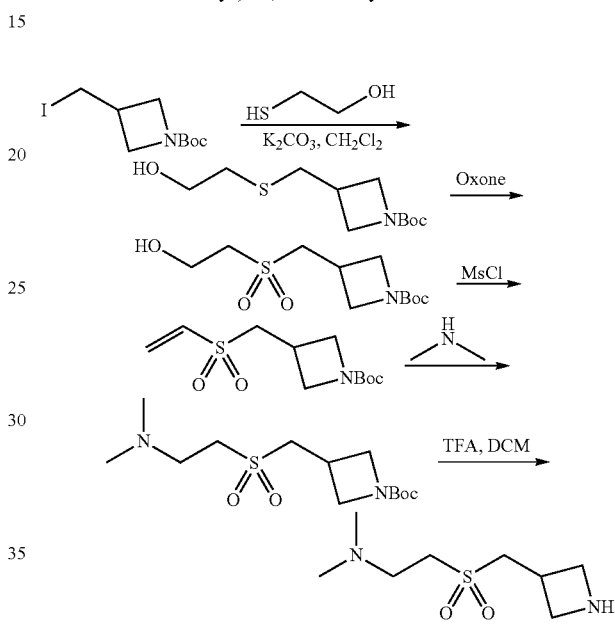

Step 1: Synthesis of tert-butyl 3-((2-hydroxyethylthio)methyl)azetidine-1-carboxylate In a 50 mL flask, was added tert-butyl 3-(iodomethyl)azetidine-1-carboxylate (3 g, 10.0 mmol) dissolved in THF (10 mL). To this was added 2-sulfanylethan-1-ol (781 mg, 10.0 mmol), K₂CO₃ (4.20 g, 30.0 mmol). The mixture was stirred overnight at rt. The reaction was quenched with water and extracted with EA. The organic layer was dried and concentrated to give the title compound (2.8 g) (crude) as brown oil.

Analytical Data: LC-MS: (ES, m/z)=248 [M+1].

Step 2: Synthesis of tert-butyl 3-((2-hydroxyethylsulfonyl)methyl)azetidine-1-carboxylate In a 50 mL flask, was added tert-butyl 3-{[(2-hydroxyethyl)sulfanyl]methyl}azetidine-1-carboxylate (2.7 g, 1.2 mmol) dissolved in THF/EtOH/H₂O (10 mL). To this was added Oxone (744 mg, 1.2 mmol). The mixture was stirred for 3 h at rt. The reaction was extracted with EA. The organic layer was dried and concentrated to give the title compound (2.4 g crude) as a yellow solid.

Step 3: Synthesis of tert-butyl 3-(vinylsulfonylmethyl)azetidine-1-carboxylate

Methanesulfonyl chloride (1.8 g) was added to the solution of tert-butyl 3-[(2-hydroxyethanesulfonyl)methyl]azetidine-1-carboxylate (2.2 g) and TEA (2.5 g) in DCM (10 mL) at 0° C. The mixture was stirred for 3 h at rt. Water was added and extracted with EA. The organic layer was dried and concentrated to give the title compound (1.8 g) a brown solid.

Analytical Data: LC-MS: (ES, m/z)=206 [M+1-56].

Step 4: Synthesis of Tert-butyl 3-((2-(dimethyl-amino)ethylsulfonyl)methyl)azetidine-1-carboxylate In a 50 mL flask, was added tert-butyl 3-[(ethenesulfonyl) methyl]azetidine-1-carboxylate (1.8 g) dissolved in DCM (10 mL). To this was added dimethylamine hydrochloride (1.2 g), TEA (2.3 g). The mixture was stirred for 3 h at rt. Water was added and extracted with DCM. The organic layers were combined and purified with DCM/MeOH (20/1) to the title compound (1.5 g) as brown solid.

Analytical Data: LC-MS: (ES, m/z)=307 [M+1].

Step 5: Synthesis of 2-(azetidin-3-ylmethylsulfo-nyl)-N,N-dimethylethanamine

Tert-butyl 3-((2-(dimethylamino)ethylsulfonyl)methyl) azetidine-1-carboxylate (1.5 g, 4.9 mmol) was added to the solution of TFA (5 mL) in DCM (15 mL). The mixture was stirred for 3 h at rt. The solvent was removed under reduced pressure to afford the title compound as the trifluoroacetic acid salt, 1.2 g (crude) as yellow solid.

Analytical Data: LC-MS: (ES, m/z)=207 [M+1].

Example B30: Synthesis of 3-(1-oxa-7-azaspiro [3.5]nonan-7-yl)-1,2,4-triazin-5-amine

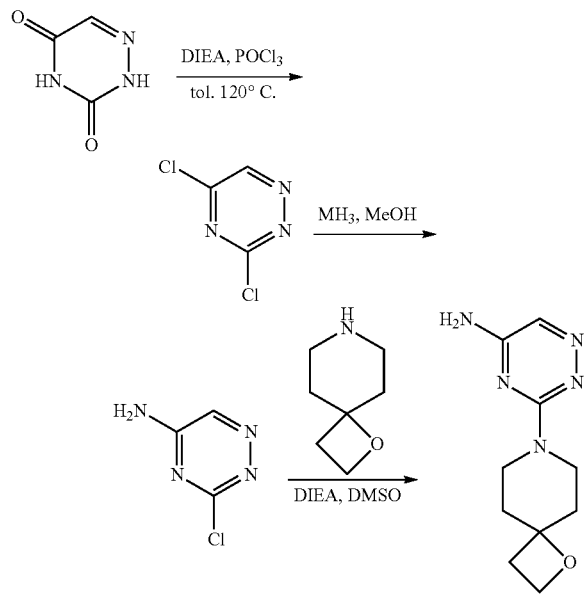

Step 1: Synthesis of 3,5-dichloro-1,2,4-triazine

To a solution of 2,3,4,5-tetrahydro-1,2,4-triazine-3,5-dione (5.0 g, 44.2 mmol) in toluene (20 mL) was added DIEA (17.1 g, 132.7 mmol) and POCl₃ (27.1 g, 176.8 mmol) at rt. Then the solution was heated at 120° C. for 3 h. Excessive POCl₃ and toluene was removed under reduced pressure and the residue was diluted with EA and water. The organic layer was washed with brine, dried over Na₂SO₄, concentrated to dryness to afford the crude product which was used for next step without further purification (200 mg, crude).

Step 2: Synthesis of 3-chloro-1,2,4-triazin-5-amine

To a solution of 3,5-dichloro-1,2,4-triazine (200 mg, 1.33 mmol) in THF (5 mL) was added NH₃/MeOH (20 mL, 7.0 M) and the resulting mixture was stirred at rt for 30 min; LC-MS showed that the reaction was completed. Evaporation to dryness and purified by Prep-HPLC to give the title compound (50 mg, 20% yield over two steps).

Analytical Data: LC-MS: (ES, m/z)=131 [M+1].

Step 3: Synthesis of 3-(1-oxa-7-azaspiro[3.5]nonan-7-yl)-1,2,4-triazin-5-amine

To a solution of 3-chloro-1,2,4-triazin-5-amine (30 mg, 229 umol) and DIPEA (88.4 mg, 686 umol) in DMSO (1 mL) was added 1-oxa-7-azaspiro[3.5]nonane (29.1 mg, 229 umol) at rt. The mixture was stirred for 2 h at 120° C. Water was added and the mixture was extracted by EA. The organic layer was combined and was dried by Na₂SO₄. The organic layer was concentrated and the residue was purified by Prep-TLC with DCM/MeOH (20:1). This resulted in 30 mg (59%) the title compound as a light-yellow solid.

Analytical Data: LC-MS: (ES, m/z)=222 [M+1].

Example B31: Synthesis of 3-(4-methoxypiperidin-1-yl)-1,2,4-triazin-5-amine

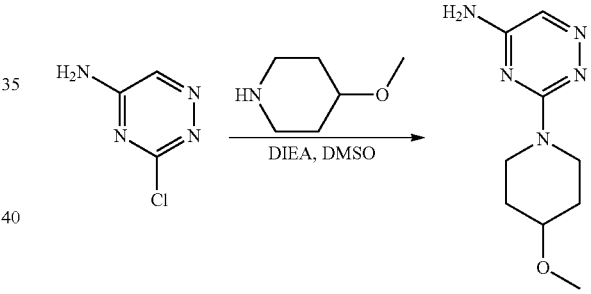

To a solution of 3-chloro-1,2,4-triazin-5-amine (30 mg, 229 umol) and DIEA (59 mg, 458 umol) in DMSO (1 mL) was added 4-methoxypiperidine (26.3 mg, 229 umol) at rt. The mixture was stirred for 2 h at 120° C. Water was added and the mixture was extracted by EA. The organic layer was combined and was dried by Na₂SO₄. The organic layer was concentrated and the residue was purified by Prep-TLC with PE/EA (5:1). This resulted in 30 mg (62%) of the title compound as a light-yellow solid.

Analytical Data: LC-MS: (ES, m/z)=210 [M+1].

Example B32: Synthesis of 2-((3R,4S)-3-fluoro-4-methoxypiperidin-1-yl)pyrimidin-4-amine

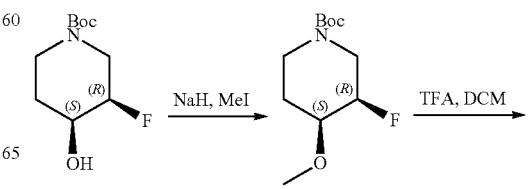

-continued

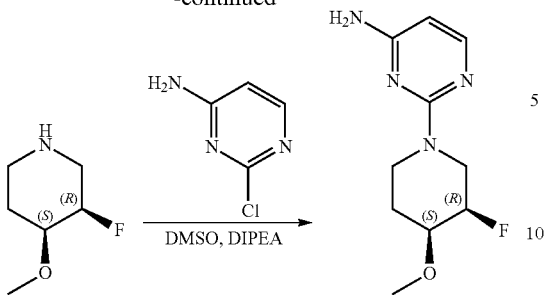

Step 1: Synthesis of (3R,4S)-tert-butyl 3-fluoro-4-methoxypiperidine-1-carboxylate To a solution of tert-butyl (3R,4S)-3-fluoro-4-hydroxypiperidine-1-carboxylate (700 mg, 3.19 mmol) in THF (5 mL), NaH (152 mg, 3.82 mmol) was added at 0° C. MeI (497 mg, 3.5 mmol) was added and the mixture was warmed to rt for and stirred for 2 h. The reaction mixture was quenched with water, extracted with EA and washed with brine. The organic layer was dried over $Na_2SO_4$, filtered and evaporated to afford the title compound (750 mg, crude) as a yellow oil.

Analytical Data: LC-MS: (ES, m/z)=178 [M+1-56].

Step 2: Synthesis of (3R,4S)-3-fluoro-4-methoxypiperidine

To a solution of tert-butyl (3R,4S)-3-fluoro-4-methoxypiperidine-1-carboxylate (750 mg, 3.21 mmol) in DCM (10 mL), TFA (2 mL) was added and stirred at rt for 3 h. The reaction mixture was evaporated to afford the title compound (700 mg crude) as a brown oil.

Step 3: Synthesis of 2-((3R,4S)-3-fluoro-4-methoxypiperidin-1-yl)pyrimidin-4-amine The mixture of (3R,4S)-3-fluoro-4-methoxypiperidine (700 mg, 5.25 mmol), 2-chloropyrimidin-4-amine (488 mg, 3.76 mmol) and DIPEA (1.44 g, 11.2 mmol) in DMSO (5 mL) was stirred at 100° C. for 2 h. The reaction mixture was diluted with water, extracted with EA and washed with brine. The organic layer was dried over $Na_2SO_4$, filtered, evaporated and purified by column chromatography (50% EA in PE) to afford the title compound (550 mg) as a yellow solid.

Example B33: Synthesis of 2-((3S,4R)-3-fluoro-4-methoxypiperidin-1-yl)pyrimidin-4-amine

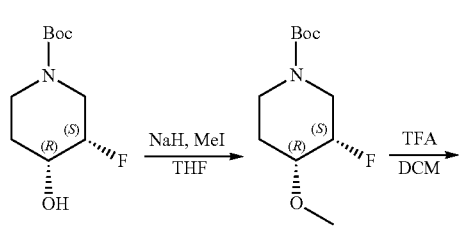

-continued

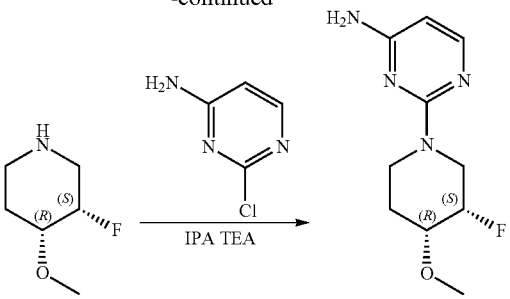

Step 1: Synthesis of (3S,4R)-tert-butyl 3-fluoro-4-methoxypiperidine-1-carboxylate Sodium hydride (218.90 mg, 9.122 mmol, 4 equiv.) was added to tert-butyl (3S,4R)-3-fluoro-4-hydroxypiperidine-1-carboxylate (500 mg, 2.280 mmol, 1 equiv.) in THF (10 mL) at 0° C. After stirring for 20 min, methyl iodide (1294.73 mg, 9.122 mmol, 4 equiv.) was added. The resulting solution was stirred for additional 1 h at 0° C. The reaction was then quenched by addition of 10 mL of water. The solids were filtered out. The resulting solution was extracted with EA and concentrated under vacuum. This resulted in 500 mg (94.1%) of the title compound as light-yellow oil.

Analytical Data: LC-MS: (ES, m/z)=178 [M+1−56].

Step 2: Synthesis of (3S,4R)-3-fluoro-4-methoxypiperidine

The solution of tert-butyl (3S,4R)-3-fluoro-4-methoxypiperidine-1-carboxylate (500 mg, 2.143 mmol, 1 equiv.) in TFA/DCM (3/10 mL) was stirred for 1 h at rt. The resulting mixture was concentrated under vacuum to afford 500 mg (crude) of the title compound as a solid.

Step 3: Synthesis of 2-((3S,4R)-3-fluoro-4-methoxypiperidin-1-yl)pyrimidin-4-amine The mixture of (3S,4R)-3-fluoro-4-methoxypiperidine (3 g, 22.528 mmol, 1 equiv.), 2-chloropyrimidin-4-amine (2.33 g, 0.018 mmol, 0.8 equiv.) and TEA (6.84 g, 0.068 mmol, 3 equiv.) in IPA (3 mL) was stirred for 12 h at 100° C. The solvent was removed under vacuum and residue was purified by FLASH (5% MeOH in DCM) to give 3.3 g (66%) of the title compound as a light-yellow solid.

Analytical Data: LC-MS: (ES, m/z)=227 [M+1]. 1H-NMR (400 MHz, 6d-DMSO) δ ppm 7.72 (d, 1H, J=5.6 Hz), 6.39 (s, 2H), 5.71 (d, 1H, J=5.6 Hz), 4.83 (d, 1H, J=49.3 Hz), 4.60-4.49 (m, 1H), 4.29 (d, 1H, J=13.3 Hz), 3.55-3.42 (m, 1H), 3.28 (d, 1H, J=13.3 Hz), 3.20-3.04 (m, 1H), 1.76-1.48 (m, 2H)

Example B34: Synthesis of 2-(8-oxa-3-aza-bicyclo[3.2.1]octan-3-yl)pyrimidin-4-amine

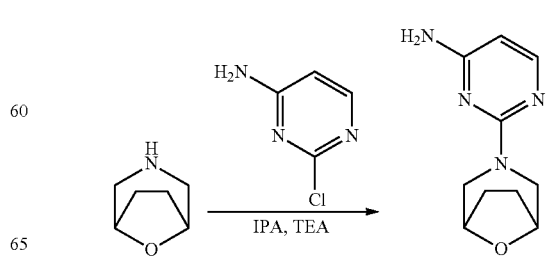

The mixture of 8-oxa-3-aza-bicyclo[3.2.1]octane (226 mg, 2.0 mmol), 2-chloropyrimidin-4-amine (260 mg, 2.0 mmol) and TEA (300 mg, 3.0 mmol) in IPA (5 mL) was stirred overnight at 100° C. The solvent was removed and the residue was purified by Prep-TLC (5% MeOH in DCM) to afford the title compound (300 mg, 73.8%) as yellow solid.

Analytical Data: LC-MS: (ES, m/z)=207 [M+1].

Example B35: Synthesis of rac-1-(4-aminopyrimidin-2-yl)-2,4-dimethylpiperidin-4-ol

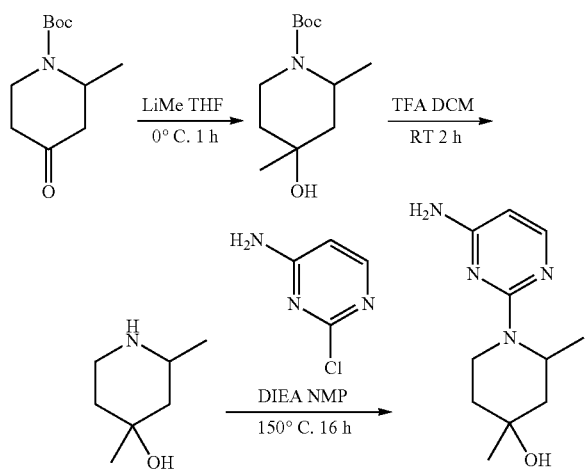

Step 1: Synthesis of rac-tert-butyl 4-hydroxy-2,4-dimethylpiperidine-1-carboxylate Methyllithium (822 mg, 37.4 mmol) was added dropwise to rac-tert-butyl 2-methyl-4-oxopiperidine-1-carboxylate (4 g, 18.7 mmol) in THF at 0° C. The mixture was stirred at 0° C. for 1 h. The reaction was quenched with water/ice and extracted with EA. Combined the organic layers and concentrated under vacuum. This resulted in 4.2 g (98.1%) of the title compound as a yellow solid.

Analytical Data: LC-MS: (ES, m/z)=230 [M+1].

Step 2: Synthesis of rac-2,4-dimethylpiperidin-4-ol

To a stirred solution of rac-tert-butyl 4-hydroxy-2,4-dimethylpiperidine-1-carboxylate (4 g, 17.4 mmol) in DCM was added TFA (10 mL). The mixture was stirred at rt for 2 h. The reaction was concentrated under vacuum. The crude product was used to nest step directly.

Analytical Data: LC-MS: (ES, m/z)=130 [M+1].

Step 3: Synthesis of rac-1-(4-aminopyrimidin-2-yl)-2,4-dimethylpiperidin-4-ol

To a stirred solution of rac-2,4-dimethylpiperidin-4-ol (2 g, 15.4 mmol) and 2-chloropyrimidin-4-amine (2.18 g, 16.9 mmol) in NMP was added DIEA (3.97 g, 30.8 mmol). The mixture was stirred overnight at 150° C. After cooling to rt, the reaction was extracted with DCM/MeOH (10:1). The residue was purified by Prep-TLC with DCM/MeOH (10:1). This resulted in 0.2 g of the title compound as a white solid.

Analytical Data: LC-MS: (ES, m/z)=223 [M+1].

Example B36: Synthesis of rac-2-(6-oxa-3-aza-bicyclo[3.2.1]octan-3-yl)pyrimidin-4-amine

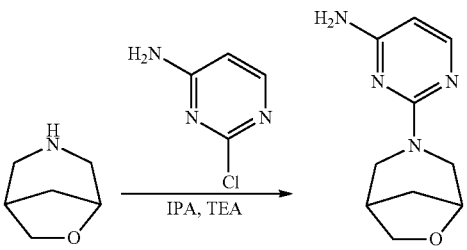 [SMILES: C1NCC2CC1CO2 ; Nc1ccnc(Cl)n1 ; Nc1ccnc(N2CC3COC(C3)C2)n1]

A mixture of 2-chloropyrimidin-4-amine (100 mg, 0.7719 mmol), rac-6-oxa-3-azabicyclo[3.2.1]octane hydrochloride (115 mg, 0.7719 mmol), TEA (233 mg, 2.31 mmol) in IPA (3 mL) was stirred at 100° C. for 3 h. The solution was concentrate and the residue was purified on prep-TLC (DCM:MeOH=10:1) to afford the title compound (100 mg) as a white solid.

Analytical Data: LC-MS: (ES, m/z)=207 [M+1].

Example B37: Synthesis of tert-butyl 3-(azetidin-3-ylmethylsulfonyl)azetidine-1-carboxylate

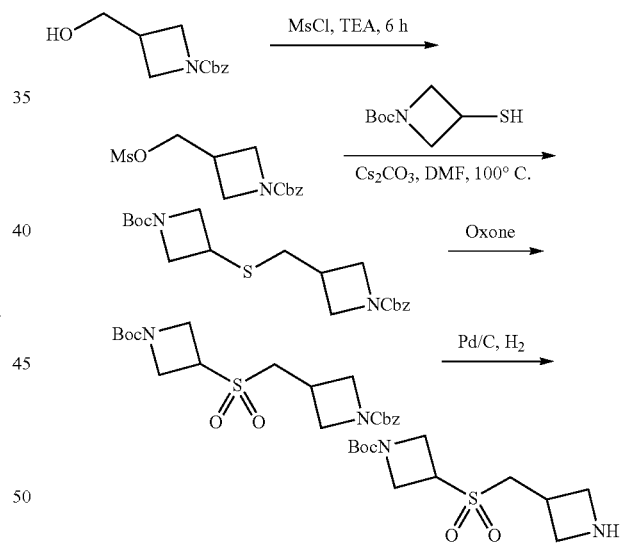

Step 1: Synthesis of benzyl 3-((methylsulfonyloxy)methyl)azetidine-1-carboxylate Into a 100 mL round bottom flask was placed benzyl 3-(hydroxymethyl)azetidine-1-carboxylate (1.2 g, 5.42 mmol) in DCM (20 mL), TEA (822 mg, 8.13 mmol) and methanesulfonyl chloride (620 mg, 5.42 mmol). The resulting solution was stirred at rt for 6 h. The solution was washed with water and purified by Prep-TLC (20% EA in PE). The resulted in 1.0 g of the title compound as a white solid.

Analytical Data: LC-MS: (ES, m/z)=300 [M+1].

Step 2: Synthesis of tert-butyl 3-((1-(benzyloxycarbonyl)azetidin-3-yl)methylthio)azetidine-1-carboxylate The mixture of benzyl 3-[(methanesulfonyloxy)methyl]azetidine-1-carboxylate (530 mg, 1.77 mmol), tert-butyl 3-sulfanylazetidine-1-carboxylate (335 mg, 1.77 mmol) and $Cs_2CO_3$ (1.15 g, 3.54 mmol) in DMF (2 mL) was stirred at 100° C. for 2 h. Water was added and the mixture was extracted by EA. The organic phase was concentrated to afford 480 mg of the title compound as a white solid.
Analytical Data: LC-MS: (ES, m/z)=293 [M+1−100].

Step 3: Synthesis of tert-butyl 3-((1-(benzyloxycarbonyl)azetidin-3-yl)methylsulfonyl)azetidine-1-carboxylate Oxone (4.21 g, 6.86 mmol) was added to the solution of benzyl 3-[({1-[(tert-butoxy)carbonyl]azetidin-3-yl}sulfanyl)methyl]azetidine-1-carboxylate (900 mg, 2.29 mmol) in EtOH/THF/$H_2O$ (3/3/3 mL). The resulting solution was stirred at rt for 2 h. The resulting solution was extracted by EA and purified by Prep-TLC with DCM/MeOH (100:1) to afford 680 mg of the title compound as white solid.
Analytical Data: LC-MS: (ES, m/z)=325 [M+1−100].

Step 4: Synthesis of tert-butyl 3-(azetidin-3-ylmethylsulfonyl)azetidine-1-carboxylate Benzyl 3-[({1-[(tert-butoxy)carbonyl]azetidin-3-yl}sulfonyl)methyl]azetidine-1-carboxylate (660 mg, 1.55 mmol) and Pd/C (199 mg, 1.55 mmol) in MeOH (12 mL) were stirred under an atmosphere of hydrogen at rt for 4 h. The solid was filtered out, mother solvent was concentrated under reduced pressure to give the title compound (480 mg) as a white solid.
Analytical Data: LC-MS: (ES, m/z)=291 [M+1].

Example B38: Synthesis of rac-1-(4-aminopyrimidin-2-yl)azepan-4-ol

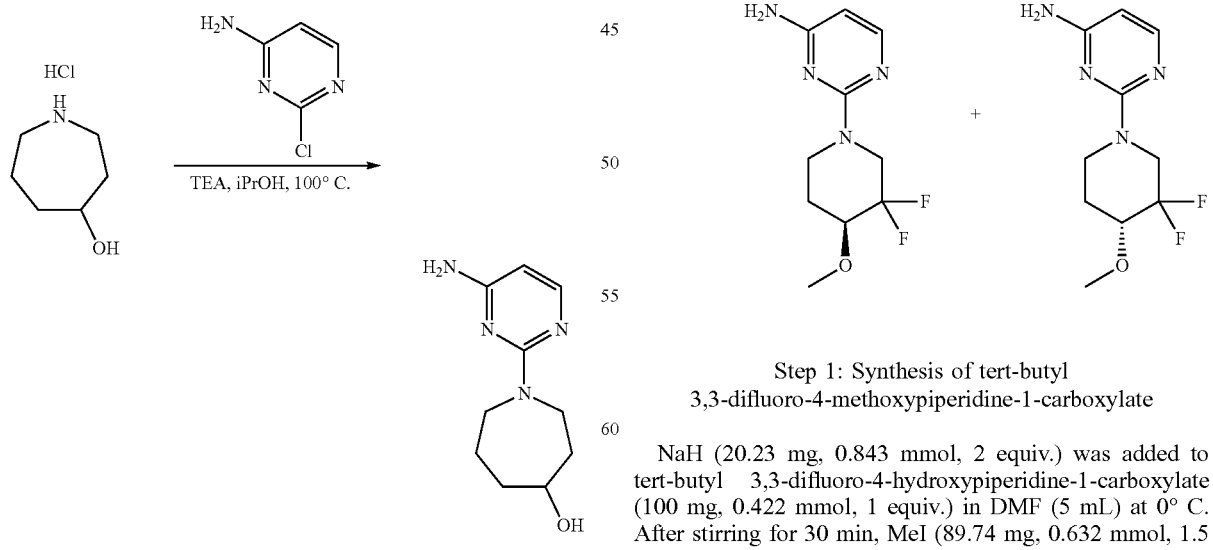

A mixture of rac-azepan-4-ol hydrochloride (150 mg, 0.9892 mmol), 2-chloropyrimidin-4-amine (128 mg, 0.989 mmol) and TEA (199 mg, 1.97 mmol) in IPA (15 mL) was stirred at 100° C. for 3 h. The reaction mixture was concentrated and purified by preparative TLC (DCM: MeOH=5:1) to afford the title compound (90 mg) as a yellow solid.
Analytical Data: LC-MS: (ES, m/z)=209 [M+1].

Example B39: Synthesis of (S)-2-(3,3-difluoro-4-methoxypiperidin-1-yl)pyrimidin-4-amine and (R)-2-(3,3-difluoro-4-methoxypiperidin-1-yl)pyrimidin-4-amine

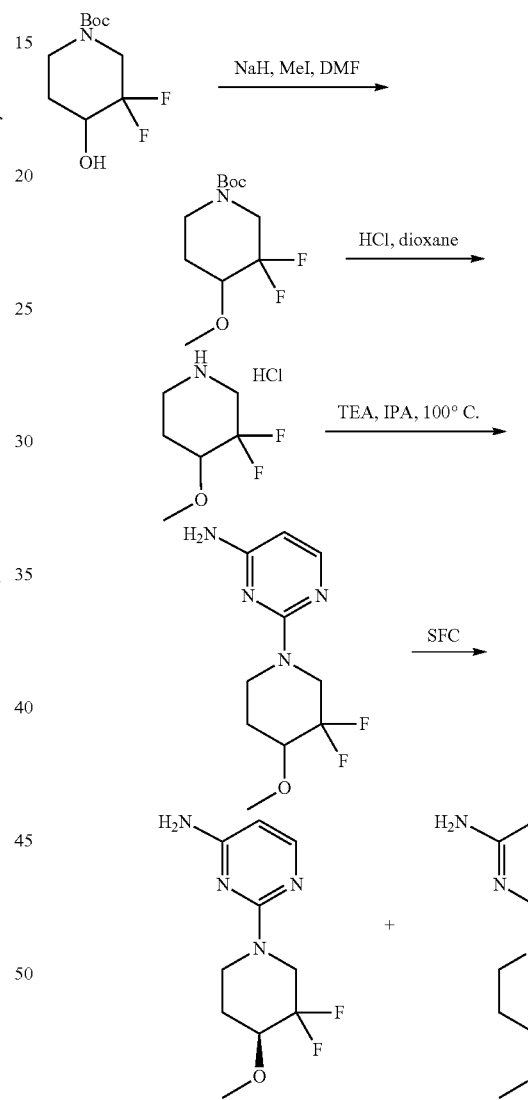

Step 1: Synthesis of tert-butyl 3,3-difluoro-4-methoxypiperidine-1-carboxylate NaH (20.23 mg, 0.843 mmol, 2 equiv.) was added to tert-butyl 3,3-difluoro-4-hydroxypiperidine-1-carboxylate (100 mg, 0.422 mmol, 1 equiv.) in DMF (5 mL) at 0° C. After stirring for 30 min, MeI (89.74 mg, 0.632 mmol, 1.5 equiv.) was added and the mixture was stirred for 2 h at rt. The reaction was then quenched by the addition of 10 mL of water. The resulting solution was extracted with EA and concentrated. This resulted in 150 mg (crude) of the title compound as a light-yellow solid.

Analytical Data: LC-MS: (ES, m/z)=252 [M+1].

Step 2: Synthesis of 3,3-difluoro-4-methoxypiperidine

The solution of tert-butyl 3,3-difluoro-4-methoxypiperidine-1-carboxylate (300 mg, 1.194 mmol) in 4M HCl/dioxane (5 mL) and DCM (15 mL) was stirred for 12 h at rt. The resulting mixture was concentrated. This resulted in 280 mg (crude) of the title compound as the HCl salt as a light-yellow solid.

Analytical Data: LC-MS: (ES, m/z)=152 [M+1].

Step 3: Synthesis of (S)-2-(3,3-difluoro-4-methoxypiperidin-1-yl)pyrimidin-4-amine and (R)-2-(3,3-difluoro-4-methoxypiperidin-1-yl)pyrimidin-4-amine The mixture of 3,3-difluoro-4-methoxypiperidine (1.5 g, 9.923 mmol, 1 equiv.), 2-chloropyrimidin-4-amine (1.29 g, 9.923 mmol, 1 equiv.) and TEA (3.01 g, 29.77 mmol, 3 equiv.) in IPA (10 mL) was stirred for 3 hr at 100° C. The resulting mixture was concentrated. The residue was applied onto a silica gel column with EA/PE (1:1). This resulted in 1.1 g (45.4%) of the title compound as a yellow solid.

2-(3,3-difluoro-4-methoxypiperidin-1-yl)pyrimidin-4-amine was separated by prep-Chiral SFC by following conditions: Column name: CHIRALCEL OJ-3, 4.6*50 mm, 3 um; Co-Solvent: MeOH (0.1% DEA) Gradient (B %): 10% to 50% in 4.0 min, hold 2.0 min at 50%; Back Pressure (psi): 1500.000; Flow (mL/min) to afford peak 1: (S)-2-(3,3-difluoro-4-methoxypiperidin-1-yl)pyrimidin-4-amine or (R)-2-(3,3-difluoro-4-methoxypiperidin-1-yl)pyrimidin-4-amine (500 mg) as pale-yellow solid and peak 2: (R)-2-(3,3-difluoro-4-methoxypiperidin-1-yl)pyrimidin-4-amine or (S)-2-(3,3-difluoro-4-methoxypiperidin-1-yl)pyrimidin-4-amine (500 mg) as pale-yellow solid.

Analytical Data: LC-MS: (ES, m/z)=245 [M+1].

Example B40: Synthesis of rac-1-(4-aminopyrimidin-2-yl)-3,3-difluoro-5,5-dimethylpiperidin-4-ol

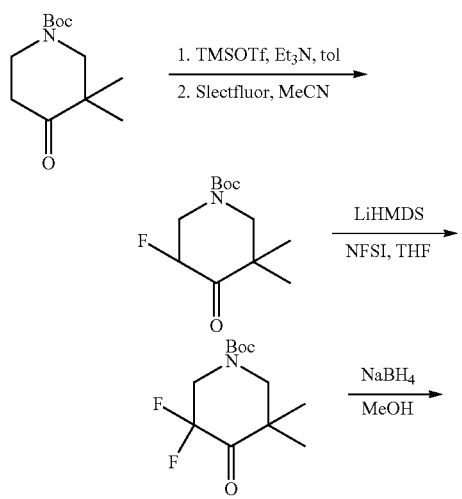

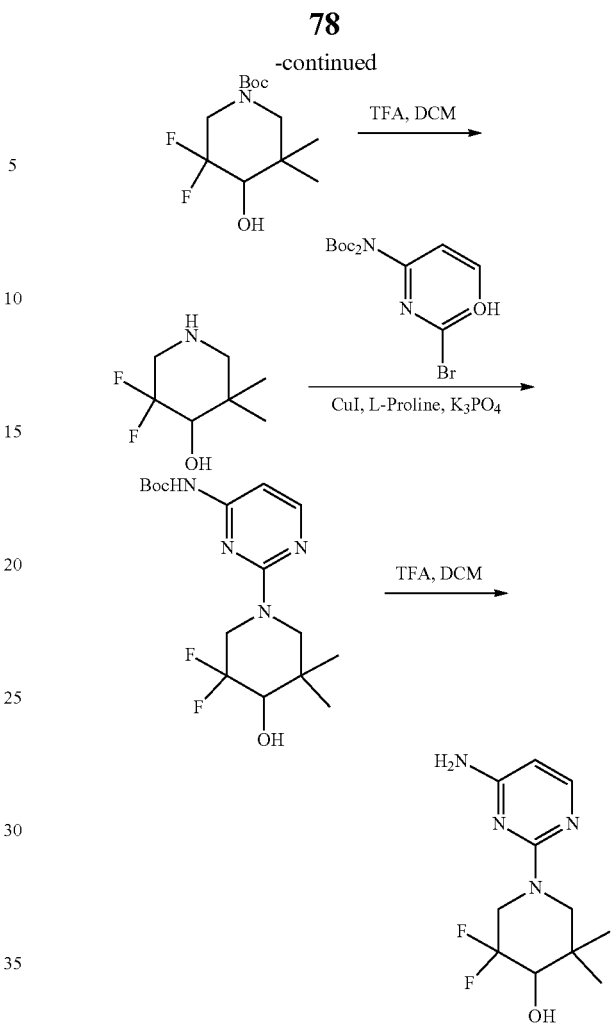

Step 1: Synthesis of rac-tert-butyl 5-fluoro-3,3-dimethyl-4-oxopiperidine-1-carboxylate To a solution of tert-butyl 3,3-dimethyl-4-oxopiperidine-1-carboxylate (7.5 g, 32.9 mmol) and TEA (13.2 g, 131 mmol) in toluene was added TMSOTf (14.6 g, 65.8 mmol) at 0° C. under $N_2$ atmosphere. The mixture was stirred for 2 h at rt. The mixture was extracted by EA and water. The organic layer was dried over $Na_2SO_4$ and concentrated under vacuum. The crude product was used directly for next step.

To a solution of tert-butyl 3,3-dimethyl-4-[(trimethylsilyl)oxy]-1,2,3,6-tetrahydropyridine-1-carboxylate (1.2 g, 4.0 mmol) in ACN was added Selectfluor (1.55 g, 4.4 mmol) at 0° C. and the mixture was stirred for 1 h at 0° C. Water was added and the mixture was extracted by EA. The organic layer was combined and was dried over $Na_2SO_4$. The organic layer was concentrated and the residue was purified by flash with PE/EA (5:1). This resulted in 500 mg (51%) of the title compound as a light-yellow solid.

Analytical Data: LC-MS: (ES, m/z)=246 [M+1].

Step 2: Synthesis of tert-butyl 3,3-difluoro-5,5-dimethyl-4-oxopiperidine-1-carboxylate To a solution of rac-tert-butyl 5-fluoro-3,3-dimethyl-4-oxopiperidine-1-carboxylate (100 mg, 407 umol) in THF was added LiHMDS (46.4 mg, 814 umol) at −78° C. under N₂ atmosphere. The mixture was stirred for 10 min at −78° C. and NFSI (117 mg, 610 umol) was added. The resulting mixture was stirred for 2 h. The mixture was extracted by EA and water. The organic layer was concentrated and the residue was purified by Prep-TLC with PE/EA (5:1). This resulted in 60 mg (56%) of the title compound as a light-yellow solid.

Analytical Data: LC-MS: (ES, m/z)=208 [M+1−56].

Step 3: Synthesis of rac-tert-butyl 3,3-difluoro-4-hydroxy-5,5-dimethylpiperidine-1-carboxylate To a solution of tert-butyl 3,3-difluoro-5,5-dimethyl-4-oxopiperidine-1-carboxylate (80 mg, 303 umol) in MeOH was added NaBH₄ (45.9 mg, 1.21 mmol) at rt. The mixture was stirred for 2 h at rt. The mixture was extracted by EA and water. The organic layer was concentrated under vacuum. The crude product 75 mg was used directly for next step.

Analytical Data: LC-MS: (ES, m/z)=210 [M+1−56].

Step 4: Synthesis of rac-3,3-difluoro-5,5-dimethylpiperidin-4-ol

Rac-tert-butyl 3,3-difluoro-4-hydroxy-5,5-dimethylpiperidine-1-carboxylate (75 mg, 282 umol) was added to DCM/TFA (5 mL/2 mL) at rt. The mixture was stirred for 2 h at rt. The resulting mixture was concentrated under vacuum to give 40 mg (86%) of the title compound as a brown liquid.

Analytical Data: LC-MS: (ES, m/z)=166 [M+1].

Step 5: Synthesis of rac-tert-butyl 2-(3,3-difluoro-4-hydroxy-5,5-dimethylpiperidin-1-yl)pyrimidin-4-ylcarbamate The mixture of rac-3,3-difluoro-5,5-dimethylpiperidin-4-ol (100 mg, 605 umol), tert-butyl N-(2-bromopyrimidin-4-yl)-N-[(tertbutoxy) carbonyl]carbamate (226 mg, 605 umol), CuI (57.3 mg, 302 umol), L-Proline (6.95 mg, 60.5 umol) and K₃PO₄ (383 mg, 1.81 mmol) in DMSO was stirred for 2 h at 100° C. under N₂ atmosphere. Water was added and the mixture was extracted with EA. The organic phase was concentrated and the residue was purified by Prep-TLC with DCM/MeOH (20:1). This resulted in 100 mg (36%) of product as a yellow solid.

Analytical Data: LC-MS: (ES, m/z)=359 [M+1].

Step 6: Synthesis of rac-1-(4-aminopyrimidin-2-yl)-3,3-difluoro-5,5-dimethylpiperidin-4-ol Rac-tert-butyl-N-[(tert-butoxy)carbonyl]-N-[2-(3,3-difluoro-4-hydroxy-5,5-dimethylpiperidin-1-yl) pyrimidin-4-yl]carbamate (200 mg, 436 umol) in DCM/TFA (10/3 mL) was stirred for 2 h at rt. The solvent was concentrated under vacuum to give 100 mg (90%) of the title compound as a brown solid.

Analytical Data: LC-MS: (ES, m/z)=259 [M+1].

Example B41: Synthesis of rac-1-(5-amino-1,2,4-triazin-3-yl)-3-fluoro-3-methylpiperidin-4-ols

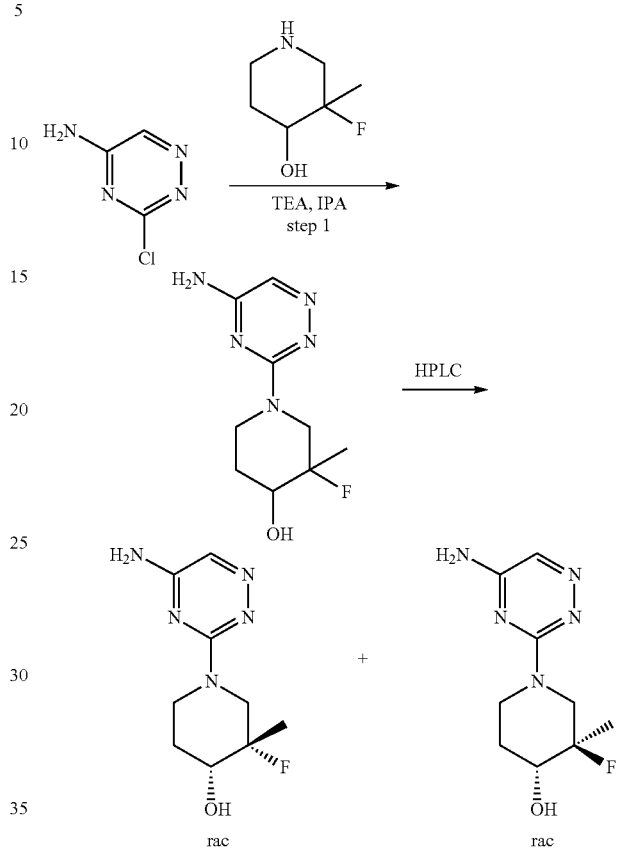

To a solution of 3-chloro-1,2,4-triazin-5-amine (280 mg, 2.14 mmol) and TEA (648 mg, 6.42 mmol) in IPA (5 mL) was added 3-fluoro-3-methylpiperidin-4-ol (Step 4, B1; 284 mg, 2.14 mmol) at rt. The mixture was stirred for 2 h at 100° C. The solvent was removed and the residue was purified by Prep-TLC with PE/EA (5:1). This resulted in 260 mg (53%) of 1-(5-amino-1,2,4-triazin-3-yl)-3-fluoro-3-methylpiperidin-4-ol as a yellow solid. The product was purified by Column: XBridge Shield RP18 OBD Column, 30*150 mm, 5 um; Mobile Phase A: Water (0.05% NH₃H₂O), Mobile Phase B: ACN; Flow rate: 60 mL/min; Gradient: 5 B to 10 B in 7 min; 254/220 nm. This resulted in 90 mg of rac-cis-1-(5-amino-1,2,4-triazin-3-yl)-3-fluoro-3-methylpiperidin-4-ol and 30 mg of rac-trans-1-(5-amino-1,2,4-triazin-3-yl)-3-fluoro-3-methylpiperidin-4-ol. Both are yellow solid.

Analytical Data: LC-MS: (ES, m/z)=228 [M+1].

Example B42: Synthesis of rac-(cis)-1-(4-aminopyrimidin-2-yl)-4-methoxy-3-methylpiperidin-3-ol and rac-(cis)-1-(4-aminopyrimidin-2-yl)-3-methoxy-3-methylpiperidin-4-ol

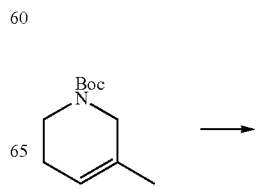

-continued

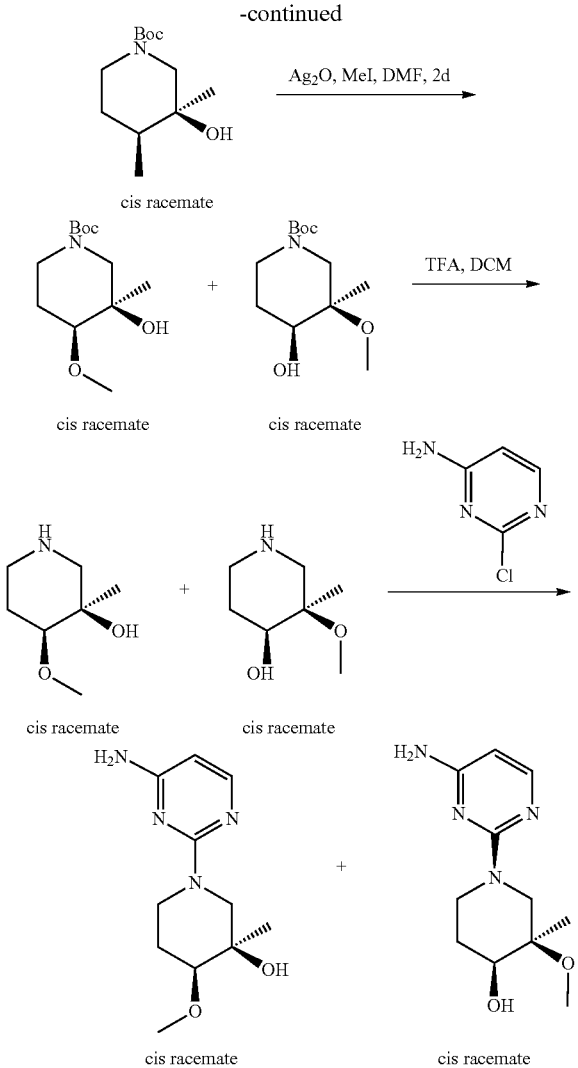

Step 1: Synthesis of rac-(cis)-tert-butyl 3,4-dihydroxy-3-methylpiperidine-1-carboxylate To a mixture of tert-butyl 5-methyl-1,2,3,6-tetrahydropyridine-1-carboxylate (200 mg, 1012 μmop, NMO (142.2 mg, 1214 μmol) in acetone (6 mL) and water (2 mL) was added $K_2OsO_4 \cdot 2H_2O$ (37.4 mg, 101.2 μmol). The mixture was stirred at rt for 2 h. The reaction mixture was extracted with EA. The organic layer was dried over $Na_2SO_4$. Filtered and concentrated to dryness to afford the title compound (180 mg) as a dark-yellow oil.

Analytical Data: LC-MS: (ES, m/z)=176 [M+1−56].

Step 2: Synthesis of rac-(cis)-tert-butyl 3-hydroxy-4-methoxy-3-methylpiperidine-1-carboxylate MeI (367 mg, 2.59 mmol) was added to the mixture of $Ag_2O$ (399 mg, 1.72 mmol) and tert-butyl (cis)-3,4-dihydroxy-3-methylpiperidine-1-carboxylate (200 mg, 864 μmol) in DMF (20 mL) at rt. The mixture was stirred at rt for 2d. The solid was filtered out and the filtrate was diluted with EA, washed with $H_2O$. The organic layer was dried over $Na_2SO_4$ and concentrated under vacuum to afford 160 mg rac-tert-butyl (cis)-3-hydroxy-4-methoxy-3-methylpiperidine-1-carboxylate mixed with rac-(cis)-tert-butyl 4-hydroxy-3-methoxy-3-methylpiperidine-1-carboxylate as a colorless oil, used in next step without further purification.

Analytical Data: LC-MS: (ES, m/z)=190 [M+1-56].

Step 3: Synthesis of rac-(cis)-4-methoxy-3-methylpiperidin-3-ol

TFA (5 mL) was added dropwise to rac-tert-butyl (cis)-3-hydroxy-4-methoxy-3-methylpiperidine-1-carboxylate mixed with rac-(cis)-tert-butyl 4-hydroxy-3-methoxy-3-methylpiperidine-1-carboxylate (160 mg, 652 μmol) in DCM (15 mL) at rt. The resulting mixture was stirred at rt for 2 h. The resulting mixture was concentrated under vacuum to afford 100 mg rac-(cis)-4-methoxy-3-methylpiperidin-3-ol mixed with rac-(cis)-3-methoxy-3-methylpiperidin-4-ol as a colorless oil.

Analytical Data: LC-MS: (ES, m/z)=146 [M+1].

Step 4: Synthesis of rac-(cis)-1-(4-aminopyrimidin-2-yl)-4-methoxy-3-methylpiperidin-3-ol and rac-(cis)-1-(4-aminopyrimidin-2-yl)-3-methoxy-3-methylpiperidin-4-ol 2-chloropyrimidin-4-amine (100 mg, 771 μmol) was added to TEA (388 mg, 385 mmol) and rac-(cis)-4-methoxy-3-methylpiperidin-3-ol (111 mg, 771 μmop/rac-(cis)-3-methoxy-3-methylpiperidin-4-ol in IPA at rt. The mixture was heated to 100° C. for 16 h. The mixture was concentrated under vacuum. The residue was purified by Prep-TLC with DCM: MeOH=25:1. The result in 120 mg rac-(cis)-1-(4-aminopyrimidin-2-yl)-4-methoxy-3-methylpiperidin-3-ol mixed with rac-(cis)-1-(4-aminopyrimidin-2-yl)-3-methoxy-3-methylpiperidin-4-ol as a brown oil.

Analytical Data: LC-MS: (ES, m/z)=239 [M+1].

Example B43: Synthesis of 3-((3R,4S)-3-fluoro-4-methoxypiperidin-1-yl)-1,2,4-triazin-5-amine

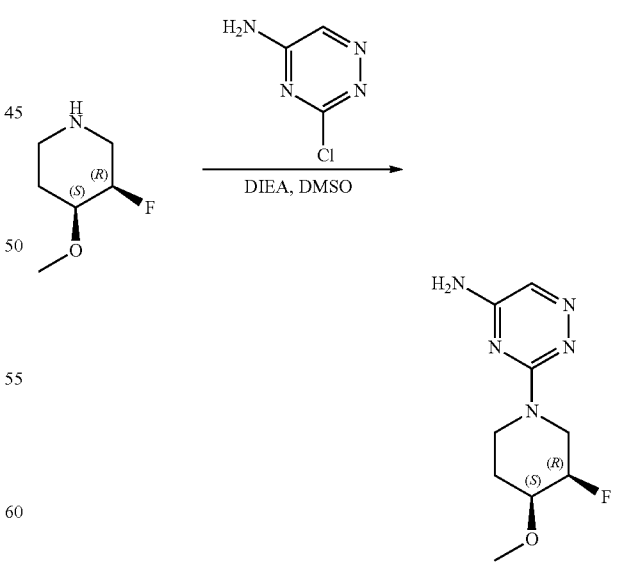

To a solution of (3R,4S)-3-fluoro-4-methoxypiperidine (60 mg, 450 umol) and DIEA (174 mg, 1.35 mmol) in DMSO (2 mL) was added 3-chloro-1,2,4-triazin-5-amine (64.6 mg, 495 umol) at rt. The mixture was stirred for 2 h at

Example B44: Synthesis of 2-(1-(4-aminopyrimidin-2-yl)piperidin-4-yloxy)ethanol

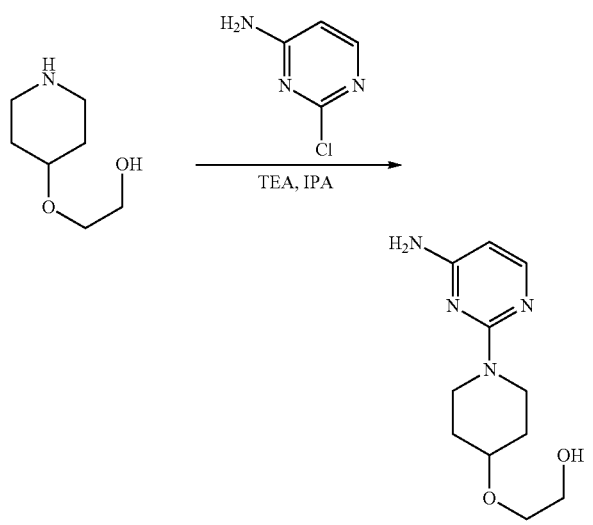

The mixture of 2-chloropyrimidin-4-amine (400 mg, 3.08 mmol), 2-(piperidin-4-yloxy)ethan-1-ol (447 mg, 3.08 mmol) and TEA (933 mg, 9.24 mmol) in IPA (10 mL) was stirred for 12 h at 100° C. The reaction mixture was diluted with water, extracted with EA. The organic layer was dried over Na$_2$SO$_4$, filtered, evaporated and purified by column chromatography (DCM:MeOH=20:1) to afford the title compound (270 mg) as a yellow solid.

Analytical Data: LC-MS: (ES, m/z)=239 [M+1].

Example B45: Synthesis of rac-(1-(4-aminopyrimidin-2-yl)-4-methoxypiperidin-3-yl)methanol

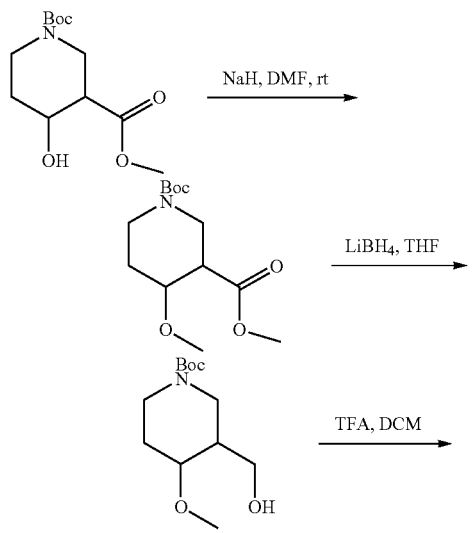

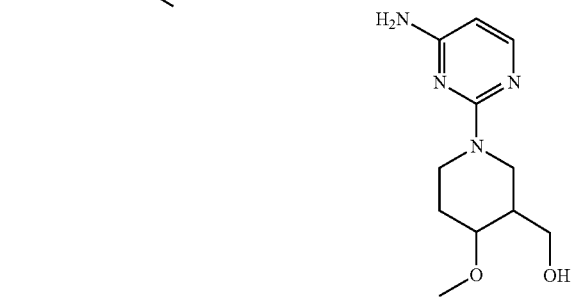

Step 1: Synthesis of rac-1-tert-butyl 3-methyl 4-methoxypiperidine-1,3-dicarboxylate NaH (1.3 g, 34.5 mmol) was added to the solution of rac-1-tert-butyl 3-methyl 4-hydroxypiperidine-1,3-dicarboxylate (6.0 g, 23.0 mmol) in DMF (50 mL) at 0° C. After stirring for 10 min, iodomethane (4.8 g, 34.5 mmol) was added. The mixture was stirred overnight at rt. Water was added and the mixture was extracted with EA. The organic phase was washed with water, dried and concentrated. The residue was purified by FLASH (20% EA in PE) to give the title compound 3.0 g (47%) as colorless oil.

Analytical Data: LC-MS: (ES, m/z)=274 [M+1].

Step 2: Synthesis of rac-tert-butyl 3-(hydroxymethyl)-4-methoxypiperidine-1-carboxylate LiBH$_4$ (2M in THF, 15 mmol) was added to the solution of rac-1-tert-butyl 3-methyl 4-methoxypiperidine-1,3-dicarboxylate (2 g, 7.3 mmol) in THF (40 mL) at 0° C. The mixture was stirred for 2 h at rt. Water was added and the mixture was extracted with EA. The organic phase was washed with water, dried and concentrated to give the title compound 1.2 g (67%) as colorless oil.

Analytical Data: LC-MS: (ES, m/z)=246 [M+1].

Step 3: Synthesis of rac-(4-methoxypiperidin-3-yl)methanol

Rac-tert-butyl 3-(hydroxymethyl)-4-methoxypiperidine-1-carboxylate 1.2 g was added to the solution of TFA/DCM (20 mL/6 mL). The mixture was stirred for 2 h at rt. The solvent was removed under reduced pressure to give the title compound trifluoroacetic acid salt 700 mg as yellow oil.

Analytical Data: LC-MS: (ES, m/z)=146 [M+1].

Step 4: Synthesis of rac-(1-(4-aminopyrimidin-2-yl)-4-methoxypiperidin-3-yl)methanol The mixture of rac-(4-methoxypiperidin-3-yl)methanol (700 mg), 2-chloropyrimidin-4-amine (376 mg, 2.89 mmol) and TEA (578 mg, 5.78 mmol) in IPA was stirred overnight at 100° C. The solvent was removed and the residue was purified by Prep-TLC (5% MeOH in DCM) to afford rac- (1-(4-aminopyrimidin-2-yl)-4-methoxypiperidin-3-yl) methanol 400 mg as pale-yellow solid.

Analytical Data: LC-MS: (ES, m/z)=239 [M+1].

Example B46: Synthesis of (1-(4-aminopyrimidin-2-yl)-4-methoxypiperidin-4-yl)methanol

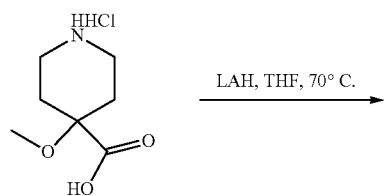

LAH, THF, 70° C.

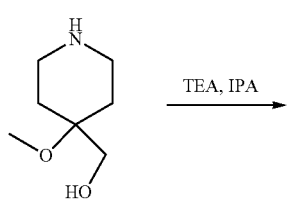

TEA, IPA

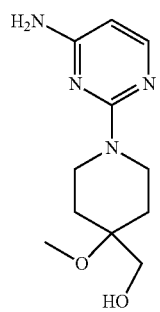

Step 1: Synthesis of (4-methoxypiperidin-4-yl)methanol

To a solution of 4-methoxypiperidine-4-carboxylic acid hydrochloride (200 mg, 1.02 mmol) in THF (25 mL) was added LiAlH$_4$ (116 mg, 3.06 mmol). The mixture was stirred at 60° C. for 16 h. The reaction mixture was quenched with ice-water. The resulting mixture was washed with EA. The aqueous layer was filtered and concentrated to dryness to afford the title compound (400 mg, crude) as a colorless oil.

Analytical Data: LC-MS: (ES, m/z)=146 [M+1].

Step 2: Synthesis of (1-(4-aminopyrimidin-2-yl)-4-methoxypiperidin-4-yl)methanol The mixture of (4-methoxypiperidin-4-yl)methanol (400 mg, crude), 4-chloropyrimidin-2-amine (130 mg, 1.01 mmol), TEA (306 mg, 3.03 mmol) in IPA (25 mL) was stirred at 100° C. for 2 h. The mixture was concentrated and the residue was purified on prep-TLC (EA:PE=2:1) to afford the title compound (35 mg) as a light-yellow solid.

Analytical Data: LC-MS: (ES, m/z)=239 [M+1].

Example B47: Synthesis of rac-1-(4-aminopyrimidin-2-yl)-2-methylpiperidin-4-ol

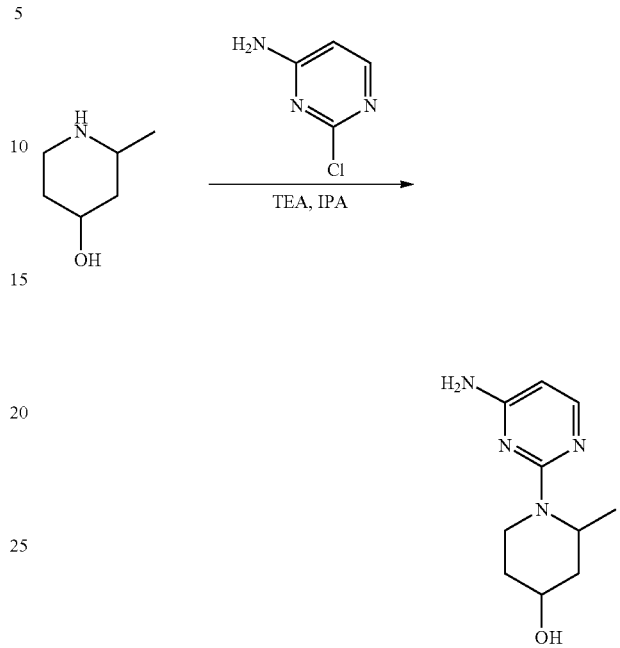

The mixture of rac-2-methylpiperidin-4-ol (575 mg, 5.0 mmol), 2-chloropyrimidin-4-amine (645 mg, 5.0 mmol) and TEA (1000 mg, 10 mmol) in IPA (5 mL) was stirred overnight at 100° C. The solvent was removed under reduced pressure. The residue was purified by Prep-TLC (5% MeOH in DCM) to afford the title compound 200 mg as yellow solid.

Analytical Data: LC-MS: (ES, m/z)=209 [M+1].

Example B48: Synthesis of tert-butyl 2-(1-(4-aminopyrimidin-2-yl)piperidin-4-yloxy)ethylcarbamate

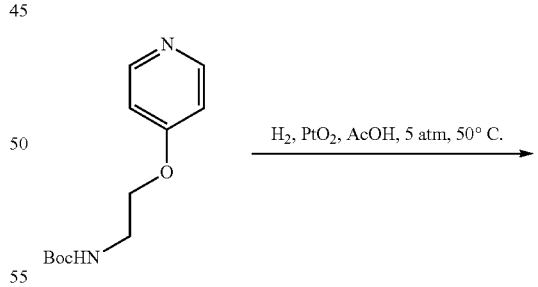

H$_2$, PtO$_2$, AcOH, 5 atm, 50° C.

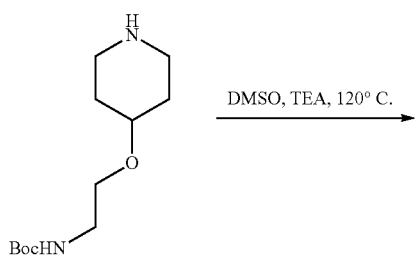

DMSO, TEA, 120° C.

-continued

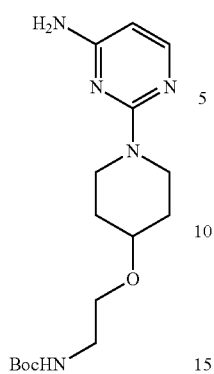

Step 1: Synthesis of tert-butyl 2-(piperidin-4-yloxy)ethylcarbamate

The mixture of tert-butyl 2-(pyridin-4-yloxy)ethylcarbamate (200 mg, 0.84 mmol) and PtO$_2$ (30 mg) in AcOH (5 mL) was stirred overnight at 50° C. under 5 atm of H2 atmosphere. The solvent was removed under reduced pressure and reside was dilute with MeOH. The solid was filtered out and the filtrate was concentrated to afford 250 mg of crude the title compound as colorless oil.

Analytical Data: LC-MS: (ES, m/z)=245 [M+1].

Step 2: Synthesis of Tert-butyl 2-(1-(4-aminopyrimidin-2-yl)piperidin-4-yloxy)ethylcarbamate The mixture of 250 mg of crude tert-butyl 2-(piperidin-4-yloxy)ethylcarbamate, 2-chloropyrimidin-4-amine (129 mg, 1.0 mmol) and TEA (200 mg, 2.0 mmol) in DMSO (1 mL) was stirred overnight at 120° C. Water was added and the mixture was extracted with EA. The organic phase was washed, concentrated and purified by Prep-TLC (5% MeOH in DCM) to afford 70 mg of the title compound as yellow oil.

Analytical Data: LC-MS: (ES, m/z)=338 [M+1].

Example B49: Synthesis of rac-cis-1-(4-aminopyrimidin-2-yl)-4-methoxypiperidine-3-carbonitrile and rac-trans-1-(4-aminopyrimidin-2-yl)-4-methoxypiperidine-3-carbonitrile

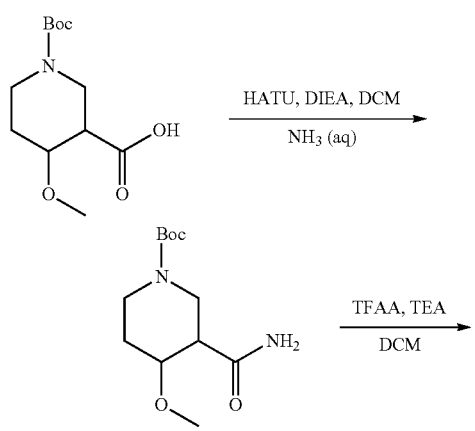

-continued

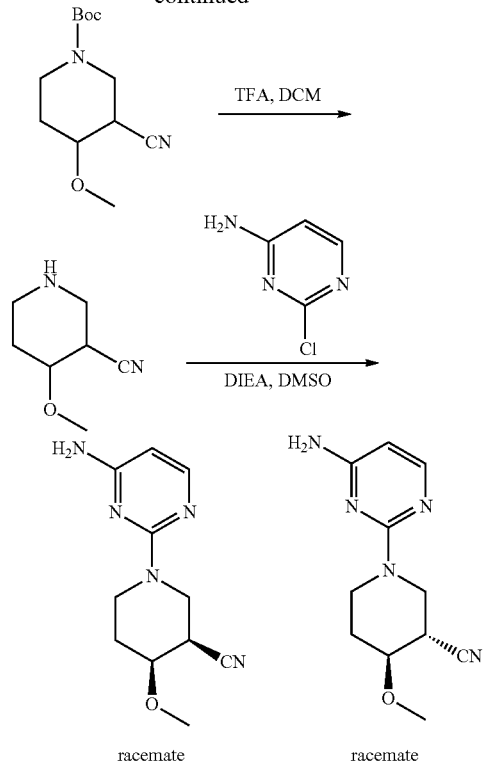

Step 1: Synthesis of rac-tert-butyl 3-carbamoyl-4-methoxypiperidine-1-carboxylate To a solution of rac-1-[(tert-butoxy)carbonyl]-4-methoxypiperidine-3-carboxylic acid (500 mg, 1.92 mmol), DIPEA (744 mg, 5.76 mmol), ammonia water (10 mL) and HATU (1.09 g, 2.88 mmol) in DCM (30 mL) was stirred for 1 h at rt. The mixture was extracted with DCM, dried and concentrated to afford the title compound (500 mg) as colorless oil.

Analytical Data: LC-MS: (ES, m/z)=259[M+1].

Step 2: Synthesis of rac-tert-butyl 3-cyano-4-methoxypiperidine-1-carboxylate

TFAA (810 mg, 3.86 mmol) was added to a solution of rac-tert-butyl 3-carbamoyl-4-methoxypiperidine-1-carboxylate (500 mg, 1.93 mmol) and TEA (585 mg, 5.79 mmol) in DCM (25 mL). The mixture was stirred for 2 h at rt. The resulting solution was washed with water and dried over Na$_2$SO$_4$. This is resulted the title compound (400 mg) as colorless oil.

Analytical Data: LC-MS: (ES, m/z)=185 [M+1−56].

Step 3: Synthesis of rac-4-methoxypiperidine-3-carbonitrile

To a solution of rac-tert-butyl 3-cyano-4-methoxypiperidine-1-carboxylate (400 mg, 1.66 mmol) in DCM (10 mL) was added TFA (5 mL). After 1 h, the solvent was removed by concentration. This is resulted the title compound (500 mg) as a light-yellow oil.

Analytical Data: LC-MS: (ES, m/z)=141[M+1].

Step 4: Synthesis of rac-cis-1-(4-aminopyrimidin-2-yl)-4-methoxypiperidine-3-carbonitrile and rac-trans-1-(4-aminopyrimidin-2-yl)-4-methoxypiperidine-3-carbonitrile A mixture of 2-chloropyrimidin-4-amine (461 mg, 3.56 mmol), rac-4-methoxypiperidine-3-carbonitrile (500 mg, 3.56 mmol), DIPEA (1.37 g, 10.6 mmol) in DMSO (20 mL) was stirred at 120° C. for 3 h. The reaction mixture was purified on prep-HPLC, Column: XBridge Shield RP18 OBD Column, 30*150 mm, 5um; Mobile Phase A: Water (0.05% NH$_3$H$_2$O), Mobile Phase B: ACN; Flow rate: 60 mL/min; Gradient: 13 B to 23 B in 7 min; 254/220 nm. This resulted in rac-cis-1-(4-aminopyrimidin-2-yl)-4-methoxypiperidine-3-carbonitrile (35 mg) as a colorless oil and rac-trans-1-(4-aminopyrimidin-2-yl)-4-methoxypiperidine-3-carbonitrile (50 mg) as a colorless oil.

rac-cis-1-(4-aminopyrimidin-2-yl)-4-methoxypiperidine-3-carbonitrile

Analytical Data: LC-MS: (ES, m/z)=234 [M+1]; 1H-NMR (300 MHz, 3d-CD$_3$Cl) δ ppm 7.94 (d, 1H, J=5.6 Hz), 5.81 (d, 1H, J=5.7 Hz), 4.68 (s, 2H), 4.37 (dd, 1H, J=13.4, 7.0 Hz), 4.14-4.00 (m, 1H), 3.85 (dd, 1H, J=13.1, 3.6 Hz), 3.68-3.57 (m, 2H), 3.49 (s, 3H), 3.04 (dtd, 1H, J=6.7, 3.8, 2.0 Hz), 1.99-1.71 (m, 2H)

rac-trans-1-(4-aminopyrimidin-2-yl)-4-methoxypiperidine-3-carbonitrile

Analytical Data: LC-MS: (ES, m/z)=234 [M+1]; 1H-NMR (300 MHz, 3d-CD$_3$Cl) δ ppm 7.93 (d, 1H, J=5.6 Hz), 5.82 (d, 1H, J=5.6 Hz), 4.78-4.71 (m, 1H), 4.69 (s, 2H), 4.51-4.37 (m, 1H), 3.61-3.51 (m, 1H), 3.49 (s, 3H), 3.40 (dd, 1H, J=13.4, 9.5 Hz), 3.19 (ddd, 1H, J=13.6, 10.4, 3.1 Hz), 2.64 (td, 1H, J=9.1, 4.0 Hz), 2.21-2.07 (m, 1H), 1.53-1.34 (m, 1H)

Example B50: Synthesis of rac-1-(4-aminopyrimidin-2-yl)-3-methoxypiperidin-4-ol

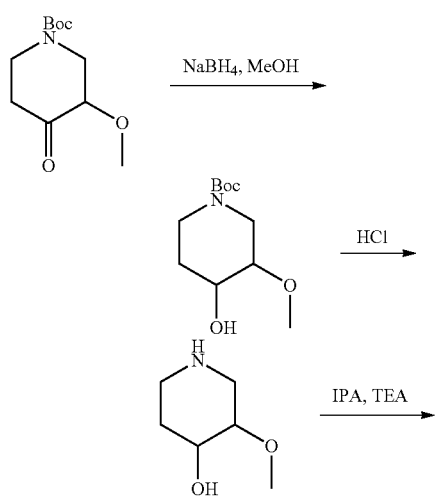

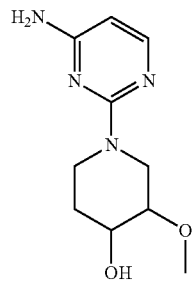

Step 1: Synthesis of rac-tert-butyl 4-hydroxy-3-methoxypiperidine-1-carboxylate

NaBH$_4$ (395 mg, 10.4 mmol) was added to a solution of rac-tert-butyl 3-methoxy-4-oxopiperidine-1-carboxylate (2 g, 8.72 mmol) in THF (50 mL) at 0° C. and stirred at rt for 2 h. The reaction mixture was diluted with water, extracted with EA and washed with brine. The organic layer was dried over Na$_2$SO$_4$, filtered, evaporated to afford the title compound (2 g, crude) as a yellow semi-solid.
Analytical Data: LC-MS: (ES, m/z)=232 [M+1].

Step 2: Synthesis of rac-3-methoxypiperidin-4-ol

The solution of rac-tert-butyl 4-hydroxy-3-methoxypiperidine-1-carboxylate (1 g, 4.32 mmol) in HCl/dioxane (50 mL) was stirred at rt for 3 h. The reaction mixture was evaporated to afford the title compound (700 mg, crude) as a yellow semi-solid.
Analytical Data: LC-MS: (ES, m/z)=132 [M+1].

Step 3: Synthesis of rac-1-(4-aminopyrimidin-2-yl)-3-methoxypiperidin-4-ol

The mixture of rac-2-chloropyrimidin-4-amine (200 mg, 1.54 mmol), 3-methoxypiperidin-4-ol (700 mg, 5.33 mmol) and TEA (1.24 g, 12.3 mmol) in IPA (8 mL) was stirred at 100° C. for 12 h. The reaction mixture was diluted with water (100 mL), and extracted with EA (150 mL×3) and washed with brine (50 mL). The organic layer was dried over Na$_2$SO$_4$, filtered, evaporated and purified by column chromatography (EA) to afford the title compound (220 mg) as a yellow solid.
Analytical Data: LC-MS: (ES, m/z)=225 [M+1].

Example B51: Synthesis of 2-((3R,4S)-1-(4-aminopyrimidin-2-yl)-3-fluoropiperidin-4-yloxy)ethanol

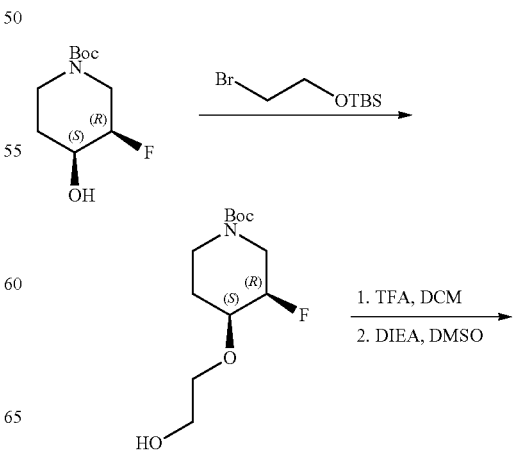

91

-continued

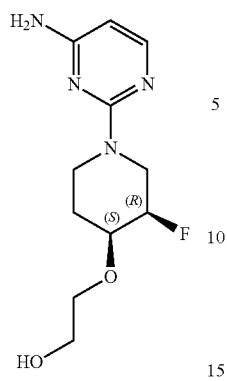

Step 1: Synthesis of (3R,4S)-tert-butyl 3-fluoro-4-(2-hydroxyethoxy)piperidine-1-carboxylate NaH (455 mg, 11.4 mmol) was added to tert-butyl (3R,4S)-3-fluoro-4-hydroxypiperidine-1-carboxylate (1.0 g, 4.56 mmol) in DMF 10 mL at 0° C. After stirring for 20 min, (2-bromoethoxy)(tert-butyl)dimethylsilane (3.25 g, 13.6 mmol) was added and the resulting mixture was stirred at rt for 16 h. The mixture was diluted with EA and washed with brine. The organic layer was dried with Na$_2$SO$_4$ and concentrated under vacuum. The residue was purified by a FLASH with PE:EA=10:1 to afford 1.1 g the title compound as a colorless oil.

Step 2: Synthesis of 2-((3R,4S)-1-(4-aminopyrimidin-2-yl)-3-fluoropiperidin-4-yloxy)ethanol TFA (5 mL) was added to tert-butyl (3R,4S)-4-{2-[(tert-butyldimethylsilyl)oxy]ethoxy}-3-fluoropiperidine-1-carboxylate (1.1 g, 2.91 mmol) in DCM (20 mL) at rt. The resulting mixture was stirred at rt for 1 h. The mixture was concentrated under vacuum and the residue was mixed with 2-chloropyrimidin-4-amine (317 mg, 2.45 mmol) and DIEA (1.26 mg, 9.80 mmol) in DMSO (10 mL). The mixture was heated to 100° C. and stirred for 16 h. The mixture was diluted with EA and washed with brine. The organic layer was dried with Na$_2$SO$_4$ and concentrated under vacuum. The residue was purified by a FLASH with MeOH:EA=1:15 to afford 450 mg the title compound as a yellow solid.

Analytical Data: LC-MS: (ES, m/z)=257 [M+1]; 1H-NMR (400 MHz, 6d-DMSO) δ ppm 7.72 (d, 1H, J=5.6 Hz), 6.41 (s, 2H), 5.71 (d, 1H, J=5.6 Hz), 4.91-4.73 (m, 1H), 4.67-4.50 (m, 2H), 4.34 (d, 1H, J=13.0 Hz), 3.69-3.46 (m, 5H), 3.30-3.17 (m, 1H), 3.06 (d, 1H, J=11.3 Hz), 1.80-1.54 (m, 2H).

Example B52: Synthesis of 2-((3S,4R)-1-(4-aminopyrimidin-2-yl)-3-fluoropiperidin-4-yloxy)ethanol

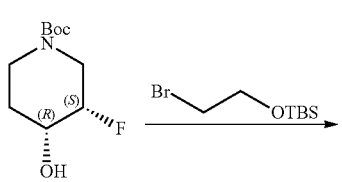

92

-continued

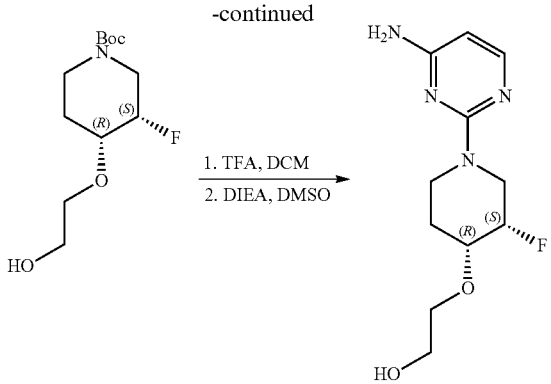

Step 1: Synthesis of (3S,4R)-tert-butyl 3-fluoro-4-(2-hydroxyethoxy)piperidine-1-carboxylate NaH (1.35 g, 33.9 mmol) was added batchwise to tert-butyl (3S,4R)-3-fluoro-4-hydroxypiperidine-1-carboxylate (3.0 g, 13.6 mmol) in DMF (10 mL) at 0° C. The mixture was stirred at 0° C. for 20 min. (2-bromoethoxy)(tert-butyl)dimethylsilane (9.76 g, 40.8 mmol) was added and the mixture was stirred at rt for 16 h. The mixture was diluted with EA and washed with brine. The organic layer was dried with Na$_2$SO$_4$ and concentrated under vacuum. The residue was purified by a FLASH with PE:EA=10:1 to afford 3.0 g the title compound as a colorless oil.

Step 2: Synthesis of 2-((3S,4R)-1-(4-aminopyrimidin-2-yl)-3-fluoropiperidin-4-yloxy)ethanol TFA (15 mL) was added to tert-butyl (3S,4R)-4-{2-[(tert-butyldimethylsilyl)oxy]ethoxy}-3-fluoropiperidine-1-carboxylate (3.0 g, 7.94 mmol) in DCM (20 mL) at rt. The resulting mixture was stirred at rt for 1 h. The mixture was concentrated under vacuum and the residue was mixed with 2-chloropyrimidin-4-amine (873 mg, 6.74 mmol) and DIEA (629 mg, 4.88 mmol) in DMSO (10 mL). The mixture was stirred overnight at 100° C. The mixture was diluted with EA 50 mL and washed with brine, the organic layer was dried with Na$_2$SO$_4$ and concentrated under vacuum. The residue was purified by a FLASH with MeOH:EA=1:15 to afford 1.1 g the title compound as a yellow solid.

Analytical Data: LC-MS: (ES, m/z)=257 [M+1]; 1H-NMR (400 MHz, 6d-DMSO) δ ppm 7.72 (d, 1H, J=5.6 Hz), 6.41 (s, 2H), 5.71 (d, 1H, J=5.6 Hz), 4.94-4.69 (m, 1H), 4.67-4.52 (m, 2H), 4.34 (d, 1H, J=13.3 Hz), 3.72-3.45 (m, 5H), 3.31-3.19 (m, 1H), 3.07 (t, 1H, J=11.4 Hz), 1.77-1.44 (m, 2H).

Example B53: Synthesis of rac-cis-tert-butyl-1-(4-aminopyrimidin-2-yl)-4-methoxypiperidin-3-ylcarbamate and rac-trans-tert-butyl-1-(4-aminopyrimidin-2-yl)-4-methoxypiperidin-3-ylcarbamate

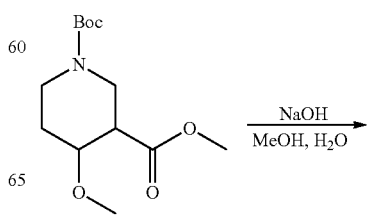

93

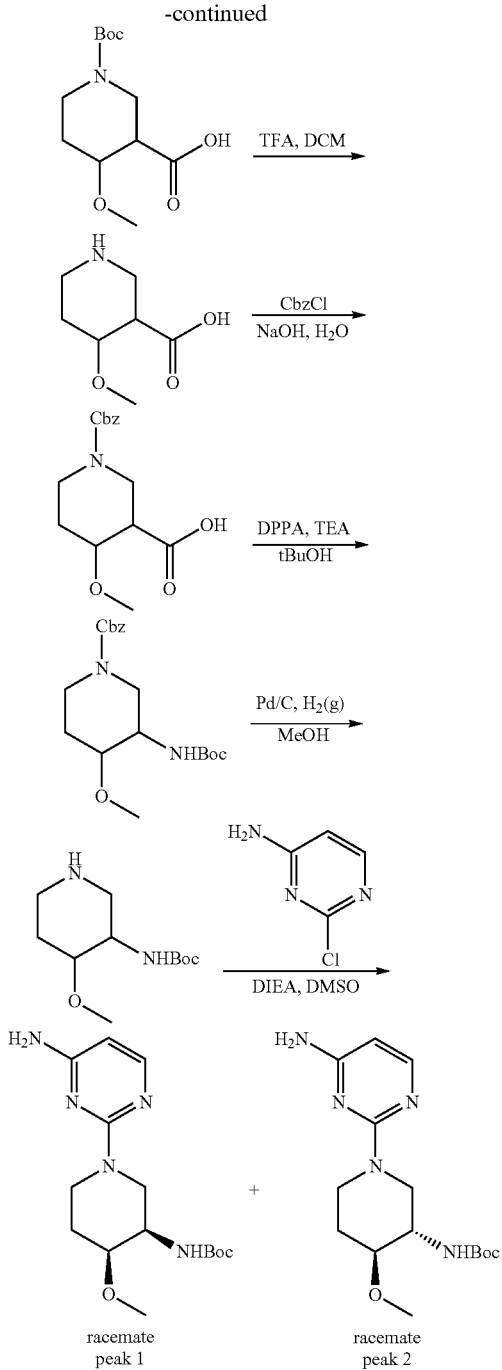

racemate peak 1     racemate peak 2

Step 1: Synthesis of rac-1-(tert-butoxycarbonyl)-4-methoxypiperidine-3-carboxylic Acid A mixture of rac-1-tert-butyl 3-methyl 4-methoxypiperidine-1,3-dicarboxylate (3 g, 10.9 mmol), NaOH (871 mg, 21.8 mmol) in MeOH (25 mL) and water (10 mL) was stirred at 80° C. for 1 h. The mixture was extracted with EA. The organic layer was dried over $Na_2SO_4$ and concentrated to dryness to afford the title compound (2.7 g, 95%) as a light-yellow oil.

Analytical Data: LC-MS: (ES, m/z)=282 [M+23].

94

Step 2: Synthesis of rac-4-methoxypiperidine-3-carboxylic Acid

To a solution of rac-1-[(tert-butoxy)carbonyl]-4-methoxypiperidine-3-carboxylic acid (1.5 g, 5.78 mmol) in DCM (20 mL) was added TFA (7 mL). The mixture was stirred at rt for 1 h. The solvent was removed by concentration to dryness to afford the title compound (1.5 g, crude) as light-yellow oil.

Analytical Data: LC-MS: (ES, m/z)=160 [M+1].

Step 3: Synthesis of rac-1-(benzyloxycarbonyl)-4-methoxypiperidine-3-carboxylic Acid To a solution of rac-4-methoxypiperidine-3-carboxylic acid (1.5 g, crude) and NaOH (931 mg, 23.3 mmol) in water (20 mL) was added CbzCl (1.49 g, 8.74 mmol). After for 1 h, the resulting mixture was washed with EA. The aqueous layer was acidified with 1N HCl and extracted with EA. The organic layer was dried over $Na_2SO_4$ and concentrated to dryness to afford the title compound (1.2 g, 70% two steps) as a colorless oil.

Analytical Data: LC-MS: (ES, m/z)=294 [M+1].

Step 4: Synthesis of rac-benzyl 3-(tert-butoxycarbonylamino)-4-methoxypiperidine-1-carboxylate To a solution of rac-1-[(tert-butoxy)carbonyl]-4-methoxypiperidine-3-carboxylic acid (1.2 g, 4.09 mmol) and TEA (1.23 g, 12.2 mmol) in tBuOH (40 mL), was added DPPA (1.49 g, 6.13 mmol). The mixture was stirred at 100° C. for 3 h. The solvent was removed by concentration and the residue was purified on silica gel column with 60% EtOAc in PE to afford the title compound (300 mg) as a colorless oil.

Analytical Data: LC-MS: (ES, m/z)=387 [M+23].

Step 5: Synthesis of rac-tert-butyl 4-methoxypiperidin-3-ylcarbamate

A mixture of rac-benzyl 3-{[(tert-butoxy)carbonyl]amino}-4-methoxypiperidine-1-carboxylate (300 mg, 823 μmol), Pd/C (87.5 mg, 82.3 μmol) in MeOH (20 mL) was stirred at rt for 2 h under $H_2$ atmosphere. The solid was filtered out and the filtrate was concentrated to dryness to afford the title compound (100 mg) as a colorless oil.

Analytical Data:LC-MS: (ES, m/z)=231 [M+1].

Step 6: Synthesis of rac-cis-tert-butyl-1-(4-aminopyrimidin-2-yl)-4-methoxypiperidin-3-ylcarbamate and rac-trans-tert-butyl-1-(4-aminopyrimidin-2-yl)-4-methoxypiperidin-3-ylcarbamate A mixture of rac-tert-butyl N-(4-methoxypiperidin-3-yl) carbamate (100 mg, 434 μmop, 2-chloropyrimidin-4-amine (56.2 mg, 434 μmol) and DIEA (168 mg, 1.30 mmol) in DMSO (8 mL) was stirred at 100° C. for 3 h. The resulting mixture was purified on prep-HPLC to afford peak 2: rac-cis-tert-butyl-1-(4-aminopyrimidin-2-yl)-4-methoxypiperidin-3-ylcarbamate (18 mg) as an off-white solid and peak 1: rac-trans-tert-butyl-1-(4-aminopyrimidin-2-yl)-4-methoxypiperidin-3-ylcarbamate (55 mg) as an off-white solid.

Analytical Data: LC-MS: (ES, m/z)=324 [M+1].

Example B54: Synthesis of (3R,4R)-1-(4-aminopyrimidin-2-yl)-5,5-difluoro-4-methoxypiperidin-3-ol and (3S,4S)-1-(4-aminopyrimidin-2-yl)-5,5-difluoro-4-methoxypiperidin-3-ol

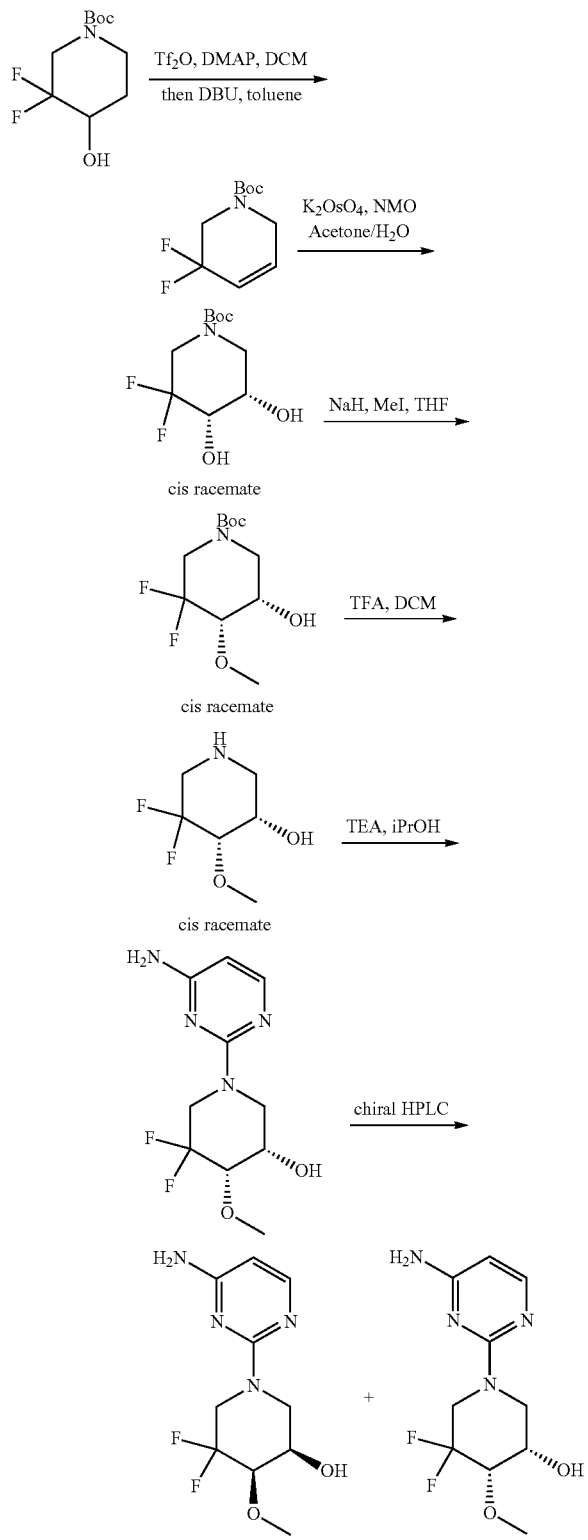

Step 1: Synthesis of tert-butyl 5,5-difluoro-5,6-dihydropyridine-1(2H)-carboxylate A solution of tert-butyl 3,3-difluoro-4-hydroxypiperidine-1-carboxylate (355 mg, 1.5 mmol, 1 equiv.) in DCM (6 mL) was added DMAP (274 mg, 2.25 mmol, 1.5 equiv.), followed by trifluoromethanesulfonyl trifluoromethanesulfonate (550 mg, 1.95 mmol, 1.3 equiv.) at 0° C. The reaction was carried on at 0° C. for 1 h before quenching with sat. NaHCO$_3$ (30 mL). The mixture was extracted with DCM (10 mL*3). The organic layer was combined and concentrated. The residue was dissolved in toluene (5 mL). DBU (569 mg, 3.75 mmol, 2.5 equiv) was added. The reaction was carried on at 70° C. for 18 h. After cooling down to r.t., the mixture was diluted with MTBE (50 mL). The mixture was washed with water (10 mL). The organic layer was combined and concentrated. The residue was purified by silica gel column chromatography (PE/EA=10:1) to afford the title compound (260 mg, 79.3%) as a light-yellow oil.

Analytical Data: 1H-NMR (400 MHz, CD$_3$Cl) δ ppm 6.23-6.17 (m, 1H), 5.98-5.92 (m, 1H), 4.06-4.00 (m, 2H), 3.91-3.65 (m, 2H), 1.51 (s, 9H).

Step 2: Synthesis of tert-butyl cis-3,3-difluoro-4,5-dihydroxypiperidine-1-carboxylate A mixture of tert-butyl 3,3-difluoro-1,2,3,6-tetrahydropyridine-1-carboxylate (153 mg, 700 μmol, 1 equiv.) in acetone (4 mL) and H$_2$O (1 mL) was added K$_2$OsO$_4$.2H$_2$O (12.8 mg, 35 μmol, 0.05 equiv.) and NMO (244 mg, 2.1 mmol, 3 equiv.) at rt. The reaction was carried on at 40° C. for 18 h. After cooling down to rt, the mixture was diluted with EA (50 mL), washed with 10% Na$_2$S$_2$O$_3$ solution (10 mL) and water (10 mL). The organic layer was concentrated, the residue was purified by silica gel column chromatography (DCM/EA=2:1) to afford the title compound (71 mg, 40.1%) as a white solid.

Analytical Data: 1H-NMR (400 MHz, 6d-DMSO) δ ppm 5.88 (d, 1H, J=5.1 Hz), 5.18 (d, 1H, J=5.9 Hz), 3.96-3.60 (m, 3H), 3.60-3.44 (m, 1H), 3.34-3.19 (m, 1H), 3.10-2.76 (m, 1H), 1.40 (s, 9H).

Step 3: Synthesis of tert-butyl cis-3,3-difluoro-5-hydroxy-4-methoxypiperidine-1-carboxylate A solution of tert-butyl cis-3,3-difluoro-4,5-dihydroxypiperidine-1-carboxylate (69.6 mg, 275 μmol, 1 equiv.) in THF (2 mL) was added NaH (10.9 mg, 275 μmol, 1 equiv., 60%) at 0° C. After 30 min, MeI (39.0 mg, 275 μmol, 1 equiv.) was added. The reaction was carried on at 0° C. for 1 h and at rt for 18 h. After quenching with sat. NH$_4$Cl (10 mL), the mixture was extracted with EA (5 mL*3). The organic layer was combined and concentrated. The residue was purified by silica gel column chromatography (DCM/EA=2:1) to afford the title compound (22 mg, 30%) as a colourless syrup.

Step 4: Synthesis of cis-5,5-difluoro-4-methoxypiperidin-3-ol

A solution of tert-butyl cis-3,3-difluoro-5-hydroxy-4-methoxypiperidine-1-carboxylate (240 mg, 900 μmol, 1 equiv.) in TFA (1 mL) and DCM (3 mL) was stirred at rt for 3 h and concentrated to afford the title compound (220 mg, crude) as colorless oil.

Analytical Data: LC-MS: (ES, m/z)=168 [M+1].

Step 5: Synthesis of cis-1-(4-aminopyrimidin-2-yl)-5,5-difluoro-4-methoxypiperidin-3-ol and (3S,4S)-1-(4-aminopyrimidin-2-yl)-5,5-difluoro-4-methoxypiperidin-3-ol 220 mg of cis-5,5-difluoro-4-methoxypiperidin-3-ol was dissolved in IPA (2 mL). 2-chloropyrimidin-4-amine (116 mg, 900 µmol, 1 equiv.) was added, followed by TEA (454 mg, 4.50 mmol, 5 equiv.). The reaction was carried on at 100° C. for 18 h. After cooling down to rt, the mixture was concentrated. The residue was purified by prep-TLC (DCM/MeOH=20:1) to afford (3S,4S)-1-(4-aminopyrimidin-2-yl)-5,5-difluoro-4-methoxypiperidin-3-ol (50 mg, 21.36%) as a white solid. The compound was separated by prep-chiral-HPLC with following conditions: CHIRAL Cellulose-SB4.6*100 mm 3 um; mobile phase: Hex(0.1% DEA): IPA=70:30; Flow: 1.0 mL/min; to afford peak 1: (3R,4R)-1-(4-aminopyrimidin-2-yl)-5,5-difluoro-4-methoxypiperidin-3-ol or (3S,4S)-1-(4-aminopyrimidin-2-yl)-5,5-difluoro-4-methoxypiperidin-3-ol (20 mg) as pale-yellow solid and peak 2: (3R,4R)-1-(4-aminopyrimidin-2-yl)-5,5-difluoro-4-methoxypiperidin-3-ol or (3S,4S)-1-(4-aminopyrimidin-2-yl)-5,5-difluoro-4-methoxypiperidin-3-ol (20 mg) as pale-yellow solid.

Analytical Data: LC-MS: (ES, m/z)=261 [M+1]; 1H-NMR (300 MHz, 3d-CD$_3$Cl) δ ppm 7.95 (d, 1H, J=5.6 Hz), 5.82 (d, 1H, J=5.6 Hz), 4.87-4.70 (m, 1H), 4.67-4.48 (m, 3H), 3.91 (s, 1H), 3.67 (d, 3H, J=1.0 Hz), 3.67-3.60 (m, 1H), 3.51 (ddd, 1H, J=29.0, 14.0, 1.8 Hz), 3.12 (dd, 1H, J=12.9, 10.1 Hz), 2.41 (s, 1H).

Example B55: Synthesis of rac-cis-1-(4-aminopyrimidin-2-yl)-4-methylpiperidine-3,4-diol

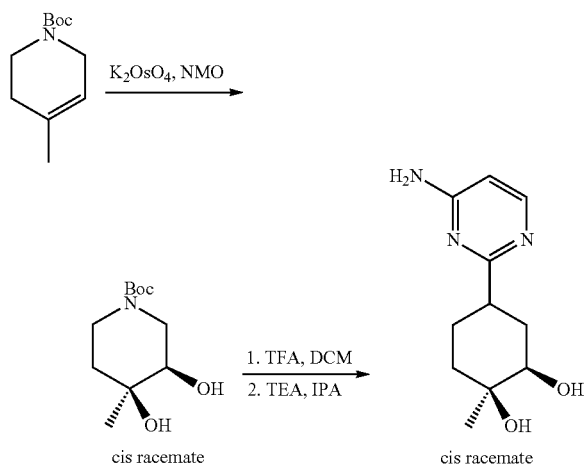

Step 1: Synthesis of rac-cis-tert-butyl 3,4-dihydroxy-4-methylpiperidine-1-carboxylate To a solution of tert-butyl 4-methyl-1,2,3,6-tetrahydropyridine-1-carboxylate (300 mg, 1.52 mmol) in THF (3 mL) and H$_2$O (1 mL), K$_2$OsO$_4$.2H$_2$O (50.4 mg, 152 umol) and NMO (533 mg, 4.56 mmol) were added at rt and stirred for 12 h. The reaction mixture was diluted with sat. Na$_2$S$_2$SO$_3$.aq, and extracted with EA and brine. The organic layer was dried over Na$_2$SO$_4$, filtered and evaporated to afford the title compound (350 mg, crude) as a yellow solid.

Analytical Data: LC-MS: (ES, m/z)=254 [M+23].

Step 2: Synthesis of rac-cis-1-(4-aminopyrimidin-2-yl)-4-methylpiperidine-3,4-diol To a solution of rac-tert-butyl cis-3,4-dihydroxy-4-methylpiperidine-1-carboxylate (350 mg, crude) in DCM (6 mL), TFA (2 mL) was added and stirred at rt for 2 h. The reaction mixture was evaporated and the residue dissolved in IPA (3 mL), 2-chloropyrimidin-4-amine (160 mg, 1.23 mmol) and TEA (621 mg, 6.15 mmol) was added and the mixture was heated to 100° C. and stirred for 12 h. The reaction mixture was diluted with water, extracted with EA and washed with brine. The organic layer was dried over Na$_2$SO$_4$, filtered and evaporated. The residue was purified by column chromatography (DCM:MeOH=20:1) to afford the title compound (200 mg, 72.7%) as a yellow solid.

Analytical Data: LC-MS: (ES, m/z)=225 [M+1].

Example B56: Synthesis of rac-trans-1-(4-aminopyrimidin-2-yl)-4-methylpiperidine-3,4-diol

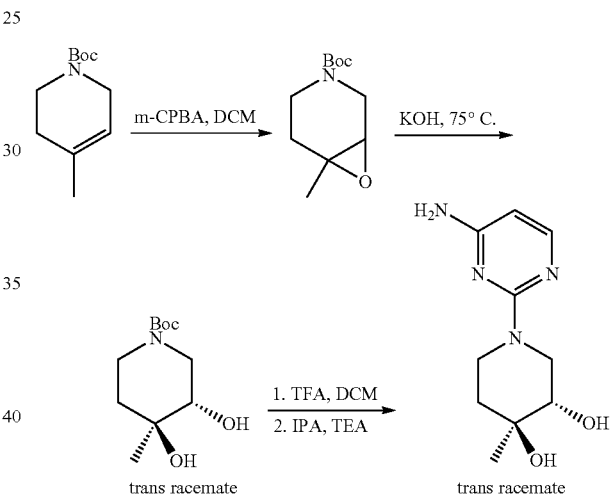

Step 1: Synthesis of tert-butyl 6-methyl-7-oxa-3-aza-bicyclo[4.1.0]heptane-3-carboxylate To a solution of tert-butyl 4-methyl-1,2,3,6-tetrahydropyridine-1-carboxylate (500 mg, 2.53 mmol) in DCM (20 mL) was added m-CPBA (870 mg, 5.06 mmol) and the mixture was stirred at rt for 2 h. The mixture was extracted with EA and water. The organic layer was concentrated and purified by FLASH (30% EA in PE) to afford the title compound of 460 mg as colorless oil.

Analytical Data: LC-MS: (ES, m/z)=214 [M+1].

Step 2: Synthesis of rac-tert-butyl trans-3,4-dihydroxy-4-methylpiperidine-1-carboxylate To a solution of rac-tert-butyl 6-methyl-7-oxa-3-azabicyclo[4.1.0]heptane-3-carboxylate (100 mg, 468 µmol) in H$_2$O (5 mL) were added KOH (448 mg, 8.00 mmol) and the solution was stirred at 75° C. for 15 h. The mixture was extracted with EA, dried and concentrated to afford the title compound 180 mg as yellow oil.

Analytical Data: LC-MS: (ES, m/z)=232 [M+1].

Step 2: Synthesis of rac-trans-1-(4-aminopyrimidin-2-yl)-4-methylpiperidine-3,4-diol To a solution of rac-tert-butyl trans-3,4-dihydroxy-4-methylpiperidine-1-carboxylate (300 mg, 1.29 mmol) in DCM (10 mL) were added TFA (3 mL) and the mixture was stirred for 1.5 h at rt. The solvent was removed under reduced pressure. The residue was dissolved in IPA (2 mL), 2-chloropyrimidin-4-amine (88.8 mg, 686 μmol) and DIEA (441 mg, 3.42 mmol) were added and the solution was heated to 120° C. for 10 h. The mixture was extracted with EA and water. The organic concentrated and was purified by FLASH (50% MeOH in DCM) to afford the title compound of 80 mg as pale-yellow solid.

Analytical Data: LC-MS: (ES, m/z)=225 [M+1].

Example B57: Synthesis of rac-tert-butyl 1-(4-aminopyrimidin-2-yl)-3,3-difluoropiperidin-4-ylcarbamate

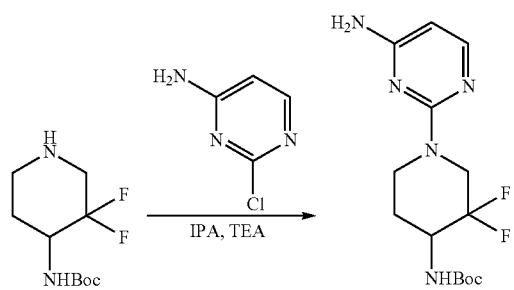 [SMILES: CC(C)(C)OC(=O)NC1CCNCC1(F)F ; Nc1ccnc(Cl)n1 ; CC(C)(C)OC(=O)NC1CCN(c2nccc(N)n2)CC1(F)F]

The mixture of rac-tert-butyl N-(3,3-difluoropiperidin-4-yl)carbamate (200 mg, 0.85 mmol, 1 equiv.), 2-chloropyrimidin-4-amine (109.67 mg, 0.847 mmol, 1 equiv.) and TEA (256.98 mg, 2.540 mmol, 3 equiv.) in IPA (3 mL) was stirred for 3 h at 100° C. The mixture was concentrated and the residue was applied onto a silica gel column with DCM/MeOH (20:1). This resulted in 100 mg (35.9%) of the title compound as a light-yellow solid.

Analytical Data: LC-MS: (ES, m/z)=330 [M+1].

Example B58: Synthesis of rac-cis-1-(5-amino-1,2,4-triazin-3-yl)-3-fluoro-4-methylpiperidin-4-ol

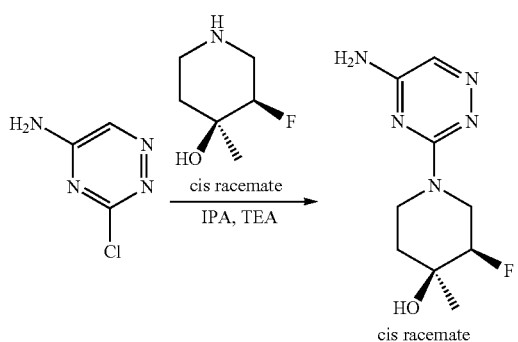

The mixture of 3-chloro-1,2,4-triazin-5-amine (200 mg, 1.53 mmol), cis-3-fluoro-4-methylpiperidin-4-ol (243 mg, 1.83 mmol) and TEA (309 mg, 3.06 mmol) in IPA (5 mL) was stirred at 100° C. for 2 h. Water was added and the reaction was extracted with EA. The organic layer was purified by Prep-TLC (DCM:MeOH=10:1). This result in 300 mg (34.4%) the title compound as grey solid.

Analytical Data: LC-MS: (ES, m/z)=228 [M+1].

Example B59: Synthesis of 2-((3S,4R)-3-fluoro-4-methoxy-3-methylpiperidin-1-yl)pyrimidin-4-amine and 2-((3R,4S)-3-fluoro-4-methoxy-3-methylpiperidin-1-yl)pyrimidin-4-amine and 2-((3R,4R)-3-fluoro-4-methoxy-3-methylpiperidin-1-yl)pyrimidin-4-amine and 2-((3S,4S)-3-fluoro-4-methoxy-3-methylpiperidin-1-yl)pyrimidin-4-amine

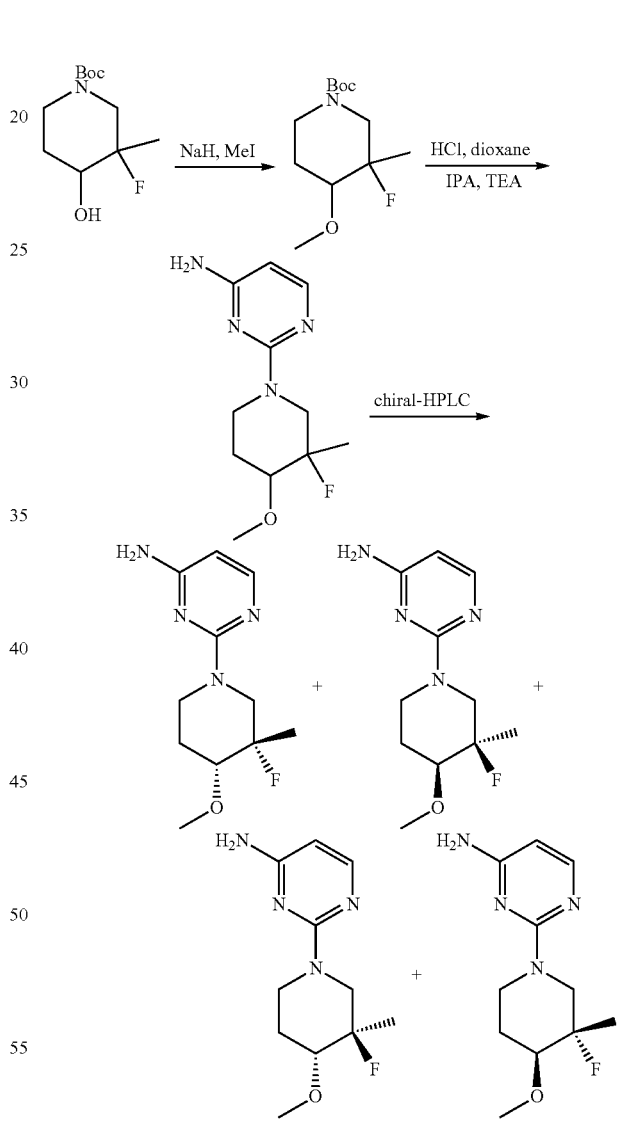

Step 1: Synthesis of rac-tert-butyl 3-fluoro-4-methoxy-3-methylpiperidine-1-carboxylate Rac-tert-butyl 3-fluoro-4-hydroxy-3-methylpiperidine-1-carboxylate (Step 3, Example B1; 4 g, 17 mmol) was dissolved in DMF (40 mL), sodium hydride (820 mg, 34.2 mmol) was added at 0° C. The mixture was stirred at rt for 1 h. Iodomethane (4.82 g, 34.2 mmol) was added and the reaction was stirred at rt for another 2 h. The reaction was quenched with water/ice, extracted with EA, washed with brine, dried over anhydrous sodium sulfate and concentrated under vacuum to afford 5.1 g of tert-butyl 3-fluoro-4-methoxy-3-methylpiperidine-1-carboxylate as colorless oil.

Step 2: Synthesis of rac-2-(3-fluoro-4-methoxy-3-methylpiperidin-1-yl)pyrimidin-4-amine Rac-tert-butyl 3-fluoro-4-methoxy-3-methylpiperidine-1-carboxylate (5.1 g) was dissolved in HCl/dioxane (4M, 50 mL). The reaction was stirred at rt for 2 h. The mixture was concentrated under vacuum. The residue was mixed with 2-chloropyrimidin-4-(4.21 g, 32.5 mmol) and TEA (5.47 g, 54.2 mmol) in IPA (30 mL). The mixture was stirred at 100° C. and stirred for 16 h. The reaction was concentrated under vacuum and the residue was purified by FLASH (DCM:MeOH=10:1). This resulted in 1.6 g of the title compound as a white solid, which was further separated to four isomers using following conditions:

Analytical Data: LC-MS: (ES, m/z)=241 [M+1].

Column name: CHIRAL ND(2) 4.6*100 mm, 3 um; Co-Solvent: MeOH (0.1% DEA); Gradient (B %): 10% to 50% in 4.0 min, hold 2.0 min at 50%; Flow (mL/min) to afford 2-((3S,4R)-3-fluoro-4-methoxy-3-methylpiperidin-1-yl)pyrimidin-4-amine or 2-((3R,4S)-3-fluoro-4-methoxy-3-methylpiperidin-1-yl)pyrimidin-4-amine (490 mg) and 2-((3R,4S)-3-fluoro-4-methoxy-3-methylpiperidin-1-yl)pyrimidin-4-amine or 2-((3 S,4R)-3-fluoro-4-methoxy-3-methylpiperidin-1-yl)pyrimidin-4-amine (440 mg). Both are pale-yellow solids.

Column name: CHIRAL ND(2) 4.6*100 mm, 3 um; Co-Solvent: MeOH (0.1% DEA); Gradient (B %): 10% to 50% in 4.0 min, hold 2.0 min at 50%; Flow (mL/min) to afford 2-((3R,4R)-3-fluoro-4-methoxy-3-methylpiperidin-1-yl)pyrimidin-4-amine or 2-((3S,4S)-3-fluoro-4-methoxy-3-methylpiperidin-1-yl)pyrimidin-4-amine (81 mg) and 2-((3S,4S)-3-fluoro-4-methoxy-3-methylpiperidin-1-yl)pyrimidin-4-amine or 2-((3R,4R)-3-fluoro-4-methoxy-3-methylpiperidin-1-yl)pyrimidin-4-amine (123 mg). Both are pale-yellow solids.

Example B60: Synthesis of rac-tert-butyl 2-(azetidin-3-yl)-2-(methylsulfonyl)ethylcarbamate

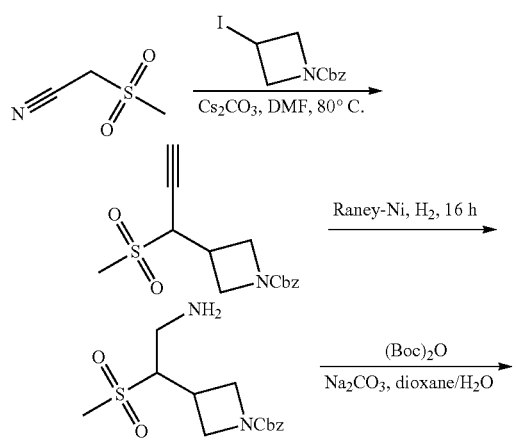

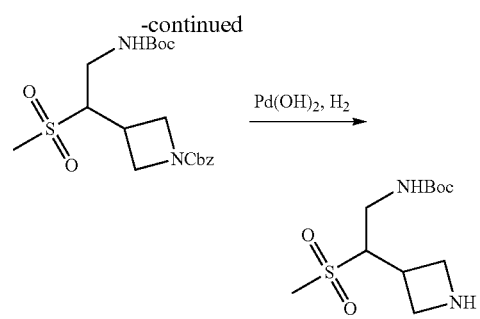

Step 1: Synthesis of rac-benzyl 3-(1-(methylsulfonyl)prop-2-ynyl)azetidine-1-carboxylate Cs₂CO₃ (544 mg, 1.67 mmol) was added to 2-methanesulfonylacetonitrile (1 g, 8.39 mmol) and benzyl 3-iodoazetidine-1-carboxylate (3.96 g, 12.5 mmol) in DMF (5 mL) at rt. The resulting mixture was stirred for 8 h at 80° C. The mixture was diluted with EA and washed with brine. The organic layer was dried with Na₂SO₄ and concentrated under vacuum. The residue was purified by a silica gel column with PE:EA=5:1 to afford 1.2 g the title compound as a colorless oil.

Analytical Data:LC-MS: (ES, m/z)=308 [M+1].

Step 2: Synthesis of rac-Benzyl 3-(2-amino-1-(methylsulfonyl)ethyl)azetidine-1-carboxylate Rac-Benzyl 3-[cyano(methanesulfonyl)methyl]azetidine-1-carboxylate (1.2 g, 3.89 mmol) and Raney-Ni (10 mg) in EtOH (4 mL) were stirred for 8 h under H2 atmosphere at rt. The solid was filtered out, filtrate was concentrated under reduced pressure to give 600 mg the title compound as colorless oil.

Analytical Data: LC-MS: (ES, m/z)=313 [M+1].

Step 3: Synthesis of rac-benzyl 3-(2-(tert-butoxycarbonylamino)-1-(methylsulfonyl)ethyl)azetidine-1-carboxylate (Boc)₂O (829 mg, 3.84 mmol) was added to Na₂CO₃ (407 mg, 3.84 mmol) rac-benzyl 3-(2-amino-1-methanesulfonylethyl)azetidine-1-carboxylate (600 mg, 1.92 mmol) in dioxane/H₂O (10 mL/3 mL) at 0° C. The resulting mixture was stirred at rt for 16 h. The mixture was diluted with EA and washed with brine. the organic layer was dried with Na₂SO₄ and concentrated under vacuum. The residue was purified by a silica gel column with PE:EA=5:1 to afford 650 mg the title compound as a colorless oil.

Analytical Data: LC-MS: (ES, m/z)=413 [M+1].

Step 4: Synthesis of rac-tert-butyl 2-(azetidin-3-yl)-2-(methylsulfonyl)ethylcarbamate The mixture of rac-benzyl-3-(2-amino-1-methanesulfonylethyl)azetidine-1-carboxylate (600 mg, 1.92 mmol) and Pd(OH)₂/C (300 mg, 2.14 mmol) in MeOH (50 mL) was stirred overnight under an atmosphere of hydrogen at rt. The solid was filtered out, filtrate was concentrated under reduced pressure to give the title compound (300 mg) as colorless oil.

Analytical Data: LC-MS: (ES, m/z)=279 [M+1].

103

Example B61: Synthesis of rac-cis-2-(hexahydro-furo[3,4-b]pyrrol-1-yl)pyrimidin-4-amine

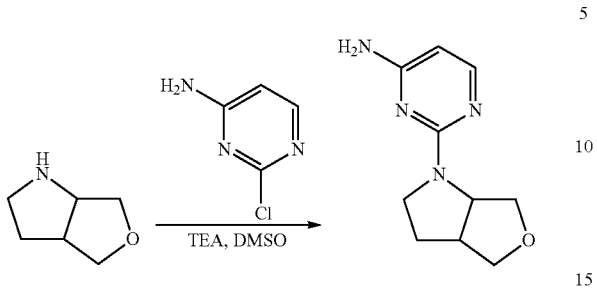

The mixture of 2-chloropyrimidin-4-amine (370 mg, 2.85 mmol), rac-cis-hexahydro-1H-furo[3,4-b]pyrrole (322 mg, 2.85 mmol) and DIPEA (1.10 g, 8.55 mmol) in DMSO (8 mL) was stirred for 12 h at 120° C. The reaction mixture was diluted with water, extracted with EA and washed with brine. The organic layer was dried over $Na_2SO_4$, filtered, evaporated and purified by column chromatography (DCM:MeOH=20:1) to afford the title compound (410 mg, 69.8%) as a yellow solid.

Analytical Data: LC-MS: (ES, m/z)=207 [M+1].

Example B62: Synthesis of tert-butyl (1-(4-amino-pyrimidin-2-yl)-4-methoxypiperidin-4-yl)methylcarbamate

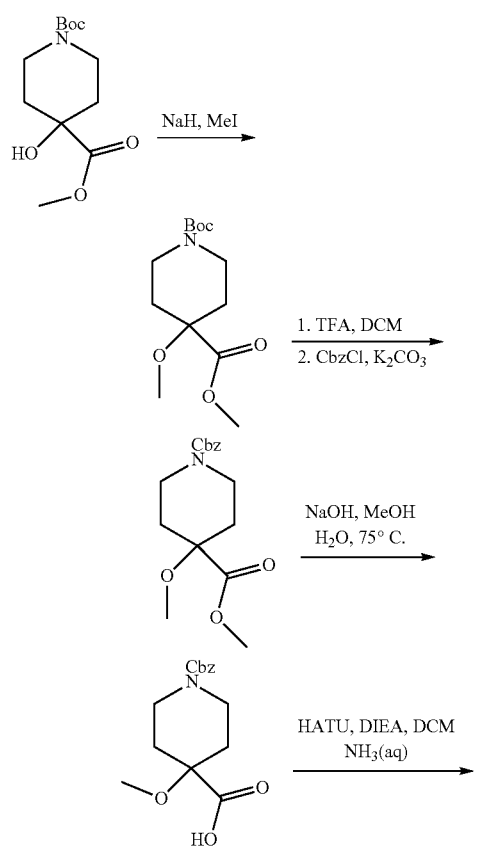

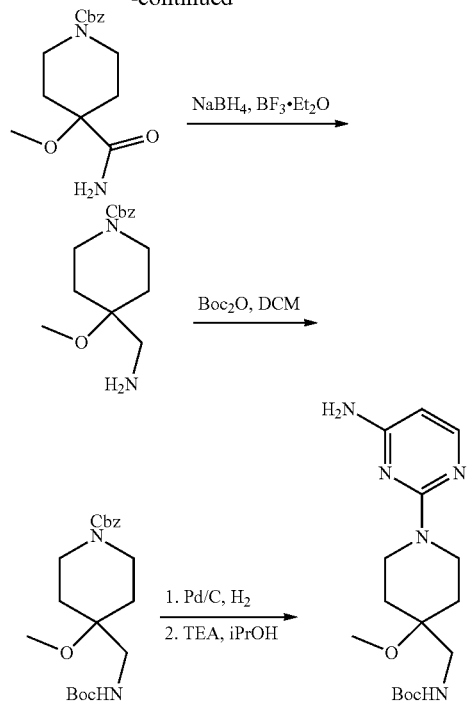

Step 1: Synthesis of 1-tert-butyl 4-methyl 4-methoxypiperidine-1,4-dicarboxylate To a solution of 1-tert-butyl 4-methyl 4-hydroxypiperidine-1,4-dicarboxylate (1.5 g, 5.78 mmol) in THF (40 mL) was added NaH (346 mg, 8.67 mmol) at 0° C. After 10 min, MeI (1.23 g, 8.67 mmol) was added and stirred for 2 h. The mixture was quenched with ice-water and extracted with EA. The organic layer was dried over $Na_2SO_4$ and concentrated to dryness. The residue was purified on silica gel column with 10% EA in PE to afford 1-tert-butyl 4-methyl 4-methoxypiperidine-1,4-dicarboxylate (1.3 g) as a light-yellow oil.

Analytical Data: LC-MS: (ES, m/z)=296 [M+23].

Step 2: Synthesis of 1-benzyl 4-methyl 4-methoxypiperidine-1,4-dicarboxylate To a solution of 1-tert-butyl 4-methyl 4-methoxypiperidine-1,4-dicarboxylate (1.3 g, 4.75 mmol) in DCM (20 mL) was added TFA (8 mL). The mixture was stirred for 1 h at rt. The reaction was concentrated. The reside was dissolved in dioxane (20 mL) and water (10 mL), $K_2CO_3$ (1.94 g, 14.1 mmol) and CbzCl (1.60 g, 9.42 mmol) was added at rt and stirred for 2 h. The reaction was extracted with EA, dried over $Na_2SO_4$ and concentrated to dryness to afford the title compound (1.2 g) as a colorless oil.

Analytical Data: LC-MS: (ES, m/z)=309 [M+1].

Step 3: Synthesis of 1-(benzyloxycarbonyl)-4-methoxypiperidine-4-carboxylic Acid To a mixture of 1-benzyl 4-methyl 4-methoxypiperidine-1,4-dicarboxylate (1.1 g, 3.57 mmol) in MeOH (20 mL) and water (5 mL) was added NaOH (285 mg, 7.14 mmol). The mixture was stirred at 70° C. for 2 h. After cooling to rt, the pH was adjusted to 5 with 1N HCl and extracted with EA.

The organic layer was dried over Na$_2$SO$_4$, filtered and concentrated to dryness to afford the title compound (1 g) as a colorless oil.

Analytical Data: LC-MS: (ES, m/z)=294 [M+1].

Step 4: Synthesis of Benzyl 4-carbamoyl-4-methoxypiperidine-1-carboxylate

The mixture of 1-[(benzyloxy)carbonyl]-4-methoxypiperidine-4-carboxylic acid (950 mg, 3.23 mmol), DIEA (834 mg, 6.46 mmol), ammonia (1.82 g, 37.4 mmol) and HATU (1.84 g, 4.84 mmol) in DCM (20 mL) was stirred for 2 h at rt. The organic layer was separated and washed with water, dried over Na$_2$SO$_4$, filtered and concentrated to dryness. The residue was purified on silica gel column with 60% EtOAc in PE to afford the title compound (900 mg) as colorless oil.

Analytical Data: LC-MS: (ES, m/z)=293 [M+1].

Step 5: Synthesis of Benzyl 4-(aminomethyl)-4-methoxypiperidine-1-carboxylate To a solution of benzyl 4-carbamoyl-4-methoxypiperidine-1-carboxylate (600 mg, 2.05 mmol) in THF (20 mL) was added NaBH$_4$ (310 mg, 8.20 mmol), followed by BF$_3$·Et$_2$O (1.16 g, 8.20 mmol) at rt. The mixture was stirred for 2 h at rt. Water was added and the mixture was extracted with EA. The organic layer was dried over Na$_2$SO$_4$, filtered and concentrated to dryness to afford the title compound (1.4 g, crude) as colorless oil.

Analytical Data: LC-MS: (ES, m/z)=279 [M+1].

Step 6: Synthesis of benzyl 4-((tert-butoxycarbonylamino)methyl)-4-methoxypiperidine-1-carboxylate The solution of benzyl 4-(aminomethyl)-4-methoxypiperidine-1-carboxylate (1.4 g, crude) and Boc$_2$O (1.21 g, 5.58 mmol) in DCM (20 mL) was stirred at rt for 1 h. Water was added and the organic layer was separated and purified on silica gel column with 60% EA in PE to afford the title compound (250 mg) as a colorless oil.

Analytical Data: LC-MS: (ES, m/z)=401 [M+23].

Step 7: Synthesis of Tert-butyl (4-methoxypiperidin-4-yl)methylcarbamate

A mixture of benzyl 4-({[(tert-butoxy)carbonyl]amino}methyl)-4-methoxypiperidine-1-carboxylate (240 mg, 634 µmol) and Pd/C (100 mg, 95.1 µmol) in MeOH (20 mL) was stirred at rt for 1 h under a H$_2$ atm. The solid was filtered out. The filtrate was concentrated to dryness to afford the title compound (130 mg) as a colorless oil.

Analytical Data: LC-MS: (ES, m/z)=245 [M+1].

Step 8: Synthesis of tert-butyl (1-(4-aminopyrimidin-2-yl)-4-methoxypiperidin-4-yl)methylcarbamate A mixture of 1-(4-methoxypiperidin-4-yl)methanamine (120 mg, 832 µmop, 2-chloropyrimidin-4-amine (107 mg, 832 µmol) and TEA (167 mg, 1.66 mmol) in iPrOH (20 mL) was stirred at 80° C. for 2 h. The mixture was concentrated and the residue was purified on prep-TLC (EtOAc:PE=1:1) to afford the title compound (95 mg) as an off-white solid.

Analytical Data: LC-MS: (ES, m/z)=338 [M+1].

Example B63: Synthesis of 2-((3S,4R)-1-(4-aminopyrimidin-2-yl)-3-fluoro-3-methylpiperidin-4-yloxy)ethanol HCl (6M, 5 mL) was added to 2-[(3S,4R)-4-{2-[(tert-butyldimethylsilyl)oxy]ethoxy}-3-fluoro-3-methylpiperidin-1-yl]-4-(2,2,12,12-tetramethyl-5,9-dioxa-7-aza-2,12-disilatridecan-7-yl)pyrimidine (600 mg, 930 µmol, from Step 2 of Example B70) in EtOH (5 mL). The mixture was stirred at 80° C. for 1 h. The mixture was concentrated under vacuum to afford 200 mg the title compound as a colorless oil.

Analytical Data: LC-MS: (ES, m/z)=271 [M+1].

Example B64: Synthesis of tert-butyl 2-(1-(4-aminopyrimidin-2-yl)-4-methoxypiperidin-4-yl)ethylcarbamate

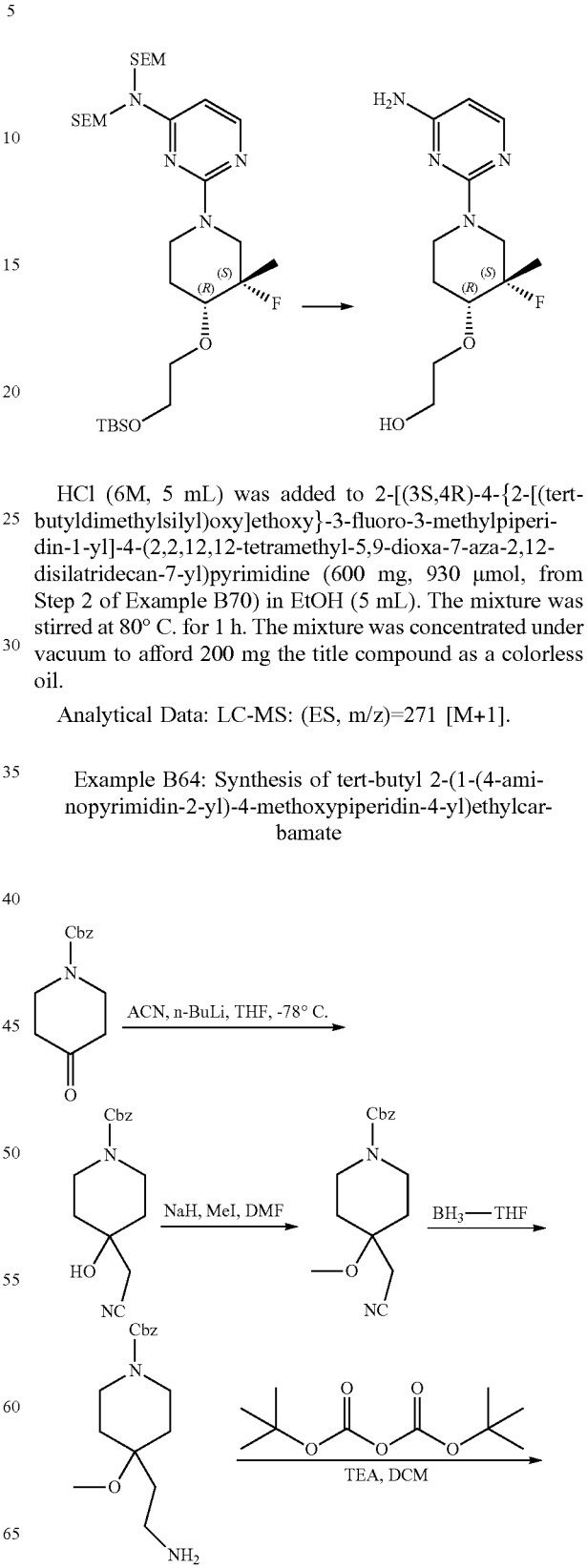

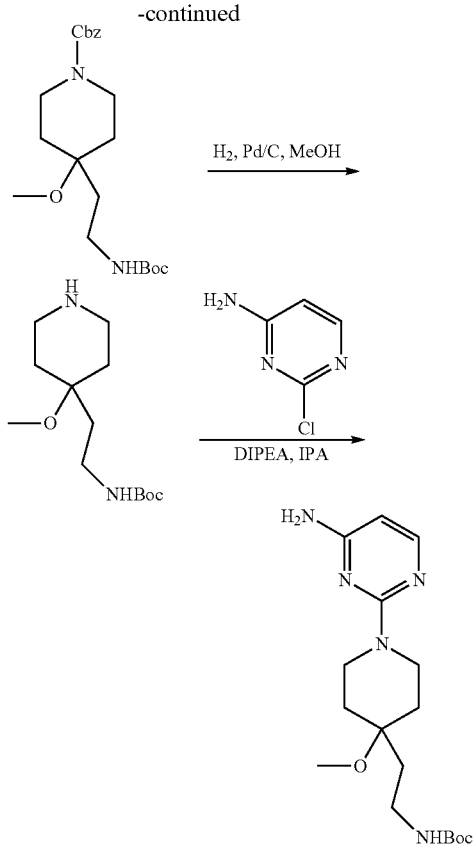

Step 1: Synthesis of benzyl 4-(cyanomethyl)-4-hydroxypiperidine-1-carboxylate To a solution of ACN (1.73 g, 42.1 mmol) in THF (80 mL) was added n-Buli (23.5 mL, 58.9 mmol, 2.5 M) at −78° C. The mixture was stirred at −78° C. for 30 min. Then a solution of benzyl 4-oxopiperidine-1-carboxylate (10.3 g, 44.2 mmol) in THF (20 mL) was added. The mixture was stirred at rt for 2 h. The mixture was quenched with H$_2$O (30 mL) and extracted with EA and washed with brine. The organic layer was dried with Na$_2$SO$_4$ and concentrated under vacuum. The residue was purified by Flash Column Silica-CS (PE:EA=10:1 to 3:2). This resulted in 1 g (90.9%) of the title compound as a light-yellow solid.

Analytical Data: LC-MS: (ES, m/z)=275 [M+1].

Step 2: synthesis of benzyl 4-(cyanomethyl)-4-methoxypiperidine-1-carboxylate To a solution of benzyl 4-(cyanomethyl)-4-hydroxypiperidine-1-carboxylate (250 mg, 911 μmol) and iodomethane (283 mg, 2 mmol) in DMF (30 mL) was added NaH (216 mg, 5.45 mmol) at 0° C. Then the mixture was stirred at rt for 13 h. The mixture was quenched with H$_2$O (4 mL) and extracted with EA and washed with brine. The organic layer was dried with Na$_2$SO$_4$ and concentrated under vacuum. The residue was purified by Flash Column Silica-CS (PE:EA=1:1). This resulted in 940 mg of benzyl 4-(cyanomethyl)-4-methoxypiperidine-1-carboxylate as a light-yellow gum.

Analytical Data: LC-MS: (ES, m/z)=311 [M+23].

Step 3: Synthesis of Benzyl 4-(2-aminoethyl)-4-methoxypiperidine-1-carboxylate To a solution of benzyl 4-(cyanomethyl)-4-methoxypiperidine-1-carboxylate (840 mg, 2.91 mmol) in THF (30 mL) was added BH$_3$-THF (8.73 mL, 8.73 mmol, 1M) at 0° C. Then the mixture was stirred at rt for 5 h. The reaction was quenched with MeOH (8 mL) and concentrated to give the crude the title compound (900 mg).

Analytical Data: LC-MS: (ES, m/z)=293 [M+1].

Step 4: Synthesis of benzyl 4-(2-(tert-butoxycarbonylamino)ethyl)-4-methoxypiperidine-1-carboxylate To a solution of benzyl 4-(2-aminoethyl)-4-methoxypiperidine-1-carboxylate (850 mg, 2.90 mmol) in DCM (30 mL) was added TEA (586 mg, 5.80 mmol) and di-tert-butyl dicarbonate (949 mg, 4.35 mmol). Then the mixture was stirred at rt for 10 h. The mixture was extracted with EA and washed with brine. The organic layer was dried and concentrated under vacuum. The residue was purified by Flash Column Silica-CS (PE:EA=10:1 to 3:2). This resulted in 900 mg (79.6%) of the title compound as a light-yellow gum.

Analytical Data: LC-MS: (ES, m/z)=415 [M+23].

Step 5: Synthesis of tert-butyl 2-(4-methoxypiperidin-4-yl)ethylcarbamate

To a solution of benzyl 4-(2-{[(tert-butoxy)carbonyl]amino}ethyl)-4-methoxypiperidine-1-carboxylate (420 mg, 1.07 mmol) in MeOH (25 mL) was added Pd/C (200 mg). Then the mixture was hydrogenated under hydrogen balloon at rt for 2 h. The reaction mixture was filtered through celite bed, washed with MeOH (100 mL) and the filtrate was concentrated to afford a crude product (250 mg) the title compound, which was used directly for the next step.

Analytical Data: LC-MS: (ES, m/z)=259 [M+1].

Step 6: synthesis of tert-butyl 2-(1-(4-aminopyrimidin-2-yl)-4-methoxypiperidin-4-yl)ethylcarbamate To a solution of tert-butyl N4-[2-(4-methoxypiperidin-4-yl)ethyl]carbamate (260 mg, 1 mmol) in IPA (16 mL), was added 2-chloropyrimidin-4-amine (116 mg, 900 μmol) and DIPEA (323 mg, 2.50 mmol). The mixture was stirred at 120° C. for 13 h. The mixture was extracted with EA and washed with brine. The organic layer was dried and concentrated under vacuum. The residue was purified by prep.TLC (DCM:MeOH=10:1). This resulted in 280 mg (79.7%) of the title compound as a light-yellow solid.

Analytical Data: LC-MS: (ES, m/z)=352 [M+1].

Example B65: Synthesis of 1-((3R,4S)-1-(4-aminopyrimidin-2-yl)-3-fluoropiperidin-4-yloxy)-2-methylpropan-2-ol

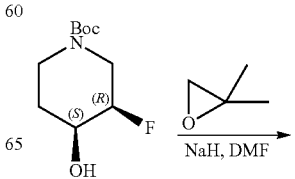

Example B66: Synthesis of 1-((3S,4R)-1-(4-aminopyrimidin-2-yl)-3-fluoropiperidin-4-yloxy)-2-methylpropan-2-ol

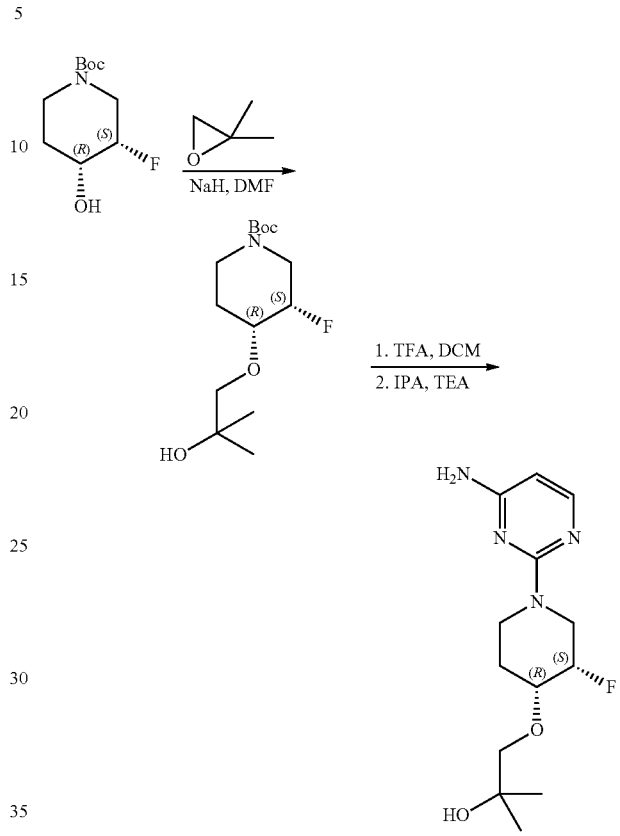

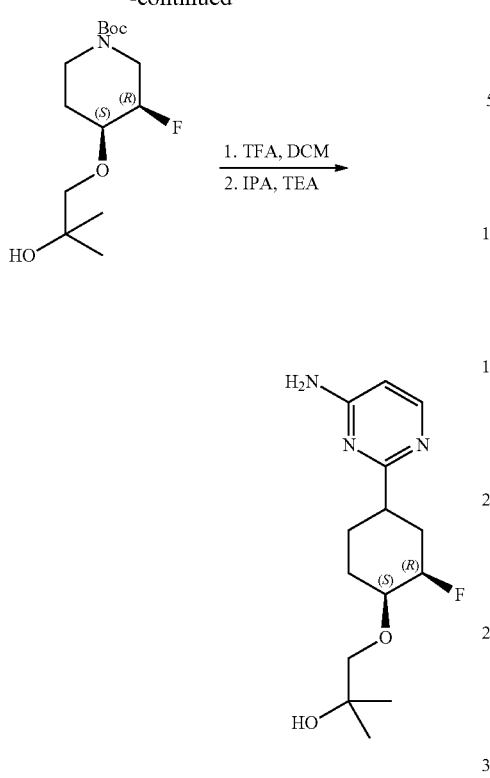

Step 1: Synthesis of (3R,4S)-tert-butyl 3-fluoro-4-(2-hydroxy-2-methylpropoxy)piperidine-1-carboxylate NaH (175.12 mg, 7.297 mmol, 8 equiv.) was added to the mixture of tert-butyl (3R,4S)-3-fluoro-4-hydroxypiperidine-1-carboxylate (200 mg, 0.912 mmol, 1 equiv.) and 2,2-dimethyloxirane (526.19 mg, 7.297 mmol, 8 equiv.) in DMF (5 mL) at 0° C. The resulting solution was stirred overnight at rt. The reaction was quenched by the addition of 10 mL of water. The resulting solution was extracted with EA, washed with brine and concentrate to afford 100 mg (37.63%) of the title compound as light-yellow oil.

Analytical Data: LC-MS: (ES, m/z)=292 [M+1].

Step 2: Synthesis of 1-((3R,4S)-1-(4-aminopyrimidin-2-yl)-3-fluoropiperidin-4-yloxy)-2-methylpropan-2-ol Tert-butyl (3R,4S)-3-fluoro-4-(2-hydroxy-2-methylpropoxy)piperidine-1-carboxylate (100.00 mg, 0.343 mmol) was added to the solution of TFA (1 mL) in DCM (3 mL). The resulting solution was stirred for 2 hr at rt. The resulting mixture was concentrated under vacuum and the residue was mixed with 2-chloropyrimidin-4-amine (50 mg, 0.386 mmol, 1 equiv.) and TEA (117.16 mg, 1.158 mmol, 3 equiv.) in IPA (2 mL). The resulting solution was stirred for 12 h at 100° C. The mixture was concentrated under vacuum and the residue was applied onto a silica gel column with DCM/MeOH (15:1). This resulted in 20 mg (18.22%) of the title compound as light-yellow oil.

Analytical Data: LC-MS: (ES, m/z)=285 [M+1].

Step 1: Synthesis of (3S,4R)-tert-butyl 3-fluoro-4-(2-hydroxy-2-methylpropoxy)piperidine-1-carboxylate NaH (262.68 mg, 10.946 mmol, 6 equiv.) was added to the solution of tert-butyl (3S,4R)-3-fluoro-4-hydroxypiperidine-1-carboxylate (400.00 mg, 1.824 mmol, 1 equiv.) and 2,2-dimethyloxirane (1315.49 mg, 18.244 mmol, 10 equiv.) in DMF (20.00 mL). The resulting solution was stirred for overnight at rt. The reaction was then quenched by the addition of 3 mL of water. The resulting solution was extracted with EA and concentrated under vacuum. This resulted in 200 mg (37.63%) of the title compound as yellow oil.

Analytical Data: LC-MS: (ES, m/z)=292 [M+1].

Step 2: Synthesis of 1-((3S,4R)-1-(4-aminopyrimidin-2-yl)-3-fluoropiperidin-4-yloxy)-2-methylpropan-2-ol Tert-butyl (3 S,4R)-3-fluoro-4-(2-hydroxy-2-methylpropoxy)piperidine-1-carboxylate (200.00 mg, 0.686 mmol, 1 equiv.) was added to DCM/TFA (8.00 mL/4.00 mL). The resulting solution was stirred for 2 h at rt. The resulting mixture was concentrated under vacuum. The residue was mixed with 2-chloropyrimidin-4-amine (67.74 mg, 0.523 mmol, 1 equiv.) and TEA (158.73 mg, 1.569 mmol, 3.0 equiv.) in IPA (3 mL) at 100° C. and stirred for 3 h. The solvent was removed and the residue was applied onto a silica gel column with DCM/MeOH (15:1). This resulted in 55 mg (37%) of the title compound as light-yellow oil.
Analytical Data: LC-MS: (ES, m/z)=285 [M+1].

Example B67: Synthesis of 2-((3R,4S)-3-fluoro-4-(methoxy-d3)piperidin-1-yl)pyrimidin-4-amine

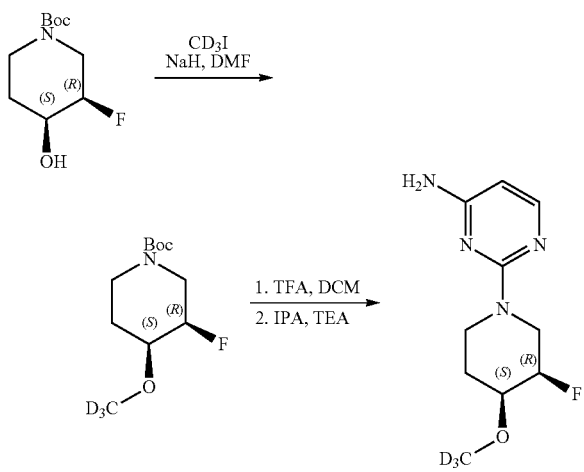

Step 1: Synthesis of tert-butyl (3R,4S)-3-fluoro-4-(methoxy-d3)piperidine-1-carboxylate NaH (218 mg, 9.08 mmol) was added to tert-butyl (3R,4S)-3-fluoro-4-hydroxypiperidine-1-carboxylate (1000 mg, 4.56 mmol) in DMF (20 mL, 22.6 mmol) at 0° C. After stirring for 20 minutes, CD$_3$I (3.30 g, 22.8 mmol) was added and the solution was stirred at rt for 16 h. The reaction was quenched by the addition of 5 mL of water. The solids were filtered out. The resulting solution was extracted with EA and washed with brine and concentrated. This is resulted 1140 mg of the title compound as a light-yellow oil.

Step 2: Synthesis of 2-((3R,4S)-3-fluoro-4-(methoxy-d3)piperidin-1-yl)pyrimidin-4-amine TFA (2 mL) was added to tert-butyl (3R,4S)-3-fluoro-4-(methoxy-d3)piperidine-1-carboxylate (1140 mg, 4.82 mmol) in DCM (6 mL) and the solution was stirred for 2 h at rt. The mixture was concentrated under vacuum and residue was dissolved in IPA (20 mL), followed by 2-chloropyrimidin-4- (496 mg, 3.83 mmol) and TEA (0.6 mL). The mixture was stirred overnight at 100° C. The mixture was concentrated and the residue was purified by FLASH (5% MeOH in EA) to afford 425 mg of the title compound as a light-yellow solid.
Analytical Data: LC-MS: (ES, m/z)=230 [M+1].

Example B68: Synthesis of 2-((3R,4S)-4-cyclopropoxy-3-fluoropiperidin-1-yl)pyrimidin-4-amine

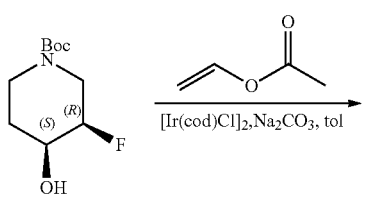

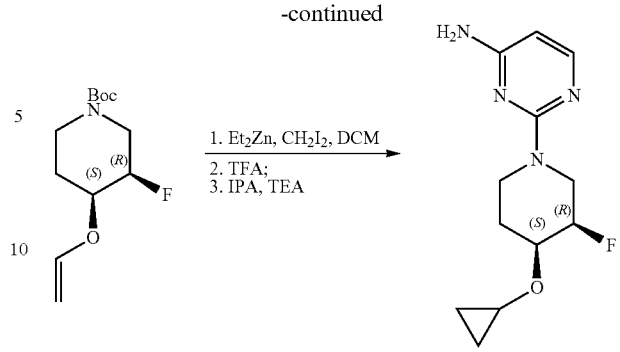

Step 1: Synthesis of (3R,4S)-tert-butyl 3-fluoro-4-(vinyloxy)piperidine-1-carboxylate A mixture of tert-butyl (3R,4S)-3-fluoro-4-hydroxypiperidine-1-carboxylate (263 mg, 1.2 mmol, 1 equiv.), ethenyl acetate (515 mg, 5.99 mmol, 5 equiv.), Ir(COD)$_2$Cl$_2$ (80.3 mg, 120 µmol, 0.1 equiv.) and Na$_2$CO$_3$ (127 mg, 1.20 mmol, 1 equiv.) in toluene (1.5 mL) was heated to 100° C. for 3 h. After cooling down to rt, the mixture was filtered. The filtrate was concentrated. The residue was purified by prep-TLC (PE/EA=4:1) to afford the title compound (200 mg, 68%) as a colourless syrup.

Step 2: Synthesis of 2-((3R,4S)-4-cyclopropoxy-3-fluoropiperidin-1-yl)pyrimidin-4-amine A solution of diiodomethane (1.17 g, 4.39 mmol, 5.5 equiv.) in DCM (2 mL) was added diethylzinc (3.59 mL, 3.59 mmol, 4.5 equiv., 1M in heptane) at 0° C. The mixture was stirred at 0° C. for 1 h. A solution of tert-butyl (3R,4S)-4-(ethenyloxy)-3-fluoropiperidine-1-carboxylate (196 mg, 800 µmol, 1 equiv.) in DCM (2 mL) was added. The reaction was carried on at rt for 2 h then concentrated. The residue was suspended in TFA (1 mL) and DCM (3 mL) and stirred for 2 h at rt. The mixture was concentrated. The residue was added TEA (404 mg, 4.00 mmol, 5 equiv.), 2-chloropyrimidin-4-amine (72.5 mg, 560 µmol, 0.7 equiv.) and IPA (2 mL). The mixture was heated to 100° C. for 18 h. After cooling down to rt, the mixture was concentrated. The residue was purified by prep-TLC (DCM/MeOH=25:1) to afford 2-[(3R,4S)-4-cyclopropoxy-3-fluoropiperidin-1-yl]pyrimidin-4-amine (80 mg, 40%) as a white solid.
Analytical Data: 1H-NMR (400 MHz, 3d-CD$_3$Cl) δ ppm 7.94 (d, 1H, J=5.6 Hz), 5.78 (d, 1H, J=5.6 Hz), 4.83 (ddt, 1H, J=48.3, 5.7, 2.7 Hz), 4.68-4.59 (m, 1H), 4.58 (s, 2H), 4.32 (dddd, 1H, J=13.4, 5.7, 4.0, 1.5 Hz), 3.84-3.71 (m, 1H), 3.61-3.42 (m, 2H), 3.35 (dddd, 1H, J=13.2, 9.3, 3.6, 1.7 Hz), 2.05-1.91 (m, 1H), 1.89-1.74 (m, 1H), 0.72-0.63 (m, 2H), 0.58-0.49 (m, 2H).

Example B69: Synthesis of rac-2-(1-(4-aminopyrimidin-2-yl)-3,3-difluoropiperidin-4-yloxy)ethanol

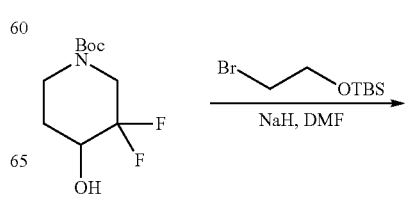

-continued

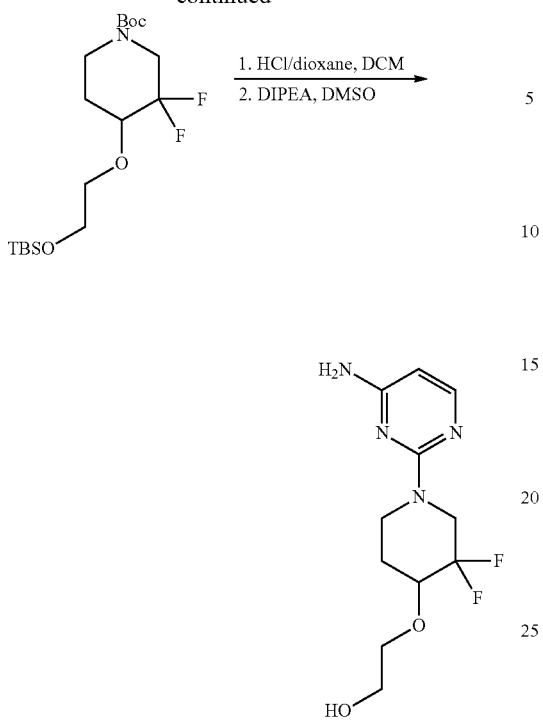

Step 1: Synthesis of rac-tert-butyl 4-(2-(tert-butyldimethylsilyloxy)ethoxy)-3,3-difluoropiperidine-1-carboxylate To a solution of rac-tert-butyl 3,3-difluoro-4-hydroxypiperidine-1-carboxylate (3 g, 12.6 mmol) in DMF (20 mL) was added NaH (1.25 g, 31.5 mmol, 60%) at 0° C. The mixture was stirred at 0° C. for 0.5 h. Then (2-bromoethoxy)(tert-butyl)dimethylsilane (9.04 g, 37.8 mmol) was added. The mixture was stirred at rt for 13 h. The mixture was extracted with EA and washed with brine. The organic layer was dried and concentrated under vacuum. The residue was purified by Flash Column Silica-CS (PE:EA=1:0 to 10:1). This resulted in 3.8 g (76.3%) of the title compound as a yellow oil.

Step 2: Synthesis of rac-2-(1-(4-aminopyrimidin-2-yl)-3,3-difluoropiperidin-4-yloxy)ethanol To a solution of rac-tert-butyl 4-{2-[(tert-butyldimethylsilyl)oxy]ethoxy}-3,3-difluoropiperidine-1-carboxylate (3.7 g, 9.35 mmol) in DCM (10 mL), was added HCl/dioxane (20 mL) at 0° C. Then the mixture was stirred at rt for 2 h. The reaction was concentrated and the residue was dissolved in IPA (4 mL), followed by TEA (278 mg, 2.75 mmol) and 2-chloropyrimidin-4-amine (84.7 mg, 654 μmol). The mixture was stirred at 120° C. for 13 h. The mixture was extracted with EA and washed with brine. The organic layer was dried and concentrated under vacuum. The residue was purified by Flash Column Silica-CS (DCM:MeOH=10:1). This resulted in 2 g (79.6%) of the title compound as a light-yellow solid.

Analytical Data: LC-MS: (ES, m/z)=275 [M+1].

Example B70: Synthesis of 2-((3S,4R)-4-(2-azidoethoxy)-3-fluoro-3-methylpiperidin-1-yl)pyrimidin-4-amine

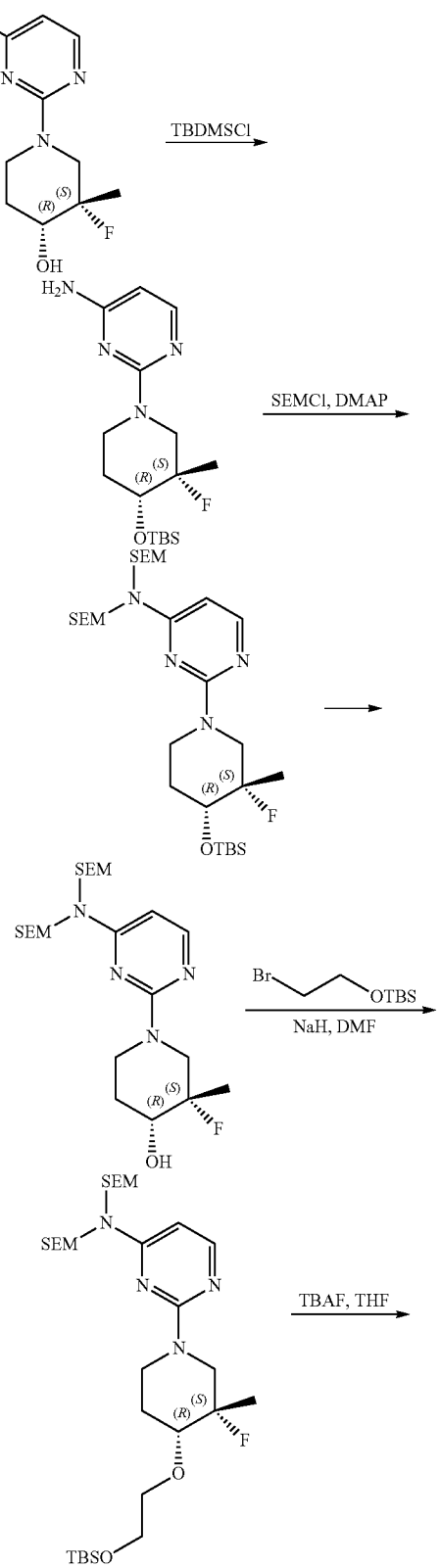

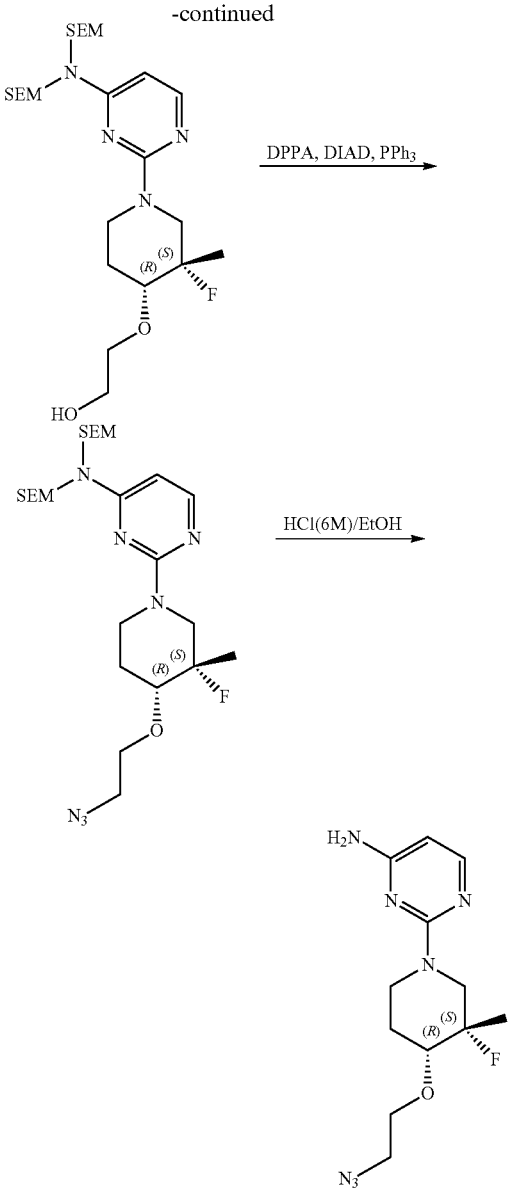

Step 1: Synthesis of 2-((3S,4R)-4-(tert-butyldimethylsilyloxy)-3-fluoro-3-methylpiperidin-1-yl)pyrimidin-4-amine:

Tert-butyl(chloro)dimethylsilane (5.98 g, 39.7 mmol) was added batchwise to 1H-imidazole (3.60 g, 53.0 mmol) and chirally pure (3 S,4R)-1-(4-aminopyrimidin-2-yl)-3-fluoro-3-methylpiperidin-4-ol (from Example B1, Step 7, 6.0 g, 26.5 mmol) in DMF at 0° C. The mixture was stirred at rt for 16 h. The mixture was diluted with EA (500 mL) and washed with brine, the organic layer was dried over Na$_2$SO$_4$ and concentrated under vacuum. The residue was purified by a flash with PE:EA=2:1 to afford 7.5 g the title compound as a colorless oil.

Analytical Data: LC-MS: (ES, m/z)=341 [M+1].

Step 2: Synthesis of 2-((3S,4R)-4-(tert-butyldimethylsilyloxy)-3-fluoro-3-methylpiperidin-1-yl)-N,N-bis((2-(trimethylsilyl)ethoxy)methyl)pyrimidin-4-amine The mixture of [2-(chloromethoxy)ethyl]trimethylsilane (11.0 g, 66.0 mmol), DIEA (8.51 g, 66 mmol) and 2-[(3S, 4R)-4-[(tert-butyldimethylsilyl)oxy]-3-fluoro-3-methylpiperidin-1-yl]pyrimidin-4-amine (7.5 g, 22.0 mmol) in DCM (200 mL) was stirred 3 h in reflux. The mixture was diluted with EA (100 mL) and washed with brine. The organic layer was dried over Na$_2$SO$_4$ and concentrated under vacuum. The residue was purified by a flash with PE:EA=5:1 to afford 10.0 g the title compound as a colorless oil.

Analytical Data: LC-MS: (ES, m/z)=601 [M+1].

Step 3: Synthesis of (3 S,4R)-1-(4-(bis((2-(trimethylsilyl)ethoxy)methyl)amino)pyrimidin-2-yl)-3-fluoro-3-methylpiperidin-4-ol TBAF (83 mL, 83 mmol) was added to 2-[(3S,4R)-4-[(tert-butyldimethylsilyl)oxy]-3-fluoro-3-methylpiperidin-1-yl]-4-(2,2,12,12-tetramethyl-5,9-dioxa-7-aza-2,12-disilatridecan-7-yl)pyrimidine (10.0 g, 16.6 mmol) in THF. The mixture was stirred at rt for 2 h. The mixture was concentrated under vacuum. The residue was purified by a Pre-TLC with PE:EA=4:1 to afford 6.5 g the title compound as a colorless oil.

Analytical Data: LC-MS: (ES, m/z)=487 [M+1].

Step 4: Synthesis of 2-((3S,4R)-4-(2-(tert-butyldimethylsilyloxy)ethoxy)-3-fluoro-3-methylpiperidin-1-yl)-N,N-bis((2-(trimethylsilyl)ethoxy)methyl)pyrimidin-4-amine NaH (310 mg, 7.75 mmol) was added to 2-[(3S,4R)-4-{2-[(tert-butyldimethylsilyl)oxy]ethoxy}-3-fluoro-3-methylpiperidin-1-yl]-4-(2,2,12,12-tetramethyl-5,9-dioxa-7-aza-2,12-disilatridecan-7-yl)pyrimidine (2 g, 3.10 mmol) in DMF at 0° C. The mixture was stirred at 0° C. for 10 min. (2-bromoethoxy)(tert-butyl)dimethylsilane (2.22 g, 9.30 mmol) was added to the mixture and the resulting solution was stirred at rt for 16 h. The mixture was diluted with EA (100 mL) and washed with brine. The organic layer was dried and concentrated under vacuum. The residue was purified by a silica gel column with PE:EA=5:1 to afford 2.1 g the title compound as a colorless oil.

Analytical Data: LC-MS: (ES, m/z)=645 [M+1].

Step 5: Synthesis of 2-((3S,4R)-1-(4-(bis((2-(trimethylsilyl)ethoxy)methyl)amino)pyrimidin-2-yl)-3-fluoro-3-methylpiperidin-4-yloxy)ethanol TBAF (10 mL, 10 mmol) was added to 2-[(3S,4R)-4-{2-[(tert-butyldimethylsilyl)oxy]ethoxy}-3-fluoro-3-methylpiperidin-1-yl]-4-(2,2,12,12-tetramethyl-5,9-dioxa-7-aza-2,12-disilatridecan-7-yl)pyrimidine (600 mg, 930 μmol) in THF (10 mL) at rt. The mixture was stirred in reflux for 1 h. The mixture was concentrated under vacuum. The residue was purified by a silica gel column with PE:EA=2:1. The result in 200 mg the title compound as a colorless oil.

Analytical Data: LC-MS: (ES, m/z)=531 [M+1].

Step 6: Synthesis of 2-((3 S,4R)-4-(2-azidoethoxy)-3-fluoro-3-methylpiperidin-1-yl)-N,N-bis((2-(trimethylsilyl) ethoxy)methyl)pyrimidin-4-amine (E)-N-{[(propan-2-yloxy)carbonyl]imino}(propan-2-yloxy)formamide (456 mg, 2.26 mmol) was added dropwise to the mixture of PPh$_3$ (885 mg, 3.38 mmol), {[azido (phenoxy)phosphoryl]oxy}benzene (930 mg, 3.38 mmol) and 2-{[3S,4R)-3-fluoro-3-methyl-1-[4-(2,2,12,12-tetramethyl-5,9-dioxa-7-aza-2,12-disilatridecan-7-yl)pyrimidin-2-yl]piperidin-4-yl]oxy}ethan-1-ol (600 mg, 1.13 mmol) in THF at 0° C. The mixture was stirred at rt for 16 h. The mixture was diluted with EA (100 mL) and washed with brine. The organic layer was dried and concentrated under vacuum. The residue was purified by a Prep-TLC with PE:EA=5:1 to afford 280 mg the title compound as a yellow solid.

Analytical Data: LC-MS: (ES, m/z)=556 [M+1].

Step 7: Synthesis of 2-((3 S,4R)-4-(2-azidoethoxy)-3-fluoro-3-methylpiperidin-1-yl)pyrimidin-4-amine HCl (6M, 5 mL) was added to 2-[(3S,4R)-4-(2-azidoethoxy)-3-fluoro-3-methylpiperidin-1-yl]-4-(2,2,12,12-tetramethyl-5,9-dioxa-7-aza-2,12-disilatridecan-7-yl)pyrimidine (260 mg, 467 μmol) in EtOH at rt. The mixture was stirred in reflux for 1 h. The mixture was concentrated under vacuum to afford 120 mg 2-[(3S,4R)-4-(2-azidoethoxy)-3-fluoro-3-methylpiperidin-1-yl]pyrimidin-4-amine as a colorless oil.

Analytical Data: LC-MS: (ES, m/z)=296 [M+1].

Example B71: Synthesis of 1-((3S,4R)-1-(4-aminopyrimidin-2-yl)-3-fluoropiperidin-4-yloxy)propan-2-ol

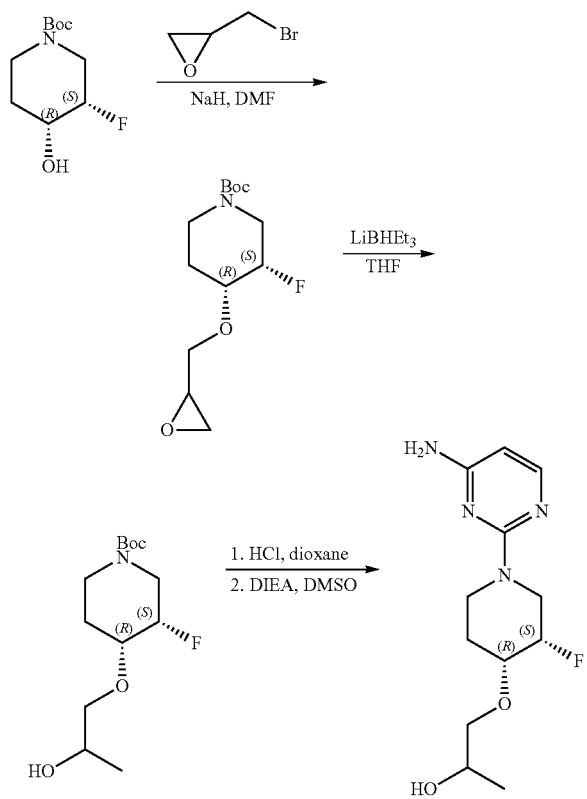

Step 1: Synthesis of (3S,4R)-tert-butyl 3-fluoro-4-(oxiran-2-ylmethoxy)piperidine-1-carboxylate To a solution of tert-butyl (3 S,4R)-3-fluoro-4-hydroxypiperidine-1-carboxylate (500 mg, 2.28 mmol) in DMF at 0° C. was added NaH (109 mg, 4.56 mmol) and the mixture was stirred for 20 min at 0° C. Then 2-(bromomethyl)oxirane (936 mg, 6.84 mmol) was added into the mixture. The resulting mixture was stirred at rt for 2 h. The mixture was extracted by EA and water. The organic layer was combined and was dried by $Na_2SO_4$. The organic layer was concentrated and the crude product was used 600 mg (95%) of the title compound as a brown solid.

Analytical Data: LC-MS: (ES, m/z)=220 [M+1-56].

Step 2: Synthesis of (3S,4R)-tert-butyl 3-fluoro-4-(2-hydroxypropoxy)piperidine-1-carboxylate To a solution of tert-butyl (3S,4R)-3-fluoro-4-[(oxiran-2-yl)methoxy]piperidine-1-carboxylate (750 mg, 2.72 mmol) in THF was added $LiBHEt_3$ (1 M in THF solution) at 0° C. under $N_2$ atmosphere. The mixture was stirred for 2 h at rt. The mixture was extracted by EA and water. The organic layer was combined and dried by $Na_2SO_4$. The organic layer was concentrated to afford 600 mg (80%) of the title compound as a yellow solid.

Analytical Data: LC-MS: (ES, m/z)=222 [M+1-56].

Step 3: Synthesis of 1-((3S,4R)-1-(4-aminopyrimidin-2-yl)-3-fluoropiperidin-4-yloxy)propan-2-ol To a solution of tert-butyl (3S,4R)-3-fluoro-4-(2-hydroxypropoxy)piperidine-1-carboxylate (600 mg, 2.16 mmol) in DCM was added HCl (4 M in dioxane solution) at rt. The mixture was stirred for 2 h at rt. The resulting mixture was concentrated under vacuum. The residue was dissolved in DMSO (3 mL), followed by 2-chloropyrimidin-4-amine (380 mg, 2.93 mmol) and DIEA (1.13 g, 8.79 mmol). The mixture was stirred for 2 h at 120° C. The mixture was extracted by EA and water. The organic layer was combined and dried by $Na_2SO_4$. The organic layer was concentrated and the residue was purified by Prep-TLC with DCM/MeOH (15:1). This resulted in 210 mg of the title compound as a yellow solid.

Analytical Data: LC-MS: (ES, m/z)=271 [M+1].

Example B72: Synthesis of 2-((3S,4R)-4-cyclopropoxy-3-fluoropiperidin-1-yl)pyrimidin-4-amine

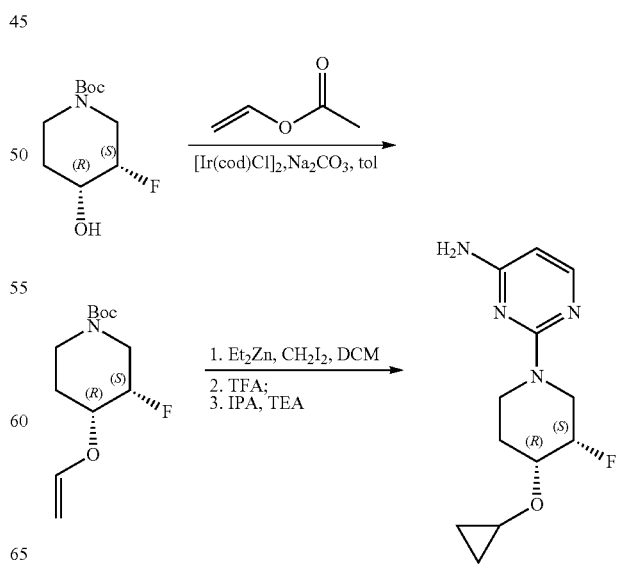

Step 1: Synthesis of (3S,4R)-tert-butyl 3-fluoro-4-(vinyloxy)piperidine-1-carboxylate A mixture of tert-butyl (3S,4R)-3-fluoro-4-hydroxypiperidine-1-carboxylate (263 mg, 1.2 mmol, 1 equiv.), ethenyl acetate (515 mg, 5.99 mmol, 5 equiv.), Ir(COD)$_2$Cl$_2$ (80.3 mg, 120 μmol, 0.1 equiv.) and Na$_2$CO$_3$ (127 mg, 1.20 mmol, 1 equiv.) in toluene (1.5 mL) was heated to 100° C. for 3 h. After cooling down to rt, the mixture was filtered. The filtrate was concentrated. The residue was purified by prep-TLC (PE/EA=4:1) to afford the title compound (200 mg, 68%) as a colourless syrup.

Step 2: Synthesis of 2-((3S,4R)-4-cyclopropoxy-3-fluoropiperidin-1-yl)pyrimidin-4-amine A solution of diiodomethane (1.17 g, 4.39 mmol, 5.5 equiv.) in DCM (2 mL) was added diethylzinc (3.59 mL, 3.59 mmol, 4.5 equiv., 1M in heptane) at 0° C. The mixture was stirred at 0° C. for 1 h. A solution of tert-butyl (3S,4R)-4-(ethenyloxy)-3-fluoropiperidine-1-carboxylate (196 mg, 800 μmol, 1 equiv.) in DCM (2 mL) was added. The reaction was carried on at rt for 2 h then concentrated. The residue was suspended in TFA (1 mL) and DCM (3 mL) and stirred for 2 h at rt. The mixture was concentrated. The residue was added triethylamine (404 mg, 4.00 mmol, 5 equiv.), 2-chloropyrimidin-4-amine (72.5 mg, 560 μmol, 0.7 equiv.) and IPA (2 mL). The mixture was heated to 100° C. for 18 h. After cooling down to rt, the mixture was concentrated. The residue was purified by prep-TLC (DCM/MeOH=25:1) to afford the title compound (80 mg, 40%) as a white solid.

Analytical Data: 1H-NMR (400 MHz, 3d-CD$_3$Cl) δ ppm 7.94 (d, 1H, J=5.6 Hz), 5.78 (d, 1H, J=5.6 Hz), 4.84 (ddd, 1H, J=48.1, 5.8, 2.8 Hz), 4.66-4.59 (m, 1H), 4.57 (s, 2H), 4.39-4.27 (m, 1H), 3.85-3.69 (m, 1H), 3.62-3.43 (m, 2H), 3.35 (dddd, 1H, J=13.3, 9.4, 3.6, 1.7 Hz), 1.98 (dddd, 1H, J=13.4, 6.8, 5.4, 3.2 Hz), 1.83 (ddd, 1H, J=9.6, 7.8, 4.6 Hz), 0.72-0.64 (m, 2H), 0.57-0.47 (m, 2H).

Example B73: Synthesis of 3-((3S,4R)-3-fluoro-4-methoxypiperidin-1-yl)-1,2,4-triazin-5-amine

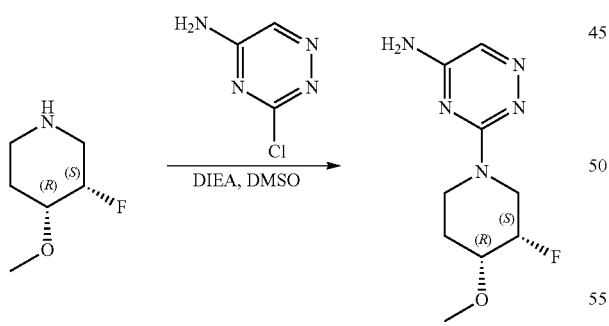

The solution of (3S,4R)-3-fluoro-4-methoxypiperidine (60 mg, 450 umol, from step 2 of Example B33), DIPEA (174 mg, 1.35 mmol) and 3-chloro-1,2,4-triazin-5-amine (64.6 mg, 495 umol, from step 2 of Example B30) in DMSO (2 mL) was stirred for 2 h at 120° C. The mixture was extracted by EA and water. The organic layer was dried, concentrated and the residue was purified by Prep-TLC with PE/EA (5:1). This resulted in 40 mg (39%) of the title compound as a yellow solid.

Analytical Data: LC-MS: (ES, m/z)=228 [M+1].

Example B74: Synthesis of rac-(all cis)-1-(4-aminopyrimidin-2-yl)-5-fluoro-4-methoxypiperidin-3-ol

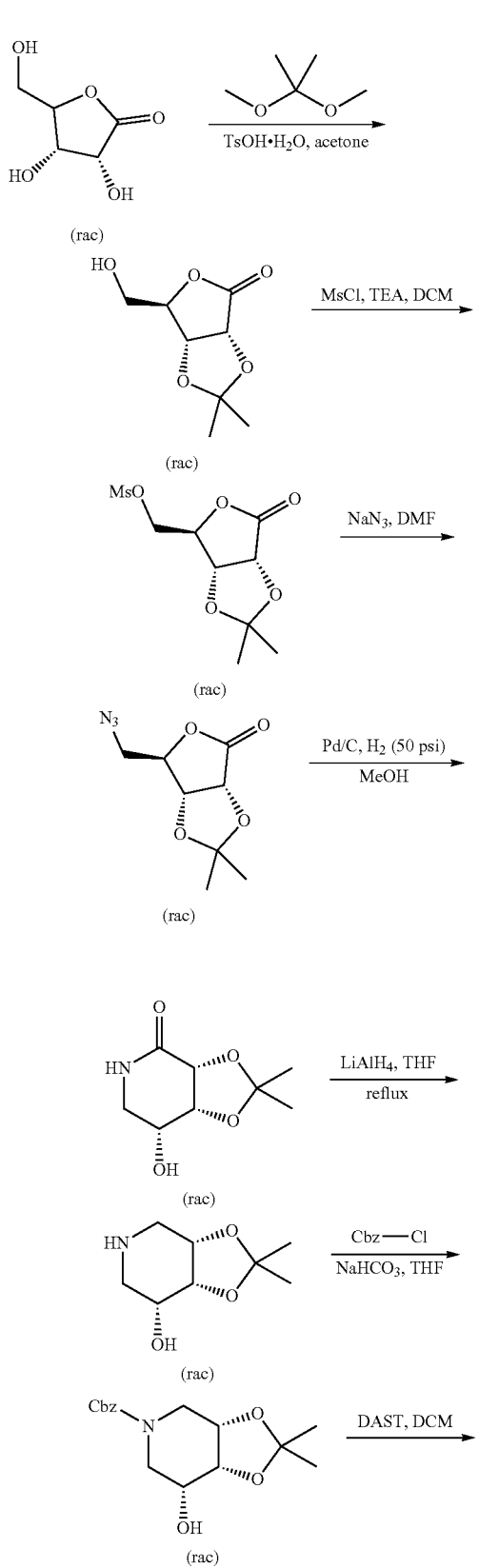

-continued

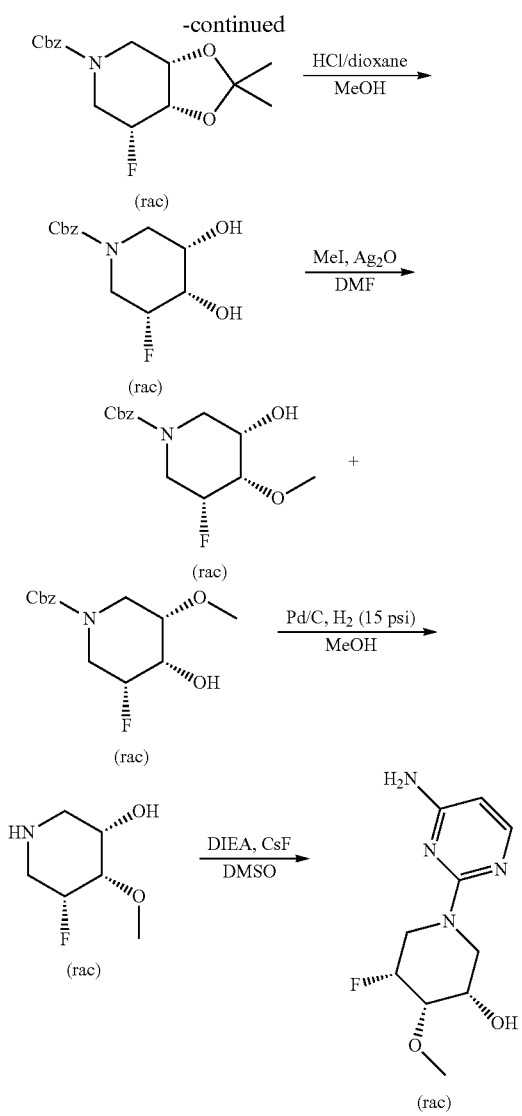

Step 1: Synthesis of rac-trans-6-(hydroxymethyl)-cis-2,2-dimethyldihydrofuro[3,4-d][1,3]dioxol-4(3aH)-one Into a 100-mL round-bottom flask was placed rac-cis-3,4-dihydroxy-trans-5-(hydroxymethyl)tetra hydrofuran-2-one (3 g, 20.2 mmol, 1 equiv), TsOH·H$_2$O (385 mg, 2.03 mmol, 0.100 equiv), and anhydrous acetone (60 mL), then 2,2-dimethoxypropane (2.53 g, 24.3 mmol, 1.20 equiv) was added at 0° C. over 5 min. The resulting solution was stirred at 25° C. for 2 h. Then the sodium bicarbonate solid (255 mg, 3.04 mmol, 0.150 equiv.) was added to the mixture and stirred for 5 min. The reaction mixture was filtered and concentrated under vacuum. This resulted in 3.8 g (100%) of the title compound as a white solid.

Step 2: Synthesis of rac-((cis)-2,2-dimethyl-6-oxo-tetrahydrofuro[3,4-d][1,3]dioxol-trans-4-yl)methyl methanesulfonate Into a 100-mL round-bottom flask was placed rac-trans-6-(hydroxymethyl)-cis-2,2-dimethyldihydrofuro[3,4-d][1,3]dioxol-4(3aH)-one (3.81 g, 20.3 mmol, 1 equiv) and TEA (4.10 g, 40.5 mmol, 2 equiv), and THF (70 mL), then MsCl (2.78 g, 24.3 mmol, 1.20 equiv) was added dropwise at 0° C. The resulting solution was stirred at 25° C. for 1 h. The mixture was diluted with DCM (20 mL) and washed with the saturated aqueous NH$_4$Cl (20 mL×3). The organic layer was dried over MgSO$_4$, filtered and concentrated under vacuum. This resulted in 5.0 g (93%) of the title compound as an orange oil, which was used directly for next step without further purification.

Analytical data: LC-MS: (ES, m/z): RT=0.274 min, LCMS: m/z=267 [M+1], $^1$H NMR (400 MHz, CDCl$_3$) δ 4.89-4.73 (m, 3H), 4.54-4.41 (m, 2H), 3.06 (s, 3H), 1.49 (s, 3H), 1.41 (s, 3H).

Step 3: Synthesis of rac-(trans)-6-(azidomethyl)-cis-2,2-dimethyldihydrofuro[3,4-d][1,3]dioxol-4(3aH)-one Into a 100-mL round-bottom flask was placed rac-((cis)-2,2-dimethyl-6-oxotetrahydrofuro[3,4-d][1,3]dioxol-trans-4-yl)methyl methanesulfonate (5.00 g, 18.8 mmol, 1 equiv), NaN$_3$ (3.66 g, 56.3 mmol, 3 equiv), and DMF (60 mL). The resulting solution was stirred at 75° C. for 3 h in an oil bath. The reaction mixture was diluted with EA (150 mL) and washed with brine (50 mL×3). The collected organic phase was dried over Na$_2$SO$_4$, filtered and concentrated under vacuum. This resulted in 3.2 g (80%) of the title compound as red oil.

Analytical Data: $^1$H NMR (400 MHz, CDCl$_3$) δ 4.85 (d, J=5.6 Hz, 1H), 4.71-4.58 (m, 2H), 3.83-3.74 (m, 1H), 3.70-3.62 (m, 1H), 1.48 (s, 3H), 1.39 (s, 3H).

Step 4: Synthesis of rac-(all cis)-7-hydroxy-2,2-dimethyltetrahydro-[1,3]dioxolo[4,5-c]pyridin-4(3aH)-one Into a 100-mL round-bottom flask was placed rac-(trans)-6-(azidomethyl)-cis-2,2-dimethyldihydrofuro[3,4-d][1,3]dioxol-4(3aH)-one (3.20 g, 15.0 mmol, 1 equiv), Pd/C (300 mg, 10% purity), and MeOH (30 mL) under N$_2$ atmosphere. The resulting solution was stirred at 25° C. for 3 h under H$_2$ (50 psi) atmosphere. The mixture was filtered and concentrated under vacuum. This resulted in 2.7 g (93%) of the title compound as colorless oil.

Analytical Data: $^1$H NMR (400 MHz, CDCl$_3$) δ 7.03-6.83 (m, 1H), 4.58-4.47 (m, 2H), 4.12-4.04 (m, 1H), 3.49-3.40 (m, 1H), 3.28-3.20 (m, 1H), 1.54 (s, 3H), 1.42 (s, 3H).

Step 5: Synthesis of rac-(all cis)-2,2-dimethylhexahydro-[1,3]dioxolo[4,5-c]pyridin-7-ol Into a 100-mL round-bottom flask was placed rac-(all cis)-7-hydroxy-2,2-dimethyltetrahydro-[1,3]dioxolo[4,5-c]pyridin-4(3aH)-one (2.55 g, 13.6 mmol, 1 equiv), LiAlH$_4$ (2.58 g, 68.1 mmol, 5.00 equiv) in THF (50 mL) was stirred at 70° C. for 6 h under N$_2$ atmosphere. The reaction mixture was quenched with H$_2$O (3 mL). The reaction mixture was diluted with EA/MeOH (100 mL, v/v=20/1), dried over Na$_2$SO$_4$, filtered and concentrated under vacuum. This resulted in 2.4 g (crude) of the title compound as a white solid.

Analytical Data: LC-MS: (ES, m/z): RT=0.086 min, LCMS: m/z=174 [M+1].

Step 6: Synthesis of rac-(all cis)-benzyl 7-hydroxy-2,2-dimethyltetrahydro-[1,3]dioxolo[4,5-c]pyridine-5(6H)-carboxylate Into a 100-mL round-bottom flask was placed rac-(all cis)-2,2-dimethylhexahydro-[1,3]dioxolo[4,5-c]pyridin-7-ol (2.36 g, 13.6 mmol, 1 equiv), NaHCO$_3$ (3.43 g, 40.9 mmol, 3 equiv), CbzCl (2.56 g, 15.0 mmol, 1.10 equiv), and THF (50 mL). The resulting solution was stirred at 50° C. for 2 h in an oil bath. The mixture was filtered and concentrated under vacuum. The residue was purified by column chromatography (SiO$_2$, PE/EA=3/1 and DCM/MeOH=20/1). This resulted in 2.3 g (53%) of the title compound as a white solid.

Analytical Data: LC-MS: (ES, m/z): RT=0.665 min, LCMS: m/z=308 [M+1], $^1$H NMR (400 MHz, CDCl$_3$) δ 7.41-7.30 (m, 5H), 5.15 (s, 2H), 4.45-4.35 (m, 2H), 4.04-3.82 (m, 1H), 3.76-3.62 (m, 2H), 3.58-3.49 (m, 1H), 3.30-3.20 (m, 1H), 2.30 (s, 1H), 1.49 (s, 3H), 1.38 (s, 3H).

Step 7: Synthesis of rac-(all cis)-benzyl 7-fluoro-2,2-dimethyltetrahydro-[1,3]dioxolo[4,5-c]pyridine-5(6H)-carboxylate Into a 50-mL round-bottom flask was placed rac-(all cis)-benzyl-7-hydroxy-2,2-dimethyltetrahydro-[1,3]dioxolo[4,5-c]pyridine-5(6H)-carboxylate (500 mg, 1.63 mmol, 1 equiv) and dry DCM (8 mL), DAST (786 mg, 4.88 mmol, 3 equiv) was added at 0~10° C. The resulting solution was stirred at 0~10° C. for 1 h. The reaction mixture was quenched with the saturated aqueous NaHCO$_3$ till pH ~8 and extracted with DCM (20 mL×3). The combined organic layer was dried over Na$_2$SO$_4$ and concentrated under vacuum. The residue was purified by column chromatography (SiO$_2$, PE/EA=3/1 and EA/MeOH=20/1). This resulted in 0.38 g (75%) of the title compound as colorless oil.

Analytical Data: LC-MS: (ES, m/z): RT=0.741 min, LCMS: m/z=310 [M+1]. $^1$H NMR (400 MHz, CDCl$_3$) δ 7.38-7.32 (m, 5H), 5.16 (s, 2H), 4.92-4.64 (m, 1H), 4.48-4.30 (m, 2H), 3.80-3.58 (m, 4H), 1.51 (s, 3H), 1.39 (s, 3H).

Step 8: Synthesis of rac-(all cis)-benzyl 3-fluoro-4,5-dihydroxypiperidine-1-carboxylate Into a 50-mL round-bottom flask was placed rac-(all cis)-benzyl-7-fluoro-2,2-dimethyltetrahydro-[1,3]dioxolo[4,5-c]pyridine-5(6H)-carboxylate (383 mg, 1.24 mmol, 1 equiv), HCl/MeOH (10.1 mL, 32.6 equiv, 4 mol/L). The resulting solution was stirred at 25° C. for 2 h. The mixture was concentrated under vacuum. This resulted in 0.28 g (84%) of the title compound as white solid.

Analytical Data: $^1$H NMR (400 MHz, CDCl$_3$) δ 7.42-7.31 (m, 5H), 5.16 (s, 2H), 4.73-4.52 (m, 1H), 4.02-3.51 (m, 6H).

Step 9: Synthesis of rac-(all cis)-benzyl 3-fluoro-5-hydroxy-4-methoxypiperidine-1-carboxylate and (3R,4S,5S)-benzyl 3-fluoro-4-hydroxy-5-methoxypiperidine-1-carboxylate Into a 25-mL round-bottom flask was placed rac-(all cis)-benzyl 3-fluoro-4,5-dihydroxypiperidine-1-carboxylate (110 mg, 409 μmol, 1 equiv), Ag$_2$O (94.7 mg, 409 μmol, 1 equiv.), MeI (145 mg, 1.02 mmol, 2.50 equiv.), and DMF (3 mL). The resulting solution was stirred at 25° C. for 24 h. The mixture was filtered, diluted with EA (30 mL) and washed with the brine (30 mL×3), the collected organic phase was dried over Na$_2$SO$_4$, filtered and concentrated under vacuum. The residue was purified by Prep-HPLC; mobile phase; water (10 mmol/L NH$_4$HCO$_3$) and ACN (18.0% ACN up to 38.0% in 10 min); detector, UV 254/220 nm. This resulted in 20 mg (17%) of the title compound as a colorless oil.

Analytical Data: LC-MS: (ES, m/z): RT=0.689 min, LCMS: m/z=284 [M+1], $^1$H NMR (400 MHz, CDCl$_3$) δ 7.43-7.30 (m, 5H), 5.20-5.10 (m, 2H), 4.65-4.43 (m, 1H), 4.10-4.05 (m, 1H), 3.86-3.82 (m, 1H), 3.76-3.29 (m, 7H), 2.68 (s, 1H). And 32 mg (28%) of the title compound B as colorless oil. [27] LC-MS: (ES, m/z): RT=0.705 min, LCMS: m/z=284 [M+1]. $^1$H NMR (400 MHz, CDCl$_3$) δ=7.43-7.29 (m, 5H), 5.20-5.09 (m, 2H), 4.76-4.51 (m, 1H), 3.89-3.61 (m, 5H), 3.59 (s, 3H), 3.40-3.30 (m, 1H), 2.50 (s, 1H).

Step 10: Synthesis of rac-(all cis)-5-fluoro-4-methoxypiperidin-3-ol

Into a 25 mL round-bottom flask was placed rac-(all cis)-benzyl 3-fluoro-5-hydroxy-4-methoxypiperidine-1-carboxylate and rac-(all cis)-benzyl 3-fluoro-4-hydroxy-5-methoxypiperidine-1-carboxylate (5.00 mg, 17.7 μmol, 1 equiv.), Pd/C (5 mg, 10% purity), and THF (1 mL). The resulting solution was stirred under H$_2$ (15 psi) at 25° C. for 2 h. The mixture was filtered and concentrated under vacuum. This resulted in 2.6 mg (100%) of the title compound as a yellow solid.

Step 11: Synthesis of rac-(all cis)-1-(4-aminopyrimidin-2-yl)-5-fluoro-4-methoxypiperidin-3-ol Into a 250-mL round-bottom flask was placed 2-chloropyrimidin-4-amine (2.28 mg, 17.6 umol, 1 equiv), rac-(all cis)-5-fluoro-4-methoxy-piperidin-3-ol (2.63 mg, 17.6 μmol, 1 equiv), DIEA (4.56 mg, 35.3 μmol, 2 equiv), and DMSO (1 mL). The resulting solution was stirred at 100° C. for 12 h. The mixture was filtered and concentrated under vacuum. The residue was purified by silica gel prep-TLC (PE:EA=1:2). This resulted in 3.5 mg (81%) of the title compound.

Analytical Data: LC-MS: (ES, m/z): RT=0.077 min, LCMS: m/z=243 [M+1].

Example B75: Synthesis of rac-(all cis)-1-(4-aminopyrimidin-2-yl)-3-fluoro-5-methoxypiperidin-4-ol

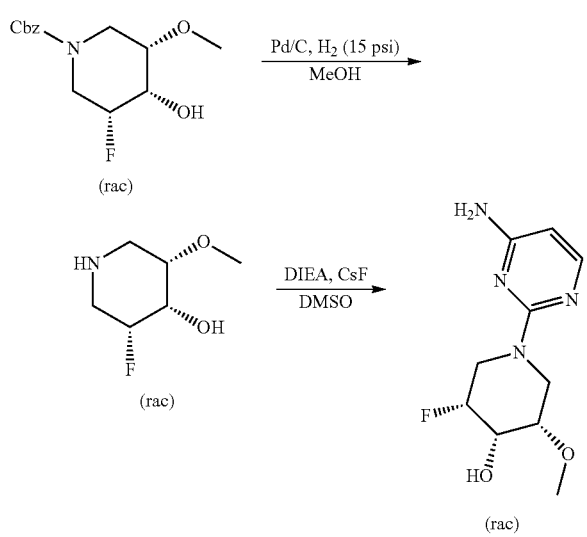

Step 1: Synthesis of rac-(all cis)-3-fluoro-5-methoxypiperidin-4-ol

Into a 25-mL round-bottom flask was placed rac-(all cis)-benzyl 3-fluoro-4-hydroxy-5-methoxypiperidine-1-carboxylate (50.0 mg, 176 μmol, 1 eq), Pd/C (15.0 mg, 10% purity), and THF (3 mL). The resulting solution was stirred under $H_2$ (15 psi) at 25° C. for 2 h. The reaction was filtered and concentrated in vacuo to give the title compound. This resulted in 28 mg (100%) of the title compound as colorless oil.

Analytical Data: $^1$H NMR (400 MHz, $CDCl_3$) δ 7.03-6.83 (m, 1H), 4.58-4.47 (m, 2H), 4.12-4.04 (m, 1H), 3.49-3.40 (m, 1H), 3.28-3.20 (m, 1H), 1.54 (s, 3H), 1.42 (s, 3H).

Step 2: Synthesis of rac-(all cis)-1-(4-aminopyrimidin-2-yl)-3-fluoro-5-methoxypiperidin-4-ol Into a 25-mL round-bottom flask was placed rac-(all cis)-3-fluoro-5-methoxypiperidin-4-ol (28.0 mg, 188 μmol, 1 eq), 2-chloropyrimidin-4-amine (36.5 mg, 282 μmol, 1.50 eq), DIEA (60.6 mg, 469 μmol, 2.50 eq), CsF (28.5 mg, 188 μmol, 1 eq), and in DMSO (1 mL). The resulting solution was stirred at 100° C. for 36 h. The reaction mixture was filtered and concentrated under vacuum. The residue was purified by Prep-HPLC; mobile phase: water (10 mmol/L $NH_4HCO_3$) and ACN (0% ACN up to 20.0% in 10 min); detector, UV 254/220 nm. This resulted in 15 mg (33%) of the title compound as yellow solid.

Analytical Data: $^1$H NMR (400 MHz, $CDCl_3$) 7.93 (d, J=5.6 Hz, 1H), 5.79 (d, J=5.6 Hz, 1H), 4.73 (s, 1H), 4.60 (s, 2H), 4.33-4.14 (m, 3H), 3.89-3.83 (m, 1H), 3.70-3.60 (m, 1H), 3.49 (s, 3H), 3.40-3.30 (m, 1H).

Example B76: Synthesis of rac-2-((all cis)-3-fluoro-4,5-dimethoxypiperidin-1-yl)pyrimidin-4-amine

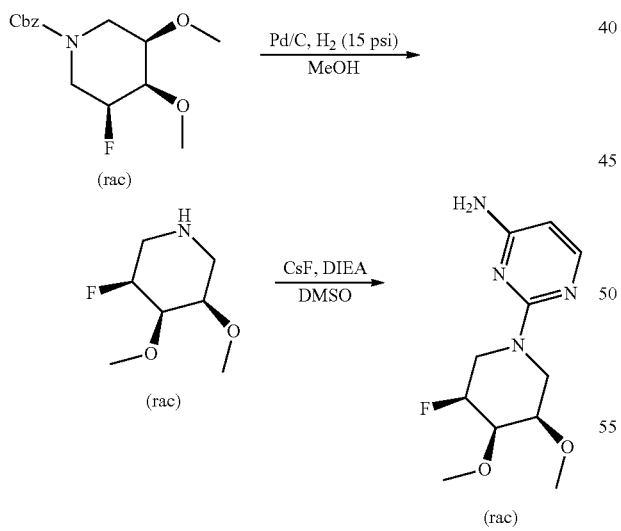

Step I: Synthesis of rac-(3S,4R,5R)-3-fluoro-4,5-dimethoxypiperidine

Into a 25-mL round-bottom flask was placed rac-benzyl-(all cis)-3-fluoro-4,5-dimethoxy-piperidine-1-carboxylate (Resulting from over-alkylation in Step 9, Example B74; 30.0 mg, 101 μmol, 1 equiv.), Pd/C (10.0 mg, 101 μmol, 10% purity), and THF (2 mL). The resulting solution was stirred at 25° C. for 2 h under $H_2$ (15 psi) atmosphere. The mixture was filtered and concentrated under vacuum. This resulted in 16 mg (100%) of the title compound as colorless oil.

Step 2: Synthesis of rac-2-((all cis)-3-fluoro-4,5-dimethoxypiperidin-1-yl)pyrimidin-4-amine Into a 25-mL round-bottom flask was placed rac-(all cis)-3-fluoro-4,5-dimethoxy-piperidine (16 mg, 98.1 μmol, 1 equiv.), 2-chloropyrimidin-4-amine (25.4 mg, 196 μmol, 2 equiv.), DIEA (38.0 mg, 294 μmol, 51.2 μL, 3 equiv.), CsF (29.8 mg, 196 μmol, 2 equiv.), and DMSO (1 mL). The resulting solution was stirred at 120° C. for 72 h. The mixture was diluted with EA (20 mL) and washed with $H_2O$ (5 mL×3). The collected water phases were concentrated under vacuum. The residue was purified by Prep-HPLC; water (10 mmol/L $NH_4HCO_3$) and ACN (0% ACN up to 30.0% in 10 min); detector, UV 254/220 nm. This resulted in 8.0 mg (32%) of the title compound as colorless oil.

Analytical Data: LC-MS: (ES, m/z): RT=1.141 min, LCMS: m/z=257 [M+1].

Example B77: Synthesis of rac-1-(4-aminopyrimidin-2-yl)-5,5-difluoro-4-methoxy-piperidin-3-ol

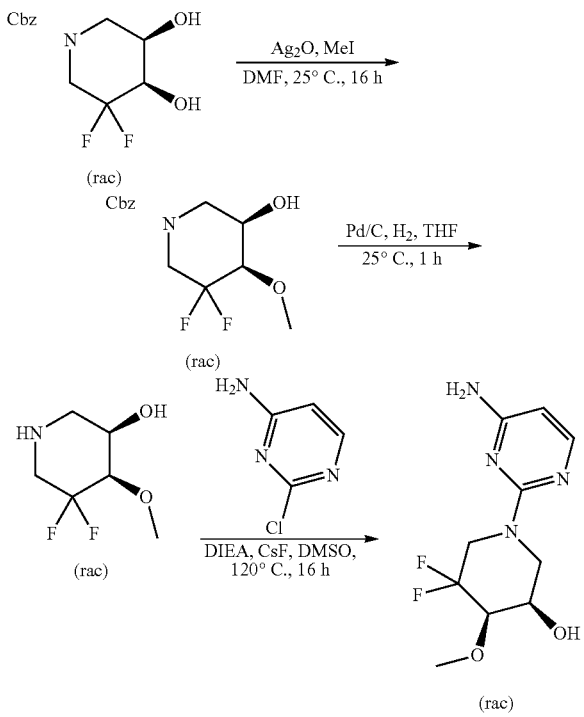

Step 1: Synthesis of rac-benzyl 3,3-difluoro-5-hydroxy-4-methoxy-piperidine-1-carboxylate To a solution of rac-benzyl 3,3-difluoro-4,5-dihydroxy-piperidine-1-carboxylate (as prepared from Step 2 (Boc-protected) Example 54, 170 mg, 591 μmol, 1 equiv.) and $Ag_2O$ (137 mg, 591 μmol, 1 equiv.) in DMF (5 mL) was added MeI (210 mg, 1.48 mmol, 92.1 μL, 2.50 equiv.) dropwise, the mixture was stirred at 25° C. for 16 h while being kept away from light. The mixture was diluted with water (60 mL) and extracted with EA (40 mL×3), the combined organic layers were washed with brine (50 mL), dried over anhydrous $Na_2SO_4$, filtered and concentrated in vacuum. The crude was purified with prep-HPLC [column: Xtimate C18 150*40 mm*10 um; mobile phase: [water (0.05% ammonia hydroxide v/v)-ACN]; B %: 31%-51%, 10 min]. This resulted in 110 mg (61%) of the title compound as a colorless oil.

Analytical Data: 1H NMR (400 MHz, $CDCl_3$) δ 7.44-7.30 (m, 5H), 5.17 (s, 2H), 4.32-3.99 (m, 2H), 3.91-3.81 (m, 1H), 3.65 (s, 3H), 3.63 (d, J=3.6 Hz, 1H), 3.53-3.27 (m, 1H), 3.07-2.88 (m, 1H), 2.37 (s, 1H).

Step 2: Synthesis of rac-5,5-difluoro-4-methoxy-piperidin-3-ol

To a solution of rac-benzyl 3,3-difluoro-5-hydroxy-4-methoxy-piperidine-1-carboxylate (100 mg, 331 μmol, 1 equiv.) in THF (5 mL) was added Pd/C (10 mg, 10% purity) under $N_2$. The mixture was stirred under $H_2$ (15 psi) at 25° C. for 1 h. The mixture was filtered and the filter was concentrated. The reaction mixture was filtered and the filter was concentrated. This resulted in 50 mg (90%) of the title compound as a colorless oil which was used for next step directly.

Step 3: Synthesis of rac-1-(4-aminopyrimidin-2-yl)-5,5-difluoro-4-methoxy-piperidin-3-ol To a solution of rac-5,5-difluoro-4-methoxy-piperidin-3-ol (50.0 mg, 299 μmol, 1 equiv) and DIEA (77.3 mg, 598 μmol, 2 equiv) in DMSO (1 mL) was added 2-chloropyrimidin-4-amine (50.3 mg, 388 μmol, 1.30 equiv), the mixture was stirred at 120° C. for 16 h. The reaction mixture was purified with prep-HPLC [column: Waters Xbridge 150*25 mm*5 um; mobile phase: [water (10 mM $NH_4HCO_3$)-ACN]; B %: 5%-38%, 10 min]. This resulted in 25 mg (32%) of the title compound as a colorless oil.

Analytical Data: 1H NMR (400 MHz, $CD_3OD$) δ 7.72 (d, J=6.0 Hz, 1H), 5.85 (d, J=6.0 Hz, 1H), 4.75-4.66 (m, 1H), 4.58 (s, 1H), 4.47 (dd, J=4.8, 12.8, Hz, 1H), 3.75 (dd, J=10.4, 4.4 Hz, 1H), 3.60 (s, 4H), 3.36 (d, J=13.6 Hz, 1H), 3.03 (dd, J=12.4, 11.2 Hz, 1H).

Example B78: S Synthesis of rac-cis-1-(4-aminopyrimidin-2-yl)-4-(2-methoxyethoxy)piperidin-3-ol

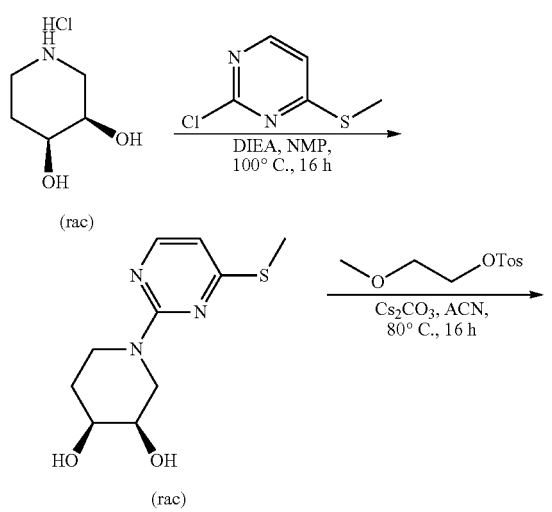

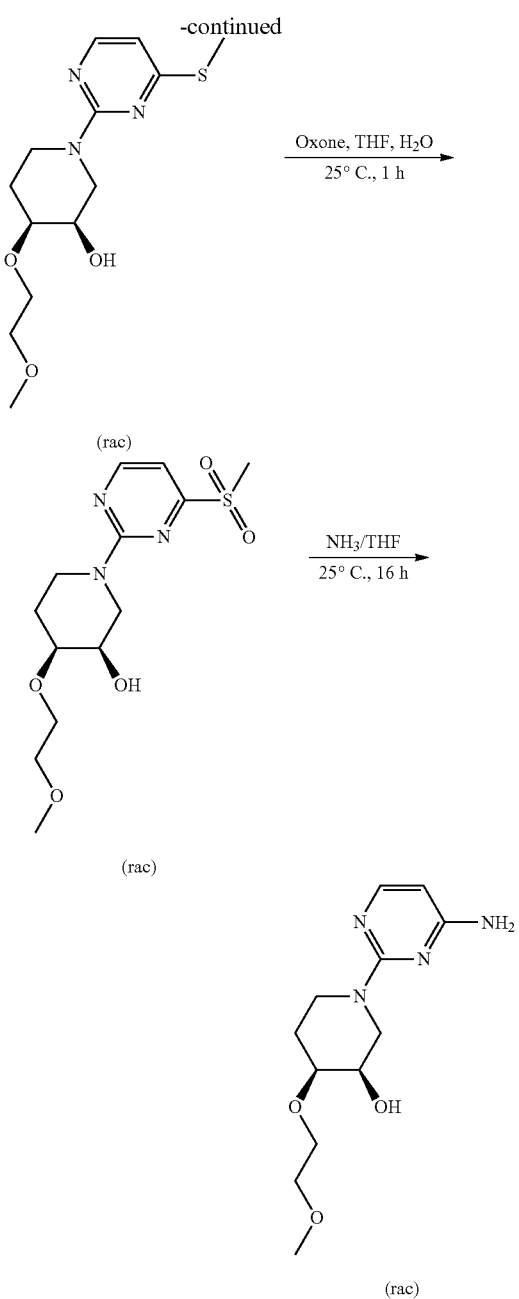

Step 1: Synthesis of rac-cis-1-(4-methylsulfanylpyrimidin-2-yl)piperidine-3,4-diol To a solution of rac-cis-piperidine-3,4-diol (0.500 g, 3.26 mmol, 1 equiv., HCl salt) and DIEA (1.68 g, 13.0 mmol, 2.27 mL, 4.00 equiv.) in DMSO (5 mL) was added 2-chloro-4-methylsulfanyl-pyrimidine (784 mg, 4.88 mmol, 1.50 equiv.), the mixture was stirred at 100° C. for 16 h. The mixture was diluted with water (120 mL) and extracted with EA (70 mL×2), the combined organic layers were washed with brine (50 mL), dried over anhydrous $Na_2SO_4$, filtered and concentrated in vacuum. The crude was purified with silica gel column chromatograph (PE:EA=2:1). This resulted in 0.68 g (96%) of the title compound as an off-white solid.

Analytical Data: 1H NMR (400 MHz, CDCl$_3$) δ 7.95 (d, J=5.2 Hz, 1H), 6.42 (d, J=5.2 Hz, 1H), 4.24-4.17 (m, 1H), 4.16-4.07 (m, 1H), 3.96-3.86 (m, 2H), 3.73 (dd, J=13.6, 3.2 Hz, 1H), 3.64-3.52 (m, 1H), 2.50 (s, 3H), 1.94-1.73 (m, 2H).

Step 2: Synthesis of rac-cis-4-(2-methoxyethoxy)-1-(4-methylsulfanylpyrimidin-2-yl)piperidin-3-ol To a solution of rac-cis-1-(4-methylsulfanylpyrimidin-2-yl)piperidine-3,4-diol (470 mg, 1.95 mmol, 1 equiv.), NaI (29.2 mg, 194 µmol, 0.100 equiv.) in ACN (10 mL) was added 2-methoxyethyl 4-methylbenzenesulfonate (897 mg, 3.90 mmol, 2 equiv.) and Cs$_2$CO$_3$ (1.90 g, 5.84 mmol, 3 equiv.), the mixture was stirred at 80° C. for 16 h. The mixture was filtered and the filtrate was concentrated in vacuo. The crude was purified with prep-HPLC [column: Phenomenex luna C18 150*40 mm*15 µm; mobile phase: [water (0.225% FA)-ACN]; B %: 1%-25%, 9 min]. This resulted in 0.18 g (30%) of the title compound as a yellow solid.

Analytical Data: 1H NMR (400 MHz, CDCl$_3$) δ 7.95 (d, J=5.2 Hz, 1H), 6.39 (d, J=5.2 Hz, 1H), 4.07-4.02 (m, 1H), 3.97-3.79 (m, 4H), 3.71-3.65 (m, 1H), 3.61-3.47 (m, 3H), 3.42-3.38 (m, 3H), 2.50 (s, 3H), 2.01-1.89 (m, 1H), 1.78-1.66 (m, 1H).

Step 3: Synthesis of rac-cis-4-(2-methoxyethoxy)-1-(4-methylsulfonylpyrimidin-2-yl)piperidin-3-ol

[8] To a solution of rac-cis-4-(2-methoxyethoxy)-1-(4-methylsulfanylpyrimidin-2-yl)piperidin-3-ol (160 mg, 534 µmol, 1 equiv.) in THF (8 mL) and H$_2$O (2 mL) was added Oxone (1.64 g, 2.67 mmol, 5.00 equiv.), the mixture was stirred at 25° C. for 1 h. The mixture was washed with saturated aqueous Na$_2$SO$_3$ (20 mL) and extracted with EA (30 mL×3), the combined organic layers were dried over anhydrous Na$_2$SO$_4$, filtered and concentrated in vacuum. The crude was purified with silica gel chromatograph (EA). This resulted in 85 mg (48%) of the title compound as a colorless oil.

Analytical Data: 1H NMR (400 MHz, CDCl$_3$) δ 8.58 (d, J=4.8 Hz, 1H), 7.07 (d, J=4.8 Hz, 1H), 4.08-3.94 (m, 3H), 3.93-3.85 (m, 2H), 3.84-3.80 (m, 1H), 3.75-3.63 (m, 2H), 3.60-3.49 (m, 3H), 3.42-3.38 (m, 3H), 3.18 (s, 3H), 2.01-1.90 (m, 1H), 1.79-1.69 (m, 1H).

Step 4: Synthesis of rac-cis-1-(4-aminopyrimidin-2-yl)-4-(2-methoxyethoxy)piperidin-3-ol A solution of rac-cis-4-(2-methoxyethoxy)-1-(4-methylsulfonylpyrimidin-2-yl)piperidin-3-ol (80.0 mg, 241 µmol, 1 equiv) in NH$_3$/THF (8 mL) was stirred at 25° C. for 16 h. The mixture concentrated in vacuo. The crude was purified with prep-HPLC [column: Waters Xbridge 150*25 mm*5 µm; mobile phase: [water (10 mM NH$_4$HCO$_3$)-ACN]; B %: 1%-30%, 10 min]. This resulted in 5.0 mg (7%) of the title compound as a mixture of enantiomers as a colorless oil.

Analytical Data: 1H NMR (400 MHz, CDCl$_3$) δ 7.91 (d, J=5.6 Hz, 1H), 5.73 (d, J=5.6 Hz, 1H), 4.57 (s, 2H), 4.00-3.93 (m, 1H), 3.91-3.82 (m, 2H), 3.82-3.72 (m, 3H), 3.71-3.60 (m, 3H), 3.59-3.56 (m, 1H), 3.40 (s, 3H), 2-1.90 (m, 1H), 1.73-1.67 (m, 1H).

Example B79: Synthesis of trans racemic (3S,4S)-1-(4-aminopyrimidin-2-yl)-4-(2-methoxyethoxy)piperidin-3-ol

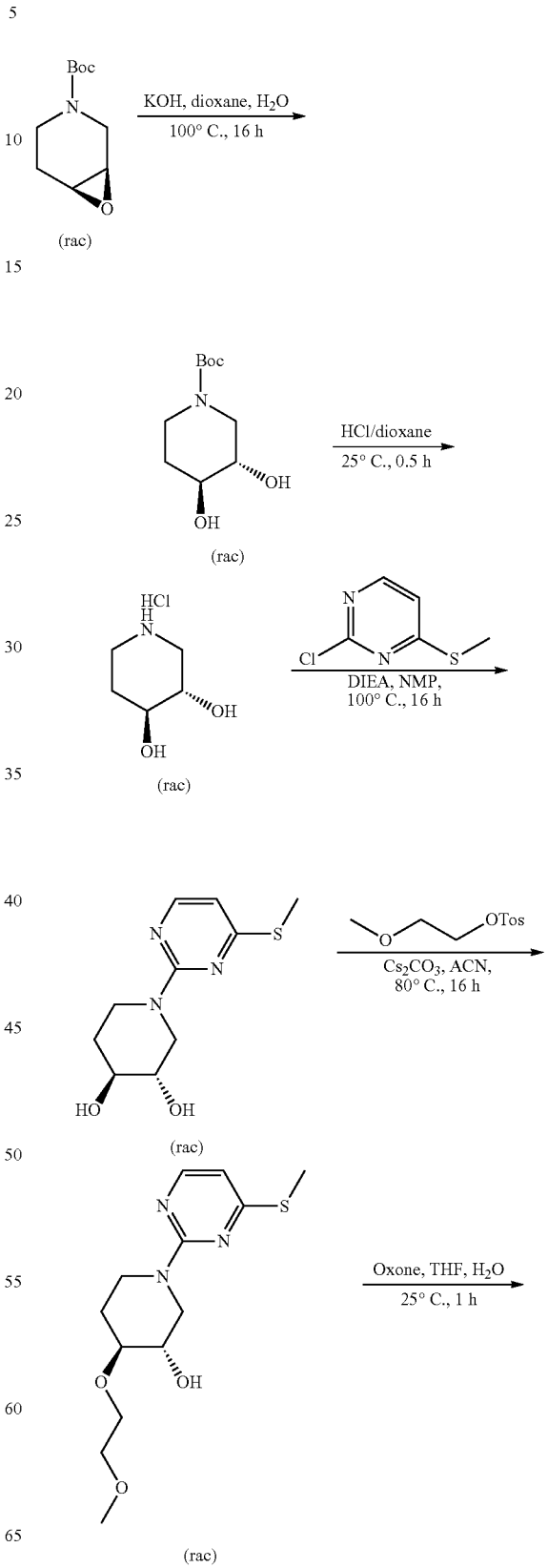

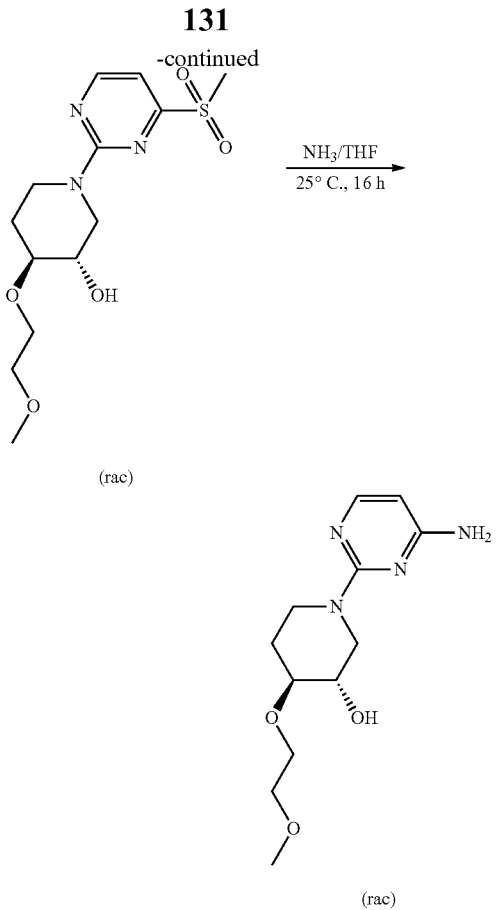

(rac)

(rac)

Step 1: Synthesis of rac-trans-tert-butyl-3,4-dihydroxypiperidine-1-carboxylate A solution of racemic tert-butyl 7-oxa-4-azabicyclo[4.1.0]heptane-4-carboxylate (2 g, 10.0 mmol, 1 equiv.) in dioxane (30 mL) was added a solution of KOH (1.13 g, 20.0 mmol, 2 equiv.) in water (15 mL), the mixture was stirred at 100° C. for 16 h. The mixture was concentrated in vacuo to give a residue. The residue was diluted with water (200 mL), extracted with EA (100 mL×3). The combined organic layers were washed with brine (80 mL), dried and concentrated in vacuo. This resulted in 2 g (90%) of the title compound as a colorless oil which was used for next step directly.

Step 2: Synthesis of (3S,4S)-piperidine-3,4-diol

A solution of rac-trans-tert-butyl-3,4-dihydroxypiperidine-1-carboxylate (2 g, 9.21 mmol, 1 equiv.) in HCl/dioxane (5 mL, 4 mol/L) was stirred at 25° C. for 30 min. The mixture was concentrated in vacuo. This resulted in 1.40 g (100%) of the title compound as a yellow solid which was used for next step directly.

Step 3: Synthesis of rac-trans-1-(4-methylsulfanylpyrimidin-2-yl)piperidine-3,4-diol To a solution of rac-trans-piperidine-3,4-diol (1.20 g, 7.81 mmol, 1 equiv., HCl salt) and DIEA (5.05 g, 39.1 mmol, 6.80 mL, 5.00 equiv.) in DMSO (12 mL) was added 2-chloro-4-methylsulfanyl-pyrimidine (1.25 g, 7.81 mmol, 1 equiv.), the mixture was stirred at 100° C. for 16 h. The mixture was diluted with water (150 mL) and extracted with EA (100 mL×2), the combined organic layers were washed with brine (80 mL), dried over anhydrous $Na_2SO_4$, filtered and concentrated in vacuum. The crude was purified with silica gel column chromatograph (PE:EA=2:1). This resulted in 1.30 g (69%) of the title compound as an off-white solid which was used for next step directly.

Step 4: Synthesis of rac-trans-4-(2-methoxyethoxy)-1-(4-methylsulfanylpyrimidin-2-yl)piperidin-3-ol To a solution of rac-trans-1-(4-methylsulfanylpyrimidin-2-yl)piperidine-3,4-diol (700 mg, 2.90 mmol, 1 equiv), NaI (43.4 mg, 290 μmol, 0.100 equiv.) in ACN (10 mL) was added 2-methoxyethyl 4-methylbenzenesulfonate (1.34 g, 5.80 mmol, 2 equiv.) and $Cs_2CO_3$ (2.84 g, 8.70 mmol, 3 equiv.), the mixture was stirred at 80° C. for 16 h. The mixture was filtered and the filtrate was concentrated in vacuo. The crude was purified with prep-HPLC [column: Waters Xbridge C18 150*50 mm*10 um; mobile phase: [water (10 mM NH4HCO3)-ACN]; B %: 20%-50%, 11.5 min]. This resulted in 300 mg (34%) of the title compound as a yellow solid.

Analytical Data: 1H NMR (400 MHz, $CDCl_3$) δ 8.00-7.93 (m, 1H), 6.46-6.39 (m, 1H), 5.03-4.83 (m, 1H), 4.81-4.62 (m, 1H), 4.02-3.88 (m, 1H), 3.74-3.57 (m, 5H), 3.42 (s, 3H), 3.38-3.14 (m, 1H), 3.03-2.65 (m, 2H), 2.50 (s, 3H), 2.08-2.01 (m, 1H), 1.56-1.46 (m, 1H).

Step 5: Synthesis of rac-trans-4-(2-methoxyethoxy)-1-(4-methylsulfonylpyrimidin-2-yl)piperidin-3-ol To a solution of rac-trans-4-(2-methoxyethoxy)-1-(4-methylsulfanylpyrimidin-2-yl)piperidin-3-ol (300 mg, 1 mmol, 1 equiv.) in THF (10 mL) and $H_2O$ (3 mL) was added Oxone (1.85 g, 3.01 mmol, 3 equiv.), the mixture was stirred at 25° C. for 3 h. The mixture was washed with saturated aqueous $Na_2SO_3$ (60 mL) and extracted with EA (50 mL×3), the combined organic layers were dried over anhydrous $Na_2SO_4$, filtered and concentrated in vacuum. The crude was purified with silica gel chromatograph (EA). This resulted in 120 mg (36%) of the title compound as a colorless oil.

Step 6: Synthesis of rac-trans-1-(4-aminopyrimidin-2-yl)-4-(2-methoxyethoxy)piperidin-3-ol A solution of rac-trans-4-(2-methoxyethoxy)-1-(4-methylsulfonylpyrimidin-2-yl)piperidin-3-ol (120 mg, 362 μmol, 1 equiv) in $NH_3$/THF (8 mL) was stirred at 25° C. for 16 h. The mixture was concentrated in vacuo. The crude was purified with prep-HPLC [column: Xtimate C18 150*40 mm*10 um; mobile phase: [water (0.05% ammonia hydroxide v/v)-ACN]; B %: 10%-20%, 10 min]. This resulted in 10.0 mg (10%) of the title compound as a mixture of enantiomers as a colorless oil.

Analytical Data: 1H NMR (400 MHz, $CDCl_3$) δ 7.90 (d, J=5.6 Hz, 1H), 5.74 (d, J=5.6 Hz, 1H), 4.74-4.64 (m, 3H), 4.57-4.49 (m, 1H), 3.90-3.84 (m, 1H), 3.70-3.65 (m, 1H), 3.60-3.55 (m, 3H), 3.40 (s, 3H), 3.39-3.29 (m, 1H), 3.01-2.94 (m, 1H), 2.88 (dd, J=13.2, 9.6 Hz, 1H), 2.03-2 (m, 1H), 1.53-1.43 (m, 1H).

Example C1: Synthesis of 1,6-dichloro-4-isopropyl-2,7-naphthyridine

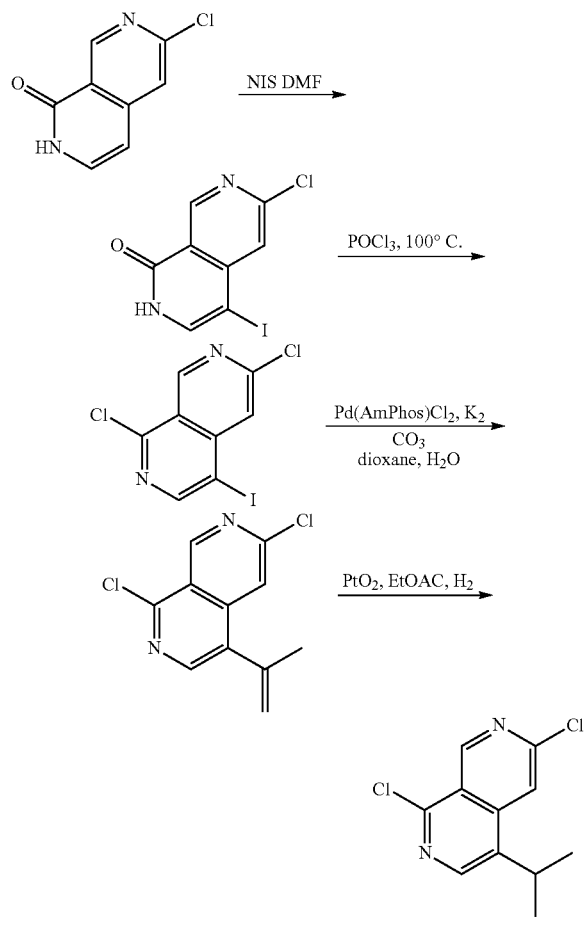

Step 1: Synthesis of 6-chloro-4-iodo-2,7-naphthyridin-1(2H)-one

To a solution of 6-chloro-1,2-dihydro-2,7-naphthyridin-1-one (50 g, 0.276 mol) in DMF (300 mL), NIS (74 g, 0.33 mol) was added at 0° C. and the mixture was stirred overnight at rt. The reaction mixture was filtered and the filtered cake was washed by water and dried under vacuum to afford the title compound (60 g, 70%) as a light-yellow solid.

Analytical Data: LC-MS: (ES, m/z)=307 [M+1]. 1H NMR (300 MHz, DMSO-d6) δ 12 (s, 1H), 9.02 (s, 1H), 7.89 (d, 1H, J=6.0 Hz), 7.44 (s, 1H).

Step 2: Synthesis of 1,6-dichloro-4-iodo-2,7-naphthyridine

A mixture of 6-chloro-4-iodo-1,2-dihydro-2,7-naphthyridin-1-one (60 g, 0.196 mol) in POCl₃ (320 mL) was stirred at 100° C. for 1.5 h. LCMS showed the starting material was consumed. The mixture was concentrated and neutralized with cooled saturated aq. NaHCO₃. The mixture was extracted with EA 3*300 mL. The combined organic layers were dried over Na₂SO₄, filtered and concentrated in reduced pressure to give 1,6-dichloro-4-iodo-2,7-naphthyridine 53 g (84%) as a yellow solid.

Analytical Data: LC-MS: (ES, m/z)=325 [M+1].

Step 3: Synthesis of 1,6-dichloro-4-(prop-1-en-2-yl)-2,7-naphthyridine

To a solution of 1,6-dichloro-4-iodo-2,7-naphthyridine (30 g, 92.5 mmol) in 1,4-dioxane/H₂O (300/70 mL) was added 4,4,5,5-tetramethyl-2-(prop-1-en-2-yl)-1,3,2-dioxaborolane (15 g, 93 mmol), K₂CO₃ (37.8 g, 276 mmol) and PdAMPhosCl₂/Bis(di-tert-butyl(4-dimethylaminophenyl)phosphine)dichloropalladium(II) (3 g, 4.2 mmol). The resulting solution was stirred for 0.5 h at 50° C. LCMS showed the reaction is complete. The mixture was cooled to rt and diluted with 200 mL of water. The resulting solution was extracted with 2×300 mL of EA and the organic layers combined. The resulting mixture was washed with 200 mL of brine. The mixture was dried over anhydrous sodium sulfate and concentrated under vacuum. The product was purified by chromatography with EA:PE (1:10). This resulted in 15 g (68.1%) of 1,6-dichloro-4-(prop-1-en-2-yl)-2,7-naphthyridine as white solid.

Analytical Data: LC-MS: (ES, m/z)=239 [M+1].

Step 4: Synthesis of 1,6-dichloro-4-isopropyl-2,7-naphthyridine

To a solution of 1,6-dichloro-4-(prop-1-en-2-yl)-2,7-naphthyridine (4 g, 16.8 mmol) in EA (300 mL) was added PtO₂ (5 g, 22 mmol). The resulting mixture was stirred at 25° C. for 24 h under H₂ atmosphere. The solid was filtered out. The filtrate was concentered under vacuum. The residue was purified by chromatography (EA:PE=1:8) to give 3 g (75%) of 1,6-dichloro-4-(propan-2-yl)-2,7-naphthyridine as a white solid.

Analytical Data: LC-MS: (ES, m/z)=241 [M+1]. 1H NMR (300 MHz, DMSO-d6) δ 9.47 (d, 1H, J=0.8 Hz), 8.47 (d, 1H, J=0.7 Hz), 8.26 (d, 1H, J=0.8 Hz), 3.64 (p, 1H, J=6.8 Hz), 1.33 (d, 6H, J=6.9 Hz).

Example C2: Synthesis of 4-bromo-7-chloro-1-isopropyl-2,6-naphthyridine

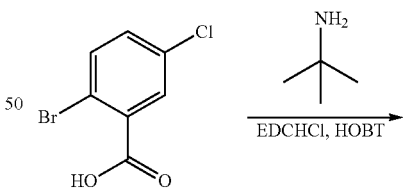

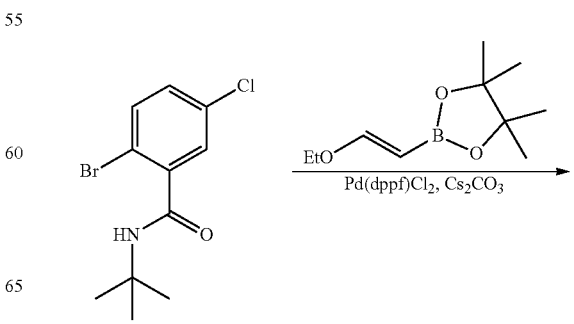

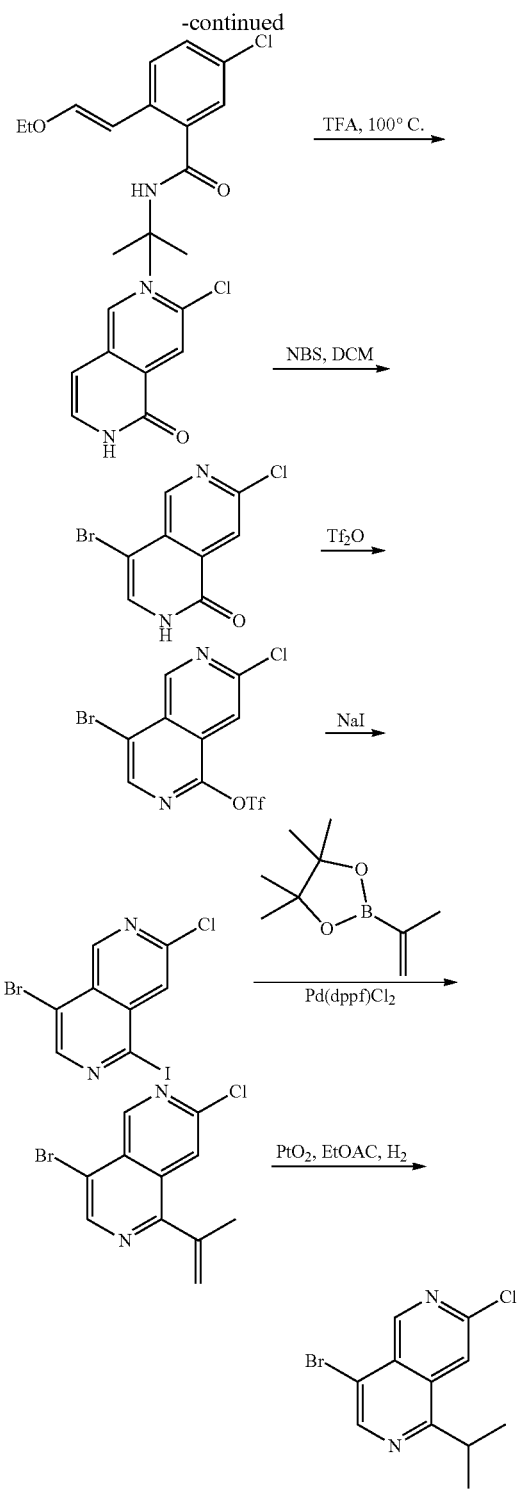

Step 1: Synthesis of
5-bromo-N-tert-butyl-2-chloroisonicotinamide

Into a 100-mL round-bottom flask purged and maintained with an inert atmosphere of nitrogen, was placed 5-bromo-2-chloropyridine-4-carboxylic acid (4 g, 16.9 mmol) in DMF (30 mL), 2-methylpropan-2-amine (1.47 g, 20.2 mmol), EDC HCl (4.85 g, 25.3 mmol) and HOBT (3.41 g, 25.3 mmol). The resulting solution was stirred overnight at rt. The resulting solution was added water and suspension was extracted with EA, and then the organic layers were combined, dried over anhydrous sodium sulfate and concentrated under vacuum. The residue was purified by FLASH with PE/EA (2:1). This resulted in 3 g (60.9%) of 5-bromo-N-tert-butyl-2-chloropyridine-4-carboxamide as a white solid.

Analytical Data: LC-MS: (ES, m/z)=293 [M+1]; 1H NMR (300 MHz, DMSO-d6) δ 8.64 (s, 1H), 8.30 (s, 1H), 7.58 (s, 1H), 1.36 (s, 9H).

Step 2: Synthesis of (E)-N-tert-butyl-2-chloro-5-(2-ethoxyvinyl)isonicotinamide

Into a 100-mL round-bottom flask purged and maintained with an inert atmosphere of nitrogen, was placed 5-bromo-N-tert-butyl-2-chloropyridine-4-carboxamide (2 g, 6.85 mmol) in dioxane (30 mL) and H₂O (6 mL), 2-[(E)-2-ethoxyethenyl]-4,4,5,5-tetramethyl-1,3,2-dioxaborolane (1.49 g, 7.53 mmol), Cs₂CO₃ (4.46 g, 13.7 mmol) and Pd(dppf)Cl₂ (501 mg, 685 µmop. The resulting solution was stirred for 2 h at 80° C. The resulting solution was diluted with water and extracted with EA, and then the organic layers combined, dried over anhydrous sodium sulfate and concentrated under vacuum. The residue was purified by FLASH with PE/EA (2:1). This resulted in 1.2 g (62.1%) of N-tert-butyl-2-chloro-5-[(E)-2-ethoxyethenyl]pyridine-4-carboxamide as a yellow solid.

Analytical Data: LC-MS: (ES, m/z)=283 [M+1]; 1H NMR (300 MHz, DMSO-d6) δ 8.55 (s, 1H), 8.20 (s, 1H), 7.35 (d, 1H, J=13.0 Hz), 7.28 (s, 1H), 5.79 (d, 1H, J=13.0 Hz), 3.90 (q, 2H, J=7.0 Hz), 1.35 (s, 9H), 1.26 (t, 3H, J=7.0 Hz).

Step 3: Synthesis of
7-chloro-2,6-naphthyridin-1(2H)-one

Into a 20-mL vial was placed N-tert-butyl-2-chloro-5-[(E)-2-ethoxyethenyl]pyridine-4-carboxamide (1.2 g, 4.24 mmol) in TFA (20 mL). The resulting solution was stirred overnight at 100° C. The resulting mixture was concentrated under vacuum. This resulted in 600 mg (91.5%) of 7-chloro-1,2-dihydro-2,6-naphthyridin-1-one as a red solid. The crude product was used directly for next step without any further purification.

Analytical Data: LC-MS: (ES, m/z)=181 [M+1].

Step 4: Synthesis of
4-bromo-7-chloro-2,6-naphthyridin-1(2H)-one

Into a 250-mL round-bottom flask was placed 7-chloro-1,2-dihydro-2,6-naphthyridin-1-one (3 g, 16.6 mmol) in DCM (40 mL) and NBS (3.54 g, 19.9 mmol). The resulting solution was stirred for 1 h at rt. The solid was collected by filtration. This resulted in 3 g (69.7%) of the title compound as a white solid.

Analytical Data: LC-MS: (ES, m/z)=261 [M+1]; H NMR (300 MHz, DMSO-d₆) δ 12.09 (s, 1H), 8.93 (s, 1H), 8.04 (s, 1H), 7.70 (d, 1H, J=6.0 Hz).

Step 5: Synthesis of
4-bromo-7-chloro-2,6-naphthyridin-1-yl
trifluoromethanesulfonate Into a 50-mL three-necked bottle was placed 4-bromo-7-chloro-1,2-dihydro-2,6-naphthyridin-1-one (1 g, 3.85 mmol) in DCM (15 mL) and TEA (777 mg, 7.70 mmol). The resulting mixture was cooled to −78° C., and then Tf₂O (4.34 g, 15.4 mmol) was added drop wise over 10 min. The resulting solution was stirred for 0.5 h at −78° C. Then the mixture was warmed to room temperature and stirred at this temperature for 0.5 h. The reaction was then quenched by the addition of 2 mL of water/ice, extracted with DCM, and then the organic layers combined, dried over anhydrous sodium sulfate and concentrated under vacuum. The residue was applied onto a silica gel column with EA/PE (0-10%). This resulted in 1 g (66.6%) of the title compound as a white solid.

Analytical Data: LC-MS: (ES, m/z)=393 [M+1]; 1H NMR (300 MHz, DMSO-d6) δ 9.47 (s, 1H), 8.78 (s, 1H), 8.14 (d, 1H, J=0.9 Hz).

Step 6: Synthesis of 4-bromo-7-chloro-1-iodo-2,6-naphthyridine

Into a 50-mL three-necked bottle was placed 4-bromo-7-chloro-2,6-naphthyridin-1-yl trifluoromethanesulfonate (500 mg, 1.27 mmol) in ACN (9 mL) and NaI (952 mg, 6.35 mmol). The resulting mixture was cooled to 0° C. and trifluoromethanesulfonate acid (381 mg, 2.54 mmol) in ACN (1 mL) was added drop wise over 10 min. The mixture was then stirred at rt for 1.5 h. After that, the resulting solution was extracted with EA, and then the organic layers combined, washed with brine, dried over anhydrous sodium sulfate and concentrated under vacuum. This resulted in 500 mg of the title compound as a dark solid. The crude compound was used directly for next without further purification.

Analytical Data: LC-MS: (ES, m/z)=369 [M+1].

Step 7: Synthesis of 4-bromo-7-chloro-1-(prop-1-en-2-yl)-2,6-naphthyridine

Into a 25-mL round-bottom flask purged and maintained with an inert atmosphere of nitrogen, was placed 4-bromo-7-chloro-1-iodo-2,6-naphthyridine (500 mg, 1.35 mmol) was added in dioxane (5 mL) and H₂O (1 mL), 4,4,5,5-tetramethyl-2-(prop-1-en-2-yl)-1,3,2-dioxaborolane (226 mg, 1.35 mmol), K₂CO₃ (372 mg, 2.7 mmol) and Pd(dppf)Cl₂ (0.99 mg, 0.135 mmol). The resulting solution was stirred for 2 h at 80° C. The resulting solution was extracted with EA, and then the organic layers combined, dried over anhydrous sodium sulfate and concentrated under vacuum. The residue was purified by Prep-TLC with PE/EA (8:1). This resulted in 200 mg (52.3%) of the title compound as a light-yellow oil.

Analytical Data: LC-MS: (ES, m/z)=285 [M+1].

Step 8: Synthesis of 4-bromo-7-chloro-1-isopropyl-2,6-naphthyridine

Into a 25-mL round-bottom flask purged and maintained with an inert atmosphere of hydrogen, was placed 4-bromo-7-chloro-1-(prop-1-en-2-yl)-2,6-naphthyridine (160 mg, 564 μmol) in EA (6 mL) and PtO₂ (166 mg, 733 μmol). The resulting solution was stirred for 3 h at rt. The solids were filtered out. The resulting mixture was concentrated under vacuum. This resulted in 100 mg (62.1%) of the title compound as a yellow solid.

Analytical Data: LC-MS: (ES, m/z)=287 [M+1].

Example C3: Synthesis of 4,7-dichloro-1-isopropylpyrido[4,3-d]pyridazine

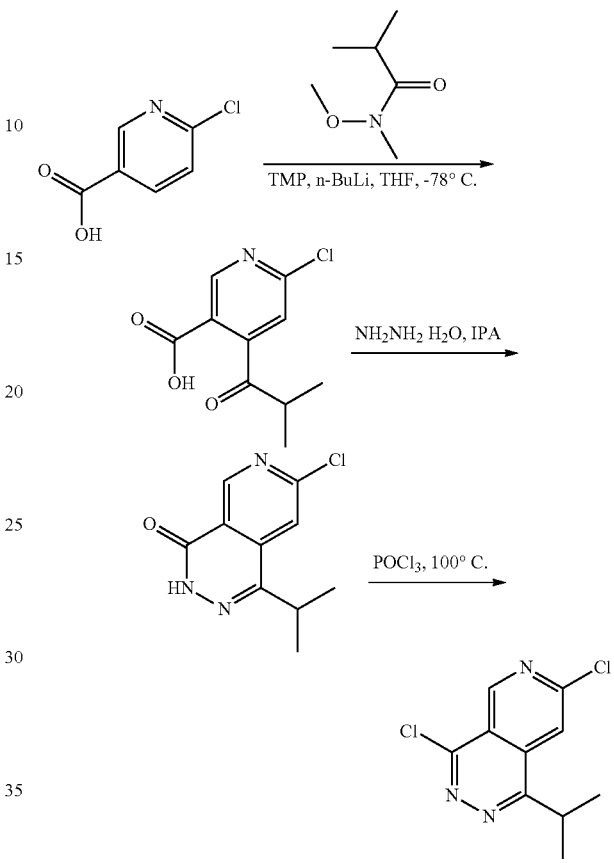

Step 1: Synthesis of 6-chloro-4-isobutyrylnicotinic Acid

To a stirred solution of n-BuLi (100 mL) in THF was added dropwise TMP (40.1 g, 285 mmol) at −78° C. The mixture was allowed to warm to 0° C. and stirred for 1 h and then recooled to −78° C. And then a solution of 6-chloropyridine-3-carboxylic acid (15 g, 95.2 mmol) in THF was added dropwise and the reaction was left to stir for 1.5 h. Then N-methoxy-N,2-dimethylpropanamide (37.3 g 285 mmol) was added and the reaction mixture was allowed to warm to rt and stirred for 4 h. The mixture was quenched by aq. NH₄Cl and PH was adjusted to 5-6 with citric acid, and then extracted with EA. The combined organic layers were washed with brine, dried over Na₂SO₄, filtered and concentrated under reduced pressure to get the target product as yellow oil without further purification.

Analytical Data: LC-MS: (ES, m/z)=228 [M+1].

Step 2: Synthesis of 7-chloro-1-isopropylpyrido[3,4-d]pyridazin-4(3H)-one

To a solution of 6-chloro-4-(2-methylpropanoyl)pyridine-3-carboxylic acid (11 g, 48.3 mmol) in IPA was added NH₂NH₂·H₂O (3.62 g, 72.4 mmol), the mixture was stirred at 70° C. for 3 h. The mixture was filtered and the solid was collected, the filtrate was concentrated to 10 mL, and then filtered. The solid was combined to get target product as yellow solid (6 g, crude).

Analytical Data: LC-MS: (ES, m/z)=224 [M+1].

Step 3: Synthesis of 4,7-dichloro-1-isopropylpyrido[4,3-d]pyridazine

To a solution of POCl$_3$ (5 mL) was added 7-chloro-1-(propan-2-yl)-3H,4H-pyrido[3,4-d]pyridazin-4-one (100 mg, 447 umol). The mixture was stirred overnight at 100° C. The mixture was concentrated and the product was used directly without further purification.

Analytical Data: LC-MS: (ES, m/z)=242 [M+1].

Example C4: Synthesis of 8-bromo-3-chloro-5-isopropylisoquinoline

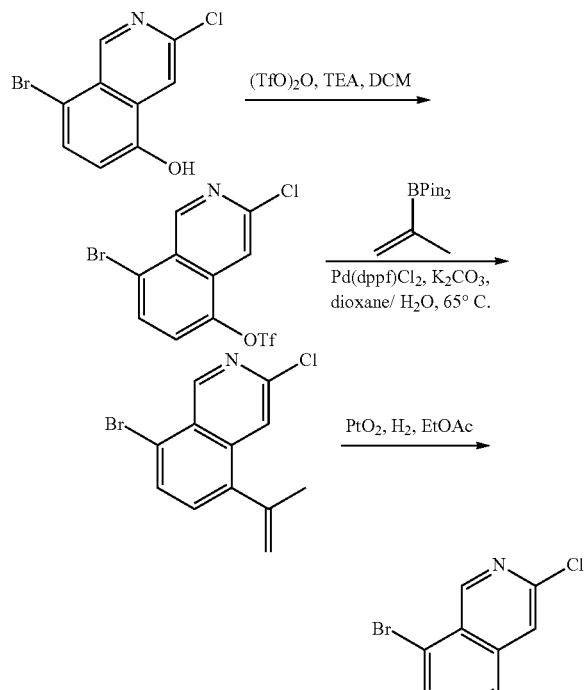

Step 1: Synthesis of 8-bromo-3-chloroisoquinolin-5-yl trifluoromethanesulfonate

Trifluoromethanesulfonyl trifluoromethanesulfonate (45.7 g, 162 mmol) was added dropwise to 8-bromo-3-chloroisoquinolin-5-ol (14 g, 54.1 mmol) and TEA (21.8 g, 216 mmol) in DCM (400 mL) at −60° C. The resulting mixture was warmed to room temperature naturally and stirred at rt for 1 h. The mixture was concentrated under vacuum. The residue was purified by a silica gel column with PE:EA=5:1 to afford 18 g (85%) the title compound as a white solid.

Analytical Data: LC-MS: (ES, m/z)=392 [M+1]; 1H NMR (400 MHz, DMSO-d6) δ 9.46 (d, 1H, J=0.8 Hz), 8.20 (d, 1H, J=8.3 Hz), 8.02 (d, 1H, J=8.4 Hz), 7.93 (d, 1H, J=0.7 Hz).

Step 2: Synthesis of 8-bromo-3-chloro-5-(prop-1-en-2-yl)isoquinoline

The mixture of K$_2$CO$_3$ (6 g, 43.5 mmol), 8-bromo-3-chloroisoquinolin-5-yl trifluoromethanesulfonate (17 g, 43.5 mmol), 4,4,5,5-tetramethyl-2-(prop-1-en-2-yl)-1,3,2-dioxaborolane (7.30 g, 43.5 mmol) and Pd(dppf)Cl$_2$·CH$_2$Cl$_2$ (2.83 g, 3.48 mmol) in dioxane/H$_2$O (200/20 mL) was stirred for 3 h at 45° C. The mixture was diluted with 500 mL of EA and washed with brine 200 mL*2. The organic layer was dried with Na$_2$SO$_4$ and concentrated under vacuum. The residue was purified by a silica gel column with PE:EA=20:1 to afford 8.0 g (67%) the title compound as an off-white solid.

Analytical Data: LC-MS: (ES, m/z)=282 [M+1].

Step 3: Synthesis of 8-bromo-3-chloro-5-isopropylisoquinoline

PtO$_2$ (1.7 g 7.04 mmol) and 8-bromo-3-chloro-5-(prop-1-en-2-yl)isoquinoline (7.1 g, 25.1 mmol) in EA (300 mL) were stirred under an atmosphere of H$_2$ balloon at rt and stirred for 1 h. The solid was filtered out. The mother solvent was concentrated under vacuum. The crude product was purified by a silica gel column with PE:EA=10:1 to get 6.7 g (93%) the title compound as a brown solid.

Analytical Data: LC-MS: (ES, m/z)=284 [M+1].

Example C5: Synthesis of rac-2-(8-bromo-3-chloroisoquinolin-5-yl)propan-1-ol

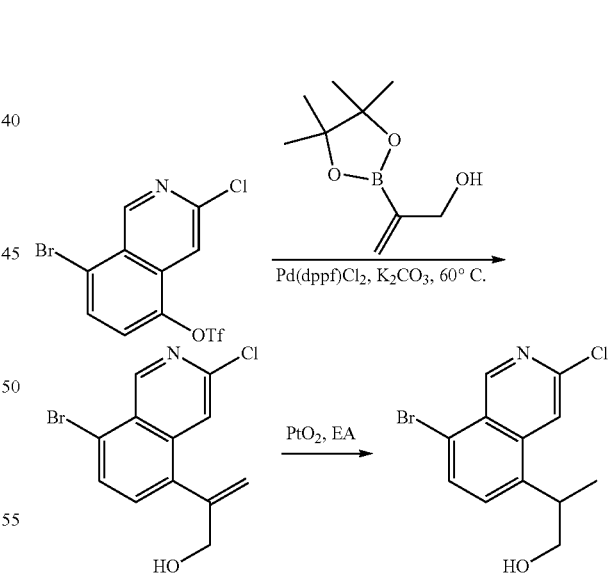

Step 1: Synthesis of 2-(8-bromo-3-chloroisoquinolin-5-yl)prop-2-en-1-ol

To a solution of 8-bromo-3-chloroisoquinolin-5-yl trifluoromethanesulfonate (5 g, 12.8 mmol, form step 1 of Example C4) in 1,4-dioxane/H$_2$O was added 2-(4,4,5,5-tetramethyl-1,3,2-dioxaborolan-2-yl)prop-2-en-1-ol (2.35 g, 12.8 mmol), K$_2$CO$_3$ (1.76 g, 12.8 mmol) and Pd(dPPf)Cl$_2$ (467 mg, 0.641 mmol). The resulting solution was stirred for 2 h at 60° C. The resulting solution was diluted with 100 mL of water and extracted with 2×100 mL of EA. The organic phase was washed with brine, dried, and concentrated. The residue was purified by Flash with PE:EA (1:1). This resulted in 2.1 g (54.9%) of the title compound as white solid.

Analytical Data: LC-MS: (ES, m/z)=298 [M+1].

Step 2: Synthesis of rac-2-(8-bromo-3-chloroisoquinolin-5-yl)propan-1-ol

The mixture of 2-(8-bromo-3-chloroisoquinolin-5-yl)prop-2-en-1-ol (2 g, 6.69 mmol) and PtO$_2$ (454 mg, 0.05 mmol) in EA (50 mL) was stirred at rt for 2 h at H$_2$ atmosphere. The resulting mixture was filtered. The filtrate was concentered under vacuum. The product was purified by Flash with PE:EA (10:1). This resulted in 1.8 g (90%) of the title compound as a yellow solid.

Analytical Data: LC-MS: (ES, m/z)=300 [M+1].

Example C6: Synthesis of 8-bromo-3-chloro-5-methylisoquinoline

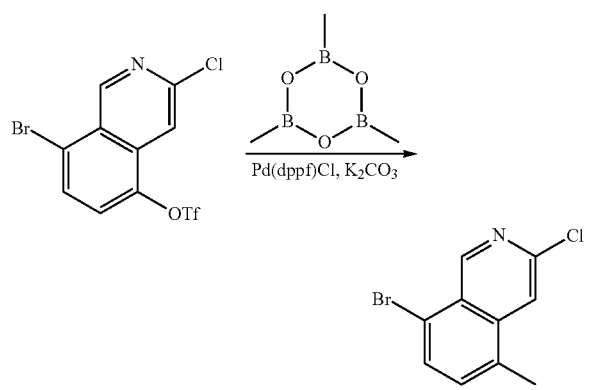

The mixture of 8-bromo-3-chloroisoquinolin-5-yl trifluoromethanesulfonate (500 mg, 1.28 mmol, from step 1 of Example C1), trimethyl-1,3,5,2,4,6-trioxatriborinane (64.2 mg, 512 μmol), Pd(dppf)Cl$_2$ (46.9 mg, 64.0 μmol) and K$_2$CO$_3$ (176 mg, 1.28 mmol) in mixture solvent (dioxane:H$_2$O=5:1, 4.8 mL) was stirred at 40° C. for 16 h under N$_2$ atmosphere. The resulting solution was concentrated under vacuum. The residue was purified by Prep-TLC with DCM/MeOH (20/1) to afford 100 mg of the title compound as an off-white solid.

Analytical Data: LC-MS: (ES, m/z)=258 [M+1].

Example C7: Synthesis of 8-bromo-3-chloroisoquinoline

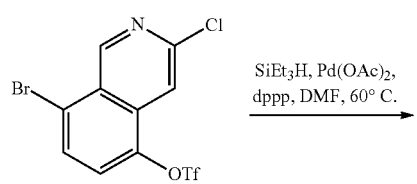

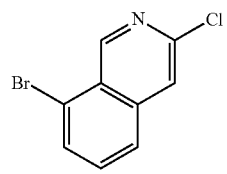

The mixture of 8-bromo-3-chloroisoquinolin-5-yl trifluoromethanesulfonate (100.00 mg, 0.256 mmol, 1 equiv., from step 1 of Example C4), [3-(diphenylphosphanyl)propyl]diphenylphosphane (2.11 mg, 0.005 mmol, 0.02 equiv.), (acetyloxy)palladio acetate (1.15 mg, 0.005 mmol, 0.02 equiv.), and triethylsilane (74.43 mg, 0.640 mmol, 2.5 equiv) in DMF (3 mL) was stirred for 1 h at 60° C. under N$_2$ atmosphere. Water was added and extracted with EA and concentrated. The residue was applied onto a Prep-TLC with DCM/MeOH (10:1). This resulted in 50 mg (80.5%) of the title compound as a light-yellow solid.

Analytical Data: LC-MS: (ES, m/z)=242 [M+1].

Example C8: Synthesis of rac-3-chloro-5-(1-fluoropropan-2-yl)-8-(3-(methylsulfonylmethyl)azetidin-1-yl)isoquinoline

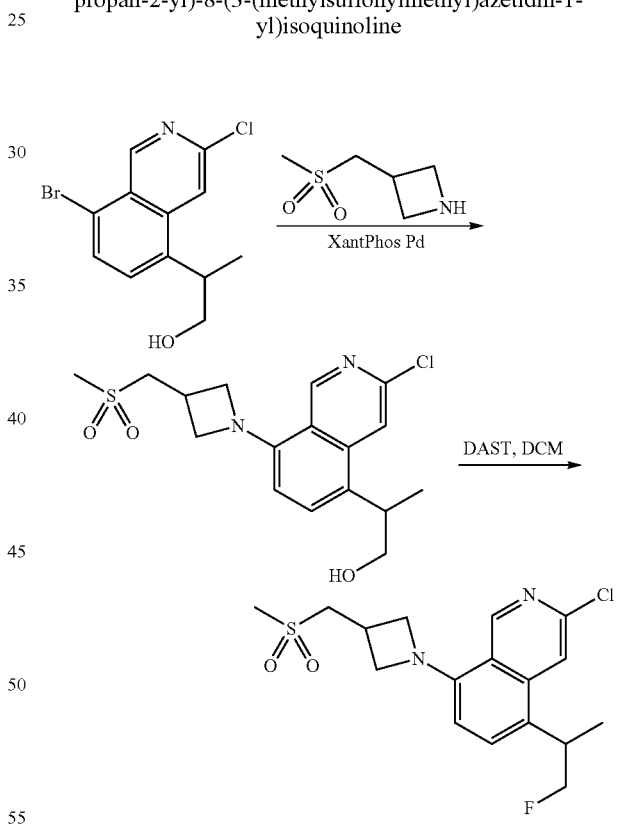

Step 1: Synthesis of rac-2-{3-chloro-8-[3-(methanesulfonylmethyl)azetidin-1-yl]isoquinolin-5-yl}propan-1-ol To a solution of rac-2-(8-bromo-3-chloroisoquinolin-5-yl)propan-1-ol (150 mg, 0.4990 mmol, from Example C5) in 1,4-dioxane was added 3-(methanesulfonylmethyl)azetidine (74.4 mg, 0.499 mmol), Cs$_2$CO$_3$ (325 mg, 0.998 mmol) and XantPhos Pd G4 (44.3 mg, 49.9 umol) under nitrogen. The mixture was stirred at 100° C. for 3 h. The resulting solution was diluted with 20 mL of water and extracted with 2×20 mL of EA. The organic phase was washed with brine, dried and concentrated under vacuum. The crude product was purified by Prep-TLC (DCM: MeOH=10:1). This resulted in 100 mg (54.3%) of the title compound as yellow solid.

Analytical Data: LC-MS: (ES, m/z)=369 [M+1].

Step 2: Synthesis of rac-bn3-chloro-5-(1-fluoropropan-2-yl)-8-(3-(methylsulfonylmethyl)azetidin-1-yl)isoquinoline To a solution of 2-{3-chloro-8-[3-(methanesulfonylmethyl)azetidin-1-yl]isoquinolin-5-yl}propan-1-ol (100 mg, 0.2710 mmol) in DCM was added DAST (87.3 mg, 0.542 mmol) at 0° C. The mixture was stirred at 0° C. for 3 h. The reaction solution was quenched with water and extracted with 2×20 mL of EA. The organic phase was washed with brine, dried and concentrated under vacuum. The crude product was purified by Prep-TLC (DCM:MeOH=15:1). This resulted in 80 mg (79.9%) of 3 the title compound as yellow solid.

Analytical Data: LC-MS: (ES, m/z)=371 [M+1].

Example C9: Synthesis of 8-bromo-3-chloro-5-ethoxyisoquinoline

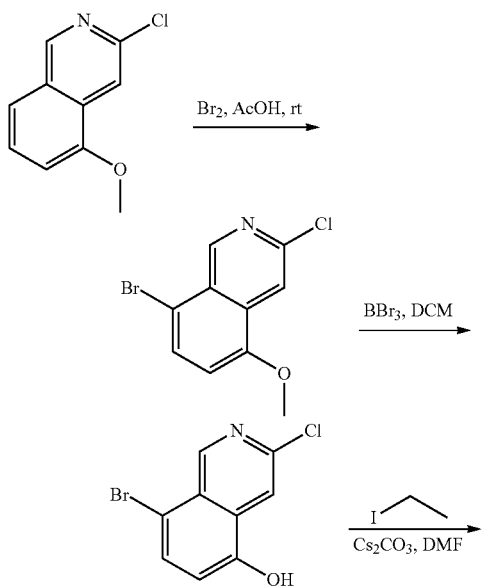

Step 1: Synthesis of 8-bromo-3-chloro-5-methoxyisoquinoline

To a mixture of 3-chloro-5-methoxyisoquinoline (2 g, 10.3 mmol) in AcOH (20 mL) was added a solution of dibromine (1.80 g, 11.3 mmol) dissolved in 10 mL AcOH over 10 min. The mixture was stirred overnight at rt. The mixture was concentrated and the residue was slowly poured into a solution of $K_2CO_3$ (5 g in 100 mL $H_2O$) with rapid stirring. Then the mixture was extracted with DCM and concentrated in reduced pressure to get the title compound 2.5 g (89.2%) as a yellow solid.

Analytical Data: LC-MS: (ES, m/z)=272 [M+1]. 1H-NMR (300 MHz, 6d-DMSO) δ ppm 9.21 (s, 1H), 8.09-7.81 (m, 2H), 7.20 (d, J=8.3 Hz, 1H), 4.00 (s, 3H).

Step 2: Synthesis of 8-bromo-3-chloroisoquinolin-5-ol

To a solution of 8-bromo-3-chloro-5-methoxyisoquinoline (2 g, 7.33 mmol) in DCM was added tribromoborane (5.48 g, 21.9 mmol). The resulting solution was stirred for 2 h at rt. The reaction mixture was slowly poured into ice/water with rapid stirring. The precipitation collected by filtration. This is resulted in 1.8 g (89%) of the title compound as a yellow solid.

Analytical Data: LC-MS: (ES, m/z)=258 [M+1].

Step 3: Synthesis of 8-bromo-3-chloro-5-ethoxyisoquinoline

To a solution of 8-bromo-3-chloroisoquinolin-5-ol (900 mg, 3.48 mmol) in DMF (20 mL) was added iodoethane (1.08 g, 6.96 mmol) and $Cs_2CO_3$ (3.39 g, 10.4 mmol). The resulting solution was stirred for 3 h at 100° C. The resulting solution was cooled to rt and diluted with water and extracted with EA. The organic phase was concentrated under vacuum and purified by chromatography with PE:EA (1:1). This resulted in 800 mg (80.2%) of the title compound as yellow solid.

Analytical Data: LC-MS: (ES, m/z)=286 [M+1]; 1H-NMR (400 MHz, 6d-DMSO) δ ppm 9.23 (d, 1H, J=0.8 Hz), 8.03 (d, 1H, J=0.8 Hz), 7.91 (d, 1H, J=8.3 Hz), 7.20 (d, 1H, J=8.4 Hz), 4.25 (q, 2H, J=7.0 Hz), 1.47 (t, 3H, J=6.9 Hz).

Example C10: Synthesis of 3-chloro-8-(3-(cyclopropylsulfonylmethyl)azetidin-1-yl)-5-isopropylisoquinoline

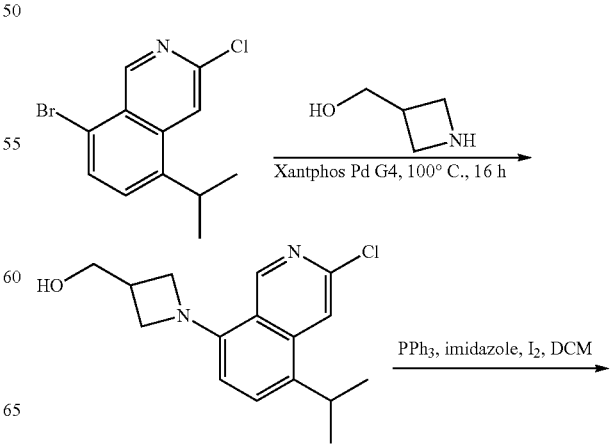

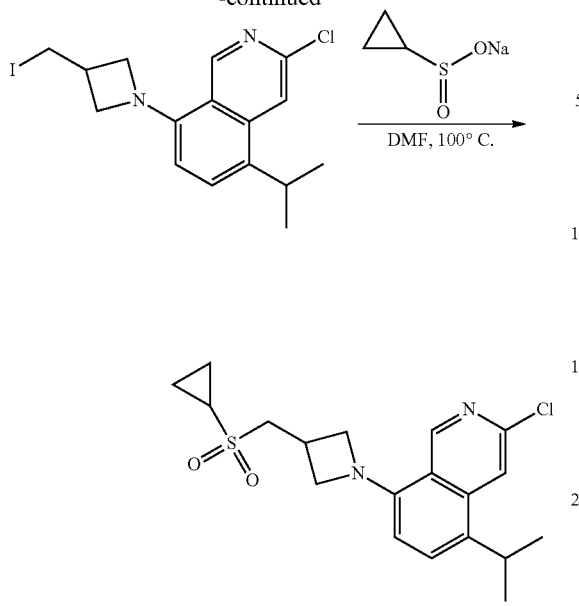

Step 1: Synthesis of (1-(3-chloro-5-isopropylisoquinolin-8-yl)azetidin-3-yl)methanol A mixture of 8-bromo-3-chloro-5-(propan-2-yl)isoquinoline (Example C4, 300 mg, 1.05 mmol, Example C4), (azetidin-3-yl)methanol hydrochloride (129 mg, 1.05 mmol), XantPhos Pd G4 (175 mg, 210 μmop, Cs$_2$CO$_3$ (684 mg, 2.10 mmol) in dioxane (25 mL) stirred at 100° C. for 16 h. The reaction was purified by preparative TLC (DCM:MeOH=15:1) to afford the title compound (230 mg, 76%) as a yellow solid.

Analytical Data: LC-MS: (ES, m/z)=291 [M+1].

Step 2: Synthesis of 3-chloro-8-(3-(iodomethyl)azetidin-1-yl)-5-isopropylisoquinoline A mixture of {1-[3-chloro-5-(propan-2-yl)isoquinolin-8-yl]azetidin-3-yl}methanol (220 mg, 756 μmop, triphenylphosphine (296 mg, 1.13 mmol), imidazole (102 mg, 1.51 mmol) and iodine (230 mg, 907 μmol) in DCM (25 mL) was stirred at rt for 2 h. The solvent was removed and the reside was purified by preparative TLC (PE:EA=20:1) to afford the title compound (190 mg, 62%) as a yellow solid.

Analytical Data: LC-MS: (ES, m/z)=401 [M+1].

Step 3: Synthesis of 3-chloro-8-(3-(cyclopropylsulfonylmethyl)azetidin-1-yl)-5-isopropylisoquinoline A mixture of 3-chloro-8-[3-(iodomethyl)azetidin-1-yl]-5-(propan-2-yl)isoquinoline (100 mg, 249 μmop, sodium cyclopropanesulfinate (127 mg, 996 μmol) in DMF (15 mL) was stirred at 80° C. for 2 h. The solvent removed and residue was purified by preparative TLC (PE:EA=2:1) to afford the title compound (100 mg, 94.5%) as a yellow solid.

Analytical Data: LC-MS: (ES, m/z)=379 [M+1].

Example C11: Synthesis of 8-bromo-3-chloro-5-cyclopropylisoquinoline

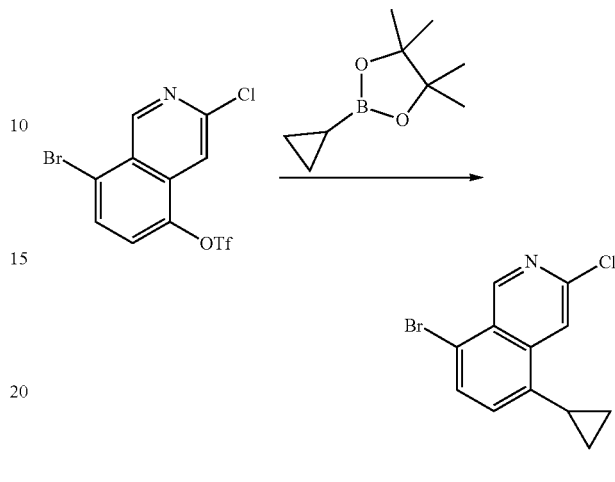

To a solution of 8-bromo-3-chloroisoquinolin-5-yl trifluoromethanesulfonate (240 mg, 614 μmol) in dioxane/H$_2$O (10 mL/2 mL) was added 2-cyclopropyl-4,4,5,5-tetramethyl-1,3,2-dioxaborolane (123 mg, 736 μmol) and K$_2$CO$_3$ (168 mg, 1.22 mmol) and Pd(dppf)Cl$_2$ (50.1 mg, 61.4 μmol). The mixture was stirred at 80° C. for 16 h under N$_2$ atmosphere. The mixture was added water and extracted with EA. The organic phase was concentrated and purified by FLASH (50% EA in PE) to give the title compound of 90 mg (52%) as yellow solid.

Analytical Data: LC-MS: (ES, m/z)=284 [M+1].

Example C12: Synthesis of 3-chloro-5-isopropyl-7-methyl-8-(3-(methylsulfonylmethyl)azetidin-1-yl)isoquinoline

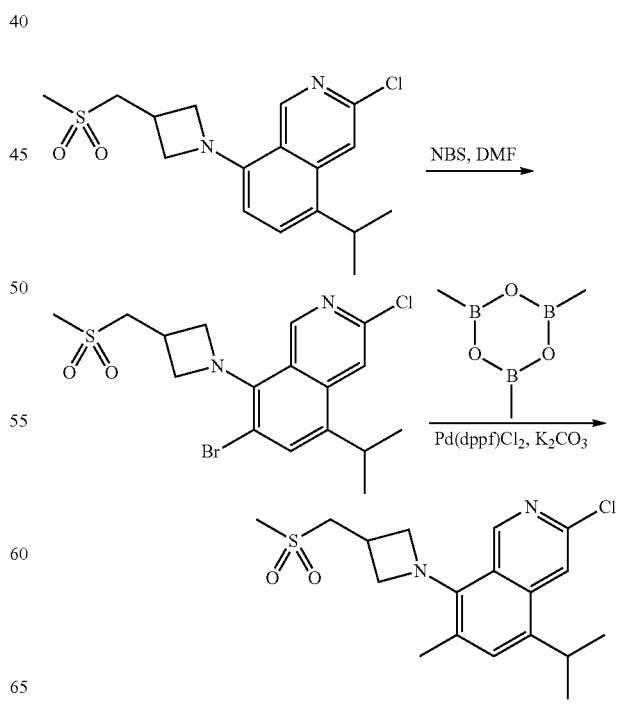

Step 1: Synthesis of 7-bromo-3-chloro-5-isopropyl-8-(3-(methylsulfonylmethyl)azetidin-1-yl)isoquinoline To a solution of 3-chloro-8-[3-(methanesulfonylmethyl)azetidin-1-yl]-5-(propan-2-yl)isoquinoline (150 mg, 425 µmol) in DMF (10 mL) were added NBS (60.1 mg, 340 µmol). The solution was stirred at rt for 16 h. The solvent was removed and the residue was purified by Prep-TLC (5% MeOH in DCM) to give the title compound of 170 mg (81.7%) as yellow solid.
Analytical Data: LC-MS: (ES, m/z)=431 [M+1].

Step 2: Synthesis of 3-chloro-5-isopropyl-7-methyl-8-(3-(methylsulfonylmethyl)azetidin-1-yl)isoquinoline The mixture of 7-bromo-3-chloro-8-[3-(methanesulfonylmethyl)azetidin-1-yl]-5-(propan-2-yl)isoquinoline (75 mg, 173 µmol), trimethyl-1,3,5,2,4,6-trioxatriborinane (8.68 mg, 69.2 µmol), K₂CO₃ (23.8 mg, 173 µmol) and Pd(dppf)Cl₂ (14.1 mg, 17.3 µmol) in dioxane/H₂O (7 mL/2 mL) was stirred for 3 h at 80° C. The mixture was extracted with EA. The organic concentrated and was purified by FLASH (5% MeOH in DCM) to give 55 mg (87%) of the title compound of as yellow solid.
Analytical Data: LC-MS: (ES, m/z)=367 [M+1].

Example C13: Synthesis of 3-chloro-7-fluoro-5-isopropyl-8-(3-(methylsulfonylmethyl)azetidin-1-yl)isoquinoline

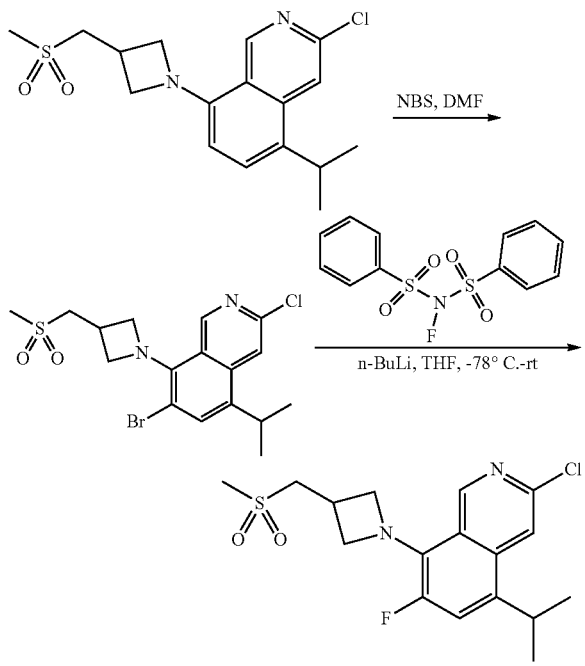

Step 1: Synthesis of 7-bromo-3-chloro-5-isopropyl-8-(3-(methylsulfonylmethyl)azetidin-1-yl)isoquinoline NBS (163 mg, 918 µmol) was added batchwise to 3-chloro-8-[3-(methanesulfonylmethyl)azetidin-1-yl]-5-(propan-2-yl)isoquinoline (360 mg, 1.02 mmol) in DMF (20 mL) at rt. The resulting mixture was stirred at rt for 16 h. The mixture was diluted with EA and washed with brine. The organic layer was dried over Na₂SO₄ and concentrated under vacuum. The residue was purified by a Pre-TLC with PE:EA=1:1 to afford 350 mg the title compound as a yellow solid.
Analytical Data: LC-MS: (ES, m/z)=431 [M+1].

Step 2: Synthesis of 3-chloro-7-fluoro-5-isopropyl-8-(3-(methylsulfonylmethyl)azetidin-1-yl)isoquinoline n-BuLi (2.5 M, 2.29 mmol, 916 µL) was dropwise to 7-bromo-3-chloro-8-[3-(methanesulfonylmethyl)azetidin-1-yl]-5-(propan-2-yl)isoquinoline (330 mg, 764 µmol) and N-(benzenesulfonyl)-N-fluorobenzenesulfonamide (479 mg, 1.52 mmol) in THF (20 mL) at −78° C. under N₂ atmosphere. The resulting mixture was stirred at rt for 1 h. The mixture was quenched with H₂O, diluted with EA and washed with brine. The organic layer was dried over Na₂SO₄ and concentrated under vacuum. The residue was purified by a Pre-TLC with DCM:MeOH=30:1 to afford 80 mg the title compound as a yellow solid.
Analytical Data: LC-MS: (ES, m/z)=371 [M+1].

Example C14: Synthesis of 3-chloro-8-((2R,3S)-2-methyl-3-(methylsulfonylmethyl)azetidin-1-yl)-5-(trifluoromethyl)isoquinoline

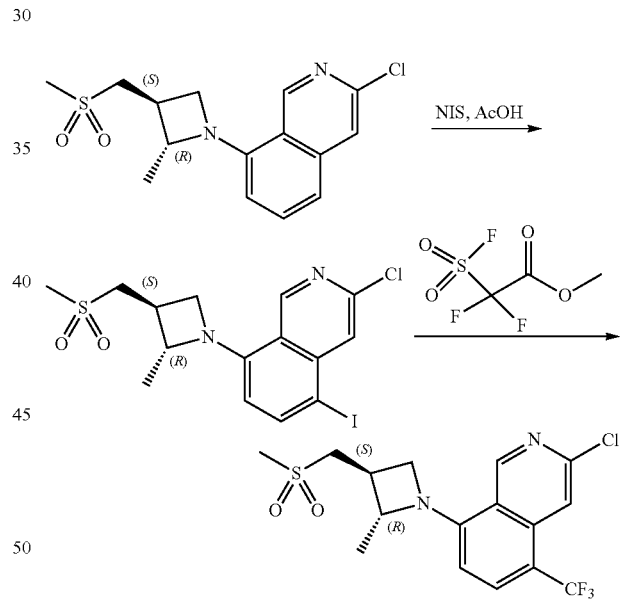

Step 1: Synthesis of 3-chloro-5-iodo-8-((2R,3S)-2-methyl-3-(methylsulfonylmethyl)azetidin-1-yl)isoquinoline To a solution of 3-chloro-8-[(2R,3S)-3-(methanesulfonylmethyl)-2-methylazetidin-1-yl]isoquinoline (100 mg, 307 umol) in AcOH (5 mL) was added iodo(sulfanyl)amine (58.6 mg, 337 umol) and stirred at rt for 1 h. Water was added and the reaction was extracted with EA. The organic phase was concentrated and purified by preparative TLC (DCM:MeOH=15:1) to give product (100 mg) as yellow solid.
Analytical Data: LC-MS: (ES, m/z)=451 [M+1].

Step 2: Synthesis of 3-chloro-8-((2R,3S)-2-methyl-3-(methylsulfonylmethyl)azetidin-1-yl)-5-(trifluoromethyl)isoquinoline The mixture of 3-chloro-5-iodo-8-[(2R,3S)-3-(methanesulfonylmethyl)-2-methylazetidin-1-yl]isoquinoline (100 mg, 221 umol), methyl 2,2-difluoro-2-(fluorosulfonyl)acetate (211 mg, 1.10 mmol) and CuI (4.18 mg, 22.0 umol) in NMP (5 mL) was heated to 80° C. for 2 h under $N_2$ atmosphere. The reaction was diluted with water and extracted with EA. The organic layer was concentrated and purified by preparative TLC (EA:PE=2:1) to give product 40 mg as a light-yellow solid.

Analytical Data: LC-MS: (ES, m/z)=393 [M+1].

Example C15: Synthesis of 2-(6-chloro-1-((2R,3S)-2-methyl-3-(methylsulfonylmethyl)azetidin-1-yl)-2,7-naphthyridin-4-yl)propan-1-ol

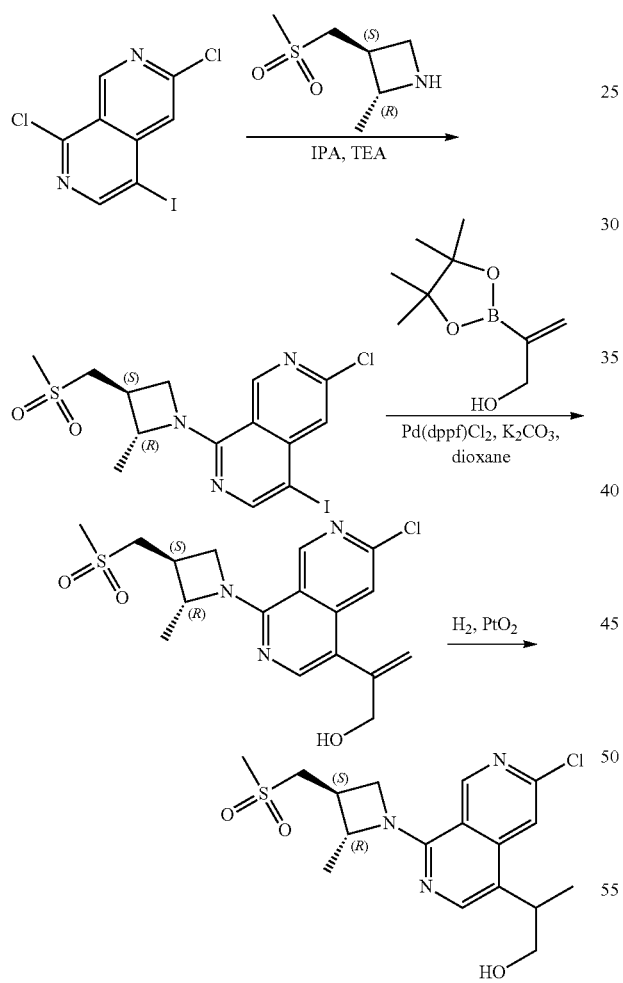

Step 1: Synthesis of 6-chloro-4-iodo-1-((2R,3S)-2-methyl-3-(methylsulfonylmethyl)azetidin-1-yl)-2,7-naphthyridine The mixture of 1,6-dichloro-4-iodo-2,7-naphthyridine (300 mg, 923 μmol), (2R,3S)-3-(methanesulfonylmethyl)-2-methylazetidine (Example A4, 179 mg, 1.10 mmol) and TEA (186 mg, 1.84 mmol) in IPA (15 mL) was stirred at 100° C. for 3 h. The mixture was diluted with EA and washed with brine. The organic layer was dried with $Na_2SO_4$ and concentrated under vacuum. The residue was purified by TLC (PE:EA=1:1). This resulted in 300 mg (72.1%) the title compound as a light-yellow solid.

Analytical Data: LC-MS: (ES, m/z)=452 [M+1].

Step 2: Synthesis of 2-(6-chloro-1-((2R,3S)-2-methyl-3-(methylsulfonylmethyl)azetidin-1-yl)-2,7-naphthyridin-4-yl)prop-2-en-1-ol Into a 50-mL sealed tube was placed 6-chloro-4-iodo-1-[(2R,3S)-3-(methanesulfonylmethyl)-2-methylazetidin-1-yl]-2,7-naphthyridine (200 mg, 663 μmol), 2-(4,4,5,5-tetrameth (122 mg, 663 μmol), $K_2CO_3$ (122 mg, 884 μmol) and Pd(dppf)Cl$_2$ (64.6 mg, 88.3 μmol) in dioxane (20 mL) and $H_2O$ (4 mL) under $N_2$ atmosphere. The resulting solution was stirred at 85° C. for 6 h. The mixture was diluted with EA and washed with brine. The organic layer was dried with $Na_2SO_4$ and concentrated under vacuum. The residue was purified by Flash Column Silica-CS (DCM:MeOH=10:1). This resulted in 150 mg (89.2%) of the title compound as a white solid.

Analytical Data: LC-MS: (ES, m/z)=382 [M+1].

Step 3: Synthesis of 2-(6-chloro-1-((2R,3S)-2-methyl-3-(methylsulfonylmethyl)azetidin-1-yl)-2,7-naphthyridin-4-yl)propan-1-ol To a solution of 2-{6-chloro-1-[(2R,3S)-3-(methanesulfonylmethyl)-2-methylazetidin-1-yl]-2,7-naphthyridin-4-yl}prop-2-en-1-ol (100 mg, 261 μmol) in EA (30 mL) was added PtO$_2$ (29.5 mg, 130 μmol). Then the mixture was hydrogenated under hydrogen balloon at rt for 1 h. The mixture was filtrated and concentrated. The residue was purified by TLC (DCM:MeOH=10:1). This resulted in 110 mg of the title compound as a yellow solid.

Analytical Data: LC-MS: (ES, m/z)=384 [M+1].

Example C16: Synthesis of 3-chloro-5,7-difluoro-8-(3-((methylsulfonyl)methyl)azetidin-1-yl)isoquinoline

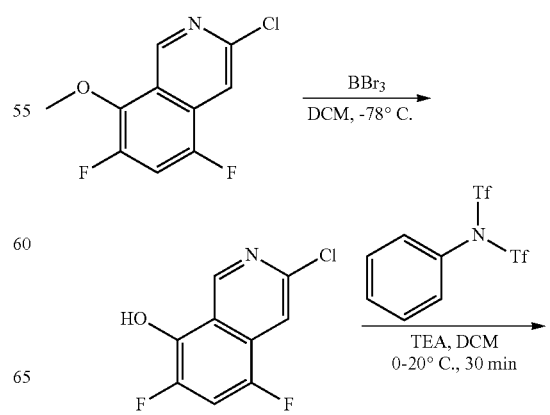

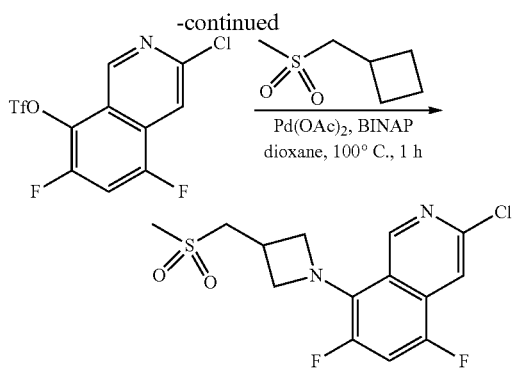

Step 1: Synthesis of 3-chloro-5,7-difluoroisoquinolin-8-ol

To the solution of 3-chloro-5,7-difluoro-8-methoxy-isoquinoline (300 mg, 1.31 mmol, 1 equiv.) in DCM (5 mL) was added BBr$_3$ (982 mg, 3.92 mmol, 3 equiv.) at −78° C., then the mixture was stirred at 25° C. for 2 h. The mixture was quenched by 10 mL of water, some solid precipitated. The solid was collected by filtration, washed with 10 mL of water. This resulted in 0.22 g (77%) of the title compound as a brown solid.

Analytical Data: LC-MS: (ES, m/z): RT=0.645 min, LCMS: m/z=215.8 [M+1].

Step 2: Synthesis of 3-chloro-5,7-difluoroisoquinolin-8-yl trifluoromethanesulfonate The mixture of 3-chloro-5,7-difluoro-isoquinolin-8-ol (200 mg, 923 μmol, 1 equiv), 1,1,1-trifluoro-N-phenyl-N-(trifluoromethylsulfonyl)methanesulfonamide (994 mg, 2.78 mmol, 3 equiv) and TEA (282 mg, 2.78 mmol, 3 equiv) in DCM (5 mL) was stirred at 20° C. for 2 h. The mixture was concentrated, the residue was purified by silica gel chromatography (from PE to PE/EA=50/1). This resulted in 0.26 g (76%) of the title compound as a white solid.

Analytical Data: LC-MS: (ES, m/z): RT=0.966 min, LCMS: m/z=348.0 [M+1]. $^1$H NMR (400 MHz, DMSO-d$_6$) δ=9.30 (s, 1H), 8.33 (dd, J=9.6, 10.4 Hz, 1H), 8.28 (s, 1H).

Step 3: Synthesis of 3-chloro-5,7-difluoro-8-(3-((methylsulfonyl)methyl)azetidin-1-yl)isoquinoline To the mixture of (3-chloro-5,7-difluoro-8-isoquinolyl) trifluoromethanesulfonate (140 mg, 403 μmol, 1 equiv), 3-(methylsulfonylmethyl)azetidine (159 mg, 604 μmol, 1.50 equiv, TFA salt) and Cs$_2$CO$_3$ (393 mg, 1.21 mmol, 3 equiv.) in toluene (1 mL) was added (1E,4E)-1,5-diphenylpenta-1,4-dien-3-one; palladium (23.2 mg, 40.3 μmol, 0.1 equiv.), BINAP (201 mg, 322 μmol, 0.8 equiv.) and Pd(OAc)$_2$ (18.1 mg, 80.5 μmol, 0.2 equiv), the mixture was degassed and purged with N$_2$ for 3 times, and then the mixture was stirred at 90° C. for 2 h. The reaction mixture was filtered and concentrated under reduced pressure to give a residue. The residue was purified by silica gel chromatography (Petroleum ether: Ethyl acetate=20:1 to 1:1). This resulted in 10 mg (7%) of the title compound as a yellow solid.

Analytical Data: LC-MS: (ES, m/z): RT=0.900 min, LCMS: m/z=347.1 [M+1]. $^1$H NMR (400 MHz, CDCl$_3$) δ=9.22 (s, 1H), 7.81 (s, 1H), 4.72-4.65 (m, 1H), 4.30-4.25 (m, 1H), 3.45-3.30 (m, 6H).

Example 1, Compound 55: Synthesis of (3S,4R)-3-fluoro-1-(4-(5-isopropyl-8-(3-(methylsulfonylmethyl)azetidin-1-yl)isoquinolin-3-ylamino)pyrimidin-2-yl)-3-methylpiperidin-4-ol

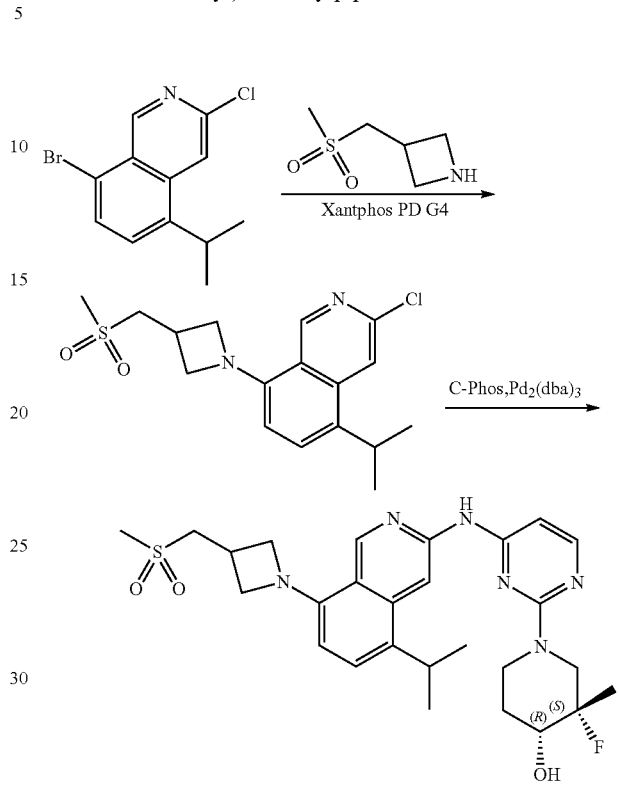

Step 1: Synthesis of 3-chloro-5-isopropyl-8-(3-(methylsulfonylmethyl)azetidin-1-yl)isoquinoline The mixture of Cs$_2$CO$_3$ (8.21 g, 25.2 mmol), 3-(methanesulfonylmethyl)azetidin-1-ium trifluoromethanesulfonate (6.91 g, 23.1 mmol), 8-bromo-3-chloro-5-(propan-2-yl)isoquinoline (from Example C4, 6.0 g, 21.0 mmol) and XantPhos Pd G3 (1.86 g, 2.10 mmol) in dioxane (100 mL) was stirred at 100° C. for 16 h under N$_2$ atmosphere. The mixture was diluted with EA (200 mL) and washed with brine. The organic layer was dried over Na$_2$SO$_4$ and concentrated under vacuum. The residue was purified by FLASH (DCM:MeOH=30:1) to afford 5.0 g (67%) of the title compound as a yellow solid.

Analytical Data: LC-MS: (ES, m/z)=353 [M+1].

Step 2: Synthesis of (3S,4R)-3-fluoro-1-(4-(5-isopropyl-8-(3-(methylsulfonylmethyl)azetidin-1-yl)isoquinolin-3-ylamino)pyrimidin-2-yl)-3-methylpiperidin-4-ol Cs$_2$CO$_3$ (3.81 g, 11.7 mmol) was added to C-Phos (627 mg, 1.07 mmol, 2-Dicyclohexylphosphino-2',6'-bis(N,N-dimethylamino)biphenyl), Pd$_2$(dba)$_3$·CHCl$_3$ (1.42 g, 1.07 mmol), 3-chloro-8-[3-(methanesulfonylmethyl)azetidin-1-yl]-5-(propan-2-yl)isoquinoline (3.8 g, 10.7 mmol) and (3S,4R)-1-(4-aminopyrimidin-2-yl)-3-fluoro-3-methylpiperidin-4-ol (2.64 g, 11.7 mmol from Example B1) in dioxane (100 mL). The mixture was stirred at 100° C. for 16 h under N$_2$ atmosphere. The mixture was diluted with EA (500 mL) and washed with brine. The organic layer was dried over Na₂SO₄ and concentrated under vacuum. The crude product was purified by Prep-HPLC Column: XBridge Prep OBD C18 Column 30×150 mm 5 um; Mobile Phase A: Water (10 MMOL/L NH₄HCO₃), Mobile Phase B: ACN; Flow rate: 60 mL/min; Gradient: 41% B to 90% B in 10 min; 254; 220 nm to get 2.80 g (70%) of the title compound as a yellow solid.

Example 2, Compound 52: Synthesis of (3S,4R)-1-(4-(5-isopropyl-8-(3-(methylsulfonylmethyl)azetidin-1-yl)isoquinolin-3-ylamino)pyrimidin-2-yl)-4-methoxypiperidin-3-ol or (3R,4S)-1-(4-(5-isopropyl-8-(3-(methylsulfonylmethyl)azetidin-1-yl)isoquinolin-3-ylamino)pyrimidin-2-yl)-4-methoxypiperidin-3-ol

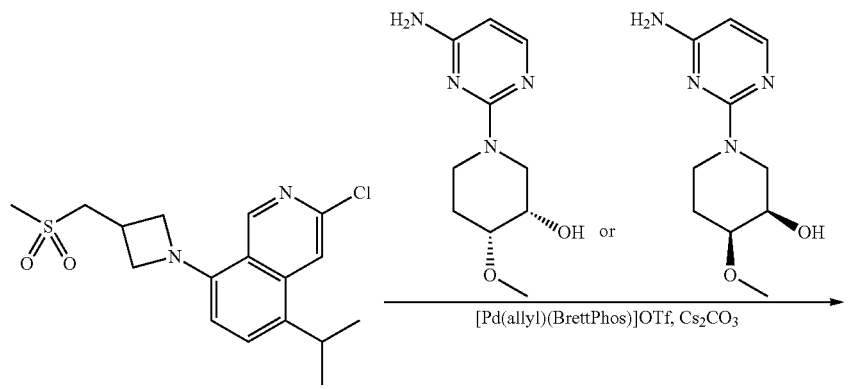

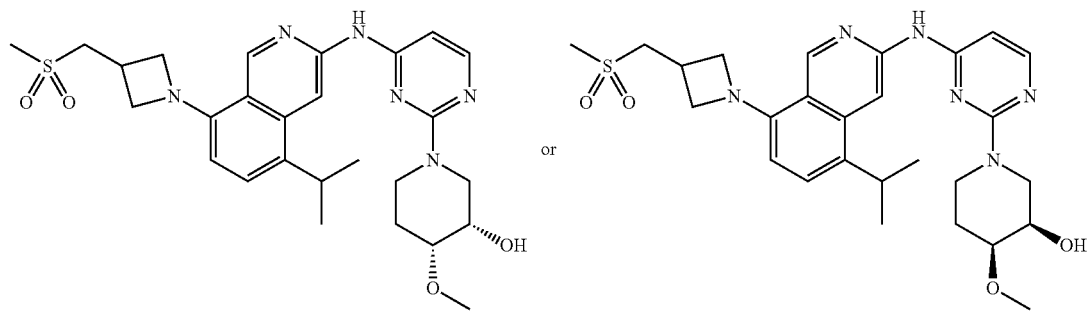

To a solution of 3-chloro-8-[3-(methanesulfonylmethyl)azetidin-1-yl]-5-(propan-2-yl)isoquinoline (70 mg, 0.1983 mmol, from Step 1 of Example 1) in 1,4-dioxane was added cis-1-(4-aminopyrimidin-2-yl)-4-methoxypiperidin-3-ol (44.4 mg, 0.1983 mmol, peak 1 from Example B10), Cs₂CO₃ (193 mg, 0.59 mmol) and Allyl BrettPhos PdOTf (16.5 mg, 19.7 umol). The mixture was stirred at 100° C. for 2 h under N₂ atmosphere. The reaction mixture was cooled to rt and diluted with 20 mL of water. The resulting solution was extracted with 2×20 mL of EA and the organic layers combined. The resulting mixture was washed with 20 mL of brine, dried over anhydrous sodium sulfate and concentrated under vacuum. The crude product was purified by Prep-HPLC with the following conditions: Column: XBridge Prep OBD C18 Column 30×150 mm Sum; Mobile Phase A: Water (10 mmol/L NH₄HCO₃), Mobile Phase B: ACN; Flow rate: 60 mL/min; Gradient: 30% B to 45% B in 8 min; 254; 220 nm; Rt: 7.17 min. This resulted in 35 mg (32.7%) of the title compound as yellow solid.

Example 3, Compound 111: Synthesis of (3S,4R)-3-fluoro-1-(4-(5-isopropyl-8-((2R,3S)-2-methyl-3-(methylsulfonylmethyl)azetidin-1-yl)isoquinolin-3-ylamino)pyrimidin-2-yl)-3-methylpiperidin-4-ol

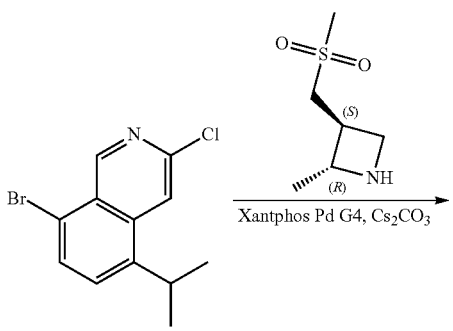

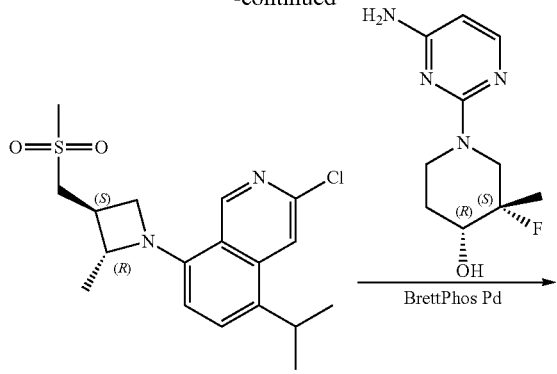

Step 1: Synthesis of 3-chloro-5-isopropyl-8-((2R, 3S)-2-methyl-3-(methylsulfonylmethyl)azetidin-1-yl)isoquinoline To a solution of 8-bromo-3-chloro-5-(propan-2-yl)isoquinoline (9 g, 31.6 mmol, from Example C4) in 1,4-dioxane (130 mL) was added (2R,3S)-3-(methanesulfonylmethyl)-2-methylazetidine (5.15 g, 31.6 mmol, from Example A4), $Cs_2CO_3$ (20.6 g, 63.2 mmol) and XantphosPd G4 (1.51 g, 1.58 mmol) under nitrogen. The mixture was stirred at 100° C. for 3 h under nitrogen. The reaction mixture was cooled to rt and diluted with 300 mL of water. The resulting solution was extracted with EA, washed with brine, dried over anhydrous sodium sulfate and concentrated under vacuum. The crude product was purified by silica gel chromatography (0-60% EA in PE) to give 7.2 g (62.6%) of 3-chloro-8-[(2R, 3S)-3-(methanesulfonylmethyl)-2-methylazetidin-1-yl]-5-(propan-2-yl)isoquinoline as yellow solid.

Analytical Data: LC-MS: (ES, m/z)=367 [M+1].

Step 2: Synthesis of (3S,4R)-3-fluoro-1-(4-(5-isopropyl-8-((2R,3S)-2-methyl-3-(methylsulfonylmethyl)azetidin-1-yl)isoquinolin-3-ylamino)pyrimidin-2-yl)-3-methylpiperidin-4-ol The mixture of 3-chloro-8-[(2R,3S)-3-(methanesulfonylmethyl)-2-methylazetidin-1-yl]-5-(propan-2-yl)isoquinoline (5 g, 13.6 mmol), (3 S,4R)-1-(4-aminopyrimidin-2-yl)-3-fluoro-3-methylpiperidin-4-ol (3.07 g, 13.6 mmol, from Example B1), $Cs_2CO_3$ (8.86 g, 27.2 mmol) and BrettphosPd G3 (616 mg, 0.68 mmol) in dioxane (60 mL) was stirred at 100° C. for 3 h under nitrogen. The reaction mixture was cooled to rt and diluted with water. The resulting solution was extracted with EA, washed with brine, dried over anhydrous sodium sulfate and concentrated under vacuum. The crude product was purified by silica gel chromatography 0-5% MeOH in DCM. This resulted in 4.6 g (60.7%) of the title compound as yellow solid.

Example 4, Compound 64: Synthesis of N-(2-((3S, 4R)-3-fluoro-4-methoxypiperidin-1-yl)pyrimidin-4-yl)-5-isopropyl-8-(3-(methylsulfonylmethyl)azetidin-1-yl)isoquinolin-3-amine

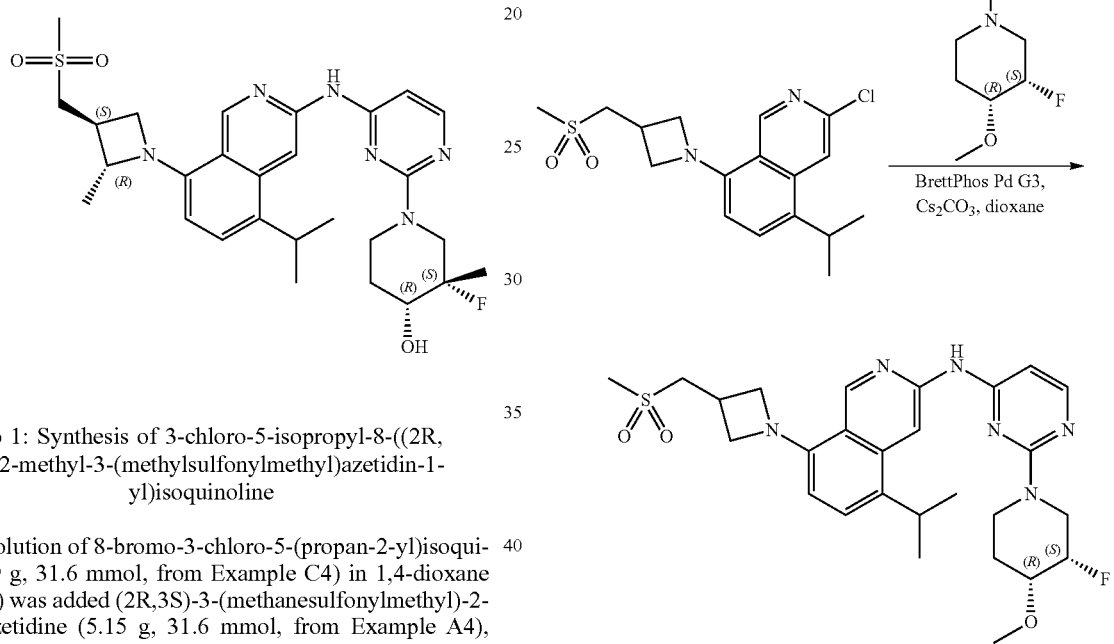

Into a 8-mL pressure tank reactor purged and maintained with an inert atmosphere of nitrogen, was placed 3-chloro-5-isopropyl-8-[3-(methanesulfonylmethyl)azetidin-1-yl]isoquinoline (30 mg, 0.085 mmol, 1 equiv. from step 1 of Example 1), 2-[(3S,4R)-3-fluoro-4-methoxypiperidin-1-yl]pyrimidin-4-amine (19.24 mg, 0.085 mmol, 1 equiv., from Example B33), BrettPhos Pd G3 (7.71 mg, 0.009 mmol, 0.1 equiv.), $Cs_2CO_3$ (55.40 mg, 0.170 mmol, 2 equiv.) in dioxane (2 mL). The resulting solution was stirred for 3 h at 110° C. The reaction was then quenched by the addition of 1 mL of water. The solids were filtered out. The resulting solution was extracted with 3×5 mL of EA concentrated under vacuum. The residue was applied onto a silica gel column with dichloromethane/methanol (15:1). The crude product was purified by Prep-HPLC with the following conditions: Column: XBridge Shield RP18 OBD Column 19*250 mm, 10 um; Mobile Phase A: Water (10 mmol/L $NH_4HCO_{3+0.1}$% $NH_3·H_2O$), Mobile Phase B: ACN; Flow rate: 25 mL/min; Gradient: 30% B to 57% B in 9 min; 254/210 nm; Rt: 8.30 min. This resulted in 20 mg (43.35%) of the title compound as a light-yellow solid.

Example 5, Compound 117: Synthesis of (3S,4R)-3-fluoro-1-(4-(5-isopropyl-8-((2R,3S)-2-methyl-3-(methylsulfonylmethyl)azetidin-1-yl)isoquinolin-3-ylamino)pyrimidin-2-yl)-4-methylpiperidin-4-ol

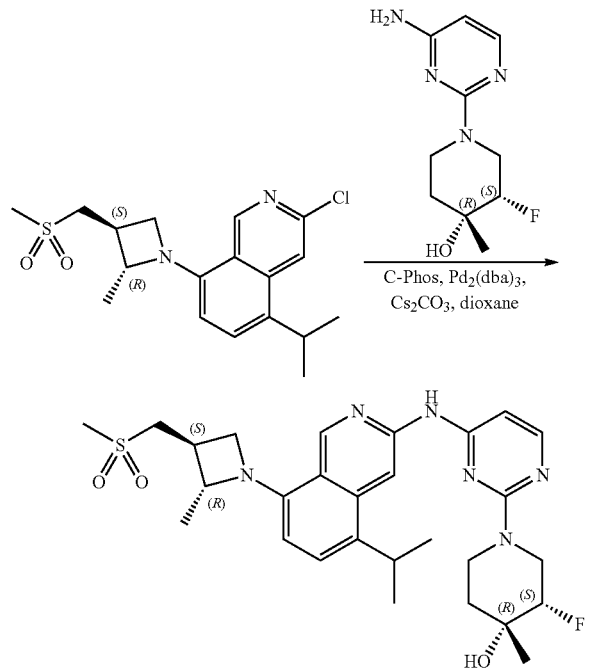

To a solution of 3-chloro-8-[(2R,3S)-3-(methanesulfonylmethyl)-2-methylazetidin-1-yl]-5-(propan-2-yl)isoquinoline (28 g, 76.3 mmol, from step 1 of Example 3), (3R,4S)-1-(4-aminopyrimidin-2-yl)-3-fluoro-4-methylpiperidin-4-ol (17.2 g, 76.3 mmol, peak 1 from Example B12), $Cs_2CO_3$ (49.8 g, 152 mmol), C-phos (4.27 g, 9.15 mmol, 2-dicyclohexylphosphino-2',6'-bis(N,N-dimethylamino)biphenyl) and $Pd_2(dba)_3$ (3.94 g, 3.81 mmol) in dioxane (400 mL) was heated to 100° C. for 16 h under $N_2$ atmosphere. The mixture reaction was filtered and the filtrate was concentration under vacuum. The residue was applied onto a silica gel column with EA/PE (2:1) to give product 28.8 g (67%) as a light-yellow solid.

Example 6, Compound 118: Synthesis of (3R,4S)-3-fluoro-1-(4-(5-isopropyl-8-02R,3S)-2-methyl-3-(methylsulfonylmethyl)azetidin-1-yl)isoquinolin-3-ylamino)pyrimidin-2-yl)-4-methylpiperidin-4-ol

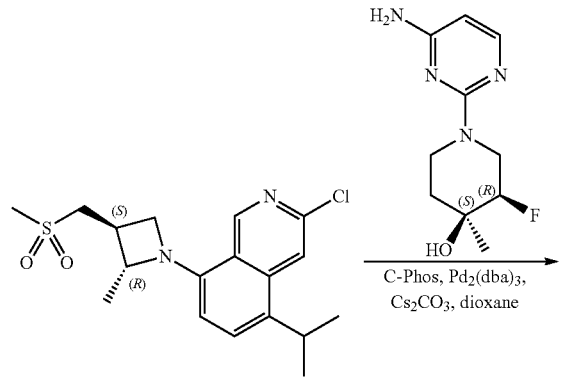

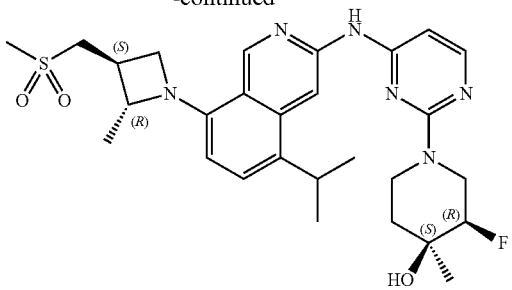

To a solution of 3-chloro-8-[(2R,3S)-3-(methanesulfonylmethyl)-2-methylazetidin-1-yl]-5-(propan-2-yl)isoquinoline (300 mg, 0.82 mmol, from step 1 of Example 3), (3R,4S)-1-(4-aminopyrimidin-2-yl)-3-fluoro-4-methylpiperidin-4-ol (185 mg, 0.82 mmol, peak 2 from Example B12), $Cs_2CO_3$ (533 mg, 1.64 mmol), C-phos (45 mg, 0.98 mmol, 2-dicyclohexylphosphino-2',6'-bis(N,N-dimethylamino)biphenyl) and Pd2(dba)3 (39 mg, 0.38 mmol) in dioxane (5 mL) was heated to 100° C. for 16 h under $N_2$ atmosphere. The mixture reaction was filtered and the filtrate was concentration under vacuum. The residue was purified by Prep-HPLC with following conditions: Column: XBridge Prep OBD C18 Column, 30×150 mm 5 um; Mobile Phase A: Water (10 mmol/L $NH_4HCO_3$+0.1% $NH_3 \cdot H_2O$), Mobile Phase B: ACN; Flow rate: 60 mL/min; Gradient: 35 B to 60 B in 7 min; 254; 220 nm to give 260 mg (57%) of the title compound as pale-yellow solid.

Example 7, Compound 63: Synthesis of N-(2-((3R,4S)-3-fluoro-4-methoxypiperidin-1-yl)pyrimidin-4-yl)-5-isopropyl-8-(3-(methylsulfonylmethyl)azetidin-1-yl)isoquinolin-3-amine

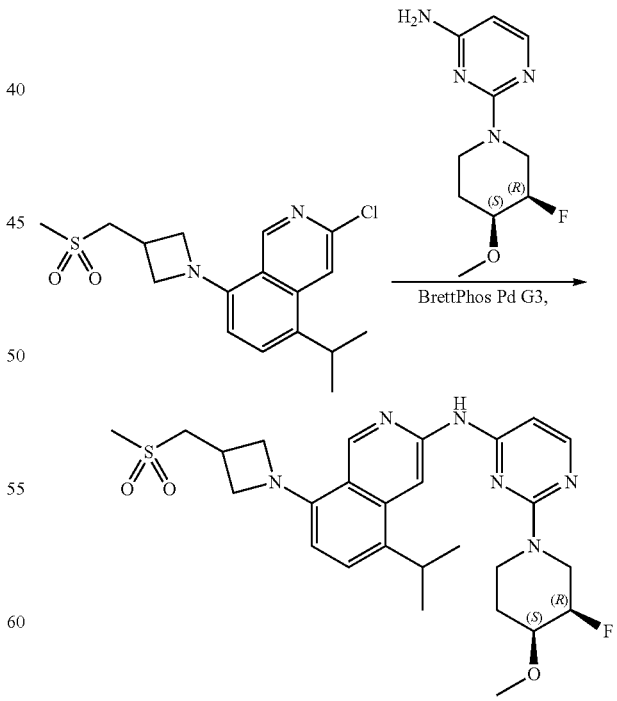

Into a 8-mL pressure tank reactor purged and maintained with an inert atmosphere of nitrogen, was placed 3-chloro-5-isopropyl-8-[3-(methanesulfonylmethyl)azetidin-1-yl]isoquinoline (30 mg, 0.085 mmol, 1 equiv., from step 1 of Example 1), 2-[(3R,4S)-3-fluoro-4-methoxypiperidin-1-yl]pyrimidin-4-amine (19.24 mg, 0.085 mmol, 1 equiv., from Example B32), BrettPhos Pd G3 (7.71 mg, 0.009 mmol, 0.10 equiv.) and $Cs_2CO_3$ (55.40 mg, 0.170 mmol, 2 equiv.) in dioxane (2 mL). The resulting solution was stirred for 3 hr at 110° C. The reaction was concentrated and the residue was applied onto Prep-TLC with DCM/MeOH (15:1) and further purified by Prep-HPLC with the following conditions: Column: XBridge Shield RP18 OBD Column 19*250 mm, 10 um; Mobile Phase A: Water(10 mmol/L $NH_4HCO_3$+ 0.1% $NH_3·H_2O$), Mobile Phase B: ACN; Flow rate: 25 mL/min; Gradient: 30% B to 57% B in 9 min; 254/210 nm; Rt: 8.30 min. This resulted in 20 mg (43.4%) of the title compound as a light-yellow solid.

Example 8, Compound 211: Synthesis of (R)-3,3-difluoro-1-(4-(5-isopropyl-8-((2R,3S)-2-methyl-3-(methylsulfonylmethyl)azetidin-1-yl)isoquinolin-3-ylamino)pyrimidin-2-yl)-4-methylpiperidin-4-ol or (S)-3,3-difluoro-1-(4-(5-isopropyl-8-((2R,3S)-2-methyl-3-(methylsulfonylmethyl)azetidin-1-yl)isoquinolin-3-ylamino)pyrimidin-2-yl)-4-methylpiperidin-4-ol

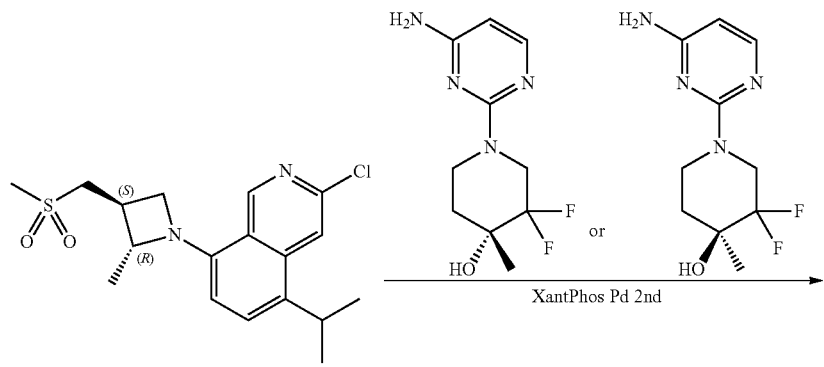

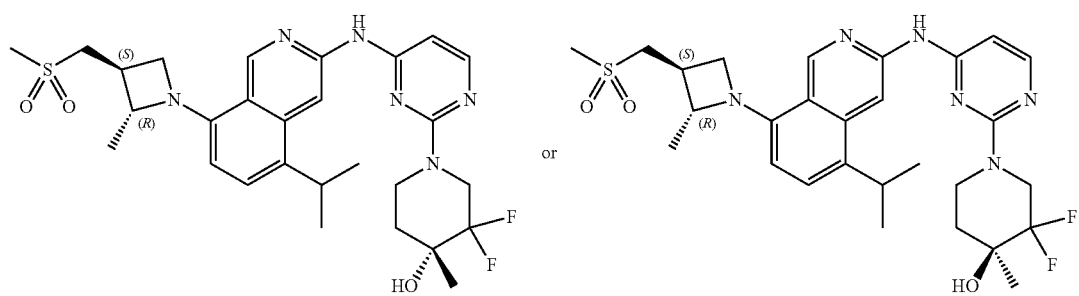

The mixture of 3-chloro-8-[(2R,3S)-3-(methanesulfonylmethyl)-2-methylazetidin-1-yl]-5-(propan-2-yl)isoquinoline (80 mg, 218 μmol, from step 1 of Example 3), (4R)-1-(4-aminopyrimidin-2-yl)-3,3-difluoro-4-methylpiperidin-4-ol or (4S)-1-(4-aminopyrimidin-2-yl)-3,3-difluoro-4-methylpiperidin-4-ol (53.2 mg, 218 μmol, peak 2 from Example B13), palladium(1+) 2'-amino-1,1'-biphenyl-2-yl xantphos chloride (38.7 mg, 43.6 μmol) and $Cs_2CO_3$ (142 mg, 436 μmol) in diaxone (4 mL) was stirred at rt for 4 h at 100° C. under $N_2$ atmosphere. The resulting solution was concentrated under vacuum. The crude product was purified by Flash-Prep-HPLC with the following conditions (Column: XBridge Shield RP18 OBD Column, 30*150 mm, 5 um; Mobile Phase A: Water (0.05% $NH_3H_2O$), Mobile Phase B: ACN; Flow rate: 60 mL/min; Gradient: 35 B to 65 B in 7 min; 254/220 nm). The resulted in 57 mg of the title compound as a yellow solid.

Example 9, Compound 92: Synthesis of (3S,4S)-1-(4-(5-isopropyl-8-(2R,3S)-2-methyl-3-(methylsulfonylmethyl)azetidin-1-yl)isoquinolin-3-ylamino)pyrimidin-2-yl)-4-methoxypiperidin-3-ol or (3R,4R)-1-(4-(5-isopropyl-8-((2R,3S)-2-methyl-3-(methylsulfonylmethyl)azetidin-1-yl)isoquinolin-3-ylamino)pyrimidin-2-yl)-4-methoxypiperidin-3-ol

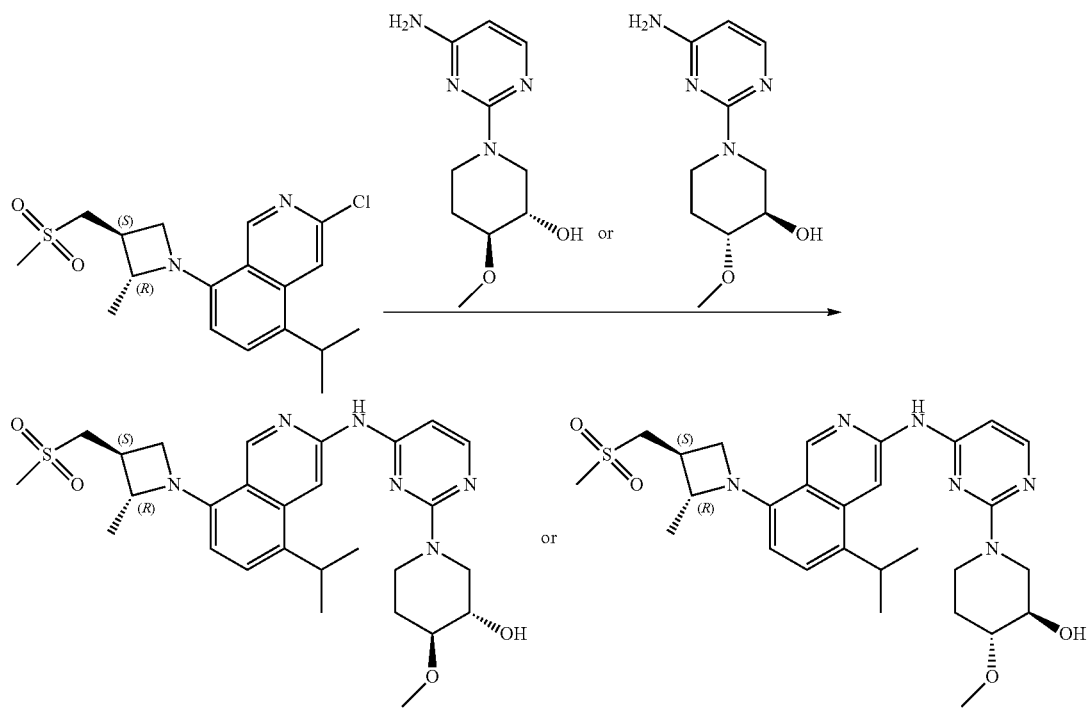

Into a 20-mL sealed tube was placed 3-chloro-8-[(2R,3S)-3-(methanesulfonylmethyl)-2-methylazetidin-1-yl]-5-(propan-2-yl)isoquinoline (100 mg, 272 μmol, from step 3 of Example 3), trans-1-(4-aminopyrimidin-2-yl)-4-methoxypiperidin-3-ol (60.9 mg, 272 μmol, peak 2 from Example B28), palladium(1+) 2'-amino-1,1'-biphenyl-2-yl xantphos chloride (36.2 mg, 40.8 μmol) and caesium carbonate (177 mg, 544 μmol). The resulting solution was stirred at 100° C. for 16 h. The resulting solution was concentrated under vacuum. The residue was purified by Prep-TLC with DCM/MeOH (20:1). The crude product was purified by Prep-Flash-HPLC with following conditions (Column: XBridge Shield RP18 OBD Column, 30*150 mm, 5 um; Mobile Phase A: Water (0.05% NH$_3$H$_2$O), Mobile Phase B: ACN; Flow rate: 60 mL/min; Gradient: 35 B to 51 B in 7 min; 254/220 nm. This resulted in 64.8 mg of the title compound as yellow solid.

Example 10, Compound 150: Synthesis of N-(2-((3S,4R)-3-fluoro-4-methoxypiperidin-1-yl)pyrimidin-4-yl)-1-isopropyl-4-((2R,3S)-2-methyl-3-(methylsulfonylmethyl)azetidin-1-yl)pyrido[4,3-d]pyridazin-7-amine

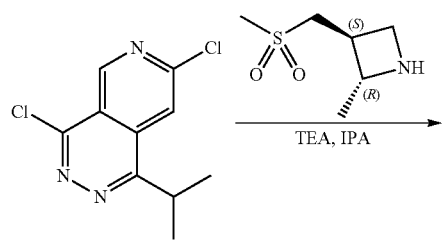

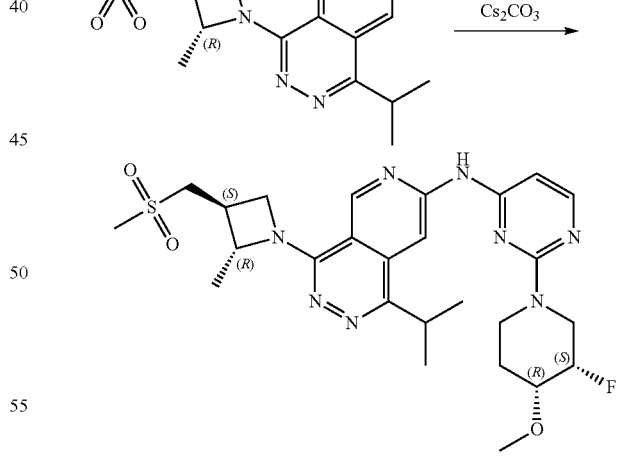

Step 1: Synthesis of 7-chloro-1-isopropyl-4-((2R,3S)-2-methyl-3-(methylsulfonylmethyl)azetidin-1-yl)pyrido[4,3-d]pyridazine To a solution of 4,7-dichloro-1-(propan-2-yl)pyrido[3,4-d]pyridazine (170 mg, 702 umol, from Example C3) and TEA (141 mg, 1.4 mmol) in IPA (3 mL) was added (2R,3S)-3-(methanesulfonylmethyl)-2-methylazetidine (126 mg, 772 umol, from Example A4). The mixture was stirred for 2 h at 100° C. The mixture was concentrated and the residue was purified by Prep-TLC with PE/EA (10:1). This resulted in 100 mg (39%) of the title compound as a yellow solid.

Analytical Data: LC-MS: (ES, m/z)=369 [M+1].

Step 2: Synthesis of N-(2-((3S,4R)-3-fluoro-4-methoxypiperidin-1-yl)pyrimidin-4-yl)-1-isopropyl-4-((2R,3S)-2-methyl-3-(methylsulfonylmethyl)azetidin-1-yl)pyrido[4,3-d]pyridazin-7-amine The mixture of (2R,3S)-1-[7-chloro-1-(propan-2-yl)pyrido[3,4-d]pyridazin-4-yl]-3-(methanesulfonylmethyl)-2-methylazetidine (100 mg, 271 umol), 2-[(3S,4R)-3-fluoro-4-methoxypiperidin-1-yl]pyrimidin-4-amine (64 mg, 284 umol, from Example B33), Brettphos Pd G3 (49 mg, 54.1 umol) and Cs$_2$CO$_3$ (176 mg, 542 umol) in dioxane was stirred for 2 h at 100° C. under N$_2$ atmosphere. The mixture was extracted with EA and water. The organic layer was dried by Na$_2$SO$_4$ and concentrated. The product was purified by Column: XBridge Shield RP18 OBD Column, 30*150 mm, 5 um; Mobile Phase A: Water (0.05% NH$_3$H$_2$O), Mobile Phase B: ACN; Flow rate: 60 mL/min; Gradient: 35 B to 45 B in 7 min; 254/220 nm. This resulted in 20 mg of the title compound as a white solid.

Example 11, Compound 93: Synthesis of (3S,4R)-1-(4-(5-isopropyl-8-((2R,3S)-2-methyl-3-(methylsulfonylmethyl)azetidin-1-yl)isoquinolin-3-ylamino)pyrimidin-2-yl)-4-methoxypiperidin-3-ol or (3R,4S)-1-(4-(5-isopropyl-8-((2R,3S)-2-methyl-3-(methylsulfonylmethyl)azetidin-1-yl)isoquinolin-3-ylamino)pyrimidin-2-yl)-4-methoxypiperidin-3-ol

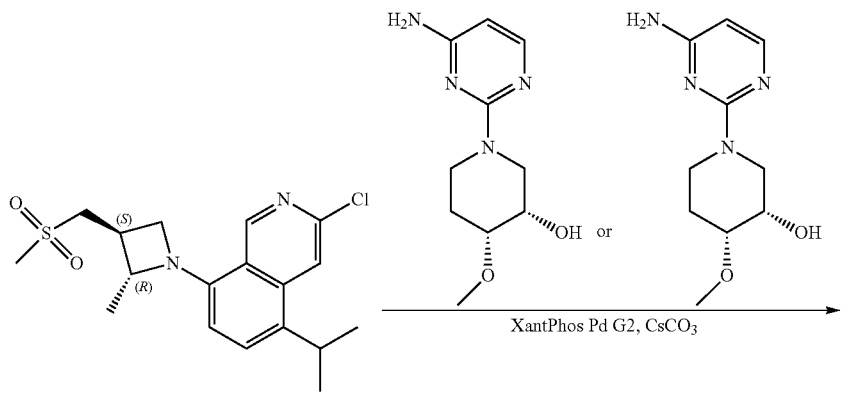

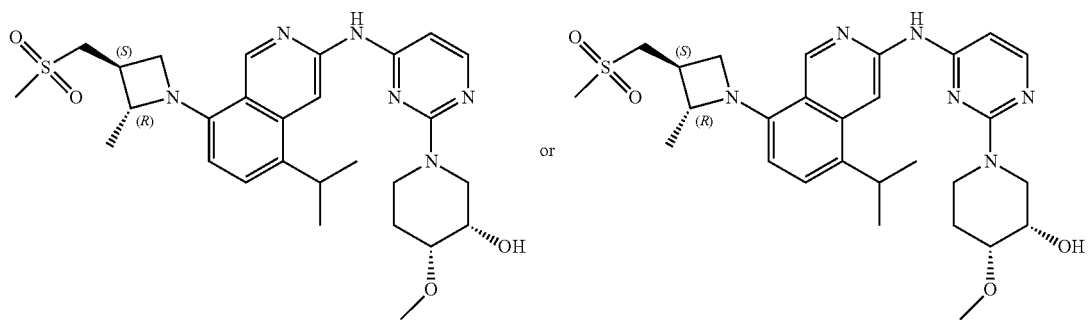

Into a 20-mL sealed tube was placed 3-chloro-8-[(2R,3S)-3-(methanesulfonylmethyl)-2-methylazetidin-1-yl]-5-(propan-2-yl)isoquinoline (100 mg, 272 μmol, from step 3 of Example 3), cis-1-(4-aminopyrimidin-2-yl)-4-methoxypiperidin-3-ol (60.9 mg, 272 μmol, peak 1 from Example B10), palladium(1+) 2'-amino-1,1'-biphenyl-2-yl xantphos chloride (24.1 mg, 27.2 μmol) and caesium carbonate (177 mg, 544 μmol) in diaxone (5 mL). The resulting solution was stirred at 100° C. for 16 h. The resulting solution was concentrated under vacuum. The residue was purified by Prep-TLC with DCM/MeOH (20:1). The crude product was purified by Prep-Flash-HPLC with following conditions (Column: XBridge Shield RP18 OBD Column, 30*150 mm, 5 um; Mobile Phase A: Water (0.05% NH$_3$H$_2$O), Mobile Phase B: ACN; Flow rate: 60 mL/min; Gradient: 35 B to 50 B in 7 min; 254/220 nm. This resulted in 64 mg of the title compound as yellow solid.

Example 12, Compound 103: Synthesis of (3S,4R)-1-(4-(5-isopropyl-8-((2R,3S)-2-methyl-3-(methylsulfonylmethyl)azetidin-1-yl)-2,6-naphthyridin-3-ylamino)pyrimidin-2-yl)-4-methoxypiperidin-3-ol or (3R,4S)-1-(4-(5-isopropyl-8-((2R,3S)-2-methyl-3-(methylsulfonylmethyl)azetidin-1-yl)-2,6-naphthyridin-3-ylamino)pyrimidin-2-yl)-4-methoxypiperidin-3-ol

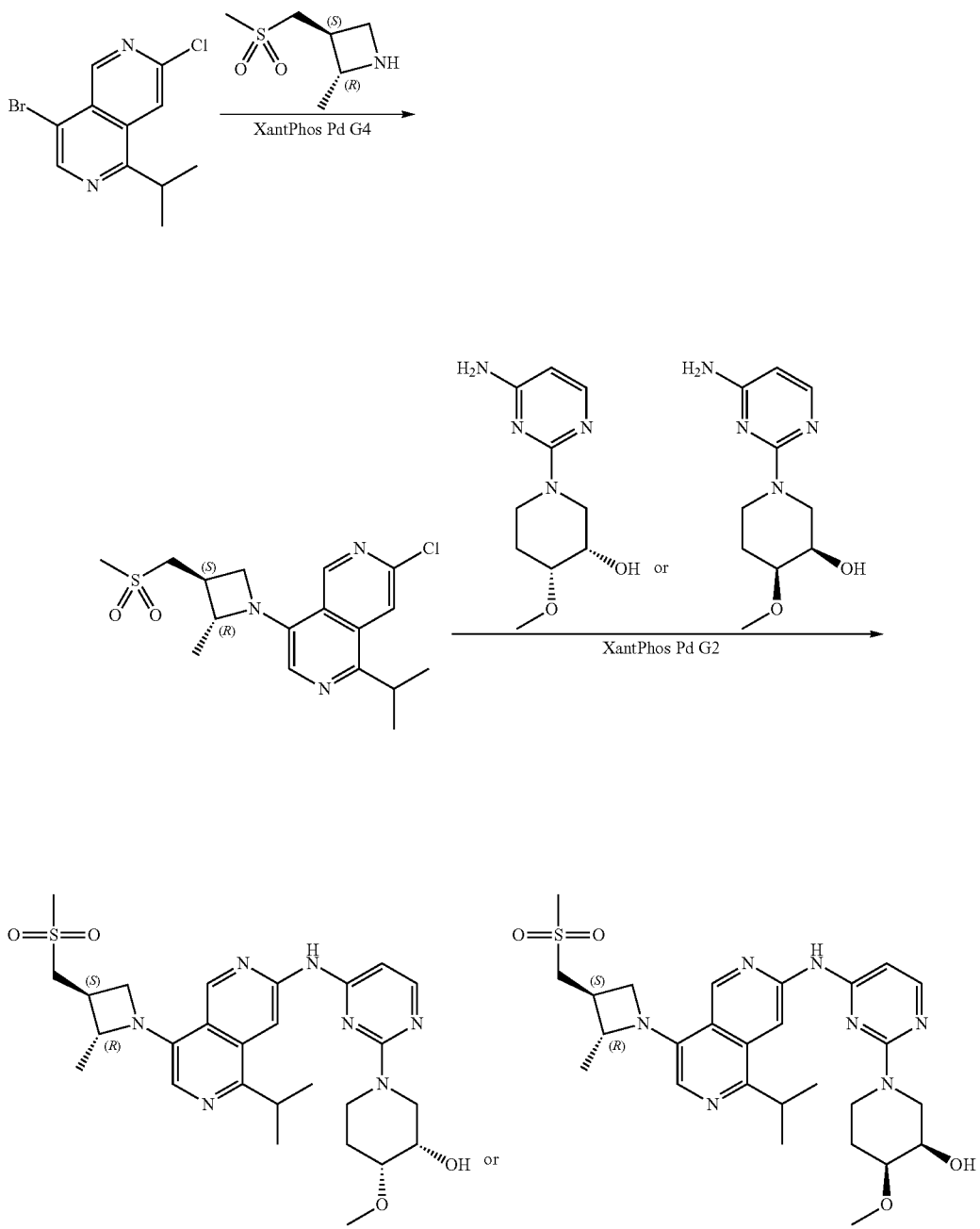

Step 1: Synthesis of 7-chloro-1-isopropyl-4-((2R,3S)-2-methyl-3-(methylsulfonylmethyl)azetidin-1-yl)-2,6-naphthyridine 4-bromo-7-chloro-1-(propan-2-yl)-2,6-naphthyridine (200 mg, 700 μmol, from Example C2), (2R,3S)-3-(methanesulfonylmethyl)-2-methylazetidine (114 mg, 700 μmol, from Example A4), XantPhos Pd G4 (66.4 mg, 70.0 μmol) and caesium carbonate (456 mg, 1.40 mmol) was dissolved in dioxane (4 mL). The resulting solution was stirred at 100° C. for 3 h under $N_2$ atmosphere. Then resulting solution was concentrated under vacuum and purified by Prep-TLC with DCM/MeOH (20:1) to afford 200 mg of the title compound as a yellow solid.

Analytical Data: LC-MS: (ES, m/z)=368 [M+1].

Step 2: Synthesis of (3S,4R)-1-(4-(5-isopropyl-8-((2R,3S)-2-methyl-3-(methylsulfonylmethyl)azetidin-1-yl)-2,6-naphthyridin-3-ylamino)pyrimidin-2-yl)-4-methoxypiperidin-3-ol Into a 20-mL sealed tube was placed 7-chloro-4-[(2R,3S)-3-(methanesulfonylmethyl)-2-methylazetidin-1-yl]-1-(propan-2-yl)-2,6-naphthyridine (90 mg, 244 μmol), cis-1-(4-aminopyrimidin-2-yl)-4-methoxypiperidin-3-ol (54.7 mg, 244 μmol, peak 1 from Example B10), palladium(1+) 2'-amino-1,1'-biphenyl-2-yl xantphos chloride (21.6 mg, 24.4 μmol) and caesium carbonate (158 mg, 488 μmol). The resulting solution was stirred at 100° C. for 16 h. The resulting solution was concentrated under vacuum. The residue was purified by Prep-TLC with DCM/MeOH (20:1). The crude product was purified by Prep-Flash-HPLC with following conditions (Column: XBridge Shield RP18 OBD Column, 30*150 mm, 5um; Mobile Phase A: Water (0.05% $NH_3H_2O$), Mobile Phase B: ACN; Flow rate: 60 mL/min; Gradient: 30 B to 38 B in 7 min; 254/220 nm. This resulted in 30 mg of the title compound as yellow solid.

Example 13, Compound 104: Synthesis of (3S,4S)-1-(4-(5-isopropyl-8-((2R,3S)-2-methyl-3-(methylsulfonylmethyl)azetidin-1-yl)-2,6-naphthyridin-3-ylamino)pyrimidin-2-yl)-4-methoxypiperidin-3-ol or (3R,4R)-1-(4-(5-isopropyl-8-((2R,3S)-2-methyl-3-(methylsulfonylmethyl)azetidin-1-yl)-2,6-naphthyridin-3-ylamino)pyrimidin-2-yl)-4-methoxypiperidin-3-ol

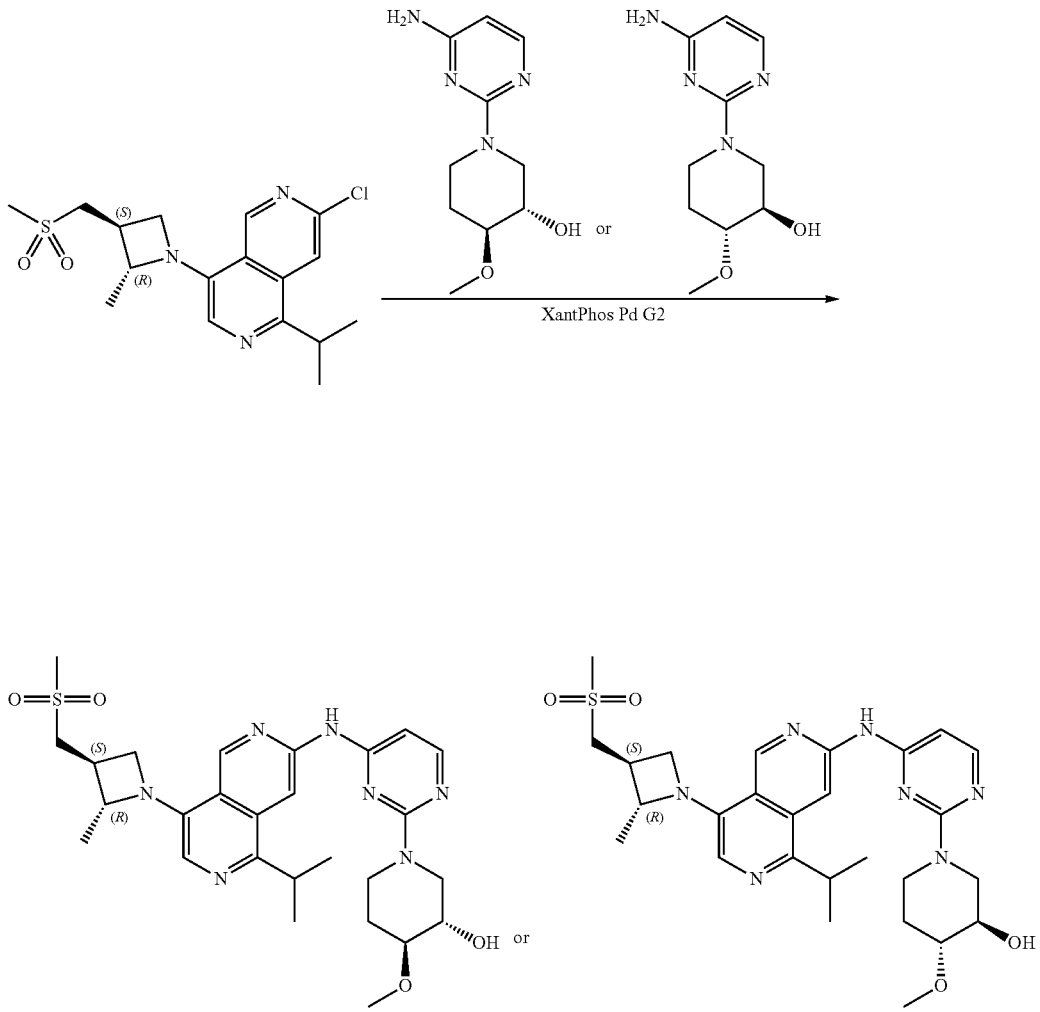

Into a 20-mL sealed tube was placed 7-chloro-4-[(2R,3S)-3-(methanesulfonylmethyl)-2-methylazetidin-1-yl]-1-(propan-2-yl)-2,6-naphthyridine (50 mg, 135 μmol, from step 1 of Example 12) in dioxane (5 mL), trans-1-(4-aminopyrimidin-2-yl)-4-methoxypiperidin-3-ol (30.2 mg, 135 μmol, peak 1 from Example B28), palladium source (11.9 mg, 13.5 μmol) and cesium carbonate (87.9 mg, 270 μmol). The resulting solution was stirred at 100° C. for 16 h under N₂ atmosphere. The resulting solution was concentrated under vacuum. The residue was purified by Prep-TLC with DCM/MeOH (20:1). The crude product was purified by Prep-Flash-HPLC with following conditions (Column: XBridge Shield RP18 OBD Column, 30*150 mm, 5um; Mobile Phase A: Water (0.05% NH₃H₂O), Mobile Phase B: ACN; Flow rate: 60 mL/min; Gradient: 30 B to 40 B in 7 min; 254/220 nm. This resulted in 30 mg of the title compound as a yellow solid.

Example 14, Compound 134: Synthesis of N-(3-((3S,4R)-3-fluoro-4-methoxypiperidin-1-yl)-1,2,4-triazin-5-yl)-5-isopropyl-8-((2R,3S)-2-methyl-3-(methylsulfonylmethyl)azetidin-1-yl)isoquinolin-3-amine

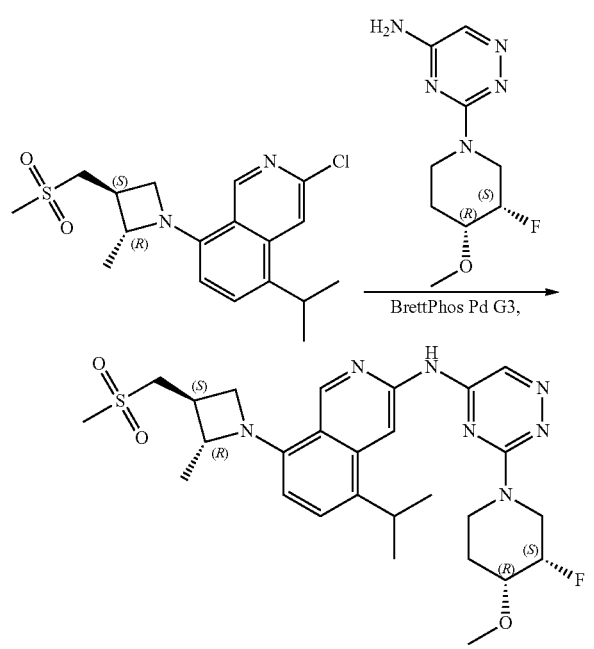

The mixture of 3-chloro-8-[(2R,3S)-3-(methanesulfonylmethyl)-2-methylazetidin-1-yl]-5-(propan-2-yl)isoquinoline (80 mg, 218 umol, from step 1 of Example 3), 3-[(3S,4R)-3-fluoro-4-methoxypiperidin-1-yl]-1,2,4-triazin-5-amine (51.8 mg, 228 umol, from Example B73), Brettphos Pd G3 (39.5 mg, 43.6 umol) and Cs₂CO₃ (142 mg, 436 umol) in dioxane (2 mL) was stirred for 2 h at 100° C. under N₂ atmosphere. The mixture was concentrated and extracted with EA and water. The organic layer was dried and concentrated. The residue was purified by Column: XBridge Prep OBD C18 Column 30×150 mm 5um; Mobile Phase A: Water (0.05% TFA), Mobile Phase B: ACN; Flow rate: 60 mL/min; Gradient: 25% B to 50% B in 7 min; 254/220 nm; Rt: 6.07 min. This resulted in 20 mg of the title compound as a yellow solid.

Example 15, Compound 135: Synthesis of (3R,4S)-3-fluoro-1-(4-(5-isopropyl-8-((2R,3S)-2-methyl-3-(methylsulfonylmethyl)azetidin-1-yl)-2,7-naphthyridin-3-ylamino)pyrimidin-2-yl)-4-methylpiperidin-4-ol

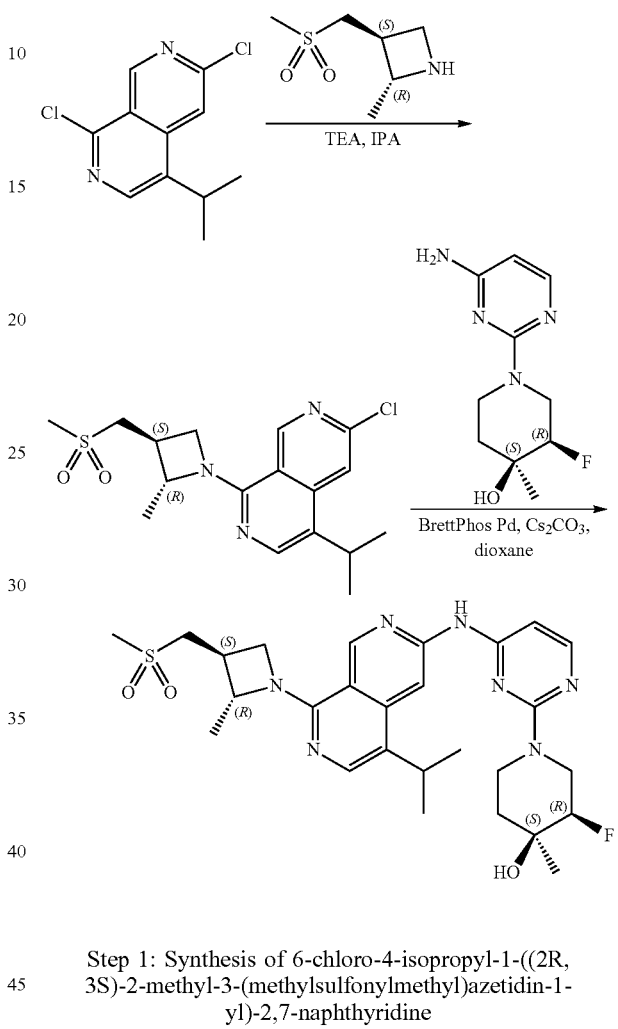

Step 1: Synthesis of 6-chloro-4-isopropyl-1-((2R,3S)-2-methyl-3-(methylsulfonylmethyl)azetidin-1-yl)-2,7-naphthyridine The mixture of 1,6-dichloro-4-isopropyl-2,7-naphthyridine (480 mg, 2.0 mmol, from Example C1), (2R,3S)-2-methyl-3-(methylsulfonylmethyl)azetidine (320 mg, 2.0 mmol, from Example A4) and TEA (400 mg, 4.0 mmol) in IPA (2 mL) was stirred overnight at 100° C. The solvent was removed the residue was purified by PLASH (20% EA in PE) to afford 6-chloro-4-isopropyl-1-((2R,3S)-2-methyl-3-(methylsulfonylmethyl)azetidin-1-yl)-2,7-naphthyridine 280 mg as yellow solid.

Analytical Data: LC-MS: (ES, m/z)=368 [M+1].

Step 2: Synthesis of (3R,4S)-3-fluoro-1-(4-(5-isopropyl-8-((2R,3S)-2-methyl-3-(methylsulfonylmethyl)azetidin-1-yl)-2,7-naphthyridin-3-ylamino)pyrimidin-2-yl)-4-methylpiperidin-4-ol The mixture of 6-chloro-1-[(2R,3S)-3-(methanesulfonylmethyl)-2-methylazetidin-1-yl]-4-(propan-2-yl)-2,7-naphthyridine (100 mg, 271 umol), (3R,4S)-1-(4-aminopyrimidin-2-yl)-3-fluoro-4-methylpiperidin-4-ol (61 mg, 271 umol, peak 2 from Example B12), Brettphos Pd G3 (24 mg, 27 umol) and Cs$_2$CO$_3$ (176 mg, 542 umol) in dioxane (5 mL) was stirred at 120° C. for 3 h under N$_2$ atmosphere. The reaction was concentrated and the residue was purified by preparative HPLC (Column: XBridge Prep OBD C18 Column, 30×150 mm 5 um; Mobile Phase A: Water(10 mmol/L NH$_4$HCO$_3$+0.1% NH$_3$·H$_2$O), Mobile Phase B: ACN; Flow rate: 60 mL/min; Gradient: 33 B to 39 B in 9 min; 254/220 nm to give the title compound (57 mg) as a light-yellow solid.

Example 16, Compound 136: Synthesis of (3R,4S)-3-fluoro-1-(4-(5-isopropyl-8-((2R,3S)-2-methyl-3-(methylsulfonylmethyl)azetidin-1-yl)-2,6-naphthyridin-3-ylamino)pyrimidin-2-yl)-4-methylpiperidin-4-ol

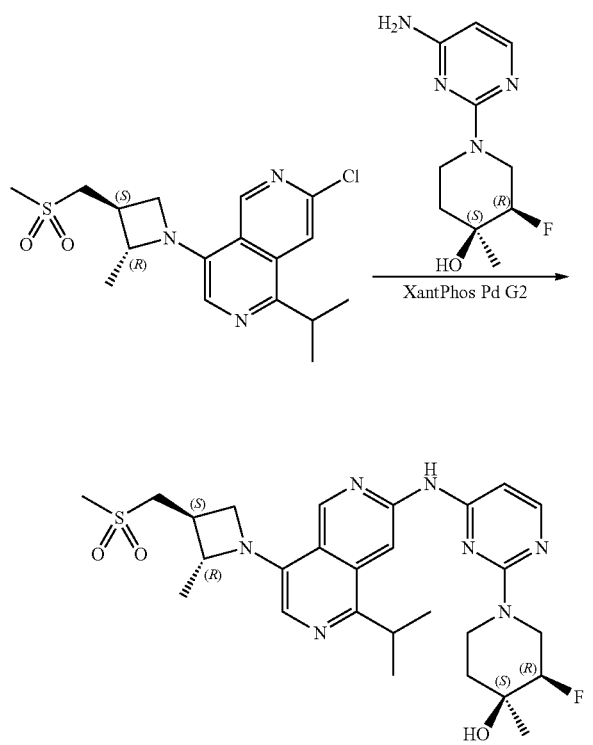

The mixture of 7-chloro-4-[(2R,3S)-3-(methanesulfonylmethyl)-2-methylazetidin-1-yl]-1-(propan-2-yl)-2,6-naphthyridine (60 mg, 163 µmol, from Step 1 of Example 12), (3R,4S)-1-(4-aminopyrimidin-2-yl)-3-fluoro-4-methylpiperidin-4-ol (36.8 mg, 163 µmol, peak 2 from Example B12), palladium(1+) 2'-amino-1,1'-biphenyl-2-yl xantphos chloride (14.4 mg, 16.3 µmol) and Cs$_2$CO$_3$ (106 mg, 326 µmop in dioxane (2 mL) was stirred at 100° C. for 16 h under N$_2$ atmosphere. The resulting solution was concentrated under vacuum and the residue was purified by Prep-TLC with DCM/MeOH (20:1). The crude product was further purified by Prep-Flash-HPLC with following conditions (Column: XBridge Shield RP18 OBD Column, 30*150 mm, Sum; Mobile Phase A: Water (0.05% NH$_3$H$_2$O), Mobile Phase B: ACN; Flow rate: 60 mL/min; Gradient: 33 B to 42 B in 7 min; 254/220 nm. This resulted in 20 mg of the title compound as yellow solid.

Example 17, Compound 190: Synthesis of (3S,4R)-1-(4-(8-((2R,3S)-3-(ethylsulfonylmethyl)-2-methylazetidin-1-yl)-5-isopropyl-2,7-naphthyridin-3-ylamino)pyrimidin-2-yl)-3-fluoro-4-methylpiperidin-4-ol

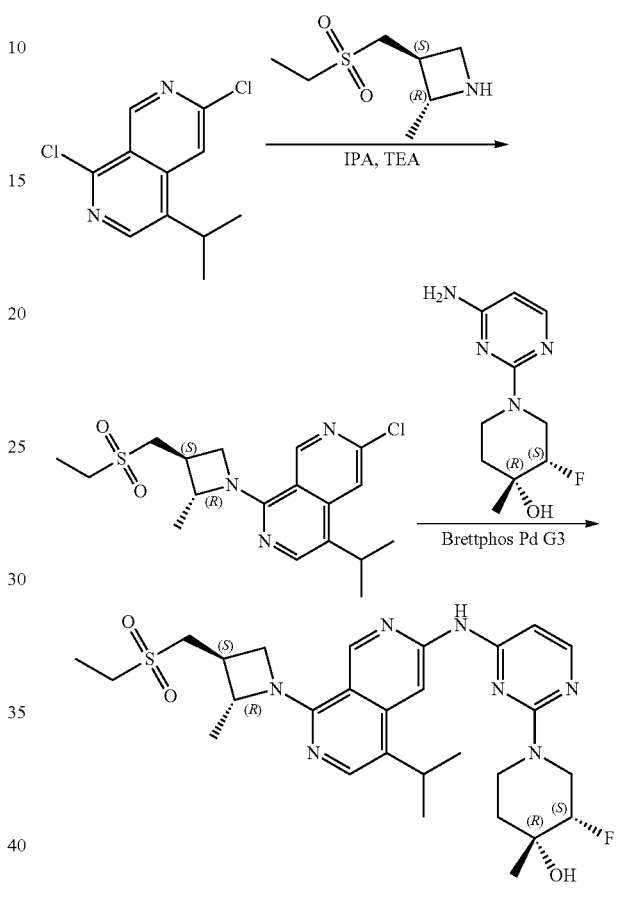

Step 1: Synthesis of 6-chloro-1-((2R,3S)-3-(ethylsulfonylmethyl)-2-methylazetidin-1-yl)-4-isopropyl-2,7-naphthyridine To a solution of (2R,3S)-3-[(ethanesulfonyl)methyl]-2-methylazetidine (300 mg, 1.69 mmol, from Example A7), 1,6-dichloro-4-(propan-2-yl)-2,7-naphthyridine (250 mg, 1.03 mmol, from Example C1) and TEA (682 mg, 6.76 mmol) in IPA (4 mL) was heated to 100° C. and stirred overnight. The reaction was concentrated and the residue was purified by preparative TLC (EA:PE=2:1) to afford the title compound (280 mg) as a light-yellow oil.

Analytical Data: LC-MS: (ES, m/z)=382 [M+1].

Step 2: Synthesis of (3S,4R)-1-(4-(8-((2R,3S)-3-(ethylsulfonylmethyl)-2-methylazetidin-1-yl)-5-isopropyl-2,7-naphthyridin-3-ylamino)pyrimidin-2-yl)-3-fluoro-4-methylpiperidin-4-ol The mixture of 6-chloro-1-[(2R,3S)-3-[(ethanesulfonyl)methyl]-2-methylazetidin-1-yl]-4-(propan-2-yl)-2,7-naphthyridine (100 mg, 261 umol), (3S,4R)-1-(4-aminopyrimidin-2-yl)-3-fluoro-4-methylpiperidin-4-ol (59 mg, 261

Example 18, Compound 137: Synthesis of (3S,4R)-3-fluoro-1-(4-(5-isopropyl-8-((2R,3S)-2-methyl-3-(methylsulfonylmethyl)azetidin-1-yl)-2,7-naphthyridin-3-ylamino)pyrimidin-2-yl)-4-methylpiperidin-4-ol

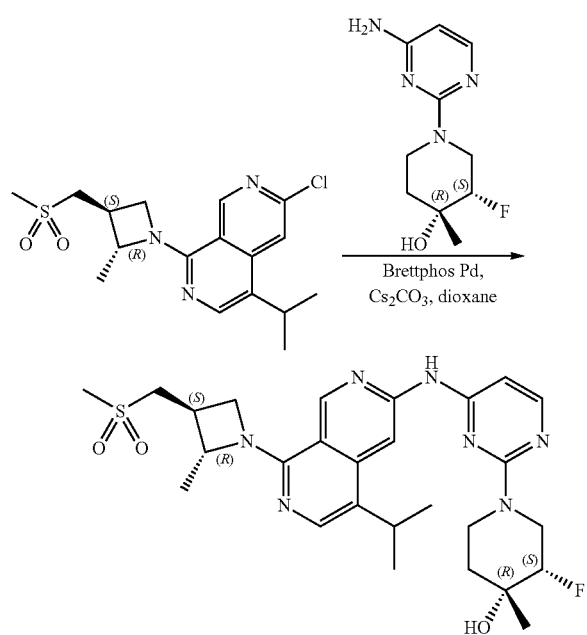

umol, peak 1 from Example B12), Cs₂CO₃ (171 mg, 522 umol) and Brettphos Pd G3 (23.6 mg, 26.1 umol) in dioxane (4 mL) was stirred at 120° C. for 3 h under N₂ atmosphere. The reaction was concentrated and the residue was purified by preparative HPLC (Column: XBridge Prep OBD C18 Column, 19*250 mm, 5 um; Mobile Phase A: Water (10 mmol/L NH₄HCO₃₊₀.₁% NH₃·H₂O), Mobile Phase B: ACN; Flow rate: 25 mL/min; Gradient: 43 B to 43 B in 9 min; 254; 220 nm) to give the title compound (21.8 mg) as light-yellow solid.

The mixture of 6-chloro-1-[(2R,3S)-3-(methanesulfonylmethyl)-2-methylazetidin-1-yl]-4-(propan-2-yl)-2,7-naphthyridine (100 mg, 271 umol, from step 1 of Example 15), (3S,4R)-1-(4-aminopyrimidin-2-yl)-3-fluoro-4-methylpiperidin-4-ol (61 mg, 271 umol, peak 1 from Example B12), Brettphos Pd G3 (24 mg, 27 umol) and Cs₂CO₃ (176 mg, 542 umol) in dioxane (5 mL) was stirred at 120° C. for 3 h under N₂. The reaction was concentrated and the purified by preparative HPLC (Column: XBridge Prep OBD C18 Column, 30×150 mm 5 um; Mobile Phase A: Water(10 mmol/L NH₄HCO₃+0.1% NH₃·H₂O), Mobile Phase B: ACN; Flow rate: 60 mL/min; Gradient: 33 B to 38 B in 10 min; 254; 220 nm) to give the title compound (70.8 mg) as a light-yellow solid.

Example 19, Compound 138: Synthesis of (3S,4R)-3-fluoro-1-(4-(5-isopropyl-8-((2R,3S)-2-methyl-3-(methylsulfonylmethyl)azetidin-1-yl)-2,6-naphthyridin-3-ylamino)pyrimidin-2-yl)-4-methylpiperidin-4-ol

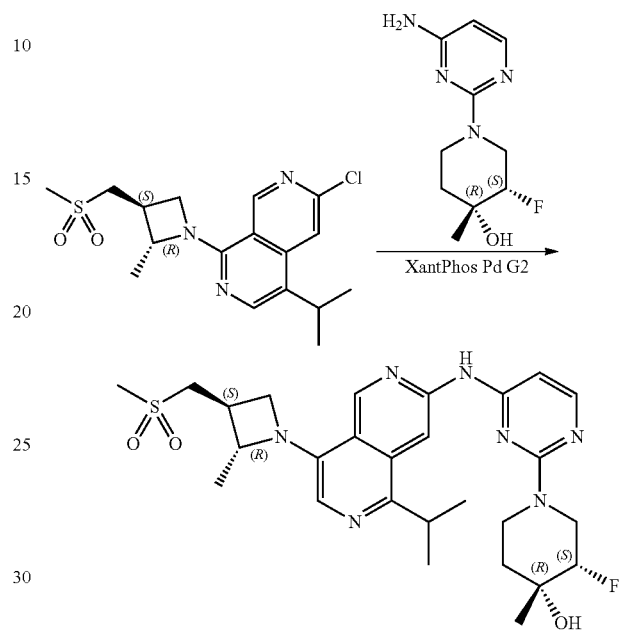

The mixture of 7-chloro-4-[(2R,3S)-3-(methanesulfonylmethyl)-2-methylazetidin-1-yl]-1-(propan-2-yl)-2,6-naphthyridine (50 mg, 135 μmol, from step 1 of Example 12), (3S,4R)-1-(4-aminopyrimidin-2-yl)-3-fluoro-4-methylpiperidin-4-ol (30.5 mg, 135 μmol, peak 1 from Example B12), palladium(1+) 2'-amino-1,1'-biphenyl2-yl xantphos chloride (23.9 mg, 27.0 μmol) and Cs₂CO₃ (87.9 mg, 270 μmol) in dioxane (2 mL) was stirred at 100° C. for 2 h under N₂ atmosphere. The resulting solution was concentrated and the residue was purified by Prep-Flash-HPLC with following conditions (Column: XBridge Shield RP18 OBD Column, 30*150 mm, 5 um; Mobile Phase A: Water (0.05% NH₃H₂O), Mobile Phase B: ACN; Flow rate: 60 mL/min; Gradient: 37 B to 43 B in 7 min; 254/220 nm). This resulted in 20 mg of the title compound as yellow-green solid.

Example 20, Compound 177: Synthesis of (3S,4S)-1-(4-(8-((2R,3S)-3-(ethylsulfonylmethyl)-2-methylazetidin-1-yl)-5-isopropylisoquinolin-3-ylamino)pyrimidin-2-yl)-4-methoxypiperidin-3-ol or (3R,4R)-1-(4-(8-((2R,3S)-3-(ethylsulfonylmethyl)-2-methylazetidin-1-yl)-5-isopropylisoquinolin-3-ylamino)pyrimidin-2-yl)-4-methoxypiperidin-3-ol

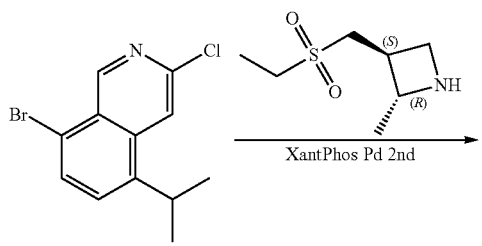

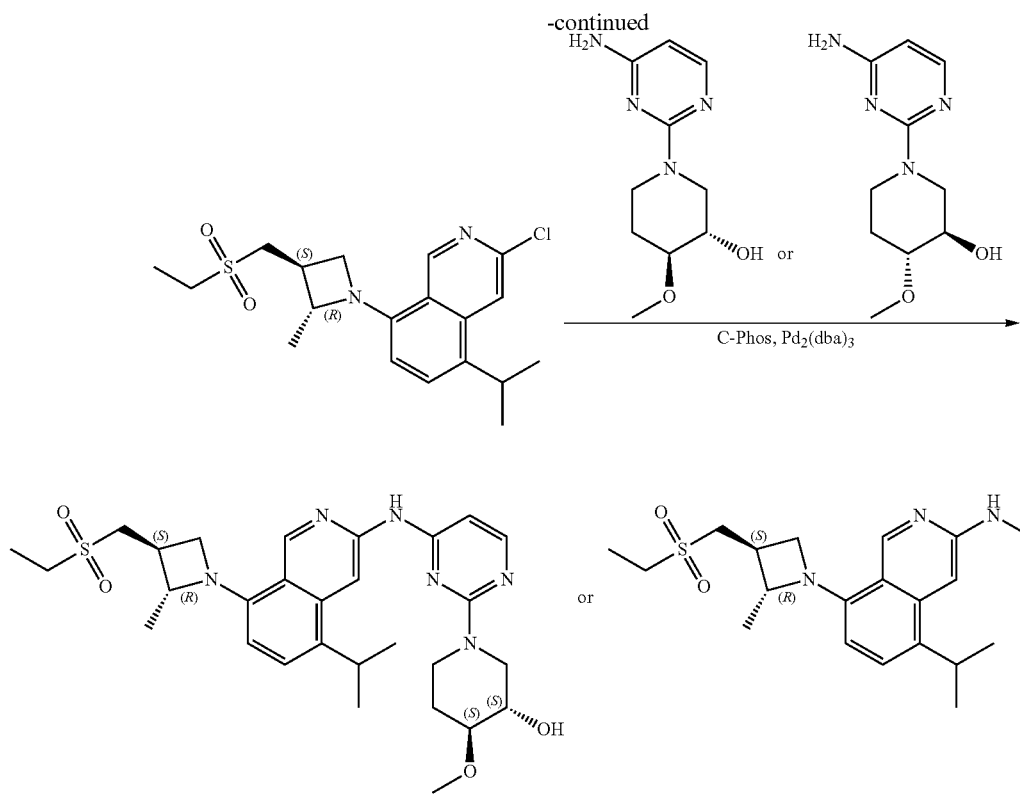

Step 1: Synthesis of 3-chloro-8-((2R,3S)-3-(ethylsulfonylmethyl)-2-methylazetidin-1-yl)-5-isopropylisoquinoline The mixture of 8-bromo-3-chloro-5-(propan-2-yl)isoquinoline (200 mg, 702 umol, from Example C4), (2R,3S)-3-[(ethanesulfonyl)methyl]-2-methylazetidine (149 mg, 842 umol, from Example A7), Xantphos Pd G2 (62.3 mg, 70.2 umol) and $Cs_2CO_3$ (458 mg, 1.40 mmol) in dioxane (5 mL) was stirred at 100° C. for 16 h under $N_2$. The reaction was concentrated and purified by preparative TLC (EA:PE=2:1) to give product 160 mg as a light-yellow solid.

Analytical Data: LC-MS: (ES, m/z)=381 [M+1].

Step 2: Synthesis of (3S,4S)-1-(4-(8-((2R,3S)-3-(ethylsulfonylmethyl)-2-methylazetidin-1-yl)-5-isopropylisoquinolin-3-ylamino)pyrimidin-2-yl)-4-methoxypiperidin-3-ol or (3R,4R)-1-(4-(8-((2R,3S)-3-(ethylsulfonylmethyl)-2-methylazetidin-1-yl)-5-isopropylisoquinolin-3-ylamino)pyrimidin-2-yl)-4-methoxypiperidin-3-ol The mixture of 3-chloro-8-[(2R,3S)-3-[(ethanesulfonyl)methyl]-2-methylazetidin-1-yl]-5-(propan-2-yl)isoquinoline (80 mg, 210 umol), trans-1-(4-aminopyrimidin-2-yl)-4-methoxypiperidin-3-ol (47 mg, 210 umol, peak 1 from Example B28), $Cs_2CO_3$ (137 mg, 420 umol), C-Phos (9.8 mg, 21 umol, 2-Dicyclohexylphosphino-2',6'-bis(N,N-dimethylamino)biphenyl) and $Pd_2(dba)_3$ (12 mg, 10.5 umol) in dioxane (4 mL) was heated to 100° C. for 16 h under $N_2$. The reaction was concentrated and purified by preparative HPLC (Column: XBridge Shield RP18 OBD Column, 30*150 mm, 5 um; Mobile Phase A: Water (0.05% $NH_3H_2O$), Mobile Phase B: ACN; Flow rate: 60 mL/min; Gradient: 40 B to 48 B in 7 min; 254/220 nm) to give the title compound 62 mg as a light-yellow solid.

Example 21, Compound 228: Synthesis of 2-((3R,4S)-3-fluoro-1-(4-(5-isopropyl-8-((2R,3S)-2-methyl-3-(methylsulfonylmethyl)azetidin-1-yl)isoquinolin-3-ylamino)pyrimidin-2-yl)piperidin-4-yloxy)ethanol

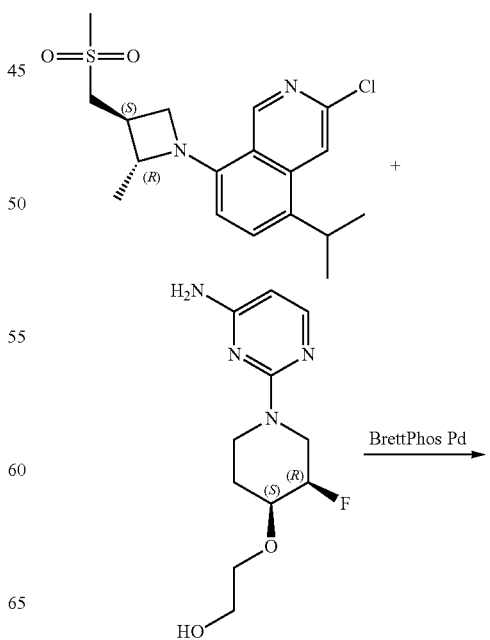

177

-continued

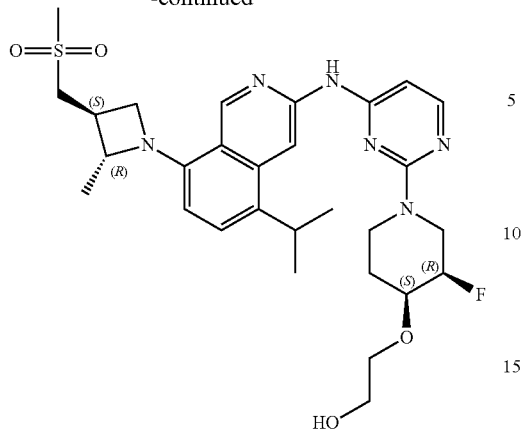

Into a 8-mL pressure tank reactor purged and maintained with an inert atmosphere of nitrogen, was placed 2-[[(3R, 4S)-1-(4-aminopyrimidin-2-yl)-3-fluoropiperidin-4-yl]oxy] ethanol (50 mg, 0.195 mmol, 1 equiv. from Example B51), 3-chloro-5-isopropyl-8-[(2R,3S)-3-(methanesulfonylmethyl)-2-methylazetidin-1-yl]isoquinoline (71.58 mg, 0.195 mmol, 1 equiv. from step 1 of Example 3), $Cs_2CO_3$ (127.53 mg, 0.390 mmol, 2 equiv.) and Brettphos Pd G3 (17.69 mg, 0.020 mmol, 0.1 equiv) in dioxane (3 mL). The resulting solution was stirred for 3 h at 100° C. The reaction was concentrated and the residue was purified by Prep-HPLC with following condition: Column: XBridge Prep Phenyl OBD Column, 5 um, 19*250 mm; Mobile Phase A: Water (10 MMOL/L $NH_4HCO_3$+0.1% $NH_3·H_2O$), Mobile Phase B: MeOH-HPLC; Flow rate: 25 mL/min; Gradient: 63 B to 67 B in 11 min; 254; 220 nm; This resulted in 20 mg (17.47%) of the title compound as a light-yellow solid.

Example 22, Compound 229: Synthesis of 2-((3S, 4R)-3-fluoro-1-(4-(5-isopropyl-8-((2R,3S)-2-methyl-3-(methylsulfonylmethyl)azetidin-1-yl)isoquinolin-3-ylamino)pyrimidin-2-yl)piperidin-4-yloxy)ethanol

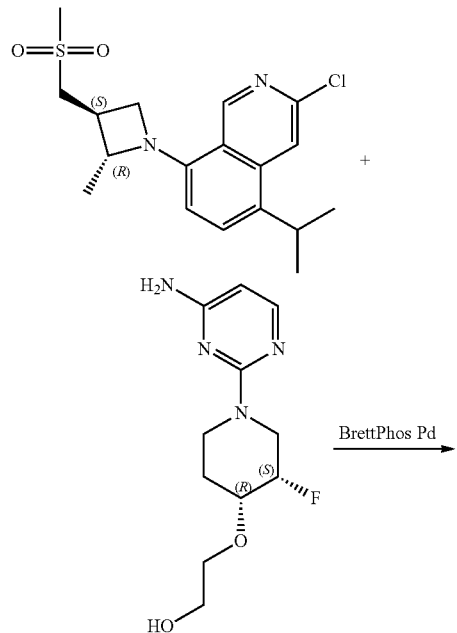

178

-continued

Into a 8-mL pressure tank reactor purged and maintained with an inert atmosphere of nitrogen, was placed 2-[[(3S, 4R)-1-(4-aminopyrimidin-2-yl)-3-fluoropiperidin-4-yl]oxy] ethanol (50.00 mg, 0.195 mmol, 1 equiv. from Example B52), 3-chloro-5-isopropyl-8-[(2R,3S)-3-(methanesulfonylmethyl)-2-methylazetidin-1-yl]isoquinoline (71.58 mg, 0.195 mmol, 1 equiv. from step 1 of Example 3), $Cs_2CO_3$ (127.53 mg, 0.390 mmol, 2 equiv.) and Brettphos Pd G3 (17.69 mg, 0.020 mmol, 0.1 equiv.) in dioxane (3 mL). The resulting solution was stirred for 3 hr at 100° C. The reaction was concentrated and the residue was purified by Prep-HPLC with following condition: Column: XBridge Prep Phenyl OBD Column, 5 um, 19*250 mm; Mobile Phase A: Water (10 mmol/L $NH_4HCO_3$+0.1% $NH_3·H_2O$), Mobile Phase B: MeOH-HPLC; Flow rate: 25 mL/min; Gradient: 63 B to 66 B in 11 min; 254; 220 nm; This resulted in 10 mg (8.74%) of the title compound as a light-yellow solid.

Example 23, Compound 232: Synthesis of (3S,4S)-5,5-difluoro-1-(4-(5-isopropyl-8-((2R,3S)-2-methyl-3-(methylsulfonylmethyl)azetidin-1-yl)isoquinolin-3-ylamino)pyrimidin-2-yl)-4-methoxypiperidin-3-ol or (3R,4R)-5,5-difluoro-1-(4-(5-isopropyl-8-((2R, 3S)-2-methyl-3-(methylsulfonylmethyl)azetidin-1-yl)isoquinolin-3-ylamino)pyrimidin-2-yl)-4-methoxypiperidin-3-ol

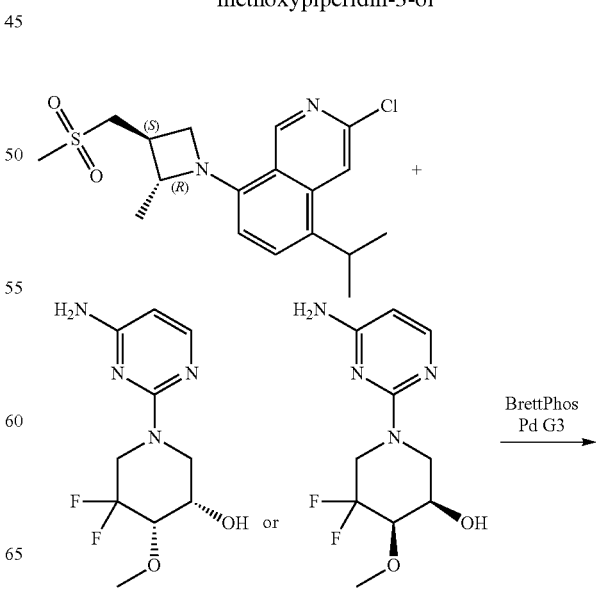

179

-continued

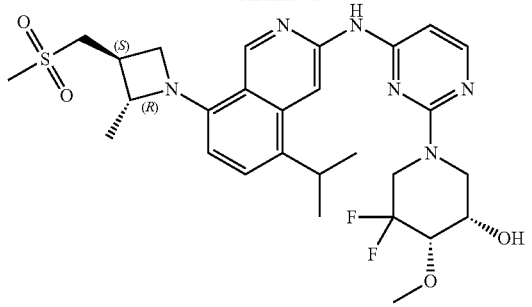

or

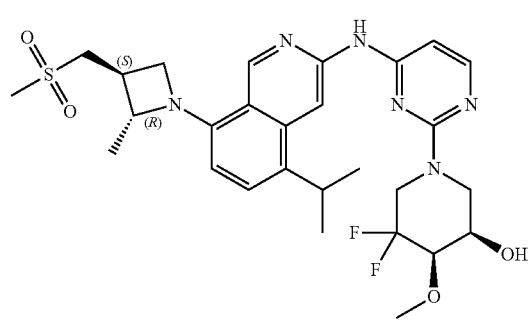

A mixture of 3-chloro-8-[(2R,3S)-3-(methanesulfonylmethyl)-2-methylazetidin-1-yl]-5-(propan-2-yl)isoquinoline (69.7 mg, 190 µmol, 1 equiv., from step 1 of Example 3), cis-1-(4-aminopyrimidin-2-yl)-5,5-difluoro-4-methoxypiperidin-3-ol (49.4 mg, 190 µmol, 1 equiv., peak 2 from Example B54), BrettPhos Pd G3 (17.1 mg, 19.0 µmol, 0.1 equiv.) and Cs₂CO₃ (123 mg, 380 µmol, 2 equiv.) in dioxane (2 mL) was heated to 100° C. for 3 h under N₂ atmosphere. After cooling down to rt, the mixture was concentrated, the residue was purified by prep-HPLC with following conditions: Column: XBridge Prep OBD C18 Column, 30×150 mm 5 um; Mobile Phase A: Water (0.05% NH₃H₂O), Mobile Phase B: ACN; Flow rate: 60 mL/min; Gradient: 41 B to 61 B in 7 min; 254/220 nm; to afford the title compound (50 mg, 44.64%) as a yellow solid.

Example 24, Compound 152: Synthesis of N-(2-((R)-4-amino-3,3-difluoropiperidin-1-yl)pyrimidin-4-yl)-5-isopropyl-8-((2R,3S)-2-methyl-3-(methylsulfonylmethyl)azetidin-1-yl(isoquinolin-3-amine or N-(2-((S)-4-amino-3,3-difluoropiperidin-1-yl)pyrimidin-4-yl)-5-isopropyl-8-((2R,3S)-2-methyl-3-((methylsulfonyl)methyl)azetidin-1-yl)isoquinolin-3-amine

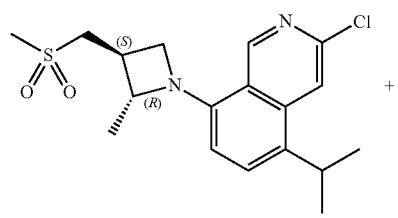

+

180

-continued

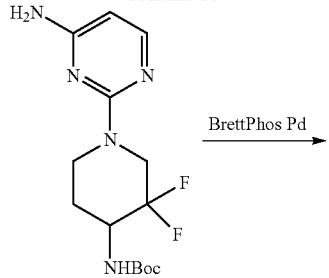

BrettPhos Pd →

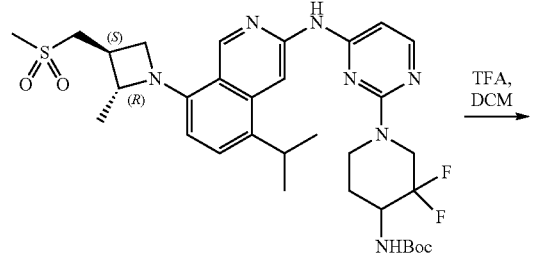

TFA, DCM →

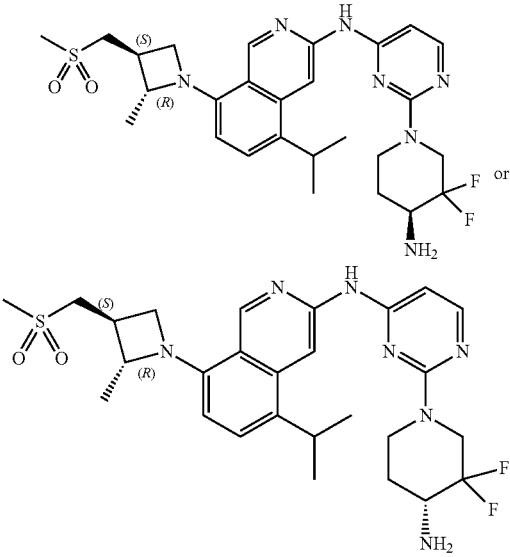

Chiral-HPLC →

Step 1: Synthesis of tert-butyl 3,3-difluoro-1-(4-(5-isopropyl-8-((2R,3S)-2-methyl-3-(methylsulfonylmethyl)azetidin-1-yl)isoquinolin-3-ylamino)pyrimidin-2-yl)piperidin-4-ylcarbamate Into a 8-mL pressure tank reactor purged and maintained with an inert atmosphere of nitrogen, was placed tert-butyl N-[1-(4-aminopyrimidin-2-yl)-3,3-difluoropiperidin-4-yl]carbamate (100 mg, 0.304 mmol, 1 equiv., from Example B57), 3-chloro-5-isopropyl-8-[(2R,3S)-3-(methanesulfonylmethyl)-2-methylazetidin-1-yl]isoquinoline (111.40 mg, 0.304 mmol, 1 equiv., from step 1 of Example 3), Cs₂CO₃

(198.47 mg, 0.607 mmol, 2 equiv.) and Brettphos Pd G3 (27.52 mg, 0.030 mmol, 0.1 equiv.) in dioxane (3 mL). The resulting solution was stirred for 3 hr at 100° C. The mixture was concentrated and the residue was purified by Prep-TLC (5% MeOH in DCM). This resulted in 100 mg (49.9%) of the title compound as a light-yellow solid.

Analytical Data: LC-MS: (ES, m/z)=660 [M+1].

Step 2: Synthesis of N-(2-((R)-4-amino-3,3-difluoropiperidin-1-yl)pyrimidin-4-yl)-5-isopropyl-8-((2R,3S)-2-methyl-3-(methylsulfonylmethyl)azetidin-1-yl)isoquinolin-3-amine The solution of tert-butyl N-[3,3-difluoro-1-[4-([5-isopropyl-8-[(2R,3S)-3-(methanesulfonylmethyl)-2-methylazetidin-1-yl]isoquinolin-3-yl]amino)pyrimidin-2-yl]piperidin-4-yl]carbamate (150 mg, 0.227 mmol, 1 equiv.) in DCM (5.00 mL)/TFA (1 mL) was stirred for 3 h at rt. The resulting mixture was concentrated and the residue was purified by Prep-TLC (5% MeOH in DCM) to afford 80 mg (62.9%) of N-[2-(4-amino-3,3-difluoropiperidin-1-yl)pyrimidin-4-yl]-5-isopropyl-8-[(2R,3S)-3-(methanesulfonylmethyl)-2-methylazetidin-1-yl]isoquinolin-3-amine as red oil, which was further separated by Chiral-HPLC to afford the N-(2-((R)-4-amino-3,3-difluoropiperidin-1-yl)pyrimidin-4-yl)-5-isopropyl-8-((2R,3S)-2-methyl-3-(methylsulfonylmethyl)azetidin-1-yl)isoquinolin-3-amine or N-(2-((S)-4-amino-3,3-difluoropiperidin-1-yl)pyrimidin-4-yl)-5-isopropyl-8-((2R,3S)-2-methyl-3-((methylsulfonyl)methyl)azetidin-1-yl)isoquinolin-3-amine (peak 2, 10 mg) as pale-yellow solid.

Example 25, Compound 194: Synthesis of (3S,4R)-1-(4-(8-((2R,3S)-3-(ethylsulfonylmethyl)-2-methylazetidin-1-yl)-5-isopropyl-2,6-naphthyridin-3-ylamino)pyrimidin-2-yl)-3-fluoro-4-methylpiperidin-4-ol

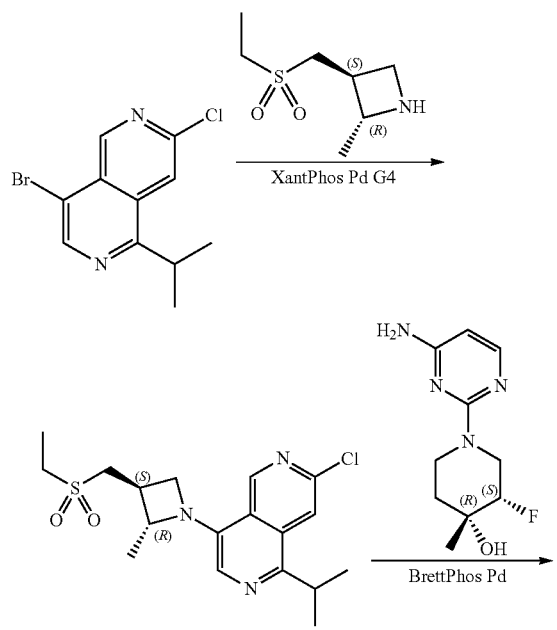

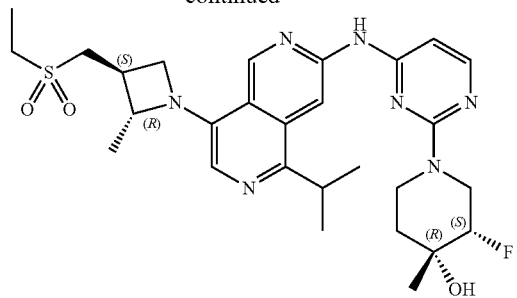

Step 1: Synthesis of 7-chloro-4-((2R,3S)-3-(ethylsulfonylmethyl)-2-methylazetidin-1-yl)-1-isopropyl-2,6-naphthyridine The mixture of 4-bromo-7-chloro-1-(propan-2-yl)-2,6-naphthyridine (150 mg, 525 umol, from Example C2), (2R,3S)-3-[(ethanesulfonyl)methyl]-2-methylazetidine (111 mg, 630 umol, from Example A7), $Cs_2CO_3$ (399 mg, 1.04 mmol) and Xantphos Pd G4 (83.9 mg, 52.5 umol) in dioxane (3 mL) was stirred overnight at 100° C. under $N_2$ atmosphere. The reaction mixture was diluted with water, extracted with EA and washed with brine. The organic layer was dried, filtered, evaporated and purified by column chromatography (DCM:MeOH=25:1) to afford the title compound (170 mg, 85.0%) as a yellow solid.

Analytical Data: LC-MS: (ES, m/z)=382 [M+1].

Step 2: Synthesis of (3S,4R)-1-(4-(8-((2R,3S)-3-(ethylsulfonylmethyl)-2-methylazetidin-1-yl)-5-isopropyl-2,6-naphthyridin-3-ylamino)pyrimidin-2-yl)-3-fluoro-4-methylpiperidin-4-ol The mixture of 7-chloro-4-[(2R,3S)-3-[(ethanesulfonyl)methyl]-2-methylazetidin-1-yl]-1-(propan-2-yl)-2,6-naphthyridine (75 mg, 196 umol), (3S,4R)-1-(4-aminopyrimidin-2-yl)-3-fluoro-4-methylpiperidin-4-ol (44.3 mg, 196 umol, peak 1 from Example B12), $Cs_2CO_3$ (127 mg, 392 umol) and BrettPhos Pd G3 (17.7 mg, 19.6 umol) in dioxane (3 mL) was stirred at 110° C. for 4 h. The reaction mixture was diluted with water, extracted with EA and brine. The organic layer was dried, filtered, evaporated and purified by column chromatography (DCM:MeOH=10:1) and followed by Prep-HPLC to afford the title compound (41.3 mg, 36.8%) as a yellow solid.

Example 26, Compound 40: Synthesis of N-(2-((3aR,6aS)-hexahydrofuro[3,4-b]pyrrol-1-yl)pyrimidin-4-yl)-5-isopropyl-8-((2R,3S)-2-methyl-3-(methylsulfonylmethyl)azetidin-1-yl)isoquinolin-3-amine and Diastereomer

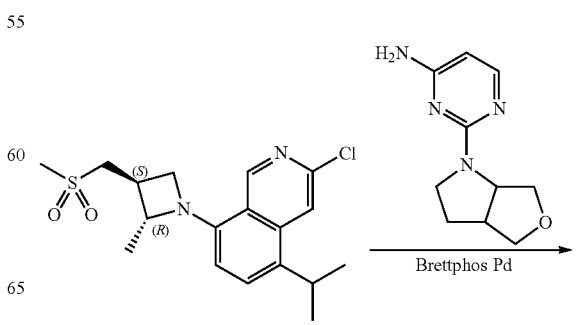

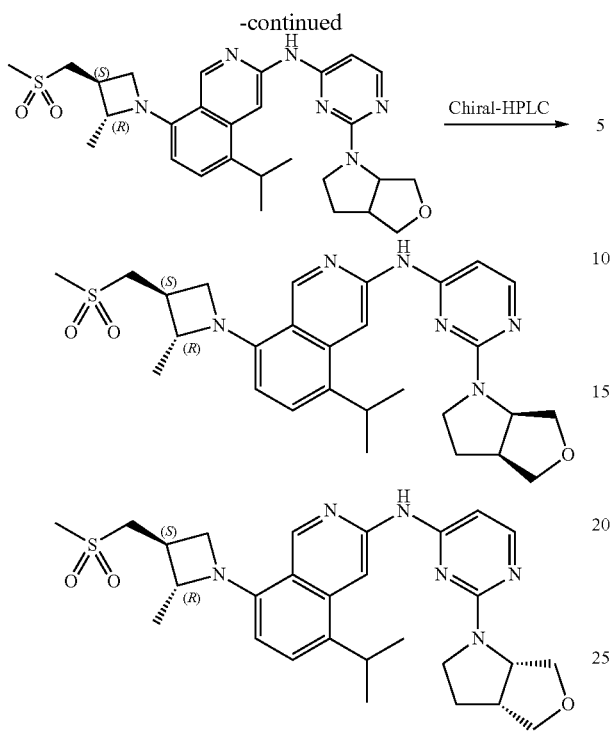

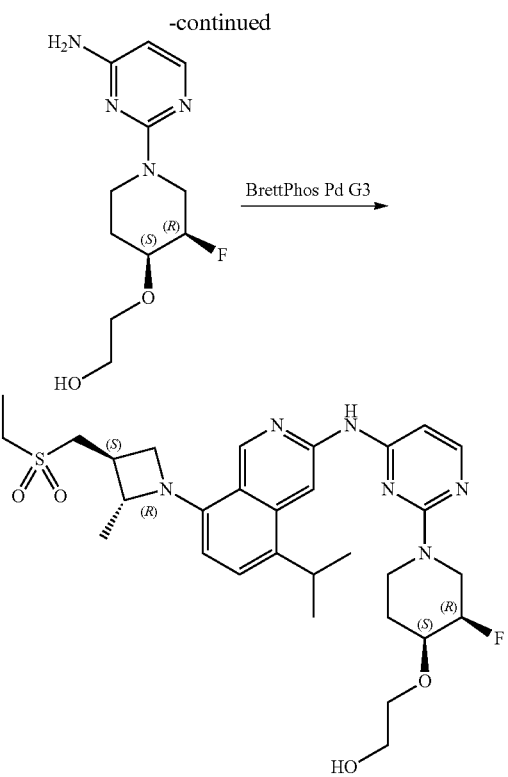

In a 20 mL sealed tube, the mixture of 3-chloro-8-[(2R, 3S)-3-(methanesulfonylmethyl)-2-methylazetidin-1-yl]-5-(propan-2-yl)isoquinoline (200 mg, 545 umol, from step 1 of Example 3), 2-{hexahydro-1H-furo[3,4-b]pyrrol-1-yl}pyrimidin-4-amine (112 mg, 545 umol, from Example B61), $Cs_2CO_3$ (355 mg, 1.09 mmol) and BrettPhos Pd G3 (49.4 mg, 54.5 umol) in dioxane (5 mL) was stirred for 5 h at 100° C. under $N_2$ atmosphere. The reaction mixture was diluted with water, extracted with EA and washed with brine. The organic layer was dried, filtered, evaporated and purified by column chromatography (DCM:MeOH=10:1) and followed by Prep-HPLC to afford N-(2-{hexahydro-1H-furo[3,4-b]pyrrol-1-yl}pyrimidin-4-yl)-8-[(2R,3S)-3-(methanesulfonylmethyl)-2-methylazetidin-1-yl]-5-(propan-2-yl)isoquinolin-3-amine (190 mg, 65.0%) as a light-yellow solid. The product was separated by Chiral HPLC to afford the title compound (peak 1) and its diastereomer as light-yellow solids.

Example 27, Compound 243: Synthesis of 2-((3R, 4S)-1-(4-(8-((2R,3S)-3-(ethylsulfonylmethyl)-2-methylazetidin-1-yl)-5-isopropylisoquinolin-3-ylamino)pyrimidin-2-yl)-3-fluoropiperidin-4-yloxy)ethanol In a 8-mL sealed tube, the mixture of 3-chloro-8-[(2R, 3S)-3-[(ethanesulfonyl)methyl]-2-methylazetidin-1-yl]-5-(propan-2-yl)isoquinoline (90 mg, 236 umol, from step 1 of Example 20), 2-{[(3R,4S)-1-(4-aminopyrimidin-2-yl)-3-fluoropiperidin-4-yl]oxy}ethan-1-ol (60.4 mg, 236 umol, from Example B51), $Cs_2CO_3$ (153 mg, 472 umol) and BrettPhos Pd G3 (21.4 mg, 23.6 umol) in dioxane (2 mL) was stirred at 100° C. for 5 h under $N_2$ atmosphere. The reaction mixture was diluted with water and extracted with EA and washed with brine. The organic layer was dried, filtered, evaporated and purified by column chromatography (DCM:MeOH=10:1) followed by Prep-HPLC to afford the title compound (39.5 mg, 28.0%) as a yellow solid.

Example 28, Compound 199: Synthesis of (3S,4R)-3-fluoro-1-(4-(5-((S)-1-hydroxypropan-2-yl)-8-((2R, 3S)-2-methyl-3-(methylsulfonylmethyl)azetidin-1-yl)isoquinolin-3-ylamino)pyrimidin-2-yl)-4-methylpiperidin-4-ol or (3S,4R)-3-fluoro-1-(4-((5-((R)-1-hydroxypropan-2-yl)-8-((2R,3S)-2-methyl-3-((methylsulfonyl)methyl)azetidin-1-yl)isoquinolin-3-yl)amino)pyrimidin-2-yl)-4-methylpiperidin-4-ol

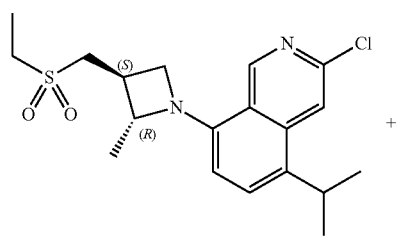

+

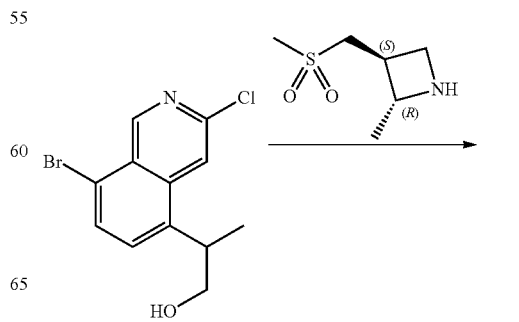

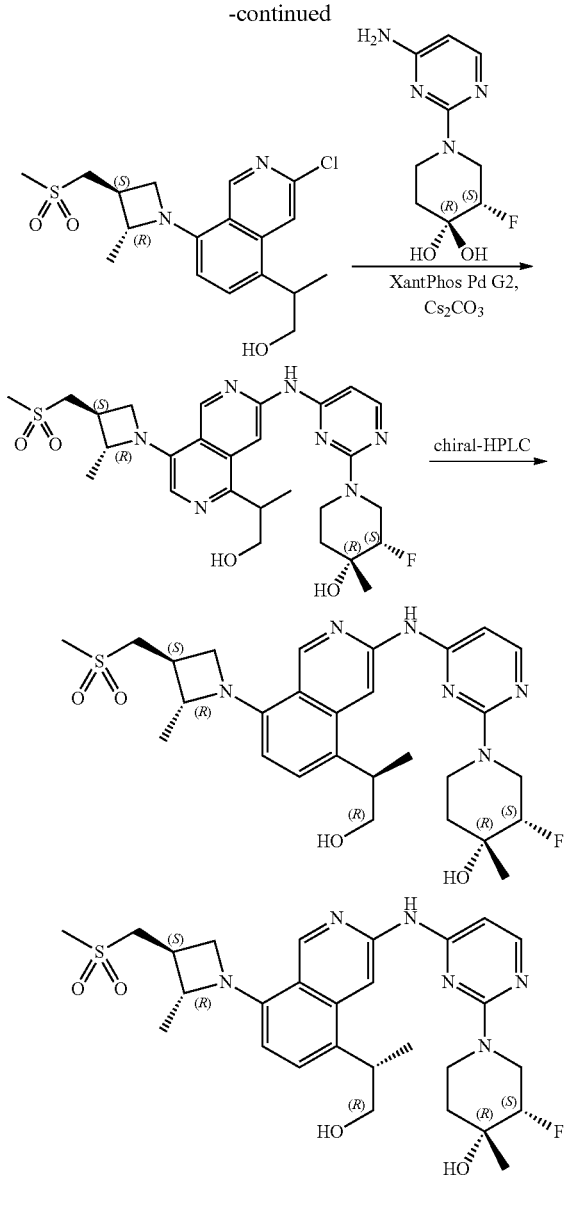

Step 1: Synthesis of 2-(3-chloro-8-((2R,3S)-2-methyl-3-(methylsulfonylmethyl)azetidin-1-yl)isoquinolin-5-yl)propan-1-ol To a solution of 2-(8-bromo-3-chloroisoquinolin-5-yl)propan-1-ol (300 mg, 0.9980 mmol, from Example C5) in 1,4-dioxane was added (2R,3S)-3-(methanesulfonylmethyl)-2-methylazetidine (162 mg, 0.998 mmol, from Example A4), Cs₂CO₃ (648 mg, 1.99 mmol) and BINAP Pd G3 (93 mg, 0.0998 mmol). The mixture was stirred for 3 h at 100° C. The reaction mixture was cooled to rt. The resulting solution was diluted with water and extracted with EA. The organic layer was concentrated and purified by PrepTLC (5% MeOH in DCM. This resulted in 270 mg (70.6%) of 2-{3-chloro-8-[(2R,3S)-3-(methanesulfonylmethyl)-2-methylazetidin-1-yl]isoquinolin-5-yl}propan-1-ol as a yellow solid.

Analytical Data: LC-MS: (ES, m/z)=383 [M+1].

Step 2: Synthesis of (3S,4R)-3-fluoro-1-(4-(5-((S)-1-hydroxypropan-2-yl)-8-((2R,3S)-2-methyl-3-(methylsulfonylmethyl)azetidin-1-yl)isoquinolin-3-ylamino)pyrimidin-2-yl)-4-methylpiperidin-4-ol To a solution of 2-{3-chloro-8-[(2R,3S)-3-(methanesulfonylmethyl)-2-methylazetidin-1-yl]isoquinolin-5-yl}propan-1-ol (220 mg, 0.5745 mmol) in 1,4-dioxane was added (3S,4R)-1-(4-aminopyrimidin-2-yl)-3-fluoro-4-methylpiperidin-4-ol (129 mg, 0.5745 mmol, peak 1 from Example B12), Cs₂CO₃ (371 mg, 1.14 mmol) and XantPhos Pd G2 (25.5 mg, 0.02872 mmol). The mixture was stirred for 3 h at 100° C. under nitrogen. The reaction mixture was cooled to rt, diluted with water and extracted with EA. The resulting mixture was washed brine, dried and concentrated under vacuum. This resulted in 200 mg (60.7%) of (3S,4R)-3-fluoro-1-(4-{[5-(1-hydroxypropan-2-yl)-8-((2R,3S)-3-(methanesulfonylmethyl)-2-methylazetidin-1-yl)isoquinolin-3-yl]amino}pyrimidin-2-yl)-4-methylpiperidin-4-ol as a yellow solid, which was further separated by chiral-HPLC to afford (3S,4R)-3-fluoro-1-(4-(5-((S)-1-hydroxypropan-2-yl)-8-((2R,3S)-2-methyl-3-((methylsulfonyl)methyl)azetidin-1-yl)isoquinolin-3-ylamino)pyrimidin-2-yl)-4-methylpiperidin-4-ol and (3S,4R)-3-fluoro-1-(4-((5-((R)-1-hydroxypropan-2-yl)-8-((2R,3S)-2-methyl-3-((methylsulfonyl)methyl)azetidin-1-yl)isoquinolin-3-yl)amino)pyrimidin-2-yl)-4-methylpiperidin-4-ol (peak 1, 70 mg) as yellow solid.

Example 29, Compound 244: Synthesis of 2-((3S,4R)-1-(4-(8-((2R,3S)-3-(ethylsulfonylmethyl)-2-methylazetidin-1-yl)-5-isopropylisoquinolin-3-ylamino)pyrimidin-2-yl)-3-fluoropiperidin-4-yloxy)ethanol

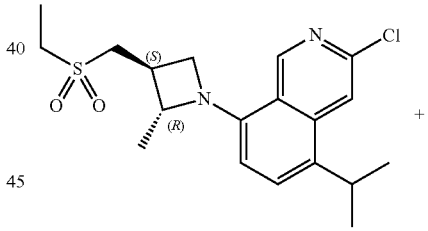

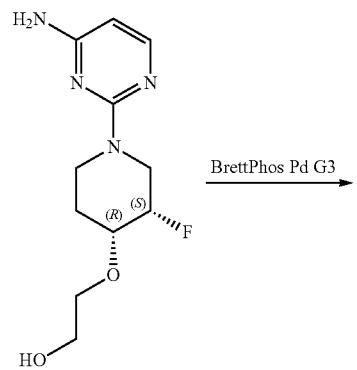

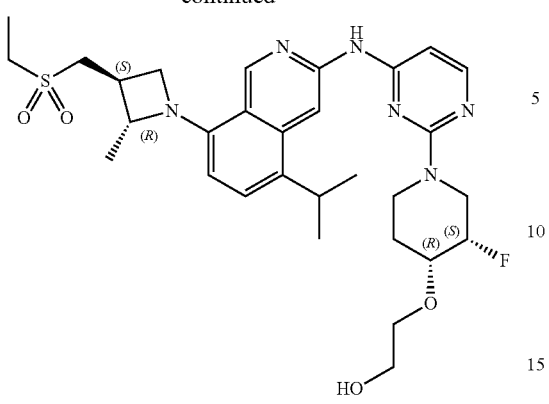

In a 8-mL sealed tube, the mixture of 3-chloro-8-[(2R,3S)-3-[(ethanesulfonyl)methyl]-2-methylazetidin-1-yl]-5-(propan-2-yl)isoquinoline (90 mg, 236 umol, from step 1 of Example 20), 2-{[(3S,4R)-1-(4-aminopyrimidin-2-yl)-3-fluoropiperidin-4-yl]oxy}ethan-1-ol (60.4 mg, 236 umol, from Example B52), $Cs_2CO_3$ (153 mg, 472 umol) and BrettPhos Pd G3 (21.4 mg, 23.6 umol) in dioxane (2 mL) was stirred at 100° C. for 5 h under nitrogen atmosphere. The reaction mixture was diluted with water, extracted with EA and washed with brine. The organic layer was dried, filtered, evaporated and purified by column chromatography (DCM:MeOH=20:1) followed by Prep-HPLC to afford the title compound (50.4 mg, 35.7%) as a yellow solid.

Example 30, Compound 251 and 252: Synthesis of 2-((R)-3,3-difluoro-1-(4-(5-isopropyl-8-((2R,3S)-2-methyl-3-(methylsulfonylmethyl)azetidin-1-yl)isoquinolin-3-ylamino)pyrimidin-2-yl)piperidin-4-yloxy)ethanol and 2-((S)-3,3-difluoro-1-(4-(5-isopropyl-8-((2R,3S)-2-methyl-3-(methylsulfonylmethyl)azetidin-1-yl)isoquinolin-3-ylamino)pyrimidin-2-yl)piperidin-4-yloxy)ethanol

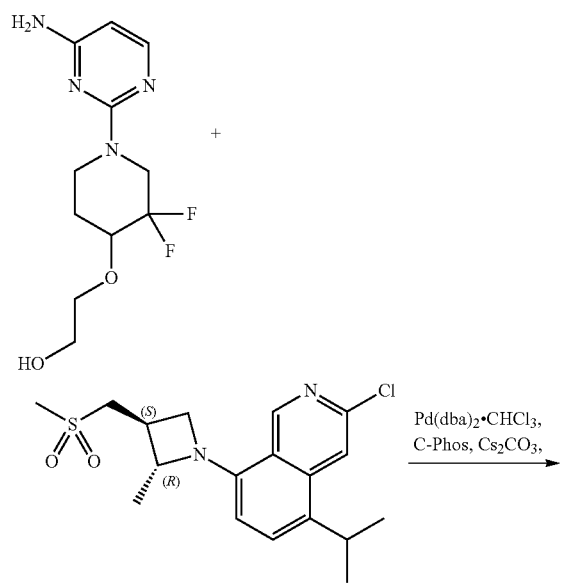

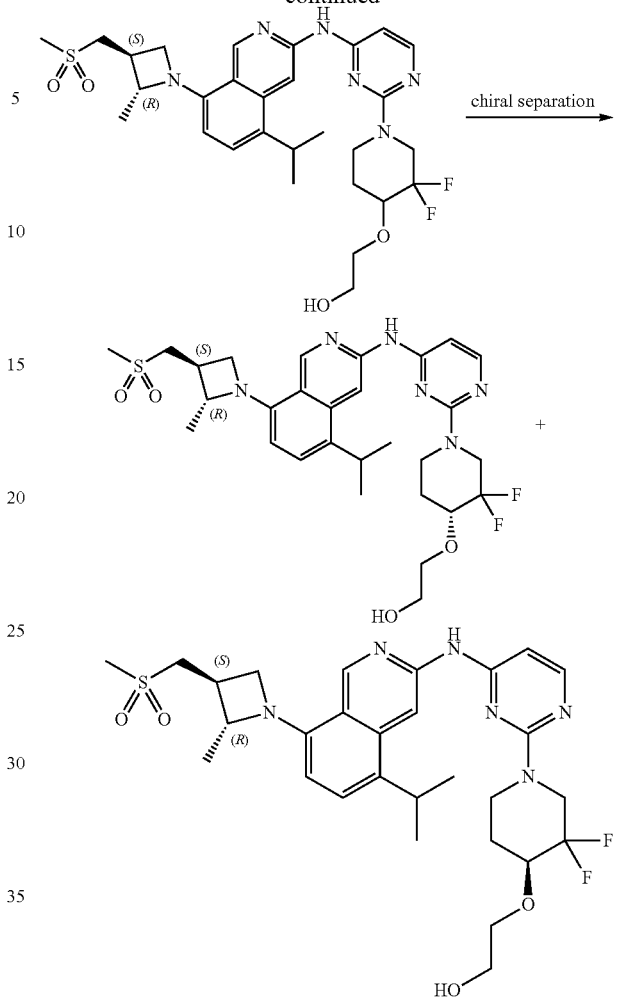

Into a 40-mL sealed tube was placed 3-chloro-8-[(2R,3S)-3-(methanesulfonylmethyl)-2-methylazetidin-1-yl]-5-(propan-2-yl)isoquinoline (900 mg, 2.45 mmol, from step 1 of Example 3) in dioxane (10 mL), was added rac-2-{[1-(4-aminopyrimidin-2-yl)-3,3-difluoropiperidin-4-yl]oxy}ethan-1-ol (671 mg, 2.45 mmol, from Example B69), $Cs_2CO_3$ (1.59 g, 4.90 mmol) and C-Phos (427 mg, 980 μmol, 2-Dicyclohexylphosphino-2',6'-bis(N,N-dimethylamino)biphenyl) and $Pd(dba)_2 \cdot CHCl_3$ (1.01 g, 980 μmol) under $N_2$. The resulting solution was stirred at 110° C. for 3 h. The mixture was diluted with EA and washed with brine. The organic layer was dried with $Na_2SO_4$ and concentrated under vacuum. The residue was purified by Flash Column Silica-CS (DCM: MeOH=1:0 to 10:1). And this resulted in 1 g (67.5%) of 2-({3,3-difluoro-1-[4-({8-[(2R,3S)-3-(methanesulfonylmethyl)-2-methylazetidin-1-yl]-5-(propan-2-yl)isoquinolin-3-yl}amino)pyrimidin-2-yl] piperidin-4-yl}oxy)ethan-1-ol a yellow solid, which was further separated by Prep-Chiral-HPLC to afford 400 mg (40%) of 2-((R)-3,3-difluoro-1-(4-(5-isopropyl-8-((2R,3S)-2-methyl-3-(methylsulfonylmethyl)azetidin-1-yl)isoquinolin-3-ylamino)pyrimidin-2-yl)piperidin-4-yloxy)ethanol or 2-((S)-3,3-difluoro-1-(4-(5-isopropyl-8-((2R,3S)-2-methyl-3-(methylsulfonylmethyl)azetidin-1-yl)isoquinolin-3-ylamino)pyrimidin-2-yl)piperidin-4-yloxy)ethanol as a yellow solid.

Example 31, Compound 146: Synthesis of (3S,4S,5R)-5-fluoro-1-(4-((5-isopropyl-8-(3-((methylsulfonyl)methyl)azetidin-1-yl)isoquinolin-3-yl)amino)pyrimidin-2-yl)-4-methoxypiperidin-3-ol and (3R,4R,5S)-5-fluoro-1-(4-((5-isopropyl-8-(3-((methylsulfonyl)methyl)azetidin-1-yl)isoquinolin-3-yl)amino)pyrimidin-2-yl)-4-methoxypiperidin-3-ol

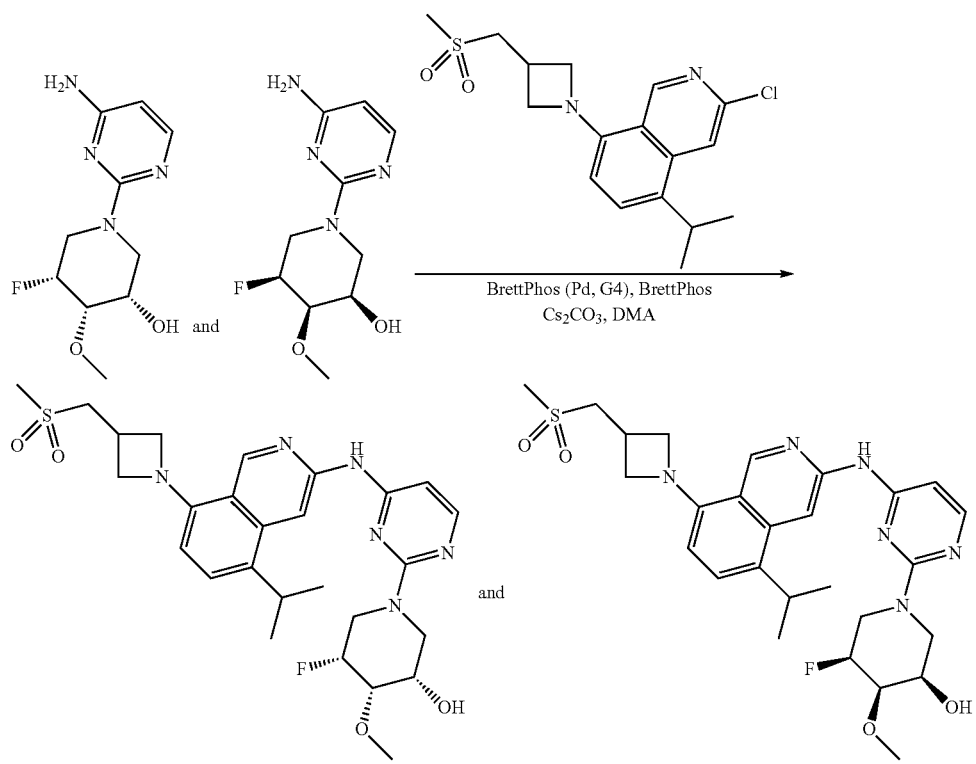

Into a 25-mL round-bottom flask was placed 3-chloro-5-isopropyl-8-[3-(methylsulfonylmethyl) azetidin-1-yl]isoquinoline (5.10 mg, 14.5 μmol, 1 equiv), (3S,4S,5R)-1-(4-aminopyrimidin-2-yl)-5-fluoro-4-methoxy-piperidin-3-ol and (3R,4R,5S)-1-(4-aminopyrimidin-2-yl)-5-fluoro-4-methoxy-piperidin-3-ol (3.5 mg, 14.5 μmol, 1 equiv.), BrettPhos (Pd, G4) (1.33 mg, 1.44 μmol, 0.100 equiv), BrettPhos (1.55 mg, 2.89 μmol, 0.20 equiv) and KOAc (7.09 mg, 72.2 μmol, 5.00 equiv), and dioxane (1 mL). The resulting solution was stirred at 100° C. for 5 h under $N_2$ atmosphere. The mixture was filtered and concentrated under vacuum. The residue was purified by Prep-HPLC; mobile phase: water (10 mmol/L FA) and ACN (14.0% ACN up to 44.0% in 10 min); UV 254/220 nm. This resulted in 1.6 mg (19%) of the title compound as a yellow solid.

Example 32, Compound 200: Synthesis of (3R,4S,5S)-3-fluoro-1-(4-((5-isopropyl-8-((2R,3S)-2-methyl-3-((methylsulfonyl)methyl)azetidin-1-yl)isoquinolin-3-yl)amino)pyrimidin-2-yl)-5-methoxypiperidin-4-ol and (3S,4R,5R)-3-fluoro-1-(4-((5-isopropyl-8-((2R,3S)-2-methyl-3-((methylsulfonyl)methyl)azetidin-1-yl)isoquinolin-3-yl)amino)pyrimidin-2-yl)-5-methoxypiperidin-4-ol

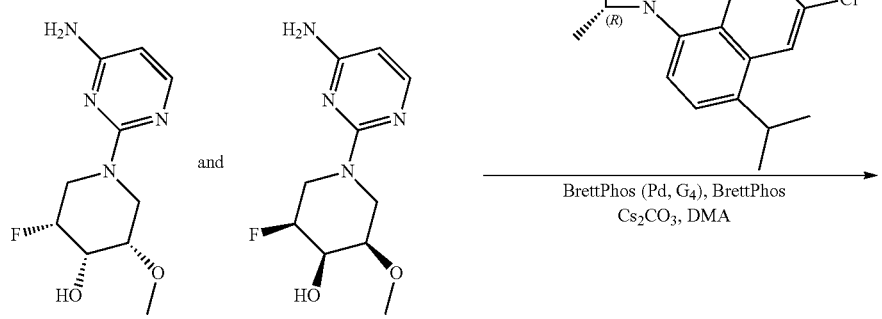

191

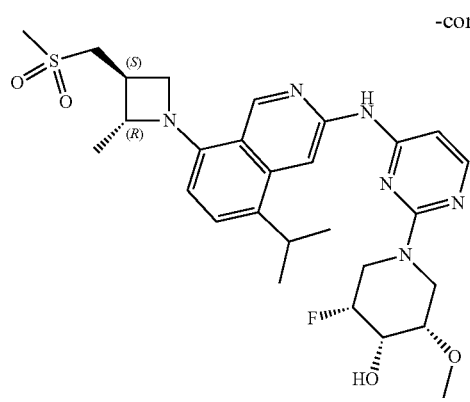

192
-continued

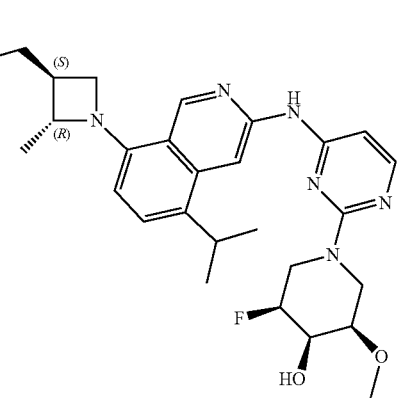

Into a 25-mL round-bottom flask was placed 3-chloro-5-isopropyl-8-[(2R,3S)-2-methyl-3-(methylsulfonylmethyl)azetidin-1-yl]isoquinoline (7.57 mg, 20.6 μmol, 1 equiv.), (3R,4S,5S)-1-(4-aminopyrimidin-2-yl)-3-fluoro-5-methoxy-piperidin-4-ol and (3 S,4R,5R)-1-(4-aminopyrimidin-2-yl)-3-fluoro-5-methoxy-piperidin-4-ol (5.00 mg, 20.6 μl equiv.), BrettPhos (Pd, G4) (1.90 mg, 2.06 μmol, 0.100 equiv.), Cs₂CO₃ (13.4 mg, 41.3 μmol, 2 equiv.), BrettPhos (2.22 mg, 4.13 μmol, 0.200 equiv.), and DMA (1.5 mL). The resulting solution was stirred at 100° C. for 3 h under N₂ atmosphere. The mixture was filtered and concentrated under vacuum. The residue was purified by Prep-HPLC; mobile phase; water (10 mmol/L FA) and ACN (17.0% ACN up to 47.0% in 10 min); detector, UV 254/220 nm. This resulted in 2.8 mg (24%) of the title compound as yellow solid.

Example 33, Compound 198: Synthesis of racemic of (3R,4R,5S)-5-fluoro-1-(4-((5-isopropyl-8-((2R,3S)-2-methyl-3-((methylsulfonyl)methyl)azetidin-1-yl)isoquinolin-3-yl)amino)pyrimidin-2-yl)-4-methoxypiperidin-3-ol and (3S,4S,5R)-5-fluoro-1-(4-((5-isopropyl-8-((2R,3S)-2-methyl-3-((methylsulfonyl)methyl)azetidin-1-yl)isoquinolin-3-yl)amino)pyrimidin-2-yl)-4-methoxypiperidin-3-ol

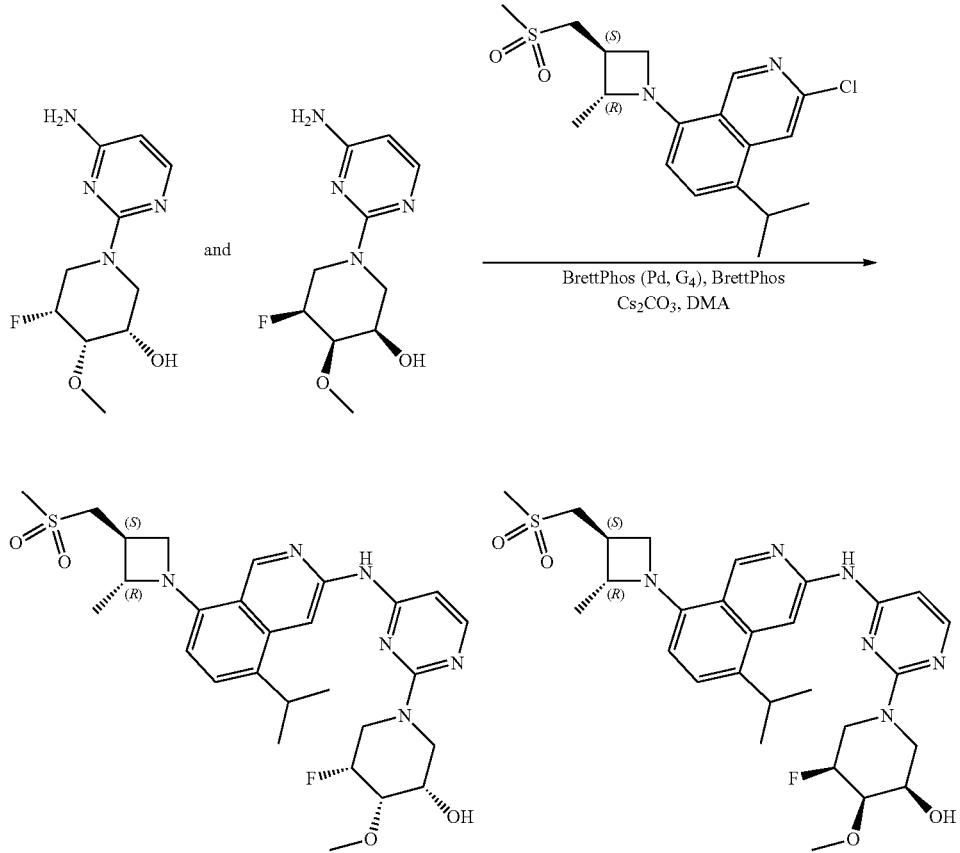

Into a 25-mL round-bottom flask was placed (3R,4R,5S)-1-(4-aminopyrimidin-2-yl)-5-fluoro-4-methoxy-piperidin-3-ol and (3S,4S,5R)-1-(4-aminopyrimidin-2-yl)-5-fluoro-4-methoxy-piperidin-3-ol (21.0 mg, 86.7 µmol, 1 equiv.), 3-chloro-5-isopropyl-8-[(2R,3S)-2-methyl-3-(methylsulfonylmethyl)azetidin-1-yl]isoquinoline (31.8 mg, 86.7 µmol, 1 equiv.), BrettPhos (Pd, G4) (7.98 mg, 8.67 µmol, 0.1 equiv.), BrettPhos (9.31 mg, 17.3 µmol, 0.2 equiv.), Cs$_2$CO$_3$ (56.5 mg, 173 µmol, 2 equiv.), and DMA (1.5 mL). The resulting solution was stirred at 100° C. for 2 h under N$_2$ atmosphere. The reaction mixture was filtered and concentrated under vacuum. The residue was purified by Prep-HPLC; mobile phase: water (10 mmol/L FA) and ACN (20.0% ACN up to 50.0% in 10 min); detector, UV 254/220 nm. This resulted in 23 mg (46%) of the title compound as a yellow solid.

Example 34, Compound 147: Synthesis of racemic (3S,4R,5R)-3-fluoro-1-(4-((5-isopropyl-8-(3-((methylsulfonyl)methyl)azetidin-1-yl)isoquinolin-3-yl)amino)pyrimidin-2-yl)-5-methoxypiperidin-4-ol and (3R,4S,5S)-3-fluoro-1-(4-((5-isopropyl-8-(3-((methylsulfonyl)methyl)azetidin-1-yl)isoquinolin-3-yl)amino)pyrimidin-2-yl)-5-methoxypiperidin-4-ol

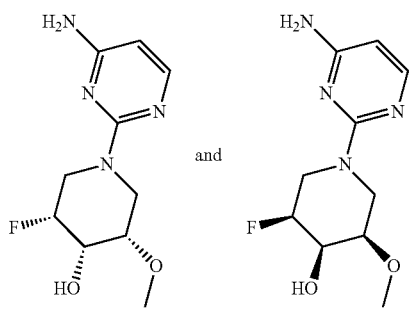
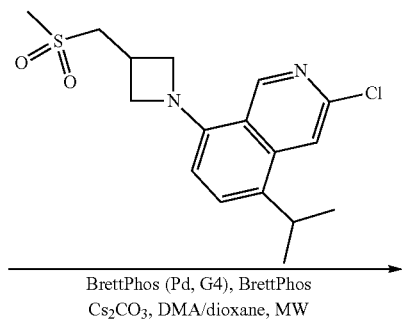

BrettPhos (Pd, G4), BrettPhos
Cs$_2$CO$_3$, DMA/dioxane, MW

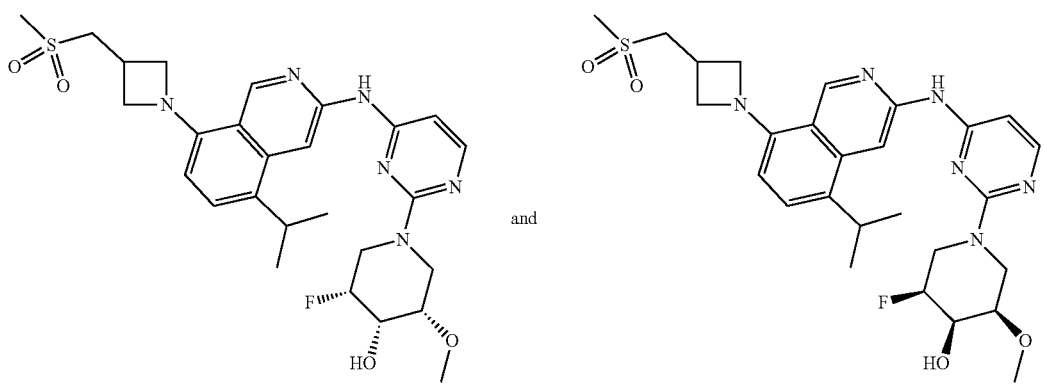

Into a 10-mL microwave tube was placed (3S,4R,5R)-1-(4-aminopyrimidin-2-yl)-3-fluoro-5-methoxy-piperidin-4-ol (32.0 mg, 132 μmol, 1 equiv.), 3-chloro-5-isopropyl-8-[3-(methylsulfonylmethyl)azetidin-1-yl]isoquinoline (46.6 mg, 132 μmol, 1 equiv.), BrettPhos (Pd, G4) (12.2 mg, 13.2 μmol, 0.1 equiv.), BrettPhos (14.2 mg, 26.4 μmol, 0.2 equiv.), $Cs_2CO_3$ (86.1 mg, 264 μmol, 2 equiv.), DMA (0.7 mL) and dioxane (0.7 mL). The resulting solution was stirred at 110° C. for 2 h under MW condition. The mixture was filtered and concentrated under vacuum. The residue was purified by Prep-HPLC; water (10 mmol/L $NH_4HCO_3$) and ACN (16.0% ACN up to 46.0% in 10 min); detector, UV 254/220 nm. This resulted in 20 mg (27%) of the title compound as yellow solid.

Example 35, Compound 201: Synthesis of (3R,4S,5S)-3-fluoro-1-(4-((5-isopropyl-8-((2R,3S)-2-methyl-3-((methylsulfonyl)methyl)azetidin-1-yl)isoquinolin-3-yl)amino)pyrimidin-2-yl)-5-methoxy piperidin-4-ol and (3S,4R,5R)-3-fluoro-1-(4-((5-isopropyl-8-((2R,3S)-2-methyl-3-((methylsulfonyl)methyl)azetidin-1-yl)isoquinolin-3-yl)amino)pyrimidin-2-yl)-5-methoxy piperidin-4-ol

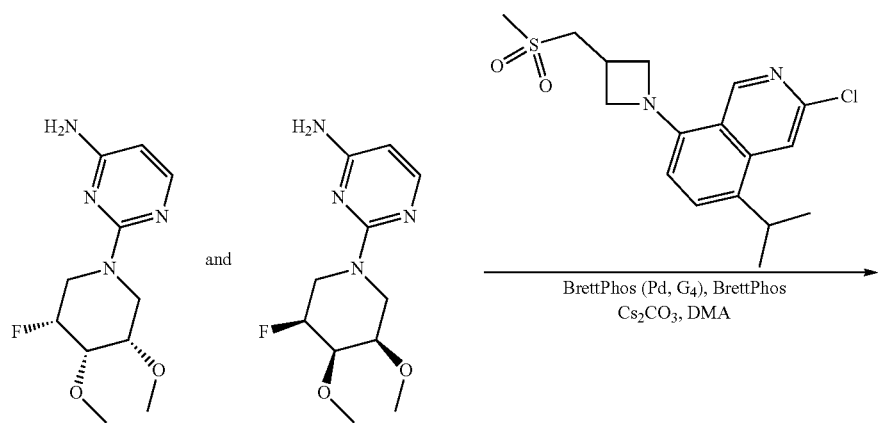

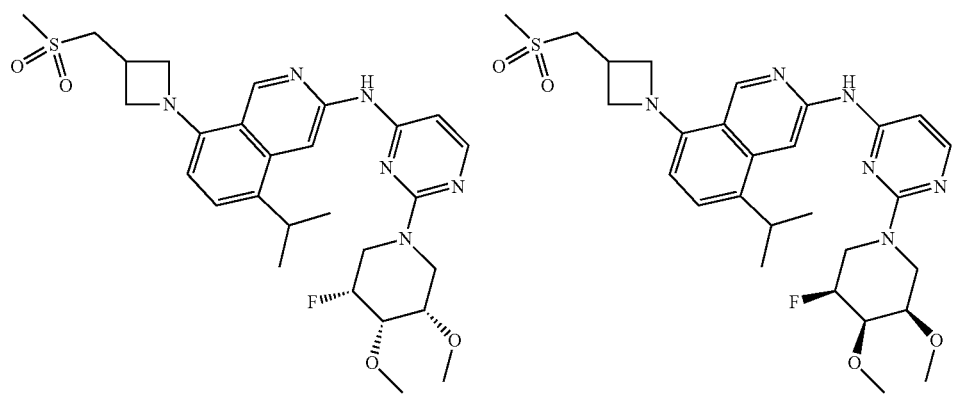

Into a 25-mL round-bottom flask was placed 3-chloro-5-isopropyl-8-[(2R,3S)-2-methyl-3-(methylsulfonylmethyl)azetidin-1-yl]isoquinoline (7.57 mg, 20.6 μmol, 1 equiv.), (3R,4S,5S)-1-(4-aminopyrimidin-2-yl)-5-fluoro-5-methoxy-piperidin-4-ol (5.00 mg, 20.6 μmol, 1 equiv.), BrettPhos (Pd, G4) (1.90 mg, 2.06 μmol, 0.10 equiv.), Cs₂CO₃ (13.5 mg, 41.3 μmol, 2 equiv.), BrettPhos (2.22 mg, 4.13 μmol, 0.200 equiv.), and DMA (1.5 mL). The resulting solution was stirred at 100° C. for 3 h under N₂ atmosphere. The mixture was filtered and concentrated under vacuum. The residue was purified by Prep-HPLC; mobile phase: water (10 mmol/L FA) and ACN (17.0% ACN up to 47.0% in 10 min); detector, UV 254/220 nm. This resulted in 2.8 mg (24%) of the title compound as yellow solid.

Example 36, Compound 218: Synthesis of rac-5,5-difluoro-1-[4-[[5-isopropyl-8-[3-(methylsulfonylmethyl)azetidin-1-yl]-3-isoquinolyl]amino]pyrimidin-2-yl]-4-methoxy-piperidin-3-ol

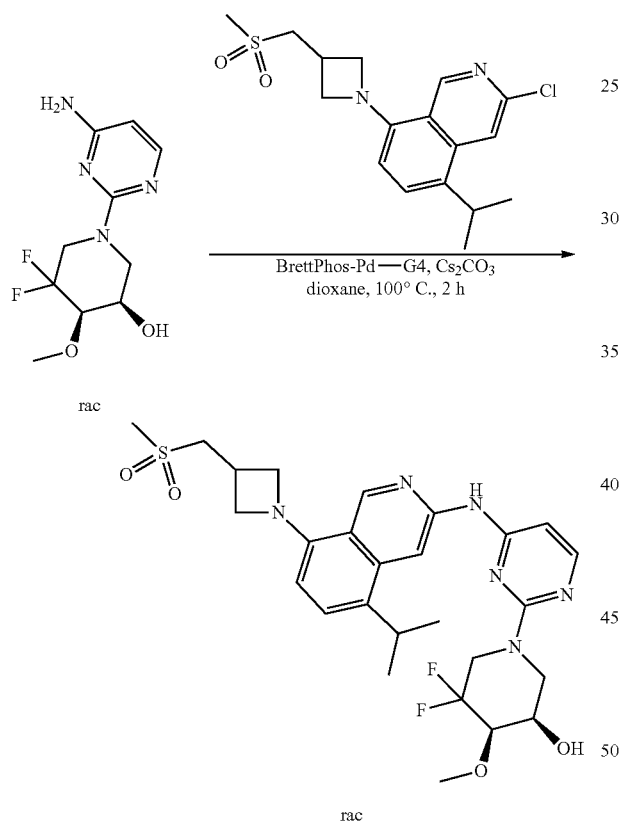

To a solution of 3-chloro-5-isopropyl-8-[3-(methylsulfonylmethyl)azetidin-1-yl]isoquinoline (20.3 mg, 57.6 μmol, 1.50 equiv), rac-cis-1-(4-aminopyrimidin-2-yl)-5,5-difluoro-4-methoxy-piperidin-3-ol (10.0 mg, 38.4 μmol, 1 equiv.) and Cs₂CO₃ (37.5 mg, 115 μmol) in dioxane (1 mL) was added BrettPhos (Pd, G4) (3.54 mg, 3.84 μmol, 0.1 equiv.) under N₂, the mixture was stirred at 100° C. for 2 h. The mixture was filtered and the filtrate was concentrated in vacuo. The crude was purified with prep-HPLC [column: Waters Xbridge 150*25 mm*5 um; mobile phase: [water (10 mM NH4HCO3)-ACN]; B %: 26%-59%, 11 min]. This resulted in 20 mg (94%) of the title compound as an orange solid.

Example 37, Compound 226: Synthesis of (3R,4S)-1-[4-[[5-isopropyl-8-[3-(methylsulfonylmethyl)azetidin-1-yl]-3-isoquinolyl]amino]pyrimidin-2-yl]-4-(2-methoxyethoxy)piperidin-3-ol and (3S,4R)-1-[4-[[5-isopropyl-8-[3-(methylsulfonylmethyl)azetidin-1-yl]-3-isoquinolyl]amino]pyrimidin-2-yl]-4-(2-methoxyethoxy)piperidin-3-ol

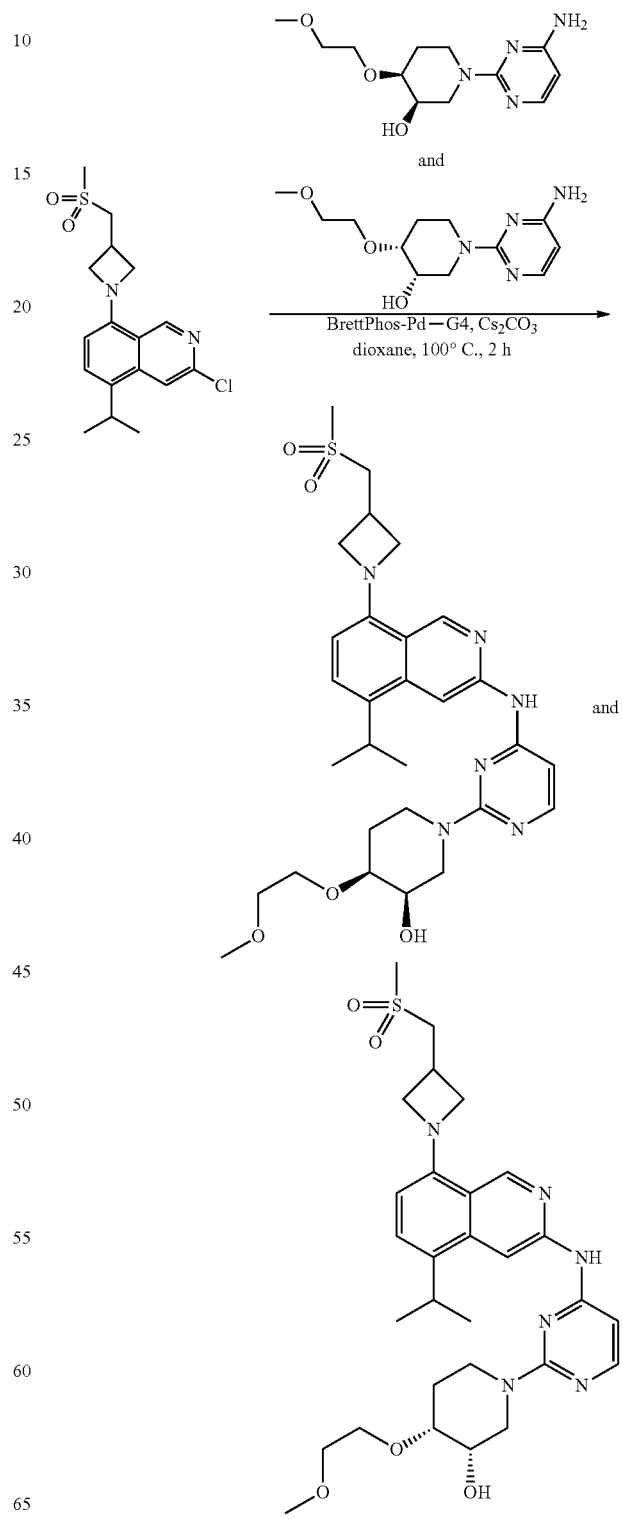

To a solution of 3-chloro-5-isopropyl-8-[3-(methylsulfonylmethyl)azetidin-1-yl]isoquinoline (6.58 mg, 18.6 µmol, 1 equiv), rac (cis)-1-(4-aminopyrimidin-2-yl)-4-(2-methoxyethoxy)piperidin-3-ol (Example B78, 5.00 mg, 18.6 µmol, 1 equiv.) and Cs$_2$CO$_3$ (18.2 mg, 55.9 µmol, 3 equiv.) in dioxane (0.5 mL) was added BrettPhos (Pd, G4) (1.72 mg, 1.86 µmol, 0.100 equiv.) under N$_2$, the mixture was stirred at 100° C. for 2 h. The mixture was filtered and concentrated in vacuo. The crude was purified with prep-TLC (DCM: MeOH=10:1) and prep-HPLC [column: Xtimate C18 150*40 mm*10 µm; mobile phase: [water (0.05% ammonia hydroxide v/v)-ACN]; B %: 28%-58%, 10 min]. This resulted in 2.0 mg (18%) of the title compound as a yellow solid.

Example 38, Compound 227: (3S,4S)-1-[4-[[5-isopropyl-8-[3-(methylsulfonylmethyl)azetidin-1-yl]-3-isoquinolyl]amino]pyrimidin-2-yl]-4-(2-methoxyethoxy)piperidin-3-ol or (3R,4R)-1-[4-[[5-isopropyl-8-[3-(methylsulfonylmethyl)azetidin-1-yl]-3-isoquinolyl]amino]pyrimidin-2-yl]-4-(2-methoxyethoxy)piperidin-3-ol

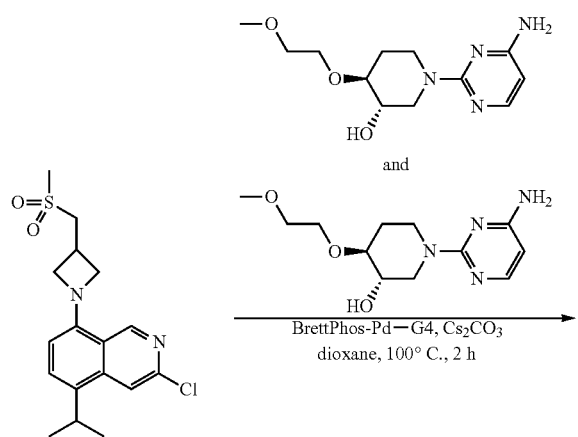

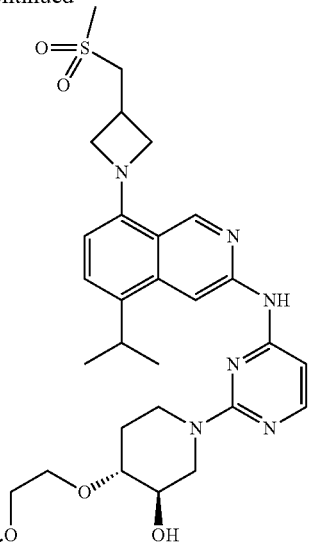

To a solution of 3-chloro-5-isopropyl-8-[3-(methylsulfonylmethyl)azetidin-1-yl]isoquinoline (13.1 mg, 37.2 µmol, 1 equiv.), rac (trans)-1-(4-aminopyrimidin-2-yl)-4-(2-methoxyethoxy)piperidin-3-ol (Example B79, 10.0 mg, 37.2 µmol, 1 equiv.) and Cs$_2$CO$_3$ (36.4 mg, 111 µmol, 3 equiv.) in dioxane (0.5 mL) was added BrettPhos (Pd, G4) (3.43 mg, 3.73 µmol, 0.1 equiv.) under N$_2$, the mixture was stirred at 100° C. for 2 h. The mixture was filtered and concentrated in vacuo. The crude was purified with prep-HPLC to afford 6.5 mg (26%) of the title compound as a yellow solid.

Example 39, Compound 86: Synthesis of (4S,5R)-1-[4-[[5,7-difluoro-8-[3-(methylsulfonylmethyl)azetidin-1-yl]-3-isoquinolyl]amino]pyrimidin-2-yl]-5-fluoro-3,3-dimethyl-piperidin-4-ol or (4R,5S)-1-[4-[[5,7-difluoro-8-[3-(methylsulfonylmethyl)azetidin-1-yl]-3-isoquinolyl]amino]pyrimidin-2-yl]-5-fluoro-3,3-dimethyl-piperidin-4-ol

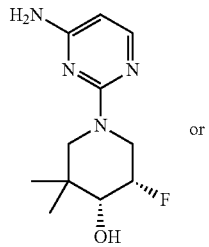

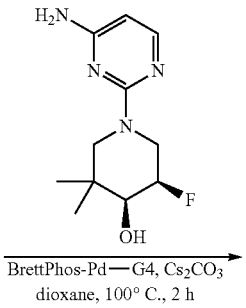

201
-continued

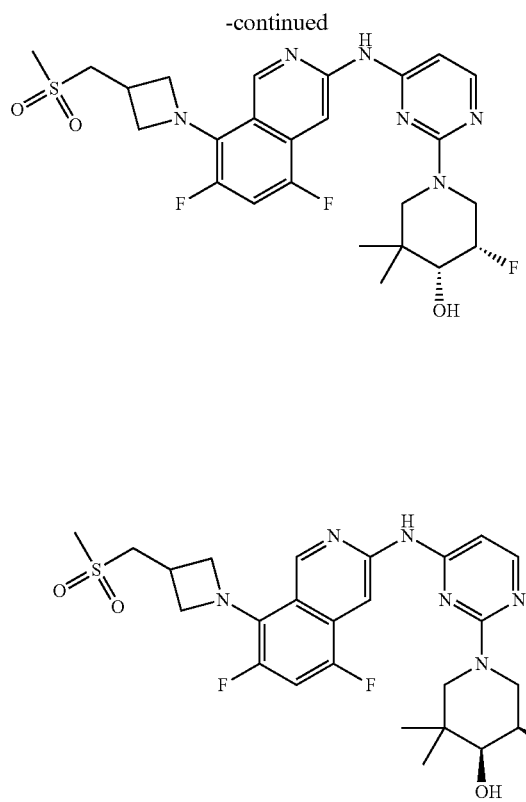

To a solution of 3-chloro-5,7-difluoro-8-[3-(methylsulfonylmethyl)azetidin-1-yl]isoquinoline (5.00 mg, 14.4 µmol, 1 equiv), (4S,5R)-1-(4-aminopyrimidin-2-yl)-5-fluoro-3,3-dimethyl-piperidin-4-ol or (4R,5S)-1-[4-[[5,7-difluoro-8-[3-(methyl sulfonylmethyl)azetidin-1-yl]-3-isoquinolyl]amino]pyrimidin-2-yl]-5-fluoro-3,3-dimethyl-piperidin-4-ol (peak 2 from Example B11, 4.16 mg, 17.3 µmol, 1.20 equiv.) and Cs$_2$CO$_3$ (14.1 mg, 43.2 µmol, 3 equiv.) in dioxane (0.5 mL) was added BrettPhos (Pd, G4) (1.33 mg, 1.44 µmol, 0.1 equiv.) under N$_2$, the mixture was stirred at 100° C. for 2 h. The mixture was diluted with EA (10 mL), filtered through a thin layer of silica and the filtrate was concentrated in vacuo. The crude was purified with prep-HPLC [column: Waters Xbridge 150*25 mm*5 µm; mobile phase: [water (10 mM NH$_4$HCO$_3$)-ACN]; B %: 25%-55%, 10 min]. This resulted in 2.3 mg (29%) of the title compound as a yellow solid.

Example 40, Compound 282: Synthesis of N-(2-((3S,4R)-3-fluoro-4-(methoxy-d3)piperidin-1-yl)pyrimidin-4-yl)-5-isopropyl-8-((2R,3S)-2-methyl-3-((methylsulfonyl)methyl)azetidin-1-yl)isoquinolin-3-amine

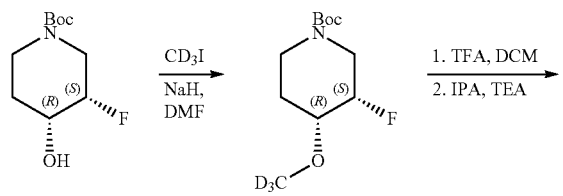

202
-continued

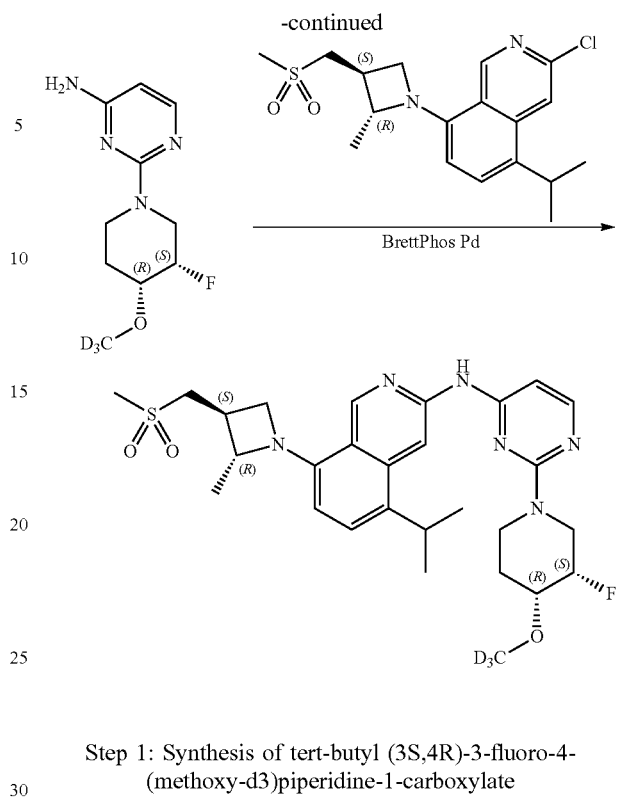

Step 1: Synthesis of tert-butyl (3S,4R)-3-fluoro-4-(methoxy-d3)piperidine-1-carboxylate NaH (218.90 mg, 9.122 mmol, 2 equiv.) was added to tert-butyl (3S,4R)-3-fluoro-4-hydroxypiperidine-1-carboxylate (1000.00 mg, 4.561 mmol, 1.00 equiv.) (Pharmablock) in DMF (20 mL) at 0° C. After stirring for 20 minutes, CD$_3$I (3305.67 mg, 22.804 mmol, 5 equiv.) was added and the resulting solution was stirred for 12 hr at rt. Water was added and the mixture was extracted with EA. The organic layer was washed with brine, dried and concentrated to afford 1000 mg of product as light yellow oil.

Step 2: Synthesis of 2-((3S,4R)-3-fluoro-4-(methoxy-d3)piperidin-1-yl)pyrimidin-4-amine TFA (3 mL) was added to tert-butyl (3S,4R)-3-fluoro-4-(methoxy-d3)piperidine-1-carboxylate (1000.00 mg, 4.232 mmol, 1.00 equiv.) in DCM (10 mL) and the solution was stirred for 2 h at rt. The mixture was concentrated under vacuum and residue was dissolved in IPA (20 mL), followed by the addition of 2-chloropyrimidin-4-amine (480 mg, 3.60 mmol) and TEA (2229.10 mg). The mixture was stirred overnight at 100° C. The mixture was concentrated and the residue was purified by FLASH (5% MeOH in EA) to afford 500 mg of the title compound as a light yellow solid.

Analytical Data: LC-MS: (ES, m/z)=230 [M+1].

Step 3: Synthesis of N-(2-((3S,4R)-3-fluoro-4-(methoxy-d3)piperidin-1-yl)pyrimidin-4-yl)-5-isopropyl-8-((2R,3S)-2-methyl-3-((methylsulfonyl)methyl)azetidin-1-yl)isoquinolin-3-amine The mixture of Cs$_2$CO$_3$ (1421.09 mg, 4.362 mmol, 2 equiv.), 3-chloro-8-[(2R,3S)-3-(methanesulfonylmethyl)-2-methylazetidin-1-yl]-5-(propan-2-yl)isoquinoline (500.00 mg, 2.181 mmol, 1.00 equiv.), 2-((3S,4R)-3-fluoro-4-(methoxy-d3)piperidin-1-yl)pyrimidin-4-amine (340 mg, 1.48 mmol) and Brettphos Pd (197.69 mg, 0.218 mmol, 0.1 equiv.) in dioxane (10 mL) was heated to 100° C. and stirred for 16 h under $N_2$ atmosphere. The mixture was diluted with EA (100 mL) and washed with brine. The organic layer was dried over $Na_2SO_4$ and concentrated under vacuum. The crude product was purified by prep-HPLC to afford the title compound, 250 mg as yellow solid.

Example 41, Compound 283: Synthesis of N-(2-((3R,4S)-3-fluoro-4-(methoxy-d3)piperidin-1-yl)pyrimidin-4-yl)-5-isopropyl-8-((2R,3S)-2-methyl-3-((methylsulfonyl)methyl)azetidin-1-yl)isoquinolin-3-amine

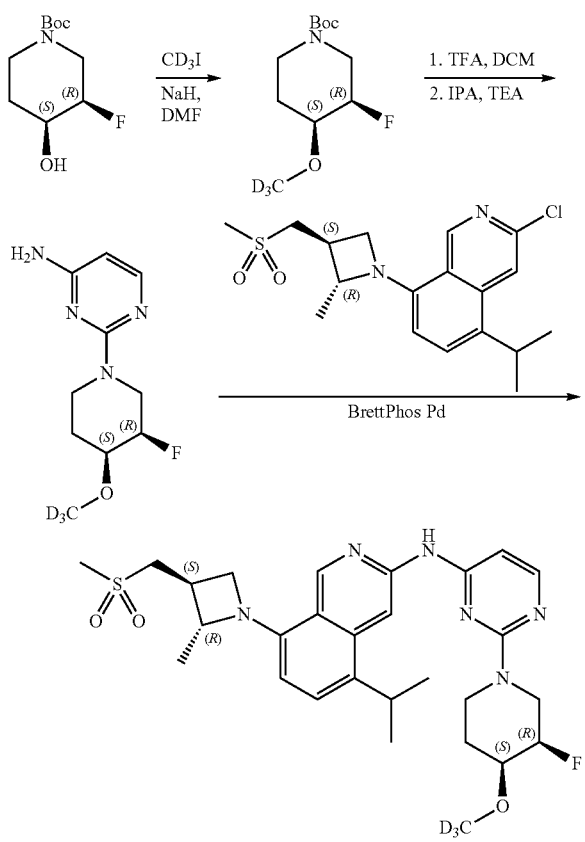

Step 1: Synthesis of tert-butyl (3R,4S)-3-fluoro-4-(methoxy-d3)piperidine-1-carboxylate NaH (218 mg, 9.08 mmol) was added to tert-butyl (3R,4S)-3-fluoro-4-hydroxypiperidine-1-carboxylate (1000 mg, 4.56 mmol) in DMF (20 mL, 22.6 mmol) at 0° C. After stirring for 20 minutes, $CD_3I$ (3.30 g, 22.8 mmol) was added and the solution was stirred at rt for 16 h. The reaction was quenched by the addition of 5 mL of water and extracted with EA and washed with brine and concentrated. This is resulted 1140 mg of the title compound as a light-yellow oil.

Step 2: Synthesis of 2-((3R,4S)-3-fluoro-4-(methoxy-d3)piperidin-1-yl)pyrimidin-4-amine TFA (2 mL) was added to tert-butyl (3R,4S)-3-fluoro-4-(methoxy-d3)piperidine-1-carboxylate (1140 mg, 4.82 mmol) in DCM (6 mL) and the solution was stirred for 2 h at rt. The mixture was concentrated under vacuum and residue was dissolved in IPA (20 mL), followed by 2-chloropyrimidin-4- (496 mg, 3.83 mmol) and TEA (0.6 mL). The mixture was stirred overnight at 100° C. The mixture was concentrated and the residue was purified by FLASH (5% MeOH in EA) to afford 425 mg of the title compound as a light-yellow solid.

Analytical Data: LC-MS: (ES, m/z)=230 [M+1].

Step 3: Synthesis of N-(2-((3R,4S)-3-fluoro-4-(methoxy-d3)piperidin-1-yl)pyrimidin-4-yl)-5-isopropyl-8-((2R,3S)-2-methyl-3-((methylsulfonyl)methyl)azetidin-1-yl)isoquinolin-3-amine The mixture of $Cs_2CO_3$ (318 mg, 0.9768 mmol), 3-chloro-8-[(2R,3S)-3-(methanesulfonylmethyl)-2-methylazetidin-1-yl]-5-(propan-2-yl)isoquinoline (543 mg, 1.47 mmol), 2-[(3R,4S)-3-fluoro- (340 mg, 1.48 mmol) and Brettphos Pd (134 mg, 0.1480 mmol) in dioxane (20 mL) was heated to 100° C. and stirred for 16 hours under $N_2$ atmosphere. The mixture was diluted with EA (100 mL) and washed with brine. The organic layer was dried over $Na_2SO_4$ and concentrated under vacuum. The crude product was purified by prep-HPLC to get 327.1 mg of the title compound as yellow solid.

Example 42, Compound 122: Synthesis of N-(2-((3S,4R)-3-fluoro-4-methoxypiperidin-1-yl)pyrimidin-4-yl)-5-isopropyl-8-((2R,3S)-2-methyl-3-((methylsulfonyl)methyl)azetidin-1-yl)isoquinolin-3-amine

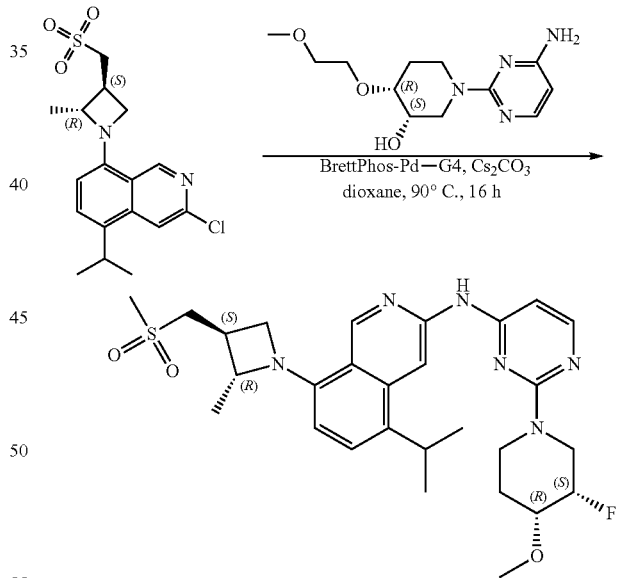

To a solution of 2-((3S,4R)-3-fluoro-4-methoxypiperidin-1-yl)pyrimidin-4-amine (18.50 mg, 0.082 mmol, 1 equiv., from Example B33), 3-chloro-5-isopropyl-8-((2R,3S)-2-methyl-3-((methylsulfonyl)methyl)azetidin-1-yl)isoquinoline (30 mg, 0.082 mmol, 1 equiv.) and $Cs_2CO_3$ (53.3 mg, 0.164 mmol, 2 equiv.) in 1,4-Dioxane (0.82 ml) was added BrettPhos Precatalyst (Gen IV) (3.76 mg, 4.09 µmol, 0.05 equiv.) under $N_2$, the mixture was stirred at 90° C. for 16 h. The mixture was filtered and concentrated in vacuo. The crude mixture was purified by reverse phase chromatography (0 to 60% acetonitrile/water containing 0.1% TFA).

Pure fractions were combined and neutralized with saturated sodium bicarbonate solution and then extracted with 10% MeOH/DCM (5 mL×3). Combined organic phases dried over sodium sulfate, filtered and evaporated to give 17.4 mg of the title compound (38%) as a yellow solid.

Example 43, Compound 123: Synthesis of N-(2-((3R,4S)-3-fluoro-4-methoxypiperidin-1-yl)pyrimidin-4-yl)-5-isopropyl-8-((2R,3S)-2-methyl-3-((methylsulfonyl)methyl)azetidin-1-yl)isoquinolin-3-amine

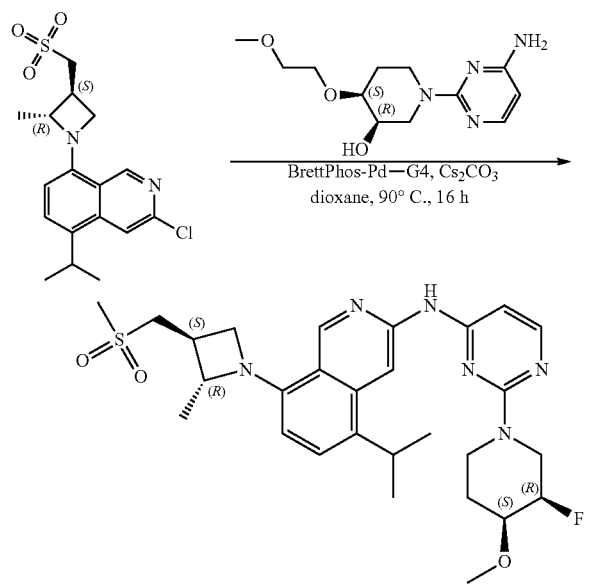

To a solution of 2-((3R,4S)-3-fluoro-4-methoxypiperidin-1-yl)pyrimidin-4-amine (18.5 mg, 0.082 mmol, 1 equiv., from Example B32), 3-chloro-5-isopropyl-8-((2R,3S)-2-methyl-3-((methylsulfonyl)methyl)azetidin-1-yl)isoquinoline (30 mg, 0.082 mmol, 1 equiv.) and $Cs_2CO_3$ (53.3 mg, 0.164 mmol, 2 equiv.) in 1,4-Dioxane (0.82 ml) was added BrettPhos Precatalyst (Gen IV) (3.76 mg, 4.09 μmol, 0.05 equiv.) under $N_2$, the mixture was stirred at 90° C. for 16 h. The mixture was filtered and concentrated in vacuo. The crude mixture was purified by reverse phase chromatography (0 to 60% acetonitrile/water containing 0.1% TFA). Pure fractions were combined and neutralized with saturated sodium bicarbonate solution and then extracted with 10% MeOH/DCM (5 mL×3). Combined organic phases dried over sodium sulfate, filtered and evaporated to give 20.4 mg of the title compound (45%) as a yellow solid.

Chiral Chromatography Conditions:
- A. Column: AD 20*250 mm, 10 um (Daicel); Mobile Phase: CO2/MeOH (0.2% ammonia in methanol)=60/40; Flow Rate: 80 g/min.
- B. Column: CHIRALPAK IC-3, 0.46*5 cm; 3 um; Mobile phase: (Hex:DCM=3:1)(0.1% DEA):EtOH=50:50; Flow Rate: 1.0 ml/min.
- C. Column: Chiral-IC 4.6*100 mm, 5 um; Mobile Phase: CO2/IPA (0.1% DEA), Gradient (B %): 10% to 50% in 4.0 min, hold 2.0 min at 50%; Flow: 4.0 ml/min.
- D. Column: CHIRALPAK IG-3, 0.46*5 cm; 3 um; Mobile phase: MtBE (0.1% DEA): EtOH=70:30; Flow Rate: 1.0 ml/min.
- E. Column name: CHIRALPAK AD-3 3*100 mm, 3 um; Mobile Phase: CO2/MeOH (0.1% DEA), 10% to 50% in 4.0 min, hold 2.0 min at 50%; Flow Rate: 2 mL/min.
- F. Column: CHIRALPAK IE-3, 0.46*5 cm; 3 um; Mobile phase: (Hex:DCM=3:1)(0.1% DEA):IPA=70:30; Flow Rate: 1.0 ml/min.
- G. Column: Reg AD Column Size: 0.46*10 cm; 5 um; Mobile phase A: Hex (0.1% DEA) Mobile phase B: Hex (0.1% FA) Mobile phase C: EtOH Mobile phase D: IPA; Flow: 1.0 mL/min.
- H. Column: CHIRAL Cellulose-SB4.6*100 mm 3 um; Mobile phase: Hex (0.1% DEA): EtOH=50:50; Flow Rate: 1 ml/min.
- I. Column: Lux Cellulose-4, 0.46*5 cm; 3 um; Mobile phase: Hex (8 mMNH3): MeOH:MeOH=40:30:30; Flow Rate: 1.0 mL/min.
- J. For intermediate stage: Column: CHIRALPAK IA (0.46*15 cm, 5 um); Mobile Phase: CO2/EtOH (0.1% DEA); Flow Rate: 4 mL/min.
- K. Column: CHIRALPAK IA-3; Size: 0.46*5 cm; 3 um; Mobile phase: (Hex:DCM=5:1)(0.1% DEA):IPA=80:20; Flow: 1.0 mL/min.
- L. Column: CHIRALPAK ID-3, 0.46*5 cm; 3 um; (Hex:DCM=3:1)(0.1% DEA):MeOH=50:50; Flow Rate: 1.0 ml/min.
- M. Column: CHIRALPAK IF-3, 0.46*5 cm; 3 um; Mobile phase: (Hex:DCM=1:1)(0.1% DEA): EtOH=92:8; Flow: 1.5 ml/min.
- N. Column: CHIRAL Cellulose-SJ 4.6*150 mm, 3 um; Mobile Phase: CO2/MeOH (0.1% DEA); Flow: 4.0 ml/min.
- O. For Intermediate: Column name: Chiral-ND 3.0*100 mm, 3 um; Mobile Phase: CO2/MeOH (0.1% DEA); Flow: 4.0 ml/min.
- P. Column: DAICEL CHIRALPAK AD (250 mm*30 mm, 10 um); mobile phase: [0.1% $NH_3H_2O$ IPA]; B %: 60%-60%, 3.5 min; 30 min.
- Q. Column: DAICEL CHIRALPAK AS (250 mm*30 mm, 10 um); mobile phase: [0.1% NH3H₂O-MEOH]; B %: 60%-60%, 4.4 min; 25 min.
- R. Column: DAICEL CHIRALCEL OJ (250 mm*50 mm, 10 um); mobile phase: [0.1% NH3H₂O MEOH]; B %: 60%-60%, 2.2 min.
- S. Column: Cellucoat 50×4.6 mm I.D., 3 um, Mobile phase: Phase A for CO2, and Phase B for MeOH+ACN (0.05% DEA); Gradient elution: 60% MeOH+ACN (0.05% DEA) in CO2, Flow rate: 3 mL/min; Detector: PDA; Column Temp: 35 C; Back Pressure: 100 Bar.
- T. Column: CHIRALPAK IF-3; Size: 0.46*5 cm; 3 um; Mobile phase: MtBE (0.1% DEA): MeOH=93:7; Flow: 1.0 mL/min.
- U. Column: CHIRALPAK IF-3; Size: 0.46*5 cm; 3 um; Mobile phase: MtBE (0.1% DEA): MeOH=50:50; Flow: 1.0 mL/min.
- V. Column: CHIRALPAK IF-3; Size: 0.46*5 cm; 3 um; Mobile phase: (Hex:DCM=3:1)(0.1% DEA):IPA=50:50; Flow: 1.0 mL/min.
- W. CHIRALPAK IF-3; Size: 0.46*5 cm; 3 um; Mobile phase: MtBE (0.1% DEA): MeOH=93:7; Flow: 1.0 mL/min X. CHIRALPAK IF-3; Size: 0.46*5 cm; 3 um; Mobile phase: (Hex:DCM=3:1)(0.1% DEA):EtOH=70:30; Flow: 1.0 mL/min.
Y. Column: CHIRALPAK IE-3, 0.46*5 cm; 3 um; Mobile phase: (Hex:DCM=3:1)(0.1% DEA):IPA=90:10; Flow Rate: 1.0 ml/min.
Z. Column: CHIRALPAK IC-3, 0.46*5 cm; 3 um; Mobile phase: Hex:DCM=3:1)(0.1% DEA):EtOH=80:20; Flow Rate: 1.0 ml/min
AA. Column: Chiralpak IG-3 50×4.6 mm I.D., 3 um Mobile phase: Phase A for CO2, and Phase B for MeOH+ACN (0.05% DEA); Gradient elution: 60% MeOH+ACN (0.05% DEA) in CO2 Flow rate: 3 mL/min; Detector: PDA; Column Temp: 35 C; Back Pressure: 100 Bar.
BB. For intermediate stage: Column: CHIRAL Cellulose-SB4.6*100 mm 3 um; mobile phase: Hex (0.1% DEA): IPA=70:30 Flow: 1.0 ml/min; Flow 1.000 mL/min.
DD. For intermediate stage: Column: CHIRALPAK IC-3, 3*100 mm 3 um; Mobile Phase A: Mobile Phase B: MeOH (0.1% DEA); Flow rate: 2 mL/min.
EE. For intermediate stage: Column: EnantioPak-A1-5 (02), 5*25 cm, 5 um; Mobile Phase A: CO2:60, Mobile Phase B: EtOH 0.1% DEA; Flow rate: 2 mL/min.
FF. For intermediate stage: Column: CHIRALPAK AD-3 3*100m m, 3 um; Co-Solvent: MeOH (0.1% DEA); Gradient (B %): 10% to 50% in 4.0 min, hold 2.0 min at 50%; Back Pressure (psi): 1500.000; Flow: 2 ml/min.
GG. For intermediate stage: Column: CHIRALPAK AD-3 3*100 m m, 3 um; Co-Solvent: MeOH (0.1% DEA); Gradient (B %): 10% to 50% in 4.0 min, hold 2.0 min at 50%; Back Pressure (psi): 1500.000; Flow: 2 ml/min.
HH. For intermediate stage: Column: CHIRALPAK IC, 2*25 cm, 5 um; Mobile Phase A: CO2, Mobile Phase B: EtOH (8 mmol/L NH3.MeOH)-HPLC; Flow rate: 40 mL/min; Gradient: 25% B; 254 nm; Injection Volume: 0.8 m.
II. For intermediate stage: Column: CHIRALPAK IA (4.6*150 mm, 5 um); solvent, CO2/10% MEOH (0.1% DEA); Flow rate, 4 mL/min.
JJ. For intermediate stage: Column: CHIRALPAK IA (4.6*150 mm, 5 um); solvent, CO2/10% MEOH (0.1% DEA); Flow rate, 4 mL/min.
KK. For intermediate stage: Column: Lux 3 um Cellulose-4 4.6*100 mm, 3 um Co-Solvent: MeOH (0.1% DEA).
LL. For intermediate stage: Column: CHIRALPAK IC, 2*25 cm, 5 um; Mobile Phase A: CO2, Mobile Phase B: EtOH (8 mmol/L NH3·MeOH)-HPLC; Flow rate: 40 mL/min; Gradient: 25% B.
MM. For intermediate stage: Column: CHIRALPAK IA (4.6*150 mm, 5 um); Co-Solvent: MEOH(0.1% DEA), Co-Solvent %: 10%; Flow (ml/min): 4.
NN. For intermediate stage: Phenomenex Lux 5 u Cellulose-3, 5*25 cm, 5 um; Mobile Phase A: $CO_2$: 50, Mobile Phase B: MEOH (0.1% DEA): 50; Flow rate: 170 mL/min; 220 nm.
OO. For intermediate stage: CHIRAL Cellulose-SJ (4.6*150 mm, 5 um); Mobile Phase: CO2/MeOH (0.1% DEA); Flow Rate: 4 g/min.
PP. For intermediate stage: CHIRALCEL OJ-3, 4.6*50 mm, 3 um; Co-Solvent: MeOH (0.1% DEA) Gradient (B %): 10% to 50% in 4.0 min, hold 2.0 m in at 50%; Back Pressure (psi): 1500.
QQ. For intermediate stage (aminopyrimidine, analogous to example B54): Column: CHIRALPAK IA-3; Size: 3.0*100 mm, 3 um; Co-solvent: MeOH (0.1% DEA); Flow rate 2 mL/min.

Table 1 lists the compounds prepared by the synthetic methods disclosed above.

TABLE 1

| # | Structure | LC/MS | NMR | Separation Conditions | Chemical Name |
|---|-----------|-------|-----|------------------------|---------------|
| 1 | 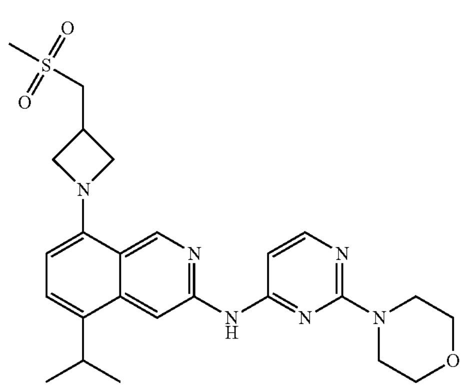 [SMILES: CC(C)c1ccc(N2CC(CS(C)(=O)=O)C2)c2cnc(Nc3ccnc(N4CCOCC4)n3)cc12] | 497 | 1H-NMR (400 MHz, 6d-DMSO) δ ppm 9.94 (s, 1H), 9.05 (s, 1H), 8.65 (s, 1H), 8.04 (d, 1H, J = 5.6 Hz), 7.42 (d, 1H, J = 8.0 Hz), 6.56-6.49 (m, 1H), 6.41 (d, 1H, J = 8.1 Hz), 4.39 (t, 2H, J = 7.6 Hz), 3.97 (t, 2H, J = 6.9 Hz), 3.75 (dd, 8H, J = 20.1, 5.2 Hz), 3.59 (d, 2H, J = 7.3 Hz), 3.48-3.40 (m, 1H), 3.32-3.22 (m, 1H), 3.02 (s, 3H), 1.28 (d, 6H, J = 6.8 Hz) | | 8-[3-(methanesulfonylmethyl)azetidin-1-yl]-N-[2-(morpholin-4-yl)pyrimidin-4-yl]-5-(propan-2-yl)isoquinolin-3-amine |

TABLE 1-continued

| # | Structure | LC/MS | NMR | Separation Conditions | Chemical Name |
|---|---|---|---|---|---|
| 2 | 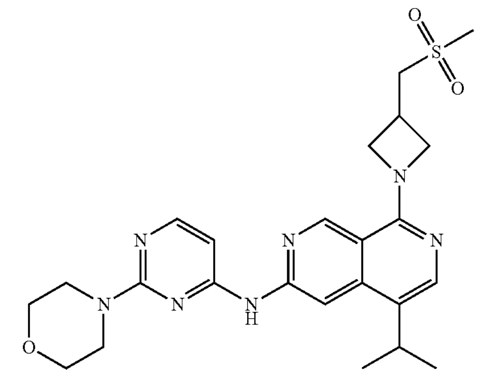 [SMILES: CC(C)c1cnc(N2CC(CS(C)(=O)=O)C2)c2cnc(Nc3ccnc(N4CCOCC4)n3)cc12] | 498 | 1H-NMR (300 MHz, 6d-DMSO) δ ppm 10.14 (s, 1H), 9.00 (s, 1H), 8.51 (s, 1H), 8.06 (d, 1H, J = 5.6 Hz), 7.96 (s, 1H), 6.53 (d, 1H, J = 5.7 Hz), 4.54 (t, 2H, J = 8.4 Hz), 4.20 (dd, 2H, J = 8.6, 6.2 Hz), 3.72 (dd, 8H, J = 11.4, 4.6 Hz), 3.57 (d, 2H, J = 7.4 Hz), 3.23 (dt, 2H, J = 13.7, 7.3 Hz), 2.99 (s, 3H), 1.27 (d, 6H, J = 6.8 Hz) | | 8-[3-(methanesulfonylmethyl)azetidin-1-yl]-N-[2-(morpholin-4-yl)pyrimidin-4-yl]-5-(propan-2-yl)-2,7-naphthyridin-3-amine |
| 3 | 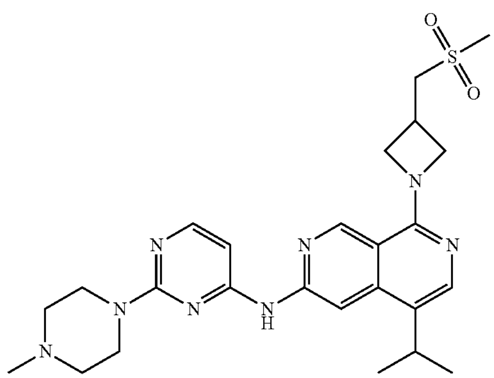 | 511 | 1H NMR (300 MHz, 6d-DMSO) δ ppm 10.13 (s, 1H), 9.02 (s, 1H), 8.06 (d, 1H, J = 5.6 Hz), 7.98 (s, 1H), 6.51 (d, 1H, J = 5.6 Hz), 4.57 (t, 2H, J = 8.4 Hz), 4.22 (dd, 2H, J = 8.6, 6.2 Hz), 3.80 (t, 4H, J = 4.9 Hz), 3.60 (d, 2H, J = 7.4 Hz), 3.54-3.23 (m, 2H), 3.01 (s, 3H), 2.41 (t, 4H, J = 4.9 Hz), 2.26 (s, 3H), 1.31 (d, 6H, J = 6.8 Hz) | | 8-[3-(methanesulfonylmethyl)azetidin-1-yl]-N-[2-(4-methylpiperazin-1-yl)pyrimidin-4-yl]-5-(propan-2-yl)-2,7-naphthyridin-3-amine |
| 4 | 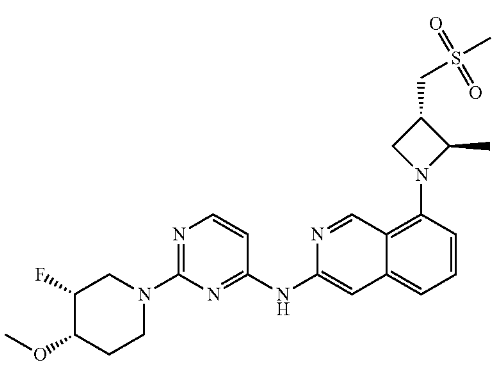 | 515 | 1H-NMR (400 MHz, 6d-DMSO) δ ppm 9.90 (s, 1H), 9.05 (s, 1H), 8.33 (s, 1H), 8.01 (d, 1H, J = 5.6 Hz), 7.48 (t, 1H, J = 7.8 Hz), 7.16 (d, 1H, J = 8.1 Hz), 6.51 (dd, 2H, J = 13.6, 6.7 Hz), 4.91 (d, 1H), 4.79-4.59 (m, 2H), 4.50-4.36 (m, 1H), 4.25 (t, 1H, J = 6.2 Hz), 3.74 (t, 1H, J = 7.0 Hz), 3.62-3.49 (m, 3H), 3.48-3.42 (m, 2H), 3.37 (s, 3H), 3.01 (s, 3H), 2.94-2.86 (m, 1H), 1.85-1.79 (m, 2H), 1.45 (d, 3H, J = 6.0 Hz), | | N-{2-[(3R,4S)-3-fluoro-4-methoxypiperidin-1-yl]pyrimidin-4-yl}-8-[(2R,3S)-3-(methanesulfonylmethyl)-2-methylazetidin-1-yl]isoquinolin-3-amine |
| 5 | 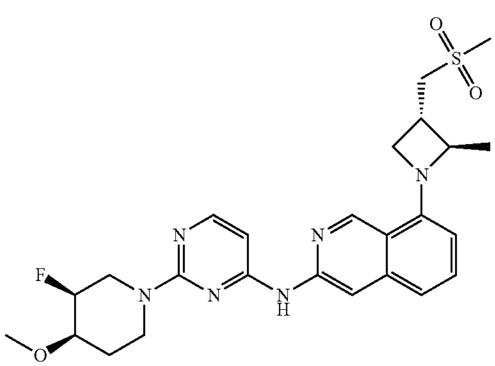 | 515 | 1H-NMR (300 MHz, 6d-DMSO) δ ppm 9.90 (s, 1H), 9.05 (s, 1H), 8.33 (s, 1H), 8.01 (d, 1H, J = 5.7 Hz), 7.48 (t, 1H, J = 7.9 Hz), 7.16 (d, 1H, J = 8.1 Hz), 6.51 (dd, 2H, J = 13.3, 6.7 Hz), 4.99 (d, 1H, J = 48.2 Hz), 4.79-4.59 (m, 2H), 4.47-4.36 (m, 1H), 4.25 (t, 1H, J = 6.2 Hz), 3.74 (t, 1H, J = 7.1 Hz), 3.66-3.39 (m, 4H), 3.37 (s, 3H), 3.30-3.21 (m, 1H), 3.01 (s, 3H), 2.90 (q, 1H, J = 7.0 Hz), 1.92-1.69 (m, 2H), 1.45 (d, 3H, J = 6.0 Hz) | | N-{2-[(3S,4R)-3-fluoro-4-methoxypiperidin-1-yl]pyrimidin-4-yl}-8-[(2R,3S)-3-(methanesulfonylmethyl)-2-methylazetidin-1-yl]isoquinolin-3-amine |

TABLE 1-continued

| # | Structure | LC/MS | NMR | Separation Conditions | Chemical Name |
|---|---|---|---|---|---|
| 6 | 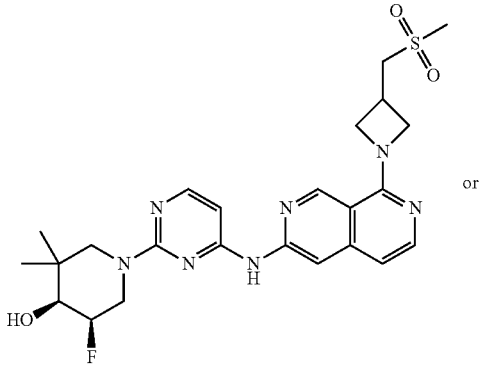 | 516 | 1H-NMR (300 MHz, 6d-DMSO) δ ppm 10.03 (s, 1H), 8.99 (s, 1H), 8.27 (s, 1H), 8.05-7.95 (m, 2H), 6.75 (d, 1H, J = 5.8 Hz), 6.46 (d, 1H, J = 5.7 Hz), 5.11 (d, 1H, J = 5.4 Hz), 4.74 (d, 1H, J = 48.6 Hz), 4.60 (t, 2H, J = 8.5 Hz), 4.25 (dd, 3H, J = 8.9, 6.1 Hz), 3.91-3.73 (m, 2H), 3.59 (d, 2H, J = 7.4 Hz), 3.45 (ddd, 1H, J = 23.1, 5.6, 2.8 Hz), 3.38-3.27 (m, 2H), 3.00 (s, 3H), 0.98-0.90 (m, 6H) | J; Peak 2 | (4S,5R)-5-fluoro-1-[4-({8-[3-(methanesulfonylmethyl)azetidin-1-yl]-2,7-naphthyridin-3-yl}amino)pyrimidin-2-yl]-3,3-dimethylpiperidin-4-ol or (4R,5S)-5-fluoro-1-[4-({8-[3-(methanesulfonylmethyl)azetidin-1-yl]-2,7-naphthyridin-3-yl}amino)pyrimidin-2-yl]-3,3-dimethylpiperidin-4-ol |
| | 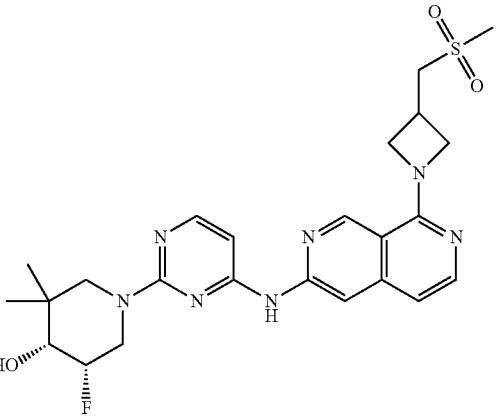 | | | | |
| 7 | 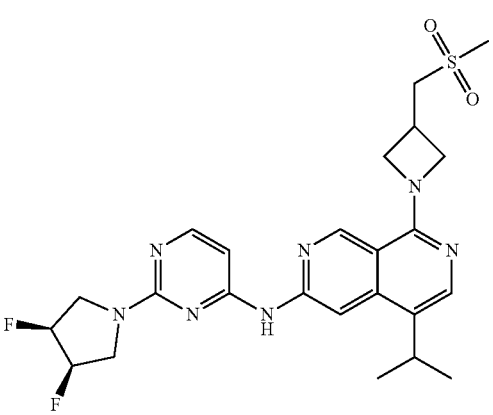 [SMILES: CC(C)c1cnc(N2CC(CS(C)(=O)=O)C2)c2cnc(Nc3ccnc(N4C[C@@H](F)[C@@H](F)C4)n3)cc12] | 518 | 1H-NMR (400 MHz, 6d-DMSO) δ ppm 10.20 (s, 1H), 9.03 (s, 1H), 8.74 (s, 1H), 8.07 (d, 1H, J = 5.7 Hz), 7.99 (s, 1H), 6.55 (d, 1H, J = 5.7 Hz), 5.56 (s, 1H), 5.43 (s, 1H), 4.57 (t, 2H, J = 8.4 Hz), 4.22 (dd, 2H, J = 8.6, 6.2 Hz), 4.14 (s, 1H), 3.91 (s, 2H), 3.76 (s, 2H), 3.60 (d, 2H, J = 7.4 Hz), 3.02 (s, 3H), 1.32 (d, 6H, J = 6.8 Hz) | B8 | N-{2-[cis-3,4-difluoropyrrolidin-1-yl]pyrimidin-4-yl}-8-[3-(methanesulfonylmethyl)azetidin-1-yl]-5-(propan-2-yl)-2,7-naphthyridin-3-amine |

TABLE 1-continued

| # | Structure | LC/MS | NMR | Separation Conditions | Chemical Name |
|---|---|---|---|---|---|
| 8 | 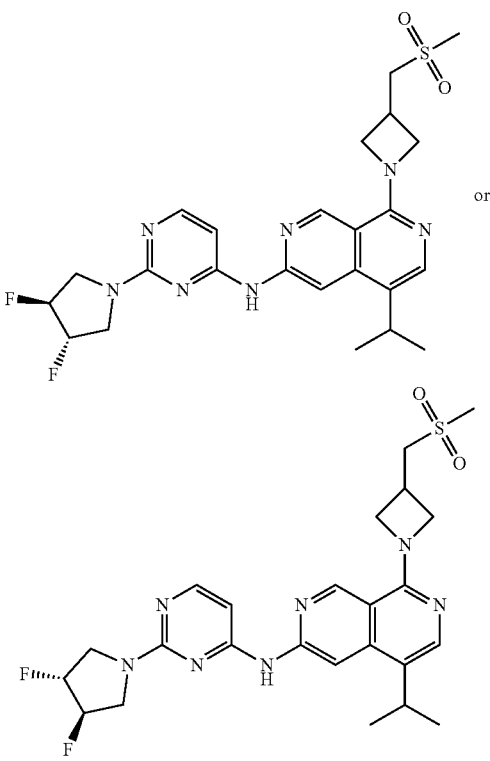 | 518 | 1H-NMR (400 MHz, 6d-DMSO) δ ppm 10.20 (s, 1H), 9.03 (s, 1H), 8.69 (s, 1H), 8.08 (d, 1H, J = 5.7 Hz), 7.99 (s, 1H), 6.59 (d, 1H, J = 5.7 Hz), 5.62 (s, 1H), 5.50 (s, 1H), 4.57 (td, 2H, J = 8.5, 2.4 Hz), 4.22 (dd, 2H, J = 8.6, 6.2 Hz), 3.97 (s, 4H), 3.86 (s, 1H), 3.60 (d, 2H, J = 7.4 Hz), 3.02 (s, 3H), 1.34 (dd, 6H, J = 9.3, 6.8 Hz) | D; Peak 1 | N-{2-[(3S,4S)-3,4-difluoropyrrolidin-1-yl]pyrimidin-4-yl}-8-[3-(methanesulfonylmethyl)azetidin-1-yl]-5-(propan-2-yl)-2,7-naphthyridin-3-amine or N-{2-[(3R,4R)-3,4-difluoropyrrolidin-1-yl]pyrimidin-4-yl}-8-[3-(methanesulfonylmethyl)azetidin-1-yl]-5-(propan-2-yl)-2,7-naphthyridin-3-amine |
|   | or 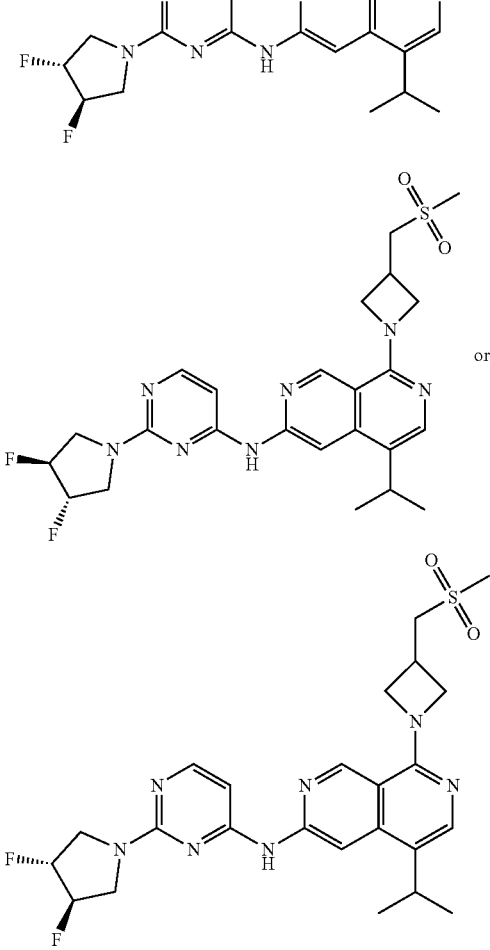 |   |   |   |   |
| 9 | 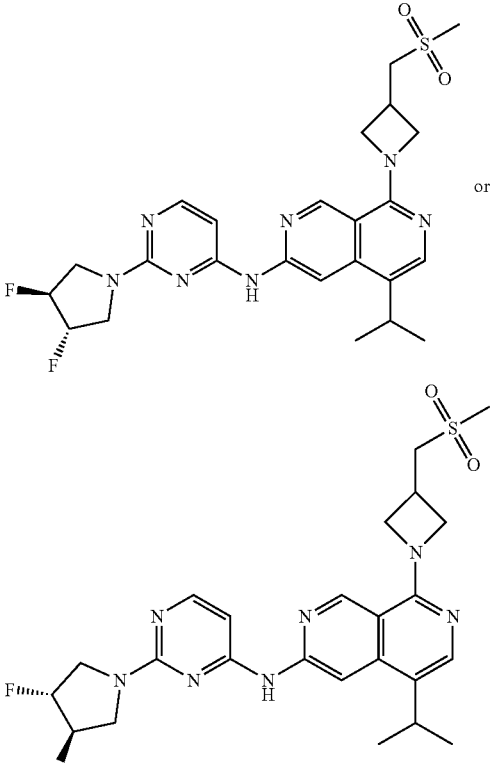 | 518 | 1H-NMR (400 MHz, 6d-DMSO) δ ppm 10.20 (s, 1H), 9.03 (s, 1H), 8.69 (s, 1H), 8.08 (d, 1H, J = 5.7 Hz), 7.99 (s, 1H), 6.59 (d, 1H, J = 5.7 Hz), 5.62 (s, 1H), 5.50 (s, 1H), 4.57 (td, 2H, J = 8.4, 2.4 Hz), 4.23 (dd, 2H, J = 8.6, 6.2 Hz), 4.08-3.87 (m, 4H), 3.60 (d, 2H, J = 7.4 Hz), 3.37-3.32 (m, 2H), 3.02 (s, 3H), 1.34 (dd, 6H, J = 9.3, 6.8 Hz) | D; Peak 2 | N-{2-[(3R,4R)-3,4-difluoropyrrolidin-1-yl]pyrimidin-4-yl}-8-[3-(methanesulfonylmethyl)azetidin-1-yl]-5-(propan-2-yl)-2,7-naphthyridin-3-amine or N-{2-[(3S,4S)-3,4-difluoropyrrolidin-1-yl]pyrimidin-4-yl}-8-[3-(methanesulfonylmethyl)azetidin-1-yl]-5-(propan-2-yl)-2,7-naphthyridin-3-amine |
|   | or 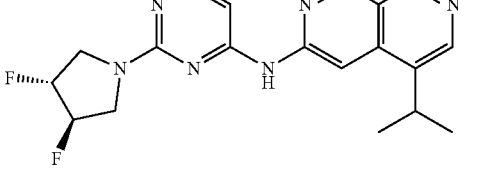 |   |   |   |   |

TABLE 1-continued

| # | Structure | LC/MS | NMR | Separation Conditions | Chemical Name |
|---|---|---|---|---|---|
| 10 | 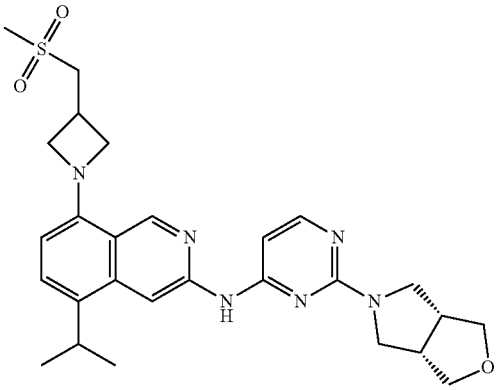 [SMILES: CC(C)c1ccc(N2CC(CS(C)(=O)=O)C2)c2cnc(Nc3ccnc(N4C[C@H]5COC[C@H]5C4)n3)cc12] | 523 | 1H-NMR (300 MHz, 6d-DMSO) δ ppm 9.86 (s, 1H), 9.01 (s, 1H), 8.85 (s, 1H), 7.96 (d, 1H, J = 5.7 Hz), 7.39 (d, 1H, J = 8.0 Hz), 6.44-6.34 (m, 2H), 4.36 (t, 2H, J = 7.6 Hz), 3.99-3.73 (m, 4H), 3.62-3.45 (m, 7H), 3.30-3.18 (m, 1H), 3.02 (d, 2H, J = 13.5 Hz), 3.00 (s, 3H), 1.26 (d, 6H, J = 6.7 Hz) | | N-{2-[(3aR,6aS)-hexahydro-1H-furo[3,4-c]pyrrol-5-yl]pyrimidin-4-yl}-8-[3-(methanesulfonyl-methyl)azetidin-1-yl]-5-(propan-2-yl)isoquinolin-3-amine |
| 11 | 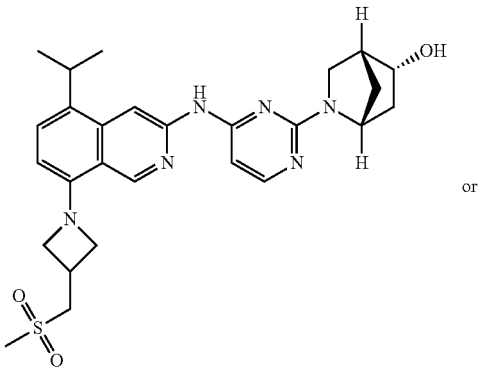 [SMILES: CC(C)c1ccc(N2CC(CS(C)(=O)=O)C2)c2cnc(Nc3ccnc(N4C[C@H]5C[C@@H]4C[C@H]5O)n3)cc12] or 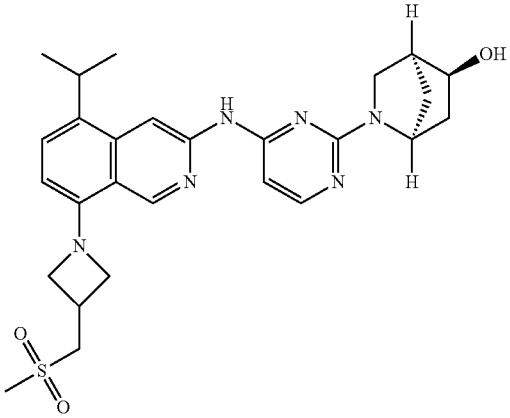 [SMILES: CC(C)c1ccc(N2CC(CS(C)(=O)=O)C2)c2cnc(Nc3ccnc(N4C[C@@H]5C[C@H]4C[C@@H]5O)n3)cc12] | 523 | 1H-NMR (300 MHz, 6d-DMSO) δ ppm 9.78 (s, 1H), 9.01 (s, 1H), 8.82 (d, 1H, J = 10.5 Hz), 7.90 (d, 1H, J = 5.6 Hz), 7.39 (d, 1H, J = 7.8 Hz), 6.36 (dd, 2H, J = 12.5, 6.8 Hz), 4.88 (s, 1H), 4.64 (d, 1H, J = 52.8 Hz), 4.36 (t, 2H, J = 7.6 Hz), 3.94 (t, 2H, J = 6.9 Hz), 3.89-3.74 (m, 1H), 3.54 (dd, 4H, J = 19.0, 7.1 Hz), 3.30-3.08 (m, 1H), 3.05-2.87 (m, 3H), 2.47-2.39 (m, 1H), 2.13-1.75 (m, 2H), 1.68-1.37 (m, 2H), 1.28 (dd, 6H, J = 6.9, 2.2 Hz) | D; Peak 2 | (1R,4R,5R)-2-[4-({8-[3-(methane-sulfonylmethyl)azetidin-1-yl]-5-(propan-2-yl)isoquinolin-3-yl}amino)pyrimidin-2-yl]-2-azabicyclo[2.2.1]heptan-5-ol or (1S,4S,5S)-2-[4-({8-[3-(methanesulfonyl-methyl)azetidin-1-yl]-5-(propan-2-yl)isoquinolin-3-yl}amino)pyrimidin-2-yl]-2-azabicyclo[2.2.1]heptan-5-ol |

TABLE 1-continued

| # | Structure | LC/MS | NMR | Separation Conditions | Chemical Name |
|---|---|---|---|---|---|
| 12 | 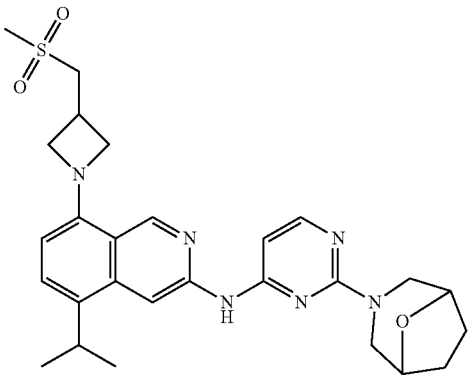 [SMILES: CC(C)c1ccc(N2CC(CS(C)(=O)=O)C2)c2cnc(Nc3ccnc(N4CC5CCC(C4)O5)n3)cc12] | 523 | 1H-NMR (400 MHz, 6d-DMSO) δ ppm 9.87 (s, 1H), 9.03 (s, 1H), 8.65 (s, 1H), 7.98 (d, 1H, J = 5.6 Hz), 7.40 (d, 1H, J = 8.0 Hz), 6.47 (d, 1H, J = 5.7 Hz), 6.39 (d, 1H, J = 8.1 Hz), 4.38 (dd, 4H, J = 14.9, 7.1 Hz), 4.25 (d, 2H, J = 12.8 Hz), 3.94 (t, 2H, J = 6.9 Hz), 3.57 (d, 2H, J = 7.3 Hz), 3.45 (p, 1H, J = 6.8 Hz), 3.28-3.20 (m, 1H), 3.11 (d, 2H, J = 12.4 Hz), 3.00 (s, 3H), 1.89-1.80 (m, 2H), 1.72 (d, 2H, J = 6.9 Hz), 1.27 (d, 6H, J = 6.8 Hz) |  | 8-[3-(methanesulfonyl-methyl)azetidin-1-yl]-N-(2-{8-oxa-3-azabicyclo[3.2.1]octan-3-yl}pyrimidin-4-yl)-5-(propan-2-yl)isoquinolin-3-amine |
| 13 | 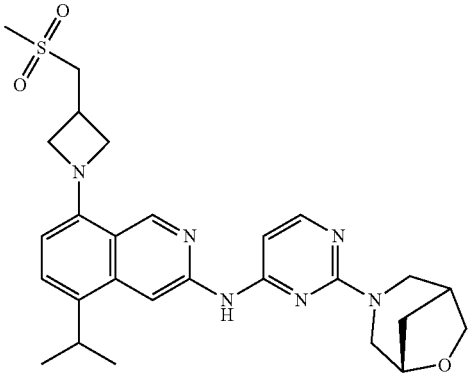<br>Racemate | 523 | 1H-NMR (400 MHz, 6d-DMSO) δ ppm 9.87 (s, 1H), 9.03 (s, 1H), 8.65 (s, 1H), 7.98 (d, 1H, J = 5.6 Hz), 7.40 (d, 1H, J = 8.0 Hz), 6.47 (d, 1H, J = 5.7 Hz), 6.39 (d, 1H, J = 8.1 Hz), 4.38 (dd, 4H, J = 14.9, 7.1 Hz), 4.25 (d, 2H, J = 12.8 Hz), 3.94 (t, 2H, J = 6.9 Hz), 3.57 (d, 2H, J = 7.3 Hz), 3.45 (p, 1H, J = 6.8 Hz), 3.28-3.20 (m, 1H), 3.11 (d, 2H, J = 12.4 Hz), 3.00 (s, 3H), 1.89-1.80 (m, 2H), 1.72 (d, 2H, J = 6.9 Hz), 1.27 (d, 6H, J = 6.8 Hz) |  | (rac)-8-[3-(methanesulfonyl-methyl)azetidin-1-yl]-N-{2-[6-oxa-3-azabicyclo[3.2.1]octan-3-yl]pyrimidin-4-yl}-5-(propan-2-yl)isoquinolin-3-amine |
| 14 | 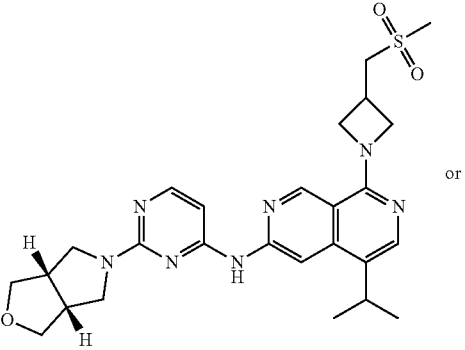 [SMILES: CC(C)c1cnc(N2CC(CS(C)(=O)=O)C2)c2cnc(Nc3ccnc(N4C[C@H]5COC[C@H]5C4)n3)cc12]<br>or | 523 | 1H-NMR (300 MHz, 6d-DMSO) δ ppm 9.91 (s, 1H), 9.05 (s, 1H), 8.76 (s, 1H), 8.00 (d, 1H, J = 5.7 Hz), 7.42 (d, 1H, J = 8.0 Hz), 6.47 (d, 1H, J = 5.7 Hz), 6.41 (d, 1H, J = 8.0 Hz), 4.39 (t, 4H, J = 7.2 Hz), 4.28 (d, 1H, J = 13.4 Hz), 3.97 (t, 2H, J = 6.9 Hz), 3.79-3.72 (m, 2H), 3.59 (d, 2H, J = 7.3 Hz), 3.55-3.44 (m, 1H), 3.31-3.21 (m, 2H), 3.09-3.04 (m, 1H), 3.02 (s, 3H), 2.66-2.60 (m, 1H), 1.97-1.91 (m, 2H), 1.30 (dd, 6H, J = 6.8, 3.8 Hz) | L; Peak 2 | N-{2-[(3aR,6aS)-hexahydro-1H-furo[3,4-c]pyrrol-5-yl]pyrimidin-4-yl}-8-[3-(methanesulfonyl-methyl)azetidin-1-yl]-5-(propan-2-yl)-2,7-naphthyridin-3-amine or N-{2-[(3aS,6aR)-hexahydro-1H-furo[3,4-c]pyrrol-5-yl]pyrimidin-4-yl}-8-[3- |

TABLE 1-continued

| # | Structure | LC/MS | NMR | Separation Conditions | Chemical Name |
|---|---|---|---|---|---|
| | 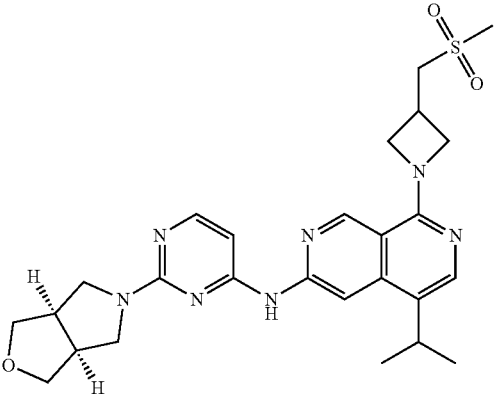 [SMILES: CC(C)c1cnc(N2CC(CS(C)(=O)=O)C2)c2cnc(Nc3ccnc(N4C[C@H]5COC[C@H]5C4)n3)cc12] | | | | (methanesulfonyl-methyl)azetidin-1-yl]-5-(propan-2-yl)-2,7-naphthyridin-3-amine |
| 15 | 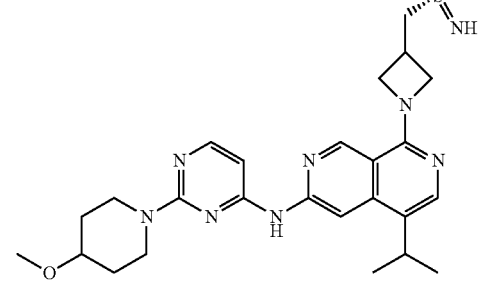 or  | 524 | 1H-NMR (300 MHz, 6d-DMSO) δ ppm 9.83 (s, 1H), 9.05 (s, 1H), 8.65 (s, 1H), 7.99 (d, J = 5.6 Hz, 1H), 7.41 (d, J = 8.0 Hz, 1H), 6.44 (d, J = 5.6 Hz, 1H), 6.39 (d, J = 8.0 Hz, 1H), 4.38 (q, J = 8.0 Hz, 2H), 4.35-4.25 (m, 2H), 4.02-3.91 (m, 2H), 3.71 (s, 1H), 3.54-3.38 (m, 6H), 3.35-3.25 (m, 1H), 3.32 (s, 3H), 2.93 (s, 3H), 1.95-1.87 (m, 2H), 1.52-1.40 (m, 2H), 1.29 (dd, J = 8.0, 3.6 Hz, 6H). | | (S)-imino((1-(5-isopropyl-3-((2-(4-methoxy-piperidin-1-yl)pyrimidin-4-yl)amino)isoquinolin-8-yl)azetidin-3-yl)methyl)(methyl)-λ⁶-sulfanone or (R)-imino((1-(5-isopropyl-3-((2-(4-methoxy-piperidin-1-yl)pyrimidin-4-yl)amino)isoquinolin-8-yl)azetidin-3-yl)methyl)(methyl)-λ⁶-sulfanone |
| 16 | 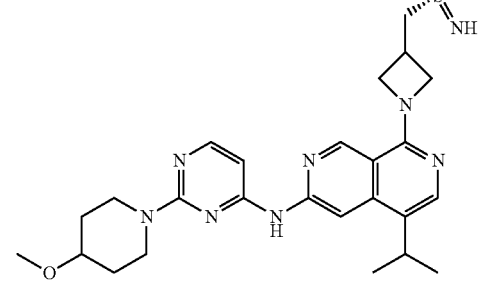 | 524 | 1H-NMR (400 MHz, 6d-DMSO) δ ppm 9.93 (s, 1H), 9.05 (s, 1H), 8.68 (s, 1H), 8.00 (d, 1H, J = 5.6 Hz), 7.41 (d, 1H, J = 8.0 Hz), 6.55 (d, 1H, J = 8.1 Hz), 6.45 (d, 1H, J = 5.6 Hz), 4.65 (t, 1H, J = 7.5 Hz), 4.18 (p, 1H, J = 6.1 Hz), 3.80 (t, 4H, J = 5.0 Hz), 3.63 (t, 1H, J = 7.2 Hz), 3.56 (dd, 1H, J = 14.2, 6.8 Hz), 3.51 (t, 1H, J = 6.9 Hz), 3.50-3.41 (m, 1H), 2.99 (s, 3H), 2.89 (p, 1H, J = 7.3 Hz), 2.41 (t, 4H, J = 5.0 Hz), 2.25 (s, 3H), 1.42 (d, 3H, J = 6.0 Hz), 1.29 (d, 6H, J = 6.7 Hz) | | 8-[(2R,3S)-3-(methanesulfonyl-methyl)-2-methylazetidin-1-yl]-N-[2-(4-methylpiperazin-1-yl)pyrimidin-4-yl]-5-(propan-2-yl)isoquinolin-3-amine |

TABLE 1-continued

| # | Structure | LC/MS | NMR | Separation Conditions | Chemical Name |
|---|---|---|---|---|---|
| 17 | 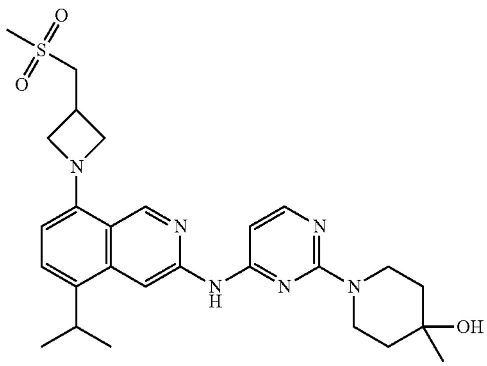 [SMILES: CC(C)c1ccc(N2CC(CS(C)(=O)=O)C2)c2cnc(Nc3ccnc(N4CCC(C)(O)CC4)n3)cc12] | 525 | 1H-NMR (400 MHz, 6d-DMSO) δ ppm 9.84 (s, 1H), 9.04 (s, 1H), 8.70 (s, 1H), 7.98 (d, 1H, J = 5.6 Hz), 7.42 (d, 1H, J = 8.1 Hz), 6.44-6.37 (m, 2H), 4.43-4.35 (m, 3H), 4.27 (d, 2H, J = 13.0 Hz), 3.97 (t, 2H, J = 6.9 Hz), 3.59 (d, 2H, J = 7.4 Hz), 3.48 (dd, 3H, J = 13.1, 7.6 Hz), 3.33-3.24 (m, 1H), 3.02 (s, 3H), 1.60-1.48 (m, 4H), 1.29 (d, 6H, J = 6.8 Hz), 1.19 (s, 3H) | | 1-[4-({8-[3-(methanesulfonyl-methyl)azetidin-1-yl]-5-(propan-2-yl)isoquinolin-3-yl}amino)pyrimidin-2-yl]-4-methylpiperidin-4-ol |
| 18 | | 525 | 1H-NMR (300 MHz, 6d-DMSO) δ ppm 9.84 (s, 1H), 9.05 (s, 1H), 8.62 (s, 1H), 7.99 (d, 1H, J = 5.6 Hz), 7.41 (d, 1H, J = 8.0 Hz), 6.45 (d, 1H, J = 5.7 Hz), 6.40 (d, 1H, J = 8.1 Hz), 4.70 (d, 1H, J = 5.4 Hz), 4.66 (s, 1H), 4.64-4.52 (m, 1H), 4.39 (td, 2H, J = 7.6, 2.4 Hz), 4.02-3.91 (m, 2H), 3.59 (d, 2H, J = 7.4 Hz), 3.49 (p, 1H, J = 6.8 Hz), 3.32-3.17 (m, 2H), 3.07 (d, 1H, J = 12.4 Hz), 3.02 (s, 3H), 2.66 (dd, 1H, J = 13.1, 10.6 Hz), 1.95-1.84 (m, 1H), 1.55-1.24 (m, 8H), 0.98 (d, 3H, J = 6.5 Hz) | E; Peak 2 | (3S,4S)-1-[4-({8-[3-(methanesulfonyl-methyl)azetidin-1-yl]-5-(propan-2-yl)isoquinolin-3-yl}amino)pyrimidin-2-yl]-3-methyl-piperidin-4-ol or (3R,4R)-1-[4-({8-[3-(methanesulfonyl-methyl)azetidin-1-yl]-5-(propan-2-yl)isoquinolin-3-yl}amino)pyrimidin-2-yl]-3-methyl-piperidin-4-ol |
| 19 | 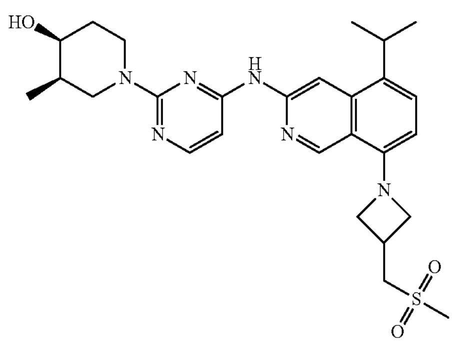 [SMILES: CC(C)c1ccc(N2CC(CS(C)(=O)=O)C2)c2cnc(Nc3ccnc(N4CC[C@@H](O)[C@H](C)C4)n3)cc12] | 525 | 1H-NMR (400 MHz, 6d-DMSO) δ ppm 9.80 (s, 1H), 9.04 (s, 1H), 8.66 (s, 1H), 7.97 (d, 1H, J = 5.6 Hz), 7.40 (d, 1H, J = 8.0 Hz), 6.44-6.36 (m, 2H), 4.63 (d, 1H, J = 3.8 Hz), 4.38 (td, 2H, J = 7.6, 2.9 Hz), 4.17-3.89 (m, 4H), 3.78 (p, 1H, J = 3.6 Hz), 3.66 (ddd, 1H, 1 = 13.1, 9.1, 4.0 Hz), 3.58 (d, 2H, J = 7.4 Hz), 3.55-3.35 (m, 2H), 3.32-3.20 (m, 1H), 3.01 (s, 3H), 1.79-1.60 (m, 2H), 1.28 (t, 6H, J = 6.5 Hz), 0.89 (d, 3H, | C; Peak 1 | (3S,4R)-1-[4-({8-[3-(methane-sulfonylmethyl)azetidin-1-yl]-5-(propan-2-yl)isoquinolin-3-yl}amino)pyrimidin-2-yl]-3-methyl-piperidin-4-ol or (3R,4S)-1-[4-({8-1,3-(methanesulfonyl-methyl)azetidin-1-yl]-5-(propan-2- |

TABLE 1-continued

| # | Structure | LC/MS | NMR | Separation Conditions | Chemical Name |
|---|---|---|---|---|---|
| | | | J = 6.8 Hz) | | yl)isoquinolin-3-yl}amino)pyrimidin-2-yl]-3-methyl-piperidin-4-ol |
| 20 | | 525 | 1H-NMR (400 MHz, 6d-DMSO) δ ppm 9.80 (s, 1H), 9.04 (s, 1H), 8.65 (s, 1H), 7.97 (d, 1H, J = 5.6 Hz), 7.41 (d, 1H, J = 8.0 Hz), 6.43-6.37 (m, 2H), 4.63 (d, 1H, J = 3.9 Hz), 4.38 (td, 2H, J = 7.6, 2.9 Hz), 4.12-4.04 (m, 1H), 4.04-3.92 (m, 3H), 3.79 (t, 1H, J = 4.3 Hz), 3.66 (ddd, 1H, J = 13.0, 9.1, 4.1 Hz), 3.59 (d, 2H, J = 7.4 Hz), 3.49 (p, 1H, J = 6.8 Hz), 3.42-3.38 (m, 1H), 3.32-3.22 (m, 1H), 3.01 (s, 3H), 1.84-1.52 (m, 3H), 1.29 (t, 6H, J = 6.5 Hz), 0.89 (d, 3H, J = 6.8 Hz) | C; Peak 2 | (3R,4S)-1-[4-({8-[3-(methane-sulfonylmethyl)azetidin-1-yl]-5-(propan-2-yl)isoquinolin-3-yl}amino)pyrimidin-2-yl]-3-methyl-piperidin-4-ol or (3S,4R)-1-[4-({8-[3-(methane-sulfonylmethyl)azetidin-1-yl]-5-(propan-2-yl)isoquinolin-3-yl}amino)pyrimidin-2-yl]-3-methyl-piperidin-4-ol |
| 21 | 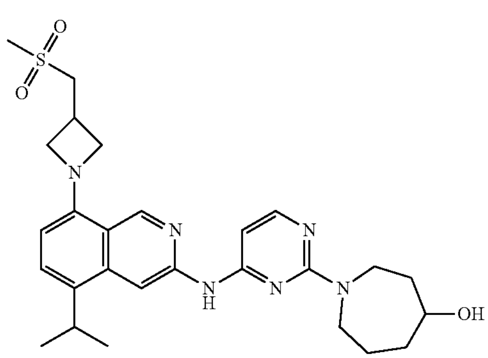 [SMILES: CC(C)c1ccc(N2CC(CS(C)(=O)=O)C2)c2cnc(Nc3ccnc(N4CCCC(O)CC4)n3)cc12] | 525 | 1H-NMR (300 MHz, 6d-DMSO) δ ppm 9.79 (s, 1H), 9.04 (s, 1H), 8.71 (s, 1H), 7.98 (d, 1H, J = 5.6 Hz), 7.41 (d, 1H, J = 8.0 Hz), 6.41 (d, 2H, J = 6.9 Hz), 4.53 (d, 1H, J = 4.0 Hz), 4.39 (t, 2H, J = 7.6 Hz), 3.96 (t, 2H, J = 6.8 Hz), 3.92-3.78 (m, 2H), 3.77-3.66 (m, 3H), 3.59 (d, 2H, J = 7.3 Hz), 3.55-3.44 (m, 1H), 3.02 (s, 3H), 1.97-1.91 (m, 2H), 1.77-1.47 (m, 4H), 1.29 (d, 6H, J = 6.7 Hz) | | (rac)-1-[4-({8-[3-(methanesulfonyl-methyl)azetidin-1-yl]-5-(propan-2-yl)isoquinolin-3-yl}amino)pyrimidin-2-yl]azepan-4-ol |

TABLE 1-continued

| # | Structure | LC/MS | NMR | Separation Conditions | Chemical Name |
|---|---|---|---|---|---|
| 22 | 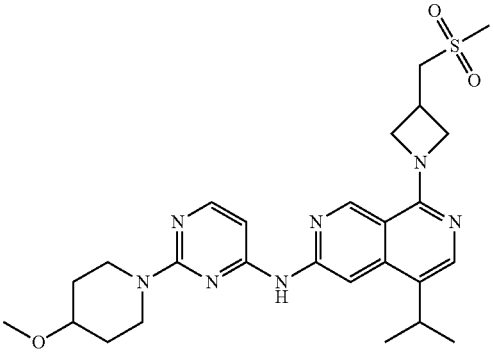 | 526 | 1H NMR (300 MHz, 6d-DMSO) δ ppm 10.10 (s, 1H), 9.02 (s, 1H), 8.55 (s, 1H), 8.05 (d, 1H, J = 5.6 Hz), 7.99 (s, 1H), 6.48 (d, 1H, J = 5.6 Hz), 4.57 (t, 2H, J = 8.4 Hz), 4.38-4.08 (m, 2H), 3.60 (d, 2H, J = 7.4 Hz), 3.54-3.37 (m, 6H), 3.31 (s, 4H), 3.01 (s, 3H), 1.93 (d, 2H, J = 12.7 Hz), 1.46 (d, 2H, J = 9.2 Hz), 1.31 (d, 6H, J = 6.8 Hz) | | 8-[3-(methanesulfonylmethyl)azetidin-1-yl]-N-[2-(4-methoxypiperidin-1-yl)pyrimidin-4-yl]-5-(propan-2-yl)-2,7-naphthyridin-3-amine |
| 23 | 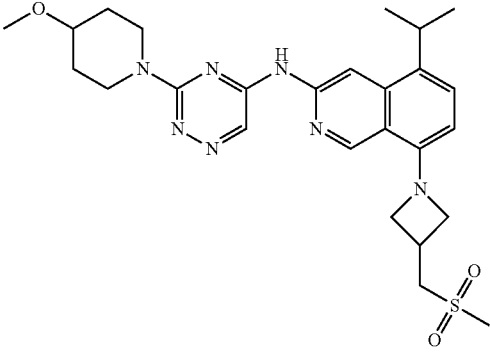 | 526 | 1H-NMR (300 MHz, 6d-DMSO) δ ppm 10.47 (s, 1H), 9.10 (s, 1H), 8.71 (s, 1H), 8.47 (s, 1H), 7.46 (d, 1H, J = 8.0 Hz), 6.46 (d, 1H, J = 8.1 Hz), 4.40 (t, 2H, J = 7.7 Hz), 4.26 (dd, 2H, J = 12.5, 6.2 Hz), 3.98 (t, 2H, J = 6.9 Hz), 3.63-3.47 (m, 4H), 3.48 (s, 2H), 3.32-3.28 (m, 1H), 3.25 (s, 3H), 3.01 (s, 3H), 2.02-1.89 (m, 2H), 1.51 (qd, 2H, J = 8.6, 4.3 Hz), 1.29 (d, 6H, J = 6.7 Hz) | | 8-[3-(methanesulfonylmethyl)azetidin-1-yl]-N-[3-(4-methoxypiperidin-1-yl)-1,2,4-triazin-5-yl]-5-(propan-2-yl)isoquinolin-3-amine |
| 24 | 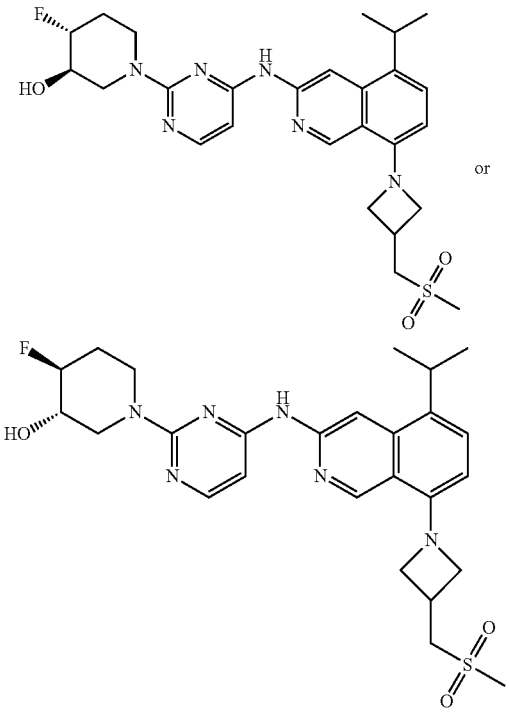 | 529 | 1H-NMR (300 MHz, 6d-DMSO) δ ppm 9.89 (s, 1H), 9.03 (s, 1H), 8.59 (s, 1H), 7.99 (d, 1H, J = 5.7 Hz), 7.39 (d, 1H, J = 8.0 Hz), 6.49 (d, 1H, J = 5.8 Hz), 6.39 (d, 1H, J = 8.1 Hz), 5.44 (d, 1H, J = 5.0 Hz), 4.52 (t, 3H, J = 17.9 Hz), 4.37 (t, 2H, J = 7.7 Hz), 3.94 (t, 2H, J = 6.8 Hz), 3.67-3.37 (m, 4H), 3.28-3.12 (m, 1H), 3.10-2.87 (m, 4H), 2.18-2.03 (m, 1H), 1.76-1.54 (m, 1H), 1.27 (dd, 6H, J = 6.8, 5.4 Hz) | F; Peak 2 | (3S,4S)-4-fluoro-1-[4-({8-[3-(methanesulfonylmethyl)azetidin-1-yl]-5-(propan-2-yl)isoquinolin-3-yl}amino)pyrimidin-2-yl]piperidin-3-ol or (3R,4R)-4-fluoro-1-[4-({8-[3-(methanesulfonylmethyl)azetidin-1-yl]-5-(propan-2-yl)isoquinolin-3-yl}amino)pyrimidin-2-yl]piperidin-3-ol |

TABLE 1-continued

| # | Structure | LC/MS | NMR | Separation Conditions | Chemical Name |
|---|---|---|---|---|---|
| 25 | 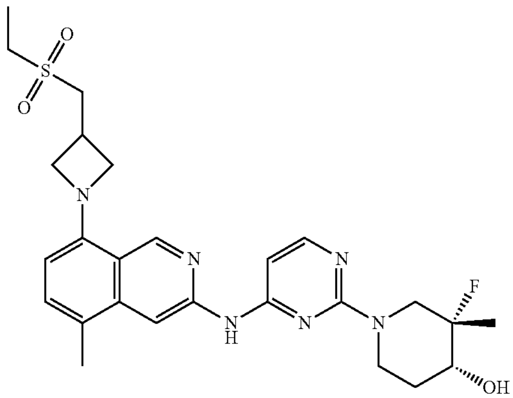 [SMILES: CCS(=O)(=O)CC1CN(c2ccc(C)c3cc(Nc4ccnc(N5CC[C@@H](O)[C@@](C)(F)C5)n4)ncc23)C1] | 529 | 1H-NMR (300 MHz, 6d-DMSO) δ ppm 9.92 (s, 1H), 9.05 (s, 1H), 8.47 (s, 1H), 7.99 (d, 1H, J = 5.7 Hz), 7.35 (d, 1H, J = 7.8 Hz), 6.44 (d, 1H, J = 5.7 Hz), 6.33 (d, 1H, J = 7.8 Hz), 5.02 (d, 1H, J = 6.4 Hz), 4.85-4.65 (m, 2H), 4.40 (dt, 2H, J = 18.2, 9.8 Hz), 3.96 (t, 2H, J = 6.9 Hz), 3.58 (d, 2H, J = 7.4 Hz), 3.55-3.43 (m, 1H), 3.32-3.22 (m, 1H), 3.13 (q, 4H, J = 7.5 Hz), 2.51 (s, 3H), 1.83-1.60 (m, 2H), 1.36 (d, 3H, J = 21.2 Hz), 1.25 (t, 3H, J = 7.4 Hz) | NN; Peak 1 | (3S,4R)-1-{4-[(8-{3-[(ethane-sulfonyl)methyl]azetidin-1-yl}-5-methylisoquinolin-3-yl)amino]pyrimidin-2-yl}-3-fluoro-3-methyl-piperidin-4-ol |
| 26 | | 529 | 1H-NMR (400 MHz, 6d-DMSO) δ ppm 9.88 (s, 1H), 9.05 (s, 1H), 8.63 (s, 1H), 8.01 (d, 1H, J = 5.6 Hz), 7.42 (d, 1H, J = 8.0 Hz), 6.49 (d, 1H, J = 5.7 Hz), 6.42 (d, 1H, J = 8.0 Hz), 5.21 (d, 1H, J = 5.4 Hz), 4.85 (d, 1H, J = 48.7 Hz), 4.39 (t, 2H, J = 7.6 Hz), 4.29-4.09 (m, 2H), 3.97 (t, 2H, J = 6.9 Hz), 3.77-3.63 (m, 1H), 3.59 (d, 2H, J = 7.5 Hz), 3.57-3.44 (m, 3H), 3.30-3.21 (m, 1H), 3.02 (s, 3H), 2.10-1.95 (m, 2H), 1.93-1.72 (m, 1H), 1.30 (dd, 6H, J = 6.8, 3.3 Hz) | H; Peak 1 | (3R,4S)-4-fluoro-1-[4-({8-[3-(methanesulfonyl-methyl)azetidin-1-yl]-5-(propan-2-yl)isoquinolin-3-yl}amino)pyrimidin-2-yl]piperidin-3-ol or (3S,4R)-4-fluoro-1-[4-({8-[3-(methanesulfonyl-methyl)azetidin-1-yl]-5-(propan-2-yl)isoquinolin-3-yl}amino)pyrimidin-2-yl]piperidin-3-ol |
| 27 | 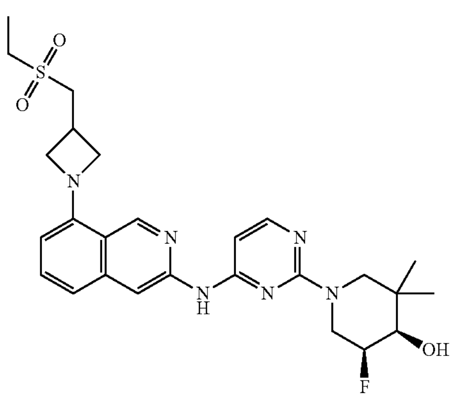 [SMILES: CCS(=O)(=O)CC1CN(c2cccc3cc(Nc4ccnc(N5C[C@@H](F)[C@@H](O)C(C)(C)C5)n4)ncc23)C1] | 529 | 1H-NMR (400 MHz, 6d-DMSO) δ ppm 9.86 (s, 1H), 9.05 (s, 1H), 8.40 (s, 1H), 7.99 (d, 1H, J = 5.6 Hz), 7.48 (t, 1H, J = 7.9 Hz), 7.06 (d, 1H, J = 8.1 Hz), 6.43 (d, 1H, J = 5.7 Hz), 6.36 (d, 1H, J = 7.6 Hz), 5.12 (d, 1H, J = 5.5 Hz), 4.76 (dt, 1H, J = 48.2, 3.7 Hz), 4.46 (t, 2H, J = 7.8 Hz), 4.25 (dt, 1H, J = 14.5, 8.1 Hz), 4.04 (dd, 2H, J = 7.6, 6.2 Hz), 3.87 (q, 2H, J = 12.7, 10.5 Hz), 3.59 (d, 2H, J = 7.4 Hz), 3.48 (ddd, 1H, J = 22.9, 5.4, 2.7 Hz), 3.39 (d, 1H, J = 13.1 Hz), 3.13 (q, 2H, J = 7.4 Hz), | J; Peak 2 | (4S,5R)-1-{4-[(8-{3-[(ethane-sulfonyl)methyl]azetidin-1-yl}isoquinolin-3-yl)amino]pyrimidin-2-yl}-5-fluoro-3,3-dimethyl-piperidin-4-ol or (4R,5S)-1-{4-[(8-{3-[(ethane-sulfonyl)methyl]azetidin-1-yl}isoquinolin-3-yl)amino]pyrimidin-2-yl}-5-fluoro-3,3-dimethyl-piperidin-4-ol |

TABLE 1-continued

| # | Structure | LC/MS | NMR | Separation Conditions | Chemical Name |
|---|---|---|---|---|---|
| | | | 1.25 (t, 3H, J = 7.4 Hz), 1.04-0.74 (m, 6H) | | |
| 28 | 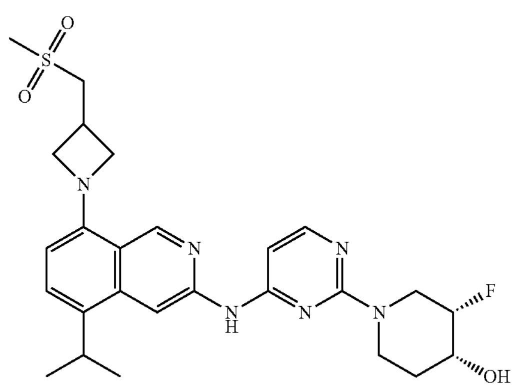 [SMILES: CC(C)c1ccc(N2CC(CS(C)(=O)=O)C2)c2cnc(Nc3ccnc(N4CC[C@@H](O)[C@@H](F)C4)n3)cc12] | 529 | 1H-NMR (300 MHz, 6d-DMSO) δ ppm 9.89 (s, 1H), 9.05 (s, 1H), 8.65 (s, 1H), 8.00 (d, 1H, J = 5.6 Hz), 7.42 (d, 1H, J = 8.0 Hz), 6.47 (d, 1H, J = 5.7 Hz), 6.42 (d, 1H, J = 8.0 Hz), 5.14 (d, 1H, J = 4.1 Hz), 4.69 (d, 2H, J = 48.1 Hz), 4.39 (t, 3H, J = 7.6 Hz), 4.04-3.76 (m, 3H), 3.56 (dd, 4H, J = 23.3, 7.4 Hz), 3.33-3.21 (m, 2H), 3.02 (s, 3H), 1.77-1.71 (m, 2H), 1.30 (dd, 6H, J = 6.8, 3.3 Hz) | | (3S,4R)-3-fluoro-1-[4-({8-[3-(methanesulfonyl-methyl)azetidin-1-yl]-5-(propan-2-yl)isoquinolin-3-yl}amino)pyrimidin-2-yl]piperidin-4-ol |
| 29 | 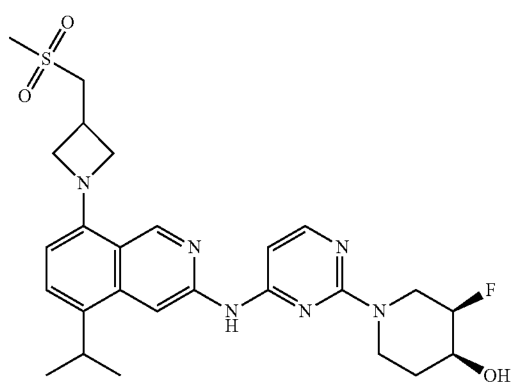 [SMILES: CC(C)c1ccc(N2CC(CS(C)(=O)=O)C2)c2cnc(Nc3ccnc(N4CC[C@H](O)[C@H](F)C4)n3)cc12] | 529 | 1H-NMR (400 MHz, 6d-DMSO) δ ppm 9.88 (s, 1H), 9.05 (s, 1H), 8.65 (s, 1H), 8.00 (d, 1H, J = 5.6 Hz), 7.42 (d, 1H, J = 8.0 Hz), 6.47 (d, 1H, J = 5.7 Hz), 6.42 (d, 1H, J = 8.1 Hz), 5.13 (d, 1H, J = 5.0 Hz), 4.84-4.53 (m, 2H), 4.39 (t, 3H, J = 7.7 Hz), 4.02-3.92 (m, 2H), 3.88-3.76 (m, 1H), 3.68-3.45 (m, 4H, J = 23.1, 7.5 Hz), 3.30-3.23 (m, 2H), 3.02 (s, 3H), 1.77-1.71 (m, 2H), 1.30 (dd, 6H, J = 6.8, 3.3 Hz) | | (3R,4S)-3-fluoro-1-[4-({8-[3-(methanesulfonyl-methyl)azetidin-1-yl]-5-(propan-2-yl)isoquinolin-3-yl}amino)pyrimidin-2-yl]piperidin-4-ol |

TABLE 1-continued

| # | Structure | LC/MS | NMR | Separation Conditions | Chemical Name |
|---|---|---|---|---|---|
| 30 | 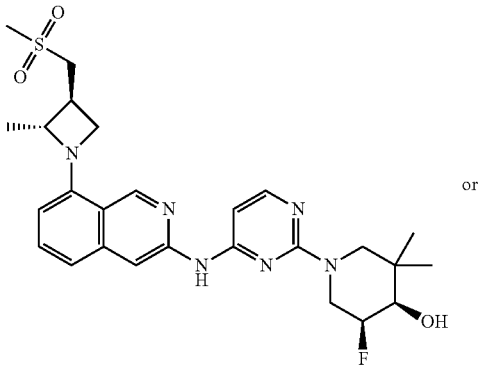 | 529 | 1H NMR (400 MHz, DMSO-d6) δ 9.85 (s, 1H), 9.02 (s, 1H), 8.38 (s, 1H), 7.96 (d, J = 5.6 Hz, 1H), 7.47 (t, J = 7.9 Hz, 1H), 7.09 (d, J = 8.1 Hz, 1H), 6.50 (d, J = 7.7 Hz, 1H), 6.39 (d, J = 5.6 Hz, 1H), 5.09 (d, J = 5.4 Hz, 1H), 4.86-4.62 (m, 2H), 4.22 (q, J = 6.4 Hz, 2H), 3.93-3.78 (m, 2H), 3.72 (t, J = 7.1 Hz, 1H), 3.60-3.34 (m, 4H), 2.98 (s, 3H), 2.88 (h, J = 7.3 Hz, 1H), 1.43 (d, J = 6.0 Hz, 3H), 0.94 (s, 6H). | J; Peak 2 | (4S,5R)-5-fluoro-1-[4-({8-[(2R,3S)-3-(methane-sulfonylmethyl)-2-methylazetidin-1-yl]isoquinolin-3-yl}amino)pyrimidin-2-yl]-3,3-dimethyl-piperidin-4-ol or (4R,5S)-5-fluoro-1-[4-({8-[(2R,3S)-3-(methanesulfonyl-methyl)-2-methylazetidin-1-yl]isoquinolin-3-yl}amino)pyrimidin-2-yl]-3,3-dimethyl-piperidin-4-ol |
|   | 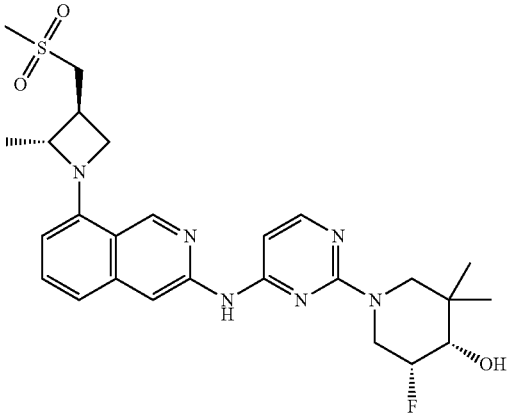 | | | | |
| 31 | 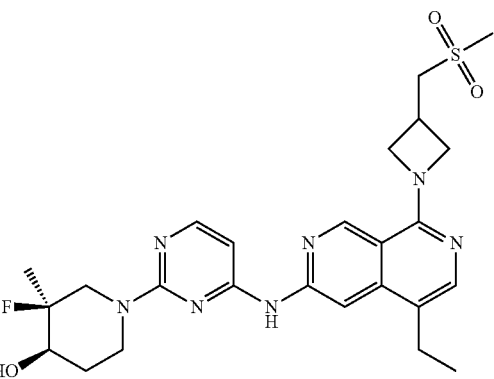 | 530 | 1H NMR (400 MHz, DMSO-d6) δ 10.06 (s, 1H), 9.01 (s, 1H), 8.39 (s, 1H), 8.01 (d, J = 5.6 Hz, 1H), 7.88 (s, 1H), 6.49 (d, J = 5.7 Hz, 1H), 5.00 (d, J = 6.4 Hz, 1H), 4.75-4.62 (m, 2H), 4.56 (t, J = 8.4 Hz, 2H), 4.21 (t, J = 7.4 Hz, 2H), 3.61-3.54 (m, 3H), 3.53-3.45 (m, 1H), 3.22-3.04 (m, 2H), 2.76 (q, J = 7.5 Hz, 2H), 1.77-1.67 (m, 2H), 1.35 (d, J = 21.2 Hz, 3H), 1.26-1.20 (m, 5H). | NN; Peak 1 | (3S,4R)-1-[4-({5-ethyl-8-[3-(methanesulfonyl-methyl)azetidin-1-yl]-2,7-naph-thyridin-3-yl}amino)pyrimidin-2-yl]-3-fluoro-3-methylpiperidin-4-ol |

TABLE 1-continued

| # | Structure | LC/MS | NMR | Separation Conditions | Chemical Name |
|---|---|---|---|---|---|
| 32 | 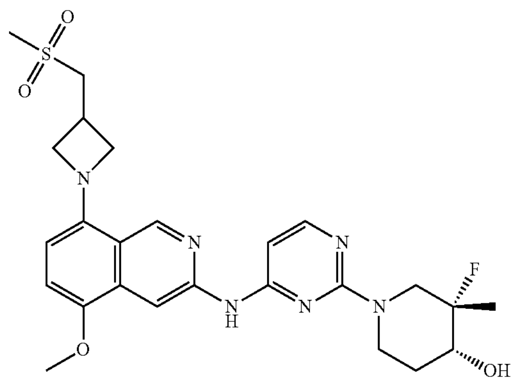 | 531 | H-NMR (300 MHz, 6d-DMSO) δ ppm 9.94 (s, 1H), 9.02 (s, 1H), 8.86 (s, 1H), 7.98 (d, 1H, J = 5.6 Hz), 7.00 (d, 1H, J = 8.3 Hz), 6.38 (dd, 2H, J = 7.0, 3.3 Hz), 5.01 (s, 1H), 4.87-4.56 (m, 2H), 4.30 (td, 2H, J = 7.6, 2.3 Hz), 3.96-3.81 (m, 5H, J = 12.8 Hz), 3.59 (d, 2H, J = 7.4 Hz), 3.51 (s, 1H), 3.32-3.08 (m, 3H), 3.02 (s, 3H), 1.88-1.62 (m, 2H), 1.38 (d, 3H, J = 21.2 Hz) | NN; Peak 1 | (3S,4R)-3-fluoro-1-[4-({8-[3-(methanesulfonyl-methyl)azetidin-1-yl]-5-methoxy-isoquinolin-3-yl}amino)pyrimidin-2-yl]-3-methyl-piperidin-4-ol |
| 33 | 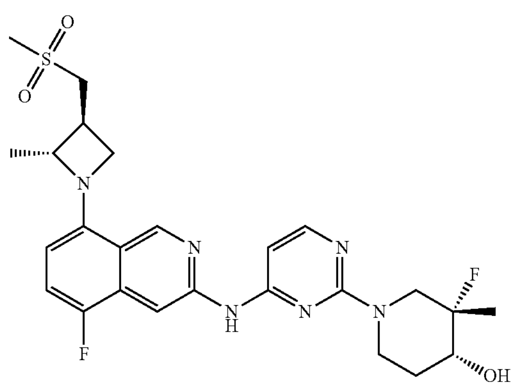 | 533 | 1H NMR (400 MHz, DMSO-d6) δ 10.06 (s, 1H), 9.07 (s, 1H), 8.67 (s, 1H), 7.99 (dd, J = 5.6, 1.1 Hz, 1H), 7.38-7.27 (m, 1H), 6.43 (dd, J = 8.5, 4.0 Hz, 1H), 6.38 (d, J = 5.7 Hz, 1H), 4.96 (d, J = 6.5 Hz, 1H), 4.82-4.71 (m, 1H), 4.71-4.60 (m, 2H), 4.20 (q, J = 6.1 Hz, 1H), 3.65 (t, J = 7.1 Hz, 1H), 3.61-3.43 (m, 3H), 2.98 (s, 5H), 2.87 (q, J = 7.3 Hz, 1H), 1.77-1.63 (m, 2H), 1.46-1.30 (m, 6H). | NN; Peak 1 | (3S,4R)-3-fluoro-1-[4-({5-fluoro-8-[(2R,3S)-3-(methanesulfonyl-methyl)-2-methylazetidin-1-yl]isoquinolin-3-yl}amino)pyrimidin-2-yl]-3-methyl-piperidin-4-ol |
| 34 | 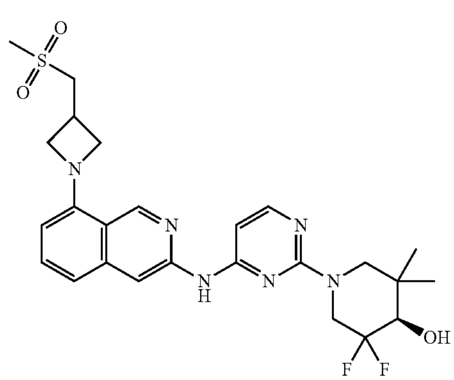 | 533 | 1H-NMR (300 MHz, 6d-DMSO) δ ppm 9.92 (s, 1H), 9.05 (s, 1H), 8.35 (s, 1H), 8.00 (d, 1H, J = 5.7 Hz), 7.49 (t, 1H, J = 7.9 Hz), 7.04 (d, 1H, J = 8.1 Hz), 6.48 (d, 1H, J = 5.7 Hz), 6.36 (d, 1H, J = 7.7 Hz), 5.70 (d, 1H, J = 6.1 Hz), 4.64 (q, 1H, J = 11.4 Hz), 4.46 (t, 2H, J = 7.8 Hz), 4.17 (d, 1H, J = 13.2 Hz), 4.04 (t, 2H, J = 6.9 Hz), 3.78-3.63 (m, 1H), 3.63-3.59 (m, 1H), 3.55 (d, 2H, J = 22.2 Hz), 3.38-3.13 (m, 1H), 3.02 (s, 3H), 1.03 (s, 3H), 0.91 (s, 3H) | L; Peak 2 | (4R)-3,3-difluoro-1-[4-({8-[3-(methanesulfonyl-methyl)azetidin-1-yl]isoquinolin-3-yl}amino)pyrimidin-2-yl]-5,5-dimethyl-piperidin-4-ol or (4S)-3,3-difluoro-1-[4-({8-[3-(methanesulfonyl-methyl)azetidin-1-yl]isoquinolin-3-yl}amino)pyrimidin-2-yl]-5,5-dimethyl- |

TABLE 1-continued

| # | Structure | LC/MS | NMR | Separation Conditions | Chemical Name |
|---|---|---|---|---|---|
| | 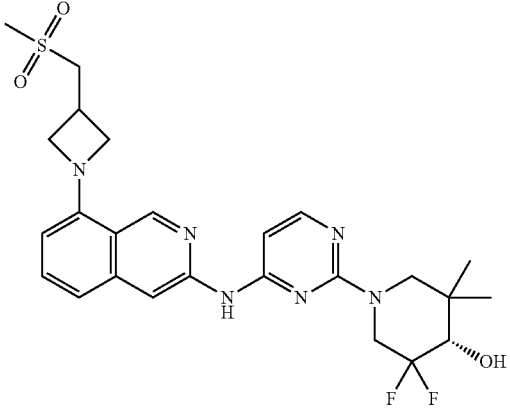 | | | | piperidin-4-ol |
| 35 | 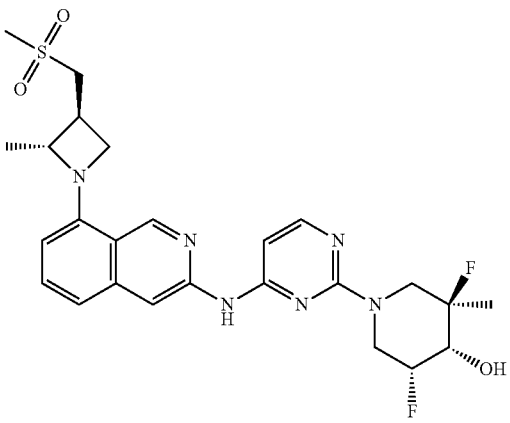 | 533 | 1H-NMR (400 MHz, 6d-DMSO) δ ppm 9.93 (s, 1H), 9.05 (s, 1H), 8.32 (s, 1H), 8.01 (d, 1H, J = 5.6 Hz), 7.49 (t, 1H, J = 7.9 Hz), 7.12 (d, 1H, J = 8.1 Hz), 6.51 (dd, 2H, J = 10.9, 6.7 Hz), 5.87 (s, 1H), 4.90-4.65 (m, 2H), 4.36-4.12 (m, 3H), 3.96-3.83 (m, 2H), 3.81-3.67 (m, 2H), 3.56 (t, 2H, J = 7.9 Hz), 3.00 (s, 3H), 2.90 (q, 1H, J = 7.2 Hz), 1.48-1.41 (m, 6H) | KK, Peak 2 | (3R,4R,5R)-3,5-difluoro-1-[4-({8-[(2R,3S)-3-(methanesulfonylmethyl)-2-methylazetidin-1-yl]isoquinolin-3-yl}amino)pyrimidin-2-yl]-3-methyl-piperidin-4-ol or (3S,4S,5S)-3,5-difluoro-1-[4-({8-[(2R,3S)-3-(methanesulfonylmethyl)-2-methylazetidin-1-yl]isoquinolin-3-yl}amino)pyrimidin-2-yl]-3-methyl-piperidin-4-ol |
| | 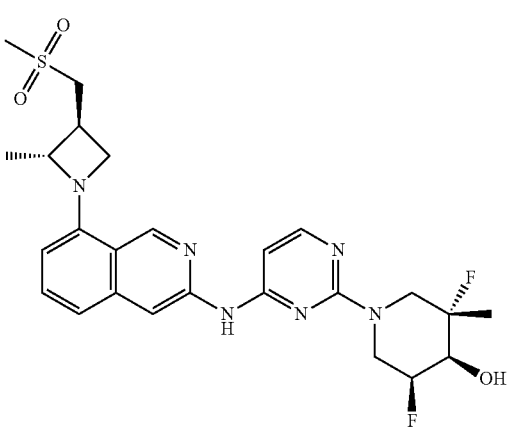 | | | | |

TABLE 1-continued

| # | Structure | LC/MS | NMR | Separation Conditions | Chemical Name |
|---|---|---|---|---|---|
| 36 | 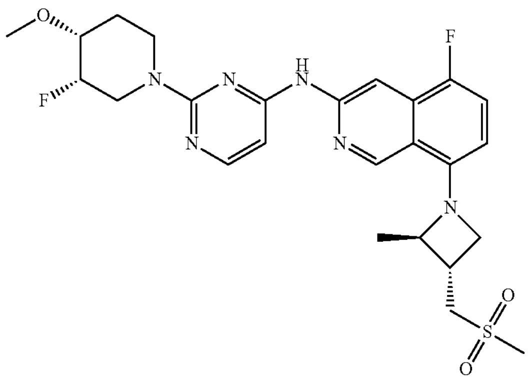 | 533 | 1H NMR (400 MHz, DMSO-d6) δ 10.07 (s, 1H), 9.07 (s, 1H), 8.64 (s, 1H), 8.01 (d, 1H, J = 5.6 Hz), 7.32 (dd, 1H, J = 10.3, 8.4 Hz), 6.44 (dd, 2H, J = 11.9, 4.7 Hz), 4.92 (d, 1H, J = 49.2 Hz), 4.67 (q, 2H, J = 9.3, 7.3 Hz), 4.45 (d, 1H, J = 12.9 Hz), 4.29-4.14 (m, 1H), 3.72-3.40 (m, 4H), 3.34 (s, 3H), 3.32-3.24 (m, 2H), 2.98 (s, 3H), 2.93-2.82 (m, 1H), 1.83-1.64 (m, 2H), 1.40 (d, 3H, J = 6.0 Hz). | | 5-fluoro-N-{2-[(3S,4R)-3-fluoro-4-methoxy-piperidin-1-yl]pyrimidin-4-yl}-8-[(2R,3S)-3-(methanesulfonyl-methyl)-2-methylazetidin-1-yl]isoquinolin-3-amine |
| 37 | 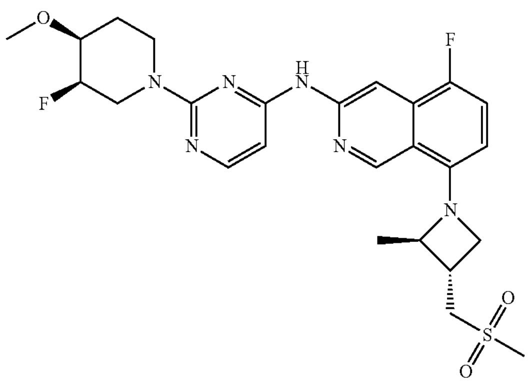 | 533 | ¹H NMR (400 MHz, DMSO-d₆) δ 10.11 (s, 1H), 9.09 (s, 1H), 8.65 (s, 1H), 8.03 (d, J = 5.6 Hz, 1H), 7.33 (dd, J = 10.3, 8.4 Hz, 1H), 6.52-6.37 (m, 2H), 4.93 (d, J = 49.3 Hz, 1H), 4.69 (t, J = 7.6 Hz, 2H), 4.44 (d, J = 13.0 Hz, 1H), 4.21 (t, J = 6.2 Hz, 1H), 3.78-3.39 (m, 4H), 3.36 (s, 3H), 3.30-3.26 (m, 2H), 3.00 (s, 3H), 2.88 (q, J = 7.3 Hz, 1H), 1.94-1.63 (m, 2H), 1.42 (d, J = 6.0 Hz, 3H) | | 5-fluoro-N-{2-[(3R,4S)-3-fluoro-4-methoxy-piperidin-1-yl]pyrimidin-4-yl}-8-[(2R,3S)-3-(methanesulfonyl-methyl)-2-methylazetidin-1-yl]isoquinolin-3-amine |
| 38 | 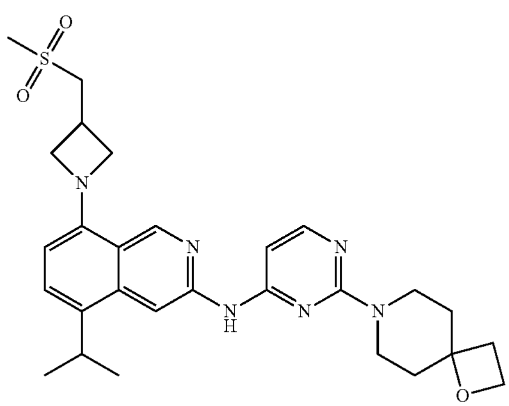 [SMILES: CC(C)c1ccc(N2CC(CS(C)(=O)=O)C2)c2cnc(Nc3ccnc(N4CCC5(CCO5)CC4)n3)cc12] | 537 | 1H-NMR (400 MHz, 6d-DMSO) δ ppm 9.87 (s, 1H), 9.05 (s, 1H), 8.65 (s, 1H), 8.00 (d, 1H, J = 5.6 Hz), 7.43 (d, 1H, J = 8.0 Hz), 6.46 (d, 1H, J = 5.7 Hz), 6.42 (d, 1H, J = 8.1 Hz), 4.46 (t, 2H, J = 7.7 Hz), 4.39 (t, 2H, J = 7.6 Hz), 3.97 (t, 2H, J = 6.9 Hz), 3.91-3.72 (m, 5H), 3.59 (d, 2H, J = 7.4 Hz), 3.48 (p, 1H, J = 6.7 Hz), 3.28 (dd, 2H, J = 14.1, 6.8 Hz), 2.43 (t, 2H, J = 7.7 Hz), 1.84 (q, 5H, J = 6.5, 5.9 Hz), 1.32 (d, 6H, J = 6.8 Hz) | | 8-[3-(methane-sulfonylmethyl)azetidin-1-yl]-N-(2-{1-oxa-7-azaspiro[3.5]nonan-7-yl}pyrimidin-4-yl)-5-(propan-2-yl)isoquinolin-3-amine |
| 39 | Racemate | 537 | 1H-NMR (300 MHz, 6d-DMSO) δ ppm 9.85 (s, 1H), 9.04 (s, 1H), 8.74 (s, 1H), 7.97 (d, 1H, J = 5.6 Hz), 7.41 (d, 1H, J = 8.0 Hz), 6.47-6.33 (m, 2H), 4.75 (d, 1H, J = 2.5 Hz), 4.57-4.27 (m, 4H), 3.95 (dd, 3H, J = 14.3, 7.4 Hz), 3.59 (d, 2H, J = 7.4 Hz), 3.55-3.42 (m, 1H), 3.08-2.94 (m, 5H), 2.25-2.05 (m, 2H), 1.93-1.73 (m, 2H), 1.40 (d, 2H, J = 7.5 Hz), 1.30 (d, 6H, J = 6.7 Hz) | | Rac (1R,5S,8S)-3-[4-({8-[3-(methanesulfonyl-methyl)azetidin-1-yl]-5-(propan-2-yl)isoquinolin-3-yl}amino)pyrimidin-2-yl]-3-azabicyclo[3.2.1]octan-8-ol |

TABLE 1-continued

| # | Structure | LC/MS | NMR | Separation Conditions | Chemical Name |
|---|---|---|---|---|---|
| 40 | 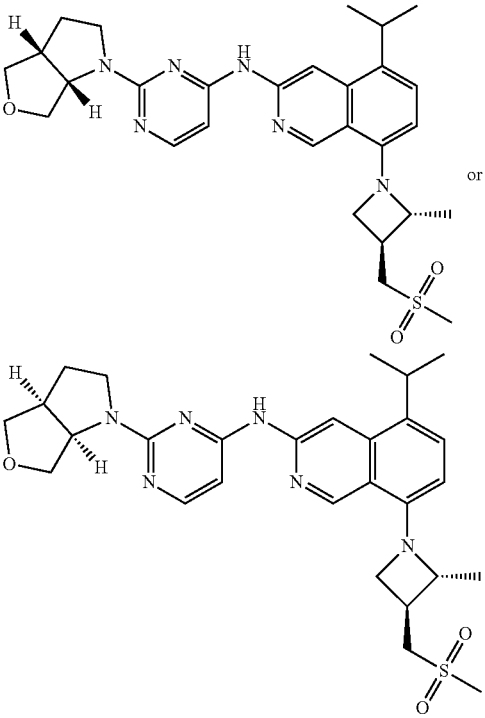 | 537 | 1H-NMR (300 MHz, 6d-DMSO) δ ppm 9.90 (s, 1H), 9.06 (s, 1H), 8.76 (s, 1H), 7.97 (d, 1H, J = 5.7 Hz), 7.42 (d, 1H, J = 8.0 Hz), 6.56 (d, 1H, J = 8.1 Hz), 4.66 (t, 1H, J = 7.5 Hz), 4.28-4.23 (m, 1H), 4.19 (t, 3H, J = 6.4 Hz), 3.93-3.59 (m, 3H), 3.59-3.36 (m, 5H), 3.00 (s, 3H), 2.89 (q, 1H, J = 7.3 Hz), 2.64 (dt, 1H, J = 11.4, 5.9 Hz), 2.13-2.03 (m, 1H), 1.91 (p, 1H, J = 10.0 Hz), 1.43 (d, 3H, J = 6.0 Hz), 1.29 (d, 6H, J = 6.6 Hz) | F; Peak 2 | N-{2-[(3aR,6aS)-hexahydro-1H-furo[3,4-b]pyrrol-1-yl]pyrimidin-4-yl}-8-[(2R,3S)-3-(methanesulfonyl-methyl)-2-methylazetidin-1-yl]-5-(propan-2-yl)isoquinolin-3-amine or N-{2-[(3aS,6aR)-hexahydro-1H-furo[3,4-b]pyrrol-1-yl]pyrimidin-4-yl}-8-[(2R,3S)-3-(methanesulfonyl-methyl)-2-methylazetidin-1-yl]-5-(propan-2-yl)isoquinolin-3-amine |
| 41 | 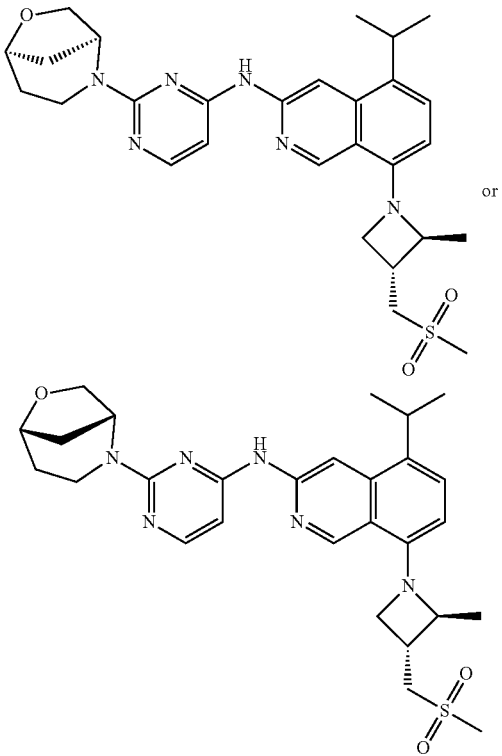 | 537 | 1H-NMR (300 MHz, 6d-DMSO) δ ppm 9.93 (s, 1H), 9.05 (s, 1H), 8.70 (s, 1H), 8.01 (d, 1H, J = 5.7 Hz), 7.42 (d, 1H, J = 8.0 Hz), 6.56 (d, 1H, J = 8.1 Hz), 6.45 (d, 1H, J = 5.5 Hz), 5.53 (s, 1H), 4.74-4.61 (m, 1H), 4.54 (s, 2H), 4.23-4.17 (m, 1H), 4.01-3.91 (m, 1H), 3.90-3.84 (m, 1H), 3.67-3.44 (m, 4H), 3.00 (s, 3H), 2.93-2.87 (m, 1H), 1.91-1.76 (m, 2H), 1.74-1.68 (m, 2H), 1.42 (d, 3H, J = 5.8 Hz), 1.33-1.24 (m, 6H) | M; Peak 2 | N-(2-((1S,5R)-6-oxa-2-azabicyclo[3.2.1]octan-2-yl)pyrimidin-4-yl)-5-isopropyl-8-((2S,3R)-2-methyl-3-((methylsulfonyl)methyl)azetidin-1-yl)isoquinolin-3-amine or N-(2-((1R,5S)-6-oxa-2-azabicyclo[3.2.1]octan-2-yl)pyrimidin-4-yl)-5-isopropyl-8-((2S,3R)-2-methyl-3-((methylsulfonyl)methyl)azetidin-1-yl)isoquinolin-3-amine |

TABLE 1-continued

| # | Structure | LC/MS | NMR | Separation Conditions | Chemical Name |
|---|---|---|---|---|---|
| 42 | 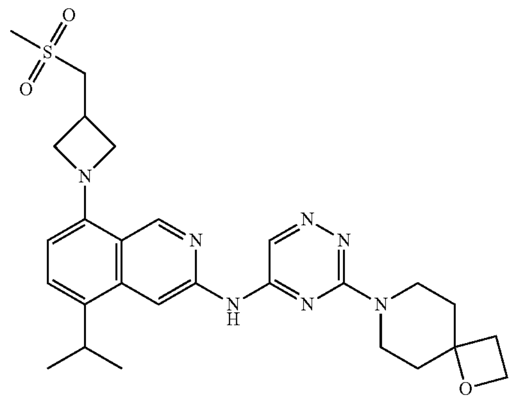 [SMILES: CC(C)c1ccc(N2CC(CS(C)(=O)=O)C2)c2cnc(Nc3cnnc(N4CCC5(CCO5)CC4)n3)cc12] | 538 | 1H-NMR (300 MHz, 6d-DMSO) δ ppm 10.45 (s, 1H), 9.09 (s, 1H), 8.68 (s, 1H), 8.46 (s, 1H), 7.45 (d, 1H, J = 8.0 Hz), 6.45 (d, 1H, J = 8.0 Hz), 4.42 (dt, 4H, J = 18.4, 7.6 Hz), 3.98 (q, 2H, J = 6.9, 6.1 Hz), 3.89-3.80 (m, 4H), 3.57 (d, 2H, J = 7.4 Hz), 3.50-3.40 (m, 1H), 3.00 (s, 3H), 2.42 (t, 2H, J = 7.7 Hz), 1.91-1.81 (m, 4H), 1.30 (d, 6H, J = 6.7 Hz) | | 8-[3-(methanesulfonylmethyl)azetidin-1-yl]-N-(3-{1-oxa-7-azaspiro[3.5]nonan-7-yl}-1,2,4-triazin-5-yl)-5-(propan-2-yl)isoquinolin-3-amine |
| 43 | | 538 | 1H-NMR (300 MHz, 6d-DMSO) δ ppm 10.14 (s, 1H), 9.13 (s, 1H), 8.90 (s, 1H), 8.01 (d, 1H, J = 5.7 Hz), 7.73 (s, 1H), 6.51 (s, 1H), 4.74 (t, 1H, J = 7.5 Hz), 4.39-4.13 (m, 4H), 3.90-3.74 (m, 1H), 3.75 (s, 3H), 3.54 (dt, 2H, J = 10.1, 5.0 Hz), 3.51-3.42 (m, 2H), 3.01 (s, 3H), 2.93 (q, 1H, J = 7.2 Hz), 2.74-2.60 (m, 1H), 2.12-2.05 (m, 1H), 1.99-1.86 (m, 1H), 1.48 (d, 3H, J = 6.0 Hz), 1.30 (dd, 6H, J = 6.7, 3.4 Hz) | F; Peak 2 | N-{2-[(3aR,6aS)-hexahydro-1H-furo[3,4-b]pyrrol-1-yl]pyrimidin-4-yl}-8-[(2R,3S)-3-(methanesulfonylmethyl)-2-methylazetidin-1-yl]-5-(propan-2-yl)-2,6-naphthyridin-3-amine or N-{2-[(3aS,6aR)-hexahydro-1H-furo[3,4-b]pyrrol-1-yl]pyrimidin-4-yl}-8-[(2R,3S)-3-(methanesulfonylmethyl)-2-methylazetidin-1-yl]-5-(propan-2-yl)-2,6-naphthyridin-3-amine |
| 44 | 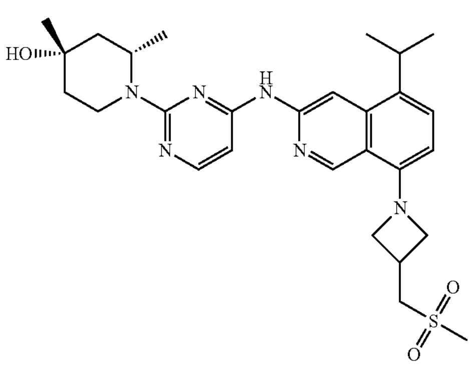 | 539 | 1H-NMR (300 MHz, 6d-DMSO) δ ppm 9.80 (s, 1H), 9.04 (s, 1H), 8.69 (s, 1H), 7.98 (d, 1H, J = 5.6 Hz), 7.42 (d, 1H, J = 8.0 Hz), 6.41 (d, 1H, J = 8.0 Hz), 6.38 (d, 1H, J = 5.6 Hz), 5.10-5.04 (m, 1H), 4.66-4.55 (m, 1H), 4.39 (t, 2H, J = 7.6 Hz), 4.31 (s, 1H), 3.97 (t, 2H, J = 6.9 Hz), 3.59 (d, 2H, J = 7.4 Hz), 3.49 (q, 1H, J = 6.8 Hz), 3.30-3.20 (m, 1H), 3.02 (s, 3H), 1.68-1.58 (m, 3H), 1.55-1.41 (m, 1H), 1.39-1.25 (m, 9H), 1.16 (s, 3H) | H; Peak 1 | (2R,4R)-1-[4-({8-[3-(methanesulfonylmethyl)azetidin-1-yl]-5-(propan-2-yl)isoquinolin-3-yl}amino)pyrimidin-2-yl]-2,4-dimethylpiperidin-4-ol or (2S,4S)-1-[4-({8-[3-(methanesulfonylmethyl)azetidin-1-yl]-5-(propan-2-yl)isoquinolin-3-yl}amino) |

TABLE 1-continued

| # | Structure | LC/MS | NMR | Separation Conditions | Chemical Name |
|---|-----------|-------|-----|----------------------|---------------|
| | | | | | pyrimidin-2-yl]-2,4-dimethyl-piperidin-4-ol |
| 45 | | 539 | 1H-NMR (300 MHz, 6d-DMSO) δ ppm 9.80 (s, 1H), 9.04 (s, 1H), 8.69 (s, 1H), 7.98 (d, 1H, J = 5.6 Hz), 7.42 (d, 1H, J = 8.0 Hz), 6.46-6.34 (m, 2H), 5.08-5.02 (m, 1H), 4.60 (d, 1H, J = 12.9 Hz), 4.39 (t, 2H, J = 7.7 Hz), 4.31 (s, 1H), 3.97 (t, 2H, J = 6.9 Hz), 3.59 (d, 2H, J = 7.4 Hz), 3.55-3.45 (m, 1H), 3.32-3.26 (m, 1H), 3.02 (s, 3H), 1.68-1.58 (m, 3H), 1.55-1.40 (m, 1H), 1.39-1.25 (m, 9H), 1.16 (s, 3H) | H; Peak 2 | (2S,4S)-1-[4-({8-[3-(methane-sulfonylmethyl)azetidin-1-yl]-5-(propan-2-yl)isoquinolin-3-yl}amino)pyrimidin-2-yl]-2,4-dimethylpiperidin-4-ol or (2R,4R)-1-[4-({8-[3-(methanesulfonyl-methyl)azetidin-1-yl]-5-(propan-2-yl)isoquinolin-3-yl}amino)pyrimidin-2-yl]-2,4-dimethyl-piperidin-4-ol |
| 46 | 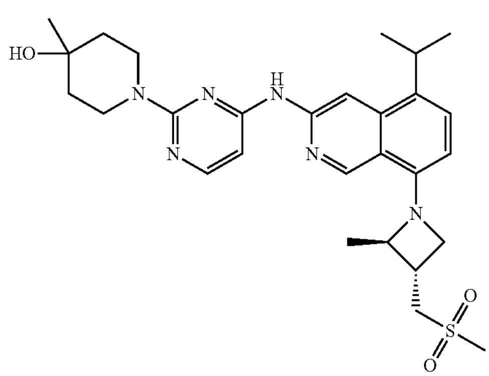 [SMILES: CC(C)c1ccc(N2C[C@H](CS(C)(=O)=O)[C@H]2C)c2cnc(Nc3ccnc(N4CCC(C)(O)CC4)n3)cc12] | 539 | 1H-NMR (400 MHz, 6d-DMSO) δ ppm 9.84 (s, 1H), 9.04 (s, 1H), 8.70 (s, 1H), 7.98 (d, 1H, J = 5.6 Hz), 7.42 (d, 1H, J = 8.0 Hz), 6.55 (d, 1H, J = 8.0 Hz), 6.39 (d, 1H, J = 5.6 Hz), 4.65 (t, 1H, J = 7.5 Hz), 4.39 (s, 1H), 4.27 (s, 1H), 4.20 (td, 2H, J = 12.6, 12.2, 5.3 Hz), 3.63 (t, 1H, J = 7.2 Hz), 3.51 (ddd, 4H, J = 16.0, 8.2, 4.8 Hz), 3.45 (d, 1H, J = 4.4 Hz), 2.99 (s, 3H), 2.88 (q, 1H, J = 7.3 Hz), 1.53 (td, 4H, J = 13.4, 12.7, 6.4 Hz), 1.42 (d, 3H, J = 6.0 Hz), 1.29 (d, 6H, J = 6.7 Hz), 1.18 (s, 3H) | K; Peak 1 | 1-[4-({8-[(2R,3S)-3-(methane-sulfonylmethyl)-2-methylazetidin-1-yl]-5-(propan-2-yl)isoquinolin-3-yl}amino)pyrimidin-2-yl]-4-methyl-piperidin-4-ol |

TABLE 1-continued

| # | Structure | LC/MS | NMR | Separation Conditions | Chemical Name |
|---|---|---|---|---|---|
| 47 | 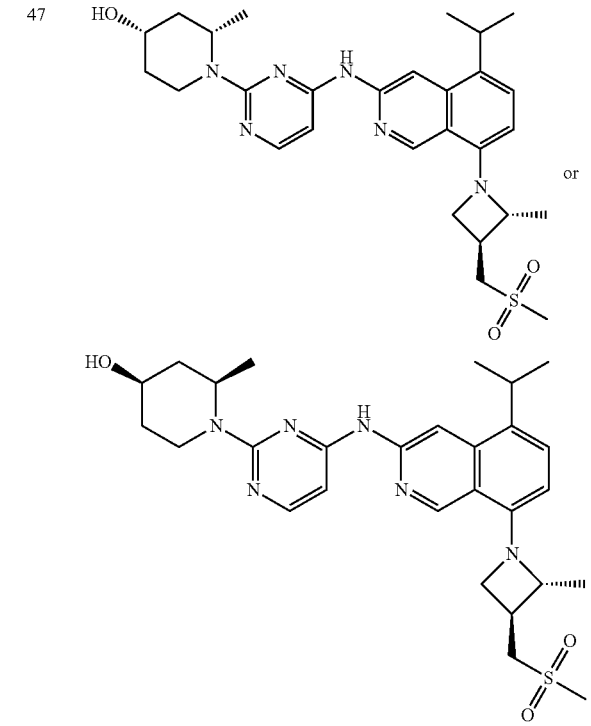 | 539 | 1H-NMR (300 MHz, 6d-DMSO) δ ppm 9.85 (s, 1H), 9.05 (s, 1H), 8.71 (s, 1H), 7.98 (d, 1H, J = 5.6 Hz), 7.43 (d, 1H, J = 7.9 Hz), 6.56 (d, 1H, J = 8.0 Hz), 6.37 (d, 1H, J = 5.6 Hz), 5.01 (s, 1H), 4.72-4.51 (m, 3H), 4.25-4.14 (m, 1H), 4.05 (s, 1H), 3.72-3.42 (m, 4H), 3.00 (s, 3H), 2.90 (t, 1H, J = 7.3 Hz), 1.83-1.67 (m, 4H), 1.43 (d, 3H, J = 5.9 Hz), 1.38-1.17 (m, 9H) | E; Peak 1 | (2S,4S)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-2-methyl-piperidin-4-ol or (2R,4R)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-2-methyl-piperidin-4-ol |
| 48 | 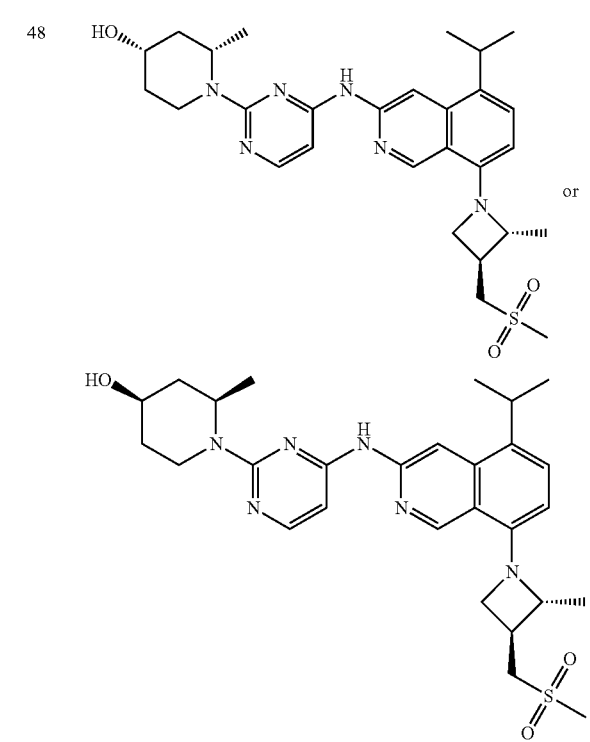 | 539 | 1H-NMR (300 MHz, CDCl3) δ ppm 9.09 (s, 1H), 8.68 (s, 1H), 8.08 (d, 1H, J = 5.6 Hz), 7.60 (s, 1H), 7.41 (d, 1H, J = 7.9 Hz), 6.54 (d, 1H, J = 8.0 Hz), 6.09 (d, 1H, J = 5.6 Hz), 5.15 (t, 1H, J = 6.8 Hz), 4.70 (q, 2H, J = 7.5, 6.5 Hz), 4.36-4.19 (m, 2H), 3.74-3.23 (m, 5H), 3.07 (p, 1H, J = 7.2 Hz), 2.97 (s, 3H), 2.14-1.65 (m, 5H), 1.51 (dd, 6H, J = 8.9, 6.5 Hz), 1.38 (dd, 6H, J = 6.8, 2.4 Hz) | E; Peak 2 | (2R,4R)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-2-methyl-piperidin-4-ol or (2S,4S)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-2-methyl-piperidin-4-ol |

TABLE 1-continued

| # | Structure | LC/MS | NMR | Separation Conditions | Chemical Name |
|---|---|---|---|---|---|
| 49 | 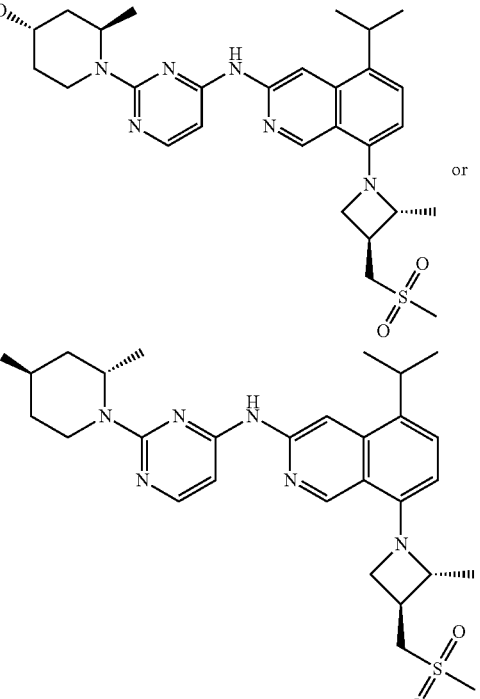 | 539 | 1H-NMR (300 MHz, CDCl3) δ ppm 9.10 (s, 1H), 8.63 (s, 1H), 8.10 (d, 1H, J = 5.7 Hz), 7.43 (d, 1H, J = 7.9 Hz), 6.56 (d, 1H, J = 8.0 Hz), 6.14 (s, 1H), 5.37 (d, 1H, J = 7.0 Hz), 4.91 (d, 1H, J = 13.3 Hz), 4.70 (t, 1H, J = 7.6 Hz), 4.33-4.23 (m, 1H), 4.20-4.14 (m, 1H), 3.63 (dt, 2H, J = 26.5, 7.0 Hz), 3.37 (t, 2H, J = 7.2 Hz), 3.21-3.01 (m, 2H), 2.98 (s, 3H), 2.13 (d, 1H, J = 12.5 Hz), 2.04 (d, 1H, J = 12.1 Hz), 1.73 (dt, 2H, J = 11.9, 5.9 Hz), 1.58-1.50 (m, 4H), 1.39 (dd, 6H, J = 6.8, 2.3 Hz), 1.31 (d, 3H, J = 7.0 Hz) | L; Peak 2 | (2R,4S)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-2-methyl-piperidin-4-ol or (2S,4R)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-2-methyl-piperidin-4-ol |
| 50 | 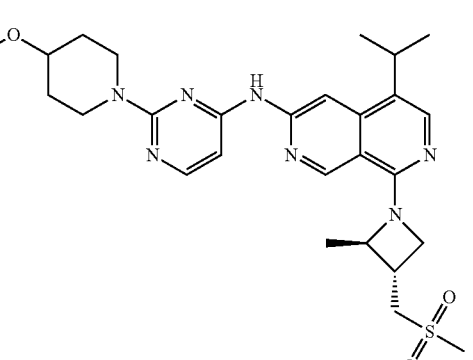 | 540 | 1H-NMR (300 MHz, 6d-DMSO) δ ppm 10.10 (s, 1H), 9.04 (s, 1H), 8.56 (s, 1H), 8.05 (d, 1H, J = 5.6 Hz), 8.01 (s, 1H), 6.48 (d, 1H, J = 5.6 Hz), 4.86 (t, 1H, J = 7.9 Hz), 4.55 (t, 1H, J = 6.2 Hz), 4.27 (d, 2H, J = 13.5 Hz), 3.98 (t, 1H, J = 7.3 Hz), 3.58-3.35 (m, 5H), 3.31 (s, 3H), 3.30-3.24 (m, 1H), 2.99 (s, 3H), 2.94-2.85 (m, 1H), 1.95-1.89 (m, 2H), 1.58-1.40 (m, 5H), 1.32 (dd, 6H, J = 6.8, 4.1 Hz) | | 8-[(2R,3S)-3-(methanesulfonyl-methyl)-2-methylazetidin-1-yl]-N-[2-(4-methoxypiperidin-1-yl)pyrimidin-4-yl]-5-(propan-2-yl)-2,7-naphthyridin-3-amine |
| 51 | 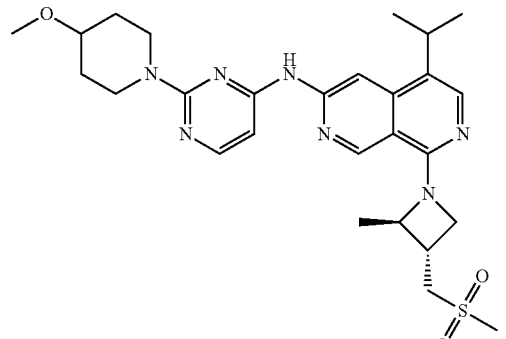 | 541 | 1H-NMR (300 MHz, 6d-DMSO) δ ppm 9.86 (s, 1H), 9.05 (s, 1H), 8.69 (s, 1H), 8.00 (d, 1H, J = 5.6 Hz), 7.24 (d, 1H, J = 7.8 Hz), 6.50 (d, 1H, J = 5.7 Hz), 6.31 (d, 1H, J = 7.9 Hz), 4.99 (d, 1H, J = 6.4 Hz), 4.72 (dt, 2H, J = 20.8, 10.7 Hz), 4.40 (t, 2H, J = 7.6 Hz), 3.97 (t, 2H, J = 6.9 Hz), 3.63-3.57 (m, 1H), 3.61-3.43 (m, 2H), 3.22-3.05 (m, 1H), 3.02 (s, 3H), 1.69-1.63 (m, 2H), 1.32 (d, 4H, J = 21.2 Hz), 1.02-0.92 (m, 2H), 0.65 (d, 2H, J = 6.1 Hz) | NN; Peak 1 | (3S,4R)-1-[4-({5-cyclopropyl-8-[3-(methanesulfonyl-methyl)azetidin-1-yl]isoquinolin-3-yl}amino)pyrimidin-2-yl]-3-fluoro-3-methylpiperidin-4-ol |

TABLE 1-continued

| # | Structure | LC/MS | NMR | Separation Conditions | Chemical Name |
|---|---|---|---|---|---|
| 52 | 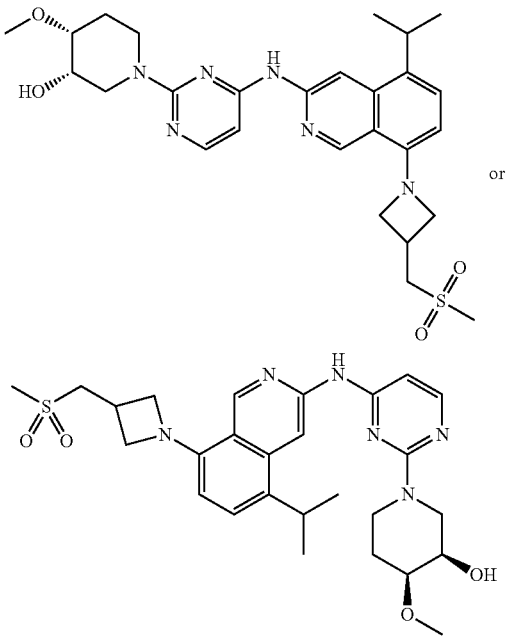 | 541 | 1H-NMR (400 MHz, 6d-DMSO) δ ppm 9.83 (s, 1H), 9.04 (s, 1H), 8.67 (s, 1H), 7.98 (d, 1H, J = 5.6 Hz), 7.41 (d, 1H, J = 8.0 Hz), 6.42 (t, 2H, J = 6.8 Hz), 4.62 (d, 1H, J = 5.0 Hz), 4.39 (t, 2H, J = 7.6 Hz), 3.96 (t, 4H, J = 6.9 Hz), 3.79 (s, 1H), 3.71 (d, 1H, J = 12.8 Hz), 3.64-3.50 (m, 4H), 3.48 (t, 1H, J = 8.6 Hz), 3.37 (s, 3H), 3.02 (s, 3H), 1.88 (s, 1H), 1.63 (s, 1H), 1.30 (d, 6H, J = 6.7 Hz) | | (3S,4R)-1-[4-({8-[3-(methane-sulfonylmethyl) azetidin-1-yl]-5-(propan-2-yl) isoquinolin-3-yl} amino)pyrimidin-2-yl]-4-methoxy-piperidin-3-ol or (3R,4S)-1-(4-((5-isopropyl-8-(3-((methyl-sulfonyl)methyl) azetidin-1-yl) isoquinolin-3-yl)amino) pyrimidin-2-yl)-4-methoxy-piperidin-3-ol |
| 53 | 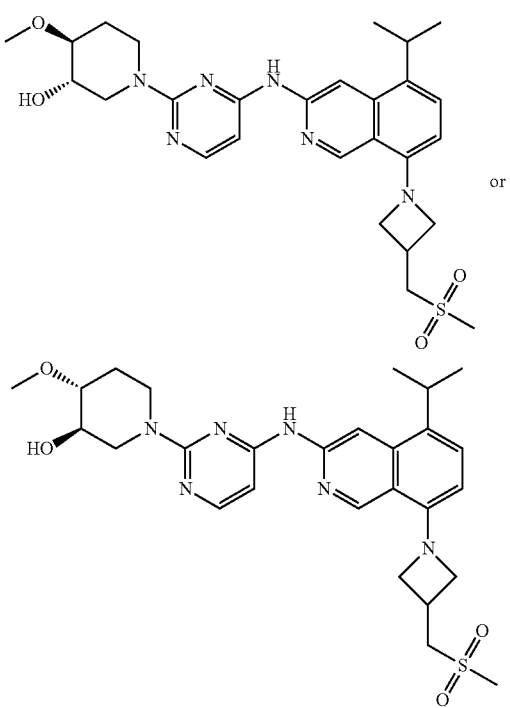 | 541 | 1H-NMR (300 MHz, 6d-DMSO) δ ppm 9.85 (s, 1H), 9.05 (s, 1H), 8.64 (s, 1H), 7.99 (d, 1H, J = 5.6 Hz), 7.41 (d, 1H, J = 8.0 Hz), 6.47 (d, 1H, J = 5.7 Hz), 6.41 (d, 1H, J = 8.1 Hz), 5.08 (d, 1H, J = 4.8 Hz), 4.39 (t, 4H, J = 7.8 Hz), 3.96 (t, 2H, J = 6.9 Hz), 3.59 (d, 2H, J = 7.4 Hz), 3.56-3.46 (m, 1H), 3.44-3.36 (m, 5H), 3.31-3.08 (m, 4H), 3.02 (s, 3H), 2.07-2.01 (m, 1H), 1.35-1.21 (m, 7H) | C; Peak 1 | (3S,4S)-1-[4-({8-[3-(methane-sulfonylmethyl) azetidin-1-yl]-5-(propan-2-yl) isoquinolin-3-yl} amino)pyrimidin-2-yl]-4-methoxy-piperidin-3-ol or (3R,4R)-1-[4-({8-[3-(methane-sulfonylmethyl) azetidin-1-yl]-5-(propan-2-yl) isoquinolin-3-yl} amino)pyrimidin-2-yl]-4-methoxy-piperidin-3-ol |

TABLE 1-continued

| # | Structure | LC/MS | NMR | Separation Conditions | Chemical Name |
|---|---|---|---|---|---|
| 54 | 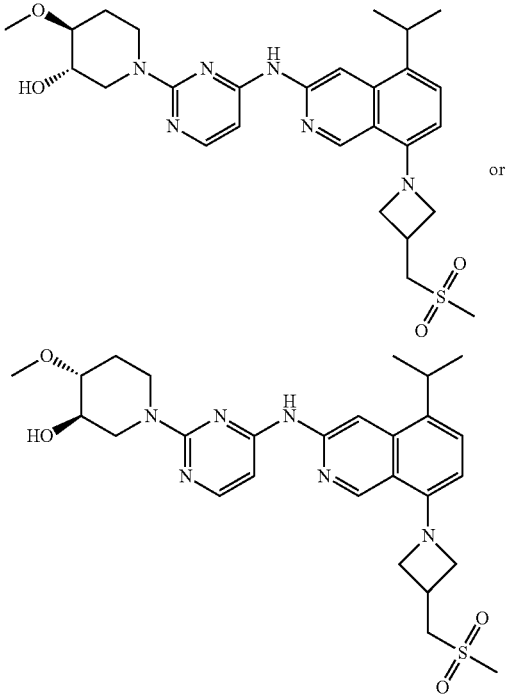 | 541 | 1H-NMR (300 MHz, 6d-DMSO) δ ppm 9.85 (s, 1H), 9.05 (s, 1H), 8.64 (s, 1H), 7.99 (d, 1H, J = 5.6 Hz), 7.41 (d, 1H, J = 8.0 Hz), 6.47 (d, 1H, J = 5.7 Hz), 6.41 (d, 1H, J = 8.1 Hz), 5.08 (d, 1H, J = 4.8 Hz), 4.39 (t, 4H, J = 7.9 Hz), 3.96 (t, 2H, J = 6.9 Hz), 3.59 (d, 2H, J = 7.4 Hz), 3.50 (dt, 1H, J = 14.2, 7.1 Hz), 3.39 (s, 3H), 3.32-3.21 (m, 1H), 3.31 (s, 3H), 3.21-3.01 (m, 1H), 3.02 (s, 3H), 2.07-2.01 (m, 1H), 1.42-1.20 (m, 7H) | C; Peak 2 | (3R,4R)-1-[4-({8-[3-(methane-sulfonylmethyl)azetidin-1-yl]-5-(propan-2-yl)isoquinolin-3-yl}amino)pyrimidin-2-yl]-4-methoxy-piperidin-3-ol or (3S,4S)-1-[4-({8-[3-(methane-sulfonylmethyl)azetidin-1-yl]-5-(propan-2-yl)isoquinolin-3-yl}amino)pyrimidin-2-yl]-4-methoxy-piperidin-3-ol |
| 55 | 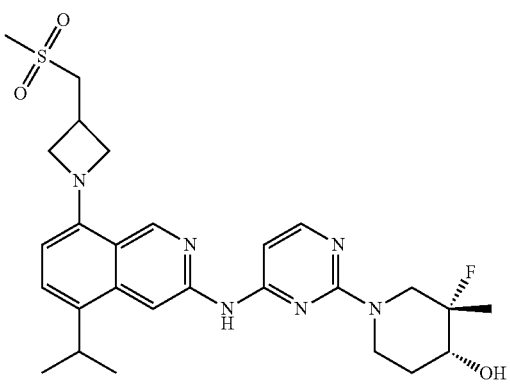 | 543 | 1H-NMR (300 MHz, 6d-DMSO) δ ppm 9.86 (s, 1H), 9.06 (s, 1H), 8.61 (s, 1H), 7.99 (d, 1H, J = 5.6 Hz), 7.41 (d, 1H, J = 8.0 Hz), 6.48 (d, 1H, J = 5.7 Hz), 6.41 (d, 1H, J = 8.1 Hz), 5.03 (d, 1H, J = 6.4 Hz), 4.92-4.58 (m, 2H), 4.39 (t, 2H, J = 7.8 Hz), 3.97 (t, 2H, J = 6.8 Hz), 3.67-3.45 (m, 4H), 3.20-3.07 (m, 3H), 3.02 (s, 3H), 1.74 (s, 2H), 1.51-1.15 (m, 9H) | NN; Peak 1 | (3S,4R)-3-fluoro-1-[4-({8-[3-(methanesulfonyl-methyl)azetidin-1-yl]-5-(propan-2-yl)isoquinolin-3-yl}amino)pyrimidin-2-yl]-3-methyl-piperidin-4-ol |
| 56 | 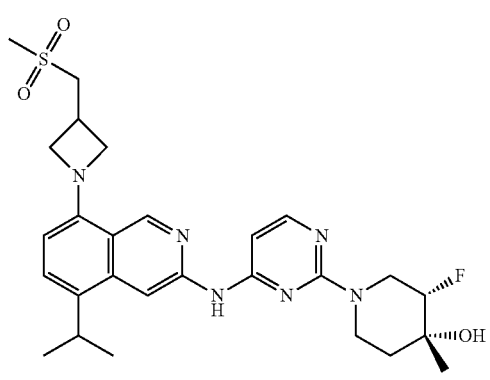 [SMILES: CC(C)c1ccc(N2CC(CS(C)(=O)=O)C2)c2cnc(Nc3ccnc(N4CC[C@@](C)(O)[C@@H](F)C4)n3)cc12] | 543 | 1H-NMR (400 MHz, 6d-DMSO) δ ppm 9.91 (s, 1H), 9.05 (s, 1H), 8.65 (s, 1H), 8.01 (d, 1H, J = 5.7 Hz), 7.42 (d, 1H, J = 8.0 Hz), 6.49 (d, 1H, J = 5.7 Hz), 6.42 (d, 1H, J = 8.0 Hz), 4.85 (s, 1H), 4.55-4.23 (m, 4H), 4.20 (d, 1H, J = 13.1 Hz), 3.97 (t, 2H, J = 6.9 Hz), 3.69-3.55 (m, 3H), 3.56-3.41 (m, 2H), 3.32-3.22 (m, 1H), 3.02 (s, 3H), 1.82-1.50 (m, 2H), 1.38-1.17 (m, 9H) | F; Peak 1 | (3S,4R)-3-fluoro-1-[4-({8-[3-(methanesulfonyl-methyl)azetidin-1-yl]-5-(propan-2-yl)isoquinolin-3-yl}amino)pyrimidin-2-yl]-4-methyl-piperidin-4-ol |

TABLE 1-continued

| # | Structure | LC/MS | NMR | Separation Conditions | Chemical Name |
|---|---|---|---|---|---|
| 57 | 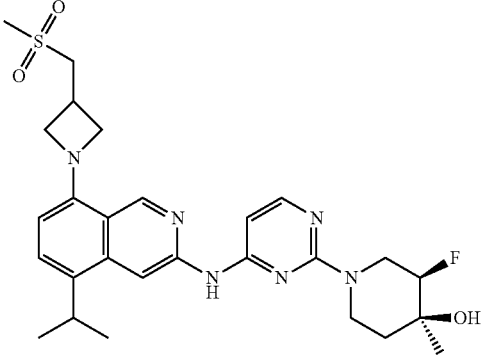 [SMILES: CC(C)c1ccc(N2CC(CS(C)(=O)=O)C2)c2cnc(Nc3ccnc(N4CC[C@](C)(O)[C@H](F)C4)n3)cc12] | 543 | 1H-NMR (400 MHz, 6d-DMSO) δ ppm 9.93 (s, 1H), 9.06 (s, 1H), 8.64 (s, 1H), 8.01 (d, 1H, J = 5.7 Hz), 7.42 (d, 1H, J = 8.0 Hz), 6.49 (d, 1H, J = 5.6 Hz), 6.42 (d, 1H, J = 8.0 Hz), 4.86 (s, 1H), 4.40 (q, 2H, J = 7.7, 6.5 Hz), 4.29 (dd, 1H, J = 9.0, 4.3 Hz), 4.19 (d, 1H, J = 13.0 Hz), 3.97 (t, 2H, J = 6.9 Hz), 3.63 (s, 1H), 3.59 (d, 2H, J = 7.4 Hz), 3.55-3.45 (m, 2H), 3.33-3.23 (m, 1H), 3.02 (s, 3H), 1.72 (d, 1H, J = 12.6 Hz), 1.57 (t, 1H, J = 10.3 Hz), 1.33-1.22 (m, 9H) | F; Peak 2 | (3R,4S)-3-fluoro-1-[4-({8-[3-(methanesulfonyl-methyl)azetidin-1-yl]-5-(propan-2-yl)isoquinolin-3-yl}amino)pyrimidin-2-yl]-4-methyl-piperidin-4-ol |
| 58 | 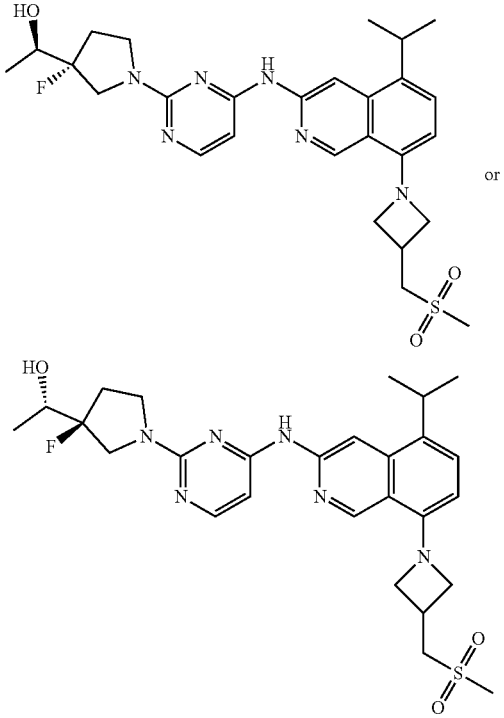 | 543 | 1H-NMR (400 MHz, 6d-DMSO) δ ppm 9.87 (s, 1H), 9.04 (d, 1H, J = 0.8 Hz), 8.82 (s, 1H), 7.99 (d, 1H, J = 5.7 Hz), 7.41 (d, 1H, J = 8.0 Hz), 6.46 (d, 1H, J = 5.7 Hz), 6.40 (d, 1H, J = 8.1 Hz), 5.20 (s, 1H), 4.38 (t, 2H, J = 7.7 Hz), 3.96 (t, 2H, J = 6.9 Hz), 3.93-3.81 (m, 2H), 3.80-3.64 (m, 2H), 3.59 (d, 2H, J = 7.4 Hz), 3.55-3.45 (m, 1H), 3.30-3.22 (m, 1H), 3.01 (s, 3H), 2.35-2.08 (m, 2H), 1.29 (dd, 6H, J = 6.7, 1.9 Hz), 1.21 (d, 3H, J = 6.4 Hz) | F; Peak 1 | (1R)-1-[(3R)-3-fluoro-1-[4-({8-[3-(methane-sulfonylmethyl)azetidin-1-yl]-5-(propan-2-yl)isoquinolin-3-yl}amino)pyrimidin-2-yl]pyrrolidin-3-yl]ethan-1-ol or (1S)-1-[(3S)-3-fluoro-1-[4-({8-[3-(methane-sulfonylmethyl)azetidin-1-yl]-5-(propan-2-yl)isoquinolin-3-yl}amino)pyrimidin-2-yl]pyrrolidin-3-yl]ethan-1-ol |
| 59 | 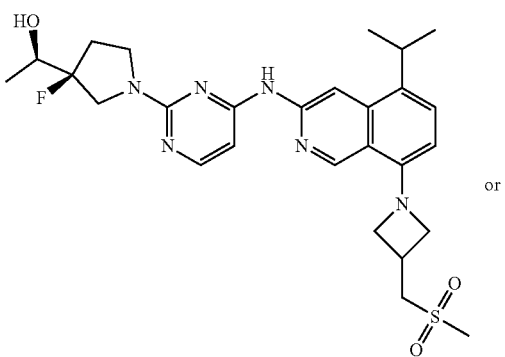 [SMILES: CC(C)c1ccc(N2CC(CS(C)(=O)=O)C2)c2cnc(Nc3ccnc(N4CC[C@@](F)([C@@H](C)O)C4)n3)cc12] | 543 | 1H-NMR (400 MHz, 6d-DMSO) δ ppm 9.85 (s, 1H), 9.04 (s, 1H), 8.81 (s, 1H), 7.99 (d, 1H, J = 5.6 Hz), 7.40 (d, 1H, J = 8.0 Hz), 6.47 (d, 1H, J = 5.6 Hz), 6.40 (d, 1H, J = 8.0 Hz), 5.16 (d, 1H, J = 5.9 Hz), 4.38 (t, 2H, J = 7.6 Hz), 3.96 (t, 2H, J = 6.9 Hz), 3.92-3.65 (m, 4H), 3.58 (d, 2H, J = 7.4 Hz), 3.54-3.41 (m, 1H), 3.31-3.17 (m, 1H), 3.01 (s, 3H), 2.35-2.04 (m, 2H), 1.29 (d, 6H, J = 6.7 Hz), 1.24-1.18 (m, 3H) | F; Peak 2 | (1R)-1-[(3S)-3-fluoro-1-[4-({8-[3-(methane-sulfonylmethyl)azetidin-1-yl]-5-(propan-2-yl)isoquinolin-3-yl}amino)pyrimidin-2-yl]pyrrolidin-3-yl]ethan-1-ol or (1S)-1-[(3R)-3-fluoro-1-[4-({8-[3-(methane-sulfonylmethyl)azetidin-1-yl]-5-(propan-2-yl) |

TABLE 1-continued

| # | Structure | LC/MS | NMR | Separation Conditions | Chemical Name |
|---|---|---|---|---|---|
| | | | | | isoquinolin-3-yl}amino)pyrimidin-2-yl]pyrrolidin-3-yl]ethan-1-ol |
| 60 | | 543 | 1H-NMR (300 MHz, 6d-DMSO) δ ppm 9.90 (s, 1H), 9.05 (s, 1H), 8.46 (s, 1H), 7.99 (d, 1H, J = 5.6 Hz), 7.57-7.32 (m, 1H), 6.44 (d, 1H, J = 5.7 Hz), 6.33 (d, 1H, J = 7.8 Hz), 5.13 (d, 1H, J = 5.4 Hz), 4.96-4.60 (m, 1H), 4.39 (t, 2H, J = 7.6 Hz), 4.24 (dt, 1H, J = 14.5, 8.0 Hz), 4.09-3.87 (m, 3H), 3.81 (d, 1H, J = 12.9 Hz), 3.58 (d, 2H, J = 7.4 Hz), 3.53-3.39 (m, 2H), 3.33-3.25 (m, 1H), 3.13 (q, 2H, J = 7.4 Hz), 2.51 (s, 3H), 1.25 (t, 3H, J = 7.4 Hz), 1.01-0.79 (m, 6H) | J; Peak 2 | (4S,5R)-1-{4-[(8-{3-[(ethanesulfonyl)methyl]azetidin-1-yl}-5-methylisoquinolin-3-yl)amino]pyrimidin-2-yl}-5-fluoro-3,3-dimethylpiperidin-4-ol or (4R,5S)-1-{4-[(8-{3-[(ethanesulfonyl)methyl]azetidin-1-yl}-5-methylisoquinolin-3-yl)amino]pyrimidin-2-yl}-5-fluoro-3,3-dimethyl-piperidin-4-ol |

TABLE 1-continued

| # | Structure | LC/MS | NMR | Separation Conditions | Chemical Name |
|---|---|---|---|---|---|
| 61 | 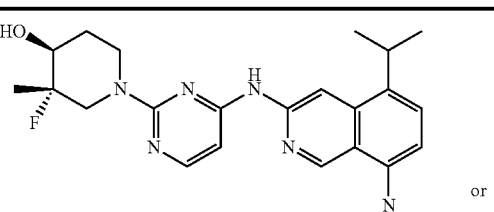 | 543 | 1H-NMR (300 MHz, 6d-DMSO) δ ppm 9.88 (s, 1H), 9.05 (s, 1H), 8.63 (s, 1H), 8.00 (d, 1H, J = 5.7 Hz), 7.42 (d, 1H, J = 7.9 Hz), 6.47 (d, 1H, J = 5.6 Hz), 6.42 (d, 1H, J = 8.1 Hz), 5.34 (d, 1H, J = 4.3 Hz), 4.39 (t, 2H, J = 7.6 Hz), 4.02-3.88 (m, 6H), 3.79-3.73 (m, 1H), 3.59 (d, 2H, J = 7.4 Hz), 3.51 (t, 1H, J = 7.0 Hz), 3.02 (s, 3H), 1.93-1.87 (m, 1H), 1.60-1.52 (m, 1H), 1.38-1.24 (m, 9H) | D; Peak 2 | (3S,4S)-3-fluoro-1-[4-({8-[3-(methanesulfonylmethyl)azetidin-1-yl]-5-(propan-2-yl)isoquinolin-3-yl}amino)pyrimidin-2-yl]-3-methylpiperidin-4-ol or (3R,4R)-3-fluoro-1-[4-({8-[3-(methanesulfonylmethyl)azetidin-1-yl]-5-(propan-2-yl)isoquinolin-3-yl}amino)pyrimidin-2-yl]-3-methylpiperidin-4-ol |
| 62 | 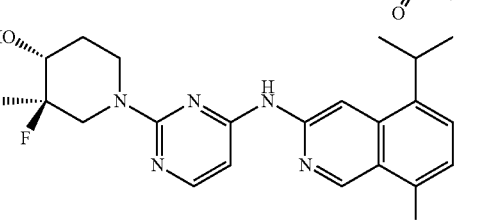 | 543 | 1H-NMR (400 MHz, 6d-DMSO) δ ppm 9.89 (s, 1H), 9.04 (s, 1H), 8.64 (s, 1H), 7.98 (d, 1H, J = 5.7 Hz), 7.41 (d, 1H, J = 8.0 Hz), 6.55 (d, 1H, J = 8.1 Hz), 6.43 (d, 1H, J = 5.7 Hz), 5.11 (d, 1H, J = 5.0 Hz), 4.79-4.53 (m, 3H), 4.36 (d, 1H, J = 13.4 Hz), 4.17 (q, 1H, J = 6.2 Hz), 3.97-3.76 (m, 1H), 3.65-3.42 (m, 5H), 3.39-3.34 (m, 1H), 2.98 (s, 3H), 2.87 (q, 1H, J = 7.2 Hz), 1.75-1.67 (m, 2H), 1.41 (d, 3H, J = 6.0 Hz), 1.29 (dd, 6H, J = 6.7, 1.9 Hz) | | (3S,4R)-3-fluoro-1-(4-((5-isopropyl-8-((2R,3S)-2-methyl-3-((methylsulfonyl)methyl)azetidin-1-yl)isoquinolin-3-yl)amino)pyrimidin-2-yl)piperidin-4-ol |
| 63 | 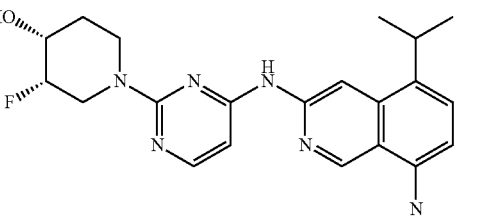 | 543 | 1H-NMR (400 MHz, 6d-DMSO) δ ppm 9.88 (s, 1H), 9.05 (s, 1H), 8.61 (s, 1H), 8.00 (d, 1H, J = 5.7 Hz), 7.42 (d, 1H, J = 8.0 Hz), 6.48 (d, 1H, J = 5.6 Hz), 6.41 (d, 1H, J = 8.0 Hz), 4.94 (d, 1H, J = 48.4 Hz), 4.73 (m, 1H), 4.48 (d, 1H, J = 12.8 Hz), 4.39 (t, 2H, J = 7.6 Hz), 3.96 (t, 2H, J = 6.9 Hz), 3.59 (d, 2H, J = 7.4 Hz), 3.65-3.40 (m, 3H), 3.37 (s, 3H), 3.40-3.15 (m, 2H), 3.01 (s, 3H), 1.78 (d, 2H, J = 25.6 Hz), 1.30 (dd, 6H, J = 6.8, 4.2 Hz) | | N-{2-[(3R,4S)-3-fluoro-4-methoxy-piperidin-1-yl]pyrimidin-4-yl}-8-[3-(methanesulfonylmethyl)azetidin-1-yl]-5-(propan-2-yl)isoquinolin-3-amine |

TABLE 1-continued

| # | Structure | LC/MS | NMR | Separation Conditions | Chemical Name |
|---|---|---|---|---|---|
| 64 | 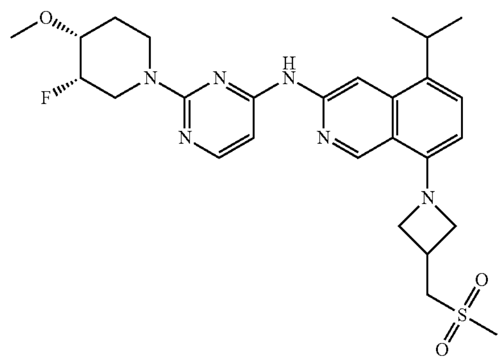 | 543 | 1H-NMR (300 MHz, 6d-DMSO) δ ppm 9.90 (s, 1H), 9.05 (s, 1H), 8.62 (s, 1H), 8.00 (d, 1H, J = 5.7 Hz), 7.42 (d, 1H, J = 7.9 Hz), 6.48 (d, 1H, J = 5.7 Hz), 6.41 (d, 1H, J = 8.1 Hz), 4.94 (d, 1H, J = 49.8 Hz), 4.74 (s, 1H), 4.49 (d, 1H, J = 13.4 Hz), 4.39 (t, 2H, J = 7.6 Hz), 3.96 (t, 2H, J = 6.9 Hz), 3.70-3.42 (m, 6H), 3.37 (s, 3H), 3.31-3.20 (m, 1H), 3.01 (s, 3H), 1.84-1.68 (m, 2H), 1.30 (dd, 6H, J = 6.8, 3.2 Hz) | | N-{2-[(3S,4R)-3-fluoro-4-methoxy-piperidin-1-yl]pyrimidin-4-yl}-8-[3-(methanesulfonylmethyl)azetidin-1-yl]-5-(propan-2-yl)isoquinolin-3-amine |
| 65 | 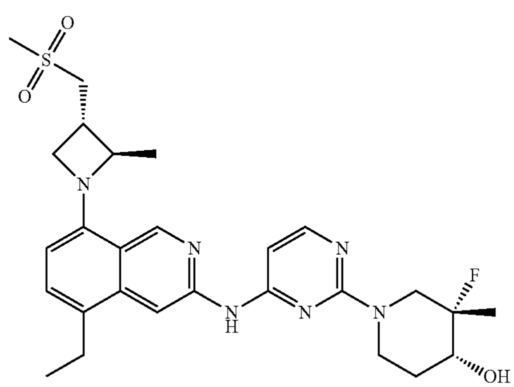 | 543 | 1H NMR (400 MHz, DMSO-d6) δ 9.86 (s, 1H), 9.03 (s, 1H), 8.51 (s, 1H), 7.96 (d, J = 5.7 Hz, 1H), 7.33 (d, J = 7.8 Hz, 1H), 6.50 (d, J = 7.9 Hz, 1H), 6.43 (d, J = 5.7 Hz, 1H), 4.99 (d, J = 6.4 Hz, 1H), 4.79-4.58 (m, 3H), 4.17 (p, J = 6.1 Hz, 1H), 3.65-3.44 (m, 4H), 3.21-3.03 (m, 2H), 2.98 (s, 3H), 2.94-2.81 (m, 3H), 1.77-1.67 (m, 2H), 1.42-1.30 (m, 6H), 1.26 (t, J = 7.4 Hz, 3H). | NN; Peak 1 | (3S,4R)-1-[4-({5-ethyl-8-[(2R,3S)-3-(methanesulfonyl-methyl)-2-methylazetidin-1-yl]isoquinolin-3-yl}amino)pyrimidin-2-yl]-3-fluoro-3-methylpiperidin-4-ol |
| 66 | | 543 | 1H NMR (400 MHz, DMSO-d6) δ 9.90 (s, 1H), 9.07 (s, 1H), 8.43 (s, 1H), 8.01 (d, J = 5.6 Hz, 1H), 7.51 (t, 1H, J = 7.9 Hz), 7.13 (d, J = 8.1 Hz), 6.54 (d, 1H, J = 7.7 Hz), 6.44 (d, 1H, J = 5.6 Hz), 5.14 (d, 1H, J = 5.4 Hz), 4.92-4.64 (m, 2H), 4.35-4.19 (m, 2H), 3.88 (d, 2H, J = 13.5 Hz), 3.76 (t, 1H, J = 7.2 Hz), 3.65-3.37 (m, 4H), 3.13 (q, 2H, J = 7.4 Hz), 2.92 (q, 1H, J = 7.1 Hz), 1.47 (d, 3H, J = 6.0 Hz), 1.26 (t, 3H, J = 7.4 Hz), 1.05-0.95 (m, 6H). | J; Peak 2 | (4S,5R)-1-[4-({8-[(2R,3S)-3-[(ethanesulfonyl)methyl]-2-methylazetidin-1-yl]isoquinolin-3-yl}amino)pyrimidin-2-yl]-5-fluoro-3,3-dimethyl-piperidin-4-ol or (4R,5S)-1-[4-({8-[(2R,3S)-3-[(ethanesulfonyl)methyl]-2-methylazetidin-1-yl]isoquinolin-3-yl}amino) | or

TABLE 1-continued

| # | Structure | LC/MS | NMR | Separation Conditions | Chemical Name |
|---|---|---|---|---|---|
| | | | | | pyrimidin-2-yl]-5-fluoro-3,3-dimethyl-piperidin-4-ol |
| 67 | 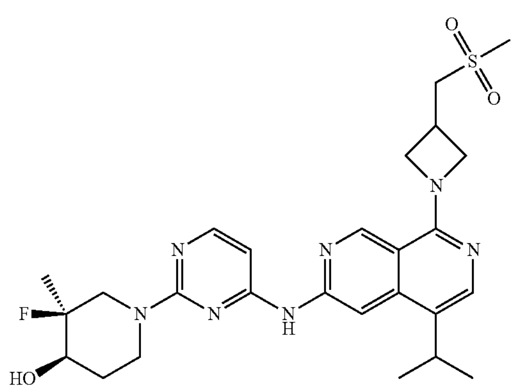 [SMILES: CC(C)c1cnc(N2CC(CS(C)(=O)=O)C2)c2cnc(Nc3ccnc(N4CC[C@@H](O)[C@@](C)(F)C4)n3)cc12] | 544 | 1H NMR (400 Hz, DMSO-d6) δ 10.08 (s, 1H), 9.05 (s, 1H), 8.50 (s, 1H), 8.06 (d, J = 5.6 Hz, 1H), 8.01 (s, 1H), 6.54 (d, J = 5.7 Hz, 1H), 5.04 (d, J = 6.4 Hz, 1H), 4.80-4.64 (m, 2H), 4.59 (t, J = 8.4 Hz, 2H), 4.25 (ddd, J = 8.5, 6.2, 1.8 Hz, 2H), 3.67-3.49 (m, 3H), 3.25-3.10 (m, 2H), 3.03 (s, 3H), 1.77 (d, J = 7.6 Hz, 2H), 1.46-1.24 (m, 9H). | NN; Peak 1 | (3S,4R)-3-fluoro-1-[4-({8-[3-(methanesulfonyl-methyl)azetidin-1-yl]-5-(propan-2-yl)-2,7-naphthyridin-3-yl}amino)pyrimidin-2-yl]-3-methyl-piperidin-4-ol |
| 70 | 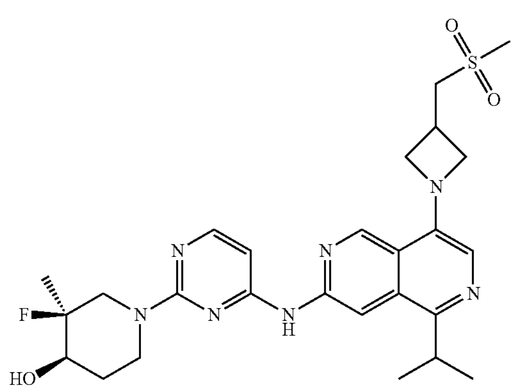 [SMILES: CC(C)c1ncc(N2CC(CS(C)(=O)=O)C2)c2cnc(Nc3ccnc(N4CC[C@@H](O)[C@@](C)(F)C4)n3)cc12] | 544 | 1H NMR (400 MHz, 6d-DMSO) δ ppm 10.12 (s, 1H), 9.13 (s, 1H), 8.73 (s, 1H), 8.03 (d, 1H, J = 5.6 Hz), 7.60 (s, 1H), 6.46 (d, 1H, J = 5.7 Hz), 5.06 (d, 1H, J = 6.4 Hz), 4.81-4.71 (m, 1H), 4.67 (s, 1H), 4.49 (t, 2H, J = 7.8 Hz), 4.08 (t, 2H, J = 13.3 Hz), 3.75-3.66 (m, 1H), 3.61 (d, 2H, J = 7.4 Hz), 3.58-3.51 (m, 1H), 3.32 (m, 1H), 3.16 (m, 2H), 3.03 (s, 3H), 1.75 (s, 2H), 1.40-1.28 (m, 9H) | NN; Peak 1 | (3S,4R)-3-fluoro-1-[4-({8-[3-(methanesulfonyl-methyl)azetidin-1-yl]-5-(propan-2-yl)-2,6-naphthyridin-3-yl}amino)pyrimidin-2-yl]-3-methyl-piperidin-4-ol |

TABLE 1-continued

| # | Structure | LC/MS | NMR | Separation Conditions | Chemical Name |
|---|---|---|---|---|---|
| 71 | 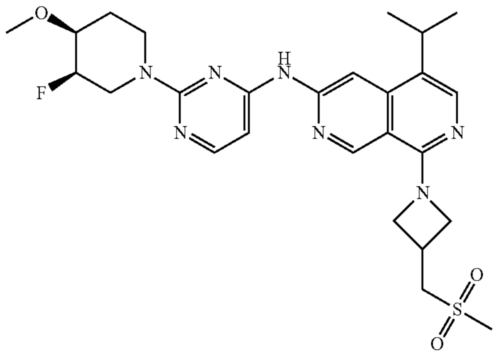 | 544 | 1H-NMR (400 MHz, 6d-DMSO) δ ppm 10.11 (s, 1H), 9.02 (s, 1H), 8.50 (s, 1H), 8.04 (d, 1H, J = 5.6 Hz), 7.98 (s, 1H), 6.52 (d, 1H, J = 5.7 Hz), 4.96 (d, 1H), 4.77-4.66 (m, 1H), 4.56 (t, 2H, J = 8.4 Hz), 4.50-4.42 (m, 1H), 4.22 (dd, 2H, J = 8.6, 6.2 Hz), 3.67-3.56 (m, 3H), 3.47 (dd, 1H, J = 31.9, 14.0 Hz), 3.37 (s, 3H), 3.33-3.26 (m, 3H), 3.01 (s, 3H), 1.87-1.69 (m, 2H), 1.31 (dd, 6H, J = 6.8, 4.3 Hz) | | N-{2-[(3R,4S)-3-fluoro-4-methoxypiperidin-1-yl]pyrimidin-4-yl}-8-[3-(methanesulfonylmethyl)azetidin-1-yl]-5-(propan-2-yl)-2,7-naphthyridin-3-amine |
| 72 | 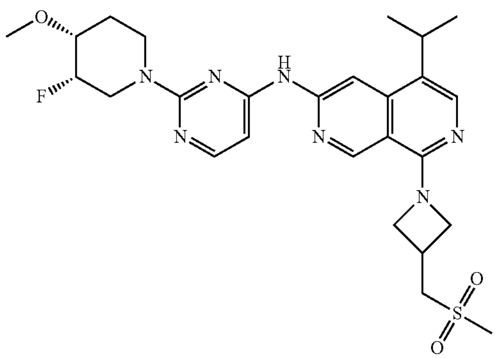 | 544 | 1H-NMR (400 MHz. 6d-DMSO) δ ppm 10.11 (s, 1H), 9.02 (s, 1H), 8.50 (s, 1H), 8.04 (d, 1H, J = 5.6 Hz), 7.98 (s, 1H), 6.52 (d, 1H, J = 5.7 Hz), 4.96 (d, 1H), 4.71 (ddd, 1H, J = 14.1, 9.4, 5.2 Hz), 4.56 (t, 2H, J = 8.4 Hz), 4.47 (d, 1H, J = 13.3 Hz), 4.22 (dd, 2H, J = 8.6, 6.2 Hz), 3.66-3.54 (m, 3H), 3.47 (dd, 1H, J = 31.9, 14.0 Hz), 3.37 (s, 3H), 3.31-3.23 (m, 3H), 3.01 (s, 3H), 1.89-1.68 (m, 2H), 1.31 (dd, 6H, J = 6.8, 4.3 Hz) | | N-{2-[(3S,4R)-3-fluoro-4-methoxypiperidin-1-yl]pyrimidin-4-yl}-8-[3-(methanesulfonylmethyl)azetidin-1-yl]-5-(propan-2-yl)-2,7-naphthyridin-3-amine |
| 73 | 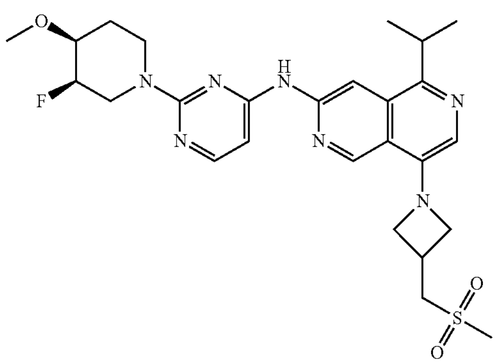 | 544 | 1H-NMR (300 MHz, 6d-DMSO) δ ppm 10.15 (s, 1H), 9.13 (s, 1H), 8.74 (s, 1H), 8.04 (d, 1H, J = 5.6 Hz), 7.60 (s, 1H), 6.48 (d, 1H, J = 5.7 Hz), 4.96 (d, 1H, J = 50.1 Hz), 4.75 (s, 1H), 4.49 (t, 3H, J = 7.7 Hz), 4.07 (t, 2H, J = 6.9 Hz), 3.82-3.42 (m, 5H), 3.38 (s, 3H), 3.35-3.23 (m, 2H), 3.03 (s, 3H), 1.86-1.73 (m, 2H), 1.31 (dd, 6H, J = 6.7, 3.5 Hz) | | N-{2-[(3R,4S)-3-fluoro-4-methoxypiperidin-1-yl]pyrimidin-4-yl}-8-[3-(methanesulfonylmethyl)azetidin-1-yl]-5-(propan-2-yl)-2,6-naphthyridin-3-amine |
| 74 | 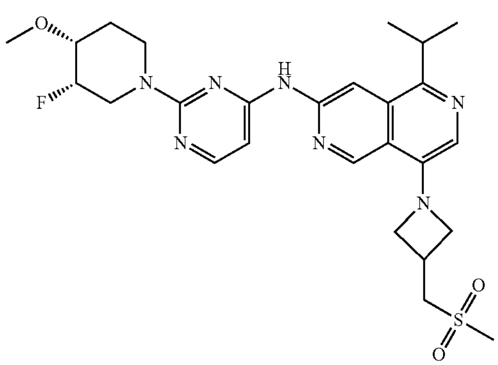 | 544 | 1H-NMR (300 MHz, 6d-DMSO) δ ppm 10.15 (s, 1H), 9.13 (s, 1H), 8.74 (s, 1H), 8.04 (d, 1H, J = 5.7 Hz), 7.60 (s, 1H), 6.48 (d, 1H, J = 5.7 Hz), 4.96 (d, 1H, J = 49.4 Hz), 4.76-4.70 (m, 1H), 4.49 (t, 2H, J = 7.7 Hz), 4.08 (t, 2H, J = 6.9 Hz), 3.78-3.40 (m, 6H), 3.38 (s, 3H), 3.33-3.24 (m, 1H), 3.03 (s, 3H), 1.87-1.74 (m, 2H), 1.31 (dd, 6H, J = 6.7, 3.5 Hz) | | N-{2-[(3S,4R)-3-fluoro-4-methoxypiperidin-1-yl]pyrimidin-4-yl}-8-[3-(methanesulfonylmethyl)azetidin-1-yl]-5-(propan-2-yl)-2,6-naphthyridin-3-amine |

TABLE 1-continued

| # | Structure | LC/MS | NMR | Separation Conditions | Chemical Name |
|---|---|---|---|---|---|
| 75 | 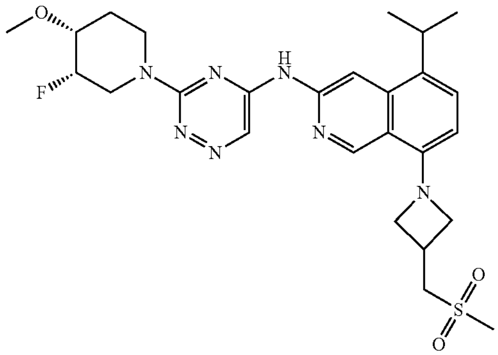 | 544 | 1H-NMR (400 MHz, 6d-DMSO) δ ppm 10.55 (s, 1H), 9.11 (s, 1H), 8.70 (s, 1H), 8.50 (s, 1H), 7.48 (d, 1H, J = 8.0 Hz), 6.48 (d, 1H, J = 8.1 Hz), 5.00 (d, 1H, J = 49.1 Hz), 4.77 (s, 1H), 4.52 (d, 1H, J = 13.5 Hz), 4.41 (t, 2H, J = 7.7 Hz), 3.99 (t, 2H, J = 6.9 Hz), 3.73-3.45 (m, 6H), 3.38-3.33 (m, 4H), 3.02 (s, 3H), 1.92-1.84 (m, 1H), 1.83-1.73 (m, 1H), 1.31 (dd, 6H, J = 6.8, 5.0 Hz) | | N-{3-[(3S,4R)-3-fluoro-4-methoxypiperidin-1-yl]-1,2,4-triazin-5-yl}-8-[3-(methanesulfonyl-methyl)azetidin-1-yl]-5-(propan-2-yl)isoquinolin-3-amine |
| 76 | 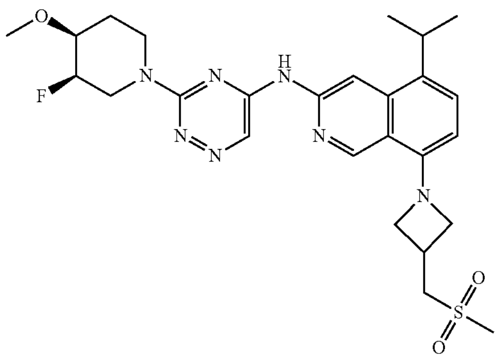 | 544 | 1H-NMR (300 MHz, 6d-DMSO) δ ppm 10.54 (s, 1H), 9.11 (s, 1H), 8.69 (s, 1H), 8.49 (s, 1H), 7.47 (d, 1H, J = 8.0 Hz), 6.47 (d, 1H, J = 8.1 Hz), 4.99 (d, 1H, J = 49.0 Hz), 4.79-4.73 (m, 1H), 4.51 (d, 1H, J = 13.5 Hz), 4.40 (t, 2H, J = 7.7 Hz), 3.98 (t, 2H, J = 6.9 Hz), 3.70-3.42 (m, 7H), 3.37-3.23 (m, 3H), 3.01 (s, 3H), 1.90-1.83 (m, 1H), 1.81-1.71 (m, 1H), 1.30 (dd, 6H, J = 6.8, 3.7 Hz) | | N-{3-[(3R,4S)-3-fluoro-4-methoxypiperidin-1-yl]-1,2,4-triazin-5-yl}-8-[3-(methanesulfonyl-methyl)azetidin-1-yl]-5-(propan-2-yl)isoquinolin-3-amine |
| 77 | 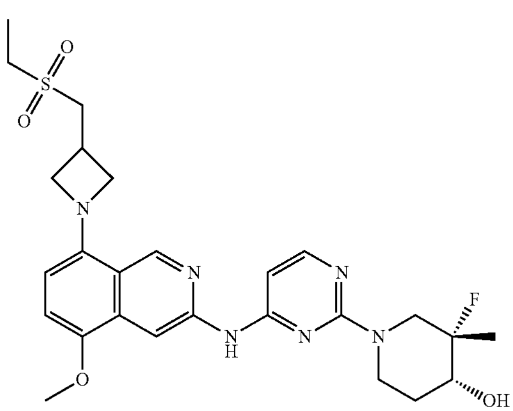 [SMILES: CCS(=O)(=O)CC1CN(c2ccc(OC)c3cc(Nc4ccnc(N5CC[C@@H](O)[C@@](C)(F)C5)n4)ncc23)C1] | 545 | 1H-NMR (300 MHz, 6d-DMSO) δ ppm 9.94 (s, 1H), 9.01 (s, 1H), 8.86 (s, 1H), 7.98 (d, 1H, J = 5.6 Hz), 7.00 (d, 1H, J = 8.3 Hz), 6.46-6.26 (m, 2H), 5.01 (d, 1H, J = 6.4 Hz), 4.76 (dd, 2H, J = 22.7, 10.0 Hz), 4.39-4.23 (m, 2H), 4.02-3.71 (m, 5H), 3.57 (d, 3H, J = 7.5 Hz), 3.31-3.19 (m, 2H), 3.13 (q, 3H, J = 7.5 Hz), 1.88-1.62 (m, 2H), 1.38 (d, 3H, J = 21.2 Hz), 1.25 (t, 3H, J = 7.4 Hz) | NN; Peak 1 | (3S,4R)-1-{4-[(8-{3-[(ethane-sulfonyl)methyl]azetidin-1-yl}-5-methoxyiso-quinolin-3-yl)amino]pyrimidin-2-yl}-3-fluoro-3-methylpiperidin-4-ol |

TABLE 1-continued

| # | Structure | LC/MS | NMR | Separation Conditions | Chemical Name |
|---|---|---|---|---|---|
| 78 | 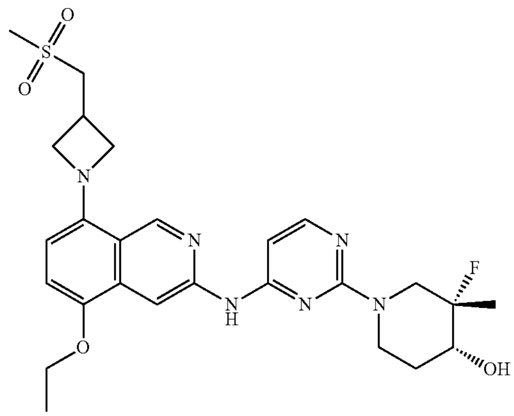 | 545 | 1H-NMR (300 MHz, 6d-DMSO) δ ppm 9.89 (s, 1H), 9.02 (s, 1H), 8.66 (s, 1H), 7.98 (d, 1H, J = 5.6 Hz), 7.01 (d, 1H, J = 8.3 Hz), 6.43 (d, 1H, J = 5.7 Hz), 6.37 (d, 1H, J = 8.3 Hz), 4.99 (d, 1H, J = 6.4 Hz), 4.78 (dd, 1H, J = 14.0, 8.8 Hz), 4.68 (d, 1H, J = 13.1 Hz), 4.30 (t, 2H, J = 7.4 Hz), 4.17 (q, 2H, J = 6.9 Hz), 3.86 (t, 2H, J = 6.8 Hz), 3.59 (d, 2H, J = 7.3 Hz), 3.56-3.42 (m, 1H), 3.31-3.04 (m, 3H), 3.02 (s, 3H), 1.75-1.68 (m, 2H), 1.52-1.18 (m, 6H) | NN; Peak 1 | (3S,4R)-1-[4-({5-ethoxy-8-[3-(methanesulfonylmethyl)azetidin-1-yl]isoquinolin-3-yl}amino)pyrimidin-2-yl]-3-fluoro-3-methylpiperidin-4-ol |
| 79 | | 545 | 1H-NMR (300 MHz, 6d-DMSO) δ ppm 9.93 (s, 1H), 9.02 (d, 1H, J = 0.9 Hz), 8.81 (s, 1H), 7.98 (d, 1H, J = 5.7 Hz), 7.00 (d, 1H, J = 8.4 Hz), 6.42-6.33 (m, 2H), 5.11 (d, 1H, J = 5.4 Hz), 4.76 (d, 1H, J = 49.8 Hz), 4.42-4.14 (m, 3H, J = 7.5 Hz), 4.09-3.71 (m, 7H), 3.59 (d, 2H, J = 7.4 Hz), 3.55-3.40 (m, 2H), 3.26 (t, 1H, J = 7.3 Hz), 3.02 (s, 3H), 0.99-0.90 (m, 6H) | J; Peak 2 | (4S,5R)-5-fluoro-1-[4-({8-[3-(methanesulfonylmethyl)azetidin-1-yl]-5-methoxy-isoquinolin-3-yl}amino)pyrimidin-2-yl]-3,3-dimethyl-piperidin-4-ol or (4R,5S)-5-fluoro-1-[4-({8-[3-(methanesulfonylmethyl)azetidin-1-yl]-5-methoxy-isoquinolin-3-yl}amino)pyrimidin-2-yl]-3,3-dimethyl-piperidin-4-ol |

| # | Structure | LC/MS | NMR | Separation Conditions | Chemical Name |
|---|---|---|---|---|---|
| 80 | 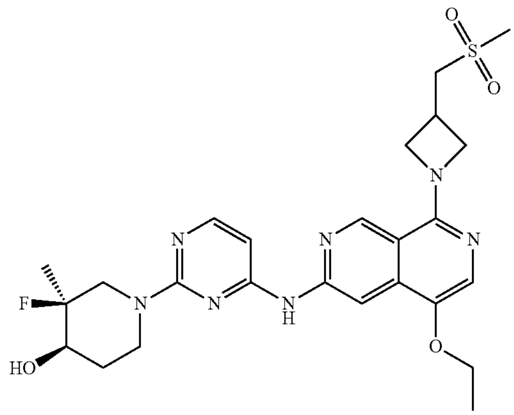 [SMILES: CCOc1cnc(N2CC(CS(C)(=O)=O)C2)c2cnc(Nc3ccnc(N4CC[C@@H](O)[C@@](C)(F)C4)n3)cc12] | 546 | 1H NMR (400 MHz, DMSO-d6) δ 10.09 (s, 1H), 8.99 (s, 1H), 8.54 (s, 1H), 8.01 (d, J = 5.6 Hz, 1H), 7.73 (s, 1H), 6.45 (d, J = 5.8 Hz, 1H), 4.96 (d, J = 6.4 Hz, 1H), 4.81-4.58 (m, 2H), 4.47 (d, J = 8.5 Hz, 2H), 4.22-4.07 (m, 4H), 3.64-3.45 (m, 3H), 3.20-3.04 (m, 2H), 2.99 (s, 3H), 1.76-1.60 (m, 2H), 1.45-1.18 (m, 8H). | NN; Peak 1 | (3S,4R)-1-[4-({5-ethoxy-8-[3-(methanesulfonylmethyl)azetidin-1-yl]-2,7-naphthyridin-3-yl}amino)pyrimidin-2-yl]-3-fluoro-3-methyl-piperidin-4-ol |
| 81 | 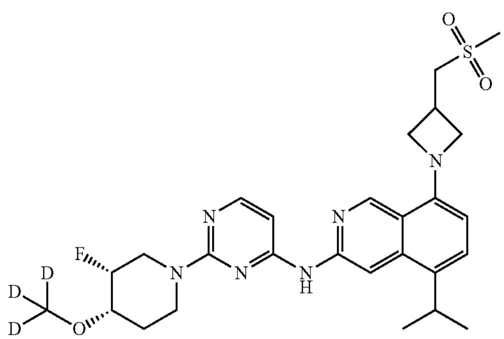 [SMILES: [2H]C([2H])([2H])O[C@H]1CCN(c2nccc(Nc3cc4c(C(C)C)ccc(N5CC(CS(C)(=O)=O)C5)c4cn3)n2)C[C@H]1F] | 546 | 1H-NMR (300 MHz, 6d-DMSO) δ ppm 9.89 (s, 1H), 9.03 (s, 1H), 8.60 (s, 1H), 7.98 (d, 1H, J = 5.7 Hz), 7.40 (d, 1H, J = 7.9 Hz), 6.46 (d, 1H, J = 5.7 Hz), 6.39 (d, 1H, J = 8.1 Hz), 4.92 (d, 1H, J = 49.6 Hz), 4.75-4.69 (m, 1H), 4.47 (d, 1H, J = 13.2 Hz), 4.37 (t, 2H, J = 7.5 Hz), 3.95-3.93 (m, 2H), 3.67-3.44 (m, 6H), 3.00 (s, 3H), 1.81-1.75 (m, 2H), 1.28 (d, 6H, J = 3.3 Hz) | K; Peak 1 | N-{2-[(3R,4S)-3-fluoro-4-(²H3)methoxy-piperidin-1-yl]pyrimidin-4-yl}-8-[3-(methanesulfonylmethyl)azetidin-1-yl]-5-(propan-2-yl)isoquinolin-3-amine |
| 82 | 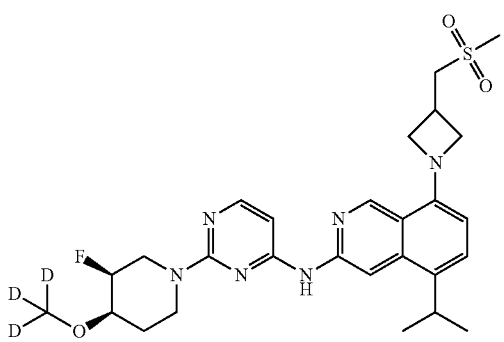 [SMILES: [2H]C([2H])([2H])O[C@@H]1CCN(c2nccc(Nc3cc4c(C(C)C)ccc(N5CC(CS(C)(=O)=O)C5)c4cn3)n2)C[C@@H]1F] | 546 | 1H-NMR (300 MHz, 6d-DMSO) δ ppm 9.89 (s, 1H), 9.03 (s, 1H), 8.60 (s, 1H), 7.98 (d, 1H, J = 5.6 Hz), 7.40 (d, 1H, J = 7.9 Hz), 6.45 (d, 1H, J = 5.7 Hz), 6.39 (d, 1H, J = 8.0 Hz), 4.92 (d, 1H, J = 49.4 Hz), 4.75-4.69 (m, 1H), 4.47 (d, 1H, J = 12.3 Hz), 4.37 (t, 2H, J = 7.6 Hz), 3.94 (t, 2H, J = 6.9 Hz), 3.66-3.43 (m, 6H), 3.00 (s, 3H), 1.81-1.69 (m, 2H), 1.28 (dd, 6H, J = 6.7, 3.2 Hz) | K; Peak 2 | N-{2-[(3S,4R)-3-fluoro-4-(²H3)methoxy-piperidin-1-yl]pyrimidin-4-yl}-8-[3-(methanesulfonylmethyl)azetidin-1-yl]-5-(propan-2-yl)isoquinolin-3-amine |
| 83 | 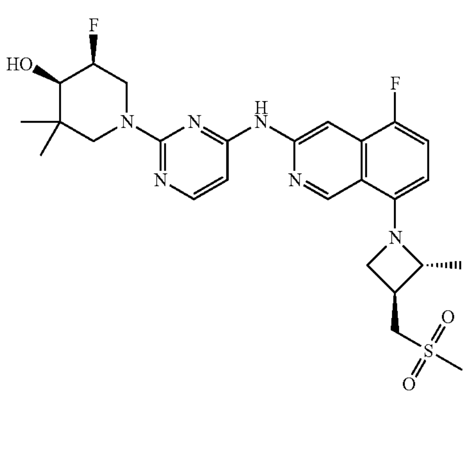 | 547 | 1H NMR (400 MHz, DMSO-d6) δ 10.11 (s, 1H), 9.11 (s, 1H), 8.71 (s, 1H), 8.03 (d, J = 5.6 Hz, 1H), 7.37 (dd, 1H, J = 10.4, 8.3 Hz), 6.48 (dd, 1H, J = 8.6, 4.0 Hz), 6.42 (d, 1H, J = 5.6 Hz), 5.12 (d, 1H, J = 5.4 Hz), 4.76-4.63 (m, 2H), 4.31-4.15 (m, 1H), 3.88 (d, 2H, J = 13.4 Hz), 3.69 (t, 1H, J = 7.1 Hz), 3.56 (td, 2H, J = 14.7, 14.2, 7.6 Hz), 3.43 (d, 1H, J = 13.8 Hz), 3.02 (s, 3H), 2.91 (q, 1H, J = 7.3 Hz), 1.44 (d, 3H, J = 6.0 Hz), 1.03-0.95 (m, 6H). | J; Peak 2 | (4S,5R)-5-fluoro-1-[4-({5-fluoro-8-[(2R,3S)-3-(methanesulfonylmethyl)-2-methylazetidin-1-yl]isoquinolin-3-yl}amino)pyrimidin-2-yl]-3,3-dimethyl-piperidin-4-ol or (4R,5S)-5-fluoro-1-[4-({5-fluoro-8-[(2R,3S)-3-(methanesulfonylmethyl)-2-methylazetidin-1- |

TABLE 1-continued

| # | Structure | LC/MS | NMR | Separation Conditions | Chemical Name |
|---|---|---|---|---|---|
| | | | | | yl]isoquinolin-3-yl}amino)pyrimidin-2-yl]-3,3-dimethyl-piperidin-4-ol |
| 84 | 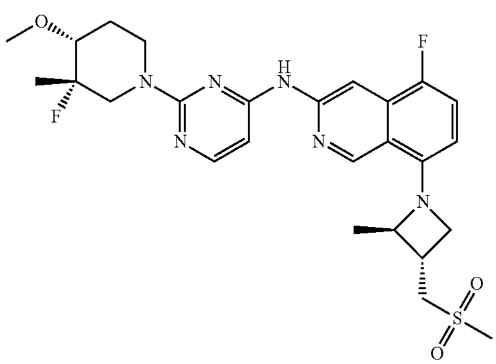 | 547 | ¹H NMR (400 MHz, DMSO-d₆) δ 10.12 (s, 1H), 9.12 (d, J = 1.7 Hz, 1H), 8.70 (s, 1H), 8.04 (d, J = 5.6 Hz, 1H), 7.38 (dd, J = 10.4, 8.4 Hz, 1H), 6.52-6.40 (m, 2H), 4.84-4.64 (m, 3H), 4.24 (p, J = 6.1 Hz, 1H), 3.70 (t, J = 7.1 Hz, 1H), 3.66-3.49 (m, 2H), 3.40 (s, 4H), 3.30-3.05 (m, 2H), 3.03 (s, 3H), 2.92 (h, J = 7.2 Hz, 1H), 2.07-1.96 (m, 1H), 1.63 (d, J = 13.2 Hz, 1H), 1.45 (dd, J = 13.6, 7.6 Hz, 6H). | NN; Peak 1 | 5-fluoro-N-{2-[(3S,4R)-3-fluoro-4-methoxy-3-methylpiperidin-1-yl]pyrimidin-4-yl}-8-[(2R,3S)-3-(methanesulfonylmethyl)-2-methylazetidin-1-yl]isoquinolin-3-amine |
| 85 | 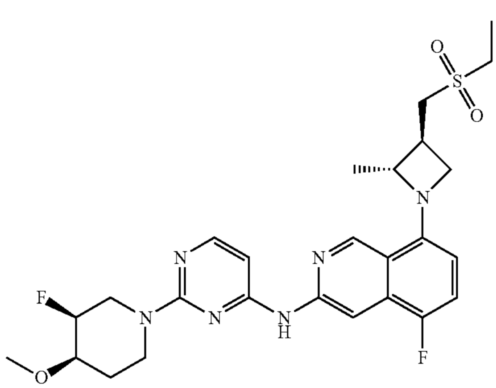 [SMILES: CCS(=O)(=O)C[C@H]1CN(c2ccc(F)c3cc(Nc4ccnc(N5CC[C@@H](OC)[C@@H](F)C5)n4)ncc23)[C@@H]1C] | 547 | 1H NMR (400 MHz, DMSO-d6) δ 10.13 (s, 1H), 9.12 (s, 1H), 8.68 (s, 1H), 8.05 (d, 1H, J = 5.5 Hz), 7.36 (dd, 1H, J = 10.3, 8.4 Hz), 6.48 (dd, 2H, J = 7.2, 4.0 Hz), 4.96 (d, 1H, J = 50.3 Hz), 4.71 (t, 2H, J = 7.4 Hz), 4.47 (d, J = 13.6 Hz, 1H), 4.24 (p, J = 6.2 Hz, 1H), 3.69 (t, J = 7.1 Hz, 1H), 3.66-3.42 (m, 4H), 3.38 (s, 3H), 3.31-3.23 (m, 1H), 3.12 (q, J = 7.4 Hz, 2H), 2.91 (q, J = 7.3 Hz, 1H), 1.94-1.68 (m, 2H), 1.45 (d, J = 6.0 Hz, 3H), 1.26 (t, J = 7.4 Hz, 3H). | | 8-[(2R,3S)-3-[(ethanesulfonyl)methyl]-2-methylazetidin-1-yl]-5-fluoro-N-{2-[(3S,4R)-3-fluoro-4-methoxy-piperidin-1-yl]pyrimidin-4-yl}isoquinolin-3-amine |

TABLE 1-continued

| # | Structure | LC/MS | NMR | Separation Conditions | Chemical Name |
|---|---|---|---|---|---|
| 86 | 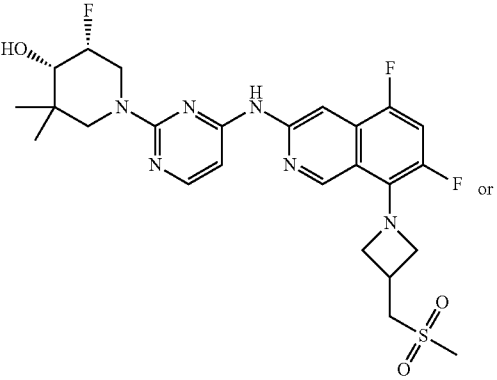 or 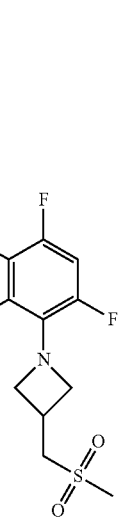 | 551 | 1H NMR (400 MHz, CDCl3) δ 9.12 (s, 1H), 8.67 (s, 1H), 8.08 (d, J = 5.6 Hz, 1H), 7.34 (s, 1H), 7.08 (dd, J = 13.2, 9.6 Hz, 1H), 6.09 (d, J = 5.6 Hz, 1H), 5.14-4.95 (m, 1H), 4.94-4.80 (m, 1H), 4.70-4.61 (m, 2H), 4.34-4.22 (m, 3H), 4.17-4.07 (m, 1H), 3.79-3.64 (m, 3H), 3.51-3.46 (m, 2H), 3.44-3.35 (m, 1H), 2.99 (s, 3H), 1.13 (s, 3H), 1.06 (s, 3H) | J; Peak 2 | (4S,5R)-1-[4-({5,7-difluoro-8-[3-(methane-sulfonylmethyl)azetidin-1-yl]isoquinolin-3-yl}amino)pyrimidin-2-yl]-5-fluoro-3,3-dimethyl-piperidin-4-ol or (4R,5S)-1-[4-({5,7-difluoro-8-[3-(methane-sulfonylmethyl)azetidin-1-yl]isoquinolin-3-yl}amino)pyrimidin-2-yl]-5-fluoro-3,3-dimethyl-piperidin-4-ol |
| 87 | 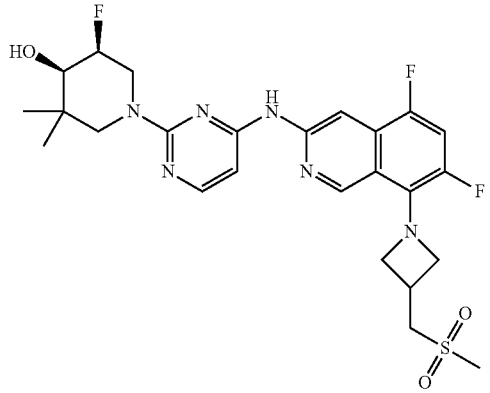 or 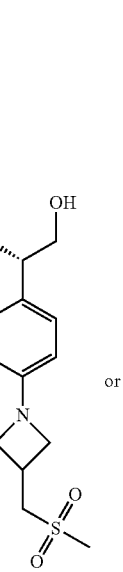 | 553 | 1H-NMR (300 MHz, 6d-DMSO) δ ppm 9.82 (s, 1H), 9.02 (s, 1H), 8.63 (s, 1H), 7.97 (d, 1H, J = 5.6 Hz), 7.36 (d, 1H, J = 8.0 Hz), 6.40 (dd, 2H, J = 10.8, 6.9 Hz), 4.71 (t, 1H, J = 5.0 Hz), 4.53-4.24 (m, 4H), 4.03-3.81 (m, 4H), 3.79-3.66 (m, 3H), 3.65-3.48 (m, 3H), 3.41 (q, 1H, J = 6.7 Hz), 3.27-3.20 (m, 1H), 3.00 (s, 3H), 2.39 (t, 2H, J = 7.7 Hz), 1.99-1.70 (m, 4H), 1.26 (d, 3H, J = 6.6 Hz) | F; Peak 2 | (2S)-2-{8-[3-(methanesulfonyl-methyl)azetidin-1-yl]-3-[(2-{1-oxa-7-azaspiro[3.5]nonan-7-yl}pyrimidin-4-yl)amino]isoquinolin-5-yl}propan-1-ol or (2R)-2-{8-[3-(methanesulfonyl-methyl)azetidin-1-yl]-3-[(2-{1-oxa-7-azaspiro[3.5]nonan-7-yl}pyrimidin-4-yl)amino] |

TABLE 1-continued

| # | Structure | LC/MS | NMR | Separation Conditions | Chemical Name |
|---|---|---|---|---|---|
| | | | | | isoquinolin-5-yl} propan-1-ol |
| 88 | 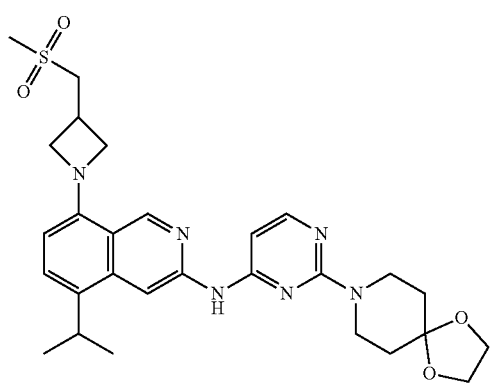 [SMILES: CC(C)c1ccc(N2CC(CS(C)(=O)=O)C2)c2cnc(Nc3ccnc(N4CCC5(CC4)OCCO5)n3)cc12] | 553 | | | N-(2-{1,4-dioxa-8-azaspiro[4.5]decan-8-yl}pyrimidin-4-yl)-8-[3-(methanesulfonylmethyl)azetidin-1-yl]-5-(propan-2-yl)isoquinolin-3-amine |
| 89 | 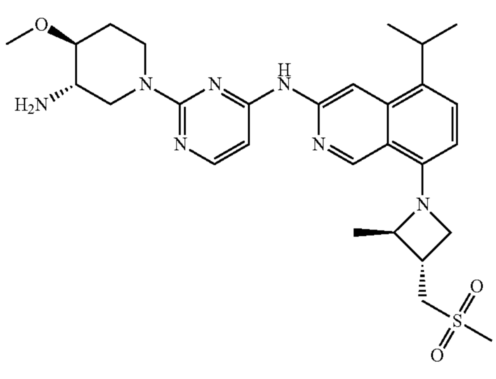 | 554 | 1H-NMR (300 MHz, 6d-DMSO) δ ppm 9.86 (s, 1H), 9.02 (s, 1H), 7.99 (d, 1H, J = 5.6 Hz), 7.39 (d, 1H, J = 8.0 Hz), 6.46 (d, 1H, J = 5.7 Hz), 6.39 (d, 1H, J = 8.2 Hz), 4.37 (t, 2H, J = 7.7 Hz), 3.92 (d, 10H, J = 10.9 Hz), 3.57 (d, 2H, J = 7.3 Hz), 3.43 (t, 1H, J = 6.8 Hz), 3.29-3.21 (m, 1H), 3.00 (s, 3H), 1.73-1.59 (m, 4H), 1.26 (d, 6H, J = 6.7 Hz) | | |
| | | | 1H-NMR (400 MHz, 4d-CD3OD) δ ppm 9.10 (s, 1H), 8.56 (s, 1H), 7.97 (d, 1H, J = 5.8 Hz), 7.46 (d, 1H, J = 8.0 Hz), 6.64 (d, 1H, J = 8.0 Hz), 6.42 (d, 1H, J = 5.8 Hz), 4.76-4.60 (m, 3H), 4.27 (t, 1H, J = 6.3 Hz), 3.67-3.46 (m, 4H), 3.45 (s, 3H), 3.18 (t, 2H, J = 9.9 Hz), 3.00 (s, 3H), 3.06-2.86 (m, 2H), 2.80-2.71 (m, 1H), 2.26-2.16 (m, 1H), 1.54-1.28 (m, 10H) | D; Peak 1 | N-{2-[(3S,4S)-3-amino-4-methoxypiperidin-1-yl]pyrimidin-4-yl}-8-[(2R,3S)-3-(methanesulfonylmethyl)-2-methylazetidin-1-yl]-5-(propan-2-yl)isoquinolin-3-amine |

TABLE 1-continued

| # | Structure | LC/MS | NMR | Separation Conditions | Chemical Name |
|---|---|---|---|---|---|
| 90 | 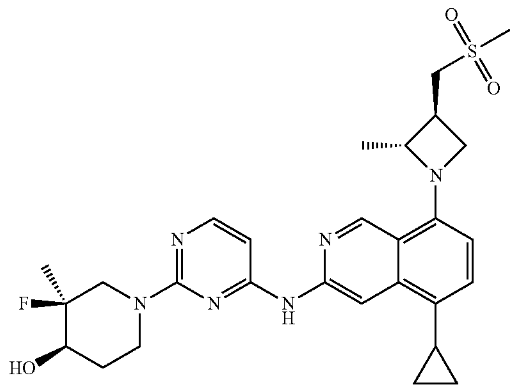 [SMILES: C[C@@H]1[C@@H](CS(C)(=O)=O)CN1c1ccc(C2CC2)c2cc(Nc3ccnc(N4CC[C@@H](O)[C@@](C)(F)C4)n3)ncc12] | 555 | 1H-NMR (400 MHz, 6d-DMSO) δ ppm 9.88 (s, 1H), 9.05 (s, 1H), 8.70 (s, 1H), 7.99 (d, 1H, J = 5.6 Hz), 7.23 (d, 1H, J = 7.9 Hz), 6.55-6.42 (m, 2H), 4.98 (t, 1H, J = 7.2 Hz), 4.78-4.62 (m, 3H), 4.19 (p, 1H, J = 6.4 Hz), 3.64 (t, 1H, J = 7.0 Hz), 3.60-3.51 (m, 2H), 3.53-3.40 (m, 1H), 3.19-3.03 (m, 2H), 2.99 (s, 3H), 2.88 (q, 1H, J = 7.3 Hz), 2.12 (td, 1H, J = 8.4, 4.1 Hz), 1.75-1.57 (m, 2H), 1.45-1.36 (m, 3H), 1.31 (d, 3H, J = 21.2 Hz), 0.97 (dd, 2H, J = 8.2, 4.1 Hz), 0.71-0.58 (m, 2H) | L; Peak 1 | (3S,4R)-1-[4-({5-cyclopropyl-8-[(2R,3S)-3-(methanesulfonyl-methyl)-2-methylazetidin-1-yl]isoquinolin-3-yl}amino)pyrimidin-2-yl]-3-fluoro-3-methylpiperidin-4-ol |
| 91 | | 555 | 1H-NMR (300 MHz, 6d-DMSO) δ ppm 9.82 (s, 1H), 9.04 (s, 1H), 8.67 (s, 1H), 7.98 (d, 1H, J = 5.6 Hz), 7.41 (d, 1H, J = 8.0 Hz), 6.47-6.36 (m, 2H), 4.61 (d, 1H, J = 5.0 Hz), 4.39 (t, 2H, J = 7.6 Hz), 3.96 (t, 4H, J = 6.9 Hz), 3.85-3.62 (m, 3H), 3.61-3.42 (m, 4H), 3.37 (s, 3H), 3.36-3.30 (m, 1H), 3.12 (q, 2H, J = 7.4 Hz), 1.92-1.86 (m, 1H), 1.66-1.60 (m, 1H), 1.40-1.06 (m, 9H) | K; Peak 1 | (3S,4R)-1-{4-[(8-{3-[(ethane-sulfonyl)methyl]azetidin-1-yl}-5-(propan-2-yl)isoquinolin-3-yl)amino]pyrimidin-2-yl}-4-methoxy-piperidin-3-ol or (3R,4S)-1-{4-[(8-{3-[(ethane-sulfonyl)methyl]azetidin-1-yl}-5-(propan-2-yl)isoquinolin-3-yl)amino]pyrimidin-2-yl}-4-methoxy-piperidin-3-ol |
| 92 | 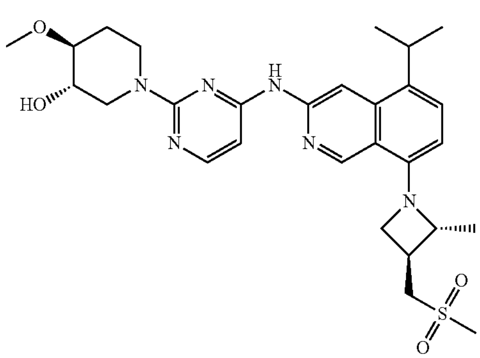 | 555 | 1H-NMR (400 MHz, 6d-DMSO) δ ppm 9.87 (s, 1H), 9.05 (s, 1H), 8.66 (s, 1H), 7.99 (d, 1H, J = 5.6 Hz), 7.42 (d, 1H, J = 8.0 Hz), 6.56 (d, 1H, J = 8.1 Hz), 6.45 (d, 1H, J = 5.7 Hz), 5.08 (d, 1H, J = 4.8 Hz), 4.66 (t, 1H, J = 7.5 Hz), 4.46-4.30 (m, 2H), 4.20 (t, 1H, J = 6.3 Hz), 3.64 (t, 1H, J = 7.1 Hz), 3.54 (t, 3H, J = 6.8 Hz), 3.39 (s, 3H), 3.29-3.19 (m, 2H), 3.22-3.07 (m, 1H), 3.00 (s, 3H), 2.89 (q, 1H, J = 7.2 Hz), 2.11-2.01 (m, 1H), 1.43 (d, 3H, J = 6.0 | LL, Peak 1 | (3S,4S)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methoxy-piperidin-3-ol or (3R,4R)-1-[4-({8-[(2R,3S)-3-(methanesulfonyl-methyl)-2-methylazetidin-1- |

TABLE 1-continued

| # | Structure | LC/MS | NMR | Separation Conditions | Chemical Name |
|---|---|---|---|---|---|
|  | 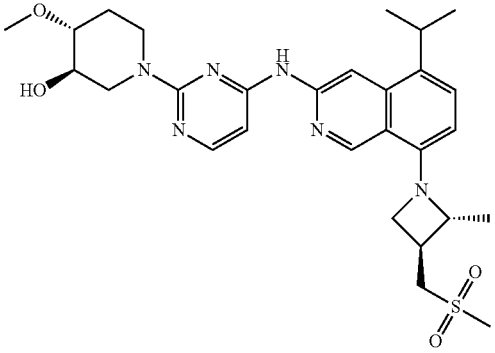 |  | Hz), 1.30 (dd, 6H, J = 6.7, 3.2 Hz) |  | yl]-5-(propan-2-yl)isoquinolin-3-yl}amino)pyrimidin-2-yl]-4-methoxy-piperidin-3-ol |
| 93 | 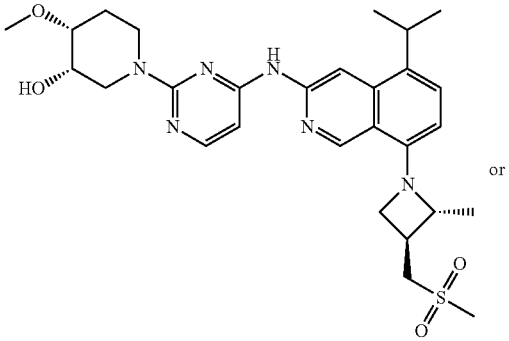 | 555 | 1H-NMR (400 MHz, 6d-DMSO) δ ppm 9.83 (s, 1H), 9.03 (s, 1H), 8.67 (s, 1H), 7.96 (d, 1H, J = 5.6 Hz), 7.40 (d, 1H, J = 7.9 Hz), 6.54 (d, 1H, J = 8.0 Hz), 6.40 (d, 1H, J = 5.7 Hz), 4.62 (dd, 2H, J = 17.2, 6.3 Hz), 4.17 (t, 1H, J = 6.2 Hz), 3.95 (s, 2H), 3.82-3.42 (m, 8H), 3.35 (s, 3H), 2.98 (s, 3H), 2.87 (q, 1H, J = 7.3 Hz), 1.88-1.82 (m, 1H), 1.64-1.58 (m, 1H), 1.41 (d, 3H, J = 6.0 Hz), 1.28 (d, 6H, J = 6.6 Hz) | JJ, Peak 1 | (3S,4R)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methoxy-piperidin-3-ol or (3R,4S)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methoxy-piperidin-3-ol |
| 94 | 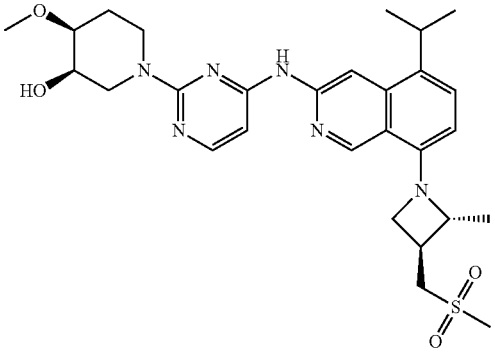 | 555 | 1H-NMR (300 MHz, 4d-CD3OD) δ ppm 9.11 (s, 1H), 8.67 (s, 1H), 7.96 (d, 1H, J = 5.8 Hz), 7.48 (d, 1H, J = 8.0 Hz), 6.53 (d, 1H, J = 8.0 Hz), 6.34 (d, 1H, J = 5.8 Hz), 4.63-4.37 (m, 5H), 4.03 (td, 2H, J = 7.6, 6.9, 1.9 Hz), 3.73-3.57 (m, 4H), 3.48-3.33 (m, 2H), 3.23 (s, 3H), 3.17 (d, 1H, J = 13.9 Hz), 3.04 (s, 3H), 1.96 (ddt, 1H, J = 13.8, 10.0, 5.0 Hz), 1.82-1.70 (m, 1H), 1.43-1.25 (m, 9H) | L; Peak 1 | (3R,4S)-1-[4-({8-[3-(methanesulfonyl-methyl)azetidin-1-yl]-5-(propan-2-yl)isoquinolin-3-yl}amino)pyrimidin-2-yl]-3-methoxy-3-methylpiperidin-4-ol or (3S,4R)-1-[4-({8-[3-(methanesulfonyl-methyl)azetidin-1-yl]-5-(propan-2-yl)isoquinolin- |

TABLE 1-continued

| # | Structure | LC/MS | NMR | Separation Conditions | Chemical Name |
|---|---|---|---|---|---|
| | | | | | 3-yl}amino)pyrimidin-2-yl]-3-methoxy-3-methyl-piperidin-4-ol |
| 95 | | 555 | 1H-NMR (300 MHz, 4d-CD3OD) δ ppm 9.11 (s, 1H), 8.67 (s, 1H), 7.96 (d, 1H, J = 5.8 Hz), 7.48 (d, 1H, J = 8.0 Hz), 6.53 (d, 1H, J = 8.0 Hz), 6.34 (d, 1H, J = 5.8 Hz), 4.58 (d, 2H, J = 15.2 Hz), 4.43 (td, 2H, J = 7.6, 2.1 Hz), 4.08-3.97 (m, 2H), 3.73-3.57 (m, 4H), 3.39 (d, 3H, J = 10.2 Hz), 3.23 (s, 3H), 3.16 (d, 1H, J = 13.9 Hz), 3.04 (s, 3H), 1.96 (ddt, 1H, J = 13.9, 9.8, 4.9 Hz), 1.82-1.70 (m, 1H), 1.38 (t, 6H, J = 6.7 Hz), 1.27 (s, 3H) | L; Peak 2 | (3S,4R)-1-[4-({8-[3-(methanesulfonyl-methyl)azetidin-1-yl]-5-(propan-2-yl)isoquinolin-3-yl}amino)pyrimidin-2-yl]-3-methoxy-3-methylpiperidin-4-ol or (3R,4S)-1-[4-({8-[3-(methanesulfonyl-methyl)azetidin-1-yl]-5-(propan-2-yl)isoquinolin-3-yl}amino)pyrimidin-2-yl]-3-methoxy-3-methylpiperidin-4-ol |
| 96 | 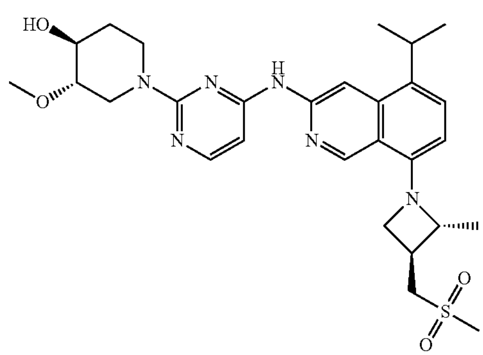 | 555 | 1H-NMR (300 MHz, 6d-DMSO) δ ppm 9.90 (s, 1H), 9.06 (s, 1H), 8.67 (s, 1H), 8.00 (d, 1H, J = 5.6 Hz), 7.42 (d, 1H, J = 7.9 Hz), 6.56 (d, 1H, J = 8.1 Hz), 6.44 (d, 1H, J = 5.7 Hz), 5.01 (d, 1H, J = 4.3 Hz), 4.66 (t, 1H, J = 7.5 Hz), 4.24-4.14 (m, 2H), 4.06 (s, 1H), 3.77-3.39 (m, 7H), 3.35 (s, 3H), 3.11-3.03 (m, 1H), 3.00 (s, 3H), 2.89 (q, 1H, J = 7.2 Hz), 1.90-1.84 (m, 1H), 1.57-1.39 (m, 4H), 1.30 (dd, 6H, J = 6.7, 2.5 Hz) | D; Peak 1 | (3S,4S)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-3-methoxy-piperidin-4-ol or (3R,4R)-1-[4-({8-[(2R,3S)-3-(methanesulfonyl-methyl)-2-methylazetidin-1- |

TABLE 1-continued

| # | Structure | LC/MS | NMR | Separation Conditions | Chemical Name |
|---|---|---|---|---|---|
|  | 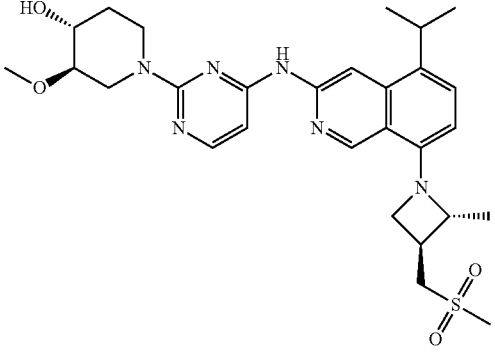 |  |  |  | yl]-5-(propan-2-yl)isoquinolin-3-yl}amino)pyrimidin-2-yl]-3-methoxy-piperidin-4-ol |
| 97 | 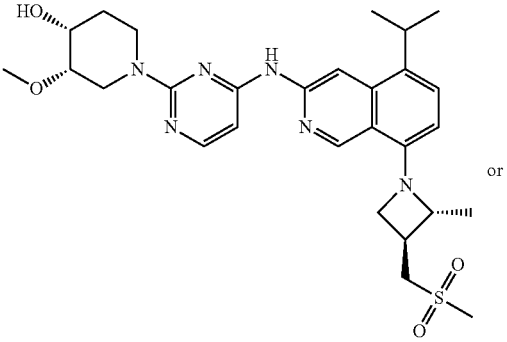 | 555 or | 1H-NMR (400 MHz, 6d-DMSO) δ ppm 9.89 (s, 1H), 9.05 (s, 1H), 8.67 (s, 1H), 7.99 (d, 1H, J = 5.6 Hz), 7.43 (d, 1H, J = 8.0 Hz), 6.56 (d, 1H, J = 8.1 Hz), 6.43 (d, 1H, J = 5.7 Hz), 4.66 (dd, 2H, J = 6.0, 3.3 Hz), 4.19 (t, 1H, J = 6.3 Hz), 4.04 (dd, 1H, J = 13.1, 7.2 Hz), 3.95 (s, 2H), 3.79 (d, 2H, J = 13.0 Hz), 3.64 (t, 1H, J = 7.2 Hz), 3.53 (h, 3H, J = 7.2 Hz), 3.33-3.25 (m, 4H), 3.00 (s, 3H), 2.89 (q, 1H, J = 7.2 Hz), 1.81-1.57 (m, 2H), 1.43 (d, 3H, J = 6.0 Hz), 1.30 (dd, 6H, J = 6.7, 1.6 Hz) | D; Peak 2 | (3S,4R)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-3-methoxy-piperidin-4-ol or (3R,4S)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-3-methoxy-piperidin-4-ol |
| 98 | 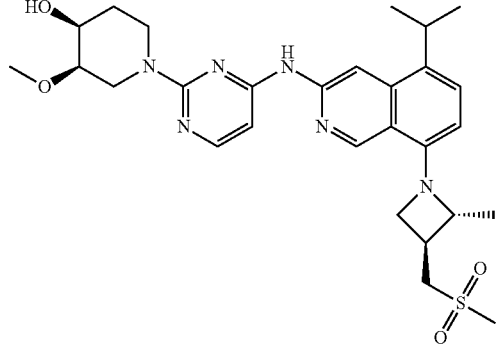 | 555 or | 1H-NMR (300 MHz, 6d-DMSO) δ ppm 9.91 (s, 1H), 9.06 (s, 1H), 8.66 (s, 1H), 8.00 (d, 1H, J = 5.6 Hz), 7.42 (d, 1H, J = 8.0 Hz), 6.56 (d, 1H, J = 8.1 Hz), 6.44 (d, 1H, J = 5.7 Hz), 5.01 (d, 1H, J = 4.3 Hz), 4.66 (t, 1H, J = 7.5 Hz), 4.35-4.00 (m, 3H), 3.73-3.41 (m, 7H), 3.35 (s, 3H), 3.09-3.02 (m, 1H), 3.00 (s, 3H), 2.89 (q, 1H, J = 7.2 Hz), 1.89-1.83 (m, 1H), 1.54-1.39 (m, 4H), 1.30 (dd, 6H, J = 6.8, 4.8 Hz) | D; Peak 1 | (3R,4R)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-3-methoxy-piperidin-4-ol or (3S,4S)-1-[4-({8-[(2R,3S)-3-(methanesulfonyl-methyl)-2-methylazetidin-1- |

TABLE 1-continued

| # | Structure | LC/MS | NMR | Separation Conditions | Chemical Name |
|---|---|---|---|---|---|
| | | | | | yl]-5-(propan-2-yl)isoquinolin-3-yl}amino)pyrimidin-2-yl]-3-methoxy-piperidin-4-ol |
| 99 | | 555 | 1H-NMR (300 MHz, 6d-DMSO) δ ppm 9.90 (s, 1H), 9.05 (s, 1H), 8.68 (s, 1H), 7.99 (d, 1H, J = 5.6 Hz), 7.42 (d, 1H, J = 8.0 Hz), 6.56 (d, 1H, J = 8.0 Hz), 6.43 (d, 1H, J = 5.7 Hz), 4.72-4.61 (m, 2H), 4.19 (t, 1H, J = 6.2 Hz), 4.13-3.89 (m, 4H), 3.75 (d, 2H, J = 13.2 Hz), 3.64 (t, 1H, J = 7.3 Hz), 3.53 (h, 3H, J = 7.3 Hz), 3.30 (s, 3H), 3.00 (s, 3H), 2.88 (p, 1H, J = 7.2 Hz), 1.82-1.53 (m, 2H), 1.43 (d, 3H, J = 6.0 Hz), 1.30 (d, 6H, J = 6.7 Hz) | D; Peak 2 | (3R,4S)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-3-methoxy-piperidin-4-ol or (3S,4R)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-3-methoxy-piperidin-4-ol |
| 100 | 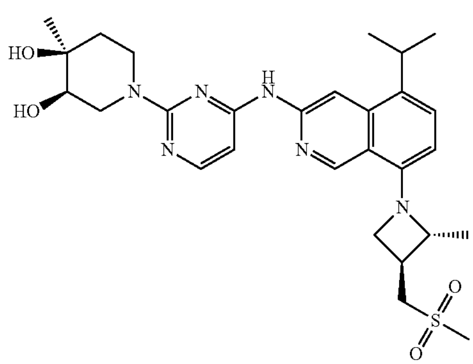 | 555 | 1H-NMR (300 MHz, 6d-DMSO) δ ppm 9.87 (s, 1H), 9.05 (s, 1H), 8.69 (s, 1H), 7.98 (d, 1H, J = 5.6 Hz), 7.41 (d, 1H, J = 8.0 Hz), 6.56 (d, 1H, J = 8.1 Hz), 6.42 (d, 1H, J = 5.7 Hz), 4.72-4.60 (m, 2H), 4.44 (dt, 2H, J = 17.1, 8.6 Hz), 4.24-4.15 (m, 2H), 3.64 (t, 1H, J = 7.3 Hz), 3.62-3.44 (m, 3H), 3.35-3.18 (m, 2H), 3.07 (t, 1H, J = 11.2 Hz), 3.00 (s, 3H), 2.89 (q, 1H, J = 7.2 Hz), 1.72-1.47 (m, 2H), 1.43 (d, 3H, J = 6.0 Hz), 1.30 (dd, 6H, J = 6.7, 4.3 | F; Peak 1 | (3R,4S)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methyl-piperidine-3,4-diol or (3S,4R)-1-[4-({8-[(2R,3S)-3-(methanesulfonyl-methyl)-2- |

| # | Structure | LC/MS | NMR | Separation Conditions | Chemical Name |
|---|---|---|---|---|---|
| | 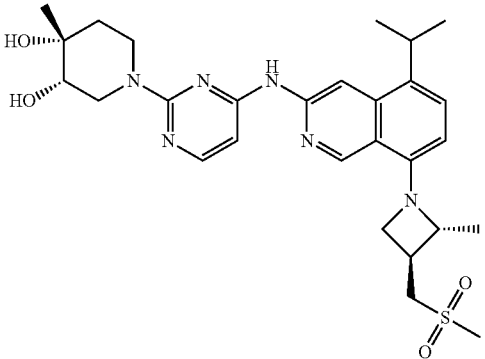 [SMILES: CC(C)c1ccc(N2C[C@H](CS(C)(=O)=O)[C@H]2C)c2cnc(Nc3ccnc(N4CC[C@@](C)(O)[C@@H](O)C4)n3)cc12] | | Hz), 1.18 (s, 3H) | | methylazetidin-1-yl]-5-(propan-2-yl)isoquinolin-3-yl}amino)pyrimidin-2-yl]-4-methyl-piperidine-3,4-diol |
| 101 | 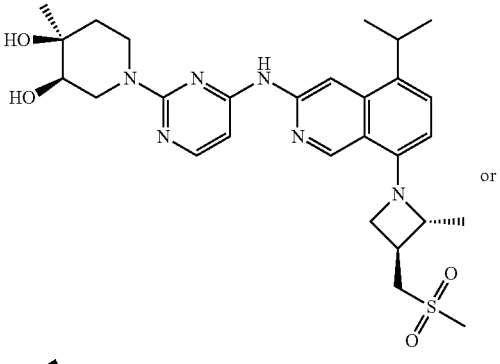 | 555 | 1H-NMR (300 MHz, 6d-DMSO) δ ppm 9.88 (s, 1H), 9.05 (s, 1H), 8.68 (s, 1H), 7.98 (d, 1H, J = 5.6 Hz), 7.41 (d, 1H, J = 8.0 Hz), 6.56 (d, 1H, J = 8.1 Hz), 6.42 (d, 1H, J = 5.6 Hz), 4.66 (s, 2H), 4.44 (dt, 2H, J = 16.5, 8.3 Hz), 4.21-4.15 (m, 2H), 3.69-3.44 (m, 4H), 3.30-3.17 (m, 2H), 3.07 (t, 1H, J = 11.2 Hz), 3.00 (s, 3H), 2.89 (q, 1H, J = 7.3 Hz), 1.66 (d, 1H, J = 13.4 Hz), 1.53 (d, 1H, J = 12.8 Hz), 1.42 (d, 3H, J = 6.0 Hz), 1.30 (t, 6H, J = 6.6 Hz), 1.19 (s, 3H) | F; Peak 2 | (4R)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methyl-piperidine-3,4-diol or (3S,4R)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methyl-piperidine-3,4-diol |
| 102 | 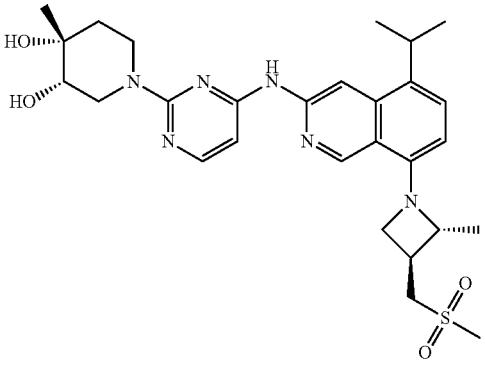 [SMILES: CC(C)c1ccc(N2C[C@H](CS(C)(=O)=O)[C@H]2C)c2cnc(Nc3ccnc(N4CC[C@@](C)(O)[C@@H](O)C4)n3)cc12] | 555 | 1H-NMR (300 MHz, 6d-DMSO) δ ppm 9.86 (s, 1H), 9.05 (s, 1H), 8.73 (s, 1H), 7.97 (d, 1H, J = 5.6 Hz), 7.42 (d, 1H, J = 8.0 Hz), 6.56 (d, 1H, J = 8.1 Hz), 6.39 (d, 1H, J = 5.7 Hz), 4.77 (d, 1H, J = 5.1 Hz), 4.66 (t, 1H, J = 7.5 Hz), 4.51 (s, 1H), 4.24-4.14 (m, 1H), 3.96 (d, 2H, J = 20.1 Hz), 3.79 (d, 1H, J = 10.8 Hz), 3.71-3.37 (m, 6H), 3.00 (s, 3H), 2.93-2.82 (m, 1H), 1.80-1.71 (m, 1H), 1.52-1.37 (m, 4H), 1.34-1.21 (m, 6H), 1.16 (s, 3H) | D; Peak 2 | (3R,4R)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methyl-piperidine-3,4-diol or (3S,4S)-1-[4-({8-[(2R,3S)-3-(methanesulfonyl-methyl)-2- |

TABLE 1-continued

| # | Structure | LC/MS | NMR | Separation Conditions | Chemical Name |
|---|---|---|---|---|---|
| | | | | | methylazetidin-1-yl]-5-(propan-2-yl)isoquinolin-3-yl}amino)pyrimidin-2-yl]-4-methyl-piperidine-3,4-diol |
| 103 | | 556 | 1H-NMR (400 MHz, 6d-DMSO) δ ppm 10.08 (s, 1H), 9.10 (s, 1H), 8.78 (s, 1H), 7.99 (d, 1H, J = 5.6 Hz), 7.70 (s, 1H), 6.39 (d, 1H, J = 5.6 Hz), 4.71 (t, 1H, J = 7.6 Hz), 4.62 (d, 1H, J = 4.9 Hz), 4.29 (t, 1H, J = 6.3 Hz), 3.99 (s, 2H), 3.83-3.49 (m, 7H), 3.45 (d, 1H, J = 7.8 Hz), 3.34 (s, 3H), 2.98 (s, 3H), 2.90 (q, 1H, J = 7.3 Hz), 1.91-1.85 (m, 1H), 1.66-1.60 (m, 1H), 1.46 (d, 3H, J = 6.0 Hz), 1.29 (dd, 6H, J = 6.7, 4.3 Hz) | II, Peak 1 | (3S,4R)-1-[4-({8-[(2R,3S)-3-(methanesulfonyl-methyl)-2-methylazetidin-1-yl]-5-(propan-2-yl)-2,6-naphthyridin-3-yl}amino)pyrimidin-2-yl]-4-methoxy-piperidin-3-ol or (3R,4S)-1-[4-({8-[(2R,3S)-3-(methanesulfonyl-methyl)-2-methylazetidin-1-yl]-5-(propan-2-yl)-2,6-naphthyridin-3-yl}amino)pyrimidin-2-yl]-4-methoxy-piperidin-3-ol |
| 104 | 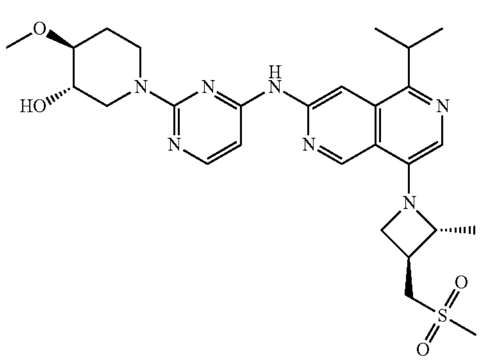 | 556 | 1H-NMR (300 MHz, 6d-DMSO) δ ppm 10.13 (s, 1H), 9.13 (s, 1H), 8.78 (s, 1H), 8.03 (d, 1H, J = 5.6 Hz), 7.73 (s, 1H), 6.44 (d, 1H, J = 5.6 Hz), 5.11 (d, 1H, J = 4.7 Hz), 4.74 (t, 1H, J = 7.6 Hz), 4.44-4.26 (m, 3H), 3.74 (dt, 2H, J = 14.2, 7.1 Hz), 3.54 (dt, 2H, J = 14.0, 6.7 Hz), 3.47-3.41 (m, 1H), 3.39 (s, 3H), 3.30-3.11 (m, 3H), 3.01 (s, 3H), 2.93 (q, 1H, J = 7.3 Hz), 2.08-2.02 (m, 1H), 1.48 (d, 3H, J = 6.0 Hz), 1.42-1.35 (m, 1H), 1.31 (dd, 6H, J = | HH, Peak 1 | (3S,4S)-1-[4-({8-[(2R,3S)-3-(methanesulfonyl-methyl)-2-methylazetidin-1-yl]-5-(propan-2-yl)-2,6-naphthyridin-3-yl}amino)pyrimidin-2-yl]-4-methoxy-piperidin-3-ol or (3R,4R)-1-[4-({8-[(2R,3S)-3-(methanesulfonyl-methyl)-2- |

TABLE 1-continued

| # | Structure | LC/MS | NMR | Separation Conditions | Chemical Name |
|---|---|---|---|---|---|
| | 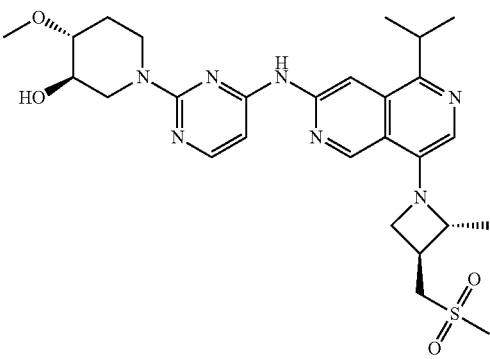 | | 8.9, 6.6 Hz) | | methylazetidin-1-yl]-5-(propan-2-yl)-2,6-naphthyridin-3-yl}amino)pyrimidin-2-yl]-4-methoxy-piperidin-3-ol |
| 105 | 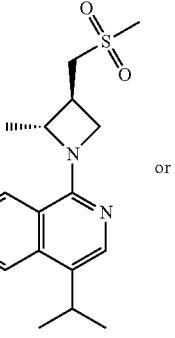 or 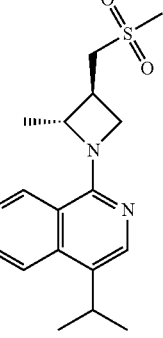 | 556 | 1H NMR (400 MHz, DMSO-d6) δ 10.07 (s, 1H), 9.06 (s, 1H), 8.60 (s, 1H), 8.08-8.01 (m, 2H), 6.49 (d, 1H, J = 5.6 Hz), 4.88 (t, 1H, J = 8.0 Hz), 4.63 (d, 1H, J = 5.1 Hz), 4.58 (t, 1H, J = 6.2 Hz), 4.08-3.91 (m, 2H), 3.82 (s, 1H), 3.75 (s, 1H), 3.60-3.53 (m, 2H), 3.49 (d, 1H, J = 7.4 Hz), 3.40 (s, 3H), 3.02 (s, 3H), 2.96-2.87 (m, 1H), 1.92-1.85 (m 1H), 1.66 (s, 1H), 1.52 (d, 3H, J = 6.2 Hz), 1.35 (dd, 6H, J = 6.8, 4.6 Hz), 1.27 (s, 3H). | JJ, Peak 1 | (3S,4R)-1-[4-({8-[(2R,3S)-3-(methanesulfonyl-methyl)-2-methylazetidin-1-yl]-5-(propan-2-yl)-2,7-naphthyridin-3-yl}amino)pyrimidin-2-yl]-4-methoxy-piperidin-3-ol or (3R,4S)-1-[4-({8-[(2R,3S)-3-(methanesulfonyl-methyl)-2-methylazetidin-1-yl]-5-(propan-2-yl)-2,7-naphthyridin-3-yl}amino)pyrimidin-2-yl]-4-methoxy-piperidin-3-ol |
| 106 | 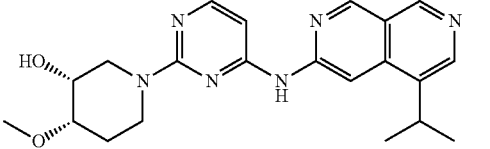 or 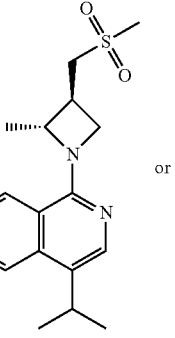 | 556 | 1H NMR (400 MHz, DMSO-d6) δ 10.09 (s, 1H), 9.06 (s, 1H), 8.57 (s, 1H), 8.06 (d, 1H, J = 5.6 Hz), 8.02 (s, 1H), 6.52 (d, J = 5.6 Hz, 1H), 5.10 (d, J = 4.9 Hz, 1H), 4.88 (t, J = 8.0 Hz, 1H), 4.58 (t, J = 6.2 Hz, 1H), 4.47-4.26 (m, 2H), 4.00 (t, J = 7.3 Hz, 1H), 3.64-3.49 (m, 2H), 3.41 (s, 5H), 3.30-3.12 (m, 2H), 3.02 (s, 3H), 2.92 (q, J = 7.3 Hz, 1H), 2.13-2.02 (m, 1H), 1.52 (d, J = 6.1 Hz, 3H), 1.45-1.21 (m, 8H). | LL, Peak 1 | (3S,4S)-1-[4-({8-[(2R,3S)-3-(methanesulfonyl-methyl)-2-methylazetidin-1-yl]-5-(propan-2-yl)-2,7-naphthyridin-3-yl}amino)pyrimidin-2-yl]-4-methoxy-piperidin-3-ol or (3R,4R)-1-[4-({8-[(2R,3S)-3-(methanesulfonyl- |

TABLE 1-continued

| # | Structure | LC/ MS | NMR | Separation Conditions | Chemical Name |
|---|---|---|---|---|---|
| | 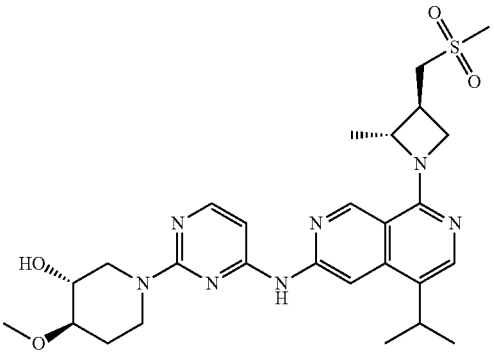 | | | | methyl)-2-methylazetidin-1-yl]-5-(propan-2-yl)-2,7-naphthyridin-3-yl} amino)pyrimidin-2-yl]-4-methoxy-piperidin-3-ol |
| 107 | 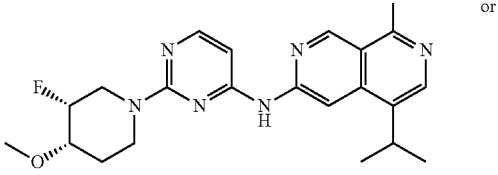 | 556 | 1H-NMR (300 MHz, 6d-DMSO) δ ppm 9.94 (s, 1H), 9.06 (s, 1H), 8.64 (s, 1H), 8.00 (d, 1H, J = 5.6 Hz), 7.43 (d, 1H, J = 7.9 Hz), 6.56 (d, 1H, J = 8.0 Hz), 6.47 (d, 1H, J = 5.7 Hz), 4.95 (d, 1H, J = 49.5 Hz), 4.81-4.69 (m, 1H), 4.64 (t, 1H, J = 7.5 Hz), 4.50 (d, 1H, J = 13.3 Hz), 4.21-4.13 (m, 1H), 3.70 (d, 2H, J = 9.8 Hz), 3.59-3.38 (m, 6H), 3.31-3.20 (m, 3H), 2.94-2.90 (m, 4H), 1.87-1.67 (m, 2H), 1.42 (d, 3H, J = 6.0 Hz), 1.31 (t, 6H, J = 6.9 Hz) | L; Peak 1 | (1S)-(((2R)-1-(6-((2-((3R,4S)-3-fluoro-4-methoxy-piperidin-1-yl)pyrimidin-4-yl)amino)-4-isopropyl-2,7-naphthyridin-1-yl)-2-methylazetidin-3-yl)methyl)(imino)(methyl)-λ$^6$-sulfanone or (1R)-(((2R)-1-(6-((2-((3R,4S)-3-fluoro-4-methoxy-piperidin-1-yl)pyrimidin-4-yl)amino)-4-isopropyl-2,7-naphthyridin-1-yl)-2-methylazetidin-3-yl)methyl)(imino)(methyl)-λ$^6$-sulfanone |
| 108 | 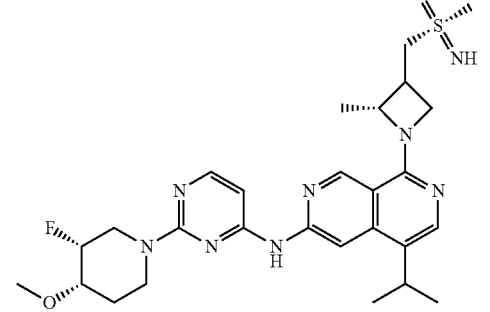 | 556 | 1H-NMR (300 MHz, 6d-DMSO) δ ppm 9.93 (s, 1H), 9.06 (s, 1H), 8.64 (s, 1H), 8.00 (d, 1H, J = 5.6 Hz), 7.43 (d, 1H, J = 7.9 Hz), 6.56 (d, 1H, J = 8.1 Hz), 6.47 (d, 1H, J = 5.7 Hz), 4.95 (d, 1H, J = 49.0 Hz), 4.80-4.70 (m, 1H), 4.66 (t, 1H, J = 7.5 Hz), 4.50 (d, 1H, J = 13.1 Hz), 4.25-4.17 (m, 1H), 3.73 (s, 1H), 3.63 (t, 1H, J = 7.1 Hz), 3.55-3.40 (m, 7H), 3.35-3.20 (m, 2H), 2.94-2.89 (m, 4H), 1.87-1.70 (m, 2H), 1.43 (d, | L; Peak 2 | (1S)-(((2R)-1-(6-((2-((3R,4S)-3-fluoro-4-methoxy-piperidin-1-yl)pyrimidin-4-yl)amino)-4-isopropyl-2,7-naphthyridin-1-yl)-2-methyl-azetidin-3-yl)methyl)(imino)(methyl)-λ$^6$- |

TABLE 1-continued

| # | Structure | LC/MS | NMR | Separation Conditions | Chemical Name |
|---|---|---|---|---|---|
| | 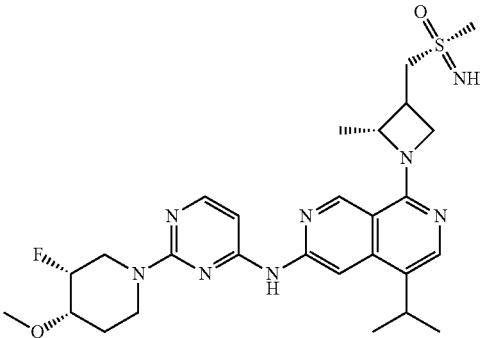 | | 3H, J = 6.0 Hz), 1.31 (t, 6H, J = 7.1 Hz) | | sulfanone or (1R)-(((2R)-1-(6-((2-((3R,4S)-3-fluoro-4-methoxy-piperidin-1-yl)pyrimidin-4-yl)amino)-4-isopropyl-2,7-naphthyridin-1-yl)-2-methyl-azetidin-3-yl)methyl)(imino)(methyl)-λ⁶-sulfanone |
| 109 | 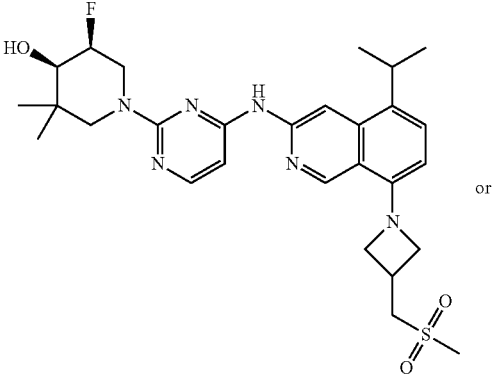 or 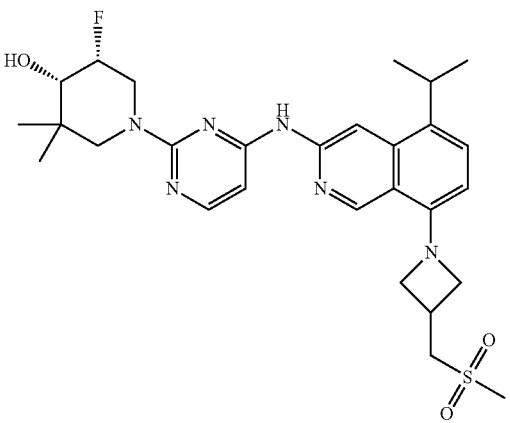 | 557 | 1H-NMR (300 MHz, 6d-DMSO) δ ppm 9.86 (s, 1H), 9.06 (s, 1H), 8.58 (s, 1H), 7.99 (d, 1H, J = 5.6 Hz), 7.41 (d, 1H, J = 8.0 Hz), 6.49 (d, 1H, J = 5.6 Hz), 6.41 (d, 1H, J = 8.0 Hz), 5.14 (d, 1H, J = 5.3 Hz), 4.89-4.61 (m, 1H), 4.39 (t, 2H, J = 7.6 Hz), 4.27 (d, 1H, J = 19.3 Hz), 3.97 (t, 3H, J = 7.0 Hz), 3.82 (d, 1H, J = 12.9 Hz), 3.68-3.18 (m, 6H), 3.29 (s, 3H), 1.30 (dd, 6H, J = 6.7, 4.1 Hz), 1.07-0.76 (m, 6H) | J; Peak 2 | (4S,5R)-5-fluoro-1-[4-({8-[3-(methanesulfonyl-methyl)azetidin-1-yl]-5-(propan-2-yl)isoquinolin-3-yl}amino)pyrimidin-2-yl]-3,3-dimethyl-piperidin-4-ol or (4R,5S)-5-fluoro-1-[4-({8-[3-(methanesulfonyl-methyl)azetidin-1-yl]-5-(propan-2-yl)isoquinolin-3-yl}amino)pyrimidin-2-yl]-3,3-dimethyl-piperidin-4-ol |

TABLE 1-continued

| # | Structure | LC/MS | NMR | Separation Conditions | Chemical Name |
|---|---|---|---|---|---|
| 110 | 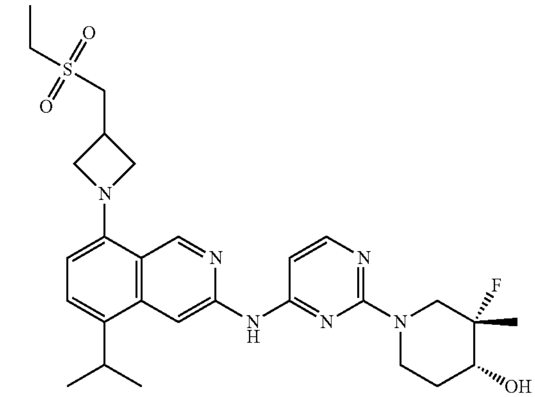 [SMILES: CCS(=O)(=O)CC1CN(c2ccc(C(C)C)c3cc(Nc4ccnc(N5CC[C@@H](O)[C@@](C)(F)C5)n4)ncc23)C1] | 557 | 1H-NMR (400 MHz, 6d-DMSO) δ ppm 9.87 (s, 1H), 9.05 (s, 1H), 8.61 (s, 1H), 7.99 (d, 1H, J = 5.7 Hz), 7.42 (d, 1H, J = 8.0 Hz), 6.47 (d, 1H, J = 5.7 Hz), 6.41 (d, 1H, J = 8.1 Hz), 5.03 (d, 1H, J = 6.4 Hz), 4.86-4.61 (m, 2H), 4.39 (td, 2H, J = 7.7, 2.3 Hz), 4.08-3.88 (m, 2H), 3.67-3.41 (m, 4H), 3.32-3.22 (m, 1H), 3.12 (q, 4H, J = 7.5 Hz), 1.83-1.65 (m, 2H), 1.49-1.15 (m, 12H) | NN; Peak 1 | (3S,4R)-1-{4-[(8-{3-[(ethanesulfonyl)methyl]azetidin-1-yl}-5-(propan-2-yl)isoquinolin-3-yl)amino]pyrimidin-2-yl}-3-fluoro-3-methyl-piperidin-4-ol |
| 111 | 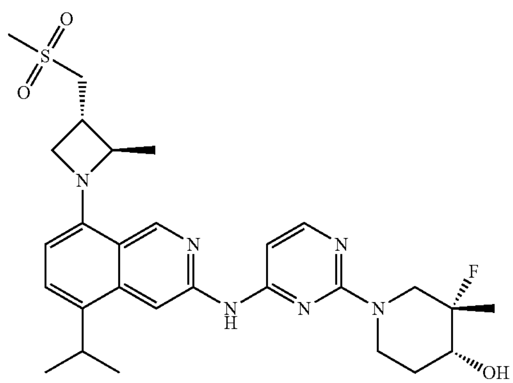 | 557 | 1H-NMR (300 MHz, 6d-DMSO) δ ppm 9.90 (s, 1H), 9.06 (s, 1H), 8.62 (s, 1H), 7.99 (d, 1H, J = 5.6 Hz), 7.43 (d, 1H, J = 8.0 Hz), 6.57 (d, 1H, J = 8.3 Hz), 6.46 (d, 1H, J = 5.7 Hz), 5.04 (d, 1H, J = 6.4 Hz), 4.92-4.47 (m, 3H), 4.20 (t, 1H, J = 6.5 Hz), 3.59 (dt, 5H, J = 28.9, 7.4 Hz), 3.26-3.06 (m, 2H), 3.00 (s, 3H), 2.89 (d, 1H, J = 7.5 Hz), 1.85-1.64 (m, 2H), 1.50-1.37 (m, 4H), 1.39-1.20 (m, 8H) | L; Peak 1 | (3S,4R)-3-fluoro-1-[4-({8-[(2R,3S)-3-(methanesulfonyl-methyl)-2-methylazetidin-1-yl]-5-(propan-2-yl)isoquinolin-3-yl}amino)pyrimidin-2-yl]-3-methyl-piperidin-4-ol |
| 112 | 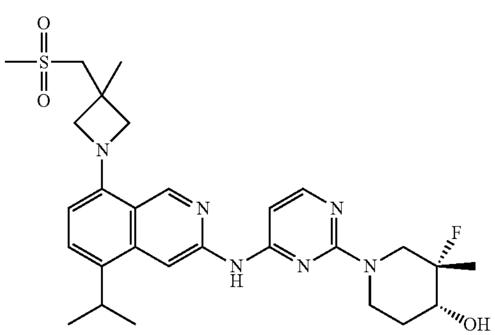 | 557 | 1H-NMR (300 MHz, 6d-DMSO) δ ppm 9.88 (s, 1H), 9.05 (s, 1H), 8.61 (s, 1H), 7.99 (d, 1H, J = 5.6 Hz), 7.41 (d, 1H, J = 8.0 Hz), 6.47 (d, 1H, J = 5.7 Hz), 6.40 (d, 1H, J = 8.1 Hz), 5.03 (d, 1H, J = 6.4 Hz), 4.83-4.64 (m, 2H), 4.17 (d, 2H, J = 7.4 Hz), 3.98 (d, 2H, J = 7.4 Hz), 3.67 (s, 2H), 3.67-3.43 (m, 2H), 3.25-3.05 (m, 2H), 3.04 (s, 3H), 1.78-1.70 (m, 2H), 1.66 (s, 3H), 1.47-1.23 (m, 9H) | NN; Peak 1 | (3S,4R)-3-fluoro-1-[4-({8-[3-(methanesulfonyl-methyl)-3-methylazetidin-1-yl]-5-(propan-2-yl)isoquinolin-3-yl}amino)pyrimidin-2-yl]-3-methyl-piperidin-4-ol |
| 113 | 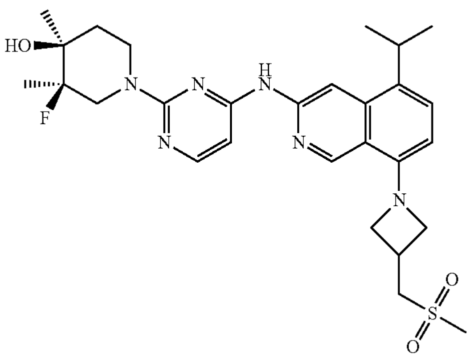 [SMILES: CC(C)c1ccc(N2CC(CS(C)(=O)=O)C2)c2cnc(Nc3ccnc(N4CC[C@@](C)(O)[C@](C)(F)C4)n3)cc12] | 557 | 1H-NMR (300 MHz, 6d-DMSO) δ ppm 9.93 (s, 1H), 9.06 (s, 1H), 8.61 (s, 1H), 8.00 (d, 1H, J = 5.7 Hz), 7.43 (d, 1H, J = 8.0 Hz), 6.50 (d, 1H, J = 5.8 Hz), 6.43 (d, 1H, J = 8.1 Hz), 4.73 (s, 1H), 4.40 (t, 2H, J = 7.6 Hz), 4.28 (dd, 1H, J = 13.4, 7.8 Hz), 4.14 (s, 1H), 3.97 (t, 2H, J = 6.9 Hz), 3.71-3.65 (m, 3H), 3.59 (d, 2H, J = 7.3 Hz), 3.56-3.45 (m, 1H), 3.02 (s, 3H), 1.89-1.83 (m, 1H), 1.61-1.55 (m, 1H), 1.39-1.20 (m, 12H) | B; Peak 2 | (3R,4S)-3-fluoro-1-[4-({8-[3-(methanesulfonyl-methyl)azetidin-1-yl]-5-(propan-2-yl)isoquinolin-3-yl}amino)pyrimidin-2-yl]-3,4-dimethyl-piperidin-4-ol or (3S,4R)-3-fluoro-1-[4-({8-[3-(methanesulfonyl-methyl)azetidin- |

TABLE 1-continued

| # | Structure | LC/MS | NMR | Separation Conditions | Chemical Name |
|---|---|---|---|---|---|
| | | | | | 1-yl]-5-(propan-2-yl)isoquinolin-3-yl}amino)pyrimidin-2-yl]-3,4-dimethyl-piperidin-4-ol |
| 114 | | 557 | 1H-NMR (300 MHz, 6d-DMSO) δ ppm 9.83 (s, 1H), 9.05 (s, 1H), 8.62 (s, 1H), 7.98 (d, 1H, J = 5.6 Hz), 7.42 (d, 1H, J = 8.0 Hz), 6.45 (d, 1H, J = 5.7 Hz), 6.41 (d, 1H, J = 8.0 Hz), 4.98 (d, 1H, J = 1.7 Hz), 4.62 (q, 2H, J = 12.7 Hz), 4.39 (t, 2H, J = 7.4 Hz), 3.97 (t, 2H, J = 6.8 Hz), 3.59 (d, 2H, J = 7.3 Hz), 3.55-3.45 (m, 1H), 3.34-3.18 (m, 3H), 3.02 (s, 3H), 1.87-1.81 (m, 1H), 1.58-1.47 (m, 1H), 1.40-1.22 (m, 9H), 1.20 (d, 3H, J = 1.6 Hz) | F; Peak 2 | (3S,4S)-3-fluoro-1-[4-({8-[3-(methanesulfonyl-methyl)azetidin-1-yl]-5-(propan-2-yl)isoquinolin-3-yl}amino)pyrimidin-2-yl]-3,4-dimethyl-piperidin-4-ol or (3R,4R)-3-fluoro-1-[4-({8-[3-(methanesulfonyl-methyl)azetidin-1-yl]-5-(propan-2-yl)isoquinolin-3-yl}amino)pyrimidin-2-yl]-3,4-dimethyl-piperidin-4-ol |
| 115 | 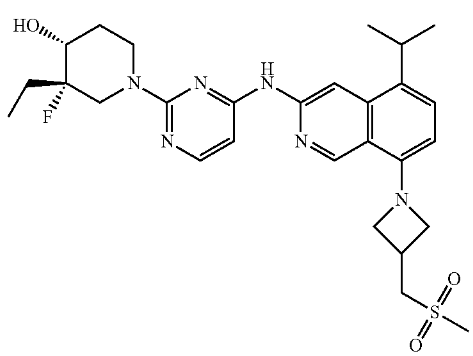 | 557 | 1H-NMR (400 MHz, 6d-DMSO) δ ppm 9.84 (s, 1H), 9.05 (s, 1H), 8.60 (s, 1H), 7.99 (d, 1H, J = 5.6 Hz), 7.41 (d, 1H, J = 8.0 Hz), 6.47 (d, 1H, J = 5.7 Hz), 6.41 (d, 1H, J = 8.1 Hz), 4.97 (d, 1H, J = 6.3 Hz), 4.68 (s, 1H), 4.58 (s, 1H), 4.39 (td, 2H, J = 7.7, 2.8 Hz), 3.96 (td, 2H, J = 6.9, 2.5 Hz), 3.73-3.55 (m, 3H), 3.53-3.44 (m, 1H), 3.30-3.18 (m, 2H), 3.01 (s, 3H), 1.92-1.59 (m, 4H), 1.30 (dd, 6H, J = 6.8, 4.6 Hz), 0.93 (t, 3H, J = 7.5 Hz) | L; Peak 1 | (3S,4R)-3-ethyl-3-fluoro-1-[4-({8-[3-(methanesulfonyl-methyl)azetidin-1-yl]-5-(propan-2-yl)isoquinolin-3-yl}amino)pyrimidin-2-yl]piperidin-4-ol or (3R,4S)-3-ethyl-3-fluoro-1-[4-({8-[3-(methanesulfonyl-methyl)azetidin-1-yl]-5-(propan- |

TABLE 1-continued

| # | Structure | LC/MS | NMR | Separation Conditions | Chemical Name |
|---|---|---|---|---|---|
| | | | | | 2-yl)isoquinolin-3-yl}amino)pyrimidin-2-yl]piperidin-4-ol |
| 116 | 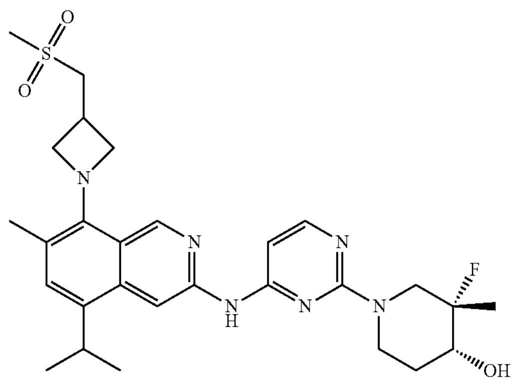 | 557 | 1H-NMR (300 MHz, 6d-DMSO) δ ppm 9.77 (s, 1H), 9.05 (s, 1H), 8.52 (s, 1H), 7.97 (d, 1H, J = 5.6 Hz), 7.21 (s, 1H), 6.45 (d, 1H, J = 5.7 Hz), 5.03 (d, 1H, J = 6.4 Hz), 4.75 (s, 1H), 4.69 (d, 1H, J = 14.1 Hz), 4.57 (t, 2H, J = 7.3 Hz), 4.17-4.06 (m, 2H), 3.52 (dd, 4H, J = 19.0, 7.0 Hz), 3.16 (t, 3H, J = 15.4 Hz), 3.00 (s, 3H), 2.38 (s, 3H), 1.77-1.71 (m, 2H), 1.50-1.14 (m, 9H) | NN; Peak 1 | (3S,4R)-3-fluoro-1-[4-({8-[3-(methanesulfonyl-methyl)azetidin-1-yl]-7-methyl-5-(propan-2-yl)isoquinolin-3-yl}amino)pyrimidin-2-yl]-3-methyl-piperidin-4-ol |
| 117 | 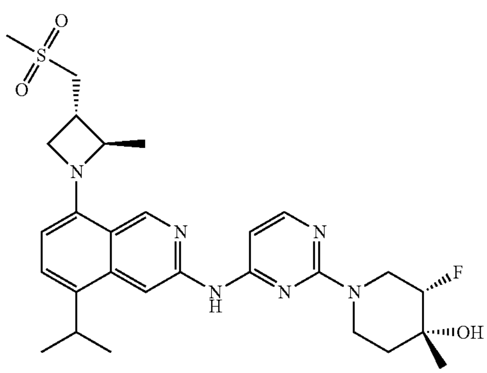 [SMILES: CC(C)c1ccc(N2C[C@H](CS(C)(=O)=O)[C@H]2C)c2cnc(Nc3ccnc(N4CC[C@@](C)(O)[C@@H](F)C4)n3)cc12] | 557 | 1H-NMR (400 MHz, 6d-DMSO) δ ppm 9.95 (s, 1H), 9.06 (s, 1H), 8.67 (s, 1H), 8.01 (d, 1H, J = 5.6 Hz), 7.42 (d, 1H, J = 8.0 Hz), 6.57 (d, 1H, J = 8.1 Hz), 6.47 (d, 1H, J = 5.7 Hz), 4.86 (s, 1H), 4.66 (t, 1H, J = 7.5 Hz), 4.52-4.36 (m, 2H), 4.25-4.14 (m, 2H), 3.69-3.47 (m, 6H), 3.00 (s, 3H), 2.89 (q, 1H, J = 7.3 Hz), 1.73-1.67 (m, 1H), 1.62-1.50 (m, 1H), 1.43 (d, 3H, J = 6.0 Hz), 1.34-1.23 (m, 9H) | N; Peak 1 | (3S,4R)-3-fluoro-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methyl-piperidin-4-ol |
| 118 | 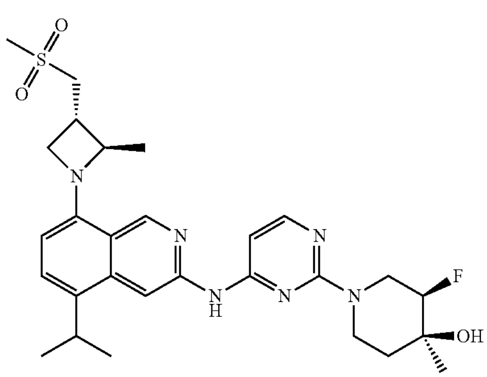 [SMILES: CC(C)c1ccc(N2C[C@H](CS(C)(=O)=O)[C@H]2C)c2cnc(Nc3ccnc(N4CC[C@](C)(O)[C@H](F)C4)n3)cc12] | 557 | 1H-NMR (300 MHz, 6d-DMSO) δ ppm 9.94 (s, 1H), 9.06 (s, 1H), 8.66 (s, 1H), 8.01 (d, 1H, J = 5.7 Hz), 7.43 (d, 1H, J = 8.0 Hz), 6.57 (d, 1H, J = 8.1 Hz), 6.47 (d, 1H, J = 5.7 Hz), 4.86 (s, 1H), 4.67 (t, 1H, J = 7.5 Hz), 4.53-4.06 (m, 4H), 3.70-3.44 (m, 6H), 3.00 (s, 3H), 2.89 (q, 1H, J = 7.3 Hz), 1.74-1.68 (m, 1H), 1.63-1.54 (m, 1H), 1.43 (d, 3H, J = 6.0 Hz), 1.35-1.23 (m, 9H) | N; Peak 2 | (3R,4S)-3-fluoro-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methyl-piperidin-4-ol |

TABLE 1-continued

| # | Structure | LC/MS | NMR | Separation Conditions | Chemical Name |
|---|---|---|---|---|---|
| 119 | 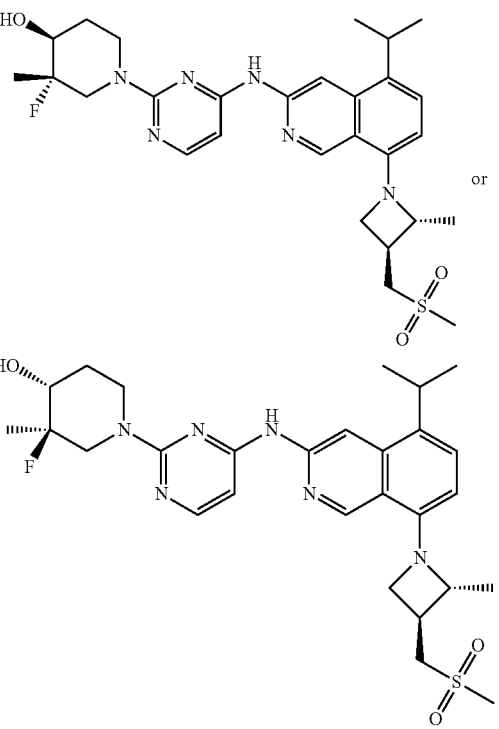 | 557 | 1H-NMR (400 MHz, 6d-DMSO) δ ppm 9.89 (s, 1H), 9.05 (s, 1H), 8.63 (s, 1H), 7.99 (d, 1H, J = 5.6 Hz), 7.42 (d, 1H, J = 8.0 Hz), 6.56 (d, 1H, J = 8.0 Hz), 6.45 (d, 1H, J = 5.7 Hz), 5.32 (d, 1H, J = 4.4 Hz), 4.65 (t, 1H, J = 7.5 Hz), 4.19 (t, 1H, J = 6.2 Hz), 3.93-3.89 (m, 4H), 3.77-3.73 (m, 1H), 3.63 (t, 1H, J = 7.2 Hz), 3.53 (hept, 3H, J = 7.8, 7.3 Hz), 2.99 (s, 3H), 2.89 (q, 1H, J = 7.2 Hz), 1.95-1.85 (m, 1H), 1.56-1.51 (m, 1H), 1.42 (d, 3H, J = 6.0 Hz), 1.35-1.21 (m, 9H) | L; Peak 1 | (3S,4S)-3-fluoro-1-[4-({8-[(2R,3S)-3-(methanesulfonylmethyl)-2-methylazetidin-1-yl]-5-(propan-2-yl)isoquinolin-3-yl}amino)pyrimidin-2-yl]-3-methylpiperidin-4-ol or (3R,4R)-3-fluoro-1-[4-({8-[(2R,3S)-3-(methanesulfonylmethyl)-2-methylazetidin-1-yl]-5-(propan-2-yl)isoquinolin-3-yl}amino)pyrimidin-2-yl]-3-methylpiperidin-4-ol |
| 120 | 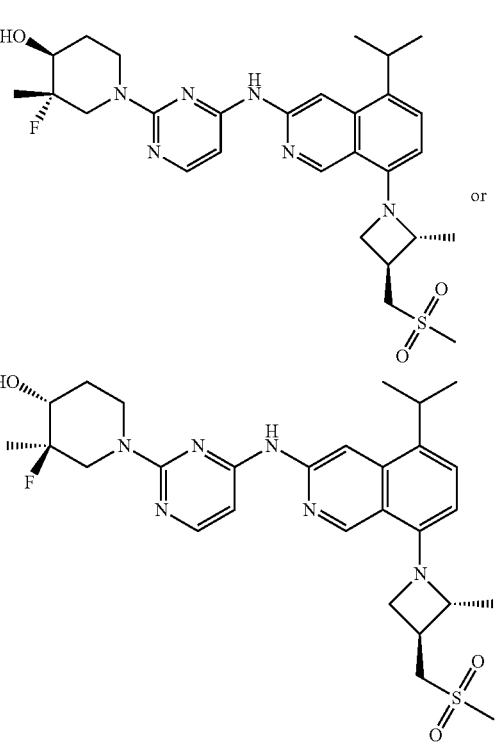 | 557 | 1H-NMR (400 MHz, 6d-DMSO) δ ppm 9.88 (s, 1H), 9.05 (s, 1H), 8.63 (s, 1H), 7.99 (d, 1H, J = 5.6 Hz), 7.42 (d, 1H, J = 8.0 Hz), 6.56 (d, 1H, J = 8.1 Hz), 6.52-6.43 (m, 1H), 5.32 (d, 1H, J = 4.4 Hz), 4.65 (t, 1H, J = 7.5 Hz), 4.19 (t, 1H, J = 6.3 Hz), 4.04-3.82 (m, 4H), 3.75 (s, 1H), 3.64 (t, 1H, J = 7.1 Hz), 3.53 (hept, 3H, J = 7.9, 7.3 Hz), 2.99 (s, 3H), 2.89 (q, 1H, J = 7.3 Hz), 1.92-1.88 (m, 1H), 1.57-1.51 (m, 1H), 1.42 (d, 3H, J = 6.1 Hz), 1.35-1.21 (m, 9H) | L; Peak 2 | (3R,4R)-3-fluoro-1-[4-({8-[(2R,3S)-3-(methanesulfonylmethyl)-2-methylazetidin-1-yl]-5-(propan-2-yl)isoquinolin-3-yl}amino)pyrimidin-2-yl]-3-methylpiperidin-4-ol or (3S,4S)-3-fluoro-1-[4-({8-[(2R,3S)-3-(methanesulfonylmethyl)-2-methylazetidin-1-yl]-5-(propan-2-yl)isoquinolin-3-yl}amino)pyrimidin-2-yl]-3-methylpiperidin-4-ol |

TABLE 1-continued

| # | Structure | LC/MS | NMR | Separation Conditions | Chemical Name |
|---|---|---|---|---|---|
| 121 | 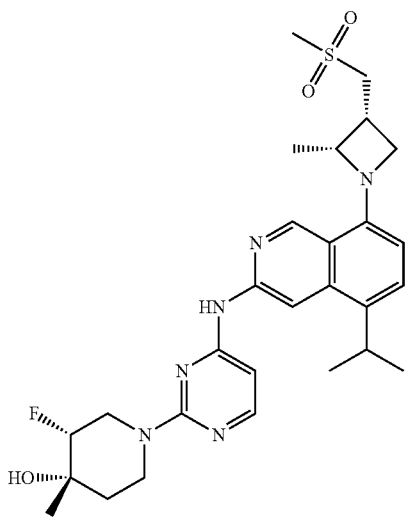 [SMILES: CC(C)c1ccc(N2C[C@@H](CS(C)(=O)=O)[C@H]2C)c2cnc(Nc3ccnc(N4CC[C@](C)(O)[C@H](F)C4)n3)cc12] | 557 | 1H-NMR (300 MHz, 6d-DMSO) δ ppm 9.94 (s, 1H), 9.05 (s, 1H), 8.66 (s, 1H), 8.00 (d, 1H, J = 5.7 Hz), 7.42 (d, 1H, J = 8.0 Hz), 6.56 (d, 1H, J = 8.0 Hz), 6.46 (s, 1H), 4.86 (s, 1H), 4.69-4.63 (m, 1H), 4.47-4.37 (m, 2H), 4.22-4.16 (m, 2H), 3.69-3.47 (m, 6H), 2.99 (s, 3H), 2.88 (d, 1H, J = 9.7 Hz), 1.73-1.67 (m, 1H), 1.59-1.53 (m, 1H), 1.42 (d, 3H, J = 5.9 Hz), 1.33-1.23 (m, 9H) | OO, Peak 2 | (3R,4S)-3-fluoro-1-[4-({8-[(2R,3R)-3-(methanesulfonyl-methyl)-2-methylazetidin-1-yl]-5-(propan-2-yl)isoquinolin-3-yl}amino)pyrimidin-2-yl]-4-methyl-piperidin-4-ol |
| 122 | 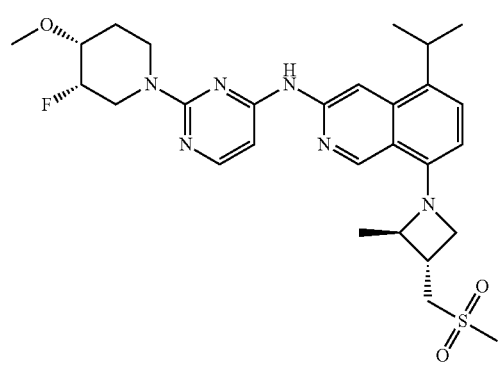 | 557 | 1H NMR (400 MHz, DMSO-d6) δ 9.90 (s, 1H), 9.06 (s, 1H), 8.63 (s, 1H), 8.00 (d, 1H, J = 5.6 Hz), 7.42 (d, 1H, J = 8.0 Hz), 6.56 (d, 1H, J = 8.1 Hz), 6.47 (d, 1H, J = 5.7 Hz), 4.94 (d, 1H, J = 49.3 Hz), 4.69 (dt, J = 25.9, 6.4 Hz, 2H), 4.47 (d, 1H, J = 13.2 Hz), 4.27-4.11 (m, 1H), 3.72-3.42 (m, 5H), 3.37 (s, 3H), 2.99 (s, 3H), 2.89 (q, 1H, J = 7.3 Hz), 1.86-1.65 (m, 2H), 1.42 (d, 3H, J = 6.0 Hz), 1.31 (dd, 6H, J = 6.8, 1.9 Hz). | | N-{2-[(3S,4R)-3-fluoro-4-methoxy-piperidin-1-yl]pyrimidin-4-yl}-8-[(2R,3S)-3-(methanesulfonyl-methyl)-2-methylazetidin-1-yl]-5-(propan-2-yl)isoquinolin-3-amine |
| 123 | 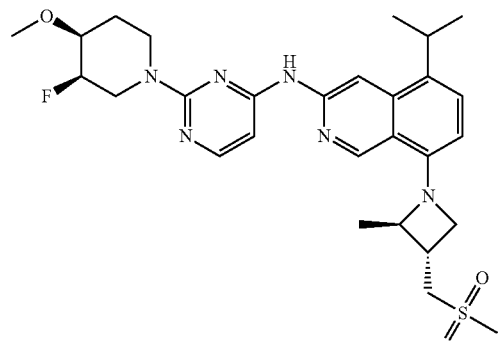 | 557 | 1H NMR (400 MHz, DMSO-d6) δ 9.94 (s, 1H), 9.09 (s, 1H), 8.66 (s, 1H), 8.03 (d, 1H, J = 5.6 Hz), 7.46 (d, 1H, J = 8.0 Hz), 6.60 (d, 1H, J = 8.0 Hz), 6.51 (d, 1H, J = 5.7 Hz), 4.97 (d, 1H, J = 49.2 Hz), 4.86-4.63 (m, 2H), 4.51 (d, 1H, J = 13.7 Hz), 4.23 (t, 1H, J = 6.3 Hz), 3.73-3.46 (m, 5H), 3.40 (s, 3H), 3.03 (s, 3H), 2.92 (q, 1H, J = 7.4 Hz), 1.85-1.79 (m, 2H), 1.46 (d, 3H, J = 6.0 Hz), 1.34 (t, 6H, J = 6.7 Hz). | | N-{2-[(3R,4S)-3-fluoro-4-methoxy-piperidin-1-yl]pyrimidin-4-yl}-8-[(2R,3S)-3-(methanesulfonyl-methyl)-2-methylazetidin-1-yl]-5-(propan-2-yl)isoquinolin-3-amine |

TABLE 1-continued

| # | Structure | LC/MS | NMR | Separation Conditions | Chemical Name |
|---|---|---|---|---|---|
| 124 | 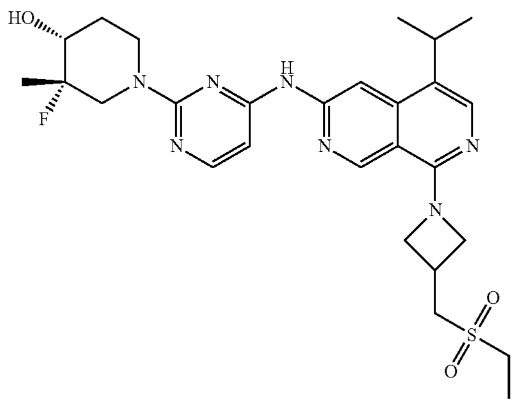 [SMILES: CCS(=O)(=O)CC1CN(c2ncc(C(C)C)c3cc(Nc4ccnc(N5CC[C@@H](O)[C@@](C)(F)C5)n4)ncc23)C1] | 558 | 1H NMR (300 MHz, 6d-DMSO) δ ppm 10.09 (s, 1H), 9.03 (s, 1H), 8.49 (s, 1H), 8.08-7.96 (m, 2H), 6.51 (d, 1H, J = 5.6 Hz), 5.05 (d, 1H, J = 6.4 Hz), 4.81-4.51 (m, 4H), 4.22 (t, 2H, J = 7.4 Hz), 3.58 (d, 3H, J = 7.4 Hz), 3.11 (q, 4H, J = 7.5 Hz), 1.74 (m, 2H), 1.41-1.19 (m, 12H) | NN; Peak 1 | (3S,4R)-1-{4-[(8-{3-[(ethanesulfonyl)methyl]azetidin-1-yl}-5-(propan-2-yl)-2,7-naphthyridin-3-yl)amino]pyrimidin-2-yl}-3-fluoro-3-methylpiperidin-4-ol |
| 126 | 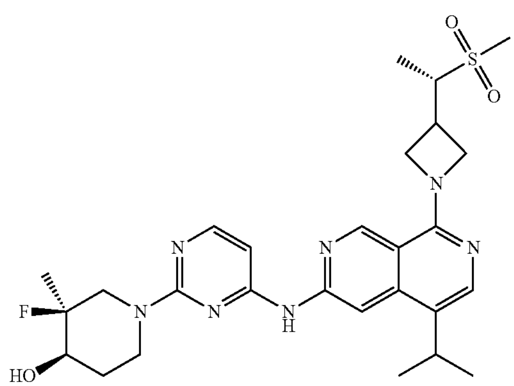 [SMILES: CC(C)c1cnc(N2CC([C@H](C)S(C)(=O)=O)C2)c2cnc(Nc3ccnc(N4CC[C@@H](O)[C@@](C)(F)C4)n3)cc12] | 558 | 1H NMR (300 MHz, 6d-DMSO) δ ppm 10.05 (s, 1H), 9.03 (s, 1H), 8.46 (s, 1H), 8.01 (d, 1H, J = 5.6 Hz), 7.97 (s, 1H), 6.50 (d, 1H, J = 5.6 Hz), 5.02 (d, 1H, J = 6.3 Hz), 4.69 (dd, 2H, J = 24.8, 16.9 Hz), 4.49 (dt, 2H, J = 16.5, 8.5 Hz), 4.26 (dt, 2H, J = 34.6, 7.8 Hz), 3.71-3.41 (m, 2H), 3.29-2.99 (m, 4H), 2.94 (s, 3H), 1.85-1.59 (m, 2H), 1.47-1.11 (m, 12H) | D; Peak 1 | (3S,4R)-3-fluoro-1-{4-[(8-{3-[(1S)-1-methanesulfonylethyl]azetidin-1-yl}-5-(propan-2-yl)-2,7-naphthyridin-3-yl)amino]pyrimidin-2-yl}-3-methyl-piperidin-4-ol |
| 127 | 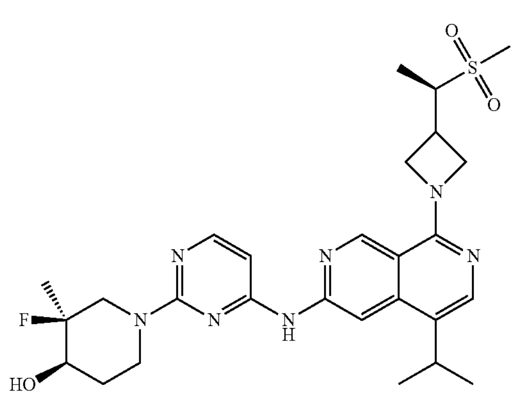 [SMILES: CC(C)c1cnc(N2CC([C@@H](C)S(C)(=O)=O)C2)c2cnc(Nc3ccnc(N4CC[C@@H](O)[C@@](C)(F)C4)n3)cc12] | 558 | 1H NMR (300 MHz, 6d-DMSO) δ ppm 10.05 (s, 1H), 9.03 (s, 1H), 8.46 (s, 1H), 8.01 (d, 1H, J = 5.6 Hz), 7.97 (s, 1H), 6.50 (d, 1H, J = 5.6 Hz), 5.02 (d, 1H, J = 6.4 Hz), 4.82-4.58 (m, 2H), 4.48 (dt, 2H, J = 17.9, 8.5 Hz), 4.26 (dt, 2H, J = 31.7, 7.8 Hz), 3.56 (dd, 2H, J = 15.6, 8.3 Hz), 3.28-3.01 (m, 4H), 2.94 (s, 3H), 1.85-1.59 (m, 2H), 1.53-1.04 (m, 12H) | D; Peak 2 | (3S,4R)-3-fluoro-1-{4-[(8-{3-[(1R)-1-methanesulfonylethyl]azetidin-1-yl}-5-(propan-2-yl)-2,7-naphthyridin-3-yl)amino]pyrimidin-2-yl}-3-methyl-piperidin-4-ol |

| # | Structure | LC/MS | NMR | Separation Conditions | Chemical Name |
|---|---|---|---|---|---|
| 128 | 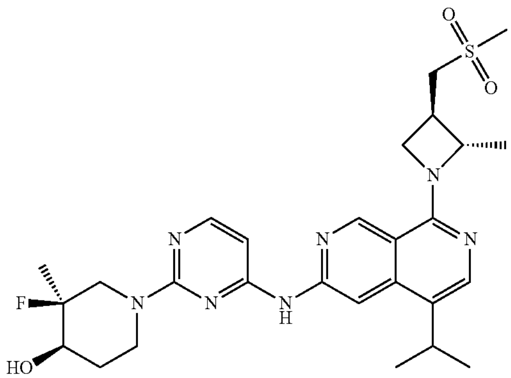 [SMILES: CC(C)c1cnc(N2C[C@@H](CS(C)(=O)=O)[C@@H]2C)c2cnc(Nc3ccnc(N4CC[C@@H](O)[C@@](C)(F)C4)n3)cc12] | 558 | 1H-NMR (300 MHz, 6d-DMSO) δ ppm 10.09 (s, 1H), 9.02 (s, 1H), 8.48 (s, 1H), 8.01 (d, 1H, J = 5.6 Hz), 7.99 (s, 1H), 6.48 (d, 1H, J = 5.6 Hz), 5.03 (d, 1H, J = 6.4 Hz), 4.84 (t, 1H, J = 8.0 Hz), 4.69 (dd, 2H, J = 26.4, 14.7 Hz), 4.53 (t, 1H, J = 6.3 Hz), 3.97 (t, 1H, J = 7.3 Hz), 3.52 (d, 3H, J = 7.5 Hz), 3.22-3.03 (m, 2H), 2.97 (s, 3H), 2.87 (q, 1H, J = 7.1 Hz), 1.71 (s, 2H), 1.47 (d, 3H, J = 6.1 Hz), 1.41-1.25 (m, 9H) | F; Peak 1 | (3S,4R)-3-fluoro-1-[4-({8-[(2S,3R)-3-(methanesulfonyl-methyl)-2-methylazetidin-1-yl]-5-(propan-2-yl)-2,7-naph-thyridin-3-yl}amino)pyrimidin-2-yl]-3-methyl-piperidin-4-ol |
| 129 | 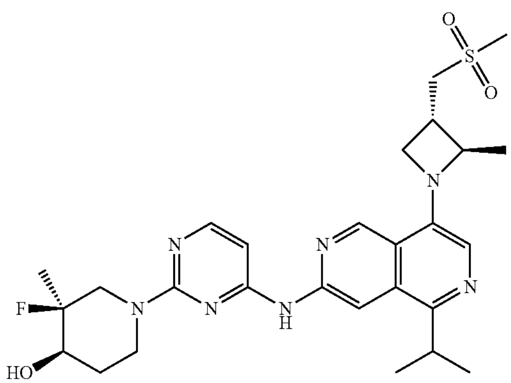 [SMILES: CC(C)c1ncc(N2C[C@H](CS(C)(=O)=O)[C@H]2C)c2cnc(Nc3ccnc(N4CC[C@@H](O)[C@@](C)(F)C4)n3)cc12] | 558 | 1H-NMR (300 MHz, 6d-DMSO) δ ppm 10.13 (s, 1H), 9.14 (s, 1H), 8.73 (s, 1H), 8.03 (d, 1H, J = 5.6 Hz), 7.74 (s, 1H), 6.46 (d, 1H, J = 5.7 Hz), 5.04 (d, 1H, J = 6.4 Hz), 4.83-4.63 (m, 3H), 4.32 (t, 1H, J = 6.2 Hz), 3.75 (dt, 2H, J = 13.7, 7.0 Hz), 3.66-3.54 (m, 2H), 3.57-3.47 (m, 1H), 3.21-3.08 (m, 2H), 3.01 (s, 3H), 2.93 (q, 1H, J = 7.3 Hz), 1.79-1.73 (m, 2H), 1.49 (d, 3H, J = 6.0 Hz), 1.43-1.24 (m, 9H) | NN; Peak 1 | (3S,4R)-3-fluoro-1-[4-({8-[(2R,3S)-3-(methanesulfonyl-methyl)-2-methylazetidin-1-yl]-5-(propan-2-yl)-2,6-naph-thyridin-3-yl}amino)pyrimidin-2-yl]-3-methyl-piperidin-4-ol |
| 130 | 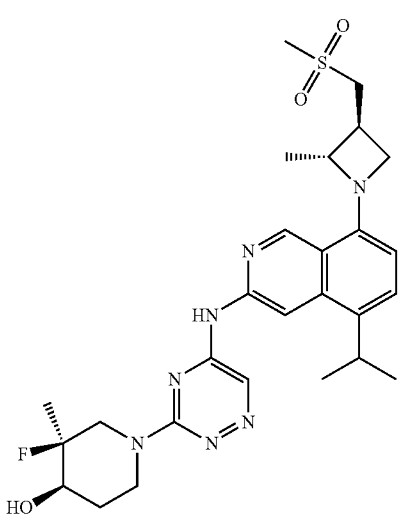 [SMILES: CC(C)c1ccc(N2C[C@H](CS(C)(=O)=O)[C@H]2C)c2cnc(Nc3cnnc(N4CC[C@@H](O)[C@@](C)(F)C4)n3)cc12] | 558 | 1H-NMR (400 MHz, 6d-DMSO) δ ppm 10.53 (s, 1H), 9.12 (s, 1H), 8.68 (s, 1H), 8.48 (s, 1H), 7.48 (d, 1H, J = 8.0 Hz), 6.63 (d, 1H, J = 8.2 Hz), 5.08 (d, 1H, J = 6.3 Hz), 4.88-4.54 (m, 3H), 4.21 (t, 1H, J = 6.2 Hz), 3.65 (t, 1H, J = 7.2 Hz), 3.59-3.36 (m, 5H), 3.28-3.10 (m, 2H), 2.99 (s, 3H), 2.89 (q, 1H, J = 7.2 Hz), 1.80-1.74 (m, 2H), 1.46-1.38 (m, 4H), 1.38-1.23 (m, 8H) | L; Peak 2 | (3S,4R)-3-fluoro-1-[5-({8-[(2R,3S)-3-(methanesulfonyl-methyl)-2-methylazetidin-1-yl]-5-(propan-2-yl)isoquinolin-3-yl}amino)-1,2,4-triazin-3-yl]-3-methyl-piperidin-4-ol |

TABLE 1-continued

| # | Structure | LC/MS | NMR | Separation Conditions | Chemical Name |
|---|---|---|---|---|---|
| 131 | 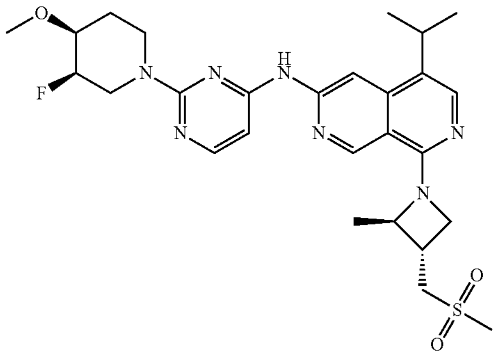 | 558 | 1H-NMR (300 MHz, 6d-DMSO) δ ppm 10.12 (s, 1H), 9.05 (s, 1H), 8.52 (s, 1H), 8.05 (d, 1H, J = 5.6 Hz), 8.01 (s, 1H), 6.53 (d, 1H, J = 5.7 Hz), 5.11-4.80 (m, 2H), 4.75-4.69 (m, 1H), 4.56 (t, 1H, J = 6.3 Hz), 4.51-4.47 (m, 1H), 4.47-4.42 (m, 1H), 3.99 (t, 1H, J = 7.3 Hz), 3.71-3.42 (m, 4H), 3.38 (s, 3H), 3.38-3.23 (m, 2H), 2.99 (s, 3H), 2.90 (q, 1H, J = 7.1 Hz), 1.87-1.70 (m, 2H), 1.50 (d, 3H, J = 6.1 Hz), 1.33 (dt, 6H, J = 6.6, 3.2 Hz) | | N-{2-[(3R,4S)-3-fluoro-4-methoxy-piperidin-1-yl]pyrimidin-4-yl}-8-[(2R,3S)-3-(methanesulfonyl-methyl)-2-methylazetidin-1-yl]-5-(propan-2-yl)-2,7-naphthyridin-3-amine |
| 132 | 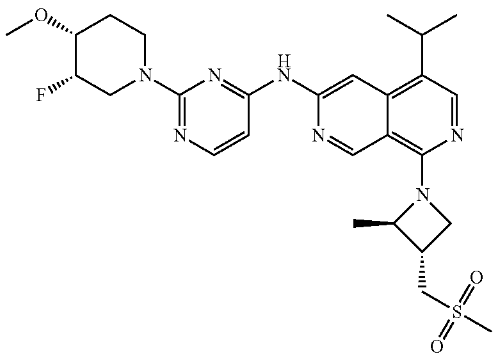 | 558 | 1H-NMR (300 MHz, 6d-DMSO) δ ppm 10.12 (s, 1H), 9.05 (s, 1H), 8.52 (s, 1H), 8.05 (d, 1H, J = 5.6 Hz), 8.01 (s, 1H), 6.53 (d, 1H, J = 5.7 Hz), 5.09-4.80 (m, 2H), 4.75-4.69 (m, 1H), 4.56 (t, 1H, J = 6.3 Hz), 4.47 (d, 1H, J = 13.3 Hz), 3.99 (t, 1H, J = 7.4 Hz), 3.71-3.49 (m, 4H), 3.47-3.41 (m, 1H), 3.38 (s, 3H), 2.99 (s, 3H), 2.96-2.85 (m, 1H), 1.84-1.78 (m, 2H), 1.50 (d, 3H, J = 6.1 Hz), 1.33 (d, 6H, J = 6.8 Hz) | | N-{2-[(3S,4R)-3-fluoro-4-methoxy-piperidin-1-yl]pyrimidin-4-yl}-8-[(2R,3S)-3-(methanesulfonyl-methyl)-2-methylazetidin-1-yl]-5-(propan-2-yl)-2,7-naphthyridin-3-amine |
| 133 | 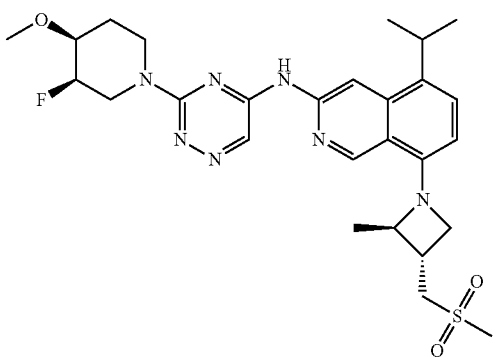 | 558 | 1H-NMR (300 MHz, 6d-DMSO) δ ppm 10.57 (s, 1H), 9.12 (s, 1H), 8.70 (s, 1H), 8.49 (s, 1H), 7.47 (d, 1H, J = 8.0 Hz), 6.63 (d, 1H, J = 8.1 Hz), 4.99 (d, 1H, J = 49.6 Hz), 4.75 (s, 1H), 4.69 (t, 1H, J = 7.5 Hz), 4.51 (d, 1H, J = 13.6 Hz), 4.21 (t, 1H, J = 6.2 Hz), 3.72-3.42 (m, 6H), 3.38 (s, 3H), 3.00 (s, 3H), 2.89 (q, 1H, J = 7.2 Hz), 1.92-1.71 (m, 2H), 1.43 (d, 3H, J = 6.0 Hz), 1.31 (dd, 6H, J = 6.7, 3.8 Hz) | | N-{3-[(3R,4S)-3-fluoro-4-methoxy-piperidin-1-yl]-1,2,4-triazin-5-yl}-8-[(2R,3S)-3-(methanesulfonyl-methyl)-2-methylazetidin-1-yl]-5-(propan-2-yl)isoquinolin-3-amine |
| 134 | 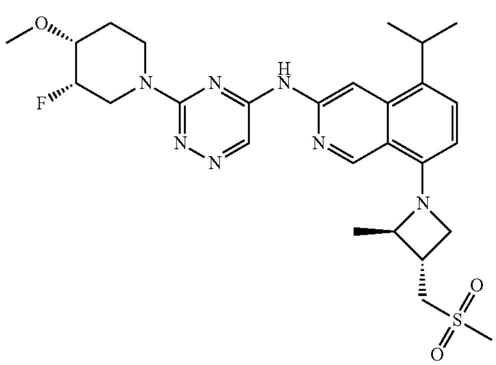 | 558 | 1H-NMR (300 MHz. 6d-DMSO) δ ppm 10.56 (s, 1H), 9.10 (s, 1H), 8.69 (s, 1H), 8.47 (s, 1H), 7.46 (d, 1H, J = 8.0 Hz), 6.61 (d, 1H, J = 8.1 Hz), 4.98 (d, 1H, J = 48.4 Hz), 4.83-4.61 (m, 2H), 4.55-4.45 (m, 1H), 4.19 (t, 1H, J = 6.3 Hz), 3.74-3.43 (m, 6H), 3.36 (s, 3H), 2.98 (s, 3H), 2.88 (q, 1H, J = 7.2 Hz), 1.88-1.71 (m, 2H), 1.41 (d, 3H, J = 6.0 Hz), 1.30 (dd, 6H, J = 6.8, 3.8 Hz) | | N-{3-[(3S,4R)-3-fluoro-4-methoxy-piperidin-1-yl]-1,2,4-triazin-5-yl}-8-[(2R,3S)-3-(methanesulfonyl-methyl)-2-methylazetidin-1-yl]-5-(propan-2-yl)isoquinolin-3-amine |

TABLE 1-continued

| # | Structure | LC/MS | NMR | Separation Conditions | Chemical Name |
|---|---|---|---|---|---|
| 135 | 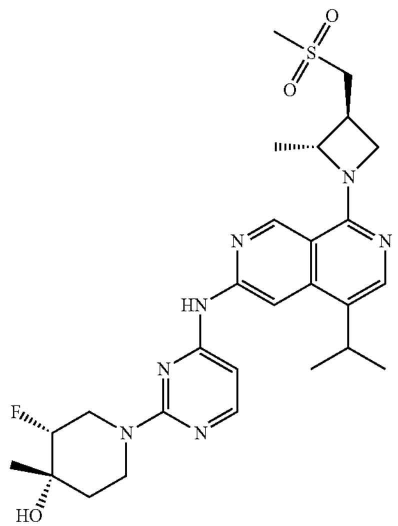 [SMILES: CC(C)c1cnc(N2C[C@H](CS(C)(=O)=O)[C@H]2C)c2cnc(Nc3ccnc(N4CC[C@](C)(O)[C@H](F)C4)n3)cc12] | 558 | 1H-NMR (300 MHz, 6d-DMSO) δ ppm 10.15 (s, 1H), 9.05 (s, 1H), 8.55 (s, 1H), 8.10-7.98 (m, 2H), 6.52 (d, 1H, J = 5.6 Hz), 4.90-4.81 (m, 2H), 4.55 (t, 1H, J = 6.3 Hz), 4.47-4.41 (m, 2H), 4.32-4.12 (m, 2H), 3.98 (t, 1H, J = 7.3 Hz), 3.70-3.38 (m, 4H), 2.99 (s, 3H), 2.89 (q, 1H, J = 7.3 Hz), 1.74-1.68 (m, 1H), 1.64-1.54 (m, 1H), 1.50 (d, 3H, J = 6.1 Hz), 1.30 (dd, 9H, J = 15.2, 8.0 Hz) | OO; Peak 2 | (3R,4S)-3-fluoro-1-[4-({8-[(2R,3S)-3-(methanesulfonylmethyl)-2-methylazetidin-1-yl]-5-(propan-2-yl)-2,7-naphthyridin-3-yl}amino)pyrimidin-2-yl]-4-methylpiperidin-4-ol |
| 136 | 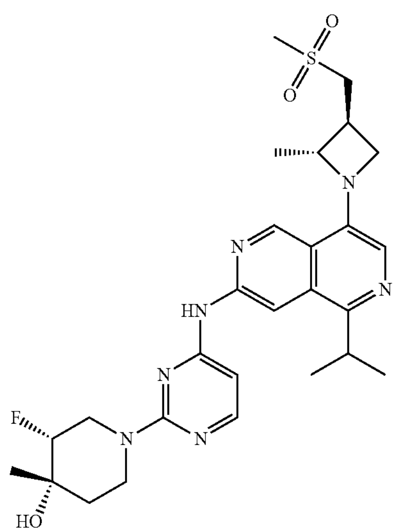 [SMILES: CC(C)c1ncc(N2C[C@H](CS(C)(=O)=O)[C@H]2C)c2cnc(Nc3ccnc(N4CC[C@](C)(O)[C@H](F)C4)n3)cc12] | 558 | 1H-NMR (300 MHz, 6d-DMSO) δ ppm 10.34 (s, 1H), 9.16 (s, 1H), 8.76 (s, 1H), 8.05 (d, 1H, J = 5.9 Hz), 7.75 (s, 1H), 6.52 (s, 1H), 4.92 (s, 1H), 4.75 (t, 1H, J = 7.6 Hz), 4.55-4.05 (m, 4H), 3.81-3.52 (m, 6H), 3.01 (s, 3H), 2.93 (q, 1H, J = 7.1 Hz), 1.80-1.56 (m, 2H), 1.49 (d, 3H, J = 6.0 Hz), 1.36-1.21 (m, 9H) | OO; Peak 2 | (3R,4S)-3-fluoro-1-[4-({8-[(2R,3S)-3-(methanesulfonylmethyl)-2-methylazetidin-1-yl]-5-(propan-2-yl)-2,6-naphthyridin-3-yl}amino)pyrimidin-2-yl]-4-methylpiperidin-4-ol |

TABLE 1-continued

| # | Structure | LC/MS | NMR | Separation Conditions | Chemical Name |
|---|---|---|---|---|---|
| 137 | 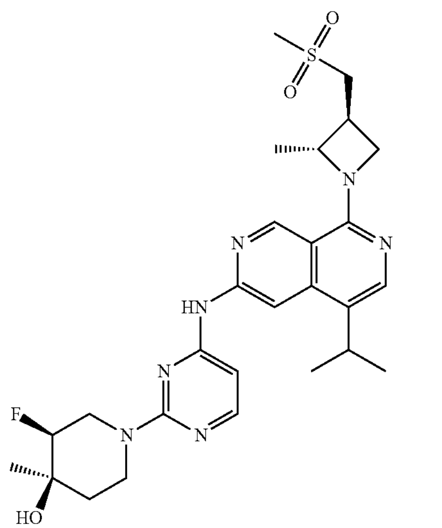 [SMILES: CC(C)c1cnc(N2C[C@H](CS(C)(=O)=O)[C@H]2C)c2cnc(Nc3ccnc(N4CC[C@@](C)(O)[C@@H](F)C4)n3)cc12] | 558 | 1H-NMR (300 MHz, 6d-DMSO) δ ppm 10.15 (s, 1H), 9.05 (s, 1H), 8.55 (s, 1H), 8.06 (d, 1H, J = 5.6 Hz), 8.01 (s, 1H), 6.52 (d, 1H, J = 5.6 Hz), 4.90-4.81 (m, 2H), 4.55 (t, 1H, J = 6.3 Hz), 4.47-4.41 (m, 2H), 4.32-4.12 (m, 2H), 3.98 (t, 1H, J = 7.3 Hz), 3.65-3.60 (m, 1H), 3.60-3.46 (m, 3H), 2.99 (s, 3H), 2.89 (q, 1H, J = 7.3 Hz), 1.74-1.68 (m, 1H), 1.62-1.46 (m, 4H), 1.30 (dd, 9H, J = 15.2, 8.0 Hz) | OO; Peak 1 | (3S,4R)-3-fluoro-1-[4-({8-[(2R,3S)-3-(methanesulfonyl-methyl)-2-methylazetidin-1-yl]-5-(propan-2-yl)-2,7-naphthyridin-3-yl}amino)pyrimidin-2-yl]-4-methyl-piperidin-4-ol |
| 138 | 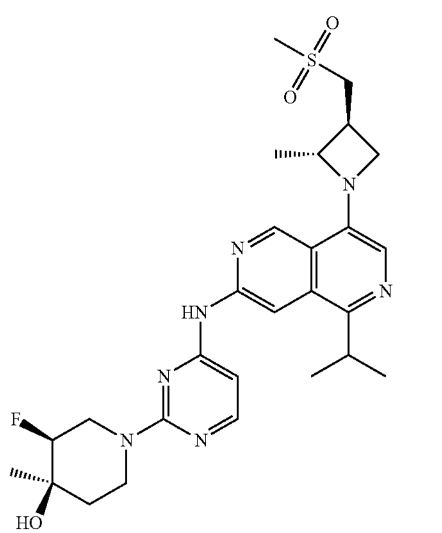 [SMILES: CC(C)c1ncc(N2C[C@H](CS(C)(=O)=O)[C@H]2C)c2cnc(Nc3ccnc(N4CC[C@@](C)(O)[C@@H](F)C4)n3)cc12] | 558 | 1H-NMR (300 MHz, 6d-DMSO) δ ppm 9.16 (s, 1H), 8.76 (s, 1H), 8.05 (d, 1H, J = 5.9 Hz), 7.75 (s, 1H), 6.52 (s, 1H), 5.01-4.82 (m, 1H), 4.75 (t, 1H, J = 7.6 Hz), 4.54-4.03 (m, 4H), 4.14 (s, 1H), 3.87-3.43 (m, 6H), 3.01 (s, 3H), 2.98-2.85 (m, 1H), 1.81-1.54 (m, 2H), 1.49 (d, 3H, J = 6.0 Hz), 1.34-1.24 (m, 9H) | OO; Peak 1 | (3S,4R)-3-fluoro-1-[4-({8-[(2R,3S)-3-(methanesulfonyl-methyl)-2-methylazetidin-1-yl]-5-(propan-2-yl)-2,6-naphthyridin-3-yl}amino)pyrimidin-2-yl]-4-methyl-piperidin-4-ol |
| 139 | 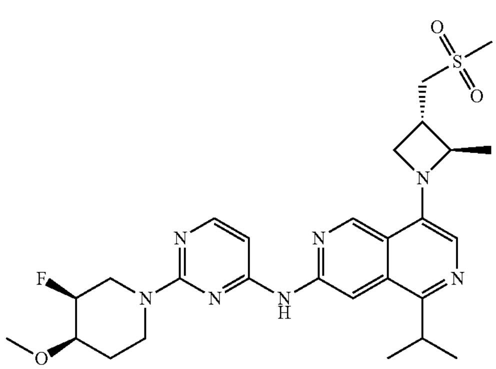 | 558 | 1H-NMR (300 MHz, 6d-DMSO) δ ppm 10.17 (s, 1H), 9.14 (s, 1H), 8.76 (s, 1H), 8.04 (d, 1H, J = 5.7 Hz), 7.74 (s, 1H), 6.47 (d, 1H, J = 5.7 Hz), 4.96 (d, 1H, J = 49.6 Hz), 4.74 (t, 2H, J = 7.6 Hz), 4.50 (d, 1H, J = 13.3 Hz), 4.37-4.27 (m, 1H), 3.82-3.44 (m, 6H), 3.38 (s, 3H), 3.01 (s, 3H), 3.05-2.86 (m, 1H), 1.95-1.69 (m, 2H), 1.48 (d, 3H, J = 6.1 Hz), 1.32 (t, 6H, J = 7.2 Hz) | | N-{2-[(3S,4R)-3-fluoro-4-methoxy-piperidin-1-yl]pyrimidin-4-yl}-8-[(2R,3S)-3-(methanesulfonyl-methyl)-2-methylazetidin-1-yl]-5-(propan-2-yl)-2,6-naphthyridin-3-amine |

TABLE 1-continued

| # | Structure | LC/MS | NMR | Separation Conditions | Chemical Name |
|---|---|---|---|---|---|
| 140 | 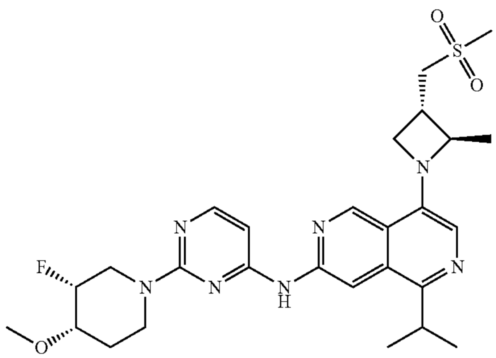 | 558 | 1H-NMR (400 MHz, 6d-DMSO) δ ppm 10.17 (s, 1H), 9.14 (s, 1H), 8.76 (s, 1H), 8.04 (d, 1H, J = 5.6 Hz), 7.74 (s, 1H), 6.47 (d, 1H, J = 5.6 Hz), 4.96 (d, 1H, J = 50.0 Hz), 4.80-4.69 (m, 2H), 4.56-4.45 (m, 1H), 4.32 (t, 1H, J = 6.3 Hz), 3.75 (dt, 3H, J = 16.2, 7.0 Hz), 3.57 (t, 3H, J = 6.7 Hz), 3.38 (s, 3H), 3.01 (s, 3H), 2.93 (q, 1H, J = 7.2 Hz), 1.91-1.68 (m, 2H), 1.48 (d, 3H, J = 6.0 Hz), 1.32 (d, 6H, J = 6.7 Hz) | | N-{2-[(3R,4S)-3-fluoro-4-methoxy-piperidin-1-yl]pyrimidin-4-yl}-8-[(2R,3S)-3-(methanesulfonyl-methyl)-2-methylazetidin-1-yl]-5-(propan-2-yl)-2,6-naphthyridin-3-amine |
| 141 | 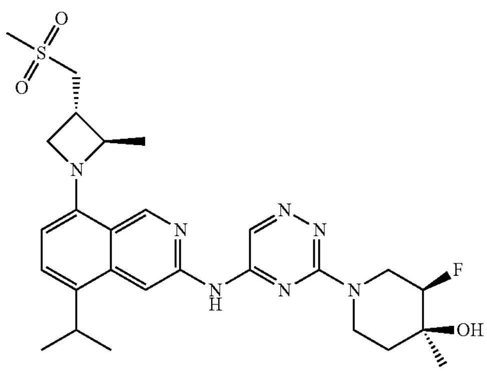 [SMILES: CC(C)c1ccc(N2C[C@H](CS(C)(=O)=O)[C@H]2C)c2cnc(Nc3cnnc(N4CC[C@](C)(O)[C@H](F)C4)n3)cc12] | 558 | 1H-NMR (300 MHz, 6d-DMSO) δ ppm 10.89 (s, 1H), 9.15 (s, 1H), 8.73 (s, 1H), 8.47 (s, 1H), 7.50 (d, 1H, J = 8.0 Hz), 6.66 (d, 1H, J = 8.1 Hz), 4.98 (s, 1H), 4.70 (t, 1H, J = 7.9 Hz), 4.56-4.29 (m, 2H), 4.29-4.07 (m, 2H), 3.67 (t, 2H, J = 7.5 Hz), 3.59-3.40 (m, 4H), 3.00 (s, 3H), 2.90 (q, 1H, J = 7.2 Hz), 1.81-1.59 (m, 2H), 1.47-1.39 (m, 3H), 1.36-1.25 (m, 9H) | M; Peak 1 | (3R,4S)-3-fluoro-1-[5-({8-[(2R,3S)-3-(methanesulfonyl-methyl)-2-methylazetidin-1-yl]-5-(propan-2-yl)isoquinolin-3-yl}amino)-1,2,4-triazin-3-yl]-4-methyl-piperidin-4-ol |
| 142 | 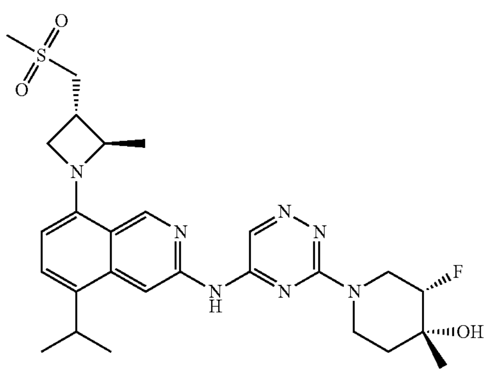 [SMILES: CC(C)c1ccc(N2C[C@H](CS(C)(=O)=O)[C@H]2C)c2cnc(Nc3cnnc(N4CC[C@@](C)(O)[C@@H](F)C4)n3)cc12] | 558 | 1H-NMR (300 MHz, 6d-DMSO) δ ppm 10.82 (s, 1H), 9.14 (s, 1H), 8.73 (s, 1H), 8.48 (s, 1H), 7.49 (d, 1H, J = 8.0 Hz), 6.66 (d, 1H, J = 8.1 Hz), 4.97 (s, 1H), 4.73-4.65 (m, 1H), 4.52-4.42 (m, 2H), 4.25-4.17 (m, 2H), 3.80-3.43 (m, 6H), 3.00 (s, 3H), 2.95-2.86 (m, 1H), 1.75 (s, 1H), 1.64 (s, 1H), 1.47-1.39 (m, 3H), 1.35-1.25 (m, 9H) | M; Peak 2 | (3S,4R)-3-fluoro-1-[5-({8-[(2R,3S)-3-(methanesulfonyl-methyl)-2-methylazetidin-1-yl]-5-(propan-2-yl)isoquinolin-3-yl}amino)-1,2,4-triazin-3-yl]-4-methyl-piperidin-4-ol |
| 143 | 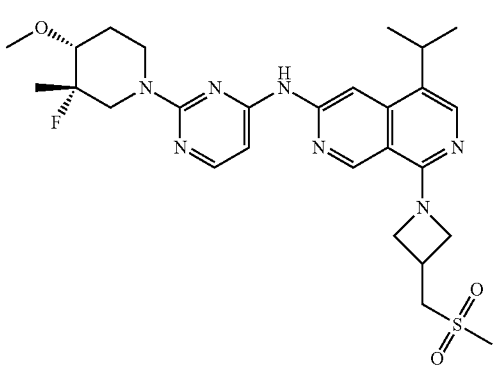 | 558 | 1H-NMR (400 MHz, 6d-DMSO) δ ppm 10.08 (s, 1H), 9.02 (s, 1H), 8.45 (s, 1H), 8.03 (d, 1H, J = 5.6 Hz), 7.98 (s, 1H), 6.53 (d, 1H, J = 5.6 Hz), 4.73-4.60 (m, 2H), 4.56 (t, 2H, J = 8.4 Hz), 4.21 (td, 2H, J = 6.7, 6.2, 3.4 Hz), 3.59 (d, 2H, J = 7.4 Hz), 3.38 (s, 3H), 3.31-3.12 (m, 5H), 3.01 (s, 3H), 1.97 (dd, 1H, J = 12.7, 4.0 Hz), 1.62 (q, 1H, J = 11.4 Hz), 1.39 (d, 3H, J = 21.2 Hz), 1.33-1.26 (m, 6H) | O; Peak 2 (intermediate stage) | N-{2-[(3S,4R)-3-fluoro-4-methoxy-3-methyl-piperidin-1-yl]pyrimidin-4-yl}-8-[3-(methanesulfonylmethyl)azetidin-1-yl]-5-(propan-2-yl)-2,7-naphthyridin-3-amine |

TABLE 1-continued

| # | Structure | LC/MS | NMR | Separation Conditions | Chemical Name |
|---|---|---|---|---|---|
| 144 | 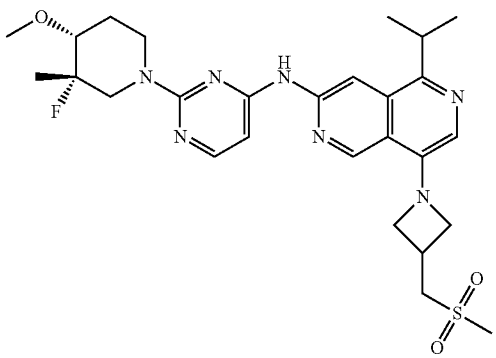 | 558 | 1H-NMR (300 MHz, 6d-DMSO) δ ppm 10.13 (s, 1H), 9.13 (s, 1H), 8.70 (s, 1H), 8.03 (d, 1H, J = 5.7 Hz), 7.60 (s, 1H), 6.48 (d, 1H, J = 5.7 Hz), 4.68 (d, 2H, J = 11.2 Hz), 4.49 (t, 2H, J = 7.7 Hz), 4.08 (t, 2H, J = 6.9 Hz), 3.71 (t, 1H, J = 6.7 Hz), 3.61 (d, 2H, J = 7.4 Hz), 3.39 (s, 3H), 3.29-3.17 (m, 4H), 3.03 (s, 3H), 2.01-1.95 (m, 1H), 1.69-1.63 (m, 1H), 1.41 (d, 3H, J = 21.3 Hz), 1.31 (dd, 6H, J = 6.7, 3.9 Hz) | | N-{2-[(3S,4R)-3-fluoro-4-methoxy-3-methyl-piperidin-1-yl]pyrimidin-4-yl}-8-[3-(methane-sulfonylmethyl)azetidin-1-yl]-5-(propan-2-yl)-2,6-naphthyridin-3-amine |
| 145 | 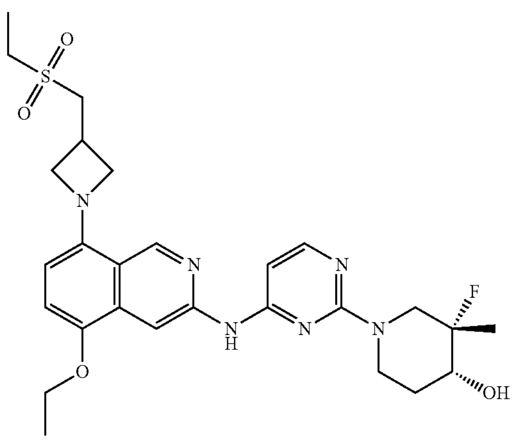 [SMILES: CCOc1ccc(N2CC(CS(=O)(=O)CC)C2)c2cnc(Nc3ccnc(N4CC[C@@H](O)[C@@](C)(F)C4)n3)cc12] | 559 | 1H-NMR (300 MHz, 6d-DMSO) δ ppm 9.89 (s, 1H), 9.01 (s, 1H), 8.67 (s, 1H), 7.98 (d, 1H, J = 5.6 Hz), 7.00 (d, 1H, J = 8.3 Hz), 6.43 (d, 1H, J = 5.7 Hz), 6.37 (d, 1H, J = 8.3 Hz), 4.99 (d, 1H, J = 6.3 Hz), 4.78 (dd, 1H, J = 14.1, 8.7 Hz), 4.68 (d, 1H, J = 13.3 Hz), 4.30 (t, 2H, J = 7.4 Hz), 4.17 (q, 2H, J = 6.9 Hz), 3.86 (t, 2H, J = 6.8 Hz), 3.61-3.43 (m, 3H), 3.24 (dd, 1H, J = 14.0, 6.9 Hz), 3.13 (q, 3H, J = 7.3 Hz), 1.75-1.69 (m, 2H), 1.47-1.35 (m, 4H), 1.34-1.19 (m, 5H) | NN; Peak 1 | (3S,4R)-1-{4-[(8-{3-[(ethane-sulfonyl)methyl]azetidin-1-yl}-5-ethoxyiso-quinolin-3-yl)amino]pyrimidin-2-yl}-3-fluoro-3-methyl-piperidin-4-ol |
| 146 | 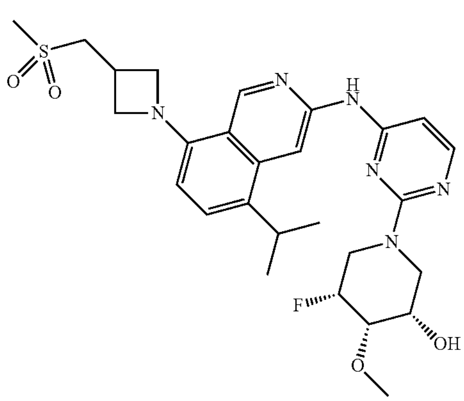 [SMILES: CO[C@@H]1[C@H](O)CN(c2nccc(Nc3cc4c(C(C)C)ccc(N5CC(CS(C)(=O)=O)C5)c4cn3)n2)C[C@@H]1F] | 559 | 1H NMR (400 MHz, MeOD-d4) δ 9.10 (s, 1H), 8.62 (s, 1H), 7.46 (d, J = 8.0 Hz, 1H), 6.52 (d, J = 8.0 Hz, 1H), 6.42 (d, J = 6.0 Hz, 1H), 4.76-4.53 (m, 2H), 4.42 (t, J = 7.2 Hz, 3H), 4.01 (t, J = 6.4 Hz, 2H), 3.85 (br d, J = 12.4 Hz, 1H), 3.73 (br s, 1H), 3.67-3.55 (m, 7H), 3.47-3.34 (m, 2H), 3.03 (s, 3H), 1.35 (d, J = 6.8 Hz, 6H) | | (3R,4R,5S)-5-fluoro-1-(4-((5-isopropyl-8-(3-((methylsulfonyl)methyl)azetidin-1-yl)isoquinolin-3-yl)amino)pyrimidin-2-yl)-4-methoxy-piperidin-3-ol and (3S,4S,5R)-5-fluoro-1-(4-((5-isopropyl-8-(3-((methyl-sulfonyl)methyl)azetidin-1-yl)isoquinolin-3- |

| # | Structure | LC/MS | NMR | Separation Conditions | Chemical Name |
|---|---|---|---|---|---|
| | | | | | yl)amino)pyrimidin-2-yl)-4-methoxy-piperidin-3-ol |
| 147 | | 559 | 1H NMR (400 MHz, MeOD-d4) δ 9.10 (s, 1H), 8.61 (s, 1H), 7.97 (d, J = 5.6 Hz, 1H), 7.46 (d, J = 8.0 Hz, 1H), 6.51 (d, J = 8.0 Hz, 1H), 6.42 (d, J = 5.6 Hz, 1H), 4.77-4.60 (m, 2H), 4.49-4.40 (m, 3H), 4.01 (t, J = 8.0 Hz, 2H), 3.86-3.80 (m, 1H), 3.76-3.70 (m, 1H), 3.65-3.57 (m, 7H), 3.44-3.36 (m, 2H), 3.02 (s, 3H), 1.35 (d, J = 6.8 Hz, 6H) | | (3S,4R,5R)-3-fluoro-1-(4-((5-isopropyl-8-(3-((methylsulfonyl)methyl)azetidin-1-yl)isoquinolin-3-yl)amino)pyrimidin-2-yl)-5-methoxy-piperidin-4-ol and (3R,4S,5S)-3-fluoro-1-(4-((5-isopropyl-8-(3-((methyl-sulfonyl)methyl)azetidin-1-yl)isoquinolin-3-yl)amino)pyrimidin-2-yl)-5-methoxy-piperidin-4-ol |
| 148 | 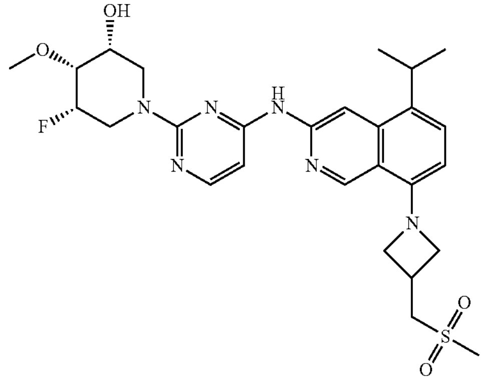 | 559 | 1H NMR (400 MHz, MeOD-d4) δ 9.10 (s, 1H), 8.61 (s, 1H), 7.97 (d, J = 5.6 Hz, 1H), 7.46 (d, J = 8.0 Hz, 1H), 6.51 (d, J = 8.0 Hz, 1H), 6.42 (d, J = 5.6 Hz, 1H), 4.77-4.60 (m, 2H), 4.49-4.40 (m, 3H), 4.01 (t, J = 8.0 Hz, 2H), 3.86-3.80 (m, 1H), 3.76-3.70 (m, 1H), 3.65-3.57 (m, 7H), 3.44-3.36 (m, 2H), 3.02 (s, 3H), 1.35 (d, J = 6.8 Hz, 6H) | P; Peak 1 | (3R,4R,5S)-5-fluoro-1-[4-({8-[3-(methanesulfonyl-methyl)azetidin-1-yl]-5-(propan-2-yl)isoquinolin-3-yl}amino)pyrimidin-2-yl]-4-methoxy-piperidin-3-ol or (3S,4S,5R)-5-fluoro-1-[4-({8-[3-(methane-sulfonylmethyl)azetidin-1-yl]-5-(propan-2-yl)isoquinolin-3- |

TABLE 1-continued

| # | Structure | LC/MS | NMR | Separation Conditions | Chemical Name |
|---|---|---|---|---|---|
| | | | | | yl}amino)pyrimidin-2-yl]-4-methoxy-piperidin-3-ol |
| 149 | | 559 | 1H NMR (400 MHz, MeOD-d4) δ 9.10 (s, 1H), 8.61 (s, 1H), 7.99 (d, J = 5.6 Hz, 1H), 7.46 (d, J = 8.0 Hz, 1H), 6.52 (d, J = 8.0 Hz, 1H), 6.42 (d, J = 5.6 Hz, 1H), 4.64-4.59 (m, 1H), 4.54-4.36 (m, 5H), 4.05-3.95 (m, 2H), 3.74-3.57 (m, 4H), 3.50-3.47 (m, 1H), 3.43 (s, 3H), 3.42-3.35 (m, 2H), 3.03 (s, 3H), 1.35 (dd, J = 3.2, 6.8 Hz, 6H) | P; Peak 2 | (3S,4R,5R)-3-fluoro-1-[4-({8-[3-(methanesulfonylmethyl)azetidin-1-yl]-5-(propan-2-yl)isoquinolin-3-yl}amino)pyrimidin-2-yl]-5-methoxy-piperidin-4-ol or (3R,4S,5S)-3-fluoro-1-[4-({8-[3-(methanesulfonylmethyl)azetidin-1-yl]-5-(propan-2-yl)isoquinolin-3-yl}amino)pyrimidin-2-yl]-5-methoxy-piperidin-4-ol |
| 150 | 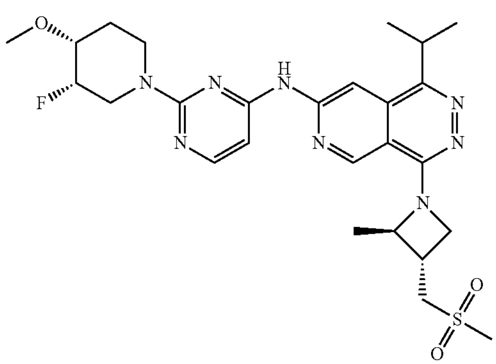 | 559 | 1H-NMR (400 MHz, 6d-DMSO) δ ppm 10.43 (s, 1H), 9.11 (s, 1H), 8.62 (s, 1H), 8.09 (d, 1H, J = 5.6 Hz), 6.54 (d, 1H, J = 5.6 Hz), 5.09-4.82 (m, 2H), 4.74-4.61 (m, 2H), 4.46 (d, 1H, J = 13.2 Hz), 4.07 (t, 1H, J = 7.3 Hz), 3.73-3.42 (m, 5H), 3.37 (s, 3H), 3.00 (s, 3H), 2.97-2.88 (m, 1H), 1.86-1.69 (m, 2H), 1.54 (d, 3H, J = 6.1 Hz), 1.37 (td, 6H, J = 6.6, 3.8 Hz) | | 2-[(3S,4R)-3-fluoro-4-methoxy-piperidin-1-yl]-N-{4-[(2R,3S)-3-(methane-sulfonylmethyl)-2-methyl-azetidin-1-yl]-1-(propan-2-yl)pyrido[3,4-d]pyridazin-7-yl}pyrimidin-4-amine |

TABLE 1-continued

| # | Structure | LC/MS | NMR | Separation Conditions | Chemical Name |
|---|---|---|---|---|---|
| 151 | 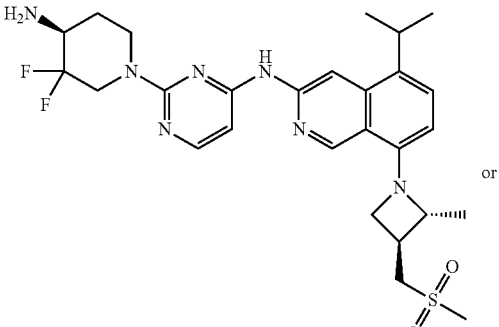 | 560 | 1H-NMR (400 MHz, 6d-DMSO) δ ppm 10.03 (s, 1H), 9.07 (s, 1H), 8.59 (s, 1H), 8.03 (d, 1H, J = 5.7 Hz), 7.43 (d, 1H, J = 8.0 Hz), 6.57 (d, 1H, J = 8.1 Hz), 6.53 (d, 1H, J = 5.8 Hz), 4.89-4.81 (m, 1H), 4.66 (t, 1H, J = 7.5 Hz), 4.55 (d, 1H, J = 13.6 Hz), 4.19 (q, 1H, J = 6.2 Hz), 3.72-3.55 (m, 2H), 3.58-3.45 (m, 4H), 3.39-3.33 (m, 1H), 3.00 (s, 3H), 2.89 (h, 1H, J = 7.2 Hz), 2.01-1.97 (m, 1H), 1.66-1.56 (m, 1H), 1.42 (d, 3H, J = 6.1 Hz), 1.30 (dd, 6H, J = 6.8, 3.9 Hz) | M; Peak 1 | N-{2-[(4S)-4-amino-3,3-difluoro-piperidin-1-yl]pyrimidin-4-yl}-8-[(2R,3S)-3-(methanesulfonyl-methyl)-2-methyl-azetidin-1-yl]-5-(propan-2-yl)isoquinolin-3-amine or N-{2-[(4R)-4-amino-3,3-difluoro-piperidin-1-yl]pyrimidin-4-yl}-8-[(2R,3S)-3-(methanesulfonyl-methyl)-2-methylazetidin-1-yl]-5-(propan-2-yl)isoquinolin-3-amine |
| | 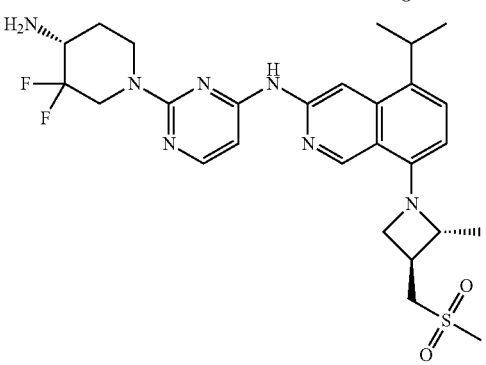 | | | | |
| 152 | 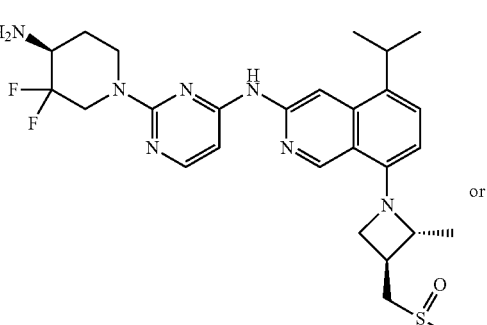 | 560 | 1H-NMR (300 MHz, 6d-DMSO) δ ppm 9.99 (s, 1H), 9.06 (s, 1H), 8.61 (s, 1H), 8.02 (d, 1H, J = 5.7 Hz), 7.43 (d, 1H, J = 8.0 Hz), 6.57 (d, 1H, J = 8.1 Hz), 6.51 (d, 1H, J = 5.6 Hz), 4.68 (q, 2H, J = 9.3, 7.3 Hz), 4.43-4.32 (m, 1H), 4.19 (t, 1H, J = 6.2 Hz), 3.79-3.56 (m, 2H), 3.57-3.35 (m, 4H), 3.24-3.18 (m, 1H), 2.99 (s, 3H), 2.88 (q, 1H, J = 7.3 Hz), 1.90-1.84 (m, 1H), 1.61-1.51 (m, 1H), 1.42 (d, 3H, J = 6.0 Hz), 1.30 (dd, 6H, J = 6.7, 1.9 Hz) | M; Peak 2 | N-{2-[(4R)-4-amino-3,3-difluoro-piperidin-1-yl]pyrimidin-4-yl}-8-[(2R,3S)-3-(methanesulfonyl-methyl)-2-methylazetidin-1-yl]-5-(propan-2-yl)isoquinolin-3-amine or N-{2-[(4S)-4-amino-3,3-difluoro-piperidin-1-yl]pyrimidin-4-yl}-8-[(2R,3S)-3-(methanesulfonyl-methyl)-2-methylazetidin-1-yl]-5-(propan-2-yl)isoquinolin-3-amine |
| | 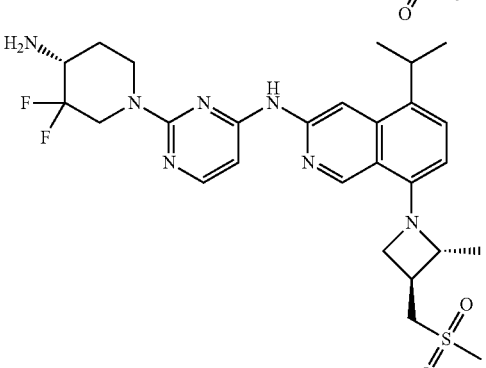 | | | | |

TABLE 1-continued

| # | Structure | LC/MS | NMR | Separation Conditions | Chemical Name |
|---|---|---|---|---|---|
| 153 | 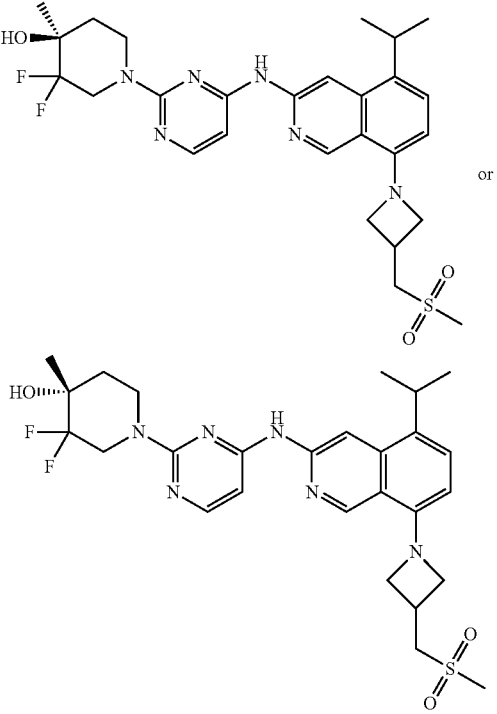 | 561 | 1H-NMR (300 MHz, 6d-DMSO) δ ppm 9.93 (s, 1H), 9.04 (s, 1H), 8.58 (s, 1H), 8.00 (d, 1H, J = 5.7 Hz), 7.40 (d, 1H, J = 8.0 Hz), 6.50 (d, 1H, J = 5.7 Hz), 6.40 (d, 1H, J = 8.0 Hz), 5.53 (s, 1H), 4.77-4.65 (m, 1H), 4.51-4.32 (m, 3H), 3.95 (t, 2H, J = 6.9 Hz), 3.64 (dd, 3H, J = 40.3, 10.4 Hz), 3.53-3.42 (m, 1H), 3.22-3.17 (m, 1H), 3.00 (s, 3H), 1.77-1.65 (m, 2H), 1.31-1.18 (m, 9H) | F; Peak 2 | (4S)-3,3-difluoro-1-[4-({8-[3-(methanesulfonyl-methyl)azetidin-1-yl]-5-(propan-2-yl)isoquinolin-3-yl}amino)pyrimidin-2-yl]-4-methyl-piperidin-4-ol or (4R)-3,3-difluoro-1-[4-({8-[3-(methanesulfonyl-methyl)azetidin-1-yl]-5-(propan-2-yl)isoquinolin-3-yl}amino)pyrimidin-2-yl]-4-methyl-piperidin-4-ol |
| 154 | 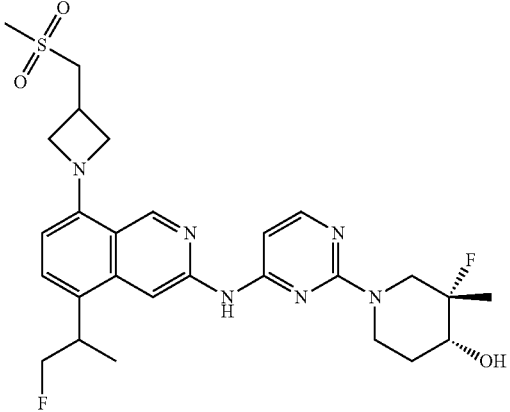 | 561 | 1H-NMR (300 MHz, 6d-DMSO) δ ppm 9.82 (s, 1H), 9.07 (s, 1H), 8.34 (s, 1H), 8.00 (d, 1H, J = 5.6 Hz), 7.41 (d, 1H, J = 7.9 Hz), 6.58 (d, 1H, J = 5.7 Hz), 6.38 (d, 1H, J = 7.9 Hz), 5.15-4.84 (m, 2H), 4.75 (dd, 2H, J = 25.4, 14.9 Hz), 4.42 (t, 2H, J = 7.7 Hz), 4.00 (t, 2H, J = 6.9 Hz), 3.60 (d, 2H, J = 7.3 Hz), 3.49 (dt, 1H, J = 11.2, 6.7 Hz), 3.31-3.06 (m, 4H), 3.02 (s, 3H), 1.83-1.55 (m, 2H), 1.44-1.12 (m, 6H) | NN; Peak 1 | (3S,4R)-3-fluoro-1-(4-{[5-(1-fluoro-propan-2-yl)-8-[3-(methanesulfonyl-methyl)azetidin-1-yl]isoquinolin-3-yl]amino}pyrimidin-2-yl)-3-methyl-piperidin-4-ol |
| 155 | 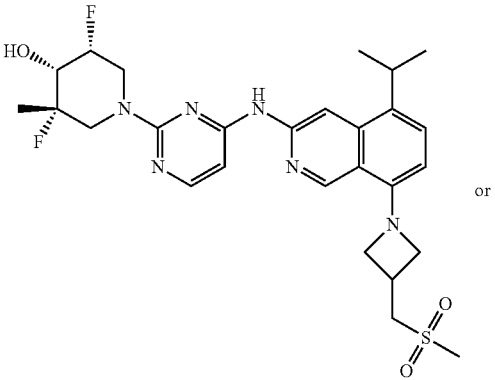 | 561 | 1H-NMR (300 MHz, 6d-DMSO) δ ppm 9.94 (s, 1H), 9.07 (s, 1H), 8.54 (s, 1H), 8.02 (d, 1H, J = 5.7 Hz), 7.42 (d, 1H, J = 8.0 Hz), 6.58 (d, 1H, J = 5.7 Hz), 6.42 (d, 1H, J = 8.1 Hz), 5.68 (d, 1H, J = 6.0 Hz), 5.10-5.00 (m, 1H), 4.92-4.78 (m, 1H), 4.66-4.44 (m, 1H), 4.40 (t, 2H, J = 7.7 Hz), 3.97 (t, 2H, J = 6.9 Hz), 3.74-3.44 (m, 5H, J = 19.8, 7.1 Hz), 3.31-3.08 (m, 3H), 3.02 (s, 3H), 1.41 (d, 3H, J = 21.5 Hz), 1.30 (d, 6H, J = 6.7 Hz) | C; Peak 1 | (3S,4R,5R)-3,5-difluoro-1-[4-({8-[3-(methanesulfonyl-methyl)azetidin-1-yl]-5-(propan-2-yl)isoquinolin-3-yl}amino)pyrimidin-2-yl]-3-methyl-piperidin-4-ol or (3R,4S,5S)-3,5-difluoro-1-[4-({8-[3-(methanesulfonyl-methyl)azetidin-1-yl]-5-(propan- |

TABLE 1-continued

| # | Structure | LC/MS | NMR | Separation Conditions | Chemical Name |
|---|---|---|---|---|---|
| | | | | | 2-yl)isoquinolin-3-yl}amino)pyrimidin-2-yl]-3-methyl-piperidin-4-ol |
| 156 | | 561 | 1H-NMR (300 MHz, 6d-DMSO) δ ppm 9.91 (s, 1H), 9.04 (s, 1H), 8.54 (s, 1H), 8.00 (d, 1H, J = 5.7 Hz), 7.40 (d, 1H, J = 8.0 Hz), 6.54 (d, 1H, J = 5.7 Hz), 6.40 (d, 1H, J = 8.1 Hz), 5.85 (d, 1H, J = 5.3 Hz), 4.89-4.62 (m, 1H), 4.37 (t, 2H, J = 7.7 Hz), 4.26-4.10 (m, 1H), 4.10-4.01 (m, 1H), 4.03-3.72 (m, 5H), 3.57 (d, 2H, J = 7.4 Hz), 3.54-3.42 (m, 1H), 3.29-3.19 (m, 1H), 3.00 (s, 3H), 1.45-1.19 (m, 9H) | I; Peak 2 | (3R,4R,5R)-3,5-difluoro-1-[4-({8-[3-(methanesulfonylmethyl)azetidin-1-yl]-5-(propan-2-yl)isoquinolin-3-yl}amino)pyrimidin-2-yl]-3-methyl-piperidin-4-ol or (3S,4S,5S)-3,5-difluoro-1-[4-({8-[3-(methanesulfonylmethyl)azetidin-1-yl]-5-(propan-2-yl)isoquinolin-3-yl}amino)pyrimidin-2-yl]-3-methyl-piperidin-4-ol |

TABLE 1-continued

| # | Structure | LC/MS | NMR | Separation Conditions | Chemical Name |
|---|---|---|---|---|---|
| 157 | 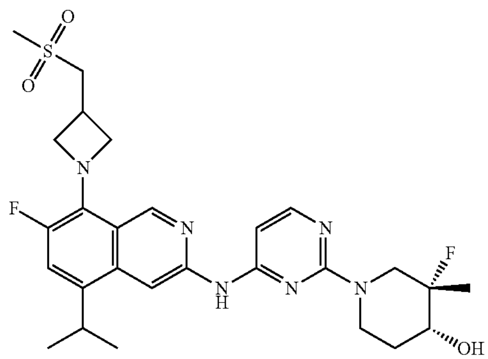 [SMILES: CC(C)c1cc(F)c(N2CC(CS(C)(=O)=O)C2)c2cnc(Nc3ccnc(N4CC[C@@H](O)[C@@](C)(F)C4)n3)cc12] | 561 | 1H-NMR (300 MHz, 6d-DMSO) δ ppm 9.84 (s, 1H), 9.07 (s, 1H), 8.56 (s, 1H), 7.97 (d, 1H, J = 5.6 Hz), 7.31 (d, 1H, J = 15.6 Hz), 6.44 (d, 1H, J = 5.6 Hz), 5.00 (d, 1H, J = 6.3 Hz), 4.71-4.65 (m, 1H), 4.63-4.57 (m, 3H), 4.24-4.18 (m, 2H), 3.56 (d, 2H, J = 7.4 Hz), 3.52-3.46 (m, 2H), 3.25-3.07 (m, 2H), 2.98 (s, 3H), 1.74-1.68 (m, 2H), 1.43-1.18 (m, 9H) | NN; Peak 1 | (3S,4R)-3-fluoro-1-[4-({7-fluoro-8-[3-(methanesulfonyl-methyl)azetidin-1-yl]-5-(propan-2-yl)isoquinolin-3-yl}amino)pyrimidin-2-yl]-3-methyl-piperidin-4-ol |
| 158 | 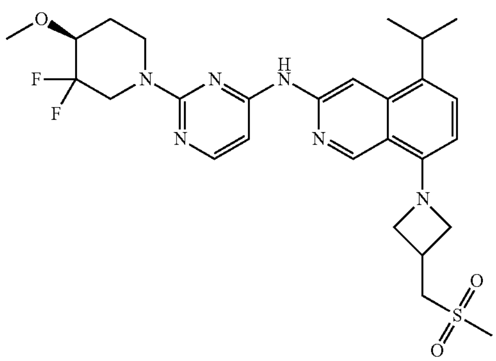 | 561 | 1H-NMR (300 MHz, 6d-DMSO) δ ppm 9.94 (s, 1H), 9.04 (s, 1H), 8.54 (s, 1H), 8.01 (d, 1H, J = 5.7 Hz), 7.41 (d, 1H, J = 8.0 Hz), 6.54 (d, 1H, J = 5.7 Hz), 6.40 (d, 1H, J = 8.0 Hz), 4.46-4.24 (m, 3H), 4.06-4.00 (m, 2H), 3.95 (t, 2H, J = 6.9 Hz), 3.75 (s, 2H), 3.57 (d, 2H, J = 7.4 Hz), 3.49 (d, 1H, J = 6.6 Hz), 3.45 (s, 3H), 3.00 (s, 3H), 1.98-1.92 (m, 1H), 1.78-1.72 (m, 1H), 1.27 (d, 6H, J = 6.7 Hz) | PP; Peak 1 | N-{2-[(4S)-3,3-difluoro-4-methoxy-piperidin-1-yl]pyrimidin-4-yl}-8-[3-(methanesulfonyl-methyl)azetidin-1-yl]-5-(propan-2-yl)isoquinolin-3-amine |
| 159 | 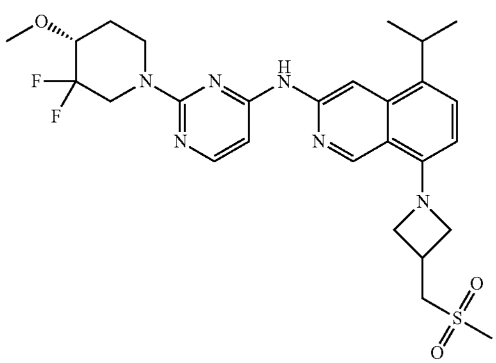 | 561 | 1H-NMR (300 MHz, 6d-DMSO) δ ppm 9.94 (s, 1H), 9.04 (s, 1H), 8.54 (s, 1H), 8.01 (d, 1H, J = 5.6 Hz), 7.41 (d, 1H, J = 7.9 Hz), 6.54 (d, 1H, J = 5.7 Hz), 6.40 (d, 1H, J = 8.0 Hz), 4.43-4.23 (m, 2H), 4.03 (s, 2H), 3.95 (t, 2H, J = 6.8 Hz), 3.79-3.68 (m, 2H), 3.57 (d, 2H, J = 7.3 Hz), 3.46-3.53 (m, 1H), 3.45 (s, 3H), 3.00 (s, 3H), 1.97-1.91 (m, 1H), 1.78-1.72 (m, 1H), 1.27 (d, 6H, J = 6.7 Hz) | PP; Peak 2 | N-{2-[(4R)-3,3-difluoro-4-methoxy-piperidin-1-yl]pyrimidin-4-yl}-8-[3-(methanesulfonyl-methyl)azetidin-1-yl]-5-(propan-2-yl)isoquinolin-3-amine |
| 160 | 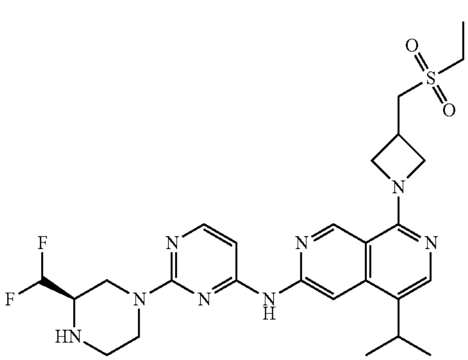 [SMILES: CCS(=O)(=O)CC1CN(c2ncc(C(C)C)c3cc(Nc4ccnc(N5CCN[C@H](C(F)F)C5)n4)ncc23)C1] | 561 | 1H-NMR (400 MHz, 6d-DMSO) δ ppm 10.12 (s, 1H), 9.02 (s, 1H), 8.47 (s, 1H), 8.08 (d, 1H, J = 5.6 Hz), 7.98 (s, 1H), 6.58 (d, 1H, J = 5.7 Hz), 5.97 (t, 1H), 4.65-4.51 (m, 3H), 4.44 (d, 1H, J = 12.5 Hz), 4.22 (td, 2H, J = 6.6, 3.3 Hz), 3.58 (d, 2H, J = 7.4 Hz), 3.31-3.25 (m, 2H), 3.11 (q, 3H, J = 7.4 Hz), 3.01 (t, 3H, J = 9.9 Hz), 2.80-2.64 (m, 2H), 1.38-1.14 (m, 9H) | I; Peak 2 | N-{2-[(3R)-3-(difluoromethyl)piperazin-1-yl]pyrimidin-4-yl}-8-{3-[(ethane-sulfonyl)methyl]azetidin-1-yl}-5-(propan-2-yl)-2,7-naph-thyridin-3-amine or N-{2-[(3S)-3-(difluoromethyl)piperazin-1-yl]pyrimidin-4-yl}-8-{3-[(ethane-sulfonyl)methyl] |

TABLE 1-continued

| # | Structure | LC/MS | NMR | Separation Conditions | Chemical Name |
|---|---|---|---|---|---|
| | | | | | azetidin-1-yl}-5-(propan-2-yl)-2,7-naphthyridin-3-amine |
| 161 | | 561 | 1H-NMR (300 MHz, 6d-DMSO) δ ppm 10.19 (s, 1H), 9.14 (s, 1H), 8.76 (s, 1H), 8.04 (d, 1H, J = 5.7 Hz), 7.74 (s, 1H), 6.47 (d, 1H, J = 5.7 Hz), 4.96 (dd, 1H, J = 49.5, 4.7 Hz), 4.74 (dd, 2H, J = 9.2, 6.0 Hz), 4.50 (d, 1H, J = 13.2 Hz), 4.32 (p, 1H, J = 6.1 Hz), 3.83-3.58 (m, 3H), 3.62-3.38 (m, 3H), 3.33-3.23 (m, 1H), 3.01 (s, 3H), 2.92 (p, 1H, J = 7.3 Hz), 1.90-1.70 (m, 2H), 1.48 (d, 3H, J = 6.0 Hz), 1.32 (d, 6H, J = 6.6 Hz) | G; Peak 1 | N-{2-[(3S,4R)-3-fluoro-4-($^2$H3)methoxypiperidin-1-yl]pyrimidin-4-yl}-8-[(2R,3S)-3-(methanesulfonylmethyl)-2-methylazetidin-1-yl]-5-(propan-2-yl)-2,6-naphthyridin-3-amine or N-{2-[(3R,4S)-3-fluoro-4-($^2$H3)methoxypiperidin-1-yl]pyrimidin-4-yl}-8-[(2R,3S)-3-(methanesulrfonylmethyl)-2-methylazetidin-1-yl]-5-(propan-2-yl)-2,6-naphthyridin-3-amine |
| 162 | 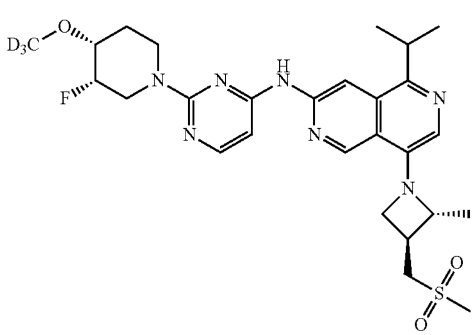 [SMILES: [2H]C([2H])([2H])O[C@H]1CCN(c2nccc(Nc3cc4c(C(C)C)ncc(N5C[C@H](CS(C)(=O)=O)[C@H]5C)c4cn3)n2)C[C@H]1F] | 561 | 1H-NMR (300 MHz, 6d-DMSO) δ ppm 10.18 (s, 1H), 9.14 (s, 1H), 8.76 (s, 1H), 8.04 (d, 1H, J = 5.6 Hz), 7.73 (s, 1H), 6.47 (d, 1H, J = 5.7 Hz), 4.96 (d, 1H, J = 50.2 Hz), 4.74 (t, 1H, J = 7.5 Hz), 4.50 (d, 1H, J = 13.6 Hz), 4.32 (p, 1H, J = 6.1 Hz), 3.83-3.71 (m, 3H), 3.75-3.43 (m, 3H), 3.33-3.23 (m, 1H), 3.01 (s, 3H), 2.93 (q, 1H, J = 7.2 Hz), 1.90-1.69 (m, 2H), 1.48 (d, 3H, J = 6.0 Hz), 1.39-1.27 (m, 6H) | G; Peak 2 | N-{2-[(3R,4S)-3-fluoro-4-($^2$H3)methoxypiperidin-1-yl]pyrimidin-4-yl}-8-[(2R,3S)-3-(methanesulfonylmethyl)-2-methylazetidin-1-yl]-5-(propan-2-yl)-2,6-naphthyridin-3-amine or N-{2-[(3S,4R)-3-fluoro-4- |

TABLE 1-continued

| # | Structure | LC/MS | NMR | Separation Conditions | Chemical Name |
|---|---|---|---|---|---|
| | | | | | (²H3)methoxypiperidin-1-yl]pyrimidin-4-yl}-8-[(2R,3S)-3-(methanesulfonylmethyl)-2-methylazetidin-1-yl]-5-(propan-2-yl)-2,6-naphthyridin-3-amine |
| 163 | 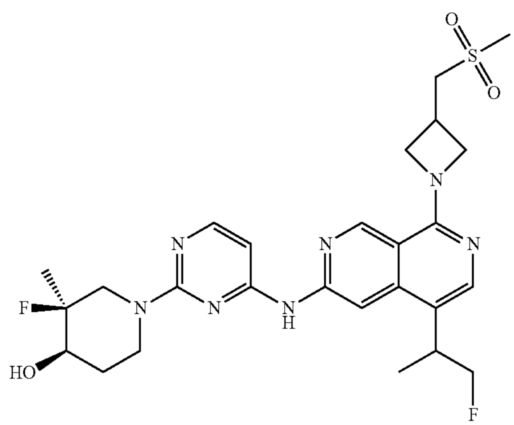 [SMILES: CC(CF)c1cnc(N2CC(CS(C)(=O)=O)C2)c2cnc(Nc3ccnc(N4CC[C@@H](O)[C@@](C)(F)C4)n3)cc12] | 562 | 1H NMR (400 MHz, DMSO-d6) δ 10.08 (s, 1H), 9.03 (s, 1H), 8.49 (s, 1H), 8.08-7.93 (m, 2H), 6.48 (d, J = 5.6 Hz, 1H), 5.00 (d, J = 6.4 Hz, 1H), 4.75-4.51 (m, 6H), 3.82 (s, 2H), 3.62-3.46 (m, 1H), 3.19-3.04 (m, 2H), 2.76 (s, 3H), 1.72 (br.s, 2H), 1.49-1.16 (m, 11H). | NN; Peak 1 | (3S,4R)-3-fluoro-1-(4-{[5-(1-fluoropropan-2-yl)-8-[3-(methanesulfonylmethyl)azetidin-1-yl]-2,7-naphthyridin-3-yl]amino}pyrimidin-2-yl)-3-methylpiperidin-4-ol |
| 164 | | 564 | 1H-NMR (300 MHz, 6d-DMSO) δ ppm 10.06 (s, 1H), 9.07 (s, 1H), 8.59 (s, 1H), 8.03 (d, 1H, J = 5.8 Hz), 7.44 (d, 1H, J = 8.0 Hz), 6.58 (d, 2H, J = 8.1 Hz), 4.81 (d, 1H, J = 13.7 Hz), 4.66 (t, 1H, J = 7.6 Hz), 4.60-4.54 (m, 1H), 4.20 (t, 1H, J = 6.5 Hz), 3.72-3.43 (m, 8H), 3.27-3.10 (m, 1H), 2.99 (s, 3H), 2.93-2.84 (m, 1H), 1.98-1.92 (m, 1H), 1.68-1.62 (m, 1H), 1.42 (d, 3H, J = 6.0 Hz), 1.32 (d, 6H, J = 6.7 Hz) | B; Peak 1 | (3S,4S)-1-[4-({8-[(2R,3S)-3-(methanesulfonylmethyl)-2-methylazetidin-1-yl]-5-(propan-2-yl)isoquinolin-3-yl}amino)pyrimidin-2-yl]-4-methoxypiperidine-3-carbonitrile or (3R,4R)-1-[4-({8-[(2R,3S)-3-(methanesulfonylmethyl)-2-methylazetidin-1-yl]-5-(propan-2-yl)isoquinolin-3-yl}amino)pyrimidin-2-yl]-4-methoxypiperidine-3-carbonitrile |

TABLE 1-continued

| # | Structure | LC/MS | NMR | Separation Conditions | Chemical Name |
|---|---|---|---|---|---|
| 165 | 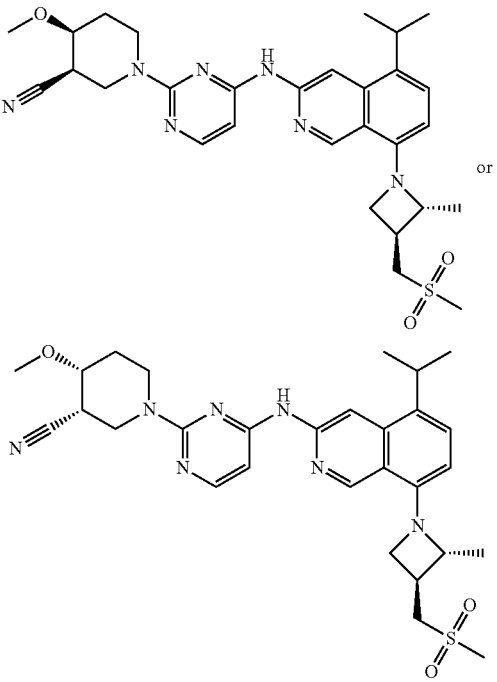 or 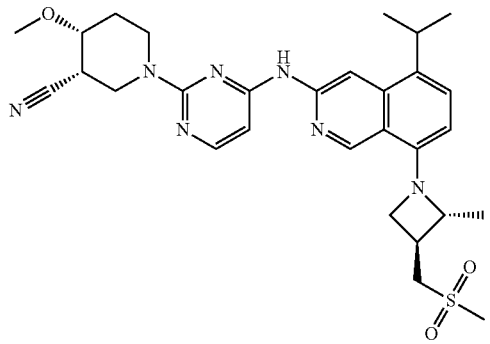 | 564 | 1H-NMR (300 MHz, 6d-DMSO) δ ppm 10.04 (s, 1H), 9.07 (s, 1H), 8.58 (s, 1H), 8.03 (d, 1H, J = 5.7 Hz), 7.44 (d, 1H, J = 8.1 Hz), 6.62-6.42 (m, 2H), 4.92-4.44 (m, 3H), 4.22-4.14 (m, 1H), 3.76-3.40 (m, 8H), 3.31-3.13 (m, 1H), 2.99 (s, 3H), 2.90-2.84 (m, 1H), 1.98-1.92 (m, 1H), 1.76-1.56 (m, 1H), 1.42 (d, 3H, J = 6.0 Hz), 1.32 (dd, 6H, J = 6.8, 2.8 Hz) | B; Peak 2 | (3R,4R)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methoxy-piperidine-3-carbonitrile or (3S,4S)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methoxy-piperidine-3-carbonitrile |
| 166 | 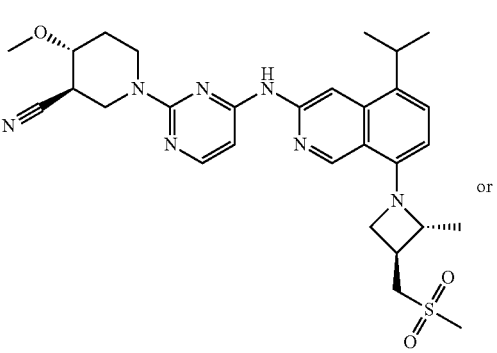 or 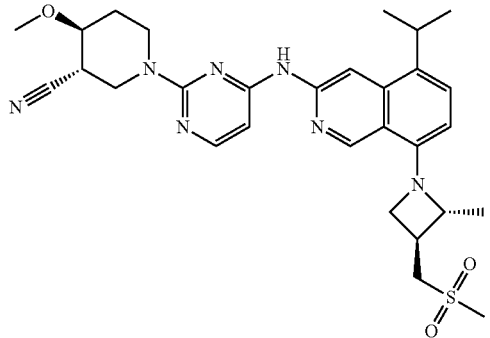 | 564 | 1H-NMR (300 MHz, 6d-DMSO) δ ppm 10.05 (s, 1H), 9.06 (s, 1H), 8.54 (s, 1H), 8.04 (d, 1H, J = 5.8 Hz), 7.43 (d, 1H, J = 8.0 Hz), 6.57 (d, 2H, J = 7.8 Hz), 4.66 (t, 1H, J = 7.4 Hz), 4.50-4.39 (m, 1H), 4.32-4.07 (m, 2H), 3.77-3.48 (m, 8H), 3.38-3.21 (m, 3H), 2.99 (s, 3H), 2.93-2.84 (m, 1H), 2.15-2.05 (m, 1H), 1.52-1.38 (m, 4H), 1.31 (dd, 6H, J = 8.9, 6.8 Hz) | K; Peak 2 | (3S,4R)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methoxy-piperidine-3-carbonitrile or (3R,4S)-1-[4-({8-[(2R,3S)-(methanesulfonyl-methyl)-2-methylazetidin-1-yl]-5-(propan-2-yl)isoquinolin-3-yl}amino)pyrimidin-2-yl]-4-methoxy-piperidine-3-carbonitrile |

TABLE 1-continued

| # | Structure | LC/MS | NMR | Separation Conditions | Chemical Name |
|---|---|---|---|---|---|
| 167 | 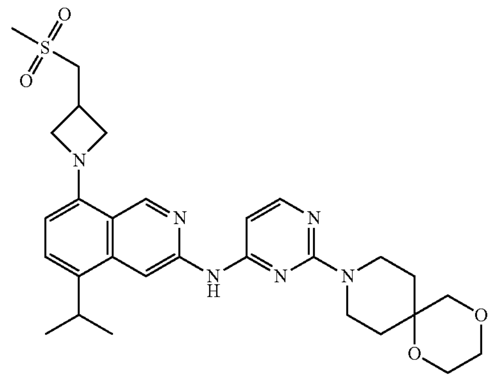 [SMILES: CC(C)c1ccc(N2CC(CS(C)(=O)=O)C2)c2cnc(Nc3ccnc(N4CCC5(CC4)COCCO5)n3)cc12] | 567 | 1H-NMR (300 MHz, 6d-DMSO) δ ppm 9.84 (s, 1H), 9.03 (s, 1H), 8.66 (s, 1H), 7.98 (d, 1H, J = 5.6 Hz), 7.40 (d, 1H, J = 8.0 Hz), 6.46-6.35 (m, 2H), 4.43-4.26 (m, 4H), 3.94 (t, 2H, J = 6.9 Hz), 3.68 (s, 2H), 3.57 (d, 4H, J = 7.4 Hz), 3.51-3.32 (m, 4H), 3.25 (d, 1H, J = 7.3 Hz), 3.00 (s, 3H), 1.92-1.81 (m, 2H), 1.59-1.45 (m, 2H), 1.28 (d, 6H, J = 6.7 Hz) | | N-(2-{1,4-dioxa-9-azaspiro[5,5]undecan-9-yl}pyrimidin-4-yl)-8-[3-(methanesulfonylmethyl)azetidin-1-yl]-5-(propan-2-yl)isoquinolin-3-amine |
| 168 | 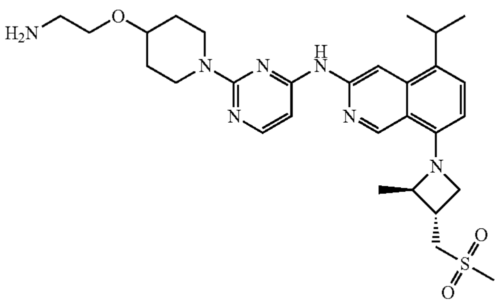 [SMILES: CC(C)c1ccc(N2C[C@H](CS(C)(=O)=O)[C@H]2C)c2cnc(Nc3ccnc(N4CCC(OCCN)CC4)n3)cc12] | 568 | 1H-NMR (300 MHz, 6d-DMSO) δ ppm 9.91 (s, 1H), 9.05 (s, 1H), 8.69 (s, 1H), 8.00 (d, 1H, J = 5.6 Hz), 7.43 (d, 1H, J = 8.0 Hz), 6.56 (d, 1H, J = 8.1 Hz), 6.43 (d, 1H, J = 5.7 Hz), 4.66 (t, 1H, J = 7.5 Hz), 4.38-4.27 (m, 2H), 4.19 (t, 1H, J = 6.2 Hz), 3.69-3.37 (m, 9H), 3.00 (s, 3H), 2.89 (q, 1H, J = 7.1 Hz), 2.71 (t, 2H, J = 5.8 Hz), 1.95-1.89 (m, 2H), 1.52-1.39 (m, 5H), 1.30 (d, 6H, J = 6.7 Hz) | | N-{2-[4-(2-aminoethoxy)piperidin-1-yl]pyrimidin-4-yl}-8-[(2R,3S)-3-(methanesulfonylmethyl)-2-methylazetidin-1-yl]-5-(propan-2-yl)isoquinolin-3-amine |
| 169 | 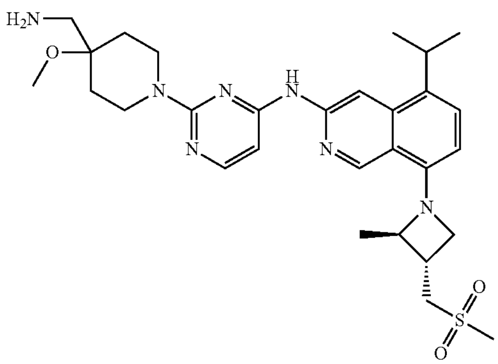 | 568 | 1H-NMR (400 MHz, 6d-DMSO) δ ppm 9.94 (s, 1H), 9.06 (s, 1H), 8.70 (s, 1H), 8.25 (s, 1H), 8.01 (d, 1H, J = 5.6 Hz), 7.43 (d, 1H, J = 8.0 Hz), 6.57 (d, 1H, J = 8.2 Hz), 6.45 (d, 1H, J = 5.6 Hz), 4.67 (t, 1H, J = 7.5 Hz), 4.42 (d, 2H, J = 13.0 Hz), 4.19 (q, 1H, J = 6.4 Hz), 3.68-3.22 (m, 11H), 3.01 (s, 3H), 2.96-2.85 (m, 3H), 1.85 (d, 2H, J = 13.6 Hz), 1.60-1.52 (m, 2H), 1.43 (d, 3H, J = 6.1 Hz), 1.31 (d, 6H, J = 6.8 Hz) | | N-{2-[4-(aminomethyl)-4-methoxypiperidin-1-yl]pyrimidin-4-yl}-8-[(2R,3S)-3-(methanesulfonylmethyl)-2-methylazetidin-1-yl]-5-(propan-2-yl)isoquinolin-3-amine |
| 170 | 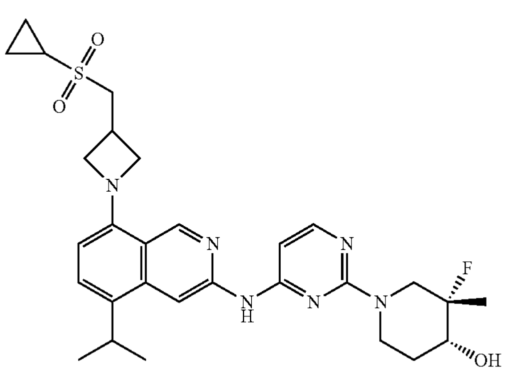 [SMILES: CC(C)c1ccc(N2CC(CS(=O)(=O)C3CC3)C2)c2cnc(Nc3ccnc(N4CC[C@@H](O)[C@@](C)(F)C4)n3)cc12] | 569 | 1H-NMR (300 MHz, 6d-DMSO) δ ppm 9.86 (s, 1H), 9.06 (s, 1H), 8.60 (s, 1H), 7.99 (d, 1H, J = 5.6 Hz), 7.42 (d, 1H, J = 8.0 Hz), 6.47 (d, 1H, J = 5.6 Hz), 6.41 (d, 1H, J = 8.0 Hz), 4.82-4.64 (m, 2H), 4.40 (t, 2H, J = 7.8 Hz), 3.98 (t, 2H, J = 6.9 Hz), 3.68-3.59 (m, 2H), 3.51 (s, 2H), 3.38-2.98 (m, 3H), 2.79-2.70 (m, 2H), 1.74 (s, 2H), 1.55-1.20 (m, 9H), 1.03 (t, 4H, J = 7.2 Hz) | | (3S,4R)-1-{4-[(8-{3-[(cyclopropanesulfonyl)methyl]azetidin-1-yl}-5-(propan-2-yl)isoquinolin-3-yl)amino]pyrimidin-2-yl}-3-fluoro-3-methylpiperidin-4-ol |

TABLE 1-continued

| # | Structure | LC/MS | NMR | Separation Conditions | Chemical Name |
|---|---|---|---|---|---|
| 171 | 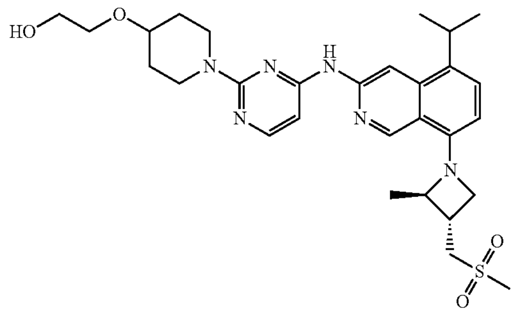 [SMILES: CC(C)c1ccc(N2C[C@H](CS(C)(=O)=O)[C@H]2C)c2cnc(Nc3ccnc(N4CCC(OCCO)CC4)n3)cc12] | 569 | 1H-NMR (300 MHz, 6d-DMSO) δ ppm 9.90 (s, 1H), 9.05 (s, 1H), 8.69 (s, 1H), 8.00 (d, 1H, J = 5.6 Hz), 7.43 (d, 1H, J = 8.0 Hz), 6.56 (d, 1H, J = 8.1 Hz), 6.43 (d, 1H, J = 5.7 Hz), 4.66 (t, 1H, J = 7.5 Hz), 4.64-4.55 (m, 1H), 4.40-4.29 (m, 2H), 4.20 (t, 1H, J = 6.3 Hz), 3.71-3.33 (m, 11H), 3.00 (s, 3H), 2.89 (q, 1H, J = 7.1 Hz), 1.99-1.88 (m, 2H), 1.57-1.39 (m, 5H), 1.30 (d, 6H, J = 6.7 Hz) | | 2-({1-[4-({8-[(2R,3S)-3-(methanesulfonyl-methyl)-2-methylazetidin-1-yl]-5-(propan-2-yl)isoquinolin-3-yl}amino)pyrimidin-2-yl]piperidin-4-yl}oxy)ethan-1-ol |
| 172 | | 569 | 1H-NMR (300 MHz, 6d-DMSO) δ ppm 9.87 (s, 1H), 9.05 (s, 1H), 8.64 (s, 1H), 8.00 (d, 1H, J = 5.7 Hz), 7.42 (d, 1H, J = 8.0 Hz), 6.56 (d, 1H, J = 8.1 Hz), 6.46 (d, 1H, J = 5.6 Hz), 4.66 (t, 1H, J = 7.5 Hz), 4.60-4.46 (m, 3H), 4.20 (t, 1H, J = 6.3 Hz), 3.55 (tdd, 7H, J = 25.6, 12.6, 6.1 Hz), 3.32 (s, 2H), 3.27-3.03 (m, 2H), 3.00 (s, 3H), 2.89 (q, 1H, J = 7.2 Hz), 2.14-2.04 (m, 1H), 1.64-1.58 (m, 1H), 1.43 (d, 3H, J = 6.0 Hz), 1.31 (t, 7H, J = 7.0 Hz) | L; Peak 2 | [(3R,4S)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methoxy-piperidin-3-yl]methanol or [(3S,4R)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methoxy-piperidin-3-yl]methanol |
| 173 | 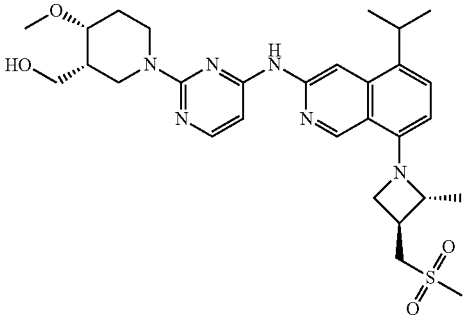 | 569 | 1H-NMR (300 MHz, 6d-DMSO) δ ppm 9.86 (s, 1H), 9.05 (s, 1H), 8.63 (s, 1H), 8.00 (d, 1H, J = 5.6 Hz), 7.42 (d, 1H, J = 8.0 Hz), 6.56 (d, 1H, J = 8.1 Hz), 6.46 (d, 1H, J = 5.6 Hz), 4.66 (t, 1H, J = 7.4 Hz), 4.59-4.40 (m, 3H), 4.20 (t, 1H, J = 6.2 Hz), 3.72-3.35 (m, 7H), 3.31 (s, 3H), 3.11-3.05 (m, 1H), 3.00 (s, 3H), 2.93-2.85 (m, 1H), 2.10-2.04 (m, 1H), 1.64-1.58 (m, 1H), 1.43 (d, 3H, J = 6.0 Hz), 1.31 (dd, 7H, J = 6.7, | F; Peak 1 | [(3R,4R)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methoxy-piperidin-3-yl]methanol or [(3S,4S)-1-[4-({8-[(2R,3S)-3-(methanesulfonyl- |

TABLE 1-continued

| # | Structure | LC/MS | NMR | Separation Conditions | Chemical Name |
|---|---|---|---|---|---|
| | | | 4.1 Hz) | | methyl)-2-methylazetidin-1-yl]-5-(propan-2-yl)isoquinolin-3-yl}amino)pyrimidin-2-yl]-4-methoxy-piperidin-3-yl]methanol |
| 174 | | 569 | 1H-NMR (300 MHz, 6d-DMSO) δ ppm 9.87 (s, 1H), 9.05 (s, 1H), 8.66 (s, 1H), 8.00 (d, 1H, J = 5.6 Hz), 7.42 (d, 1H, J = 8.0 Hz), 6.60-6.50 (m, 1H), 6.45 (d, 1H, J = 5.7 Hz), 4.66 (t, 1H, J = 7.4 Hz), 4.42 (t, 1H, J = 5.3 Hz), 4.27-4.17 (m, 3H), 3.69-3.40 (m, 7H), 3.33 (s, 3H), 3.00 (s, 3H), 2.93-2.85 (m, 1H), 1.90-1.84 (m, 2H), 1.61-1.55 (m, 1H), 1.43 (d, 3H, J = 6.0 Hz), 1.34-1.21 (m, 6H) | F; Peak 2 | [(3S,4R)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methoxy-piperidin-3-yl]methanol or [(3R,4S)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methoxy-piperidin-3-yl]methanol |
| 175 | 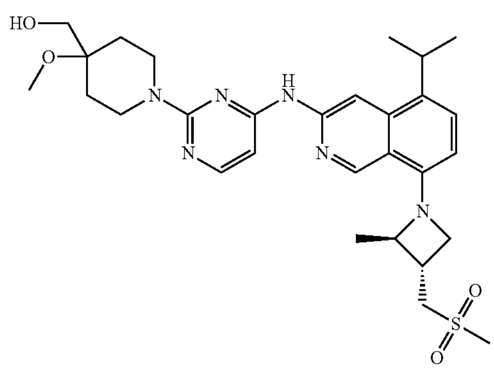 | 569 | 1H-NMR (300 MHz, 6d-DMSO) δ ppm 9.88 (s, 1H), 9.04 (s, 1H), 8.71 (s, 1H), 7.99 (d, 1H, J = 5.6 Hz), 7.42 (d, 1H, J = 8.0 Hz), 6.55 (d, 1H, J = 8.0 Hz), 6.40 (d, 1H, J = 5.7 Hz), 4.71-4.54 (m, 2H), 4.46-4.36 (m, 2H), 4.19 (t, 1H, J = 6.2 Hz), 3.69-3.43 (m, 4H), 3.40 (d, 2H, J = 5.5 Hz), 3.31-3.24 (m, 2H), 3.22 (s, 3H), 2.99 (s, 3H), 2.88 (q, 1H, J = 6.9 Hz), 1.79-1.68 (m, 2H), 1.55-1.49 (m, 2H), 1.42 (d, 3H, J = 6.1 Hz), 1.29 (d, 6H, J = 6.7 Hz) | | {1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methoxy-piperidin-4-yl}methanol |

TABLE 1-continued

| # | Structure | LC/MS | NMR | Separation Conditions | Chemical Name |
|---|---|---|---|---|---|
| 176 | 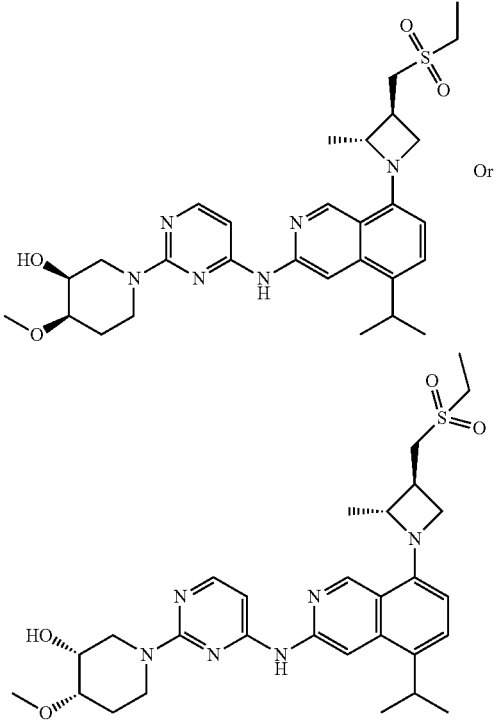 | 569 | 1H-NMR (300 MHz, 6d-DMSO) δ ppm 9.87 (s, 1H), 9.05 (s, 1H), 8.69 (s, 1H), 7.98 (d, 1H, J = 5.6 Hz), 7.42 (d, 1H, J = 8.0 Hz), 6.56 (d, 1H, J = 8.1 Hz), 6.41 (d, 1H, J = 5.6 Hz), 4.71-4.60 (m, 2H), 4.25-4.15 (m, 1H), 4.01-3.95 (m, 2H), 3.82-3.76 (m, 2H), 3.76-3.42 (m, 6H), 3.37 (s, 3H), 3.10 (q, 2H, J = 7.4 Hz), 2.89 (q, 1H, J = 7.3 Hz), 1.94-1.57 (m, 2H), 1.43 (d, 3H, J = 6.0 Hz), 1.34-1.18 (m, 9H) | JJ Peak 1 | (3S,4R)-1-[4-({8-[(2R,3S)-3-[(ethanesulfonyl)methyl]-2-methylazetidin-1-yl]-5-(propan-2-yl)isoquinolin-3-yl}amino)pyrimidin-2-yl]-4-methoxy-piperidin-3-ol, or (3R,4S)-1-[4-({8-[(2R,3S)-3-[(ethanesulfonyl)methyl]-2-methylazetidin-1-yl]-5-(propan-2-yl)isoquinolin-3-yl}amino)pyrimidin-2-yl]-4-methoxy-piperidin-3-ol |
| 177 | 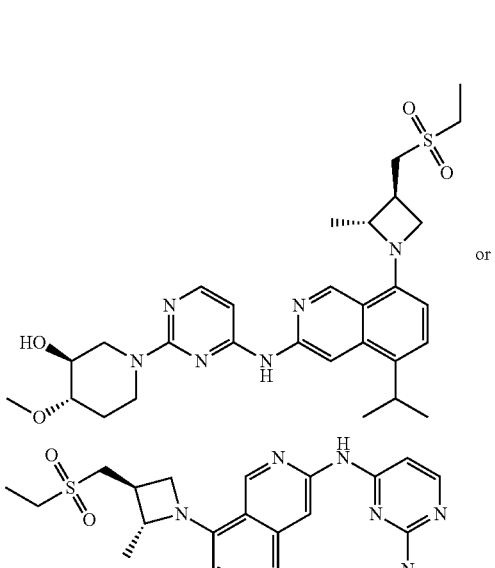 | 569 | 1H-NMR (300 MHz, 6d-DMSO) δ ppm 9.90 (s, 1H), 9.05 (s, 1H), 8.66 (s, 1H), 7.99 (d, 1H, J = 5.6 Hz), 7.42 (d, 1H, J = 8.0 Hz), 6.56 (d, 1H, J = 8.1 Hz), 6.45 (d, 1H, J = 5.7 Hz), 5.11 (d, 1H, J = 4.8 Hz), 4.66 (t, 1H, J = 7.5 Hz), 4.39 (dt, 2H, J = 17.0, 8.5 Hz), 4.19 (q, 1H, J = 6.2 Hz), 3.64 (t, 1H, J = 7.1 Hz), 3.58-3.42 (m, 3H), 3.37 (s, 3H), 3.30-3.16 (m, 2H), 3.10 (q, 3H), 2.89 (q, 1H, J = 7.2 Hz), 2.11-2.01 (m, 1H), 1.43 (d, 3H, J = 6.0 Hz), 1.40-1.34 (m, 1H), 1.32-1.11 (m, 9H) | LL, Peak 1 | (3S,4S)-1-[4-({8-[(2R,3S)-3-[(ethanesulfonyl)methyl]-2-methylazetidin-1-yl]-5-(propan-2-yl)isoquinolin-3-yl}amino)pyrimidin-2-yl]-4-methoxy-piperidin-3-ol or (3R,4R)-1-(4-((8-((2R,3S)-3-((ethylsulfonyl)methyl)-2-methylazetidin-1-yl)-5-isopropylisoquinolin-3-yl)amino)pyrimidin-2-yl)-4-methoxy-piperidin-3-ol |

TABLE 1-continued

| # | Structure | LC/MS | NMR | Separation Conditions | Chemical Name |
|---|---|---|---|---|---|
| 178 | 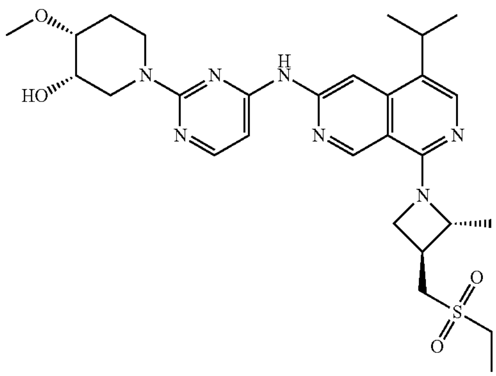 [SMILES: CCS(=O)(=O)C[C@H]1CN(c2ncc(C(C)C)c3cc(Nc4ccnc(N5CC[C@@H](OC)[C@@H](O)C5)n4)ncc23)[C@@H]1C] | 570 | 1H-NMR (300 MHz, 6d-DMSO) δ ppm 10.06 (s, 1H), 9.02 (s, 1H), 8.57 (s, 1H), 8.02 (d, 1H, J = 5.6 Hz), 7.99 (s, 1H), 6.44 (d, 1H, J = 5.6 Hz), 4.85 (t, 1H, J = 8.1 Hz), 4.65 (d, 1H, J = 5.0 Hz), 4.55 (t, 1H, J = 6.3 Hz), 4.10-3.87 (m, 3H), 3.81-3.62 (m, 4H), 3.55-3.39 (m, 6H), 3.07 (t, 2H, J = 7.4 Hz), 2.88 (d, 1H, J = 7.1 Hz), 1.91-1.82 (m, 1H), 1.65-1.59 (m, 1H), 1.49 (d, 3H, J = 6.1 Hz), 1.36-1.16 (m, 9H) | JJ, Peak 1 | (3S,4R)-1-[4-({8-[(2R,3S)-3-[(ethanesulfonyl)methyl]-2-methylazetidin-1-yl]-5-(propan-2-yl)-2,7-naphthyridin-3-yl}amino)pyrimidin-2-yl]-4-methoxy-piperidin-3-ol |
| 179 | 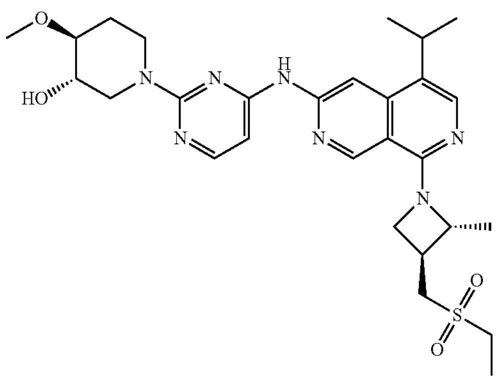 [SMILES: CCS(=O)(=O)C[C@H]1CN(c2ncc(C(C)C)c3cc(Nc4ccnc(N5CC[C@H](OC)[C@@H](O)C5)n4)ncc23)[C@@H]1C] | 570 | 1H-NMR (300 MHz, 6d-DMSO) δ ppm 10.09 (s, 1H), 9.03 (s, 1H), 8.54 (s, 1H), 8.03 (d, 1H, J = 5.6 Hz), 7.99 (s, 1H), 6.48 (d, 1H, J = 5.7 Hz), 5.10 (d, 1H, J = 4.9 Hz), 4.85 (t, 1H, J = 8.0 Hz), 4.55 (t, 1H, J = 6.2 Hz), 4.42-4.26 (m, 2H), 3.97 (t, 1H, J = 7.3 Hz), 3.51 (d, 2H, J = 7.4 Hz), 3.38 (s, 3H), 3.24 (d, 5H, J = 9.1 Hz), 3.08 (q, 2H, J = 7.5 Hz), 2.95-2.84 (m, 1H), 2.10-2.00 (m, 1H), 1.49 (d, 3H, J = 6.1 Hz), 1.44-1.32 (m, 1H), 1.31 (t, 6H, J = 7.6 Hz), 1.22 (t, 3H, J = 7.4 Hz) | LL, Peak 1 | (3S,4S)-1-[4-({8-[(2R,3S)-3-[(ethanesulfonyl)methyl]-2-methylazetidin-1-yl]-5-(propan-2-yl)-2,7-naphthyridin-3-yl}amino)pyrimidin-2-yl]-4-methoxy-piperidin-3-ol |
| 180 | | 571 | 1H-NMR (300 MHz, 6d-DMSO) δ ppm 9.91 (s, 1H), 9.06 (s, 1H), 8.58 (s, 1H), 8.02 (d, 1H, J = 5.7 Hz), 7.42 (d, 1H, J = 8.0 Hz), 6.54 (d, 1H, J = 5.8 Hz), 6.42 (d, 1H, J = 8.0 Hz), 4.64-4.32 (m, 4H), 4.19 (d, 1H, J = 14.0 Hz), 4.07-3.93 (m, 6H), 3.93-3.79 (m, 1H), 3.70 (d, 1H, J = 9.0 Hz), 3.59 (d, 2H, J = 7.4 Hz), 3.48 (p, 1H, J = 6.7, 6.1 Hz), 3.28-3.22 (m, 1H, J = 6.9 Hz), 3.02 (s, 3H), 2.00-1.82 (m, 1H), 1.72-1.61 (m, 1H), 1.39-1.21 (m, 6H) | M; Peak 1 | N-{2-[(6R)-6-fluoro-1,4-dioxa-8-azaspiro[4.5]decan-8-yl]pyrimidin-4-yl}-8-[3-(methanesulfonylmethyl)azetidin-1-yl]-5-(propan-2-yl)isoquinolin-3-amine or N-{2-[(6S)-6-fluoro-1,4-dioxa-8-azaspiro[4.5]decan-8-yl]pyrimidin-4-yl}-8-[3-(methanesulfonylmethyl)azetidin-1-yl]-5-(propan-2-yl)isoquinolin-3-amine |

TABLE 1-continued

| # | Structure | LC/MS | NMR | Separation Conditions | Chemical Name |
|---|---|---|---|---|---|
| 181 | 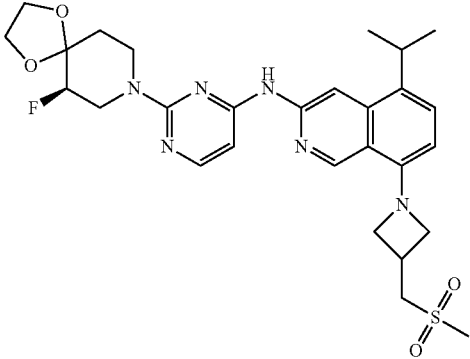 [SMILES: CC(C)c1ccc(N2CC(CS(C)(=O)=O)C2)c2cnc(Nc3ccnc(N4CCC5(OCCO5)[C@@H](F)C4)n3)cc12] | 571 | 1H-NMR (300 MHz, 6d-DMSO) δ ppm 9.91 (s, 1H), 9.06 (s, 1H), 8.58 (s, 1H), 8.02 (d, 1H, J = 5.7 Hz), 7.42 (d, 1H, J = 8.0 Hz), 6.54 (d, 1H, J = 5.7 Hz), 6.42 (d, 1H, J = 8.0 Hz), 4.63-4.30 (m, 4H), 4.24-4.13 (m, 1H), 4.07-3.79 (m, 7H), 3.69 (t, 1H, J = 9.9 Hz), 3.59 (d, 2H, J = 7.4 Hz), 3.55-3.40 (m, 1H), 3.28 (d, 1H, J = 8.1 Hz), 3.02 (s, 3H), 1.94-1.88 (m, 1H), 1.72-1.61 (m, 1H), 1.39-1.21 (m, 6H) | M; Peak 2 | N-{2-[(6R)-6-fluoro-1,4-dioxa-8-azaspiro[4.5]decan-8-yl]pyrimidin-4-yl}-8-[3-(methanesulfonylmethyl)azetidin-1-yl]-5-(propan-2-yl)isoquinolin-3-amine or N-{2-[(6S)-6-fluoro-1,4-dioxa-8-azaspiro[4.5]decan-8-yl]pyrimidin-4-yl}-8-[3-(methanesulfonylmethyl)azetidin-1-yl]-5-(propan-2-yl)isoquinolin-3-amine |
| | 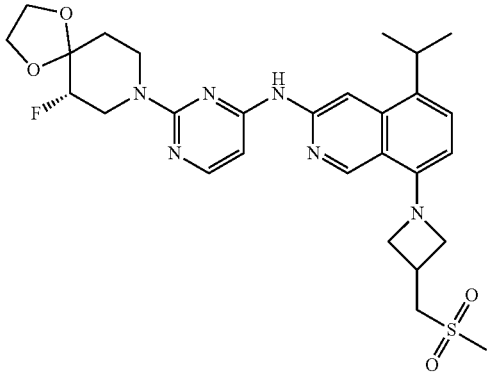 [SMILES: CC(C)c1ccc(N2CC(CS(C)(=O)=O)C2)c2cnc(Nc3ccnc(N4CCC5(OCCO5)[C@@H](F)C4)n3)cc12] | | | | |
| 182 | 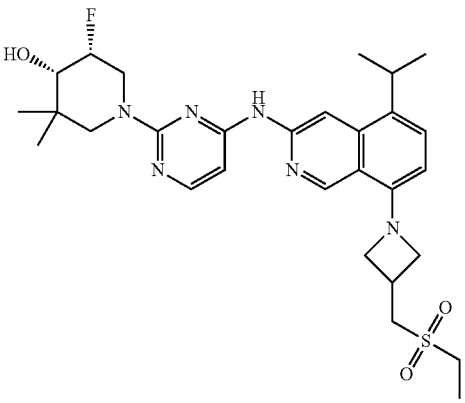 [SMILES: CCS(=O)(=O)CC1CN(c2ccc(C(C)C)c3cc(Nc4ccnc(N5C[C@H](F)[C@H](O)C(C)(C)C5)n4)ncc23)C1] | 571 | 1H-NMR (300 MHz, 6d-DMSO) δ ppm (s, 1H), 9.05 (s, 1H), 8.58 (s, 1H), 7.99 (d, 1H, J = 5.6 Hz), 7.42 (d, 1H, J = 8.0 Hz), 6.49 (d, 1H, J = 5.6 Hz), 6.41 (d, 1H, J = 8.1 Hz), 5.14 (d, 1H, J = 5.3 Hz), 4.76 (d, 1H, J = 48.7 Hz), 4.39 (t, 2H, J = 7.6 Hz), 4.33-4.17 (m, 1H), 4.12-3.89 (m, 3H), 3.66-3.39 (m, 6H), 3.31-3.21 (m, 1H), 3.12 (q, 2H, J = 7.4 Hz), 1.36-1.16 (m, 9H), 1.03-0.84 (m, 6H) | J; Peak 2 | (4S,5R)-1-{4-[(8-{3-[(ethanesulfonyl)methyl]azetidin-1-yl}-5-(propan-2-yl)isoquinolin-3-yl)amino]pyrimidin-2-yl}-5-fluoro-3,3-dimethylpiperidin-4-ol or (4R,5S)-1-{4-[(8-{3-[(ethanesulfonyl)methyl]azetidin-1-yl}-5-(propan-2-yl)isoquinolin-3-yl)amino] |

| # | Structure | LC/MS | NMR | Separation Conditions | Chemical Name |
|---|---|---|---|---|---|
| | | | | | pyrimidin-2-yl}-5-fluoro-3,3-dimethyl-piperidin-4-ol |
| 183 | | 571 | 1H-NMR (400 MHz, 6d-DMSO) δ ppm 9.89 (s, 1H), 9.06 (s, 1H), 8.60 (s, 1H), 7.99 (d, 1H, J = 5.7 Hz), 7.43 (d, 1H, J = 8.0 Hz), 6.57 (d, 1H, J = 8.1 Hz), 6.47 (d, 1H, J = 5.6 Hz), 5.13 (d, 1H, J = 5.4 Hz), 4.92-4.55 (m, 2H), 4.31-4.15 (m, 2H), 3.97 (dd, 1H, J = 23.3, 13.5 Hz), 3.84 (d, 1H, J = 12.9 Hz), 3.64 (t, 1H, J = 7.3 Hz), 3.54 (p, 3H, J = 6.8 Hz), 3.47-3.37 (m, 2H), 3.00 (s, 3H), 2.89 (q, 1H, J = 7.2 Hz), 1.43 (d, 3H, J = 6.0 Hz), 1.30 (t, 6H, J = 7.1 Hz), 0.98-0.90 (m, 6H) | L; Peak 2 | (4S,5R)-5-fluoro-1-[4-({8-[(2S,3R)-3-(methanesulfonyl-methyl)-2-methylazetidin-1-yl]-5-(propan-2-yl)isoquinolin-3-yl}amino)pyrimidin-2-yl]-3,3-dimethyl-piperidin-4-ol or (4R,5S)-5-fluoro-1-[4-({8-[(2S,3R)-3-(methanesulfonyl-methyl)-2-methylazetidin-1-yl]-5-(propan-2-yl)isoquinolin-3-yl}amino)pyrimidin-2-yl]-3,3-dimethyl-piperidin-4-ol |

TABLE 1-continued

| # | Structure | LC/MS | NMR | Separation Conditions | Chemical Name |
|---|---|---|---|---|---|
| 184 | 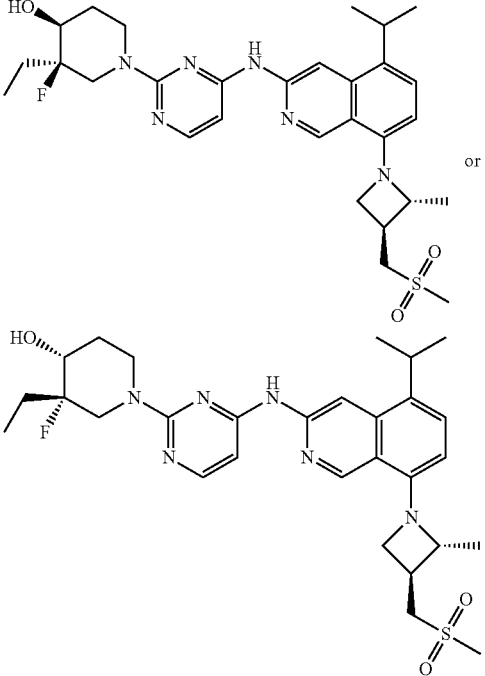 | 571 | 1H-NMR (400 MHz, 6d-DMSO) δ ppm 10.03 (s, 1H), 9.07 (s, 1H), 8.60 (s, 1H), 7.99 (d, 1H, J = 5.8 Hz), 7.43 (d, 1H, J = 8.0 Hz), 6.57 (d, 1H, J = 8.1 Hz), 6.50 (d, 1H, J = 5.8 Hz), 5.00 (s, 1H), 4.71-4.54 (m, 3H), 4.20 (p, 1H, J = 6.1 Hz), 3.66 (dt, 2H, J = 20.7, 7.2 Hz), 3.61-3.44 (m, 3H), 3.31-3.19 (m, 2H), 2.99 (s, 3H), 2.96-2.84 (m, 1H), 1.86 (dt, 1H, J = 16.6, 7.8 Hz), 1.80-1.60 (m, 3H), 1.42 (d, 3H, J = 6.1 Hz), 1.34-1.26 (m, 6H), 0.93 (t, 3H, J = 7.5 Hz) | D; Peak 2 | (3R,4S)-3-ethyl-3-fluoro-1-[4-({8-[(2R,3S)-3-(methanesulfonyl-methyl)-2-methylazetidin-1-yl]-5-(propan-2-yl)isoquinolin-3-yl}amino) pyrimidin-2-yl] piperidin-4-ol or (3S,4R)-3-ethyl-3-fluoro-1-[4-({8-[(2R,3S)-3-(methanesulfonyl-methyl)-2-methylazetidin-1-yl]-5-(propan-2-yl)isoquinolin-3-yl}amino) pyrimidin-2-yl] piperidin-4-ol |
| 185 | 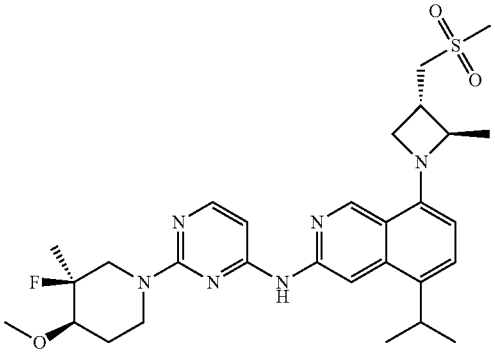 | 571 | 1H-NMR (300 MHz, 6d-DMSO) δ ppm 9.92 (s, 1H), 9.06 (s, 1H), 8.60 (s, 1H), 7.99 (d, 1H, J = 5.6 Hz), 7.43 (d, 1H, J = 7.9 Hz), 6.57 (d, 1H, J = 8.1 Hz), 6.48 (d, 1H, J = 5.7 Hz), 4.73-4.64 (m, 3H), 4.25-4.15 (m, 1H), 3.59 (dt, 4H, J = 29.1, 7.5 Hz), 3.39 (s, 3H), 3.30-3.16 (m, 3H), 3.00 (s, 3H), 2.89 (q, 1H, J = 7.4, 6.7 Hz), 2.03-1.93 (m, 1H), 1.68-1.62 (m, 1H), 1.47-1.26 (m, 12H) | NN; Peak 1 | N-{2-[(3S,4R)-3-fluoro-4-methoxy-3-methylpiperidin-1-yl]pyrimidin-4-yl}-8-[(2R,3S)-3-(methanesulfonyl-methyl)-2-methylazetidin-1-yl]-5-(propan-2-yl)isoquinolin-3-amine |
| 186 | 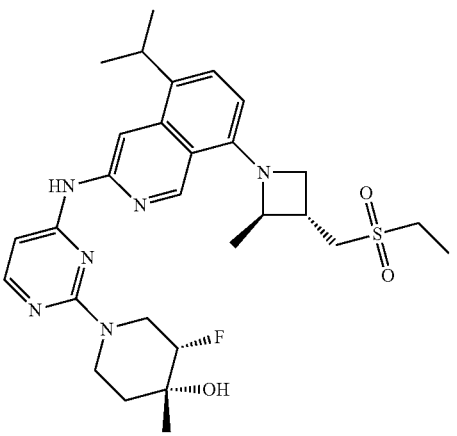 [SMILES: CCS(=O)(=O)C[C@H]1CN(c2ccc(C(C)C)c3cc(Nc4ccnc(N5CC[C@@](C)(O)[C@@H](F)C5)n4)ncc23)[C@@H]1C] | 571 | 1H NMR (400 MHz, DMSO-d6) δ 9.94 (s, 1H), 9.08 (s, 1H), 8.68 (s, 1H), 8.03 (d, 1H, J = 5.5 Hz), 7.45 (d, 1H, J = 8.0 Hz), 6.59 (d, 1H, J = 8.0 Hz), 6.50 (d, 1H, J = 5.6 Hz), 4.85 (s, 1H), 4.68 (t, 1H, J = 7.5 Hz), 4.57-4.39 (m, 1H), 4.32-4.14 (m, 2H), 3.67 (t, 2H, J = 7.1 Hz), 3.53 (q, 4H, J = 6.7 Hz), 3.12 (q, 2H, J = 7.4 Hz), 2.91 (q, 1H, J = 7.1 Hz), 1.66 (m, 2H), 1.46 (d, 3H, J = 6.0 Hz), 1.39-1.20 (m, 12H). | OO; Peak 1 | (3S,4R)-1-[4-({8-[(2R,3S)-3-[(ethanesulfonyl) methyl]-2-methylazetidin-1-yl]-5-(propan-2-yl) isoquinolin-3-yl}amino) pyrimidin-2-yl]-3-fluoro-4-methyl-piperidin-4-ol |

TABLE 1-continued

| # | Structure | LC/MS | NMR | Separation Conditions | Chemical Name |
|---|---|---|---|---|---|
| 187 | 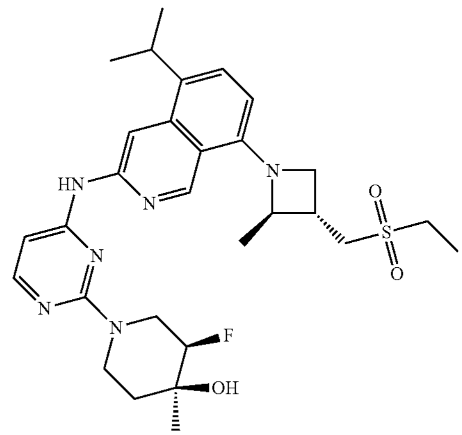 [SMILES: CCS(=O)(=O)C[C@H]1CN(c2ccc(C(C)C)c3cc(Nc4ccnc(N5CC[C@](C)(O)[C@H](F)C5)n4)ncc23)[C@@H]1C] | 571 | 1H NMR (400 MHz, DMSO-d6) δ 9.94 (s, 1H), 9.09 (s, 1H), 8.72-8.61 (m, 1H), 8.04 (d, 1H, J = 5.6 Hz), 7.45 (d, 1H, J = 7.9 Hz), 6.59 (d, 1H, J = 8.1 Hz), 6.50 (d, 1H, J = 5.6 Hz), 4.85 (s, 1H), 4.68 (t, 1H, J = 7.5 Hz), 4.55-4.37 (m, 1H), 4.23 (dd, 2H, J = 12.3, 6.0 Hz), 3.67 (t, 2H, J = 7.1 Hz), 3.54 (t, 4H, J = 7.1 Hz), 3.12 (q, 2H, J = 7.4 Hz), 1.66 (m, 2H), 1.46 (d, 3H, J = 6.1 Hz), 1.37-1.20 (m, 12H). | OO; Peak 2 | (3R,4S)-1-[4-({8-[(2R,3S)-3-[(ethanesulfonyl)methyl]-2-methylazetidin-1-yl]-5-(propan-2-yl)isoquinolin-3-yl}amino)pyrimidin-2-yl]-3-fluoro-4-methyl-piperidin-4-ol |
| 188 | 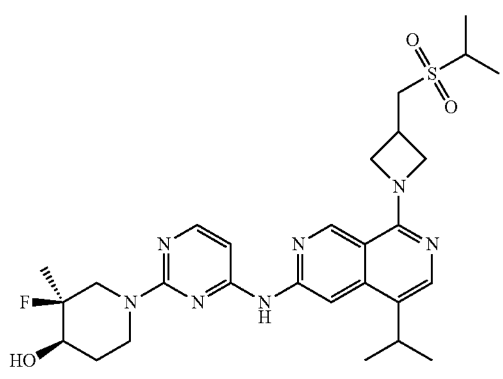 [SMILES: CC(C)c1cnc(N2CC(CS(=O)(=O)C(C)C)C2)c2cnc(Nc3ccnc(N4CC[C@@H](O)[C@@](C)(F)C4)n3)cc12] | 572 | $^1$H NMR (400 MHz, 6d-DMSO) δ ppm 10.08 (s, 1H), 9.02 (s, 1H), 8.48 (s, 1H), 8.03 (d, 1H, J = 5.6 Hz), 7.99 (s, 1H), 6.50 (d, 1H, J = 5.6 Hz), 5.03 (d, 1H, J = 6.4 Hz), 4.84-4.63 (m, 2H), 4.56 (t, 2H, J = 8.4 Hz), 4.22 (td, 2H, J = 7.3, 6.9, 3.4 Hz), 3.70-3.45 (m, 3H), 3.29-3.00 (m, 3H), 1.74 (d, 2H, J = 9.4 Hz), 1.45-1.28 (m, 9H), 1.26 (d, 6H, J = 6.8 Hz) | NN; Peak 1 | (3S,4R)-3-fluoro-3-methyl-1-(4-{[5-(propan-2-yl)-8-3-[(propane-2-sulfonyl)methyl]azetidin-1-yl]-2,7-naphthyridin-3-yl]amino}pyrimidin-2-yl)piperidin-4-ol |
| 189 | 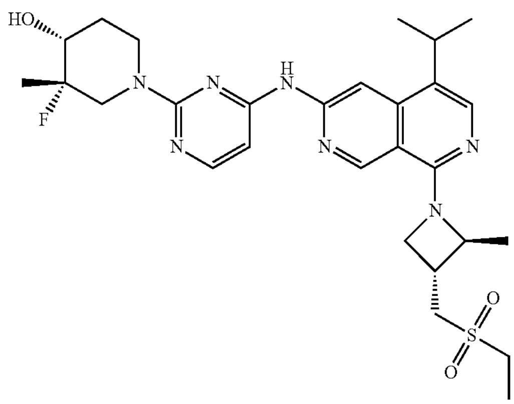 [SMILES: CCS(=O)(=O)C[C@@H]1CN(c2ncc(C(C)C)c3cc(Nc4ccnc(N5CC[C@@H](O)[C@@](C)(F)C5)n4)ncc23)[C@H]1C] | 572 | 1H-NMR (300 MHz, 6d-DMSO) δ ppm 10.10 (s, 1H), 9.05 (s, 1H), 8.50 (s, 1H), 8.09-7.98 (m, 2H), 6.51 (d, 1H, J = 5.6 Hz), 5.04 (d, 1H, J = 6.4 Hz), 4.86 (t, 1H, J = 8.0 Hz), 4.81-4.49 (m, 3H), 3.98 (t, 1H, J = 7.3 Hz), 3.67-3.47 (m, 3H), 3.34 (d, 1H, J = 13.8 Hz), 3.18 (s, 1H), 3.09 (q, 3H, J = 7.4 Hz), 2.91 (p, 1H, J = 7.2 Hz), 1.80-1.67 (m, 2H), 1.50 (d, 3H, J = 6.1 Hz), 1.43-1.29 (m, 9H), 1.23 (t, 3H, J = 7.4 Hz) | D; Peak 2 | (3S,4R)-1-[4-({8-[(2S,3R)-3-[(ethanesulfonyl)methyl]-2-methylazetidin-1-yl]-5-propan-2-yl)-2,7-naphthyridin-3-yl}amino)pyrimidin-2-yl]-3-fluoro-3-methyl-piperidin-4-ol |

TABLE 1-continued

| # | Structure | LC/MS | NMR | Separation Conditions | Chemical Name |
|---|---|---|---|---|---|
| 190 | 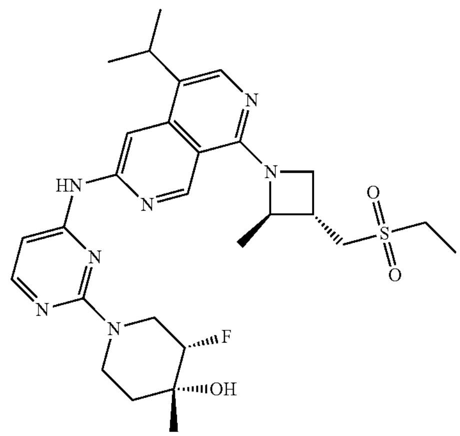 [SMILES: CCS(=O)(=O)C[C@H]1CN(c2ncc(C(C)C)c3cc(Nc4ccnc(N5CC[C@@](C)(O)[C@@H](F)C5)n4)ncc23)[C@@H]1C] | 572 | 1H-NMR (300 MHz, 6d-DMSO) δ ppm 10.15 (s, 1H), 9.04 (s, 1H), 8.55 (s, 1H), 8.10-7.98 (m, 2H), 6.51 (d, 1H, J = 5.7 Hz), 4.91-4.80 (m, 2H), 4.55 (q, 1H, J = 6.2 Hz), 4.50-4.11 (m, 3H), 3.98 (t, 1H, J = 7.3 Hz), 3.62 (td, 1H, J = 12.6, 11.4, 5.0 Hz), 3.52 (d, 2H, J = 7.5 Hz), 3.46 3.38 (m, 1H), 3.09 (q, 2H, J = 7.4 Hz), 2.89 (q, 1H, J = 7.2 Hz), 1.73-1.67 (m, 1H), 1.59-1.53 (m, 1H), 1.50 (d, 3H, J = 6.1 Hz), 1.32 (t, 6H, J = 7.4 Hz), 1.29-1.17 (m, 6H) | OO; Peak 1 | (3S,4R)-1-[4-({8-[(2R,3S)-3-[(ethanesulfonyl)methyl]-2-methylazetidin-1-yl]-5-(propan-2-yl)-2,7-naphthyridin-3-yl}amino)pyrimidin-2-yl]-3-fluoro-4-methyl-piperidin-4-ol |
| 191 | 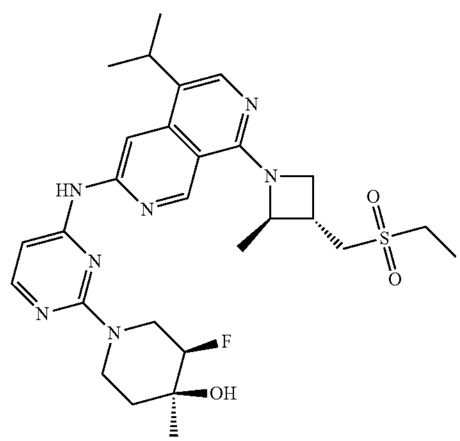 [SMILES: CCS(=O)(=O)C[C@H]1CN(c2ncc(C(C)C)c3cc(Nc4ccnc(N5CC[C@](C)(O)[C@H](F)C5)n4)ncc23)[C@@H]1C] | 572 | 1H-NMR (300 MHz, 6d-DMSO) δ ppm 10.15 (s, 1H), 9.04 (s, 1H), 8.55 (s, 1H), 8.06 (d, 1H, J = 5.6 Hz), 8.01 (s, 1H), 6.51 (d, 1H, J = 5.7 Hz), 4.92-4.80 (m, 2H), 4.56 (p, 1H, J = 6.1 Hz), 4.43 (q, 1H, J = 7.1, 5.4 Hz), 4.32-4.12 (m, 2H), 3.98 (t, 1H, J = 7.3 Hz), 3.62 (ddd, 1H, J = 13.5, 9.7, 5.1 Hz), 3.52 (d, 3H, J = 7.6 Hz), 3.35-3.27 (m, 1H), 3.09 (q, 2H, J = 7.4 Hz), 2.89 (q, 1H, J = 7.2 Hz), 1.73-1.67 (m, 1H), 1.60-1.54 (m, 1H), 1.50 (d, 3H, J = 6.1 Hz), 1.36-1.17 (m, 12H) | OO; Peak 2 | (3R,4S)-1-[4-({8-[(2R,3S)-3-[(ethanesulfonyl)methyl]-2-methylazetidin-1-yl]-5-propan-2-yl)-2,7-naphthyridin-3-yl}amino)pyrimidin-2-yl]-3-fluoro-4-methyl-piperidin-4-ol |
| 192 | | 572 | 1H-NMR (300 MHz, 6d-DMSO) δ ppm 9.86 (s, 1H), 9.03 (s, 1H), 8.39 (s, 1H), 7.96 (d, 1H, J = 5.6 Hz), 7.46 (t, 1H, J = 7.9 Hz), 7.03 (d, 1H, J = 8.1 Hz), 6.39 (d, 1H, J = 5.6 Hz), 6.33 (d, 1H, J = 7.7 Hz), 5.12 (d, 1H, J = 5.4 Hz), 4.74 (d, 1H, J = 49.7 Hz), 4.44 (t, 2H, J = 7.8 Hz), 4.27-4.21 (m, 1H), 4.01 (t, 2H, J = 6.9 Hz), 3.89 (d, 1H, J = 11.5 Hz), 3.80 (d, 1H, J = 14.4 Hz), 3.63 (d, 2H, J = 7.4 Hz), 3.54-3.35 (m, 5H), 2.64 (t, 2H, J = 6.9 Hz), 2.17 (s, 6H), 0.95 (d, 6H, J = 5.9 Hz) | EE, Peak 2 | (4S,5R)-1-(4-{[8-(3-{[2-(dimethylamino)ethanesulfonyl]methyl}azetidin-1-yl)isoquinolin-3-yl]amino}pyrimidin-2-yl)-5-fluoro-3,3-dimethyl-piperidin-4-ol or (4R,5S)-1-(4-{[8-(3-{[2-(dimethylamino)ethanesulfonyl]methyl}azetidin-1-yl)isoquinolin-3-yl]amino}pyrimidin-2-yl)-5-fluoro-3,3-dimethyl-piperidin-4-ol |

TABLE 1-continued

| # | Structure | LC/MS | NMR | Separation Conditions | Chemical Name |
|---|---|---|---|---|---|
| 193 | 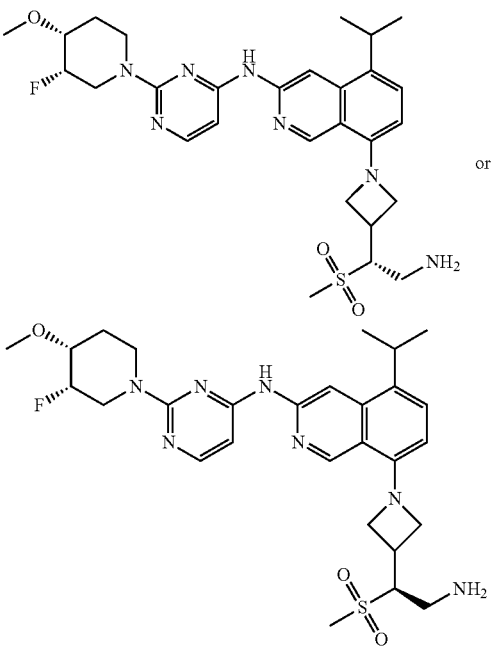 | 572 | 1H-NMR (300 MHz, 6d-DMSO) δ ppm 9.91 (s, 1H), 9.07 (s, 1H), 8.63 (s, 1H), 8.01 (d, 1H, J = 5.7 Hz), 7.43 (d, 1H, J = 8.0 Hz), 6.49 (d, 1H, J = 5.8 Hz), 6.43 (d, 1H, J = 8.0 Hz), 4.95 (d, 1H, J = 49.7 Hz), 4.74 (s, 1H), 4.57-4.31 (m, 3H), 4.08 (t, 1H, J = 7.5 Hz), 3.97 (t, 1H, J = 7.3 Hz), 3.68-3.39 (m, 5H), 3.37 (s, 3H), 3.33-3.19 (m, 3H), 3.06 (s, 3H), 3.01 (d, 2H, J = 4.8 Hz), 1.84-1.73 (m, 2H), 1.31 (dd, 6H, J = 6.8, 2.8 Hz) | K; Peak 1 (Precusor stage) | 8-{3-[(1R)-2-amino-1-methanesulfonyl-ethyl]azetidin-1-yl}-N-{2-[(3S,4R)-3-fluoro-4-methoxy-piperidin-1-yl]pyrimidin-4-yl}-5-(propan-2-yl)isoquinolin-3-amine or 8-{3-[(1S)-2-amino-1-methanesulfonyl-ethyl]azetidin-1-yl}-N-{2-[(3S,4R)-3-fluoro-4-methoxy-piperidin-1-yl]pyrimidin-4-yl}-5-(propan-2-yl)isoquinolin-3-amine |
| 194 | 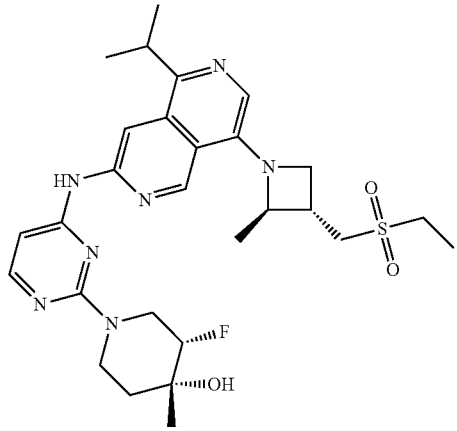 [SMILES: CCS(=O)(=O)C[C@H]1CN(c2cnc(C(C)C)c3cc(Nc4ccnc(N5CC[C@@](C)(O)[C@@H](F)C5)n4)ncc23)[C@@H]1C] | 572 | 1H-NMR (300 MHz, 6d-DMSO) δ ppm 10.18 (s, 1H), 9.13 (s, 1H), 8.77 (s, 1H), 8.05 (d, 1H, J = 5.7 Hz), 7.73 (s, 1H), 6.47 (d, 1H, J = 5.7 Hz), 4.89 (s, 1H), 4.74 (t, 1H, J = 7.6 Hz), 4.51-4.11 (m, 4H), 3.83-3.57 (m, 3H), 3.57-3.40 (m, 3H), 3.10 (q, 2H, J = 7.4 Hz), 2.92 (q, 1H, J = 7.3 Hz), 1.75-1.69 (m, 1H), 1.64-1.54 (m, 1H), 1.49 (d, 3H, J = 6.0 Hz), 1.36-1.18 (m, 12H) | OO; Peak 1 | (3S,4R)-1-[4-({8-[(2R,3S)-3-[(ethanesulfonyl)methyl]-2-methylazetidin-1-yl]-5-(propan-2-yl)-2,6-naphthyridin-3-yl}amino)pyrimidin-2-yl]-3-fluoro-4-methyl-piperidin-4-ol |
| 195 | 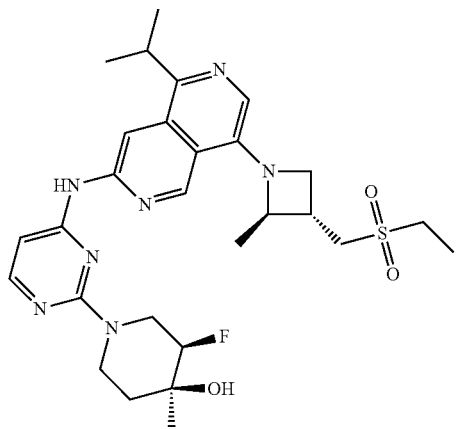 | 572 | 1H-NMR (300 MHz, 6d-DMSO) δ ppm 10.19 (s, 1H), 9.14 (s, 1H), 8.77 (s, 1H), 8.05 (d, 1H, J = 5.6 Hz), 7.73 (s, 1H), 6.47 (d, 1H, J = 5.6 Hz), 4.88 (s, 1H), 4.74 (t, 1H, J = 7.6 Hz), 4.51-4.38 (m, 1H), 4.37-4.09 (m, 3H), 3.82-3.43 (m, 6H), 3.10 (q, 2H, J = 7.4 Hz), 2.92 (q, 1H, J = 7.3 Hz), 1.75-1.69 (m, 1H), 1.64-1.55 (m, 1H), 1.49 (d, 3H, J = 6.0 Hz), 1.35-1.26 (m, 6H), 1.30-1.18 (m, 6H) | OO; Peak 2 | (3R,4S)-1-[4-({8-[(2R,3S)-3-[(ethanesulfonyl)methyl]-2-methylazetidin-1-yl]-5-(propan-2-yl)-2,6-naphthyridin-3-yl}amino)pyrimidin-2-yl]-3-fluoro-4-methyl-piperidin-4-ol |

TABLE 1-continued

| # | Structure | LC/MS | NMR | Separation Conditions | Chemical Name |
|---|---|---|---|---|---|
| 196 | 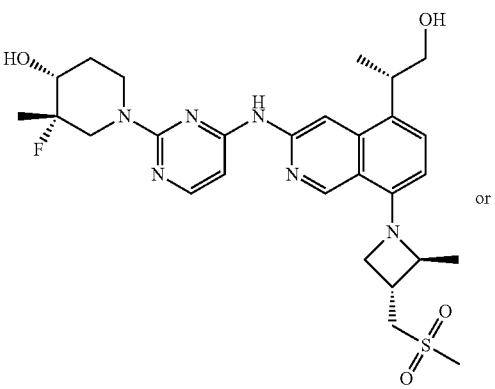 or 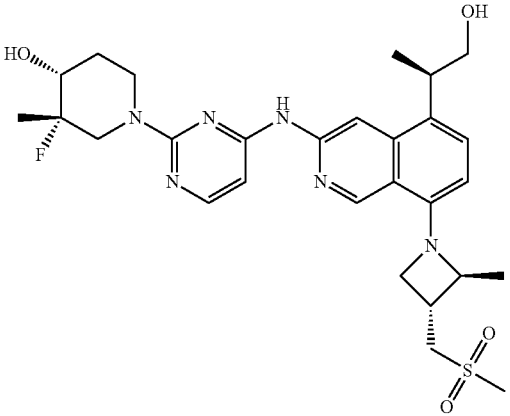 | 573 | 1H-NMR (400 MHz, 6d-DMSO) δ ppm 9.85 (s, 1H), 9.04 (s, 1H), 8.60 (s, 1H), 7.98 (d, 1H, J = 5.6 Hz), 7.39 (d, 1H, J = 8.0 Hz), 6.56 (d, 1H, J = 8.1 Hz), 6.44 (d, 1H, J = 5.7 Hz), 5.00 (d, 1H, J = 6.5 Hz), 4.86-4.51 (m, 4H), 4.19 (t, 1H, J = 6.3 Hz), 3.75-3.37 (m, 7H), 3.20-3.01 (m, 6H), 2.89 (q, 1H, J = 7.3 Hz), 1.84-1.63 (m, 2H), 1.49-1.20 (m, 9H) | B; Peak 2 | (3S,4R)-3-fluoro-1-[4-({5-[(2S)-1-hydroxypropan-2-yl]-8-[(2S,3R)-3-(methanesulfonyl-methyl)-2-methylazetidin-1-yl]isoquinolin-3-yl}amino)pyrimidin-2-yl]-3-methyl-piperidin-4-ol or (3S,4R)-3-fluoro-1-[4-({5-[(2R)-1-hydroxypropan-2-yl]-8-[(2S,3R)-3-(methanesulfonyl-methyl)-2-methylazetidin-1-yl]isoquinolin-3-yl}amino)pyrimidin-2-yl]-3-methyl-piperidin-4-ol |
| 197 | 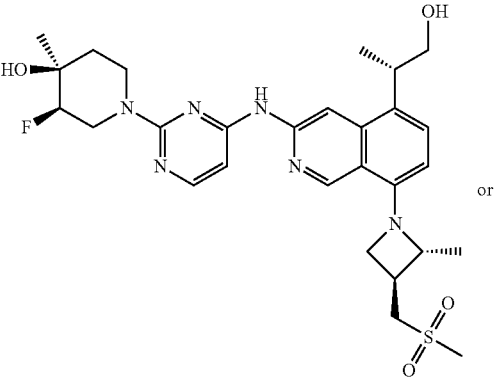 [SMILES: C[C@H](CO)c1ccc(N2C[C@H](CS(C)(=O)=O)[C@H]2C)c2cnc(Nc3ccnc(N4CC[C@](C)(O)[C@H](F)C4)n3)cc12] or | 573 | 1H-NMR (300 MHz, 6d-DMSO) δ ppm 9.94 (s, 1H), 9.05 (s, 1H), 8.63 (s, 1H), 8.01 (d, 1H, J = 5.7 Hz), 7.40 (d, 1H, J = 7.9 Hz), 6.57 (d, 1H, J = 8.0 Hz), 6.47 (d, 1H, J = 5.7 Hz), 4.84 (s, 1H), 4.73-4.59 (m, 2H), 4.46-4.06 (m, 4H), 3.59 (m, 8H), 3.00 (s, 3H), 2.89 (q, 1H, J = 7.1 Hz), 1.77-1.71 (m, 1H), 1.64-1.55 (m, 1H), 1.43 (d, 3H, J = 6.0 Hz), 1.31-1.21 (m, 6H) | B; Peak 2 | (3R,4S)-3-fluoro-1-[4-({5-[(2S)-1-hydroxypropan-2-yl]-8-[(2R,3S)-3-(methanesulfonyl-methyl)-2-methylazetidin-1-yl]isoquinolin-3-yl}amino)pyrimidin-2-yl]-4-methyl-piperidin-4-ol or (3R,4S)-3-fluoro-1-[4-({5-[(2R)-1- |

| # | Structure | LC/MS | NMR | Separation Conditions | Chemical Name |
|---|---|---|---|---|---|
| | 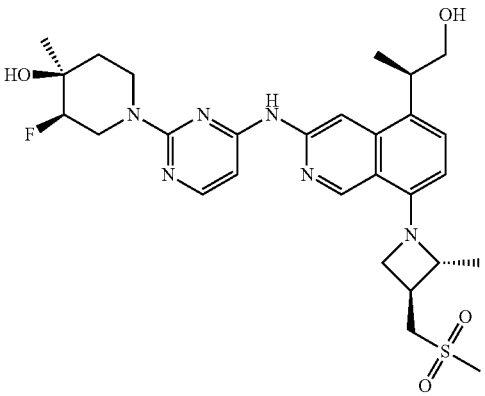 [SMILES: C[C@@H]1[C@@H](CS(C)(=O)=O)CN1c1ccc([C@@H](C)CO)c2cc(Nc3ccnc(N4CC[C@](C)(O)[C@H](F)C4)n3)ncc12] | | | | hydroxypropan-2-yl]-8-[(2R,3S)-3-(methanesulfonyl-methyl)-2-methylazetidin-1-yl]isoquinolin-3-yl}amino)pyrimidin-2-yl]-4-methyl-piperidin-4-ol |
| 198 | 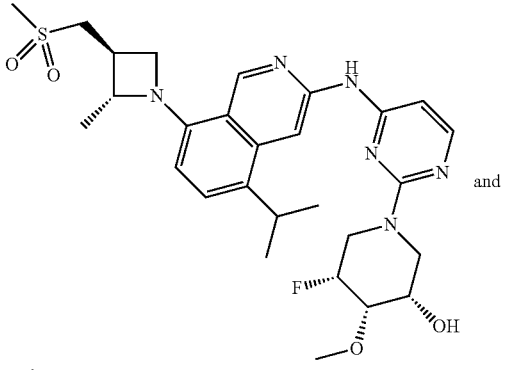 | 573 | 1H NMR (400 MHz, MeOD-d4) δ 9.10 (s, 1H), 8.62 (s, 1H), 7.97 (d, J = 5.6 Hz, 1H), 7.46 (d, J = 8.0 Hz, 1H), 6.65 (d, J = 8.0 Hz, 1H), 6.41 (d, J = 5.6 Hz, 1H), 4.74-4.55 (m, 4H), 4.45-4.40 (m, 1H), 4.32-4.25 (m, 1H), 3.89-3.85 (m, 1H), 3.80-3.70 (m, 1H), 3.66-3.47 (m, 8H), 3.39-3.33 (m, 1H), 3.01 (s, 3H), 1.49 (d, J = 6.0 Hz, 3H), 1.35 (d, J = 6.8 Hz, 6H) | | (3R,4R,5S)-5-fluoro-1-(4-((5-isopropyl-8-((2R,3S)-2-methyl-3-((methylsulfonyl)methyl)azetidin-1-yl)isoquinolin-3-yl)amino)pyrimidin-2-yl)-4-methoxy-piperidin-3-ol and (3S,4S,5R)-5-fluoro-1-(4-((5-isopropyl-8-((2R,3S)-2-methyl-3-((methylsulfonyl)methyl)azetidin-1-yl)isoquinolin-3-yl)amino)pyrimidin-2-yl)-4-methoxy-piperidin-3-ol |
| 199 | 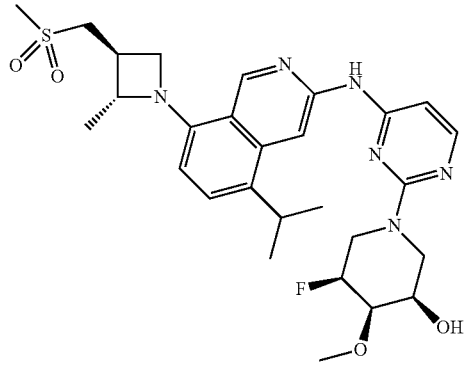 [SMILES: CO[C@@H]1[C@H](O)CN(c2nccc(Nc3cc4c(C(C)C)ccc(N5C[C@H](CS(C)(=O)=O)[C@H]5C)c4cn3)n2)C[C@@H]1F] | 573 | 1H-NMR (300 MHz, 6d-DMSO) δ ppm 9.89 (s, 1H), 9.02 (s, 1H), 8.61 (s, 1H), 7.98 (d, 1H, J = 5.7 Hz), 7.38 (d, 1H, J = 8.0 Hz), 6.54 (d, 1H, J = 8.0 Hz), 6.45 (d, 1H, J = 5.6 Hz), 4.81 (s, 1H), 4.67-4.59 (m, 2H), 4.49-3.98 (m, 4H), 3.76-3.39 (m, 8H), 2.98 (s, 3H), 2.87 (q, 1H, J = 7.6 Hz), 1.74-1.68 (m, 1H), 1.55-1.49 (m, 1H), 1.40 (d, 3H, J = 6.0 Hz), 1.28-1.19 (m, 6H) | B; Peak 2 | (3S,4R)-3-fluoro-1-[4-({5-[(2S)-1-hydroxypropan-2-yl]-8-[(2R,3S)-3-(methanesulfonyl-methyl)-2-methylazetidin-1-yl]isoquinolin-3-yl}amino)pyrimidin-2-yl]-4-methyl-piperidin-4-ol or (3S,4R)-3-fluoro-1-[4-({5-[(2R)-1-hydroxypropan- |

TABLE 1-continued

| # | Structure | LC/MS | NMR | Separation Conditions | Chemical Name |
|---|---|---|---|---|---|
| | | | | | 2-yl]-8-[(2R,3S)-3-(methanesulfonyl-methyl)-2-methylazetidin-1-yl]isoquinolin-3-yl}amino)pyrimidin-2-yl]-4-methyl-piperidin-4-ol |
| 200 | | 573 | 1H NMR (400 MHz, CDCl3) δ 9.11 (s, 1H), 8.62 (s, 1H), 7.98 (d, J = 5.6 Hz, 1H), 7.47 (d, J = 7.6 Hz, 1H), 6.66 (d, J = 7.6 Hz, 1H), 6.42 (d, J = 5.6 Hz, 1H), 4.65-4.60 (m, 2H), 4.54-4.21 (m, 4H), 3.72-3.65 (m, 1H), 3.64-3.61 (m, 2H), 3.56-3.44 (m, 5H), 3.43 (s, 3H), 3.01 (s, 3H), 1.49 (d, J = 6.0 Hz, 3H), 1.36 (d, J = 6.7 Hz, 6H) | | (3R,4S,5S)-3-fluoro-1-(4-((5-isopropyl-8-((2R,3S)-2-methyl-3-((methylsulfonyl)methyl)azetidin-1-yl)isoquinolin-3-yl)amino)pyrimidin-2-yl)-5-methoxy-piperidin-4-ol and (3S,4R,5R)-3-fluoro-1-(4-((5-isopropyl-8-((2R,3S)-2-methyl-3-((methylsulfonyl)methyl)azetidin-1-yl)isoquinolin-3-yl)amino)pyrimidin-2-yl)-5-methoxy-piperidin-4-ol |
| 201 | 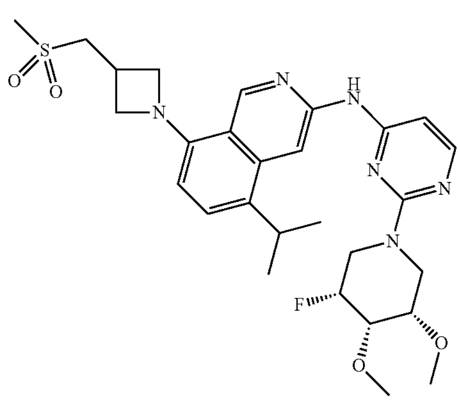 [SMILES: CO[C@H]1[C@@H](F)CN(c2nccc(Nc3cc4c(C(C)C)ccc(N5CC(CS(C)(=O)=O)C5)c4cn3)n2)C[C@H]1OC] | 573 | 1H NMR (400 MHz, MeOD-d4) δ 9.12 (s, 1H), 8.61 (s, 1H), 8.00 (d, J = 5.6 Hz, 1H), 7.48 (d, J = 7.6 Hz, 1H), 6.55 (d, J = 7.6 Hz, 1H), 6.44 (d, J = 5.6 Hz, 1H), 4.46-4.34 (m, 4H), 4.10-4.01 (m, 3H), 3.75-3.70 (m, 1H), 3.63-3.60 (m, 6H), 3.56-3.49 (m, 2H), 3.45 (s, 3H), 3.44-3.40 (m, 2H), 3.08-3.06 (m, 1H), 3.04 (s, 3H), 1.37 (dd, J = 2.8, 6.8 Hz, 6H) | | (3R,4S,5S)-3-fluoro-1-(4-((5-isopropyl-8-((2R,3S)-2-methyl-3-((methylsulfonyl)methyl)azetidin-1-yl)isoquinolin-3-yl)amino)pyrimidin-2-yl)-5-methoxy piperidin-4-ol and (3S,4R,5R)-3-fluoro-1-(4-((5-isopropyl-8-((2R,3S)-2-methyl-3-((methylsulfonyl) |

TABLE 1-continued

| # | Structure | LC/MS | NMR | Separation Conditions | Chemical Name |
|---|---|---|---|---|---|
| | | | | | methyl)azetidin-1-yl)isoquinolin-3-yl)amino)pyrimidin-2-yl)-5-methoxy piperidin-4-ol |
| 202 | | 573 | 1H NMR (400 MHz, MeOD-d4) δ 9.10 (s, 1H), 8.61 (s, 1H), 7.97 (d, J = 5.6 Hz, 1H), 7.45 (d, J = 8.0 Hz, 1H), 6.65 (d, J = 8.0 Hz, 1H), 6.40 (d, J = 5.6 Hz, 1H), 4.74-4.55 (m, 4H), 4.45-4.40 (m, 1H), 4.32-4.25 (m, 1H), 3.89-3.85 (m, 1H), 3.80-3.70 (m, 1H), 3.66-3.47 (m, 8H), 3.39-3.33 (m, 1H), 3.01 (s, 3H), 1.49 (d, J = 6.0 Hz, 3H), 1.35 (d, J = 6.8 Hz, 6H) | P; Peak 2 | (3S,4S,5R)-5-fluoro-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methoxy-piperidin-3-ol or (3R,4R,5S)-5-fluoro-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methoxy-piperidin-3-ol |
| 203 | 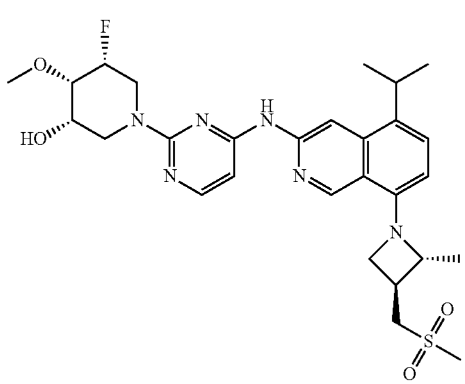 | 573 | 1H NMR (400 MHz, MeOD-d4) δ 9.10 (s, 1H), 8.62 (s, 1H), 7.97 (d, J = 5.6 Hz, 1H), 7.46 (d, J = 8.0 Hz, 1H), 6.65 (d, J = 8.0 Hz, 1H), 6.41 (d, J = 5.6 Hz, 1H), 4.74-4.55 (m, 4H), 4.45-4.40 (m, 1H), 4.32-4.25 (m, 1H), 3.89-3.85 (m, 1H), 3.80-3.70 (m, 1H), 3.66-3.47 (m, 8H), 3.39-3.33 (m, 1H), 3.01 (s, 3H), 1.49 (d, J = 6.0 Hz, 3H), 1.35 (d, J = 6.8 Hz, 6H) | P; Peak 1 | (3R,4R,5S)-5-fluoro-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methoxy-piperidin-3-ol or (3S,4S,5R)-5-fluoro-1-[4-({8-[(2R,3S)-3-(methanesulfonyl-methyl)-2- |

TABLE 1-continued

| # | Structure | LC/MS | NMR | Separation Conditions | Chemical Name |
|---|---|---|---|---|---|
| | | | | | methylazetidin-1-yl]-5-(propan-2-yl)isoquinolin-3-yl}amino)pyrimidin-2-yl]-4-methoxy-piperidin-3-ol |
| 204 | | 573 | 1H NMR (400 MHz, MeOD-d4) δ 9.01 (s, 1H), 8.52 (s, 1H), 7.88 (d, J = 5.6 Hz, 1H), 7.37 (d, J = 8.0 Hz, 1H), 6.55 (d, J = 8.0 Hz, 1H), 6.32 (d, J = 5.6 Hz, 1H), 4.59-4.48 (m, 4H), 4.43-4.26 (m, 2H), 4.20-4.05 (m, 1H), 3.61-3.56 (m, 1H), 3.56-3.45 (m, 3H), 3.45-3.32 (m, 6H), 3.30-3.24 (m, 1H), 2.91 (s, 3H), 1.39 (d, J = 6.0 Hz, 3H), 1.26 (dd, J = 3.2, 6.8 Hz, 6H) | Q; Peak 1 | (3S,4R,5R)-3-fluoro-1-[4-({8-[(2R,3S)-3-(methanesulfonyl-methyl)-2-methylazetidin-1-yl]-5-(propan-2-yl)isoquinolin-3-yl}amino)pyrimidin-2-yl]-5-methoxy-piperidin-4-ol or (3R,4S,5S)-3-fluoro-1-[4-({8-[(2R,3S)-3-(methanesulfonyl-methyl)-2-methylazetidin-1-yl]-5-(propan-2-yl)isoquinolin-3-yl}amino)pyrimidin-2-yl]-5-methoxy-piperidin-4-ol |
| 205 | 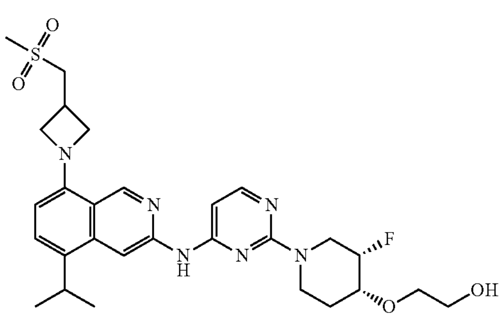 [SMILES: CC(C)c1ccc(N2CC(CS(C)(=O)=O)C2)c2cnc(Nc3ccnc(N4CC[C@@H](OCCO)[C@@H](F)C4)n3)cc12] | 573 | 1H-NMR (300 MHz, 6d-DMSO) δ ppm 9.91 (s, 1H), 9.05 (s, 1H), 8.63 (s, 1H), 8.00 (d, 1H, J = 5.6 Hz), 7.43 (d, 1H, J = 8.1 Hz), 6.48 (d, 1H, J = 5.6 Hz), 6.42 (d, 1H, J = 8.1 Hz), 5.08-4.72 (m, 2H), 4.66 (t, 1H, J = 5.2 Hz), 4.52 (s, 1H), 4.39 (t, 2H, J = 7.7 Hz), 3.97 (t, 2H, J = 6.8 Hz), 3.82-3.65 (m, 1H), 3.64-3.43 (m, 7H), 3.29-3.23 (m, 3H), 3.02 (s, 3H), 1.85-1.79 (m, 2H), 1.31 (dd, 6H, J = 6.8, 3.2 Hz) | | 2-{[(3S,4R)-3-fluoro-1-[4-({8-[3-(methanesulfonyl-methyl)azetidin-1-yl]-5-(propan-2-yl)isoquinolin-3-yl}amino)pyrimidin-2-yl]piperidin-4-yl]oxy}ethan-1-ol |

TABLE 1-continued

| # | Structure | LC/MS | NMR | Separation Conditions | Chemical Name |
|---|---|---|---|---|---|
| 206 | 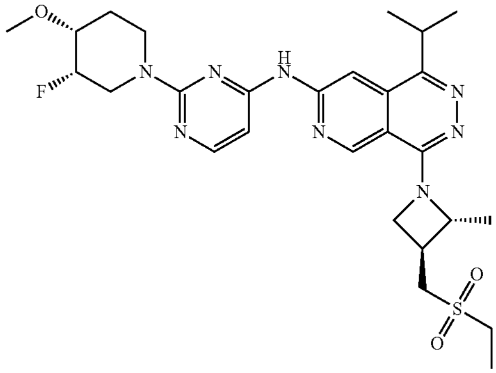 [SMILES: CCS(=O)(=O)C[C@H]1CN(c2nnc(C(C)C)c3cc(Nc4ccnc(N5CC[C@@H](OC)[C@@H](F)C5)n4)ncc23)[C@@H]1C] | 573 | 1H-NMR (300 MHz, 6d-DMSO) δ ppm 10.45 (s, 1H), 9.10 (s, 1H), 8.62 (s, 1H), 8.09 (d, 1H, J = 5.6 Hz), 6.52 (d, 1H, J = 5.6 Hz), 5.11-4.81 (m, 2H), 4.75-4.61 (m, 2H), 4.46 (d, 1H, J = 13.3 Hz), 4.06 (t, 1H, J = 7.3 Hz), 3.72-3.41 (m, 5H), 3.37 (s, 3H), 3.09 (q, 2H, J = 7.5 Hz), 2.95 (p, 1H, J = 7.1 Hz), 1.89-1.69 (m, 2H), 1.54 (d, 3H, J = 6.2 Hz), 1.36 (dd, 6H, J = 11.0, 6.7 Hz), 1.23 (t, 3H, J = 7.4 Hz) | | N-{4-[(2R,3S)-3-[(ethanesulfonyl)methyl]-2-methylazetidin-1-yl]-1-(propan-2-yl)pyrido[3,4-d]pyridazin-7-yl}-2-[(3S,4R)-3-fluoro-4-methoxypiperidin-1-yl]pyrimidin-4-amine |
| 207 | 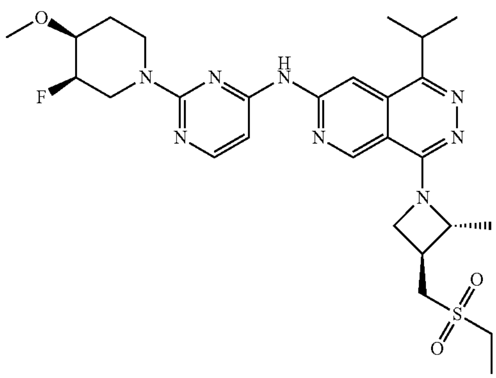 [SMILES: CCS(=O)(=O)C[C@H]1CN(c2nnc(C(C)C)c3cc(Nc4ccnc(N5CC[C@H](OC)[C@H](F)C5)n4)ncc23)[C@@H]1C] | 573 | 1H-NMR (300 MHz, 6d-DMSO) δ ppm 10.44 (s, 1H), 9.10 (s, 1H), 8.61 (s, 1H), 8.09 (d, 1H, J = 5.6 Hz), 6.52 (d, 1H, J = 5.6 Hz), 5.13-4.82 (m, 2H), 4.67 (td, 3H, J = 12.6, 11.9, 5.9 Hz), 4.47 (d, 1H, J = 13.6 Hz), 4.06 (t, 1H, J = 7.3 Hz), 3.69-3.48 (m, 7H), 3.40-3.34 (m, 2H), 3.09 (q, 2H, J = 7.4 Hz), 2.94 (q, 1H, J = 7.2 Hz), 1.85-1.65 (m, 2H), 1.54 (d, 3H, J = 6.1 Hz), 1.36 (dd, 6H, J = 6.8, 2.9 Hz), 1.23 (t, 3H, J = 7.4 Hz) | | N-{4-[(2R,3S)-3-[(ethanesulfonyl)methyl]-2-methylazetidin-1-yl]-1-(propan-2-yl)pyrido[3,4-d]pyridazin-7-yl}-2-[(3R,4S)-3-fluoro-4-methoxypiperidin-1-yl]pyrimidin-4-amine |
| 208 | | 574 | 1H-NMR (400 MHz, 6d-DMSO) δ ppm 10.12 (s, 1H), 9.04 (s, 1H), 8.54 (s, 1H), 8.05 (d, 1H, J = 5.6 Hz), 7.97 (s, 1H), 6.59-6.46 (m, 1H), 4.99 (d, 1H, J = 53.8 Hz), 4.87-4.65 (m, 3H), 4.60-4.46 (m, 2H), 3.99 (t, 1H, J = 7.3 Hz), 3.74-3.42 (m, 6H), 3.36 (s, 3H), 3.30-3.24 (m, 1H), 2.99 (s, 3H), 2.89 (q, 1H, J = 7.2 Hz), 1.89-1.64 (m, 2H), 1.50 (d, 3H, J = 6.1 Hz), 1.29 (d, 3H, J = 6.8 Hz) | F; Peak 1 | (2R)-2-[6-({2-[(3R,4S)-3-fluoro-4-methoxypiperidin-1-yl]pyrimidin-4-yl}amino)-1-[(2R,3S)-3-(methanesulfonylmethyl)-2-methylazetidin-1-yl]-2,7-naphthyridin-4-yl]propan-1-ol or (2S)-2-[6-({2-[(3R,4S)-3-fluoro-4-methoxypiperidin-1-yl]pyrimidin-4-yl}amino)-1-[(2R,3S)-3-(methanesulfonylmethyl)-2-methylazetidin-1-yl]-2,7-naphthyridin-4-yl]propan-1-ol |

TABLE 1-continued

| # | Structure | LC/MS | NMR | Separation Conditions | Chemical Name |
|---|---|---|---|---|---|
| 209 | 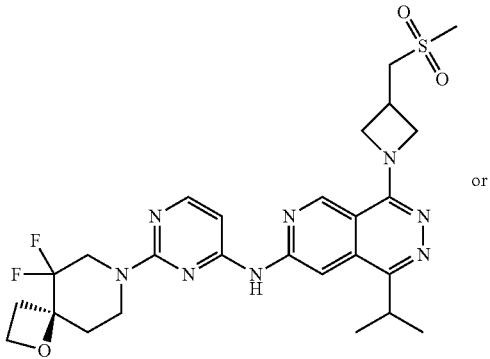 [SMILES: CC(C)c1nnc(N2CC(CS(C)(=O)=O)C2)c2cnc(Nc3ccnc(N4CC[C@]5(CCO5)C(F)(F)C4)n3)cc12]<br>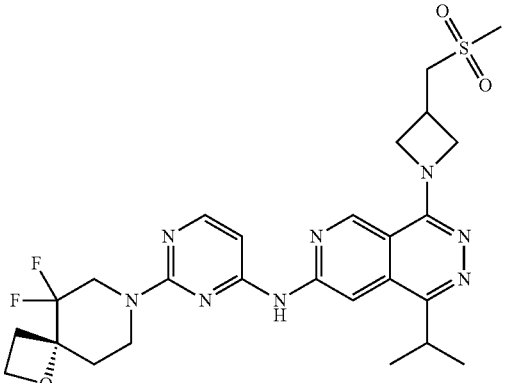 | 575 | 1H NMR (400 MHz, 6d-DMSO) δ ppm 10.46 (s, 1H), 9.05 (s, 1H), 8.48 (s, 1H), 8.09 (d, 1H, J = 5.6 Hz), 6.59 (d, 1H, J = 5.7 Hz), 4.62 (t, 2H, J = 8.4 Hz), 4.49 (t, 2H, J = 7.7 Hz), 4.41-4.21 (m, 3H), 4.11-3.84 (m, 2H), 3.77-3.48 (m, 4H), 3.01 (s, 3H), 2.77 (dt, 1H, J = 11.5, 7.5 Hz), 2.53 (t, 1H, J = 5.9 Hz), 2.06 (m, 2H), 1.41-1.28 (m, 6H) | MM, Peak 2 | (S)-N-(2-(5,5-difluoro-1-oxa-7-azaspiro[3.5]nonan-7-yl)pyrimidin-4-yl)-1-isopropyl-4-(3-((methylsulfonyl)methyl)azetidin-1-yl)pyrido[3,4-d]pyridazin-7-amine or (R)-N-(2-(5,5-difluoro-1-oxa-7-azaspiro[3.5]nonan-7-yl)pyrimidin-4-yl)-1-isopropyl-4-(3-((methylsulfonyl)methyl)azetidin-1-yl)pyrido[3,4-d]pyridazin-7-amine |
| 210 | 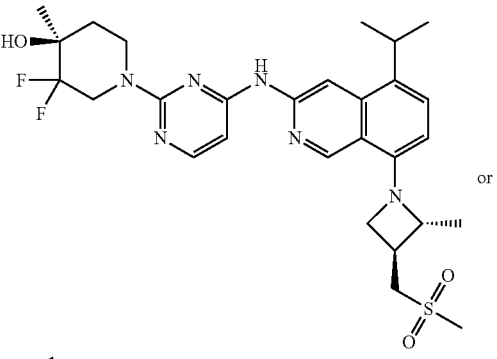<br>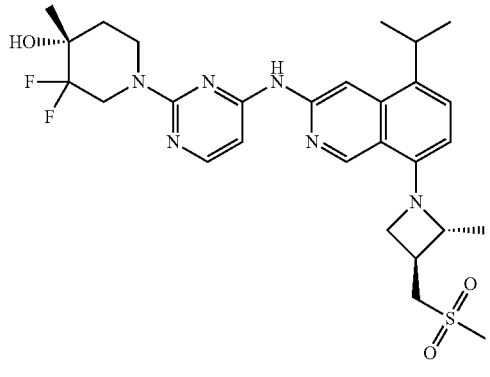 [SMILES: CC(C)c1ccc(N2C[C@H](CS(C)(=O)=O)[C@H]2C)c2cnc(Nc3ccnc(N4CC[C@@](C)(O)C(F)(F)C4)n3)cc12] | 575 | 1H-NMR (300 MHz, 6d-DMSO) δ ppm 9.95 (s, 1H), 9.04 (s, 1H), 8.59 (s, 1H), 8.00 (d, 1H, J = 5.7 Hz), 7.41 (d, 1H, J = 8.0 Hz), 6.55 (d, 1H, J = 8.1 Hz), 6.49 (d, 1H, J = 5.6 Hz), 5.53 (s, 1H), 4.73 (d, 1H, J = 10.4 Hz), 4.64 (t, 1H, J = 7.6 Hz), 4.46 (d, 1H, J = 12.3 Hz), 4.18 (t, 1H, J = 6.2 Hz), 3.76-3.36 (m, 5H), 2.98 (s, 3H), 2.87 (q, 1H, J = 7.1 Hz), 1.75-1.69 (m, 2H), 1.41 (d, 3H, J = 6.0 Hz), 1.32-1.19 (m, 9H) ppm | E; Peak 1 | (4S)-3,3-difluoro-1-[4-({8-[(2R,3S)-3-(methanesulfonylmethyl)-2-methylazetidin-1-yl]-5-(propan-2-yl)isoquinolin-3-yl}amino)pyrimidin-2-yl]-4-methyl-piperidin-4-ol or (4R)-3,3-difluoro-1-[4-({8-[(2R,3S)-3-(methanesulfonylmethyl)-2-methylazetidin-1-yl]-5-(propan-2-yl)isoquinolin-3-yl}amino)pyrimidin-2-yl]-4-methyl-piperidin-4-ol |

TABLE 1-continued

| # | Structure | LC/MS | NMR | Separation Conditions | Chemical Name |
|---|---|---|---|---|---|
| 211 | 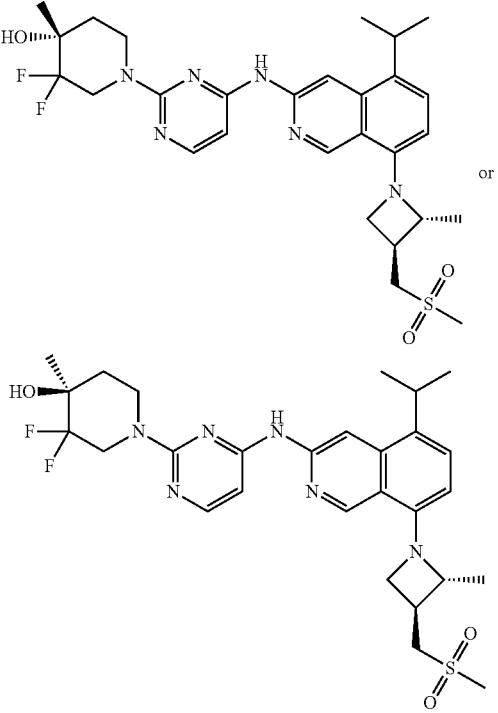 | 575 | 1H-NMR (300 MHz, 6d-DMSO) δ ppm 9.96 (s, 1H), 9.04 (s, 1H), 8.59 (s, 1H), 8.00 (d, 1H, J = 5.7 Hz), 7.41 (d, 1H, J = 8.0 Hz), 6.55 (d, 1H, J = 8.1 Hz), 6.49 (d, 1H, J = 5.7 Hz), 5.52 (s, 1H), 4.73 (s, 1H), 4.64 (t, 1H, J = 7.5 Hz), 4.46 (d, 1H, J = 13.2 Hz), 4.18 (t, 1H, J = 6.3 Hz), 3.76-3.53 (m, 2H), 3.57-3.31 (m, 3H), 2.98 (s, 3H), 2.87 (q, 1H, J = 7.1 Hz), 1.74-1.68 (m, 2H), 1.41 (d, 3H, J = 6.0 Hz), 1.32-1.22 (m, 9H) | E; Peak 2 | (4R)-3,3-difluoro-1-[4-({8-[(2R,3S)-3-(methanesulfonylmethyl)-2-methylazetidin-1-yl]-5-(propan-2-yl)isoquinolin-3-yl}amino)pyrimidin-2-yl]-4-methyl-piperidin-4-ol or (4S)-3,3-difluoro-1-[4-({8-[(2R,3S)-3-(methanesulfonylmethyl)-2-methylazetidin-1-yl]-5-(propan-2-yl)isoquinolin-3-yl}amino)pyrimidin-2-yl]-4-methyl-piperidin-4-ol |
| 212 | 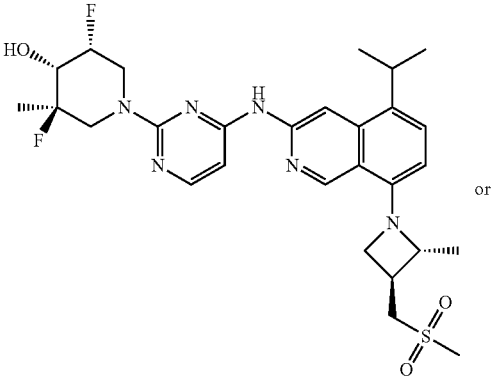 | 575 | 1H-NMR (400 MHz, 6d-DMSO) δ ppm 9.97 (s, 1H), 9.07 (s, 1H), 8.58 (s, 1H), 8.02 (d, 1H, J = 5.6 Hz), 7.43 (d, 1H, J = 8.0 Hz), 6.62-6.50 (m, 2H), 5.87 (d, 1H, J = 5.2 Hz), 4.93-4.56 (m, 2H), 4.35-3.78 (m, 6H), 3.71-3.46 (m, 4H), 3.00 (s, 3H), 2.96-2.85 (m, 1H), 1.43 (d, 4H, J = 5.2 Hz), 1.38-1.25 (m, 8H) | I; Peak 2 | (3R,4R,5R)-3,5-difluoro-1-[4-({8-[(2R,3S)-3-(methanesulfonylmethyl)-2-methylazetidin-1-yl]-5-(propan-2-yl)isoquinolin-3-yl}amino)pyrimidin-2-yl]-3-methyl-piperidin-4-ol or (3S,4S,5S)-3,5-difluoro-1-[4-({8-[(2R,3S)-3-(methanesulfonylmethyl)-2-methylazetidin-1-yl]-5-(propan-2-yl)isoquinolin-3-yl}amino)pyrimidin-2-yl]-3-methyl-piperidin-4-ol |

TABLE 1-continued

| # | Structure | LC/MS | NMR | Separation Conditions | Chemical Name |
|---|---|---|---|---|---|
| 213 | 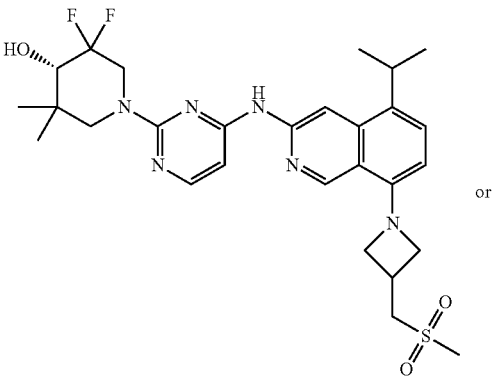 | 575 | 1H-NMR (300 MHz, 6d-DMSO) δ ppm 10.13 (s, 1H), 9.08 (s, 1H), 8.50 (s, 1H), 8.01 (d, 1H, J = 5.9 Hz), 7.43 (d, 1H, J = 8.0 Hz), 6.60 (s, 1H), 6.44 (d, 1H, J = 8.1 Hz), 5.75 (s, 1H), 4.70 (q, 1H, J = 11.5 Hz), 4.39 (t, 2H, J = 7.6 Hz), 4.17 (d, 1H, J = 13.3 Hz), 3.97 (t, 2H, J = 6.9 Hz), 3.87-3.67 (m, 1H), 3.68-3.45 (m, 4H), 3.32-3.22 (m, 2H), 3.01 (s, 3H), 1.29 (dd, 6H, J = 6.7, 3.3 Hz), 1.00 (s, 3H), 0.89 (s, 3H) | L; Peak 1 | (4S)-3,3-difluoro-1-[4-({8-[3-(methanesulfonylmethyl)azetidin-1-yl]-5-(propan-2-yl)isoquinolin-3-yl}amino)pyrimidin-2-yl]-5,5-dimethylpiperidin-4-ol or (4R)-3,3-difluoro-1-[4-({8-[3-(methanesulfonylmethyl)azetidin-1-yl]-5-(propan-2-yl)isoquinolin-3-yl}amino)pyrimidin-2-yl]-5,5-dimethylpiperidin-4-ol |
| 214 | 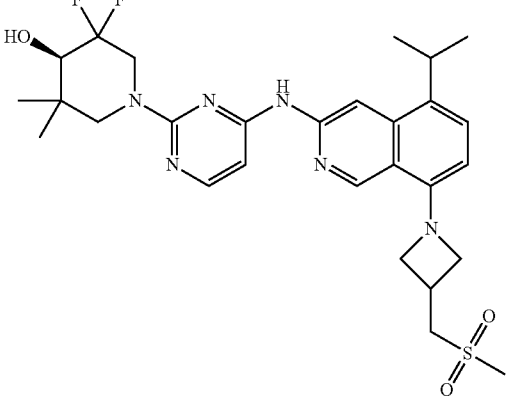 | 576 | 1H-NMR (300 MHz, 6d-DMSO) δ ppm 10.23 (s, 1H), 9.14 (s, 1H), 8.73 (s, 1H), 8.06 (d, 1H, J = 5.7 Hz), 7.74 (s, 1H), 6.51 (d, 1H, J = 5.7 Hz), 5.58 (s, 1H), 4.74 (t, 2H, J = 7.6 Hz), 4.54-4.44 (m, 1H), 4.27 (dt, 1H, J = 27.4, 6.4 Hz), 3.83-3.38 (m, 6H), 3.01 (s, 3H), 2.93 (q, 1H, J = 7.4 Hz), 1.77-1.71 (m, 2H), 1.49 (d, 3H, J = 6.1 Hz), 1.35-1.25 (m, 9H) | FF, Peak 2 | (4R)-3,3-difluoro-1-[4-({8-[(2R,3S)-3-(methanesulfonylmethyl)-2-methylazetidin-1-yl]-5-(propan-2-yl)-2,6-naphthyridin-3-yl}amino)pyrimidin-2-yl]-4-methylpiperidin-4-ol or (4S)-3,3-difluoro-1-[4-({8-[(2R,3S)-3-(methanesulfonylmethyl)-2-methylazetidin-1-yl]-5-(propan-2-yl)-2,6-naphthyridin-3-yl}amino)pyrimidin-2-yl]-4-methylpiperidin-4-ol |

TABLE 1-continued

| # | Structure | LC/MS | NMR | Separation Conditions | Chemical Name |
|---|---|---|---|---|---|
| 215 | 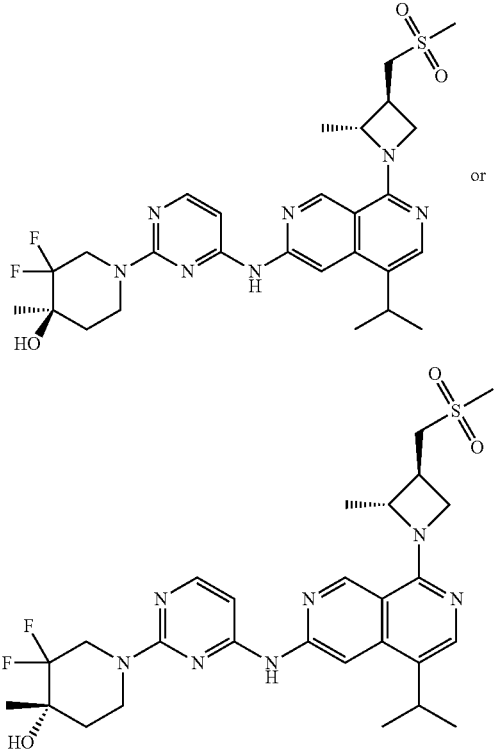 | 576 | 1H-NMR (300 MHz, 6d-DMSO) δ ppm 10.17 (s, 1H), 9.04 (s, 1H), 8.49 (s, 1H), 8.06 (d, 1H, J = 5.6 Hz), 8.00 (s, 1H), 6.55 (d, 1H, J = 5.6 Hz), 5.56 (s, 1H), 4.86 (t, 1H, J = 8.0 Hz), 4.75-4.69 (m, 1H), 4.60-4.40 (m, 2H), 3.98 (t, 1H, J = 7.3 Hz), 3.67 (dd, 1H, J = 30.1, 13.3 Hz), 3.57-3.48 (m, 2H), 3.38 (dd, 2H, J = 13.4, 6.7 Hz), 2.98 (s, 3H), 2.89 (q, 1H, J = 7.2 Hz), 1.75-1.69 (m, 2H), 1.49 (d, 3H, J = 6.1 Hz), 1.35-1.23 (m, 9H) | DD, Peak 2 | (4R)-3,3-difluoro-1-[4-({8-[(2R,3S)-3-(methanesulfonyl-methyl)-2-methylazetidin-1-yl]-5-(propan-2-yl)-2,7-naphthyridin-3-yl}amino)pyrimidin-2-yl]-4-methyl-piperidin-4-ol or (4S)-3,3-difluoro-1-[4-({8-[(2R,3S)-3-(methanesulfonyl-methyl)-2-methylazetidin-1-yl]-5-(propan-2-yl)-2,7-naphthyridin-3-yl}amino)pyrimidin-2-yl]-4-methyl-piperidin-4-ol |
| 216 | 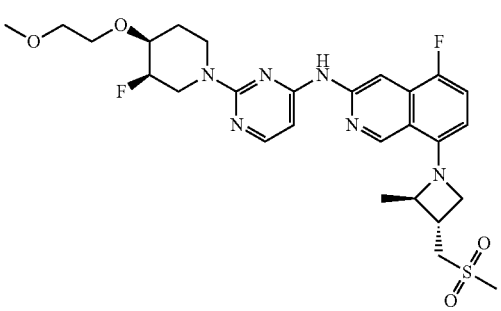 | 577 | 1H-NMR (300 MHz, 6d-DMSO) δ ppm 10.13 (s, 1H), 9.10 (s, 1H), 8.67 (s, 1H), 8.03 (d, 1H, J = 5.7 Hz), 7.34 (t, 1H, J = 9.3 Hz), 6.45 (d, 2H, J = 6.7 Hz), 4.91 (d, 1H, J = 50.0 Hz), 4.73-4.67 (m, 2H), 4.47 (d, 1H, J = 13.5 Hz), 4.21 (s, 1H), 3.81-3.39 (m, 10H), 3.27 (s, 3H), 3.01 (s, 3H), 2.93-2.87 (m, 1H), 1.83-1.77 (m, 2H), 1.42 (d, 3H, J = 5.9 Hz) | M; Peak 1 | 5-fluoro-N-{2-[(3R,4S)-3-fluoro-4-(2-methoxyethoxy)piperidin-1-yl]pyrimidin-4-yl}-8-[(2R,3S)-3-(methanesulfonyl-methyl)-2-methylazetidin-1-yl]isoquinolin-3-amine |
| 217 | 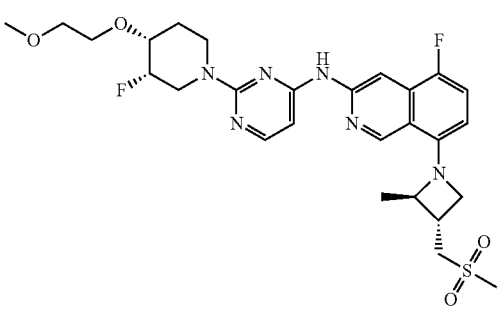 | 577 | 1H-NMR (300 MHz, 6d-DMSO) δ ppm 10.13 (s, 1H), 9.10 (s, 1H), 8.67 (s, 1H), 8.03 (d, 1H, J = 5.6 Hz), 7.40-7.28 (m, 1H), 6.46 (t, 2H, J = 5.4 Hz), 4.91 (d, 1H, J = 49.0 Hz), 4.75-4.64 (m, 2H), 4.46 (d, 1H, J = 13.1 Hz), 4.21 (t, 1H, J = 6.0 Hz), 3.77-3.72 (m, 2H), 3.67 (q, 3H, J = 4.8, 3.9 Hz), 3.61-3.43 (m, 5H), 3.28 (s, 3H), 3.01 (s, 3H), 2.89 (d, 1H, J = 7.3 Hz), 1.83-1.77 (m, 2H), 1.42 (d, 3H, J = 6.0 Hz) | M; Peak 2 | 5-fluoro-N-{2-[(3S,4R)-3-fluoro-4-(2-methoxyethoxy)piperidin-1-yl]pyrimidin-4-yl}-8-[(2R,3S)-3-(methanesulfonyl-methyl)-2-methylazetidin-1-yl]isoquinolin-3-amine |

TABLE 1-continued

| # | Structure | LC/MS | NMR | Separation Conditions | Chemical Name |
|---|---|---|---|---|---|
| 218 | 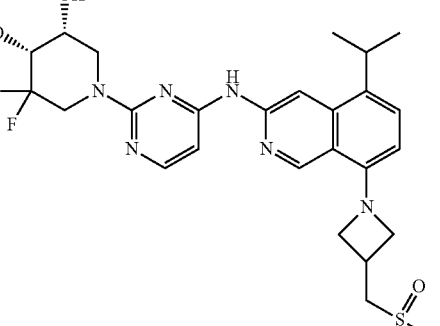 or 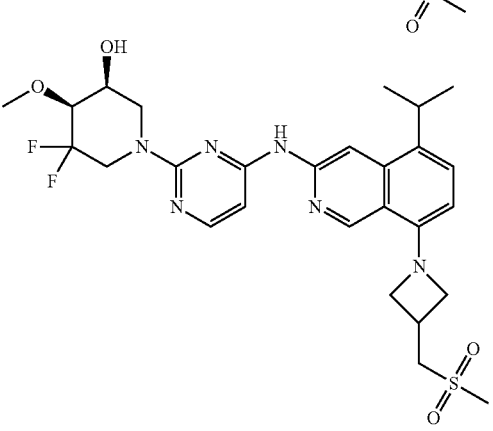 | 576.2 | 1H NMR (400 MHz, CDCl3) δ 9.07 (s, 1H), 8.48 (s, 1H), 8.08 (d, J = 5.6 Hz, 1H), 7.46-7.37 (m, 2H), 6.43 (d, J = 7.6 Hz, 1H), 6.28 (d, J = 5.5 Hz, 1H), 4.96-4.83 (m, 1H), 4.71 (dd, J = 13.2, 4.4 Hz, 1H), 4.46 (t, J = 7.2 Hz, 2H), 4.07-3.94 (m, 3H), 3.70 (s, 3H), 3.69-3.55 (m, 3H), 3.50-3.38 (m, 3H), 3.28-3.18 (m, 1H), 2.99 (s, 3H), 2.45 (d, J = 10.2 Hz, 1H), 1.37 (t, J = 6.8 Hz, 6H) | BB Peak 2 | (3R,4R)-5,5-difluoro-1-[4-({8-[3-(methanesulfonyl-methyl)azetidin-1-yl]-5-(propan-2-yl)isoquinolin-3-yl}amino)pyrimidin-2-yl]-4-methoxy-piperidin-3-ol or (3S,4S)-5,5-difluoro-1-[4-({8-[3-(methane-sulfonylmethyl)azetidin-1-yl]-5-(propan-2-yl)isoquinolin-3-yl}amino)pyrimidin-2-yl]-4-methoxy-piperidin-3-ol |
| 219 | 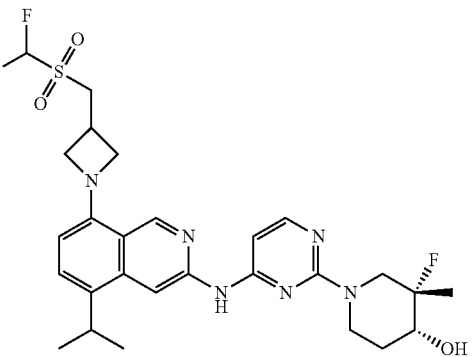 | 579 | 1H-NMR (300 MHz, 6d-DMSO) δ ppm 9.86 (s, 1H), 9.05 (s, 1H), 8.61 (s, 1H), 7.99 (d, 1H, J = 5.6 Hz), 7.43 (d, 1H, J = 7.9 Hz), 7.17 (t, 1H, J = 51.8 Hz), 6.51-6.38 (m, 2H), 5.04 (d, 1H, J = 6.3 Hz), 4.82-4.64 (m, 2H), 4.39 (t, 2H, J = 7.4 Hz), 4.05-3.90 (m, 4H), 3.66-3.45 (m, 2H), 3.23-3.02 (m, 3H), 1.77-1.70 (m, 2H), 1.49-1.25 (m, 9H) | NN; Peak 1 | (3S,4R)-1-[4-({8-[3-(difluoro-methanesulfonyl-methyl)azetidin-1-yl]-5-(propan-2-yl)isoquinolin-3-yl}amino)pyrimidin-2-yl]-3-fluoro-3-methyl-piperidin-4-ol |
| 220 | 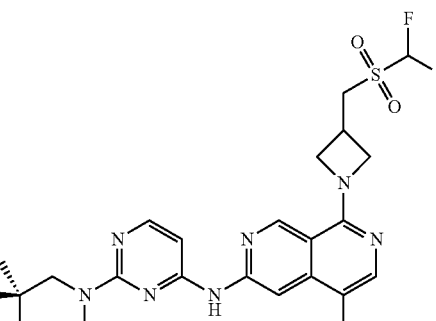 | 580 | 1H NMR (300 MHz, 6d-DMSO) δ ppm 10.06 (s, 1H), 9.00 (s, 1H), 8.47 (s, 1H), 8.01 (d, 1H, J = 5.7 Hz), 7.98 (s, 1H), 7.14 (t, 1H, J = 51.9 Hz), 6.49 (d, 1H, J = 5.7 Hz), 5.02 (d, 1H, J = 6.4 Hz), 4.83-4.45 (m, 3H), 4.23 (t, 2H, J = 7.5 Hz), 3.92 (d, 2H, J = 7.4 Hz), 3.66-3.46 (m, 1H), 3.45-3.02 (m, 4H), 1.71 (s, 2H), 1.46-1.18 (m, 9H) | NN; Peak 1 | (3S,4R)-1-[4-({8-[3-(difluoro-methanesulfonyl-methyl)azetidin-1-yl]-5-(propan-2-yl)-2,7-naph-thyridin-3-yl}amino)pyrimidin-2-yl]-3-fluoro-3-methyl-piperidin-4-ol |

TABLE 1-continued

| # | Structure | LC/MS | NMR | Separation Conditions | Chemical Name |
|---|---|---|---|---|---|
| 221 | 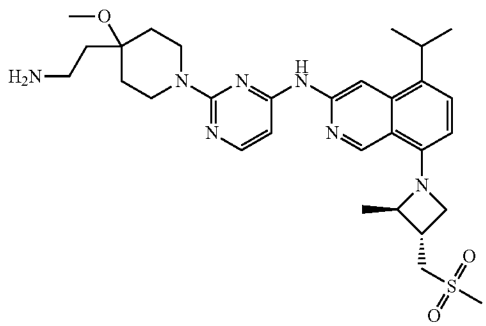 [SMILES: COC1(CCN)CCN(c2nccc(Nc3cc4c(C(C)C)ccc(N5C[C@H](CS(C)(=O)=O)[C@H]5C)c4cn3)n2)CC1] | 582 | 1H-NMR (300 MHz, 6d-DMSO) δ ppm 9.04 (s, 1H), 8.68 (s, 1H), 8.40 (s, 2H), 8.00 (d, 1H, J = 5.7 Hz), 7.43 (d, 1H, J = 8.0 Hz), 6.56 (d, 1H, J = 8.1 Hz), 6.42 (d, 1H, J = 5.7 Hz), 4.65 (t, 1H, J = 7.5 Hz), 4.36 (d, 2H, J = 12.8 Hz), 4.24-4.14 (m, 1H), 3.69-3.59 (m, 3H), 3.27 (t, 2H, J = 11.9 Hz), 3.18 (s, 3H), 2.99 (s, 3H), 2.90-2.77 (m, 3H), 1.84-1.74 (m, 4H), 1.53-1.47 (m, 2H), 1.42 (d, 3H, J = 6.0 Hz), 1.29 (d, 6H, J = 6.6 Hz) | | N-{2-[4-(2-aminoethyl)-4-methoxy-piperidin-1-yl]pyrimidin-4-yl}-8-[(2R,3S)-3-(methanesulfonyl-methyl)-2-methylazetidin-1-yl]-5-(propan-2-yl)isoquinolin-3-amine |
| 222 | 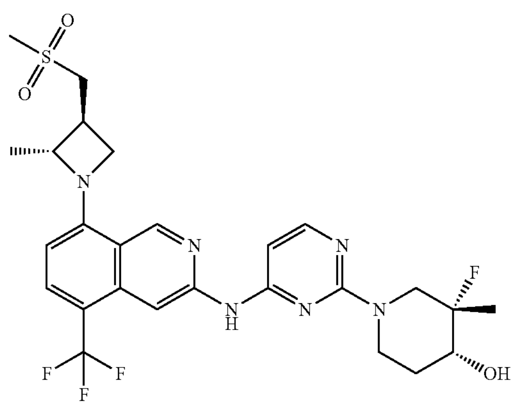 | 583 | 1H-NMR (400 MHz, 6d-DMSO) δ ppm 10.01 (s, 1H), 9.12 (s, 1H), 8.54 (s, 1H), 8.01 (d, 1H, J = 5.6 Hz), 7.84 (d, 1H, J = 8.5 Hz), 6.53-6.43 (m, 3H), 4.97 (d, 1H, J = 6.4 Hz), 4.88 (t, 1H, J = 8.2 Hz), 4.73 (dd, 2H, J = 23.9, 15.2 Hz), 4.40 (t, 1H, J = 6.1 Hz), 3.97 (t, 1H, J = 7.2 Hz), 3.65-3.45 (m, 3H), 3.09-2.98 (m, 5H), 2.93 (d, 1H, J = 7.5 Hz), 1.73-1.68 (m, 2H), 1.49 (d, 3H, J = 6.1 Hz), 1.35 (d, 3H, J = 21.2 Hz) | NN; Peak 1 | (3S,4R)-3-fluoro-1-[4-({8-[(2R,3S)-3-(methanesulfonyl-methyl)-2-methylazetidin-1-yl]-5-(trifluoromethyl)isoquinolin-3-yl}amino)pyrimidin-2-yl]-3-methyl-piperidin-4-ol |
| 223 | 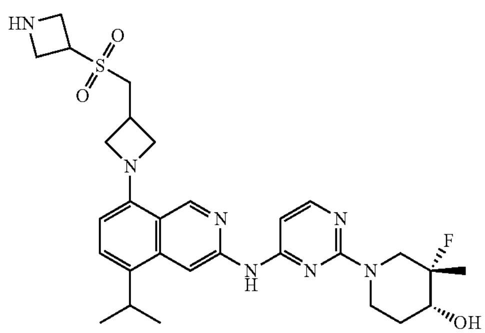 [SMILES: CC(C)c1ccc(N2CC(CS(=O)(=O)C3CNC3)C2)c2cnc(Nc3ccnc(N4CC[C@@H](O)[C@@](C)(F)C4)n3)cc12] | 584 | 1H-NMR (400 MHz, 6d-DMSO) δ ppm 9.85 (s, 1H), 9.05 (s, 1H), 8.60 (s, 1H), 7.99 (d, 1H, J = 5.6 Hz), 7.42 (d, 1H, J = 8.0 Hz), 6.47 (d, 1H, J = 5.7 Hz), 6.41 (d, 1H, J = 8.0 Hz), 5.02 (d, 1H, J = 6.4 Hz), 4.82-4.64 (m, 2H), 4.38 (dd, 3H, J = 8.9, 6.1 Hz), 3.95 (t, 2H, J = 6.9 Hz), 3.79 (dd, 2H, J = 8.7, 6.7 Hz), 3.64 (t, 2H, J = 8.6 Hz), 3.62-3.45 (m, 4H), 3.29-3.04 (m, 4H), 1.78-1.70 (m, 2H), 1.46-1.24 (m, 9H) | NN; Peak 1 | (3S,4R)-1-{4-[(8-{3-[(azetidine-3-sulfonyl)methyl]azetidin-1-yl}-5-(propan-2-yl)isoquinolin-3-yl)amino]pyrimidin-2-yl}-3-fluoro-3-methyl-piperidin-4-ol |
| 224 | 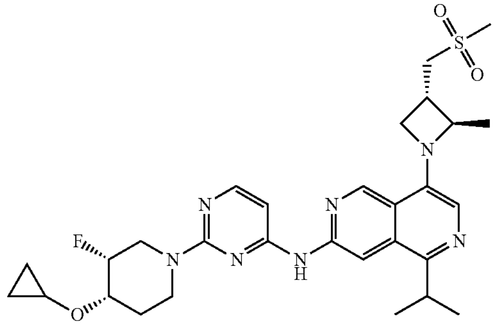 [SMILES: CC(C)c1ncc(N2C[C@H](CS(C)(=O)=O)[C@H]2C)c2cnc(Nc3ccnc(N4CC[C@H](OC5CC5)[C@H](F)C4)n3)cc12] | 584 | 1H-NMR (300 MHz, 6d-DMSO) δ ppm 10.17 (s, 1H), 9.14 (s, 1H), 8.75 (s, 1H), 8.04 (d, 1H, J = 5.6 Hz), 7.73 (s, 1H), 6.47 (d, 1H, J = 5.7 Hz), 5.00 (d, 1H, J = 49.9 Hz), 4.88-4.69 (m, 2H), 4.56 (d, 1H, J = 13.7 Hz), 4.32 (t, 1H, J = 6.2 Hz), 3.93-3.65 (m, 3H), 3.66-3.40 (m, 4H), 3.01 (s, 3H), 2.93 (q, 1H, J = 7.3 Hz), 1.87-1.76 (m, 2H), 1.48 (d, 3H, J = 6.0 Hz), 1.32 (d, 6H, J = 6.6 Hz), 0.58-0.44 (m, 4H) | | N-{2-[(3R,4S)-4-cyclopropoxy-3-fluoro-piperidin-1-yl]pyrimidin-4-yl}-8-[(2R,3S)-3-(methanesulfonyl-methyl)-2-methylazetidin-1-yl]-5-(propan-2-yl)-2,6-naphthyridin-3-amine |

TABLE 1-continued

| # | Structure | LC/MS | NMR | Separation Conditions | Chemical Name |
|---|---|---|---|---|---|
| 225 | 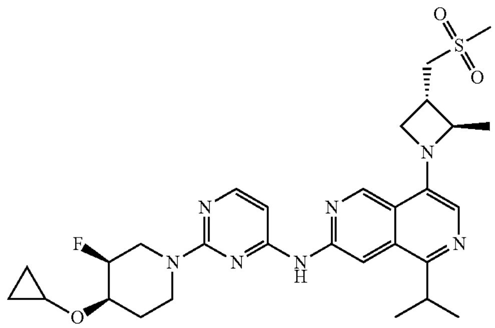 [SMILES: CC(C)c1ncc(N2C[C@H](CS(C)(=O)=O)[C@H]2C)c2cnc(Nc3ccnc(N4CC[C@@H](OC5CC5)[C@@H](F)C4)n3)cc12] | 584 | 1H-NMR (300 MHz, 6d-DMSO) δ ppm 10.15 (s, 1H), 9.11 (s, 1H), 8.73 (s, 1H), 8.02 (d, 1H, J = 5.7 Hz), 7.71 (s, 1H), 6.44 (d, 1H, J = 5.7 Hz), 4.97 (d, 1H, J = 49.4 Hz), 4.81-4.66 (m, 2H), 4.54 (d, 1H, J = 14.2 Hz), 4.34-4.24 (m, 1H), 3.92-3.63 (m, 3H), 3.59-3.36 (m, 4H), 2.98 (s, 3H), 2.90 (q, 1H, J = 7.4 Hz), 1.84-1.78 (m, 2H), 1.46 (d, 3H, J = 6.0 Hz), 1.35-1.18 (m, 6H), 0.56-0.44 (m, 4H) | | N-{2-[(3S,4R)-4-cyclopropoxy-3-fluoro-piperidin-1-yl]pyrimidin-4-yl}-8-[(2R,3S)-3-(methanesulfonyl-methyl)-2-methylazetidin-1-yl]-5-(propan-2-yl-2,6-naphthyridin-3-amine |
| 226 | | 585 | 1H NMR (400 MHz, CDCl3) δ 9.05 (s, 1H), 8.59 (s, 1H), 8.07 (d, J = 5.6 F Hz, 1H), 7.41 (d, J = 8.0 Hz, 1H), 7.30-7.28 (m, 1H), 6.42 (d, J = 8.0 Hz, 1H), 6.16 (d, J = 5.6 Hz, 1H), 4.46 (t, J = 7.6 Hz, 2H), 4.20-4.06 (m, 2H), 4.04-3.99 (m, 2H), 3.98-3.91 (m, 2H), 3.90-3.81 (m, 2H), 3.78-3.69 (m, 3H), 3.64-3.58 (m, 3H), 3.50-3.46 (m, 2H), 3.43 (s, 3H), 3.10-3.04 (m, 1H), 2.99 (s, 3H), 2.09-2.01 (m, 1H), 1.83-1.74 (m, 1H), 1.37 (dd, J = 6.8, 2.0 Hz, 6H) | and | (3R,4S)-1-[4-({8-[3-(methanesulfonyl-methyl)azetidin-1-yl]-5-(propan-2-yl)isoquinolin-3-yl}amino)pyrimidin-2-yl]-4-(2-methoxyethoxy)piperidin-3-ol and (3S,4R)-1-[4-({8-[3-(methanesulfonyl-methyl)azetidin-1-yl]-5-(propan-2-yl)isoquinolin-3-yl}amino)pyrimidin-2-yl]-4-(2-methoxyethoxy)piperidin-3-ol |
| 227 | | 585.3 | 1H NMR (400 MHz, CD3OD) δ = 9.11 (s, 1H), 8.67 (s, 1H), 7.98 (d, J = 6.0 Hz, 1H), 7.48 (d, J = 8.0 Hz, 1H), 6.53 (d, J = 8.0 Hz, 1H), 6.38 (d, J = 5.6 Hz, 1H), 4.66-4.63 (m, 1H), 4.57-4.54 (m, 1H), 4.43 (t, J = 7.6 Hz, 2H), 4.03 (t, J = 6.8 Hz, 2H), 3.89-3.74 (m, 2H), 3.67-3.56 (m, 6H), 3.51-3.44 (m, 1H), 3.42 (s, 3H), 3.39-3.35 (m, 1H), 3.27-3.22 (m, 1H), 3.16-3.11 (m, 1H), 3.04 (s, 3H), 2.21-2.14 (m, 1H), 1.58-1.48 (m, 1H), 1.38 (dd, J = 6.8, 5.2 Hz, 6H) | and | (3S,4S)-1-[4-({8-[3-(methanesulfonyl-methyl)azetidin-1-yl]-5-(propan-2-yl)isoquinolin-3-yl}amino)pyrimidin-2-yl]-4-(2-methoxyethoxy)piperidin-3-ol and (3R,4R)-1-[4-({8-[3-(methanesulfonyl-methyl)azetidin-1-yl]-5-(propan-2-yl)isoquinolin-3-yl}amino)pyrimidin-2-yl]-4-(2-methoxyethoxy)piperidin-3-ol |

TABLE 1-continued

| # | Structure | LC/MS | NMR | Separation Conditions | Chemical Name |
|---|---|---|---|---|---|
| 228 | 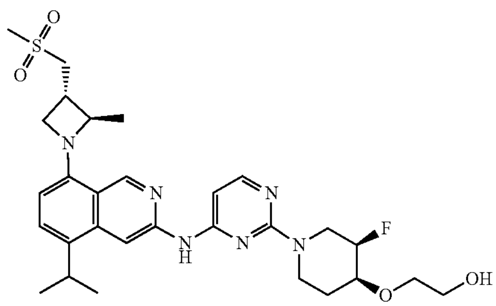 [SMILES: CC(C)c1ccc(N2C[C@H](CS(C)(=O)=O)[C@H]2C)c2cnc(Nc3ccnc(N4CC[C@H](OCCO)[C@H](F)C4)n3)cc12] | 587 | 1H-NMR (400 MHz, 6d-DMSO) δ ppm 9.93 (s, 1H), 9.05 (s, 1H), 8.64 (s, 1H), 7.99 (d, 1H, J = 5.7 Hz), 7.43 (d, 1H, J = 8.0 Hz), 6.56 (d, 1H, J = 8.1 Hz), 6.46 (d, 1H, J = 5.7 Hz), 4.93 (d, 1H, J = 50.4 Hz), 4.82-4.72 (m, 1H), 4.70-4.61 (m, 2H), 4.53 (d, 1H, J = 13.0 Hz), 4.19 (p, 1H, J = 6.2 Hz), 3.73 (dd, 1H, J = 26.1, 9.6 Hz), 3.67-3.35 (m, 9H), 3.24 (d, 1H, J = 11.5 Hz), 2.99 (s, 3H), 2.89 (p, 1H, J = 7.4 Hz), 1.89-1.69 (m, 2H), 1.42 (d, 3H, J = 6.0 Hz), 1.31 (t, 6H, J = 6.5 Hz) | | 2-{[(3R,4S)-3-fluoro-1-[4-({8-[(2R,3S)-3-(methanesulfonyl-methyl)-2-methylazetidin-1-yl]-5-(propan-2-yl)isoquinolin-3-yl}amino)pyrimidin-2-yl]piperidin-4-yl]oxy}ethan-1-ol |
| 229 | 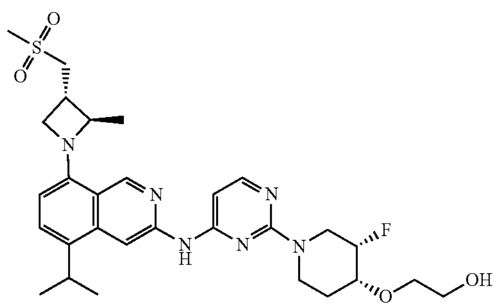 [SMILES: CC(C)c1ccc(N2C[C@H](CS(C)(=O)=O)[C@H]2C)c2cnc(Nc3ccnc(N4CC[C@@H](OCCO)[C@@H](F)C4)n3)cc12] | 587 | 1H-NMR (400 MHz, 6d-DMSO) δ ppm 9.93 (s, 1H), 9.05 (s, 1H), 8.64 (s, 1H), 7.99 (d, 1H, J = 5.7 Hz), 7.42 (d, 1H, J = 8.0 Hz), 6.56 (d, 1H, J = 8.1 Hz), 6.46 (d, 1H, J = 5.7 Hz), 5.04-4.84 (m, 1H), 4.76 (t, 1H, J = 7.9 Hz), 4.70-4.61 (m, 2H), 4.53 (d, 1H, J = 13.1 Hz), 4.19 (p, 1H, J = 6.1 Hz), 3.81-3.67 (m, 1H), 3.67-3.57 (m, 1H), 3.61-3.38 (m, 8H), 3.29-3.17 (m, 1H), 2.99 (s, 3H), 2.88 (h, 1H, J = 7.3 Hz), 1.83 (dd, 1H, J = 13.1, 4.4 Hz), 1.76 (d, 1H, J = 10.9 Hz), 1.42 (d, 3H, J = 6.1 Hz), 1.31 (dd, 6H, J = 6.8, 2.5 Hz) | | 2-{[(3S,4R)-3-fluoro-1-[4-({8-[(2R,3S)-3-(methanesulfonyl-methyl)-2-methylazetidin-1-yl]-5-(propan-2-yl)isoquinolin-3-yl}amino)pyrimidin-2-yl]piperidin-4-yl]oxy}ethan-1-ol |
| 230 | 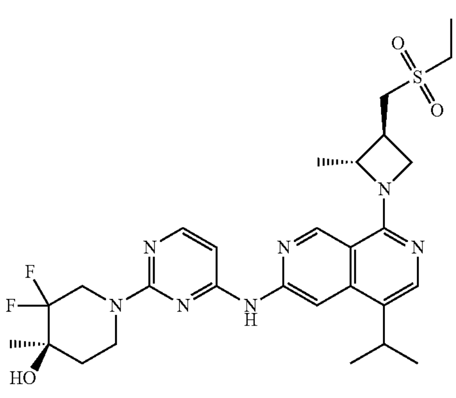 | 590 | 1H-NMR (300 MHz, 6d-DMSO) δ ppm 10.20 (s, 1H), 9.05 (s, 1H), 8.50 (s, 1H), 8.07 (d, 1H, J = 5.7 Hz), 8.02 (s, 1H), 6.55 (d, 1H, J = 5.7 Hz), 5.58 (s, 1H), 4.86 (t, 1H, J = 8.0 Hz), 4.76-4.70 (m, 1H), 4.56 (t, 1H, J = 6.3 Hz), 4.47 (d, 1H, J = 13.4 Hz), 3.98 (t, 1H, J = 7.3 Hz), 3.68 (dd, 1H, J = 30.1, 13.3 Hz), 3.52 (d, 2H, J = 7.4 Hz), 3.45-3.39 (m, 1H), 3.09 (q, 2H, J = 7.4 Hz), 2.89 (q, 1H, J = 7.3 Hz), 1.76-1.70 (m, 2H), 1.50 (d, 3H, J = 6.1 Hz), 1.36-1.17 (m, 12H) | GG, Peak 2 | (4R)-1-[4-({8-[(2R,3S)-3-[(ethanesulfonyl)methyl]-2-methylazetidin-1-yl]-5-(propan-2-yl)-2,7-naphthyridin-3-yl}amino)pyrimidin-2-yl]-3,3-difluoro-4-methyl-piperidin-4-ol or (4S)-1-[4-({8-[(2R,3S)-3-[(ethanesulfonyl)methyl]-2- |

| # | Structure | LC/MS | NMR | Separation Conditions | Chemical Name |
|---|---|---|---|---|---|
| | 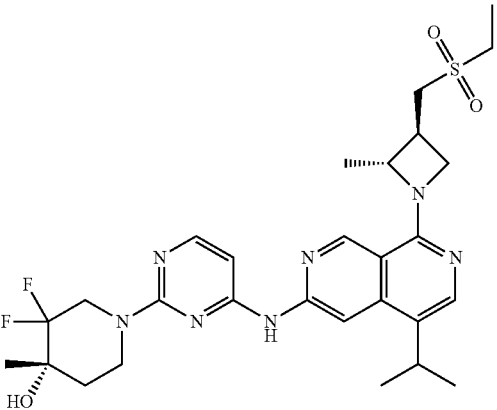 [SMILES: CCS(=O)(=O)C[C@H]1CN(c2ncc(C(C)C)c3cc(Nc4ccnc(N5CC[C@](C)(O)C(F)(F)C5)n4)ncc23)[C@@H]1C] | | | | methylazetidin-1-yl]-5-(propan-2-yl)-2,7-naphthyridin-3-yl}amino)pyrimidin-2-yl]-3,3-difluoro-4-methyl-piperidin-4-ol |
| 231 | 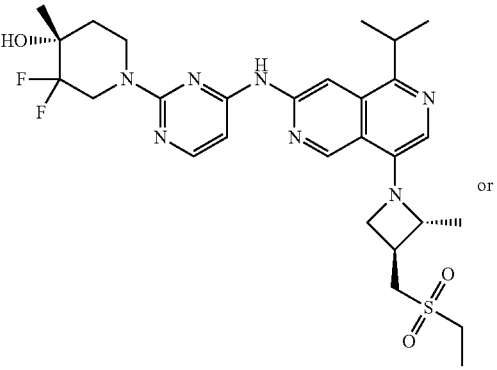 [SMILES: CCS(=O)(=O)C[C@H]1CN(c2cnc(C(C)C)c3cc(Nc4ccnc(N5CC[C@@](C)(O)C(F)(F)C5)n4)ncc23)[C@@H]1C]<br><br>or<br><br>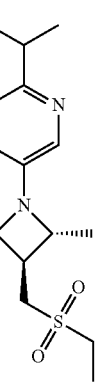 | 590 | 1H-NMR (300 MHz, 6d-DMSO) δ ppm 10.23 (s, 1H), 9.14 (s, 1H), 8.73 (s, 1H), 8.06 (d, 1H, J = 5.6 Hz), 7.74 (s, 1H), 6.51 (d, 1H, J = 5.7 Hz), 5.59 (s, 1H), 4.74 (t, 2H, J = 7.5 Hz), 4.49 (d, 1H, J = 13.0 Hz), 4.32 (t, 1H, J = 6.3 Hz), 3.83-3.58 (m, 3H), 3.61-3.45 (m, 2H), 3.40-3.34 (m, 1H), 3.10 (q, 2H, J = 7.4 Hz), 2.92 (q, 1H, J = 7.3 Hz), 1.78-1.72 (m, 2H), 1.49 (d, 3H, J = 6.0 Hz), 1.35-1.18 (m, 12H) | O; Peak 1 (intermediate) | (4R)-1-[4-({8-[(2R,3S)-3-[(ethanesulfonyl)methyl]-2-methylazetidin-1-yl]-5-(propan-2-yl)-2,6-naphthyridin-3-yl}amino)pyrimidin-2-yl]-3,3-difluoro-4-methyl-piperidin-4-ol or (4S)-1-[4-({8-[(2R,3S)-3-[(ethanesulfonyl)methyl]-2-methylazetidin-1-yl]-5-(propan-2-yl)-2,6-naphthyridin-3-yl}amino)pyrimidin-2-yl]-3,3-difluoro-4-methyl-piperidin-4-ol |

TABLE 1-continued

| # | Structure | LC/MS | NMR | Separation Conditions | Chemical Name |
|---|---|---|---|---|---|
| 232 | 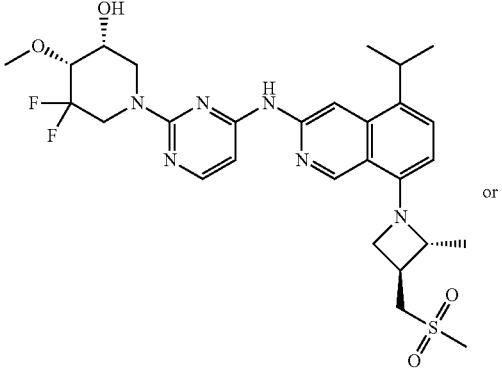 | 591 | 1H-NMR (400 MHz, 6d-DMSO) δ ppm 10.00 (s, 1H), 9.06 (s, 1H), 8.53 (s, 1H), 8.02 (d, 1H, J = 5.7 Hz), 7.42 (d, 1H, J = 8.0 Hz), 6.60-6.53 (m, 2H), 5.31 (d, 1H, J = 5.8 Hz), 4.83-4.78 (m, 1H), 4.66 (t, 1H, J = 7.5 Hz), 4.52 (dd, 1H, J = 12.5, 4.4 Hz), 4.19 (p, 1H, J = 6.1 Hz), 3.79-3.66 (m, 2H), 3.63 (t, 1H, J = 7.1 Hz), 3.57 (s, 3H), 3.55-3.44 (m, 4H), 3.18 (t, 1H, J = 11.5 Hz), 2.99 (s, 3H), 2.88 (h, 1H, J = 7.3 Hz), 1.42 (d, 3H, J = 6.0 Hz), 1.29 (dd, 6H, J = 14.0, 6.7 Hz) | F; Peak 1 | (3R,4R)-5,5-difluoro-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methoxy-piperidin-3-ol or (3S,4S)-5,5-difluoro-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methoxy-piperidin-3-ol |
| 233 | 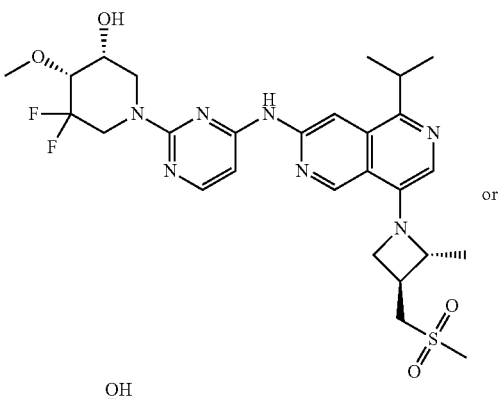 | 592 | 1H-NMR (300 MHz, 6d-DMSO) δ ppm 10.24 (s, 1H), 9.14 (s, 1H), 8.65 (s, 1H), 8.07 (d, 1H, J = 5.6 Hz), 7.74 (s, 1H), 6.56 (d, 1H, J = 5.7 Hz), 5.33 (d, 1H, J = 5.7 Hz), 4.74 (t, 2H, J = 7.6 Hz), 4.52 (d, 1H, J = 11.8 Hz), 4.32 (t, 1H, J = 6.3 Hz), 3.82-3.67 (m, 5H), 3.58 (s, 4H), 3.52 (d, 1H, J = 13.9 Hz), 3.29-3.14 (m, 1H), 3.01 (s, 3H), 2.93 (q, 1H, J = 7.1 Hz), 1.48 (d, 3H, J = 6.0 Hz), 1.35-1.20 (m, 6H) | K; Peak 1 | (3R,4R)-5,5-difluoro-1-[4-({8-[(2R,3S)-3-(methanesulfonyl-methyl)-2-methylazetidin-1-yl]-5-(propan-2-yl)-2,6-naphthyridin-3-yl}amino)pyrimidin-2-yl]-4-methoxy-piperidin-3-ol or (3S,4S)-5,5-difluoro-1-[4-({8-[(2R,3S)-3-(methanesulfonyl-methyl)-2-methylazetidin-1-yl]-5-(propan-2-yl)-2,6-naphthyridin-3-yl}amino)pyrimidin-2-yl]-4-methoxy-piperidin-3-ol |

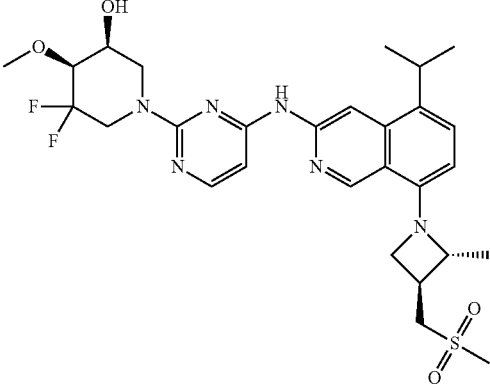

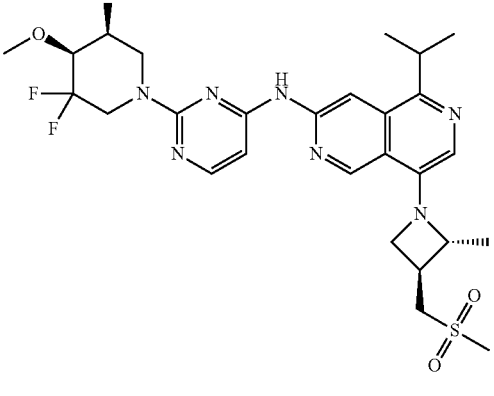

TABLE 1-continued

| # | Structure | LC/MS | NMR | Separation Conditions | Chemical Name |
|---|---|---|---|---|---|
| 234 | 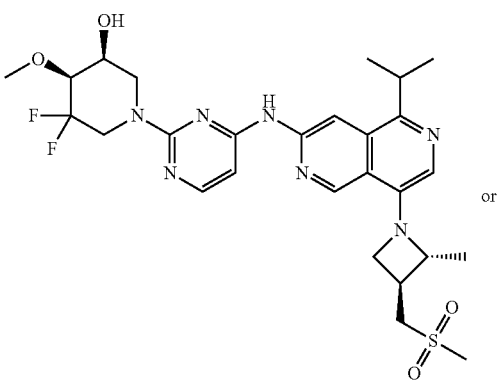 or 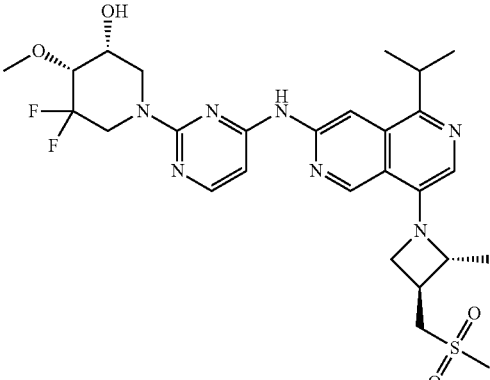 | 592 | 1H-NMR (300 MHz, 6d-DMSO) δ ppm 10.23 (s, 1H), 9.15 (s, 1H), 8.66 (s, 1H), 8.07 (d, 1H, J = 5.6 Hz), 7.74 (s, 1H), 6.56 (d, 1H, J = 5.7 Hz), 5.33 (d, 1H, J = 5.8 Hz), 4.74 (t, 2H, J = 7.6 Hz), 4.51 (d, 1H, J = 13.0 Hz), 4.32 (t, 1H, J = 6.2 Hz), 3.87-3.64 (m, 4H), 3.64-3.44 (m, 6H), 3.29-3.14 (m, 1H), 3.01 (s, 3H), 2.93 (q, 1H, J = 7.2 Hz), 1.48 (d, 3H, J = 6.0 Hz), 1.31 (dd, 6H, J = 11.0, 6.6 Hz) | K; Peak 2 | (3S,4S)-5,5-difluoro-1-[4-({8-[(2R,3S)-3-(methanesulfonyl-methyl)-2-methylazetidin-1-yl]-5-(propan-2-yl)-2,6-naphthyridin-3-yl}amino)pyrimidin-2-yl]-4-methoxy-piperidin-3-ol or (3R,4R)-5,5-difluoro-1-[4-({8-[(2R,3S)-3-(methanesulfonyl-methyl)-2-methylazetidin-1-yl]-5-(propan-2-yl)-2,6-naphthyridin-3-yl}amino)pyrimidin-2-yl]-4-methoxy-piperidin-3-ol |
| 235 | 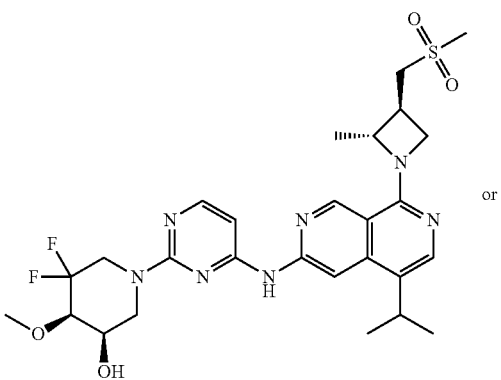 or 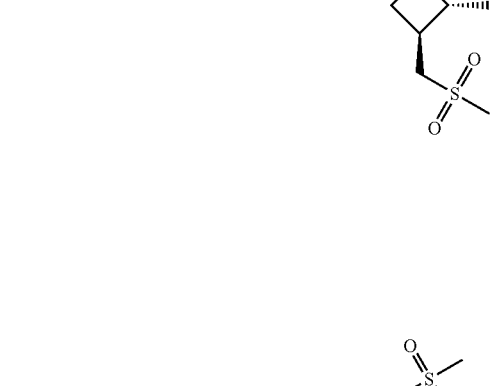 | 592 | 1H-NMR (300 MHz, 6d-DMSO) δ ppm 10.19 (s, 1H), 9.03 (s, 1H), 8.40 (s, 1H), 8.05 (d, 1H, J = 5.6 Hz), 7.98 (s, 1H), 6.58 (d, 1H, J = 5.7 Hz), 5.31 (d, 1H, J = 5.8 Hz), 4.84 (t, 1H, J = 7.9 Hz), 4.74 (s, 1H), 4.58-4.43 (m, 2H), 3.95 (t, 1H, J = 7.3 Hz), 3.73-3.63 (m, 3H), 3.58-3.47 (m, 5H), 3.18 (t, 1H, J = 11.1 Hz), 2.97 (s, 3H), 2.87 (q, 1H, J = 7.5 Hz), 1.47 (d, 3H, J = 6.0 Hz), 1.29 (t, 6H, J = 6.3 Hz) | K; Peak 1 | (3R,4R)-5,5-difluoro-1-[4-({8-[(2R,3S)-3-(methanesulfonyl-methyl)-2-methylazetidin-1-yl]-5-(propan-2-yl)-2,7-naphthyridin-3-yl}amino)pyrimidin-2-yl]-4-methoxy-piperidin-3-ol or (3S,4S)-5,5-difluoro-1-[4-({8-[(2R,3S)-3-(methanesulfonyl- |

TABLE 1-continued

| # | Structure | LC/MS | NMR | Separation Conditions | Chemical Name |
|---|-----------|-------|-----|----------------------|---------------|
|   | 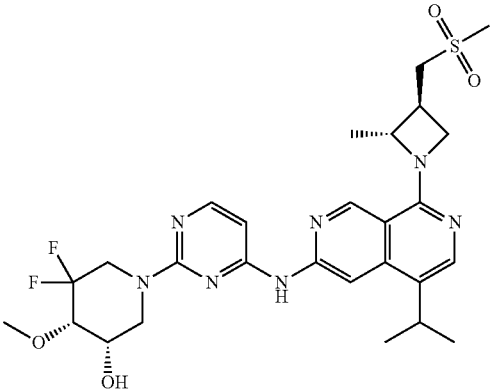 |   |   |   | methyl)-2-methylazetidin-1-yl]-5-(propan-2-yl)-2,7-naphthyridin-3-yl}amino)pyrimidin-2-yl]-4-methoxypiperidin-3-ol |
| 236 | 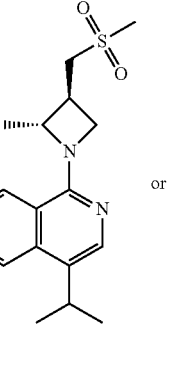 or 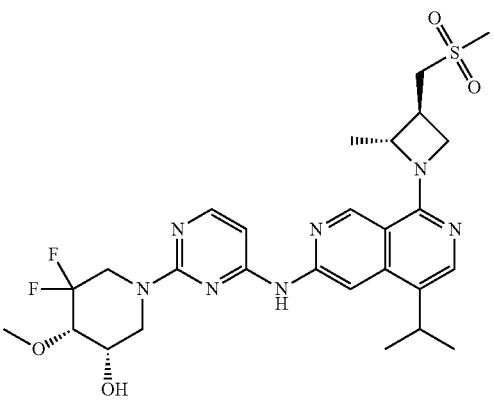 | 592 | 1H-NMR (300 MHz, 6d-DMSO) δ ppm 10.19 (s, 1H), 9.03 (s, 1H), 8.41 (s, 1H), 8.06 (d, 1H, J = 5.6 Hz), 7.96 (s, 1H), 6.59 (d, 1H, J = 5.7 Hz), 5.32 (d, 1H, J = 5.8 Hz), 4.88-4.82 (m, 1H), 4.76-4.70 (m, 1H), 4.57-4.52 (m, 1H), 4.52-4.42 (m, 1H), 3.98 (s, 1H), 3.72-3.66 (m, 3H), 3.58-3.48 (m, 5H), 3.22-3.16 (m, 1H), 2.97 (s, 3H), 2.94-2.83 (m, 1H), 1.48 (d, 3H, J = 6.1 Hz), 1.29 (dd, 6H, J = 8.7, 6.7 Hz) | K; Peak 2 | (3S,4S)-5,5-difluoro-1-[4-({8-[(2R,3S)-3-(methanesulfonylmethyl)-2-methylazetidin-1-yl]-5-(propan-2-yl)-2,7-naphthyridin-3-yl}amino)pyrimidin-2-yl]-4-methoxypiperidin-3-ol or (3R,4R)-5,5-difluoro-1-[4-({8-[(2R,3S)-3-(methanesulfonylmethyl)-2-methylazetidin-1-yl]-5-(propan-2-yl)-2,7-naphthyridin-3-yl}amino)pyrimidin-2-yl]-4-methoxypiperidin-3-ol |

TABLE 1-continued

| # | Structure | LC/MS | NMR | Separation Conditions | Chemical Name |
|---|---|---|---|---|---|
| 237 | 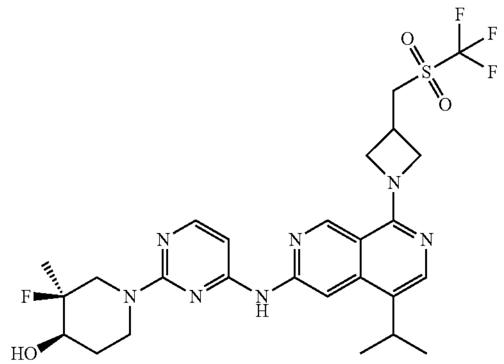 [SMILES: CC(C)c1cnc(N2CC(CS(=O)(=O)C(F)(F)F)C2)c2cnc(Nc3ccnc(N4CC[C@@H](O)[C@@](C)(F)C4)n3)cc12] | 598 | 1H-NMR (400 MHz, 4d-CD3OD) δ ppm 9.21 (d, 1H, J = 0.7 Hz), 8.55 (s, 1H), 8.01 (d, 1H, J = 5.8 Hz), 7.89 (s, 1H), 6.44 (d, 1H, J = 5.8 Hz), 4.84-4.65 (m, 2H), 3.81 (dd, 1H, J = 14.4, 5.4 Hz), 3.70 (ddd, 1H, J = 22.5, 10.0, 5.0 Hz), 3.58-3.49 (m, 1H), 3.44 (p, 1H, J = 6.9 Hz), 3.31-3.13 (m, 3H), 3.00 (dt, 1H, J = 8.6, 4.6 Hz), 2.30 (s, 1H), 1.90 (t, 1H, J = 4.4 Hz), 1.64 (dt, 1H, J = 10.0, 5.2 Hz), 1.57-1.51 (m, 1H), 1.48 (d, 3H, J = 21.1 Hz), 1.43-1.36 (m, 6H) | NN; Peak 1 | (3S,4R)-3-fluoro-3-methyl-1-(4-{[5-(propan-2-yl)-8-[3-(trifluoromethanesulfonylmethyl)azetidin-1-yl]-2,7-naphthyridin-3-yl]amino}pyrimidin-2-yl)piperidin-4-ol |
| 238 | 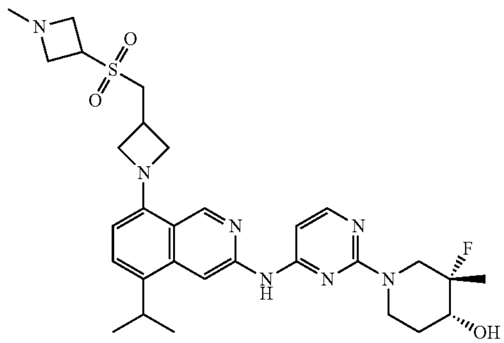 | 598 | 1H-NMR (300 MHz, 6d-DMSO) δ ppm 9.85 (s, 1H), 9.05 (s, 1H), 8.60 (s, 1H), 7.99 (d, 1H, J = 5.6 Hz), 7.42 (d, 1H, J = 8.0 Hz), 6.47 (d, 1H, J = 5.7 Hz), 6.41 (d, 1H, J = 8.0 Hz), 5.02 (d, 1H, J = 6.4 Hz), 4.82-4.64 (m, 2H), 4.37 (t, 2H, J = 7.6 Hz), 4.18 (t, 2H, J = 6.7 Hz), 3.95 (t, 2H, J = 7.1 Hz), 3.53 (d, 6H, J = 9.7 Hz), 3.25-3.14 (m, 2H), 3.14-3.04 (m, 1H), 2.24 (s, 3H), 1.77-1.71 (m, 2H), 1.44-1.24 (m, 10H) | NN; Peak 1 | (3S,4R)-3-fluoro-3-methyl-1-(4-{[8-(3-{[(1-methylazetidin-3-yl)sulfonyl]methyl}azetidin-1-yl)-5-(propan-2-yl)isoquinolin-3-yl]amino}pyrimidin-2-yl)piperidin-4-ol |
| 239 | 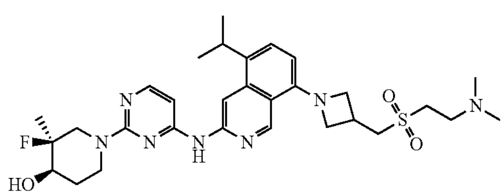 [SMILES: CC(C)c1ccc(N2CC(CS(=O)(=O)CCN(C)C)C2)c2cnc(Nc3ccnc(N4CC[C@@H](O)[C@@](C)(F)C4)n3)cc12] | 600 | 1H-NMR (300 MHz, 6d-DMSO) δ ppm 9.83 (s, 1H), 9.03 (s, 1H), 8.58 (s, 1H), 7.97 (d, 1H, J = 5.6 Hz), 7.40 (d, 1H, J = 8.0 Hz), 6.45 (d, 1H, J = 5.7 Hz), 6.39 (d, 1H, J = 8.0 Hz), 5.00 (d, 1H, J = 6.4 Hz), 4.80-4.61 (m, 2H), 4.37 (t, 2H, J = 7.4 Hz), 4.00-3.89 (m, 2H), 3.61 (d, 2H, J = 7.4 Hz), 3.58-3.41 (m, 2H), 3.38-2.97 (m, 4H), 2.65 (t, 2H, J = 6.9 Hz), 2.17 (s, 6H), 1.75-1.68 (m, 2H), 1.42-1.21 (m, 9H) | NN; Peak 1 | (3S,4R)-1-(4-{[8-(3-{[2-(dimethylamino)ethanesulfonyl]methyl}azetidin-1-yl)-5-(propan-2-yl)isoquinolin-3-yl]amino}pyrimidin-2-yl)-3-fluoro-3-methylpiperidin-4-ol |
| 240 | 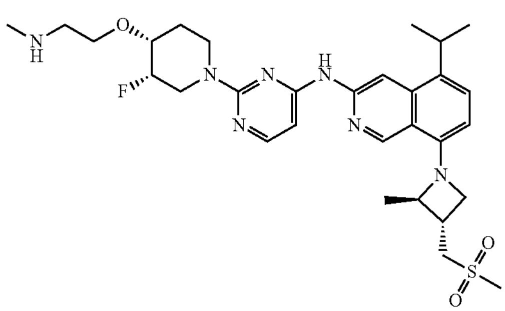 | 600 | 1H-NMR (300 MHz, 4d-CD3OD) δ ppm 9.11 (s, 1H), 8.68 (s, 1H), 7.97 (d, 1H, J = 5.8 Hz), 7.48 (d, 1H, J = 8.0 Hz), 6.66 (d, 1H, J = 8.0 Hz), 6.38 (d, 1H, J = 5.8 Hz), 4.70-4.61 (m, 2H), 4.35 (s, 1H), 4.33-4.23 (m, 1H), 3.89-3.41 (m, 9H), 3.02 (s, 3H), 3.08-2.94 (m, 1H), 2.83 (t, 2H, J = 5.3 Hz), 2.46 (s, 3H), 2.01-1.82 (m, 2H), 1.50 (d, 3H, J = 6.1 Hz), 1.37 (dd, 6H, J = 6.8, 4.4 Hz) | | N-{2-[(3S,4R)-3-fluoro-4-[2-(methylamino)ethoxy]piperidin-1-yl]pyrimidin-4-yl}-8-[(2R,3S)-3-(methanesulfonylmethyl)-2-methylazetidin-1-yl]-5-(propan-2-yl)isoquinolin-3-amine |

TABLE 1-continued

| # | Structure | LC/MS | NMR | Separation Conditions | Chemical Name |
|---|---|---|---|---|---|
| 241 | 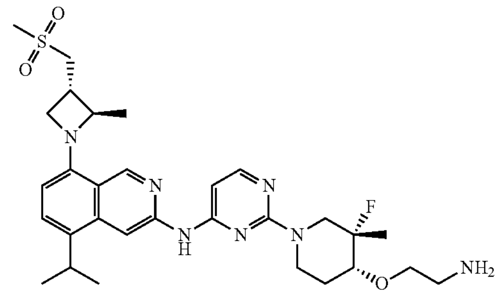 [SMILES: CC(C)c1ccc(N2C[C@H](CS(C)(=O)=O)[C@H]2C)c2cnc(Nc3ccnc(N4CC[C@@H](OCCN)[C@@](C)(F)C4)n3)cc12] | 600 | 1H-NMR (300 MHz, 6d-DMSO) δ ppm 9.92 (s, 1H), 9.06 (s, 1H), 8.60 (s, 1H), 7.99 (d, 1H, J = 5.6 Hz), 7.43 (d, 1H, J = 8.0 Hz), 6.57 (d, 1H, J = 8.1 Hz), 6.48 (d, 1H, J = 5.6 Hz), 4.80-4.60 (m, 3H), 4.20 (t, 1H, J = 6.3 Hz), 3.69-3.46 (m, 6H), 3.44 (dd, 2H, J = 10.5, 4.7 Hz), 3.24-3.07 (m, 3H), 3.00 (s, 3H), 2.89 (q, 1H, J = 7.2 Hz), 2.71 (t, 2H, J = 5.8 Hz), 1.99-1.90 (m, 1H), 1.73-1.63 (m, 1H), 1.55-1.36 (m, 6H), 1.31 (t, 6H, J = 7.2 Hz) | | N-{2-[(3S,4R)-4-(2-aminoethoxy)-3-fluoro-3-methylpiperidin-1-yl]pyrimidin-4-yl}-8-[(2R,3S)-3-(methanesulfonyl-methyl)-2-methylazetidin-1-yl]-5-(propan-2-yl)isoquinolin-3-amine |
| 242 | 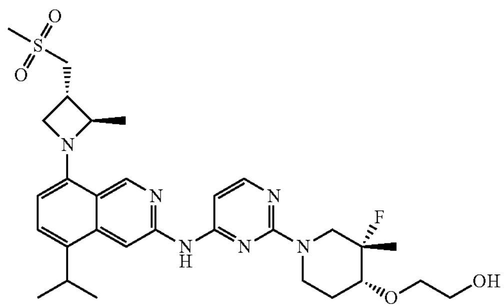 [SMILES: CC(C)c1ccc(N2C[C@H](CS(C)(=O)=O)[C@H]2C)c2cnc(Nc3ccnc(N4CC[C@@H](OCCO)[C@@](C)(F)C4)n3)cc12] | 601 | 1H-NMR (300 MHz, 6d-DMSO) δ ppm 9.92 (s, 1H), 9.06 (s, 1H), 8.60 (s, 1H), 7.99 (d, 1H, J = 5.7 Hz), 7.43 (d, 1H, J = 8.0 Hz), 6.57 (d, 1H, J = 8.1 Hz), 6.47 (d, 1H, J = 5.7 Hz), 4.83-4.60 (m, 4H), 4.20 (t, 1H, J = 6.3 Hz), 3.64 (dd, 2H, J = 9.9, 4.9 Hz), 3.59-3.37 (m, 7H), 3.24-3.07 (m, 2H), 3.00 (s, 3H), 2.89 (q, 1H, J = 7.1 Hz), 2.01-1.91 (m, 1H), 1.73-1.63 (m, 1H), 1.48-1.26 (m, 12H) | NN; Peak 1 | 2-{[(3S,4R)-3-fluoro-1-[4-({8-[(2R,3S)-3-(methanesulfonyl-methyl)-2-methylazetidin-1-yl]-5-(propan-2-yl)isoquinolin-3-yl}amino)pyrimidin-2-yl]-3-methyl-piperidin-4-yl]oxy}ethan-1-ol |
| 243 | 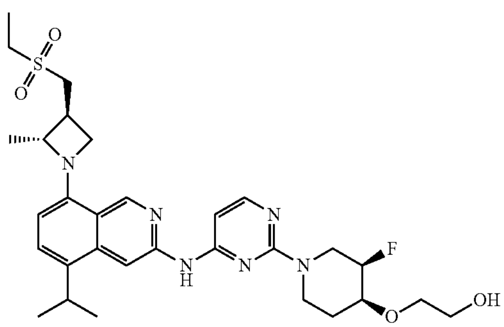 [SMILES: CCS(=O)(=O)C[C@H]1CN(c2ccc(C(C)C)c3cc(Nc4ccnc(N5CC[C@H](OCCO)[C@H](F)C5)n4)ncc23)[C@@H]1C] | 601 | 1H-NMR (300 MHz, 6d-DMSO) δ ppm 9.95 (s, 1H), 9.06 (s, 1H), 8.65 (s, 1H), 8.00 (d, 1H, J = 5.7 Hz), 7.43 (d, 1H, J = 8.0 Hz), 6.57 (d, 1H, J = 8.1 Hz), 6.47 (d, 1H, J = 5.7 Hz), 4.94 (d, 1H, J = 50.4 Hz), 4.78 (s, 1H), 4.67 (q, 2H, J = 5.7, 4.4 Hz), 4.55 (d, 1H, J = 13.3 Hz), 4.20 (t, 1H, J = 6.3 Hz), 3.83-3.56 (m, 3H), 3.60-3.45 (m, 7H), 3.35-3.19 (m, 1H), 3.10 (q, 2H, J = 7.4 Hz), 2.89 (q, 1H, J = 7.2 Hz), 1.85-1.74 (m, 2H), 1.43 (d, 3H, J = 6.0 Hz), 1.36-1.18 (m, 9H) | | 2-{[(3R,4S)-1-[4-({8-[(2R,3S)-3-[(ethanesulfonyl)methyl]-2-methylazetidin-1-yl]-5-(propan-2-yl)isoquinolin-3-yl}amino)pyrimidin-2-yl]-3-fluoro-piperidin-4-yl]oxy}ethan-1-ol |
| 244 | 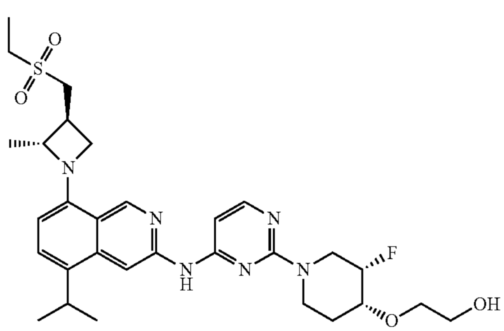 [SMILES: CCS(=O)(=O)C[C@H]1CN(c2ccc(C(C)C)c3cc(Nc4ccnc(N5CC[C@@H](OCCO)[C@@H](F)C5)n4)ncc23)[C@@H]1C] | 601 | 1H-NMR (300 MHz, 6d-DMSO) δ ppm 9.95 (s, 1H), 9.06 (s, 1H), 8.66 (s, 1H), 8.00 (d, 1H, J = 5.7 Hz), 7.43 (d, 1H, J = 8.0 Hz), 6.56 (d, 1H, J = 8.0 Hz), 6.47 (d, 1H, J = 5.7 Hz), 5.06-4.82 (m, 1H), 4.81-4.75 (m, 1H), 4.66 (q, 2H, J = 4.7, 3.2 Hz), 4.55 (d, 1H, J = 13.2 Hz), 4.21 (q, 1H, J = 6.5 Hz), 3.81-3.38 (m, 10H), 3.25 (t, 1H, J = 10.9 Hz), 3.10 (q, 2H, J = 7.4 Hz), 2.90 (p, 1H, J = 7.1 Hz), 1.86-1.71 (m, 2H), 1.43 (d, 3H, J = 6.0 Hz), 1.31 (dd, 6H, J = 6.8, 2.4 Hz), 1.23 (t, 3H, J = 7.4 Hz) | | 2-{[(3S,4R)-1-[4-({8-[(2R,3S)-3-[(ethane-sulfonyl)methyl]-2-methyl-azetidin-1-yl]-5-(propan-2-yl)isoquinolin-3-yl}amino)pyrimidin-2-yl]-3-fluoro-piperidin-4-yl]oxy}ethan-1-ol |

| # | Structure | LC/MS | NMR | Separation Conditions | Chemical Name |
|---|---|---|---|---|---|
| 245 | 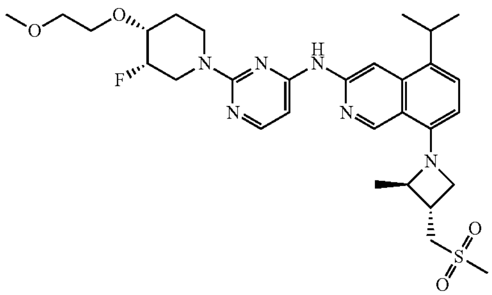 | 601 | 1H-NMR (300 MHz, 6d-DMSO) δ ppm 9.94 (s, 1H), 9.06 (s, 1H), 8.65 (s, 1H), 8.00 (d, 1H, J = 5.6 Hz), 7.43 (d, 1H, J = 8.0 Hz), 6.57 (d, 1H, J = 8.1 Hz), 6.47 (d, 1H, J = 5.7 Hz), 4.92 (d, 1H, J = 50.1 Hz), 4.79-4.62 (m, 2H), 4.52 (d, 1H, J = 13.2 Hz), 4.25-4.15 (m, 1H), 3.78-3.59 (m, 5H), 3.56-3.44 (m, 5H), 3.28 (s, 3H), 3.00 (s, 3H), 2.93-2.85 (m, 1H), 1.83-1.77 (m, 2H), 1.43 (d, 3H, J = 6.0 Hz), 1.36-1.26 (m, 6H) | K; Peak 1 | N-{2-[(3S,4R)-3-fluoro-4-(2-methoxyethoxy)piperidin-1-yl]pyrimidin-4-yl}-8-[(2R,3S)-3-(methanesulfonylmethyl)-2-methylazetidin-1-yl]-5-(propan-2-yl)isoquinolin-3-amine |
| 246 | 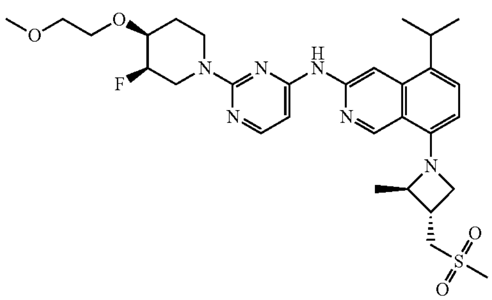 | 601 | 1H-NMR (300 MHz, 6d-DMSO) δ ppm 9.94 (s, 1H), 9.06 (s, 1H), 8.65 (s, 1H), 8.00 (d, 1H, J = 5.5 Hz), 7.43 (d, 1H, J = 7.7 Hz), 6.57 (d, 1H, J = 8.1 Hz), 6.47 (d, 1H, J = 5.7 Hz), 4.92 (d, 1H, J = 50.6 Hz), 4.80-4.60 (m, 2H), 4.52 (d, 1H, J = 12.6 Hz), 4.23-4.17 (m, 1H), 3.71-3.65 (m, 4H), 3.70-3.61 (m, 1H), 3.57-3.44 (m, 5H), 3.28 (s, 3H), 3.00 (s, 3H), 2.89 (d, 1H, J = 7.2 Hz), 1.84-1.78 (m, 2H), 1.43 (d, 3H, J = 5.9 Hz), 1.35-1.27 (m, 6H), | K; Peak 2 | N-{2-[(3R,4S)-3-fluoro-4-(2-methoxyethoxy)piperidin-1-yl]pyrimidin-4-yl}-8-[(2R,3S)-3-(methanesulfonylmethyl)-2-methylazetidin-1-yl]-5-(propan-2-yl)isoquinolin-3-amine |
| 247 | | 601 | 1H-NMR (300 MHz, 6d-DMSO) δ ppm 9.94 (s, 1H), 9.06 (s, 1H), 8.65 (s, 1H), 8.00 (d, 1H, J = 5.7 Hz), 7.43 (d, 1H, J = 8.0 Hz), 6.57 (d, 1H, J = 8.2 Hz), 6.47 (d, 1H, J = 5.7 Hz), 4.93 (d, 1H, J = 49.6 Hz), 4.75-4.60 (m, 3H), 4.49-4.43 (m, 1H), 4.25-4.15 (m, 1H), 3.82-3.40 (m, 10H), 3.00 (s, 3H), 2.94-2.85 (m, 1H), 1.86-1.72 (m, 2H), 1.43 (d, 3H, J = 6.0 Hz), 1.36-1.27 (m, 6H), 1.07 (d, 3H, J = 6.3 Hz) | L; Peak 1 | (2S)-1-{[(3S,4R)-3-fluoro-1-[4-({8-[(2R,3S)-3-(methanesulfonylmethyl)-2-methylazetidin-1-yl]-5-(propan-2-yl)isoquinolin-3-yl}amino)pyrimidin-2-yl]piperidin-4-yl]oxy}propan-2-ol or (2R)-1-{[(3S,4R)-3-fluoro-1-[4-({8-[(2R,3S)-3-(methanesulfonylmethyl)-2-methylazetidin-1-yl]-5-(propan-2-yl)isoquinolin-3-yl}amino)pyrimidin-2-yl]piperidin-4-yl]oxy}propan-2-ol |

TABLE 1-continued

| # | Structure | LC/MS | NMR | Separation Conditions | Chemical Name |
|---|---|---|---|---|---|
| 248 | | 601 | 1H-NMR (300 MHz, 6d-DMSO) δ ppm 10.2 (s, 1H), 9.07 (s, 1H), 8.65 (s, 1H), 8.00 (d, 1H, J = 5.8 Hz), 7.44 (d, 1H, J = 8.0 Hz), 6.58 (d, 1H, J = 8.0 Hz), 6.49 (s, 1H), 4.93 (d, 1H, J = 48.1 Hz), 4.73-4.61 (m, 3H), 4.52-4.49 (m, 1H), 4.27-4.15 (m, 1H), 3.86-3.39 (m, 10H), 3.00 (s, 3H), 2.91-2.89 (m, 1H), 1.85-1.79 (m, 2H), 1.43 (d, 3H, J = 6.0 Hz), 1.31 (d, 6H, J = 6.6 Hz), 1.07 (d, 3H, J = 6.3 Hz) | L; Peak 2 | (2R)-1-{[(3S,4R)-3-fluoro-1-[4-({8-[(2R,3S)-3-(methanesulfonyl-methyl)-2-methylazetidin-1-yl]-5-(propan-2-yl)isoquinolin-3-yl}amino)pyrimidin-2-yl]piperidin-4-yl]oxy}propan-2-ol or (2S)-1-{[(3S,4R)-3-fluoro-1-[4-({8-[(2R,3S)-3-(methanesulfonyl-methyl)-2-methylazetidin-1-yl]-5-(propan-2-yl)isoquinolin-3-yl}amino)pyrimidin-2-yl]piperidin-4-yl]oxy}propan-2-ol |
| 249 | 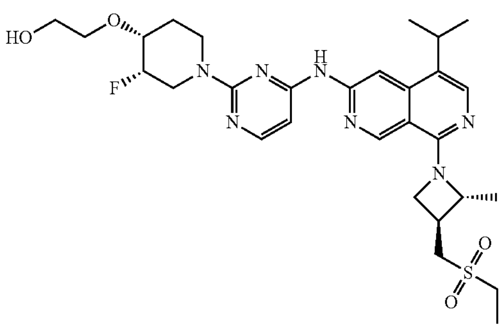 [SMILES: CCS(=O)(=O)C[C@H]1CN(c2ncc(C(C)C)c3cc(Nc4ccnc(N5CC[C@@H](OCCO)[C@@H](F)C5)n4)ncc23)[C@@H]1C] | 602 | 1H-NMR (300 MHz, 6d-DMSO) δ ppm 10.12 (s, 1H), 9.03 (s, 1H), 8.52 (s, 1H), 8.04 (d, 1H, J = 5.6 Hz), 8.00 (s, 1H), 6.50 (d, 1H, J = 5.6 Hz), 5.05-4.80 (m, 2H), 4.78-4.63 (m, 2H), 4.60-4.46 (m, 2H), 3.97 (t, 1H, J = 7.2 Hz), 3.80-3.63 (m, 1H), 3.62-3.44 (m, 7H), 3.37-3.16 (m, 2H), 3.08 (q, 2H, J = 7.4 Hz), 2.88 (d, 1H, J = 7.1 Hz), 1.85-1.79 (m, 2H), 1.49 (d, 3H, J = 6.1 Hz), 1.32 (t, 6H, J = 6.9 Hz), 1.22 (t, 3H, J = 7.4 Hz) | | 2-{[(3S,4R)-1-[4-({8-[(2R,3S)-3-[(ethanesulfonyl)methyl]-2-methylazetidin-1-yl]-5-(propan-2-yl)-2,7-naphthyridin-3-yl}amino)pyrimidin-2-yl]-3-fluoro-piperidin-4-yl]oxy}ethan-1-ol |
| 250 | 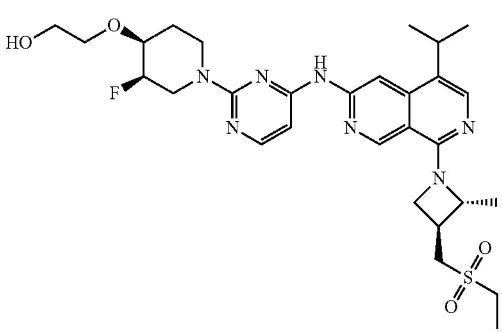 [SMILES: CCS(=O)(=O)C[C@H]1CN(c2ncc(C(C)C)c3cc(Nc4ccnc(N5CC[C@H](OCCO)[C@H](F)C5)n4)ncc23)[C@@H]1C] | 602 | 1H-NMR (300 MHz, 6d-DMSO) δ ppm 10.13 (s, 1H), 9.03 (s, 1H), 8.52 (s, 1H), 8.04 (d, 1H, J = 5.6 Hz), 8.00 (s, 1H), 6.50 (d, 1H, J = 5.7 Hz), 4.93 (d, 1H, J = 48.7 Hz), 4.89-4.47 (m, 5H), 3.97 (t, 1H, J = 7.3 Hz), 3.73 (dd, 1H, J = 25.2, 8.6 Hz), 3.52 (dd, 7H, J = 12.3, 7.1 Hz), 3.35-3.18 (m, 2H), 3.08 (q, 2H, J = 7.4 Hz), 2.88 (q, 1H, J = 7.2 Hz), 1.88-1.68 (m, 2H), 1.49 (d, 3H, J = 6.1 Hz), 1.32 (d, 6H, J = 6.7 Hz), 1.22 (t, 3H, J = 7.4 Hz) | | 2-{[(3R,4S)-1-[4-({8-[(2R,3S)-3-[(ethanesulfonyl)methyl]-2-methylazetidin-1-yl]-5-(propan-2-yl)-2,7-naphthyridin-3-yl}amino)pyrimidin-2-yl]-3-fluoro-piperidin-4-yl]oxy}ethan-1-ol |

TABLE 1-continued

| # | Structure | LC/MS | NMR | Separation Conditions | Chemical Name |
|---|---|---|---|---|---|
| 251 | 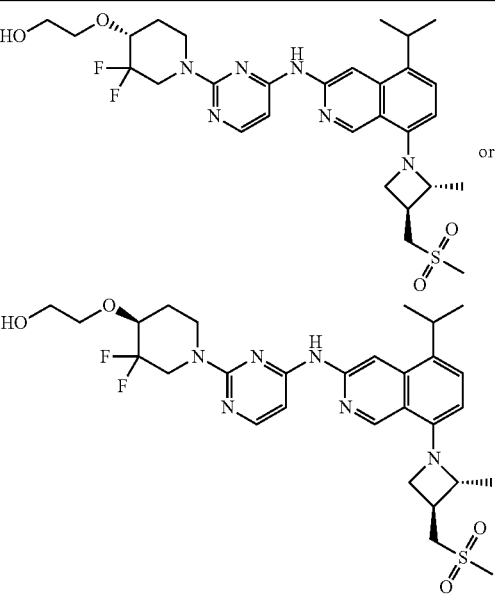 | 605 | 1H-NMR (300 MHz, 6d-DMSO) δ ppm 10.01 (s, 1H), 9.06 (s, 1H), 8.59 (s, 1H), 8.02 (d, 1H, J = 5.7 Hz), 7.43 (d, 1H, J = 8.0 Hz), 6.55 (dd, 2H, J = 10.9, 6.7 Hz), 4.69 (t, 2H, J = 7.0 Hz), 4.47-3.86 (m, 5H), 3.60 (s, 9H), 2.99 (s, 3H), 2.93-2.87 (m, 1H), 2.00-1.94 (m, 1H), 1.81-1.75 (m, 1H), 1.42 (d, 3H, J = 6.0 Hz), 1.29 (dd, 6H, J = 7.2, 3.5 Hz) | M; Peak 1 | 2-{[(4R)-3,3-difluoro-1-[4-({8-[(2R,3S)-3-(methanesulfonylmethyl)-2-methylazetidin-1-yl]-5-(propan-2-yl)isoquinolin-3-yl}amino)pyrimidin-2-yl]piperidin-4-yl]oxy}ethan-1-ol or 2-{[(4S)-3,3-difluoro-1-[4-({8-[(2R,3S)-3-(methanesulfonylmethyl)-2-methylazetidin-1-yl]-5-(propan-2-yl)isoquinolin-3-yl}amino)pyrimidin-2-yl]piperidin-4-yl]oxy}ethan-1-ol |
| 252 | 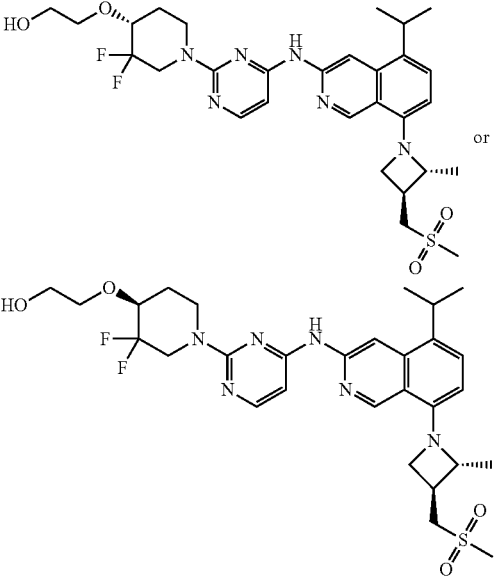 | 605 | 1H-NMR (300 MHz, 4d-CD3OD) δ ppm 9.14 (s, 1H), 8.62 (s, 1H), 7.99 (d, 1H, J = 5.9 Hz), 7.49 (d, 1H, J = 8.0 Hz), 6.68 (d, 1H, J = 8.0 Hz), 6.47 (d, 1H, J = 5.9 Hz), 4.68 (t, 1H, J = 7.5 Hz), 4.43 3.99 (m, 4H), 3.87 (dd, 3H, J = 13.0, 6.8 Hz), 3.83-3.42 (m, 7H), 3.14-2.91 (m, 4H), 2.05-2.02 (m, 2H), 1.51 (d, 3H, J = 6.1 Hz), 1.37 (dd, 6H, J = 6.8, 1.3 Hz) | M; Peak 2 | 2-{[(4S)-3,3-difluoro-1-[4-({8-[(2R,3S)-3-(methanesulfonylmethyl)-2-methylazetidin-1-yl]-5-(propan-2-yl)isoquinolin-3-yl}amino)pyrimidin-2-yl]piperidin-4-yl]oxy}ethan-1-ol or 2-{[(4R)-3,3-difluoro-1-[4-({8-[(2R,3S)-3-(methanesulfonylmethyl)-2-methylazetidin-1-yl]-5-(propan-2-yl)isoquinolin-3-yl}amino)pyrimidin-2-yl]piperidin-4-yl]oxy}ethan-1-ol |
| 253 | 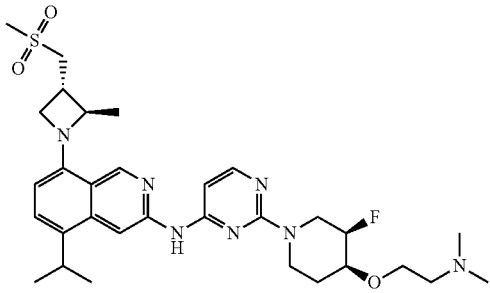 | 614 | 1H-NMR (300 MHz, 6d-DMSO) δ ppm 9.94 (s, 1H), 9.06 (s, 1H), 8.64 (s, 1H), 8.00 (d, 1H, J = 5.6 Hz), 7.43 (d, 1H, J = 8.0 Hz), 6.57 (d, 1H, J = 8.1 Hz), 6.46 (d, 1H, J = 5.7 Hz), 4.92 (d, 1H, J = 49.8 Hz), 4.76-4.61 (m, 2H), 4.49 (d, 1H, J = 13.3 Hz), 4.19 (t, 1H, J = 6.3 Hz), 3.79-3.47 (m, 9H), 3.00 (s, 3H), 2.89 (d, 1H, J = 7.3 Hz), 2.46 (t, 2H, J = 6.0 Hz), 2.19 (s, 6H), 1.83-1.71 (m, 2H), 1.43 (d, 3H, J = 6.0 Hz), 1.31 (dd, 6H, J = 6.7, | | N-{2-[(3R,4S)-4-[2-(dimethylamino)ethoxy]-3-fluoropiperidin-1-yl]pyrimidin-4-yl}-8-[(2R,3S)-3-(methanesulfonylmethyl)-2-methylazetidin-1-yl]-5-(propan-2-yl)isoquinolin-3-amine |

TABLE 1-continued

| # | Structure | LC/MS | NMR | Separation Conditions | Chemical Name |
|---|---|---|---|---|---|
| | | | 5.0 Hz) | | |
| 254 | 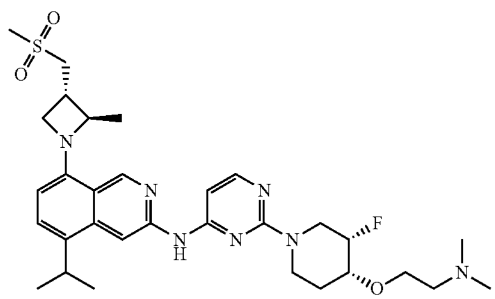 | 614 | 1H-NMR (300 MHz, 6d-DMSO) δ ppm 9.93 (s, 1H), 9.05 (s, 1H), 8.64 (s, 1H), 8.00 (d, 1H, J = 5.7 Hz), 7.42 (d, 1H, J = 8.0 Hz), 6.56 (d, 1H, J = 8.0 Hz), 6.46 (d, 1H, J = 5.7 Hz), 4.92 (d, 1H, J = 49.5 Hz), 4.74-4.60 (m, 2H), 4.47 (d, 1H, J = 13.4 Hz), 4.19 (t, 1H, J = 6.3 Hz), 3.80-3.43 (m, 9H), 2.99 (s, 3H), 2.88 (q, 1H, J = 7.2 Hz), 2.44 (t, 2H, J = 6.0 Hz), 2.17 (s, 6H), 1.82-1.76 (m, 2H), 1.42 (d, 3H, J = 6.0 Hz), 1.30 (dd, 6H, J = 6.8, 1.9 Hz) | | N-{2-[(3S,4R)-4-[2-(dimethylamino)ethoxy]-3-fluoropiperidin-1-yl]pyrimidin-4-yl}-8-[(2R,3S)-3-(methanesulfonylmethyl)-2-methylazetidin-1-yl]-5-(propan-2-yl)isoquinolin-3-amine |
| 255 | 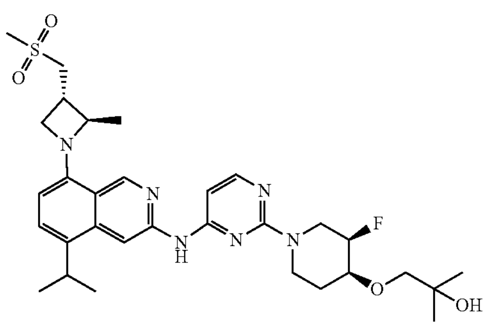 [SMILES: CC(C)c1ccc(N2C[C@H](CS(C)(=O)=O)[C@H]2C)c2cnc(Nc3ccnc(N4CC[C@H](OCC(C)(C)O)[C@H](F)C4)n3)cc12] | 615 | 1H-NMR (400 MHz, 6d-DMSO) δ ppm 9.93 (s, 1H), 9.05 (s, 1H), 8.65 (s, 1H), 8.00 (d, 1H, J = 5.6 Hz), 7.43 (d, 1H, J = 8.0 Hz), 6.56 (d, 1H, J = 8.1 Hz), 6.46 (d, 1H, J = 5.7 Hz), 4.90 (d, 1H, J = 48.1 Hz), 4.66 (s, 2H), 4.39 (d, 1H, J = 13.1 Hz), 4.35 (s, 1H), 4.23-4.15 (m, 1H), 3.82-3.68 (m, 1H), 3.67-3.37 (m, 7H), 2.99 (s, 3H), 2.88 (q, 1H, J = 7.3 Hz), 1.82-1.78 (m, 2H), 1.42 (d, 3H, J = 6.1 Hz), 1.30 (t, 6H, J = 6.5 Hz), 1.11 (d, 6H, J = 1.1 Hz) | | 1-{[(3R,4S)-3-fluoro-1-[4-({8-[(2R,3S)-3-(methanesulfonylmethyl)-2-methylazetidin-1-yl]-5-(propan-2-yl)isoquinolin-3-yl}amino)pyrimidin-2-yl]piperidin-4-yl]oxy}-2-methylpropan-2-ol |
| 256 | 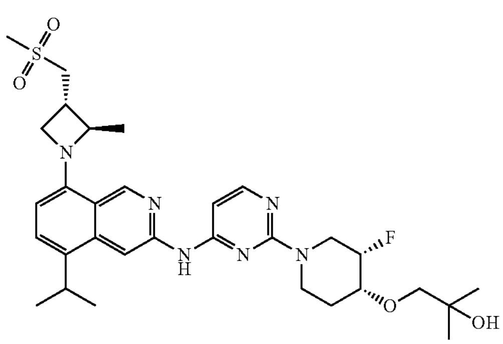 [SMILES: CC(C)c1ccc(N2C[C@H](CS(C)(=O)=O)[C@H]2C)c2cnc(Nc3ccnc(N4CC[C@@H](OCC(C)(C)O)[C@@H](F)C4)n3)cc12] | 615 | 1H-NMR (300 MHz, 6d-DMSO) δ ppm 9.93 (s, 1H), 9.05 (s, 1H), 8.65 (s, 1H), 8.00 (d, 1H, J = 5.6 Hz), 7.42 (d, 1H, J = 8.0 Hz), 6.56 (d, 1H, J = 8.1 Hz), 6.47 (d, 1H, J = 5.6 Hz), 4.90 (d, 1H, J = 50.5 Hz), 4.66 (t, 1H, J = 7.5 Hz), 4.64-4.60 (m, 1H), 4.44-4.32 (m, 2H), 4.19 (t, 1H, J = 6.3 Hz), 3.75 (d, 1H, J = 24.1 Hz), 3.68-3.35 (m, 7H), 2.99 (s, 3H), 2.88 (q, 1H, J = 7.4 Hz), 1.83-1.78 (m, 2H), 1.42 (d, 3H, J = 6.0 Hz), 1.30 (dd, 6H, J = 6.8, 2.1 Hz), 1.11 (d, 6H, J = 1.6 Hz) | | 1-{[(3S,4R)-3-fluoro-1-[4-({8-[(2R,3S)-3-(methanesulfonylmethyl)-2-methylazetidin-1-yl]-5-(propan-2-yl)isoquinolin-3-yl}amino)pyrimidin-2-yl]piperidin-4-yl]oxy}-2-methylpropan-2-ol |

TABLE 1-continued

| # | Structure | LC/MS | NMR | Separation Conditions | Chemical Name |
|---|---|---|---|---|---|
| 257 | 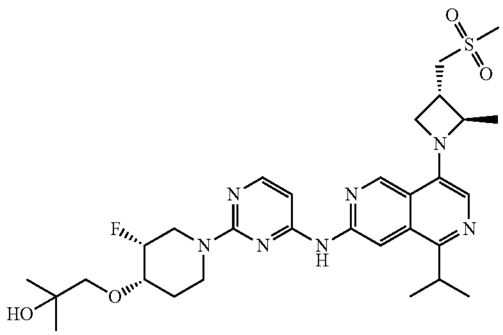 [SMILES: CC(C)c1ncc(N2C[C@H](CS(C)(=O)=O)[C@H]2C)c2cnc(Nc3ccnc(N4CC[C@H](OCC(C)(C)O)[C@H](F)C4)n3)cc12] | 616 | 1H-NMR (400 MHz, 6d-DMSO) δ ppm 10.16 (s, 1H), 9.13 (s, 1H), 8.76 (s, 1H), 8.04 (d, 1H, J = 5.6 Hz), 7.73 (s, 1H), 6.46 (d, 1H, J = 5.8 Hz), 4.92 (d, 1H, J = 50.7 Hz), 4.73 (t, 1H, J = 7.6 Hz), 4.65 (dd, 1H, J = 14.0, 7.5 Hz), 4.40 (d, 1H, J = 13.4 Hz), 4.35 (s, 1H), 4.30 (q, 1H, J = 6.3 Hz), 3.74 (dt, 3H, J = 18.9, 6.9 Hz), 3.57 (tq, 3H, J = 14.0, 7.8, 6.8 Hz), 3.44-3.32 (m, 2H), 3.00 (s, 3H), 2.93 (p, 1H, J = 7.4 Hz), 1.81 (d, 2H, J = 4.7 Hz), 1.48 (d, 3H, J = 6.0 Hz), 1.31 (d, 6H, J = 6.6 Hz), 1.11 (d, 6H, J = 1.1 Hz) | | 1-{[(3R,4S)-3-fluoro-1-[4-({8-[(2R,3S)-3-(methanesulfonylmethyl)-2-methylazetidin-1-yl]-5-(propan-2-yl)-2,6-naphthyridin-3-yl}amino)pyrimidin-2-yl]piperidin-4-yl]oxy}-2-methylpropan-2-ol |
| 258 | 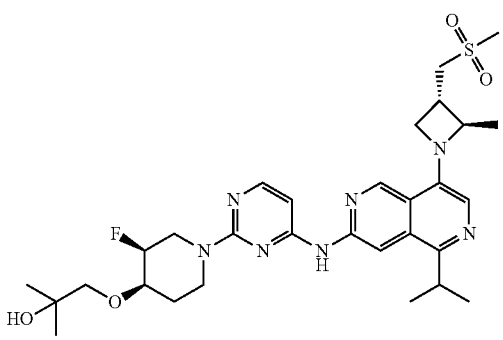 [SMILES: CC(C)c1ncc(N2C[C@H](CS(C)(=O)=O)[C@H]2C)c2cnc(Nc3ccnc(N4CC[C@@H](OCC(C)(C)O)[C@@H](F)C4)n3)cc12] | 616 | 1H-NMR (300 MHz, 6d-DMSO) δ ppm 10.18 (s, 1H), 9.14 (s, 1H), 8.77 (s, 1H), 8.04 (d, 1H, J = 5.6 Hz), 7.73 (s, 1H), 6.47 (d, 1H, J = 5.6 Hz), 4.92 (d, 1H, J = 48.7 Hz), 4.73 (q, 1H, J = 6.6, 5.6 Hz), 4.68-4.60 (m, 1H), 4.46-4.27 (m, 3H), 3.83-3.50 (m, 6H), 3.45-3.36 (m, 2H), 3.01 (s, 3H), 2.92 (p, 1H, J = 7.3 Hz), 1.85-1.79 (m, 2H), 1.48 (d, 3H, J = 6.0 Hz), 1.32 (t, 6H, J = 7.1 Hz), 1.12 (s, 6H) | | 1-{[(3S,4R)-3-fluoro-1-[4-({8-[(2R,3S)-3-(methanesulfonylmethyl)-2-methylazetidin-1-yl]-5-(propan-2-yl)-2,6-naphthyridin-3-yl}amino)pyrimidin-2-yl]piperidin-4-yl]oxy}-2-methylpropan-2-ol |
| 259 | 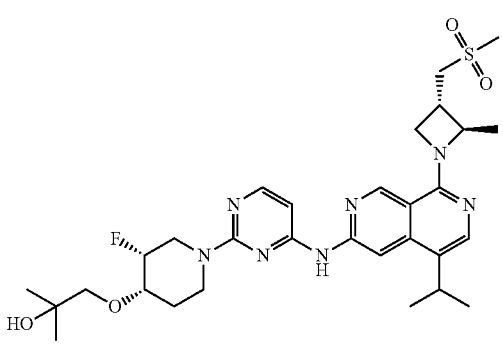 [SMILES: CC(C)c1cnc(N2C[C@H](CS(C)(=O)=O)[C@H]2C)c2cnc(Nc3ccnc(N4CC[C@H](OCC(C)(C)O)[C@H](F)C4)n3)cc12] | 616 | 1H-NMR (400 MHz, 6d-DMSO) δ ppm 10.13 (s, 1H), 9.04 (s, 1H), 8.52 (s, 1H), 8.05 (d, 1H, J = 5.6 Hz), 8.01 (s, 1H), 6.51 (d, 1H, J = 5.6 Hz), 5.01-4.79 (m, 2H), 4.66-4.49 (m, 2H), 4.38 (d, 1H, J = 13.2 Hz), 4.34 (s, 1H), 3.98 (t, 1H, J = 7.3 Hz), 3.75 (d, 1H, J = 23.4 Hz), 3.64-3.50 (m, 3H), 3.49-3.35 (m, 4H), 2.99 (s, 3H), 2.89 (q, 1H, J = 7.2 Hz), 1.83-1.77 (m, 2H), 1.49 (d, 3H, J = 6.1 Hz), 1.32 (d, 6H, J = 6.8 Hz), 1.11 (s, 6H) | | 1-{[(3R,4S)-3-fluoro-1-[4-({8-[(2R,3S)-3-(methanesulfonylmethyl)-2-methylazetidin-1-yl]-5-(propan-2-yl)-2,7-naphthyridin-3-yl}amino)pyrimidin-2-yl]piperidin-4-yl]oxy}-2-methylpropan-2-ol |

TABLE 1-continued

| # | Structure | LC/MS | NMR | Separation Conditions | Chemical Name |
|---|---|---|---|---|---|
| 260 | 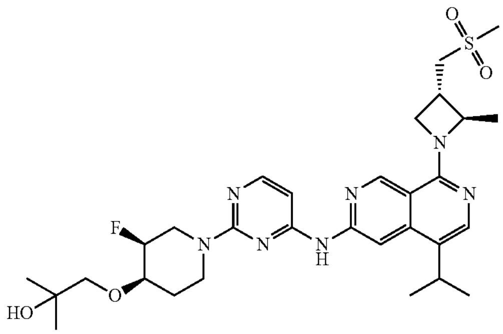 [SMILES: CC(C)c1cnc(N2C[C@H](CS(C)(=O)=O)[C@H]2C)c2cnc(Nc3ccnc(N4CC[C@@H](OCC(C)(C)O)[C@@H](F)C4)n3)cc12] | 616 | 1H-NMR (400 MHz, 6d-DMSO) δ ppm 10.12 (s, 1H), 9.04 (s, 1H), 8.52 (s, 1H), 8.05 (d, 1H, J = 5.6 Hz), 8.00 (s, 1H), 6.51 (d, 1H, J = 5.6 Hz), 5.04-4.79 (m, 2H), 4.62 (dd, 1H, J = 14.0, 7.5 Hz), 4.55 (p, 1H, J = 5.8 Hz), 4.41-4.37 (m, 1H), 4.34 (s, 1H), 3.98 (t, 1H, J = 7.3 Hz), 3.83-3.68 (m, 1H), 3.64-3.50 (m, 3H), 3.49-3.34 (m, 4H), 2.99 (s, 3H), 2.90 (p, 1H, J = 7.1 Hz), 1.83-1.77 (m, 2H), 1.49 (d, 3H, J = 6.1 Hz), 1.32 (dd, 6H, J = 8.4, 6.8 Hz), 1.11 (s, 6H) | | 1-{[(3S,4R)-3-fluoro-1-[4-({8-[(2R,3S)-3-(methanesulfonyl-methyl)-2-methylazetidin-1-yl]-5-(propan-2-yl)-2,7-naphthyridin-3-yl}amino)pyrimidin-2-yl]piperidin-4-yl]oxy}-2-methyl-propan-2-ol |
| 261 | 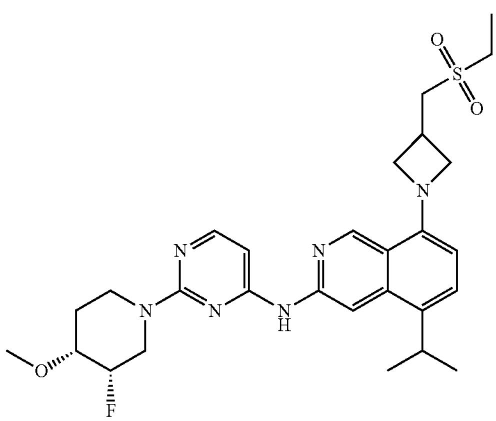 [SMILES: CCS(=O)(=O)CC1CN(c2ccc(C(C)C)c3cc(Nc4ccnc(N5CC[C@@H](OC)[C@@H](F)C5)n4)ncc23)C1] | 557 | $^1$H NMR (400 MHz, DMSO-d$_6$) δ 9.85 (s, 1H), 9.03 (s, 1H), 8.59 (s, 1H), 7.98 (d, J = 5.7 Hz, 1H), 7.40 (d, J = 8.0 Hz, 1H), 6.46 (d, J = 5.7 Hz, 1H), 6.39 (d, J = 8.0 Hz, 1H), 4.92 (d, J = 49.3 Hz, 1H), 4.70 (s, 1H), 4.46 (d, J = 13.0 Hz, 1H), 4.37 (t, J = 7.7 Hz, 2H), 3.94 (t, J = 6.9 Hz, 2H), 3.67-3.38 (m, 4H), 3.35 (s, 2H), 3.32-3.22 (m, 4H), 3.10 (q, J = 7.4 Hz, 2H), 1.86-1.64 (m, 2H), 1.34-1.14 (m, 9H). | | 8-{3-[(ethanesulfonyl)methyl]azetidin-1-yl}-N-{2-[(3S,4R)-3-fluoro-4-methoxy-piperidin-1-yl]pyrimidin-4-yl}-5-(propan-2-yl)isoquinolin-3-amine |
| 262 | 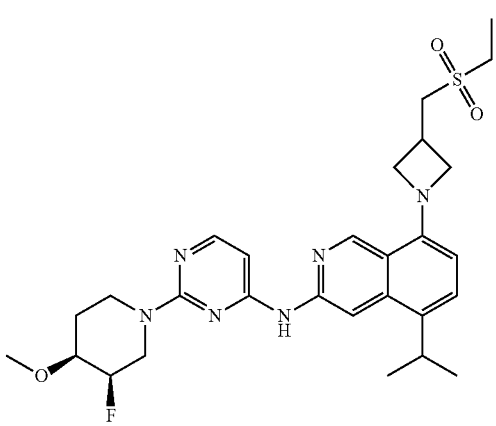 [SMILES: CCS(=O)(=O)CC1CN(c2ccc(C(C)C)c3cc(Nc4ccnc(N5CC[C@H](OC)[C@H](F)C5)n4)ncc23)C1] | 557 | $^1$H NMR (400 MHz, DMSO-d$_6$) δ 9.87 (s, 1H), 9.04 (s, 1H), 8.61 (s, 1H), 8.00 (d, J = 5.6 Hz, 1H), 7.42 (d, J = 8.0 Hz, 1H), 6.48 (d, J = 5.7 Hz, 1H), 6.41 (d, J = 8.0 Hz, 1H), 4.93 (d, J = 49.5 Hz, 1H), 4.79-4.67 (m, 1H), 4.48 (d, J = 13.5 Hz, 1H), 4.38 (t, J = 7.6 Hz, 2H), 3.96 (t, J = 6.9 Hz, 2H), 3.67-3.41 (m, 4H), 3.37 (s, 2H), 3.32-3.23 (m, 4H), 3.11 (q, J = 7.4 Hz, 2H), 1.92-1.62 (m, 2H), 1.37-1.15 (m, 9H). | | 8-{3-[(ethanesulfonyl)methyl]azetidin-1-yl}-N-{2-[(3R,4S)-3-fluoro-4-methoxy-piperidin-1-yl]pyrimidin-4-yl}-5-(propan-2-yl)isoquinolin-3-amine |

TABLE 1-continued

| # | Structure | LC/MS | NMR | Separation Conditions | Chemical Name |
|---|---|---|---|---|---|
| 263 | 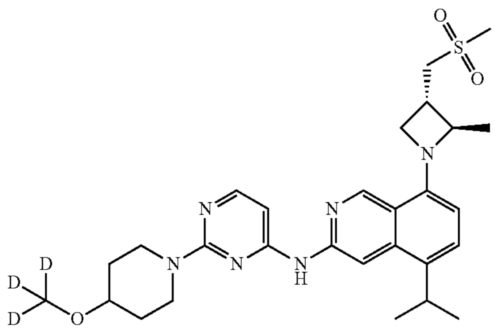 [SMILES: [2H]C([2H])([2H])OC1CCN(c2nccc(Nc3cc4c(C(C)C)ccc(N5C[C@H](CS(C)(=O)=O)[C@H]5C)c4cn3)n2)CC1] | 542 | 1H NMR (400 MHz, DMSO-d6) δ 9.87 (s, 1H), 9.05 (s, 1H), 8.67 (s, 1H), 8.00 (d, J = 5.6 Hz, 1H), 7.42 (d, J = 7.9 Hz, 1H), 6.56 (d, J = 8.0 Hz, 1H), 6.43 (d, J = 5.7 Hz, 1H), 4.66 (t, J = 7.5 Hz, 1H), 4.35-4.11 (m, 3H), 3.73-3.34 (m, 7H), 2.89 (q, J = 7.2 Hz, 1H), 1.96 (d, J = 27.6 Hz, 2H), 1.52-1.37 (m, 5H), 1.32-1.16 (m, 10H), 0.85 (dt, J = 9.3, 6.7 Hz, 3H) | | 8-[(2R,3S)-3-(methanesulfonyl-methyl)-2-methylazetidin-1-yl]-N-{2-[4-($^2$H3)methoxy-piperidin-1-yl] pyrimidin-4-yl}-5-(propan-2-yl)isoquinolin-3-amine |
| 264 | 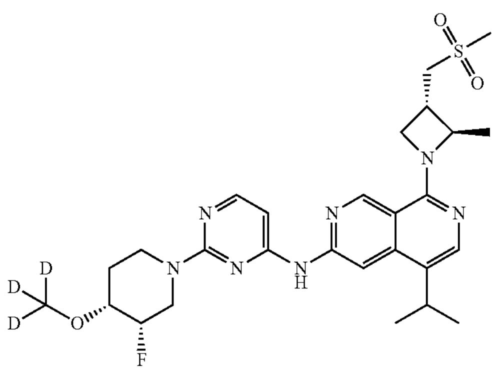 [SMILES: [2H]C([2H])([2H])O[C@@H]1CCN(c2nccc(Nc3cc4c(C(C)C)cnc(N5C[C@H](CS(C)(=O)=O)[C@H]5C)c4cn3)n2)C[C@@H]1F] | 547 | 1H NMR (400 MHz, DMSO-d6) δ 10.12 (s, 1H), 9.06 (s, 1H), 8.53 (s, 1H), 8.08 (d, J = 5.5 Hz, 1H), 8.02 (s, 1H), 6.56 (d, J = 5.7 Hz, 1H), 4.97 (d, J = 49.7 Hz, 1H), 4.74 (s, 1H), 4.66-4.51 (m, 2H), 4.49 (d, J = 13.6 Hz, 1H), 4.25 (dd, J = 8.6, 6.2 Hz, 2H), 3.69-3.43 (m, 4H), 3.04 (s, 3H), 1.92-1.64 (m, 2H), 1.35 (dd, J = 6.8, 4.2 Hz, 6H). | | N-{2-[(3S,4R)-3-fluoro-4-($^2$H3)methoxy-piperidin-1-yl] pyrimidin-4-yl}-8-[3-(methanesulfonyl-methyl)azetidin-1-yl]-5-(propan-2-yl)-2,7-naph-thyridin-3-amine |
| 265 | 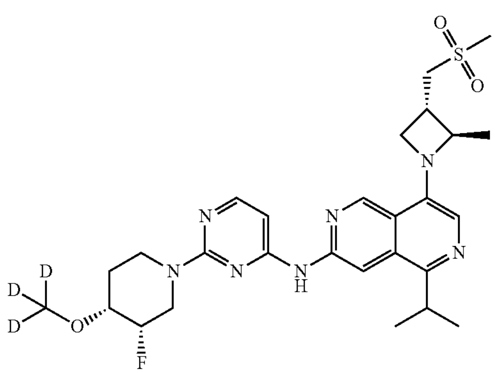 | 547 | 1H NMR (400 MHz, DMSO-d6) δ 10.13 (s, 1H), 9.15 (s, 1H), 8.75 (s, 1H), 8.06 (dd, J = 5.7, 1.9 Hz, 1H), 7.62 (d, J = 2.3 Hz, 1H), 6.50 (d, J = 5.9 Hz, 1H), 4.97 (d, J = 49.3 Hz, 1H), 4.76 (s, 1H), 4.51 (t, J = 7.8 Hz, 3H), 4.10 (t, J = 6.9 Hz, 2H), 3.78-3.47 (m, 4H), 3.04 (d, J = 2.1 Hz, 3H), 1.82 (d, J = 23.3 Hz, 2H), 1.34 (d, J = 7.1 Hz, 6H) | | N-{2-[(3S,4R)-3-fluoro-4-($^2$H3)methoxy-piperidin-1-yl] pyrimidin-4-yl}-8-[3-(methane-sulfonylmethyl) azetidin-1-yl]-5-(propan-2-yl)-2,6-naph-thyridin-3-amine |
| 266 | or | 538 | 1H-NMR (400 MHz, 6d-DMSO) δ ppm 10.09 (s, 1H), 9.03 (s, 1H), 8.68 (s, 1H), 8.01 (d, 2H, J = 10.0 Hz), 6.56 (s, 1H), 4.85 (t, 1H, J = 8.0 Hz), 4.54 (p, 1H, J = 6.1 Hz), 4.32-4.15 (m, 3H), 3.98 (t, 1H, J = 7.3 Hz), 3.84 (t, 1H, J = 6.8 Hz), 3.75 (td, 1H, J = 10.5, 6.0 Hz), 3.60-3.47 (m, 3H), 3.44 (t, 1H, J = 8.5 Hz), 2.99 (s, 3H), 2.88 (p, 1H, J = 7.2 Hz), 2.73-2.53 (m, 1H), 2.09 (dd, 1H, | V; Peak 2 | N-{2-[(3aR,6aS)-hexahydro-1H-furo[3,4-b] pyrrol-1-yl] pyrimidin-4-yl}-8-[(2R,3S)-3-(methanesulfonyl-methyl)-2-methylazetidin-1-yl]-5-(propan-2-yl)-2,7-naph-thyridin-3-amine or N-{2-[(3aS,6aR)-hexahydro-1H- |

TABLE 1-continued

| # | Structure | LC/MS | NMR | Separation Conditions | Chemical Name |
|---|---|---|---|---|---|
|  | 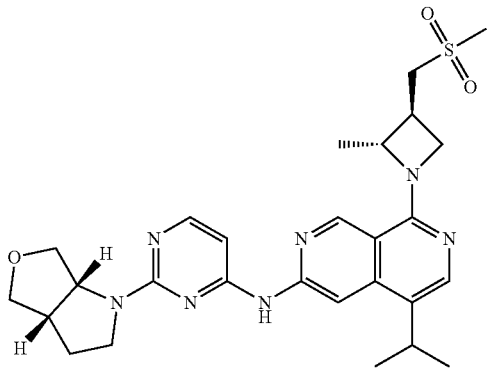 [SMILES: CC(C)c1cnc(N2C[C@H](CS(C)(=O)=O)[C@H]2C)c2cnc(Nc3ccnc(N4CC[C@@H]5COC[C@@H]54)n3)cc12] |  | J = 11.2, 5.8 Hz), 1.91 (p, 1H, J = 10.5 Hz), 1.49 (d, 3H, J = 6.1 Hz), 1.31 (dd, 6H, J = 6.8, 3.3 Hz) |  | furo[3,4-b]pyrrol-1-yl}pyrimidin-4-yl}-8-[(2R,3S)-3-(methanesulfonylmethyl)-2-methylazetidin-1-yl]-5-(propan-2-yl)-2,7-naphthyridin-3-amine |
| 267 | 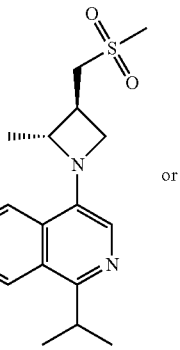 | 538 | 1H-NMR (300 MHz, 6d-DMSO) δ ppm 10.14 (s, 1H), 9.13 (s, 1H), 8.90 (s, 1H), 8.01 (d, 1H, J = 5.7 Hz), 7.73 (s, 1H), 6.51 (s, 1H), 4.74 (t, 1H, J = 7.5 Hz), 4.41-4.13 (m, 4H), 3.90-3.66 (m, 4H), 3.62-3.42 (m, 4H), 3.01 (s, 3H), 2.93 (q, 1H, J = 7.2 Hz), 2.77-2.59 (m, 1H), 2.14-1.86 (m, 2H), 1.48 (d, 3H, J = 6.0 Hz), 1.30 (dd, 6H, J = 6.7, 3.4 Hz) | V; Peak 2 | N-(2-((3aR,6aS)-hexahydro-1H-furo[3,4-b]pyrrol-1-yl)pyrimidin-4-yl)-5-isopropyl-8-((2R,3S)-2-methyl-3-((methylsulfonyl)methyl)azetidin-1-yl)-2,6-naphthyridin-3-amine or N-(2-((3aS,6aR)-hexahydro-1H-furo[3,4-b]pyrrol-1-yl)pyrimidin-4-yl)-5-isopropyl-8-((2R,3S)-2-methyl-3-((methylsulfonyl)methyl)azetidin-1-yl)-2,6-naphthyridin-3-amine |
| 268 | 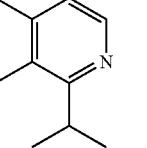 | 543 | 1H-NMR (300 MHz, 6d-DMSO) δ ppm 9.89 (s, 1H), 9.03 (s, 1H), 8.63 (s, 1H), 7.98 (d, 1H, J = 5.7 Hz), 7.40 (d, 1H, J = 7.9 Hz), 6.54 (d, 1H, J = 8.0 Hz), 6.45 (d, 1H, J = 5.7 Hz), 5.21 (d, 1H, J = 5.4 Hz), 4.83 (d, 1H, J = 50.3 Hz), 4.64 (t, 1H, J = 7.5 Hz), 4.25-4.08 (m, 3H), 3.77-3.39 (m, 8H), 2.98 (s, 3H), 2.87 (q, 1H, J = 7.3 Hz), 2.09-1.66 (m, 2H), 1.40 (d, 3H, J = 5.9 Hz), 1.28 (d, 6H, J = 6.6 Hz) | W; Peak 1 | (3R,4S)-4-fluoro-1-[4-({8-[(2R,3S)-3-(methanesulfonylmethyl)-2-methylazetidin-1-yl]-5-(propan-2-yl)isoquinolin-3-yl}amino)pyrimidin-2-yl]piperidin-3-ol or (3S,4R)-4-fluoro-1-[4-({8-[(2R,3S)-3-(methanesulfonylmethyl)-2- |

| # | Structure | LC/MS | NMR | Separation Conditions | Chemical Name |
|---|---|---|---|---|---|
| | | | | | methylazetidin-1-yl]-5-(propan-2-yl)isoquinolin-3-yl}amino)pyrimidin-2-yl]piperidin-3-ol |
| 269 | | 543 | 1H-NMR (300 MHz, 6d-DMSO) δ ppm 9.90 (s, 1H), 9.03 (s, 1H), 8.63 (s, 1H), 7.98 (d, 1H, J = 5.7 Hz), 7.40 (d, 1H, J = 8.0 Hz), 6.54 (d, 1H, J = 8.2 Hz), 6.44 (d, 1H, J = 5.7 Hz), 5.20 (d, 1H, J = 5.4 Hz), 4.83 (d, 1H, J = 51.0 Hz), 4.64 (t, 1H, J = 7.5 Hz), 4.26-4.12 (m, 3H), 3.74-3.40 (m, 8H), 2.98 (s, 3H), 2.93-2.82 (m, 1H), 2.02-1.62 (m, 2H), 1.40 (d, 3H, J = 6.0 Hz), 1.28 (dd, 6H, J = 6.8, 3.6 Hz) | W; Peak 1 | (3S,4R)-4-fluoro-1-[4-({8-[(2R,3S)-3-(methanesulfonyl-methyl)-2-methylazetidin-1-yl]-5-(propan-2-yl)isoquinolin-3-yl}amino)pyrimidin-2-yl]piperidin-3-ol or (3R,4S)-4-fluoro-1-[4-({8-[(2R,3S)-3-(methanesulfonyl-methyl)-2-methylazetidin-1-yl]-5-(propan-2-yl)isoquinolin-3-yl}amino)pyrimidin-2-yl]piperidin-3-ol |
| 270 | 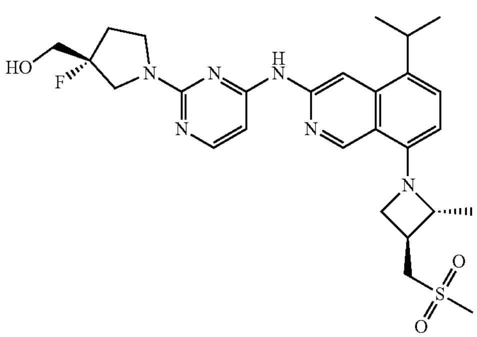 [SMILES: CC(C)c1ccc(N2C[C@H](CS(C)(=O)=O)[C@H]2C)c2cnc(Nc3ccnc(N4CC[C@@](F)(CO)C4)n3)cc12] | 543 | 1H-NMR (300 MHz, 6d-DMSO) δ ppm 9.93 (s, 1H), 9.05 (s, 1H), 8.87 (s, 1H), 8.00 (d, 1H, J = 5.7 Hz), 7.42 (d, 1H, J = 8.0 Hz), 6.56 (d, 1H, J = 8.2 Hz), 6.44 (d, 1H, J = 5.7 Hz), 5.32 (s, 1H), 4.66 (t, 1H, J = 7.5 Hz), 4.24-4.14 (m, 1H), 3.88-3.44 (m, 10H), 3.00 (s, 3H), 2.96-2.85 (m, 1H), 2.36-2.14 (m, 2H), 1.43 (d, 3H, J = 6.1 Hz), 1.30 (dd, 6H, J = 6.8, 2.5 Hz) | F; Peak 1 | [(3R)-3-fluoro-1-[4-({8-[(2R,3S)-3-(methanesulfonyl-methyl)-2-methylazetidin-1-yl]-5-(propan-2-yl)isoquinolin-3-yl}amino)pyrimidin-2-yl]pyrrolidin-3-yl]methanol or [(3S)-3-fluoro-1-[4-({8-[(2R,3S)-3- |

TABLE 1-continued

| # | Structure | LC/MS | NMR | Separation Conditions | Chemical Name |
|---|---|---|---|---|---|
|  |  |  |  |  | (methanesulfonyl-methyl)-2-methylazetidin-1-yl]-5-(propan-2-yl)isoquinolin-3-yl}amino)pyrimidin-2-yl]pyrrolidin-3-yl]methanol |
| 271 | 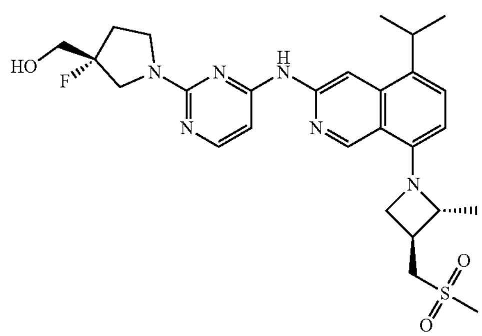 [SMILES: CC(C)c1ccc(N2C[C@H](CS(C)(=O)=O)[C@H]2C)c2cnc(Nc3ccnc(N4CC[C@@](F)(CO)C4)n3)cc12] | 543 | 1H-NMR (300 MHz, 6d-DMSO) δ ppm 9.93 (s, 1H), 9.05 (s, 1H), 8.86 (s, 1H), 8.00 (d, 1H, J = 5.7 Hz), 7.42 (d, 1H, J = 8.0 Hz), 6.56 (d, 1H, J = 8.1 Hz), 6.44 (d, 1H, J = 5.7 Hz), 5.35-5.29 (m, 1H), 4.66 (t, 1H, J = 7.5 Hz), 4.24-4.14 (m, 1H), 3.93-3.41 (m, 10H), 3.00 (s, 3H), 2.89 (q, 1H, J = 8.2, 7.6 Hz), 2.33-2.15 (m, 2H), 1.43 (d, 3H, J = 6.0 Hz), 1.34-1.21 (m, 6H) | F; Peak 2 | [(3S)-3-fluoro-1-[4-({8-[(2R,3S)-3-(methanesulfonyl-methyl)-2-methylazetidin-1-yl]-5-(propan-2-yl)isoquinolin-3-yl}amino)pyrimidin-2-yl]pyrrolidin-3-yl]methanol or [(3R)-3-fluoro-1-[4-({8-[(2R,3S)-3-(methanesulfonyl-methyl)-2-methylazetidin-1-yl]-5-(propan-2-yl)isoquinolin-3-yl}amino)pyrimidin-2-yl]pyrrolidin-3-yl]methanol |
| 272 | 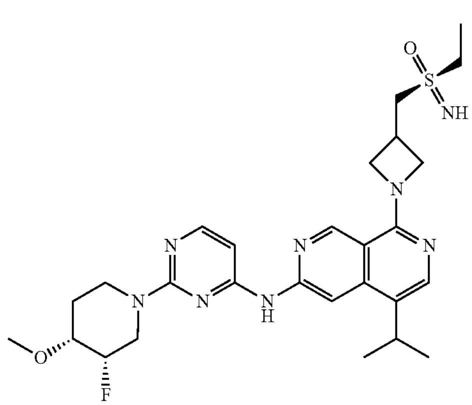 | 556 | 1H-NMR (300 MHz, 6d-DMSO) δ ppm 9.89 (s, 1H), 9.03 (s, 1H), 8.60 (s, 1H), 7.98 (d, 1H, J = 5.7 Hz), 7.40 (d, 1H, J = 8.0 Hz), 6.46 (d, 1H, J = 5.7 Hz), 6.38 (d, 1H, J = 8.1 Hz), 4.93 (d, 1H, J = 49.8 Hz), 4.74 (d, 1H, J = 13.5 Hz), 4.47 (d, 1H, J = 13.3 Hz), 4.35 (q, 2H, J = 7.5 Hz), 3.95 (dt, 2H, J = 13.2, 6.9 Hz), 3.70-3.33 (m, 10H), 2.99 (q, 2H, J = 7.3 Hz), 1.86-1.63 (m, 2H), 1.33-1.16 (m, 9H) | U; Peak 1 | (R)-ethyl({1-[3-({2-[(3S,4R)-3-fluoro-4-methoxy-piperidin-1-yl]pyrimidin-4-yl}amino)-5-(propan-2-yl)isoquinolin-8-yl]azetidin-3-yl}methyl)imino-$\lambda^6$-sulfanone or (S)-ethyl({1-[3-({2-[(3S,4R)-3-fluoro-4-methoxy- |

TABLE 1-continued

| # | Structure | LC/MS | NMR | Separation Conditions | Chemical Name |
|---|---|---|---|---|---|
| | | | | | piperidin-1-yl]pyrimidin-4-yl}amino)-5-(propan-2-yl)isoquinolin-8-yl]azetidin-3-yl}methyl)imino-λ⁶-sulfanone |
| 273 | | 556 | 1H-NMR (300 MHz, 6d-DMSO) δ ppm 9.88 (s, 1H), 9.03 (s, 1H), 8.60 (s, 1H), 7.98 (d, 1H, J = 5.7 Hz), 7.40 (d, 1H, J = 8.0 Hz), 6.46 (d, 1H, J = 5.7 Hz), 6.38 (d, 1H, J = 8.0 Hz), 4.92 (d, 1H, J = 50.3 Hz), 4.81-4.59 (m, 1H), 4.48 (d, 1H, J = 13.3 Hz), 4.35 (q, 2H, J = 7.3 Hz), 3.95 (dt, 2H, J = 13.2, 6.8 Hz), 3.74-3.55 (m, 10H), 2.98 (t, 2H, J = 7.4 Hz), 1.89-1.59 (m, 2H), 1.34-1.09 (m, 9H) | U; Peak 2 | (S)-ethyl({1-[3-({2-[(3S,4R)-3-fluoro-4-methoxy-piperidin-1-yl]pyrimidin-4-yl}amino)-5-(propan-2-yl)isoquinolin-8-yl]azetidin-3-yl}methyl)imino-λ⁶-sulfanone or (R)-ethyl({1-[3-({2-[(3S,4R)-3-fluoro-4-methoxy-piperidin-1-yl}pyrimidin-4-yl}amino)-5-(propan-2-yl)isoquinolin-8-yl]azetidin-3-yl}methyl)imino-λ⁶-sulfanone |

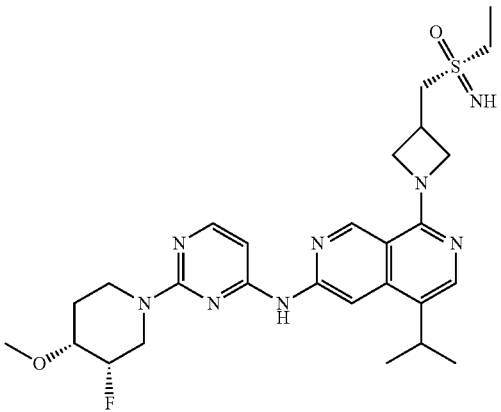 [SMILES: CC[S@@](=N)(=O)CC1CN(c2ncc(C(C)C)c3cc(Nc4ccnc(N5CC[C@@H](OC)[C@@H](F)C5)n4)ncc23)C1]
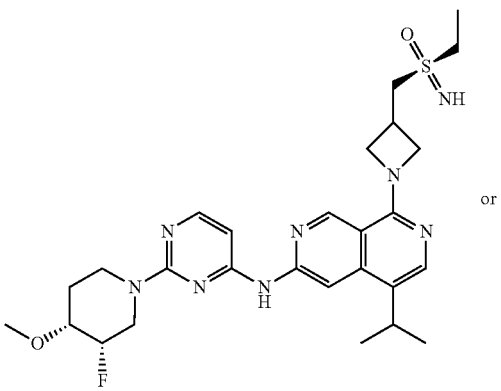 [SMILES: CC[S@](=N)(=O)CC1CN(c2ncc(C(C)C)c3cc(Nc4ccnc(N5CC[C@@H](OC)[C@@H](F)C5)n4)ncc23)C1]

TABLE 1-continued

| # | Structure | LC/MS | NMR | Separation Conditions | Chemical Name |
|---|---|---|---|---|---|
| 274 | 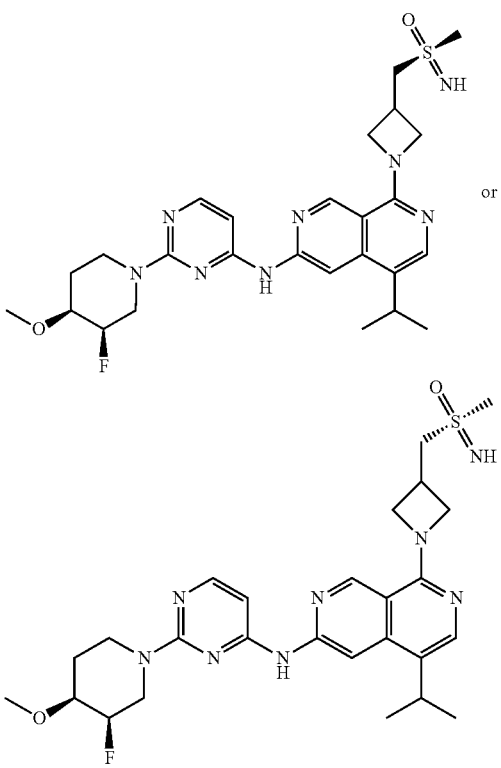 | 556 | 1H-NMR (300 MHz, 6d-DMSO) δ ppm 9.89 (s, 1H), 9.03 (s, 1H), 8.60 (s, 1H), 7.98 (d, 1H, J = 5.7 Hz), 7.40 (d, 1H, J = 8.0 Hz), 6.46 (d, 1H, J = 5.7 Hz), 6.38 (d, 1H, J = 8.1 Hz), 4.92 (d, 1H, J = 49.3 Hz), 4.72 (s, 1H), 4.47 (d, 1H, J = 13.2 Hz), 4.35 (q, 2H, J = 7.4 Hz), 3.95 (dt, 2H, J = 12.8, 6.7 Hz), 3.74-3.38 (m, 10H), 3.00 (q, 2H, J = 7.4 Hz), 1.83-1.67 (m, 2H), 1.33-1.16 (m, 9H) | U; Peak 1 | (R)-methyl({1-[3-({2-[(3R,4S)-3-fluoro-4-methoxy-piperidin-1-yl]pyrimidin-4-yl}amino)-5-(propan-2-yl)isoquinolin-8-yl]azetidin-3-yl}methyl) imino-λ⁶-sulfanone or (S)-methyl({1-[3-({2-[(3R,4S)-3-fluoro-4-methoxy-piperidin-1-yl]pyrimidin-4-yl}amino)-5-(propan-2-yl)isoquinolin-8-yl]azetidin-3-yl}methyl) imino-λ⁶-sulfanone |
| 275 | 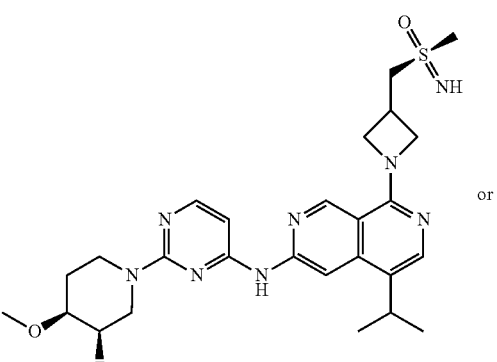 | 556 | 1H-NMR (300 MHz, 6d-DMSO) δ ppm 9.89 (s, 1H), 9.03 (s, 1H), 8.60 (s, 1H), 7.98 (d, 1H, J = 5.7 Hz), 7.39 (d, 1H, J = 8.0 Hz), 6.46 (d, 1H, J = 5.7 Hz), 6.38 (d, 1H, J = 8.1 Hz), 5.06-4.79 (m, 1H), 4.72 (dt, 1H, J = 13.6, 7.6 Hz), 4.47 (d, 1H, J = 13.5 Hz), 4.35 (td, 2H, J = 7.6, 4.6 Hz), 3.95 (dt, 2H, J = 11.7, 6.8 Hz), 3.66-3.41 (m, 7H), 3.30-3.16 (m, 3H), 3.00 (q, 2H, J = 7.4 Hz), 1.87-1.67 (m, 2H), 1.34-1.16 (m, 9H) | U; Peak 2 | (S)-ethyl({1-[3-({2-[(3R,4S)-3-fluoro-4-methoxy-piperidin-1-yl]pyrimidin-4-yl}amino)-5-(propan-2-yl)isoquinolin-8-yl]azetidin-3-yl}methyl) imino-λ⁶-sulfanone or (R)-ethyl({1-[3-({2-[(3R,4S)-3-fluoro-4-methoxy-piperidin-1-yl]pyrimidin-4-yl}amino)-5-(propan-2-yl)isoquinolin-8-yl]azetidin-3-yl}methyl) imino-λ⁶-sulfanone |

TABLE 1-continued

| # | Structure | LC/MS | NMR | Separation Conditions | Chemical Name |
|---|---|---|---|---|---|
| 276 | 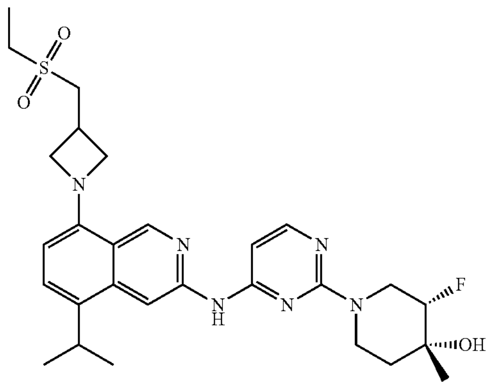 [SMILES: CCS(=O)(=O)CC1CN(c2ccc(C(C)C)c3cc(Nc4ccnc(N5CC[C@@](C)(O)[C@@H](F)C5)n4)ncc23)C1] | 557 | 1H-NMR (300 MHz, 6d-DMSO) δ ppm 9.90 (s, 1H), 9.02 (s, 1H), 8.62 (s, 1H), 7.99 (d, 1H, J = 5.6 Hz), 7.39 (d, 1H, J = 8.0 Hz), 6.46 (d, 1H, J = 5.7 Hz), 6.39 (d, 1H, J = 8.0 Hz), 4.84 (s, 1H), 4.38 (q, 3H, J = 8.1 Hz), 4.30-4.12 (m, 2H), 3.94 (t, 2H, J = 6.9 Hz), 3.62-3.42 (m, 5H), 3.10 (q, 2H, J = 7.5 Hz), 1.75-1.48 (m, 2H), 1.32-1.17 (m, 12H) | | (3S,4R)-1-{4-[(8-{3-[(ethanesulfonyl)methyl]azetidin-1-yl}-5-(propan-2-yl)isoquinolin-3-yl)amino]pyrimidin-2-yl}-3-fluoro-4-methyl-piperidin-4-ol |
| 277 | 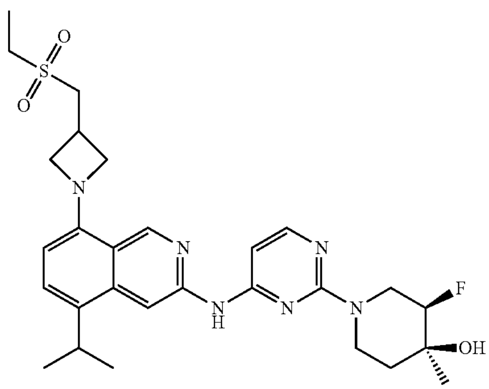 [SMILES: CCS(=O)(=O)CC1CN(c2ccc(C(C)C)c3cc(Nc4ccnc(N5CC[C@](C)(O)[C@H](F)C5)n4)ncc23)C1] | 557 | 1H-NMR (300 MHz, 6d-DMSO) δ ppm 9.89 (s, 1H), 9.03 (s, 1H), 8.62 (s, 1H), 7.99 (d, 1H, J = 5.7 Hz), 7.39 (d, 1H, J = 8.0 Hz), 6.46 (d, 1H, J = 5.7 Hz), 6.39 (d, 1H, J = 8.1 Hz), 4.84 (s, 1H), 4.38 (q, 3H, J = 8.1 Hz), 4.27-4.09 (m, 2H), 3.94 (t, 2H, J = 6.9 Hz), 3.68-3.40 (m, 5H), 3.29-3.20 (m, 1H), 3.10 (q, 2H, J = 7.4 Hz), 1.71-1.42 (m, 2H), 1.32-1.17 (m, 12H) | OO; Peak 2 | (3R,4S)-1-{4-[(8-{3-[(ethanesulfonyl)methyl]azetidin-1-yl}-5-(propan-2-yl)isoquinolin-3-yl)amino]pyrimidin-2-yl}-3-fluoro-4-methyl-piperidin-4-ol |
| 278 | | 557 | 1H-NMR (300 MHz, 6d-DMSO) δ ppm 9.98 (s, 1H), 9.06 (s, 1H), 8.63 (s, 1H), 8.02 (d, 1H, J = 5.6 Hz), 7.43 (d, 1H, J = 8.0 Hz), 6.57 (d, 1H, J = 8.1 Hz), 6.50 (d, 1H, J = 5.8 Hz), 4.72-4.37 (m, 3H), 4.20 (t, 2H, J = 6.3 Hz), 3.69-3.45 (m, 7H), 3.41 (s, 3H), 3.00 (s, 3H), 2.96-2.85 (m, 1H), 2.09-2.03 (m, 1H), 1.57-1.47 (m, 1H), 1.43 (d, 3H, J = 6.0 Hz), 1.30 (t, 6H, J = 6.2 Hz) | X; Peak 1 | N-{2-[(3R,4R)-3-fluoro-4-methoxy-piperidin-1-yl]pyrimidin-4-yl}-8-[(2R,3S)-3-(methanesulfonyl-methyl)-2-methylazetidin-1-yl]-5-(propan-2-yl)isoquinolin-3-amine or N-{2-[(3S,4S)-3-fluoro-4-methoxy-piperidin-1-yl]pyrimidin-4-yl}-8-[(2R,3S)-3-(methanesulfonyl-methyl)-2-methylazetidin-1-yl]-5-(propan-2-yl)isoquinolin-3-amine |

TABLE 1-continued

| # | Structure | LC/MS | NMR | Separation Conditions | Chemical Name |
|---|-----------|-------|-----|----------------------|---------------|
| 279 | 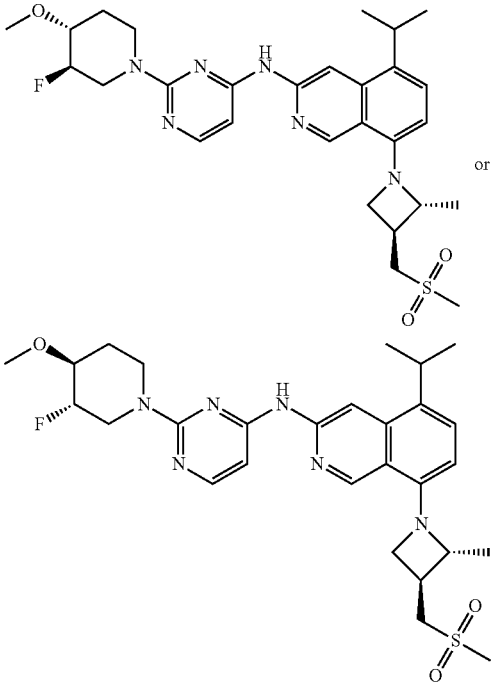 | 557 | 1H-NMR (300 MHz, 6d-DMSO) δ ppm 9.98 (s, 1H), 9.06 (s, 1H), 8.63 (s, 1H), 8.02 (d, 1H, J = 5.7 Hz), 7.43 (d, 1H, J = 8.0 Hz), 6.57 (d, 1H, J = 8.1 Hz), 6.50 (d, 1H, J = 5.6 Hz), 4.72-4.38 (m, 3H), 4.29-4.15 (m, 2H), 3.70-3.43 (m, 7H), 3.41 (s, 3H), 3.00 (s, 3H), 2.89 (q, 1H, J = 7.0 Hz), 2.08-2.02 (m, 1H), 1.52-1.46 (m, 1H), 1.43 (d, 3H, J = 6.0 Hz), 1.30 (dd, 6H, J = 6.8, 3.0 Hz) | X; Peak 2 | N-{2-[(3S,4S)-3-fluoro-4-methoxy-piperidin-1-yl]pyrimidin-4-yl}-8-[(2R,3S)-3-(methanesulfonyl-methyl)-2-methylazetidin-1-yl]-5-(propan-2-yl)isoquinolin-3-amine or N-{2-[(3R,4R)-3-fluoro-4-methoxy-piperidin-1-yl]pyrimidin-4-yl}-8-[(2R,3S)-3-(methanesulfonyl-methyl)-2-methylazetidin-1-yl]-5-(propan-2-yl)isoquinolin-3-amine |
| 280 | 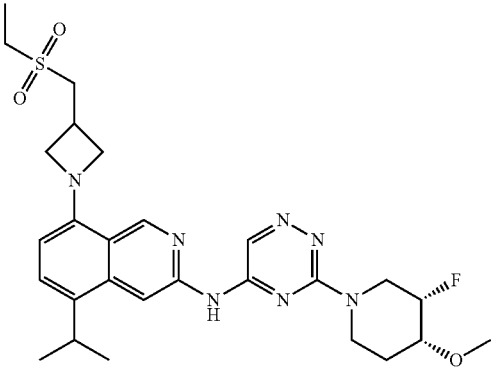 [SMILES: CCS(=O)(=O)CC1CN(c2ccc(C(C)C)c3cc(Nc4cnnc(N5CC[C@@H](OC)[C@@H](F)C5)n4)ncc23)C1] | 558 | 1H-NMR (300 MHz, 6d-DMSO) δ ppm 10.54 (s, 1H), 9.11 (s, 1H), 8.69 (s, 1H), 8.50 (s, 1H), 7.46 (d, 1H, J = 8.0 Hz), 6.47 (d, 1H, J = 8.1 Hz), 4.99 (d, 1H, J = 49.0 Hz), 4.75 (s, 1H), 4.58-4.46 (m, 1H), 4.41 (t, 2H, J = 7.7 Hz), 3.98 (t, 2H, J = 6.9 Hz), 3.71-3.43 (m, 5H), 3.37 (s, 3H), 3.33-3.24 (m, 2H), 3.12 (q, 2H, J = 7.4 Hz), 1.92-1.62 (m, 2H), 1.30 (dd, 6H, J = 6.7, 3.7 Hz), 1.24 (t, 3H, J = 7.4 Hz) | | 8-{3-[(ethanesulfonyl)methyl]azetidin-1-yl}-N-{3-[(3S,4R)-3-fluoro-4-methoxy-piperidin-1-yl]-1,2,4-triazin-5-yl}-5-(propan-2-yl)isoquinolin-3-amine |
| 281 | 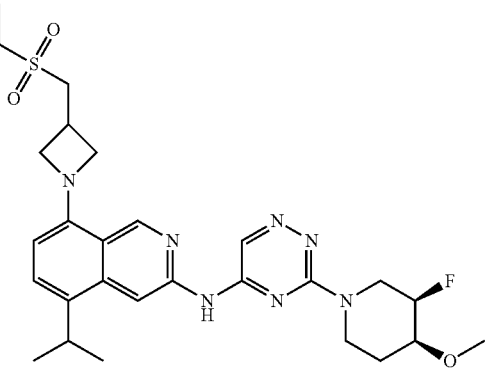 | 558 | 1H-NMR (300 MHz, 6d-DMSO) δ ppm 10.53 (s, 1H), 9.10 (s, 1H), 8.69 (s, 1H), 8.49 (s, 1H), 7.46 (d, 1H, J = 8.0 Hz), 6.47 (d, 1H, J = 8.1 Hz), 4.99 (d, 1H, J = 50.3 Hz), 4.79-4.73 (m, 1H), 4.56-4.46 (m, 1H), 4.40 (t, 2H, J = 7.6 Hz), 3.98 (t, 2H, J = 6.9 Hz), 3.70-3.43 (m, 8H), 3.37-3.20 (m, 2H), 3.12 (q, 2H, J = 7.4 Hz), 1.88-1.66 (m, 2H), 1.35-1.18 (m, 9H) | | 8-{3-[(ethanesulfonyl)methyl]azetidin-1-yl}-N-{3-[(3R,4S)-3-fluoro-4-methoxy-piperidin-1-yl]-1,2,4-triazin-5-yl}-5-(propan-2-yl)isoquinolin-3-amine |

TABLE 1-continued

| # | Structure | LC/MS | NMR | Separation Conditions | Chemical Name |
|---|---|---|---|---|---|
| 282 | 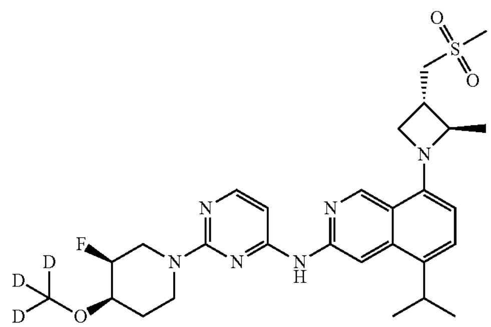 [SMILES: [2H]C([2H])([2H])O[C@@H]1CCN(c2nccc(Nc3cc4c(C(C)C)ccc(N5C[C@H](CS(C)(=O)=O)[C@H]5C)c4cn3)n2)C[C@@H]1F] | 560 | 1H-NMR (300 MHz, 6d-DMSO) δ ppm 9.94 (s, 1H), 9.06 (s, 1H), 8.65 (s, 1H), 8.00 (d, 1H, J = 5.6 Hz), 7.43 (d, 1H, J = 8.0 Hz), 6.57 (d, 1H, J = 8.1 Hz), 6.47 (d, 1H, J = 5.7 Hz), 4.95 (d, 1H, J = 49.9 Hz), 4.77-4.61 (m, 2H), 4.49 (d, 1H, J = 13.6 Hz), 4.20 (t, 1H, J = 6.3 Hz), 3.74-3.38 (m, 6H), 3.32-3.21 (m, 1H), 3.00 (s, 3H), 2.89 (q, 1H, J = 7.2 Hz), 1.84-1.70 (m, 2H), 1.43 (d, 3H, J = 6.0 Hz), 1.31 (dd, 6H, J = 6.9, 1.7 Hz) | Z; Peak 1 | N-{2-[(3S,4R)-3-fluoro-4-($^2$H3)methoxypiperidin-1-yl]pyrimidin-4-yl}-8-[(2R,3S)-3-(methanesulfonylmethyl)-2-methylazetidin-1-yl]-5-(propan-2-yl)isoquinolin-3-amine |
| 283 | 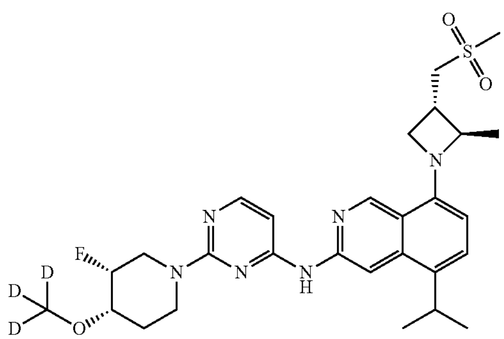 [SMILES: [2H]C([2H])([2H])O[C@H]1CCN(c2nccc(Nc3cc4c(C(C)C)ccc(N5C[C@H](CS(C)(=O)=O)[C@H]5C)c4cn3)n2)C[C@H]1F] | 560 | 1H-NMR (300 MHz, 6d-DMSO) δ ppm 9.94 (s, 1H), 9.06 (s, 1H), 8.65 (s, 1H), 8.00 (d, 1H, J = 5.7 Hz), 7.43 (d, 1H, J = 8.0 Hz), 6.57 (d, 1H, J = 8.1 Hz), 6.47 (d, 1H, J = 5.7 Hz), 4.95 (d, 1H, J = 49.4 Hz), 4.78-4.61 (m, 2H), 4.49 (d, 1H, J = 13.3 Hz), 4.20 (t, 1H, J = 6.3 Hz), 3.70-3.38 (m, 6H), 3.33-3.21 (m, 1H), 3.00 (s, 3H), 2.89 (q, 1H, J = 7.3 Hz), 1.85-1.63 (m, 2H), 1.43 (d, 3H, J = 6.0 Hz), 1.31 (dd, 6H, J = 6.8, 4.8 Hz) | Z; Peak 2 | N-{2-[(3R,4S)-3-fluoro-4-($^2$H3)methoxypiperidin-1-yl]pyrimidin-4-yl}-8-[(2R,3S)-3-(methanesulfonylmethyl)-2-methylazetidin-1-yl]-5-(propan-2-yl)isoquinolin-3-amine |
| 284 | 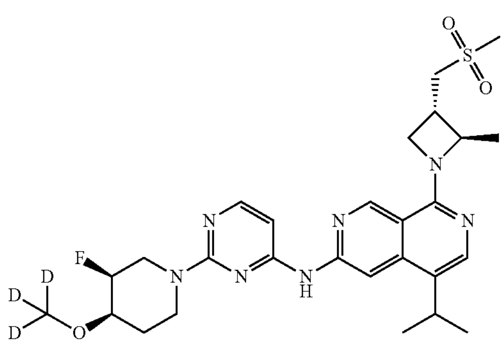 | 561 | 1H-NMR (300 MHz, 6d-DMSO) δ ppm 10.14 (s, 1H), 9.05 (s, 1H), 8.52 (s, 1H), 8.05 (d, 1H, J = 5.6 Hz), 8.01 (s, 1H), 6.52 (d, 1H, J = 5.7 Hz), 5.08-4.81 (m, 2H), 4.75-4.69 (m, 1H), 4.61-4.40 (m, 2H), 3.99 (t, 1H, J = 7.3 Hz), 3.69-3.42 (m, 5H), 2.99 (s, 3H), 2.96-2.83 (m, 1H), 1.84-1.72 (m, 2H), 1.50 (d, 3H, J = 6.1 Hz), 1.33 (t, 6H, J = 6.7 Hz) | Z; Peak 1 | N-{2-[(3S,4R)-3-fluoro-4-($^2$H3)methoxypiperidin-1-yl]pyrimidin-4-yl}-8-[(2R,3S)-3-(methanesulfonylmethyl)-2-methylazetidin-1-yl]-5-(propan-2-yl)-2,7-naphthyridin-3-amine |
| 285 | 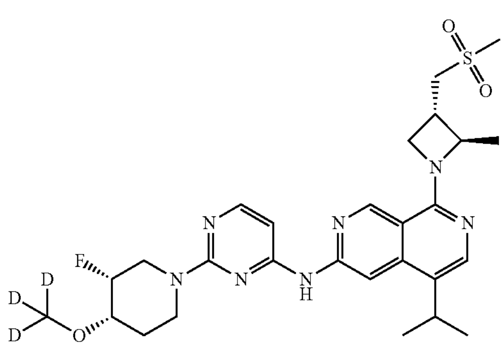 [SMILES: [2H]C([2H])([2H])O[C@H]1CCN(c2nccc(Nc3cc4c(C(C)C)cnc(N5C[C@H](CS(C)(=O)=O)[C@H]5C)c4cn3)n2)C[C@H]1F] | 561 | 1H-NMR (300 MHz, 6d-DMSO) δ ppm 10.14 (s, 1H), 9.05 (s, 1H), 8.52 (s, 1H), 8.05 (d, 1H, J = 5.6 Hz), 8.01 (s, 1H), 6.52 (d, 1H, J = 5.7 Hz), 5.09-4.81 (m, 2H), 4.76-4.36 (m, 3H), 3.98 (t, 1H, J = 7.3 Hz), 3.67-3.36 (m, 5H), 2.99 (s, 3H), 2.89 (d, 1H, J = 7.1 Hz), 1.85-1.79 (m, 2H), 1.50 (d, 3H, J = 6.1 Hz), 1.33 (d, 6H, J = 6.8 Hz) | Z; Peak 2 | N-{2-[(3R,4S)-3-fluoro-4-($^2$H3)methoxypiperidin-1-yl]pyrimidin-4-yl}-8-[(2R,3S)-3-(methanesulfonylmethyl)-2-methylazetidin-1-yl]-5-(propan-2-yl)-2,7-naphthyridin-3-amine |

TABLE 1-continued

| # | Structure | LC/MS | NMR | Separation Conditions | Chemical Name |
|---|---|---|---|---|---|
| 286 | 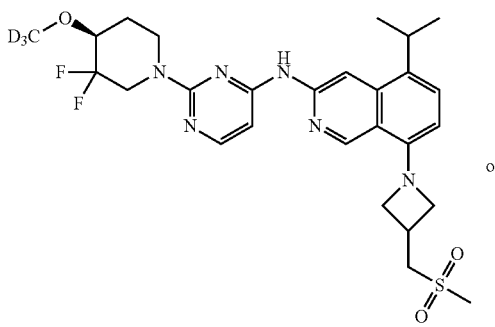 or 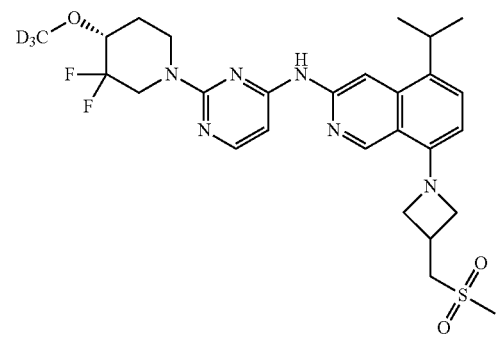 [SMILES: [2H]C([2H])([2H])O[C@@H]1CCN(c2nccc(Nc3cc4c(C(C)C)ccc(N5CC(CS(C)(=O)=O)C5)c4cn3)n2)CC1(F)F] | 564 | 1H-NMR (300 MHz, 6d-DMSO) δ ppm 9.99 (s, 1H), 9.06 (s, 1H), 8.57 (s, 1H), 8.03 (d, 1H, J = 5.6 Hz), 7.43 (d, 1H, J = 8.2 Hz), 6.55 (d, 1H, J = 5.9 Hz), 6.43 (d, 1H, J = 8.0 Hz), 4.45-4.28 (m, 3H), 4.16-3.90 (m, 4H), 3.88-3.69 (m, 2H), 3.64-3.42 (m, 4H), 3.02 (s, 3H), 2.00-1.63 (m, 2H), 1.30 (d, 6H, J = 6.7 Hz) | Z; Peak 1 | N-{2-[(4S)-3,3-difluoro-4-(²H3)methoxy-piperidin-1-yl]pyrimidin-4-yl}-8-[3-(methanesulfonylmethyl)azetidin-1-yl]-5-(propan-2-yl)isoquinolin-3-amine or N-{2-[(4R)-3,3-difluoro-4-(²H3)methoxy-piperidin-1-yl]pyrimidin-4-yl}-8-[3-(methanesulfonylmethyl)azetidin-1-yl]-5-(propan-2-yl)isoquinolin-3-amine |
| 287 | 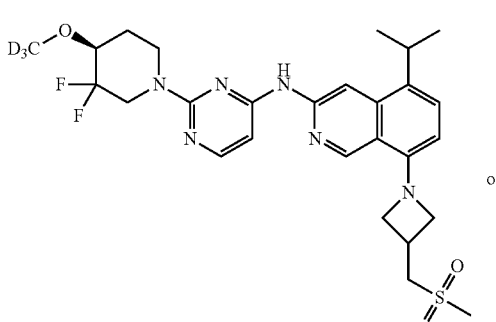 or 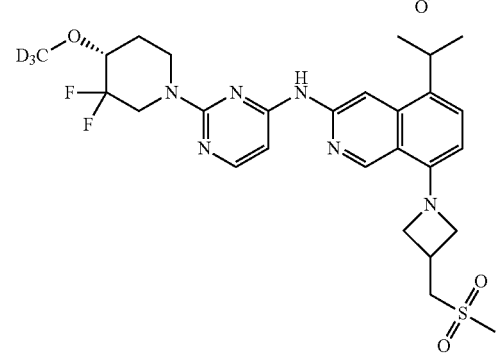 | 564 | 1H-NMR (300 MHz, 6d-DMSO) δ ppm 9.99 (s, 1H), 9.06 (s, 1H), 8.57 (s, 1H), 8.03 (d, 1H, J = 5.7 Hz), 7.43 (d, 1H, J = 8.0 Hz), 6.55 (d, 1H, J = 5.8 Hz), 6.43 (d, 1H, J = 8.1 Hz), 4.51-4.19 (m, 3H), 4.17-3.89 (m, 4H), 3.79 (d, 2H, J = 16.4 Hz), 3.64-3.31 (m, 4H), 2.11-1.58 (m, 2H), 1.30 (d, 6H, J = 6.7 Hz) | Z; Peak 2 | N-{2-[(4R)-3,3-difluoro-4-(²H3)methoxy-piperidin-1-yl]pyrimidin-4-yl}-8-[3-(methanesulfonylmethyl)azetidin-1-yl]-5-(propan-2-yl)isoquinolin-3-amine or N-{2-[(4S)-3,3-difluoro-4-(²H3)methoxy-piperidin-1-yl]pyrimidin-4-yl}-8-[3-(methanesulfonylmethyl)azetidin-1-yl]-5-(propan-2-yl)isoquinolin-3-amine |

TABLE 1-continued

| # | Structure | LC/MS | NMR | Separation Conditions | Chemical Name |
|---|---|---|---|---|---|
| 288 | 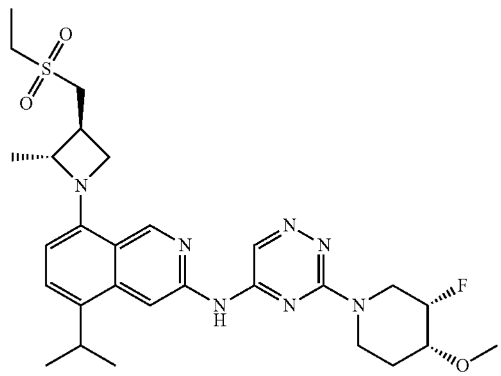 [SMILES: CCS(=O)(=O)C[C@H]1CN(c2ccc(C(C)C)c3cc(Nc4cnnc(N5CC[C@@H](OC)[C@@H](F)C5)n4)ncc23)[C@@H]1C] | 572 | 1H-NMR (300 MHz, 6d-DMSO) δ ppm 10.57 (s, 1H), 9.11 (s, 1H), 8.70 (s, 1H), 8.48 (s, 1H), 7.47 (d, 1H, J = 8.0 Hz), 6.62 (d, 1H, J = 8.1 Hz), 4.99 (d, 1H, J = 49.6 Hz), 4.79-4.62 (m, 2H), 4.51 (d, 1H, J = 13.4 Hz), 4.21 (t, 1H, J = 6.3 Hz), 3.70-3.43 (m, 9H), 3.37-3.22 (m, 1H), 3.09 (q, 2H, J = 7.4 Hz), 2.89 (q, 1H, J = 7.2 Hz), 1.88-1.65 (m, 2H), 1.42 (d, 3H, J = 6.0 Hz), 1.35-1.17 (m, 9H) | | 8-[(2R,3S)-3-[(ethanesulfonyl)methyl]-2-methylazetidin-1-yl]-N-{3-[(3S,4R)-3-fluoro-4-methoxy-piperidin-1-yl]-1,2,4-triazin-5-yl}-5-(propan-2-yl)isoquinolin-3-amine |
| 289 | 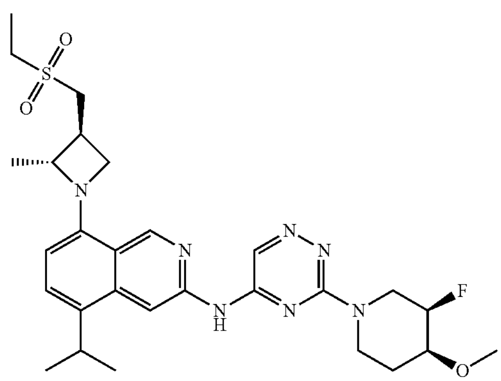 [SMILES: CCS(=O)(=O)C[C@H]1CN(c2ccc(C(C)C)c3cc(Nc4cnnc(N5CC[C@H](OC)[C@H](F)C5)n4)ncc23)[C@@H]1C] | 572 | 1H-NMR (300 MHz, 6d-DMSO) δ ppm 10.57 (s, 1H), 9.11 (s, 1H), 8.70 (s, 1H), 8.49 (s, 1H), 7.48 (d, 1H, J = 8.0 Hz), 6.63 (d, 1H, J = 8.1 Hz), 5.00 (d, 1H, J = 49.3 Hz), 4.79-4.63 (m, 2H), 4.52 (d, 1H, J = 13.7 Hz), 4.21 (t, 1H, J = 6.2 Hz), 3.71-3.46 (m, 7H), 3.40-3.30 (m, 3H), 3.09 (q, 2H, J = 7.5 Hz), 2.89 (q, 1H, J = 7.2 Hz), 1.89-1.64 (m, 2H), 1.43 (d, 3H, J = 6.0 Hz), 1.36-1.17 (m, 9H) | | 8-[(2R,3S)-3-[(ethanesulfonyl)methyl]-2-methylazetidin-1-yl]-N-{3-[(3R,4S)-3-fluoro-4-methoxy-piperidin-1-yl]-1,2,4-triazin-5-yl}-5-(propan-2-yl)isoquinolin-3-amine |
| 290 | 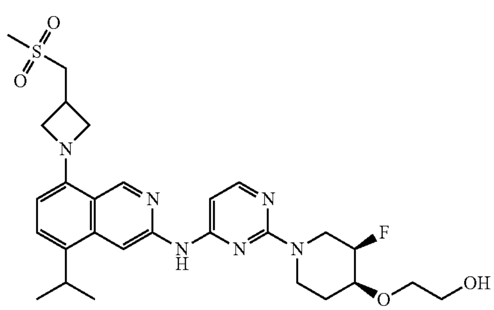 [SMILES: CC(C)c1ccc(N2CC(CS(C)(=O)=O)C2)c2cnc(Nc3ccnc(N4CC[C@H](OCCO)[C@H](F)C4)n3)cc12] | 573 | 1H-NMR (300 MHz, 6d-DMSO) δ ppm 9.91 (s, 1H), 9.05 (s, 1H), 8.00 (d, 1H, J = 5.7 Hz), 7.43 (d, 1H, J = 8.0 Hz), 6.48 (d, 1H, J = 5.7 Hz), 6.42 (d, 1H, J = 8.0 Hz), 5.08-4.62 (m, 3H), 4.54 (d, 1H, J = 13.1 Hz), 4.39 (t, 2H, J = 7.7 Hz), 3.97 (t, 2H, J = 6.9 Hz), 3.74 (d, 1H, J = 24.5 Hz), 3.65-3.45 (m, 8H), 3.22-3.17 (m, 2H), 3.02 (s, 3H), 1.91-1.68 (m, 2H), 1.31 (dd, 6H, J = 6.8, 3.2 Hz) | | 2-{[(3R,4S)-3-fluoro-1-[4-({8-[3-(methanesulfonyl-methyl)azetidin-1-yl]-5-(propan-2-yl)isoquinolin-3-yl}amino)pyrimidin-2-yl]piperidin-4-yl]oxy}ethan-1-ol |
| 291 | 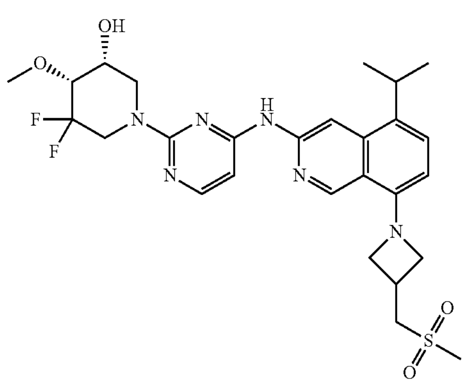 | 577 | 1H-NMR (400 MHz, 6d-DMSO) δ ppm 9.96 (s, 1H), 9.05 (s, 1H), 8.52 (s, 1H), 8.02 (d, 1H, J = 5.6 Hz), 7.41 (d, 1H, J = 8.1 Hz), 6.57 (d, 1H, J = 5.7 Hz), 6.42 (d, 1H, J = 8.1 Hz), 5.31 (d, 1H, J = 5.9 Hz), 4.82-4.77 (m, 1H), 4.56-4.48 (m, 1H), 4.38 (td, 2H, J = 7.5, 2.6 Hz), 3.96 (td, 2H, J = 7.1, 2.8 Hz), 3.71 (dd, 2H, J = 13.1, 8.4 Hz), 3.64-3.55 (m, 5H), 3.55-3.48 (m, 2H), 3.33-3.29 (m, 1H), 3.20-3.13 (m, 1H), 3.01 (s, 3H), 1.28 (dd, 6H, J = 9.8, 6.7 Hz) | BB, Peak 1 | (3R,4R)-5,5-difluoro-1-[4-({8-[3-(methanesulfonyl-methyl)azetidin-1-yl]-5-(propan-2-yl)isoquinolin-3-yl}amino)pyrimidin-2-yl]-4-methoxy-piperidin-3-ol or (3S,4S)-5,5-difluoro-1-[4-({8-[3-(methanesulfonyl-methyl)azetidin-1-yl]-5-(propan- |

TABLE 1-continued

| # | Structure | LC/MS | NMR | Separation Conditions | Chemical Name |
|---|---|---|---|---|---|
| | | | | | 2-yl)isoquinolin-3-yl}amino)pyrimidin-2-yl]-4-methoxy-piperidin-3-ol |
| 292 | 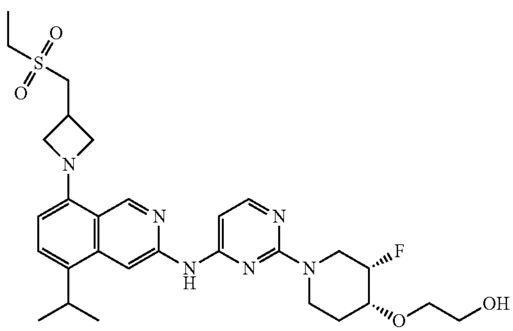 [SMILES: CCS(=O)(=O)CC1CN(c2ccc(C(C)C)c3cc(Nc4ccnc(N5CC[C@@H](OCCO)[C@@H](F)C5)n4)ncc23)C1] | 587 | 1H-NMR (300 MHz, 6d-DMSO) δ ppm 9.89 (s, 1H), 9.03 (s, 1H), 8.61 (s, 1H), 7.98 (d, 1H, J = 5.6 Hz), 7.40 (d, 1H, J = 8.0 Hz), 6.46 (d, 1H, J = 5.7 Hz), 6.39 (d, 1H, J = 8.1 Hz), 5.05-4.70 (m, 2H), 4.63 (t, 1H, J = 5.2 Hz), 4.52 (d, 1H, J = 13.5 Hz), 4.37 (t, 2H, J = 7.6 Hz), 3.94 (t, 2H, J = 6.9 Hz), 3.83-3.66 (m, 1H), 3.62-3.37 (m, 9H), 3.25 (d, 1H, J = 7.9 Hz), 3.10 (q, 2H, J = 7.4 Hz), 1.86-1.63 (m, 2H), 1.37-1.12 (m, 9H) | | 2-{[(3S,4R)-1-{4-[(8-{3-[(ethanesulfonyl)methyl]azetidin-1-yl}-5-(propan-2-yl)isoquinolin-3-yl)amino]pyrimidin-2-yl}-3-fluoro-piperidin-4-yl]oxy}ethan-1-ol |
| 293 | 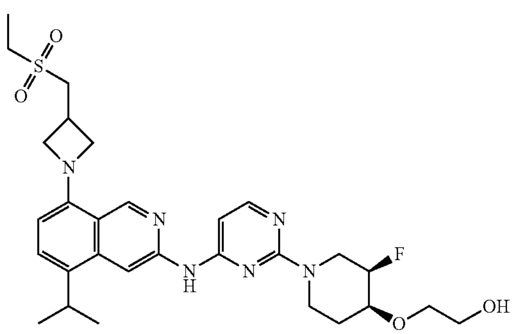 [SMILES: CCS(=O)(=O)CC1CN(c2ccc(C(C)C)c3cc(Nc4ccnc(N5CC[C@H](OCCO)[C@H](F)C5)n4)ncc23)C1] | 587 | 1H-NMR (300 MHz, 6d-DMSO) δ ppm 9.89 (s, 1H), 9.03 (s, 1H), 8.61 (s, 1H), 7.98 (d, 1H, J = 5.6 Hz), 7.40 (d, 1H, J = 8.1 Hz), 6.45 (d, 1H, J = 5.7 Hz), 6.39 (d, 1H, J = 8.1 Hz), 5.08-4.69 (m, 2H), 4.64 (d, 1H, J = 5.3 Hz), 4.52 (d, 1H, J = 13.4 Hz), 4.37 (t, 2H, J = 7.6 Hz), 3.94 (t, 2H, J = 6.9 Hz), 3.79-3.63 (m, 1H), 3.63-3.37 (m, 8H), 3.29-3.17 (m, 1H), 3.10 (q, 2H, J = 7.4 Hz), 1.92-1.60 (m, 2H), 1.35-1.08 (m, 9H) | | 2-{[(3R,4S)-1-{4-[(8-{3-[(ethanesulfonyl)methyl]azetidin-1-yl}-5-(propan-2-yl)isoquinolin-3-yl)amino]pyrimidin-2-yl}-3-fluoro-piperidin-4-yl]oxy}ethan-1-ol |
| 294 | 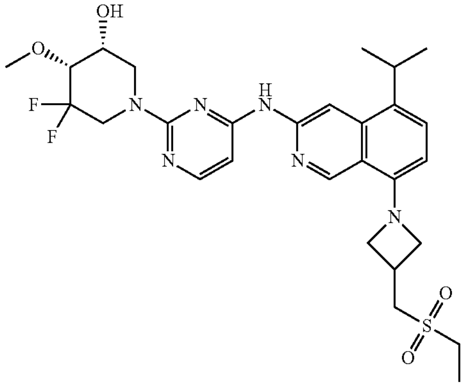 [SMILES: CCS(=O)(=O)CC1CN(c2ccc(C(C)C)c3cc(Nc4ccnc(N5C[C@H](O)[C@H](OC)C(F)(F)C5)n4)ncc23)C1] | 591 | 1H-NMR (400 MHz, 6d-DMSO) δ ppm 9.97 (s, 1H), 9.05 (s, 1H), 8.52 (s, 1H), 8.02 (d, 1H, J = 5.7 Hz), 7.41 (d, 1H, J = 8.0 Hz), 6.57 (d, 1H, J = 5.5 Hz), 6.41 (d, 1H, J = 8.1 Hz), 5.31 (d, 1H, J = 5.8 Hz), 4.80 (s, 1H), 4.56-4.48 (m, 1H), 4.43-4.34 (m, 2H), 3.96 (td, 2H, J = 7.0, 2.7 Hz), 3.82-3.66 (m, 2H), 3.64-3.51 (m, 6H), 3.54-3.48 (m, 1H), 3.30-3.23 (m, 1H), 3.22-3.04 (m, 3H), 1.33-1.20 (m, 9H) | BB, Peak 1 | (3R,4R)-1-{4-[(8-{3-[(ethanesulfonyl)methyl]azetidin-1-yl}-5-(propan-2-yl)isoquinolin-3-yl)amino]pyrimidin-2-yl}-5,5-difluoro-4-methoxy-piperidin-3-ol or (3S,4S)-1-{4-[(8-{3-[(ethanesulfonyl)methyl]azetidin-1-yl}-5-(propan-2-yl)isoquinolin-3-yl)amino] |

TABLE 1-continued

| # | Structure | LC/MS | NMR | Separation Conditions | Chemical Name |
|---|---|---|---|---|---|
| | | | | | pyrimidin-2-yl}-5,5-difluoro-4-methoxy-piperidin-3-ol |
| 295 | 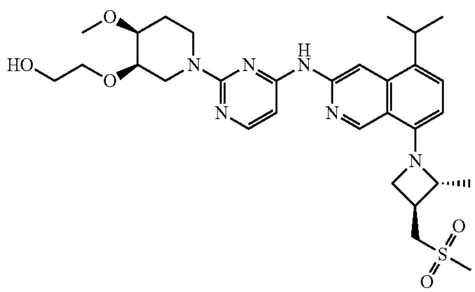 [SMILES: CO[C@@H]1CCN(c2nccc(Nc3cc4c(C(C)C)ccc(N5C[C@H](CS(C)(=O)=O)[C@H]5C)c4cn3)n2)C[C@@H]1OCCO] | 599 | 1H-NMR (300 MHz, 6d-DMSO) δ ppm 9.93 (s, 1H), 9.06 (s, 1H), 8.64 (s, 1H), 7.99 (d, 1H, J = 5.7 Hz), 7.43 (d, 1H, J = 8.0 Hz), 6.57 (d, 1H, J = 8.1 Hz), 6.46 (d, 1H, J = 5.8 Hz), 4.67 (t, 1H, J = 7.6 Hz), 4.55-4.49 (m, 1H), 4.19 (t, 1H, J = 6.3 Hz), 4.12-4.06 (m, 2H), 4.03-3.97 (m, 1H), 3.83-3.39 (m, 12H), 3.36 (s, 3H), 3.00 (s, 3H), 2.89 (q, 1H, J = 7.0 Hz), 1.89-1.58 (m, 2H), 1.43 (d, 3H, J = 6.0 Hz), 1.31 (d, 6H, J = 6.7 Hz) | Y; Peak 1 | 2-{[(3R,4S)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methoxy-piperidin-3-yl]oxy}ethan-1-ol or 2-{[(3S,4R)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methoxy-piperidin-3-yl]oxy}ethan-1-ol |
| 296 | 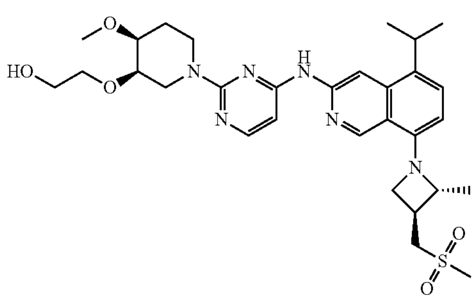 [SMILES: CO[C@@H]1CCN(c2nccc(Nc3cc4c(C(C)C)ccc(N5C[C@H](CS(C)(=O)=O)[C@H]5C)c4cn3)n2)C[C@@H]1OCCO] | 599 | 1H-NMR (300 MHz, 6d-DMSO) δ ppm 9.90 (s, 1H), 9.05 (s, 1H), 8.65 (s, 1H), 7.99 (d, 1H, J = 5.6 Hz), 7.43 (d, 1H, J = 8.0 Hz), 6.56 (d, 1H, J = 8.1 Hz), 6.45 (d, 1H, J = 5.6 Hz), 4.66 (t, 1H, J = 7.5 Hz), 4.54-4.48 (m, 1H), 4.19 (t, 1H, J = 6.3 Hz), 4.08-4.02 (m, 2H), 3.73-3.38 (m, 12H), 3.36 (s, 3H), 3.00 (s, 3H), 2.89 (q, 1H, J = 7.1 Hz), 1.88-1.58 (m, 2H), 1.43 | Y; Peak 2 | 2-{[(3S,4R)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methoxy-piperidin-3-yl]oxy}ethan-1-ol |

TABLE 1-continued

| # | Structure | LC/MS | NMR | Separation Conditions | Chemical Name |
|---|---|---|---|---|---|
|  |  |  | (d, 3H, J = 6.0 Hz), 1.31 (d, 6H, J = 6.6 Hz) |  | or 2-{[(3R,4S)-1-[4-({8-[(2R,3S)-3-(methanesulfonyl-methyl)-2-methylazetidin-1-yl]-5-(propan-2-yl)isoquinolin-3-yl}amino)pyrimidin-2-yl]-4-methoxy-piperidin-3-yl]oxy}ethan-1-ol |
| 297 | 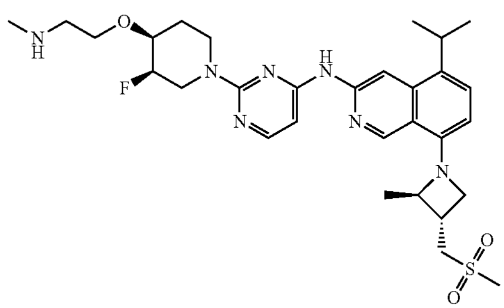 | 600 | 1H-NMR (300 MHz, 6d-DMSO) δ ppm 9.94 (s, 1H), 9.06 (s, 1H), 8.65 (s, 1H), 8.00 (d, 1H, J = 5.7 Hz), 7.43 (d, 1H, J = 8.0 Hz), 6.57 (d, 1H, J = 8.1 Hz), 6.47 (d, 1H, J = 5.7 Hz), 4.93 (d, 1H, J = 49.9 Hz), 4.77-4.61 (m, 2H), 4.49 (d, 1H, J = 13.3 Hz), 4.20 (t, 1H, J = 6.3 Hz), 3.82-3.43 (m, 8H), 3.00 (s, 3H), 2.89 (d, 1H, J = 7.5 Hz), 2.70 (t, 2H, J = 5.7 Hz), 2.34 (s, 3H), 1.84-1.78 (m, 2H), 1.43 (d, 3H, J = 6.0 Hz), 1.39-1.21 (m, 6H) |  | N-{2-[(3R,4S)-3-fluoro-4-[2-(methylamino)ethoxy]piperidin-1-yl]pyrimidin-4-yl}-8-[(2R,3S)-3-(methanesulfonyl-methyl)-2-methylazetidin-1-yl]-5-(propan-2-yl)isoquinolin-3-amine |
| 298 | 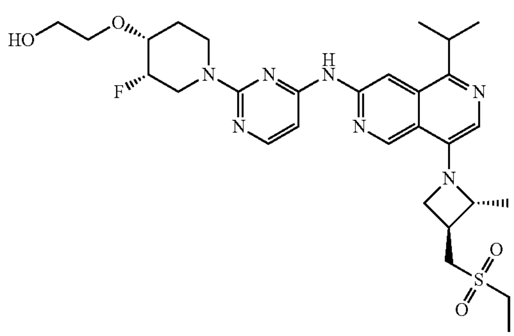 [SMILES: CCS(=O)(=O)C[C@H]1CN(c2cnc(C(C)C)c3cc(Nc4ccnc(N5CC[C@@H](OCCO)[C@@H](F)C5)n4)ncc23)[C@@H]1C] | 602 | 1H-NMR (300 MHz, 6d-DMSO) δ ppm 10.17 (s, 1H), 9.14 (s, 1H), 8.76 (s, 1H), 8.04 (d, 1H, J = 5.6 Hz), 7.73 (s, 1H), 6.46 (d, 1H, J = 5.7 Hz), 4.95 (d, 1H, J = 49.8 Hz), 4.81-4.62 (m, 3H), 4.55 (d, 1H, J = 13.4 Hz), 4.32 (t, 1H, J = 6.3 Hz), 3.83-3.67 (m, 3H), 3.64-3.49 (m, 7H), 3.30-3.24 (m, 1H), 3.10 (q, 2H, J = 7.4 Hz), 2.92 (q, 1H, J = 7.4 Hz), 1.86-1.76 (m, 2H), 1.49 (d, 3H, J = 6.0 Hz), 1.32 (dd, 6H, J = 8.3, 6.7 Hz), 1.24 (t, 3H, J = 7.4 Hz) |  | 2-{[(3S,4R)-1-[4-({8-[(2R,3S)-3-[(ethanesulfonyl)methyl]-2-methylazetidin-1-yl]-5-(propan-2-yl)-2,6-naph-thyridin-3-yl}amino)pyrimidin-2-yl]-3-fluoro-piperidin-4-yl]oxy}ethan-1-ol |
| 299 | 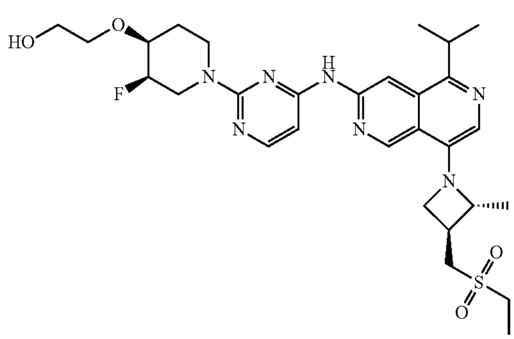 [SMILES: CCS(=O)(=O)C[C@H]1CN(c2cnc(C(C)C)c3cc(Nc4ccnc(N5CC[C@H](OCCO)[C@H](F)C5)n4)ncc23)[C@@H]1C] | 602 | 1H-NMR (300 MHz, 6d-DMSO) δ ppm 10.17 (s, 1H), 9.13 (s, 1H), 8.76 (s, 1H), 8.04 (d, 1H, J = 5.6 Hz), 7.73 (s, 1H), 6.46 (d, 1H, J = 5.7 Hz), 4.95 (d, 1H, J = 50.6 Hz), 4.81-4.62 (m, 3H), 4.55 (d, 1H, J = 13.5 Hz), 4.32 (t, 1H, J = 6.3 Hz), 3.83-3.67 (m, 3H), 3.64-3.51 (m, 7H), 3.31-3.21 (m, 1H), 3.09 (q, 2H, J = 7.3 Hz), 2.92 (q, 1H, J = 7.3 Hz), 1.86-1.80 (m, 2H), 1.49 (d, 3H, J = 6.0 Hz), 1.38-1.18 (m, 9H) |  | 2-{[(3R,4S)-1-[4-({8-[(2R,3S)-3-[(ethanesulfonyl)methyl]-2-methylazetidin-1-yl]-5-(propan-2-yl)-2,6-naph-thyridin-3-yl}amino)pyrimidin-2-yl]-3-fluoro-piperidin-4-yl]oxy}ethan-1-ol |

TABLE 1-continued

| # | Structure | LC/MS | NMR | Separation Conditions | Chemical Name |
|---|---|---|---|---|---|
| 300 | 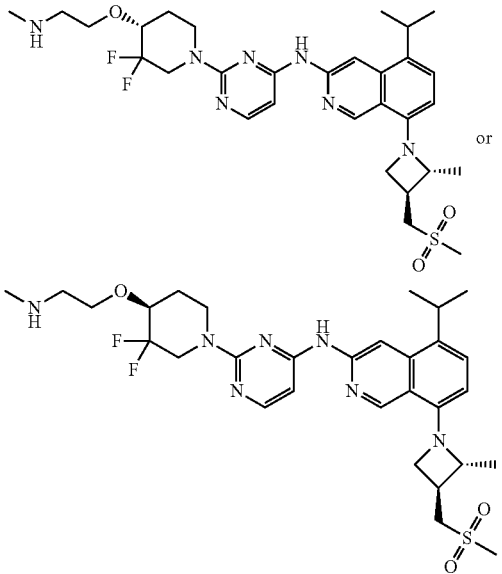 | 618 | 1H-NMR (300 MHz, 6d-DMSO) δ ppm 10.02 (s, 1H), 9.07 (s, 1H), 8.59 (s, 1H), 8.03 (d, 1H, J = 5.7 Hz), 7.43 (d, 1H, J = 8.0 Hz), 6.62-6.50 (m, 2H), 4.67 (t, 1H, J = 7.5 Hz), 4.42-3.83 (m, 5H), 3.83-3.36 (m, 8H), 3.00 (s, 3H), 2.89 (q, 1H, J = 7.1 Hz), 2.66 (td, 2H, J = 5.6, 1.5 Hz), 2.31 (s, 3H), 1.99-1.68 (m, 2H), 1.43 (d, 3H, J = 6.0 Hz), 1.30 (dd, 6H, J = 6.7, 3.6 Hz) | G; Peak 1 | N-{2-[(4R)-3,3-difluoro-4-[2-(methylamino)ethoxy]piperidin-1-yl]pyrimidin-4-yl}-8-[(2R,3S)-3-(methanesulfonylmethyl)-2-methylazetidin-1-yl]-5-(propan-2-yl)isoquinolin-3-amine or N-{2-[(4S)-3,3-difluoro-4-[2-(methylamino)ethoxy]piperidin-1-yl]pyrimidin-4-yl}-8-[(2R,3S)-3-(methanesulfonylmethyl)-2-methylazetidin-1-yl]-5-(propan-2-yl)isoquinolin-3-amine |
| 301 | 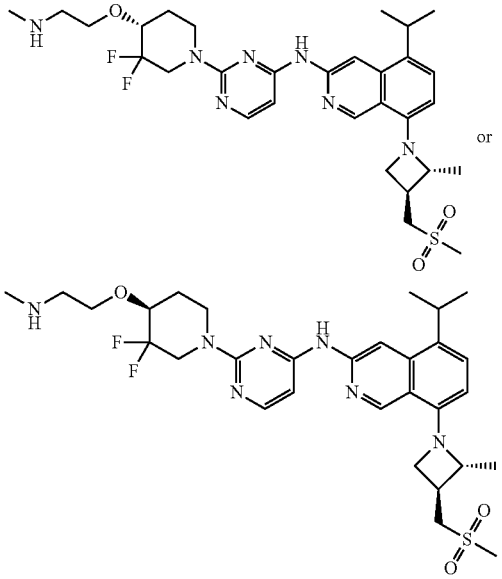 | 618 | 1H-NMR (300 MHz, 6d-DMSO) δ ppm 10.02 (s, 1H), 9.07 (s, 1H), 8.59 (s, 1H), 8.03 (d, 1H, J = 5.7 Hz), 7.44 (d, 1H, J = 8.0 Hz), 6.62-6.50 (m, 2H), 4.67 (t, 1H, J = 7.5 Hz), 4.40-4.29 (m, 1H), 4.20 (t, 1H, J = 6.2 Hz), 4.14-3.98 (m, 2H), 3.95-3.89 (m, 1H), 3.81-3.42 (m, 8H), 3.00 (s, 3H), 2.89 (q, 1H, J = 7.2 Hz), 2.72 (t, 2H, J = 5.7 Hz), 2.34 (s, 3H), 2.00-1.69 (m, 2H), 1.43 (d, 3H, J = 6.0 Hz), 1.30 (d, 6H, J = 6.7 Hz) | G; Peak 2 | N-{2-[(4S)-3,3-difluoro-4-[2-(methylamino)ethoxy]piperidin-1-yl]pyrimidin-4-yl}-8-[(2R,3S)-3-(methanesulfonylmethyl)-2-methylazetidin-1-yl]-5-(propan-2-yl)isoquinolin-3-amine or N-{2-[(4R)-3,3-difluoro-4-[2-(methylamino)ethoxy]piperidin-1-yl]pyrimidin-4-yl}-8-[(2R,3S)-3-(methanesulfonylmethyl)-2-methylazetidin-1-yl]-5-(propan-2-yl)isoquinolin-3-amine |
| 302 | 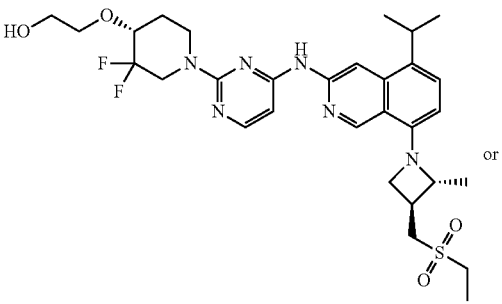 [SMILES: CCS(=O)(=O)C[C@H]1CN(c2ccc(C(C)C)c3cc(Nc4ccnc(N5CC[C@@H](OCCO)C(F)(F)C5)n4)ncc23)[C@@H]1C] | 619 | 1H-NMR (300 MHz, 6d-DMSO) δ ppm 10.02 (s, 1H), 9.07 (s, 1H), 8.59 (s, 1H), 8.03 (d, 1H, J = 5.6 Hz), 7.44 (d, 1H, J = 8.0 Hz), 6.62-6.50 (m, 2H), 4.68 (dt, 2H, J = 12.0, 6.4 Hz), 4.40 (d, 1H, J = 13.6 Hz), 4.25-3.85 (m, 4H), 3.77-3.39 (m, 9H), 3.08 (t, 2H, J = 7.4 Hz), 2.89 (q, 1H, J = 7.2 Hz), 2.01-1.66 (m, 2H), 1.43 (d, 3H, J = 5.9 Hz), 1.34-1.18 (m, | G; Peak 1 | 2-{[(4R)-1-[4-({8-[(2R,3S)-3-[(ethanesulfonyl)methyl]-2-methylazetidin-1-yl]-5-(propan-2-yl)isoquinolin-3-yl}amino)pyrimidin-2-yl]-3,3-difluoropiperidin-4-yl]oxy}ethan-1-ol or 2-{[(4S)-1-[4-({8- |

TABLE 1-continued

| # | Structure | LC/MS | NMR | Separation Conditions | Chemical Name |
|---|---|---|---|---|---|
| | | | 9H) | | [(2R,3S)-3-[(ethanesulfonyl)methyl]-2-methylazetidin-1-yl]-5-(propan-2-yl)isoquinolin-3-yl}amino)pyrimidin-2-yl]-3,3-difluoro-piperidin-4-yl]oxy}ethan-1-ol |
| 303 | 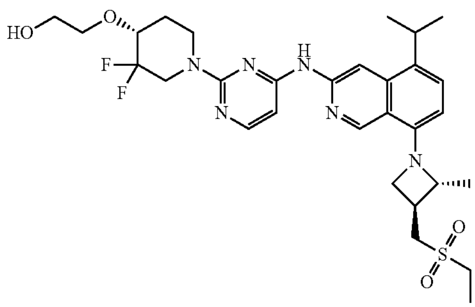 [SMILES: CCS(=O)(=O)C[C@H]1CN(c2ccc(C(C)C)c3cc(Nc4ccnc(N5CC[C@H](OCCO)C(F)(F)C5)n4)ncc23)[C@@H]1C] | 619 | 1H-NMR (300 MHz, 6d-DMSO) δ ppm 10.02 (s, 1H), 9.07 (s, 1H), 8.59 (s, 1H), 8.03 (d, 1H, J = 5.7 Hz), 7.43 (d, 1H, J = 8.0 Hz), 6.62-6.50 (m, 2H), 4.75-4.61 (m, 2H), 4.44-4.33 (m, 1H), 4.26-3.83 (m, 4H), 3.81-3.41 (m, 9H), 3.10 (q, 2H, J = 7.4 Hz), 2.93-2.84 (m, 1H), 2.01-1.67 (m, 2H), 1.43 (d, 3H, J = 5.9 Hz), 1.38-1.18 (m, 9H) | G; Peak 2 | 2-{[(4S)-1-[4-({8-[(2R,3S)-3-[(ethanesulfonyl)methyl]-2-methylazetidin-1-yl]-5-(propan-2-yl)isoquinolin-3-yl}amino)pyrimidin-2-yl]-3,3-difluoro-piperidin-4-yl]oxy}ethan-1-ol or 2-{[(4R)-1-[4-({8- |
| | | | | | [(2R,3S)-3-[(ethanesulfonyl)methyl]-2-methylazetidin-1-yl]-5-(propan-2-yl)isoquinolin-3-yl}amino)pyrimidin-2-yl]-3,3-difluoro-piperidin-4-yl]oxy}ethan-1-ol |
| 304 | 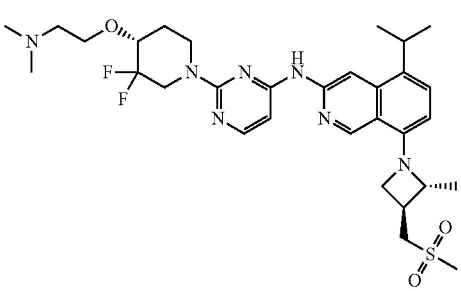 | 632 | 1H-NMR (300 MHz, 6d-DMSO) δ ppm 10.02 (s, 1H), 9.07 (s, 1H), 8.59 (s, 1H), 8.03 (d, 1H, J = 5.7 Hz), 7.43 (d, 1H, J = 8.0 Hz), 6.62-6.50 (m, 2H), 4.67 (t, 1H, J = 7.5 Hz), 4.43-3.86 (m, 6H), 3.81-3.44 (m, 6H), 3.00 (s, 3H), 2.89 (q, 1H, J = 7.2 Hz), 2.51-2.43 (m, 1H), 2.20 (s, 6H), 2.00-1.75 (m, 2H), 1.43 (d, 3H, | G; Peak 1 | N-{2-[(4R)-4-[2-(dimethylamino)ethoxy]-3,3-difluoro-piperidin-1-yl]pyrimidin-4-yl}-8-[(2R,3S)-3-(methanesulfonyl-methyl)-2-methylazetidin-1-yl]-5-(propan-2-yl)isoquinolin-3-amine or N- |

TABLE 1-continued

| # | Structure | LC/MS | NMR | Separation Conditions | Chemical Name |
|---|---|---|---|---|---|
| | | | J = 6.0 Hz), 1.30 (dd, 6H, J = 6.7, 3.4 Hz) | | {2-[(4S)-4-[2-(dimethylamino)ethoxy]-3,3-difluoro-piperidin-1-yl]pyrimidin-4-yl}-8-[(2R,3S)-3-(methanesulfonylmethyl)-2-methylazetidin-1-yl]-5-(propan-2-yl)isoquinolin-3-amine |
| 305 | 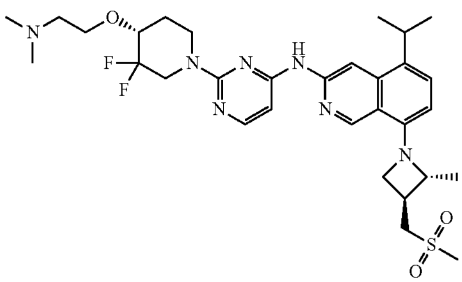 | 632 | 1H-NMR (300 MHz, 6d-DMSO) δ ppm 10.02 (s, 1H), 9.07 (s, 1H), 8.59 (s, 1H), 8.03 (d, 1H, J = 5.7 Hz), 7.43 (d, 1H, J = 8.0 Hz), 6.62-6.50 (m, 2H), 4.67 (t, 1H, J = 7.5 Hz), 4.46-4.27 (m, 1H), 4.20 (t, 1H, J = 6.3 Hz), 4.12-4.06 (m, 2H), 4.01-3.89 (m, 2H), 3.81-3.46 (m, 6H), 3.00 (s, 3H), 2.89 (q, 1H, J = 7.2 Hz), 2.57 | G; Peak 2 | N-{2-[(4S)-4-[2-(dimethylamino)ethoxy]-3,3-difluoro-piperidin-1-yl]pyrimidin-4-yl}-8-[(2R,3S)-3-(methanesulfonylmethyl)-2-methylazetidin-1-yl]-5-(propan-2-yl)isoquinolin-3-amine or N- |
| | | | (t, 2H, J = 5.8 Hz), 2.26 (s, 6H), 2.01-1.68 (m, 2H), 1.43 (d, 3H, J = 6.0 Hz), 1.30 (d, 6H, J = 6.7 Hz) | | {2-[(4R)-4-[2-(dimethylamino)ethoxy]-3,3-difluoro-piperidin-1-yl]pyrimidin-4-yl}-8-[(2R,3S)-3-(methanesulfonylmethyl)-2-methylazetidin-1-yl]-5-(propan-2-yl)isoquinolin-3-amine |
| 306 | 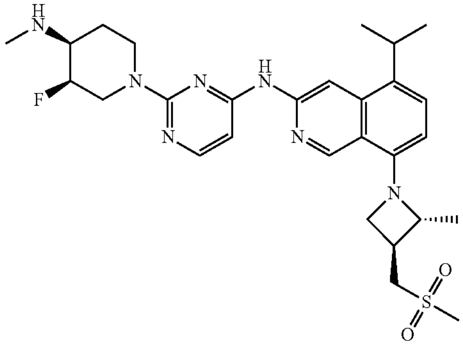 | 556 | 1H NMR (400 MHz, CDCl3) δ 9.08 (s, 1H), 8.61 (s, 1H), 8.07 (d, J = 5.6 Hz, 1H), 7.46-7.37 (m, 2H), 6.53 (d, J = 8.0 Hz, 1H), 6.16 (d, J = 5.6 Hz, 1H), 5.22-5.08 (m, 1H), 5.03-4.82 (m, 2H), 4.71-4.65 (m, 1H), 4.29-4.22 (m, 1H), 3.69-3.56 (m, 2H), 3.41-3.19 (m, 3H), 3.17-3.09 (m, 1H), 3.08-3.01 (m, 1H), 2.96 (s, 3H), 2.83-2.70 (m, 1H), 2.54 (s, 3H), 1.98-1.89 (m, | E; Peak 2 | N-{2-[(3R,4S)-3-fluoro-4-(methylamino)piperidin-1-yl]pyrimidin-4-yl}-8-[(2R,3S)-3-(methanesulfonylmethyl)-2-methylazetidin-1-yl]-5-(propan-2-yl)isoquinolin-3-amine or N-{2-[(3S,4R)-3-fluoro-4-(methylamino)piperidin-1-yl] |

| # | Structure | LC/MS | NMR | Separation Conditions | Chemical Name |
|---|---|---|---|---|---|
| | | | 1H), 1.83-1.74 (m, 1H), 1.52 (d, J = 6.0 Hz, 3H), 1.39-1.34 (m, 6H). | | pyrimidin-4-yl}-8-[(2R,3S)-3-(methanesulfonyl-methyl)-2-methylazetidin-1-yl]-5-(propan-2-yl)isoquinolin-3-amine |
| 307 | 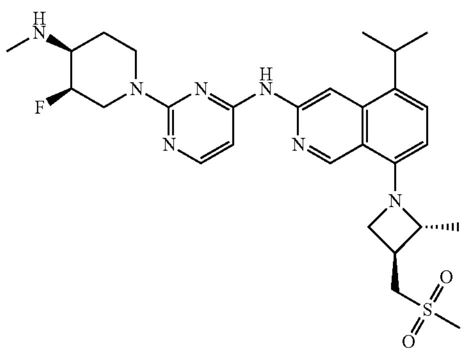 | 556 | 1H NMR (400 MHz, CDCl3) δ 9.08 (s, 1H), 8.61 (s, 1H), 8.07 (d, J = 5.6 Hz, 1H), 7.48 (s, 1H), 7.40 (d, J = 8.0 Hz, 1H), 6.53 (d, J = 8.0 Hz, 1H), 6.16 (d, J = 5.6 Hz, 1H), 5.22-5.12 (m, 1H), 5.03-4.81 (m, 2H), 4.70-4.64 (m, 1H), 4.29-4.22 (m, 1H), 3.68-3.57 (m, 2H), 3.43-3.27 (m, 3H), 3.16-3.09 (m, 1H), 3.07-3.01 (m, 1H), 2.96 (s, 3H), 2.83-2.71 (m, 1H), 2.55 (s, 3H), 1.98-1.90 (m, 1H), 1.83-1.75 (m, 1H), 1.51 (d, J = 6.0 Hz, 3H), 1.38-1.34 (m, 6H). | E; Peak 1 | N-{2-[(3S,4R)-3-fluoro-4-(methylamino)piperidin-1-yl]pyrimidin-4-yl}-8-[(2R,3S)-3-(methanesulfonyl-methyl)-2-methylazetidin-1-yl]-5-(propan-2-yl)isoquinolin-3-amine or N-{2-[(3R,4S)-3-fluoro-4-(methylamino)piperidin-1-yl]pyrimidin-4-yl}-8-[(2R,3S)-3-(methanesulfonyl-methyl)-2-methylazetidin-1-yl]-5-(propan-2-yl)isoquinolin-3-amine |
| 308 | 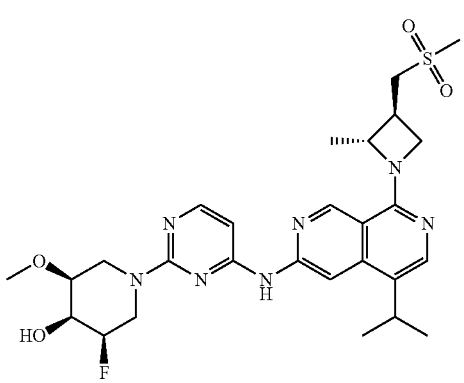 | 574 | 1H NMR (400 MHz, DMSO-d6) δ 10.07 (s, 1H), 8.96 (s, 1H), 8.40 (s, 1H), 7.99 (d, J = 5.6 Hz, 1H), 7.92 (s, 1H), 6.50 (d, J = 5.6 Hz, 1H), 5.09 (d, J = 4.4 Hz, 1H), 4.77 (t, J = 8.0 Hz, 1H), 4.54-4.38 (m, 5H), 4.35-4.26 (m, 2H), 4.26-4.16 (m, 1H), 3.89 (t, J = 7.2 Hz, 3H), 3.53-3.35 (m, 3H), 3.32-3.15 (m, 3H), 2.90 (s, 3H), 2.85-2.76 (m, 1H), 1.41 (d, J = 6.0 Hz, 3H), 1.22 (t, J = 6.8 Hz, 6H). | S; Peak 1 | (3R,4S,5S)-3-fluoro-1-[4-({8-[(2R,3S)-3-(methanesulfonyl-methyl)-2-methylazetidin-1-yl]-5-(propan-2-yl)-2,7-naphthyridin-3-yl}amino)pyrimidin-2-yl]-5-methoxy-piperidin-4-ol or (3S,4R,5R)-3-fluoro-1-[4-({8-[(2R,3S)-(methanesulfonyl- |

TABLE 1-continued

| # | Structure | LC/MS | NMR | Separation Conditions | Chemical Name |
|---|---|---|---|---|---|
| | | | | | methyl)-2-methylazetidin-1-yl]-5-(propan-2-yl)-2,7-naphthyridin-3-yl}amino)pyrimidin-2-yl]-5-methoxypiperidin-4-ol |
| 309 | | 574 | 1H NMR (400 MHz, CDCl3) δ 9.08 (s, 1H), 8.58 (s, 1H), 8.07 (d, J = 5.6 Hz, 1H), 7.60 (s, 1H), 7.41 (d, J = 8.0 Hz, 1H), 6.53 (d, J = 8.0 Hz, 1H), 6.20 (d, J = 5.6 Hz, 1H), 4.79 (dt, J = 9.2, 12.9 Hz, 1H), 4.84-4.73 (m, 1H), 4.54-4.45 (m, 1H), 4.29-4.19 (m, 1H), 3.74-3.55 (m, 3H), 3.50-3.41 (m, 1H), 3.40-3.27 (m, 2H), 3.09-2.97 (m, 2H), 2.96 (s, 3H), 2.60 (s, 3H), 2.14-2.02 (m, 1H), 1.80-1.69 (m, 2H), 1.51 (d, J = 6.0 Hz, 3H), 1.40-1.32 (m, 6H). | AA; Peak 1 | N-{2-[(4S)-3,3-difluoro-4-(methylamino)piperidin-1-yl]pyrimidin-4-yl}-8-[(2R,3S)-3-(methanesulfonylmethyl)-2-methylazetidin-1-yl]-5-(propan-2-yl)isoquinolin-3-amine or N-{2-[(4R)-3,3-difluoro-4-(methylamino)piperidin-1-yl]pyrimidin-4-yl}-8-[(2R,3S)-3-(methanesulfonylmethyl)-2-methylazetidin-1-yl]-5-(propan-2-yl)isoquinolin-3-amine |
| 310 | 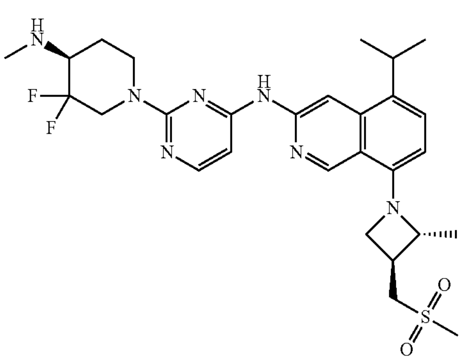 | 574 | 1H NMR (400 MHz, CDCl3) δ 9.09 (s, 1H), 8.58 (s, 1H), 8.07 (d, J = 5.6 Hz, 1H), 7.57 (s, 1H), 7.41 (d, J = 8.0 Hz, 1H), 6.53 (d, J = 8.0 Hz, 1H), 6.20 (d, J = 5.6 Hz, 1H), 4.83-4.72 (m, 1H), 4.70-4.64 (m, 1H), 4.54-4.45 (m, 1H), 4.30-4.21 (m, 1H), 3.75-3.56 (m, 3H), 3.52-3.42 (m, 1H), 3.41-3.29 (m, 2H), 3.08-2.97 (m, 2H), 2.96 (s, 3H), 2.60 (s, 3H), 2.12-2.04 (m, 1H), 1.78-1.69 (m, | AA; Peak 1 | N-{2-[(4R)-3,3-difluoro-4-(methylamino)piperidin-1-yl]pyrimidin-4-yl}-8-[(2R,3S)-3-(methanesulfonylmethyl)-2-methylazetidin-1-yl]-5-(propan-2-yl)isoquinolin-3-amine or N-{2-[(4S)-3,3-difluoro-4(methylamino)piperidin-1-yl] |

TABLE 1-continued

| # | Structure | LC/MS | NMR | Separation Conditions | Chemical Name |
|---|---|---|---|---|---|
| | | | 2H), 1.51 (d, J = 6.0 Hz, 3H), 1.39-1.34 (m, 6H). | | pyrimidin-4-yl}-8-[(2R,3S)-3-(methanesulfonyl-methyl)-2-methylazetidin-1-yl]-5-(propan-2-yl)isoquinolin-3-amine |
| 311 | 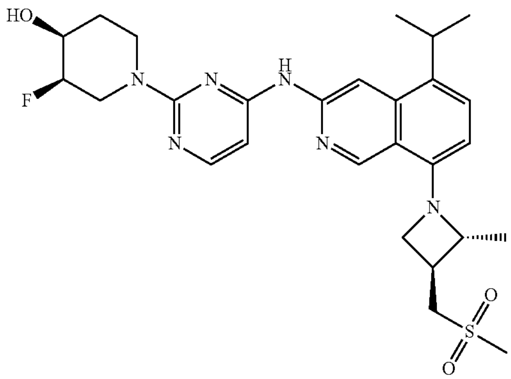 [SMILES: CC(C)c1ccc(N2C[C@H](CS(C)(=O)=O)[C@H]2C)c2cnc(Nc3ccnc(N4CC[C@H](O)[C@H](F)C4)n3)cc12] | 543 | 1H-NMR (300 MHz, 6d-DMSO) δ ppm 9.92 (s, 1H), 9.06 (s, 1H), 8.67 (s, 1H), 8.00 (d, 1H, J = 5.6 Hz), 7.43 (d, 1H, J = 8.0 Hz), 6.57 (d, 1H, J = 8.0 Hz), 6.46 (d, 1H, J = 5.7 Hz), 5.15 (d, 1H, J = 5.0 Hz), 4.81-4.59 (m, 3H), 4.39 (d, 1H, J = 13.2 Hz), 4.19 (q, 1H, J = 6.2 Hz), 3.97-3.79 (m, 1H), 3.57 (ddt, 5H, J = 27.5, 13.9, 7.3 Hz), 3.43-3.33 (m, 1H), 3.00 (s, 3H), 2.89 (q, 1H, J = 7.2 Hz), 1.77-1.69 (m, 2H), 1.43 (d, 3H, J = 6.0 Hz), 1.31 (dd, 6H, J = 6.7, 4.9 Hz). | | (3R,4S)-3-fluoro-1-[4-({8-[(2R,3S)-3-(methanesulfonyl-methyl)-2-methylazetidin-1-yl]-5-(propan-2-yl)isoquinolin-3-yl}amino)pyrimidin-2-yl]piperidin-4-ol |
| 312 | 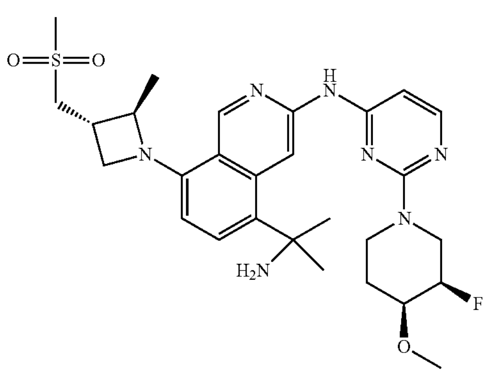 [SMILES: CO[C@H]1CCN(c2nccc(Nc3cc4c(C(C)(C)N)ccc(N5C[C@H](CS(C)(=O)=O)[C@H]5C)c4cn3)n2)C[C@H]1F] | 572 | 1H-NMR (400 MHz, 6d-DMSO) δ ppm 9.70 (s, 1H), 9.04 (d, 2H, J = 8.9 Hz), 7.99 (d, 1H, J = 5.7 Hz), 7.60 (d, 1H, J = 8.2 Hz), 6.70 (d, 1H, J = 5.7 Hz), 6.51 (d, 1H, J = 8.2 Hz), 5.11-4.84 (m, 3H), 4.64 (t, 1H, J = 7.5 Hz), 4.60-4.50 (m, 1H), 4.19 (t, 1H, J = 6.3 Hz), 3.73-3.41 (m, 5H), 3.36 (s, 3H), 3.28-3.14 (m, 1H), 3.00 (s, 4H), 2.89 (q, 1H, J = 7.2 Hz), 2.01-1.95 (m, 2H), 1.86-1.76 (m, 2H), 1.63 (s, 6H), 1.42 (d, 3H, J = 6.0 Hz). | No chiral separation | 5-(2-amino-propan-2-yl)-N-(2-((3R,4S)-3-fluoro-4-methoxy-piperidin-1-yl)pyrimidin-4-yl)-8-((2R,3S)-2-methyl-3-((methylsulfonyl)methyl)azetidin-1-yl)isoquinolin-3-amine |
| 313 | 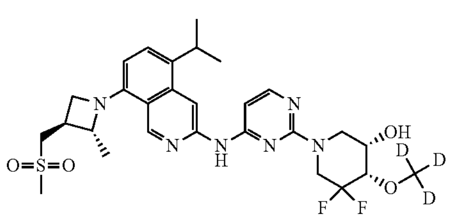 [SMILES: [2H]C([2H])([2H])O[C@@H]1[C@H](O)CN(c2nccc(Nc3cc4c(C(C)C)ccc(N5C[C@H](CS(C)(=O)=O)[C@H]5C)c4cn3)n2)CC1(F)F] | 594 | 1H-NMR (400 MHz, 6d-DMSO) δ ppm 10.00 (s, 1H), 9.07 (s, 1H), 8.54 (s, 1H), 8.03 (d, 1H, J = 5.7 Hz), 7.43 (d, 1H, J = 8.0 Hz), 6.62-6.53 (m, 2H), 5.31 (d, 1H, J = 5.8 Hz), 4.84-4.78 (m, 1H), 4.66 (t, 1H, J = 7.5 Hz), 4.53 (dd, | QQ; Peak 2 | (3S,4S)-5,5-difluoro-1-(4-((5-isopropyl-8-((2R,3S)-2-methyl-3-((methylsulfonyl)methyl)azetidin-1-yl)isoquinolin-3-yl)amino) |

| # | Structure | LC/MS | NMR | Separation Conditions | Chemical Name |
|---|---|---|---|---|---|
| | | | 1H, J = 12.2, 4.4 Hz), 4.20 (p, 1H, J = 6.0 Hz), 3.85-3.44 (m, 7H), 3.25-3.12 (m, 1H), 3.00 (s, 3H), 2.89 (h, 1H, J = 7.3 Hz), 1.43 (d, 3H, J = 6.0 Hz), 1.30 (dd, 6H, J = 10.5, 6.7 Hz). | | pyrimidin-2-yl)-4-($^2$H3) methoxy-piperidin-3-ol or (3R,4R)-5,5-difluoro-1-(4-((5-isopropyl-8-((2R,3S)-2-methyl-3-((methylsulfonyl)methyl)azetidin-1-yl)isoquinolin-3-yl)amino) pyrimidin-2-yl)-4-($^2$H3) methoxy-piperidin-3-ol |
| 314 | | 594 | 1H-NMR (400 MHz, 6d-DMSO) δ ppm 9.99 (s, 1H), 9.07 (s, 1H), 8.54 (s, 1H), 8.03 (d, 1H, J = 5.7 Hz), 7.43 (d, 1H, J = 8.0 Hz), 6.62-6.53 (m, 2H), 5.30 (d, 1H, J = 5.8 Hz), 4.84-4.78 (m, 1H), 4.67 (t, 1H, J = 7.5 Hz), 4.58-4.48 (m, 1H), 4.20 (t, 1H, J = 6.2 Hz), 3.79-3.44 (m, 7H), 3.26-3.13 (m, 1H), 3.00 (s, 3H), 2.89 (q, 1H, J = 7.3 Hz), 1.43 (d, 3H, J = 6.0 Hz), 1.30 (dd, 6H, J = 6.7, 4.1 Hz). | QQ; Peak 1 | (3S,4S)-5,5-difluoro-1-(4-((5-isopropyl-8-((2R,3S)-2-methyl-3-((methylsulfonyl)methyl)azetidin-1-yl)isoquinolin-3-yl)amino) pyrimidin-2-yl)-4-($^2$H3) methoxy-piperidin-3-ol or (3R,4R)-5,5-difluoro-1-(4-((5-isopropyl-8-((2R,3S)-2-methyl-3-((methylsulfonyl)methyl)azetidin-1-yl)isoquinolin-3-yl)amino) pyrimidin-2-yl)-4-($^2$H3)methoxy-piperidin-3-ol |
| 315 | 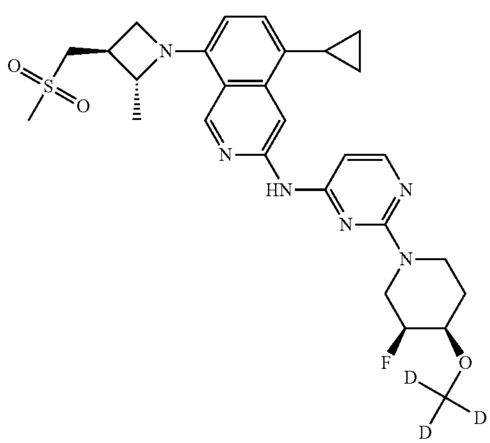 [SMILES: [2H]C([2H])([2H])O[C@@H]1CCN(c2nccc(Nc3cc4c(C5CC5)ccc(N5C[C@H](CS(C)(=O)=O)[C@H]5C)c4cn3)n2)C[C@@H]1F] | 558 | 1H-NMR (300 MHz, 6d-DMSO) δ ppm 9.91 (s, 1H), 9.03 (s, 1H), 8.71 (s, 1H), 7.98 (d, 1H, J = 5.7 Hz), 7.22 (d, 1H, J = 7.9 Hz), 6.45 (dd, 2H, J = 8.5, 6.8 Hz), 4.86 (d, 1H, J = 50.9 Hz), 4.64 (t, 2H, J = 7.3 Hz), 4.41 (d, 1H, J = 13.3 Hz), 4.17 (p, 1H, J = 6.1 Hz), 3.67-3.46 (m, 5H), 3.33-3.27 (m, 1H), 2.97 (s, 3H), 2.85 (p, 1H, J = 7.3 Hz), 2.13-2.07 (m, 1H), 1.79-1.56 (m, 2H), 1.39 (d, 3H, J = 6.0 Hz), 1.00-0.91 (m, 2H), 0.67-0.58 (m, 2H). | No Chiral Separation | 5-cyclopropyl-N-(2-((3S,4R)-3-fluoro-4-($^2$H3)piperidin-1-yl) pyrimidin-4-yl)-8-((2R,3S)-2-methyl-3-((methylsulfonyl)methyl)azetidin-1-yl)isoquinolin-3-amine |

TABLE 1-continued

| # | Structure | LC/MS | NMR | Separation Conditions | Chemical Name |
|---|---|---|---|---|---|
| 316 | (structure) | 558 | 1H-NMR (300 MHz, 6d-DMSO) δ ppm 9.91 (s, 1H), 9.03 (s, 1H), 8.71 (s, 1H), 7.98 (d, 1H, J = 5.6 Hz), 7.22 (d, 1H, J = 7.8 Hz), 6.50-6.39 (m, 2H), 4.85 (d, 1H, J = 49.2 Hz), 4.64 (t, 2H, J = 7.4 Hz), 4.41 (d, 1H, J = 13.2 Hz), 4.17 (t, 1H, J = 6.2 Hz), 3.69-3.46 (m, 5H), 3.32-3.26 (m, 1H), 2.97 (s, 3H), 2.86 (q, 1H, J = 7.1 Hz), 2.22-1.99 (m, 1H), 1.74-1.68 (m, 2H), 1.39 (d, 3H, J = 5.9 Hz), 0.95 (d, 2H, J = 8.4 Hz), 0.61 (t, 2H, J = 5.2 Hz). | No Chiral Separation | 5-cyclopropyl-N-(2-((3R,4S)-3-fluoro-4-($^2$H3)piperidin-1-yl)pyrimidin-4-yl)-8-((2R,3S)-2-methyl-3-((methylsulfonyl)methyl)azetidin-1-yl)isoquinolin-3-amine |

Biological Example 1. Biochemical EGFR Inhibition Assays

Inhibitory effects of the compounds of the disclosure were measured in biochemical assays that measure the phosphorylation activity of EGFR enzyme phosphorylates 2.5 micromolar 5-FAM-EEPLYWSFPAKKK-CONH$_2$ peptide substrate (FL-Peptide 22, PerkinElmer, 760366) in the presence of adenosine-5'-triphosphate (ATP) and varying concentrations of the test compound in 100 mM 2-[4-(2-hydroxyethyl)piperazin-1-yl] ethanesulfonic acid (HEPES), pH 7.5, 10 mM MgCl$_2$, 0.015% Brij-35, 1 mM dithiothreitol (DTT), 1.0% dimethylsulfoxide (DMSO). Assays were performed at 1.0 mM ATP or at ATP Km of the EGFR enzymes. Reactions proceeded until between 10% to 20% total peptides were phosphorylated at room temperature (25° C.) and were terminated with 35 mM 2,2',2'',2'''-(ethane-1,2-diyldinitrilo) tetraacetic acid (EDTA). Product was detected using the Caliper mobility shift detection method where the phosphorylated peptide (product) and substrate were electrophoretically separated and measured. Percent activity was plotted against log concentration of compound and points to generate an apparent IC$_{50}$. The following enzyme forms of EGFR were examples that were used in these assays: EGFR WT (SignalChem, E10-112G)

EGFR (L858R T790M C797S) (SignalChem, E10-122VG)
    EGFR (d746-750) T790M C797S (SignalChem, E10-122UG)
    EGFR L858R (SignalChem, E10-122BG)
    EGFR (d746-750) (SignalChem, E10-122JG)

Biological Example 2. NCI-H$_{1975}$ pEGFR AlphaLISA Assays

Inhibitory effects of the compounds of the disclosure were evaluated in cellular assays that measure level of intracellular phosphorylation of EGFR in NCI-H1975 cell line that harbors the EGFR L858R T790M mutations (ATCC, CRL-5908) using AlphaLISA sureFire ultra p-EGFR (Tyr1068) assay kit (PerkinElmer, ALSU-PEGFR-A50K). The NCI-H1975 cells were seeded at 12.5K/well in 22 μL into 384 well opti plate (PerkinElmer, 6007299) and adhering overnight at 37 C/5% CO$_2$. On the next day, the test compounds and DMSO control were added into H1975 cell plate followed by incubation at 37 C/5% CO$_2$ for 4-5 hours. The cells were then spin down in the 384-well plate and lysed with 10 μL of 1×AlphaLISA lysis buffer followed by shaking at 600 rpm for 10 minutes at room temperature. After that, 5 μL of an acceptor bead mix was added to each well followed by incubation at room temperature for 1.5-2 h in dark. Then 5 μL of a donor bead mix was added to each well followed by overnight incubation at room temperature in dark. On the next day, the plate was read at a compatible plate reader to obtain pEGFR signal. Percent of pEGFR inhibition was plotted against log concentration of compounds to generate IC$_{50}$ values.

Biological assay data of the test compounds are provided in Table 2 below. For inhibitory activity against EGFR LRTMCS mutant, the following designations are used: ≤15 nM=A; 15.1-20 nM=B; 20.1-30 nM=C; and 30.1-100 nM=D. For inhibition of phosphorylation of mutant EGFR in cells: ≤10 nM=A; 10.1-20 nM=B; 20.1-30 nM=C; and 30.1-50 nM=D.

TABLE 2

Tabularized Data:

| Compound Number | Ext Enz LRTMCS (nM) | Ext pEGFR H1975 (nM) |
|---|---|---|
| 1 | B | D |
| 2 | A | D |
| 3 | C | D |
| 4 | A | D |
| 5 | A | B |
| 6 | A | C |
| 7 | A | B |
| 8 | A | D |
| 9 | A | B |
| 10 | A | D |
| 11 | A | D |
| 12 | A | D |

TABLE 2-continued

Tabularized Data:

| Compound Number | Ext Enz LRTMCS (nM) | Ext pEGFR H1975 (nM) |
|---|---|---|
| 13 | A | D |
| 14 | B | D |
| 15 | A | D |
| 16 | C | B |
| 17 | A | B |
| 18 | A | A |
| 19 | B | B |
| 20 | B | D |
| 21 | C | D |
| 22 | A | A |
| 23 | A | B |
| 24 | A | C |
| 25 | A | D |
| 26 | A | A |
| 27 | A | B |
| 28 | A | A |
| 29 | A | A |
| 30 | A | A |
| 31 | A | B |
| 32 | A | C |
| 33 | A | A |
| 34 | A | B |
| 35 | A | D |
| 36 | A | A |
| 37 | A | B |
| 38 | A | A |
| 39 | A | D |
| 40 | A | A |
| 41 | A | A |
| 42 | A | B |
| 44 | A | A |
| 45 | A | B |
| 46 | A | A |
| 47 | B | A |
| 48 | A | A |
| 49 | A | A |
| 50 | A | A |
| 51 | A | C |
| 52 | A | A |
| 53 | A | A |
| 54 | A | D |
| 55 | A | A |
| 56 | A | B |
| 57 | A | B |
| 58 | B | C |
| 59 | A | B |
| 60 | A | C |
| 61 | A | D |
| 62 | A | A |
| 63 | A | A |
| 64 | A | A |
| 65 | A | A |
| 66 | A | A |
| 67 | A | A |
| 70 | A | A |
| 71 | A | A |
| 72 | A | A |
| 73 | A | A |
| 74 | A | A |
| 75 | A | A |
| 76 | A | A |
| 77 | B | D |
| 78 | A | C |
| 79 | A | B |
| 80 | A | D |
| 81 | A | A |
| 82 | A | A |
| 83 | A | A |
| 84 | A | B |
| 85 | A | B |
| 86 | C | D |
| 87 | A | C |
| 88 | A | C |
| 89 | A | A |
| 90 | A | A |
| 91 | A | A |
| 92 | A | A |
| 93 | A | A |
| 94 | A | C |
| 95 | C | B |
| 96 | C | B |
| 97 | A | A |
| 98 | A | B |
| 99 | A | B |
| 100 | A | A |
| 101 | A | B |
| 102 | A | C |
| 103 | A | B |
| 104 | A | B |
| 105 | A | A |
| 106 | A | A |
| 107 | A | B |
| 108 | A | A |
| 109 | A | A |
| 110 | A | A |
| 111 | A | A |
| 112 | A | B |
| 113 | A | B |
| 114 | D | D |
| 115 | A | A |
| 116 | A | B |
| 117 | A | A |
| 118 | A | A |
| 119 | B | C |
| 120 | B | B |
| 121 | B | A |
| 122 | A | A |
| 123 | A | A |
| 124 | A | A |
| 126 | A | A |
| 127 | A | A |
| 128 | A | A |
| 129 | A | A |
| 130 | A | A |
| 131 | A | A |
| 132 | A | A |
| 133 | A | A |
| 134 | A | A |
| 135 | A | A |
| 136 | A | B |
| 137 | A | A |
| 138 | A | A |
| 139 | A | A |
| 140 | A | A |
| 141 | A | B |
| 142 | A | C |
| 143 | A | A |
| 144 | A | A |
| 145 | B | C |
| 146 | B | B |
| 147 | A | B |
| 148 | A | A |
| 149 | B | B |
| 150 | A | C |
| 151 | A | A |
| 152 | A | A |
| 153 | A | B |
| 154 | A | C |
| 155 | A | A |
| 156 | A | A |
| 157 | A | A |
| 158 | B | B |
| 159 | B | C |
| 160 | B | D |
| 161 | A | A |
| 162 | A | A |
| 163 | A | D |
| 164 | B | A |
| 165 | A | C |
| 166 | D | D |

TABLE 2-continued

Tabularized Data:

| Compound Number | Ext Enz LRTMCS (nM) | Ext pEGFR H1975 (nM) |
|---|---|---|
| 167 | A | B |
| 168 | A | B |
| 169 | B | D |
| 170 | A | A |
| 171 | A | A |
| 172 | A | C |
| 173 | B | C |
| 174 | A | B |
| 175 | A | A |
| 176 | A | A |
| 177 | A | A |
| 178 | A | A |
| 179 | A | A |
| 180 | A | B |
| 181 | A | B |
| 182 | A | A |
| 183 | B | A |
| 184 | A | A |
| 185 | C | A |
| 186 | A | A |
| 187 | D | B |
| 188 | A | A |
| 189 | A | A |
| 190 | A | A |
| 191 | A | A |
| 192 | A | B |
| 193 | A | A |
| 194 | A | A |
| 195 | A | A |
| 196 | A | B |
| 197 | A | D |
| 198 | B | A |
| 199 | A | B |
| 200 | B | A |
| 201 | C | A |
| 202 | C | B |
| 203 | B | A |
| 204 | A | A |
| 205 | A | A |
| 206 | A | A |
| 207 | A | B |
| 208 | A | B |
| 209 | A | D |
| 210 | C | B |
| 211 | C | A |
| 212 | A | A |
| 213 | A | A |
| 214 | A | A |
| 215 | A | A |
| 216 | A | B |
| 217 | A | C |
| 218 | A | A |
| 219 | A | A |
| 220 | A | A |
| 221 | A | D |
| 222 | A | A |
| 223 | C | D |
| 224 | B | A |
| 225 | A | A |
| 226 | D | D |
| 227 | C | D |
| 228 | A | A |
| 229 | A | A |
| 230 | B | A |
| 231 | A | A |
| 232 | D | A |
| 233 | A | A |
| 234 | C | C |
| 235 | A | A |
| 236 | A | B |
| 237 | D | C |
| 238 | A | A |
| 239 | A | A |
| 240 | A | A |
| 241 | A | B |
| 242 | A | A |
| 243 | A | A |
| 244 | A | A |
| 245 | A | A |
| 246 | A | A |
| 247 | A | A |
| 248 | A | A |
| 249 | A | A |
| 250 | A | A |
| 251 | B | A |
| 252 | C | A |
| 253 | A | A |
| 254 | A | A |
| 255 | C | A |
| 256 | C | A |
| 257 | B | B |
| 258 | A | A |
| 259 | A | A |
| 260 | A | A |
| 261 | A | A |
| 262 | A | A |
| 263 | B | B |
| 264 | A | A |
| 265 | A | A |
| 266 | A | A |
| 267 | A | A |
| 268 | D | C |
| 269 | A | A |
| 270 | A | B |
| 271 | A | A |
| 272 | A | A |
| 273 | A | C |
| 274 | B | B |
| 275 | B | D |
| 276 | A | A |
| 277 | A | B |
| 278 | C | C |
| 279 | D | C |
| 280 | A | A |
| 281 | A | A |
| 282 | A | A |
| 283 | A | A |
| 284 | A | A |
| 285 | A | A |
| 286 | B | B |
| 287 | C | B |
| 288 | A | A |
| 289 | A | A |
| 290 | A | A |
| 291 | A | A |
| 292 | A | A |
| 293 | A | A |
| 294 | C | A |
| 295 | A | A |
| 296 | D | B |
| 297 | A | A |
| 298 | A | A |
| 299 | A | A |
| 300 | A | A |
| 301 | A | A |
| 302 | B | A |
| 303 | B | A |
| 304 | A | A |
| 305 | A | A |
| 306 | C | C |
| 307 | C | B |
| 308 | A | B |
| 309 | B | A |
| 310 | A | A |
| 311 | A | A |
| 312 | A | N/A |
| 313 | C | A |
| 314 | D | A |

TABLE 2-continued

Tabularized Data:

| Compound Number | Ext Enz LRTMCS (nM) | Ext pEGFR H1975 (nM) |
|---|---|---|
| 315 | A | A |
| 316 | A | A |

Biological Example 3. Biochemical EGFR Inhibition Assays

Inhibitory effects of the compounds of the disclosure were measured in biochemical assays that measure the phosphorylation activity of EGFR enzyme phosphorylates 2.5 micromolar 5-FAM-EEPLYWSFPAKKK-CONH$_2$ peptide substrate (FL-Peptide 22, PerkinElmer, 760366) in the presence of adenosine-5′-triphosphate (ATP) and varying concentrations of the test compound. Kinase reaction was initiated by mixing of EGFR enzyme, fluorescent labeled substrate peptide, ATP, and the test compound in 100 mM 2-[4-(2-hydroxyethyl)piperazin-1-yl] ethanesulfonic acid (HEPES), pH 7.5, 10 mM MgCl$_2$, 0.015% Brij-35, 1 mM dithiothreitol (DTT), 1.0% dimethylsulfoxide (DMSO). Assays were performed at 1.0 mM ATP or at ATP Km of the EGFR enzymes. Reactions proceeded until between 10% to 20% total peptides were phosphorylated at room temperature (25° C.) and were terminated with 35 mM 2,2′,2″,2‴-(ethane-1,2-diyldinitrilo)tetraacetic acid (EDTA). EGFR enzymatic activity was monitored using the Perkin Elmer electrophoretic mobility shift technology platform (the Caliper mobility shift detection method) where the phosphorylated peptide (product) and substrate were electrophoretically separated and measured. Percent activity was plotted against log concentration of compound and points to generate an apparent IC$_{50}$. The following enzyme forms of EGFR were examples that were used in these assays:

EGFR WT (SignalChem, E10-112G)

EGFR (L858R T790M C797S) (SignalChem, E10-122VG)

EGFR (d746-750) T790M C797S (SignalChem, E10-122UG)

EGFR L858R (SignalChem, E10-122BG)

EGFR (d746-750) (SignalChem, E10-122JG)

EGFR (D770_N771insNPG T790M) (SignalChem, E10-132TG)

EGFR (D770_N771insNPG) (SignalChem, E10-132GG)

Biological assay data of the test compounds are provided in the table below. For inhibitory activity against EGFR_D770_N771insNPG/T790M mutant, the following designations are used: ≤20 nM=A; 20.1-100 nm=B; 100.1 nM-250 nM=C; and 250.1-750 nM=D.

TABLE 3

| Compound Number | Enz EGFR_D770_N771insNPG/T790M |
|---|---|
| 2 | D |
| 7 | D |
| 128 | B |
| 265 | C |

Biological Example 4. pEGFR_LR/TM/G796S AlphaLISA Assay

Mutant EGFR expressing Ba/F3 cells were resuspended in fresh 10% FBS RPMI and plated at 1.0×10$^6$ cells/mL. On the next day, the cells were harvested and diluted in fresh medium at 1.25×10$^6$ cells/mL. 40 µL of cells were added to each well of a 384-well microplate (Corning 3764). In a clear 384-well polypropylene microplate, test compounds and DMSO were added. DMSO was a negative control and staurosporine was a positive control. The cell plate was placed in a humidified 37° C. incubator for 4 hrs. The cell plate was spun to pellet the cells and the media was removed. 10 µL of 1×AlphaLISA Lysis Buffer with 1× protease and phosphatase inhibitors was added to the cells and plate was shaken at 600 rpm for 30 min. The cell lysates were transferred from cell plate to a white opaque 384-well microplate (OptiPlate-384). 5 µL of acceptor mix was added to the cell lysate and the plate was shaken at 600 rpm for 10 min, gently tapped and sealed with foil. It was then incubated at RT for 1.5-2 hr. Under low light conditions, 1x donor mix was prepared right prior to use. 5 µL of donor mix was added to the plate under subdued lighting or green filters. The plate was shaken at 600 rpm for 10 min, gently tapped and sealed with foil. It was then incubated overnight at RT in dark. After overnight incubation, the plate was read on an EnVision Multilabel Reader. All IC$_{50}$ representative curves were plotted using GraphPad Prism (version 8.00 for Windows, GraphPad Software, San Diego California USA). The percentage of inhibition on EGFR phosphorylation was calculated following equation below:

$$\% \text{ Inhibition} = 100 \times \frac{pEGFR_{HC} - pEGFR_{cpds}}{pEGFR_{HC} - pEGFR_{LC}}$$

An IC$_{50}$ was calculated by fitting the curve using Nonliner fit with log(inhibitor) vs. response−Variable slope (four parameters) model.

Biological assay data of the test compounds are provided in Table 4 below. For inhibitory activity against pEGFR_LR/TM/G796S mutant, the following designations are used: ≤20 nM=A; 20.1-100 nm=B; 100.1 nM-250 nM=C; and 250.1-750 nM=D.

TABLE 4

| Compound Number | Ext pEGFR_LR/TM/G796S GMean IC$_{50}$ (nM) |
|---|---|
| 55 | A |
| 111 | B |
| 117 | D |
| 118 | D |
| 282 | B |
| 283 | B |

The invention claimed is:
1. A compound of Formula (I):

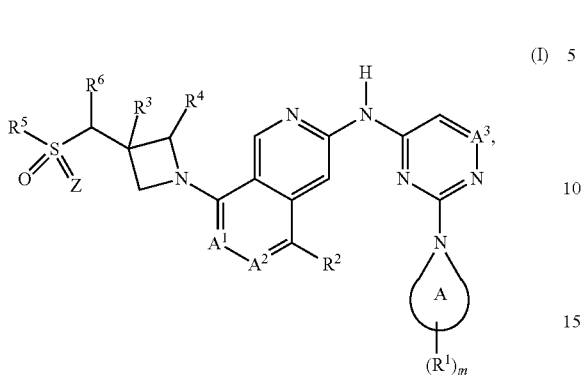

or a pharmaceutically acceptable salt thereof, wherein:
Z is O or NH;
each $A^1$, $A^2$, and $A^3$ is independently N or CR; wherein each R is independently H, halogen, or $CH_3$;
Ring A is 4-12 membered heterocyclyl;
each $R^1$ is independently halogen, CN, OH, $NR_aR_b$, $C_1$-$C_4$ alkyl, $C_1$-$C_4$ alkoxy, $C_3$-$C_6$ cycloalkyl or —O—$C_3$-$C_6$ cycloalkyl, wherein the alkyl, alkoxy or cycloalkyl represented by $R^1$ or in the group represented by $R^1$ is optionally substituted with 1 to 3 groups selected from deuterium, halogen, OH, $NR_aR_b$, $C_1$-$C_2$ alkyl, and $C_1$-$C_2$ alkoxy; and/or
m is 0, 1, 2, 3, 4, 5, or 6;
$R^2$ is H, halogen, $C_1$-$C_4$ alkyl, $C_1$-$C_4$ alkoxy, or $C_3$-$C_6$ cycloalkyl, wherein the alkyl, alkoxy or cycloalkyl represented by $R^2$ is optionally substituted with 1 to 3 groups selected from halogen and OH;
$R^3$ is H or methyl;
$R^4$ is H or methyl;
$R^5$ is H, $C_1$-$C_4$ alkyl, $C_3$-$C_6$ cycloalkyl or 4-6 membered monocyclic heterocyclyl, wherein the alkyl, cycloalkyl or heterocyclyl represented by $R^5$ is optionally substituted with 1 to 3 three groups selected from halogen, CN, OH, $NR_aR_b$, $C_1$-$C_2$ alkyl, and $C_1$-$C_2$ alkoxy;
$R^6$ is H or $C_1$-$C_4$ alkyl optionally substituted with 1 to 3 three groups selected from halogen, CN, OH, $NR_aR_b$, and $C_1$-$C_2$ alkoxy; and
each Ra and $R_b$ is independently H or $C_1$-$C_4$ alkyl.

2. The compound of claim 1, wherein the compound is represented by structural formula (II-A), (II-B), (II-C), (II-D), or (II-E):

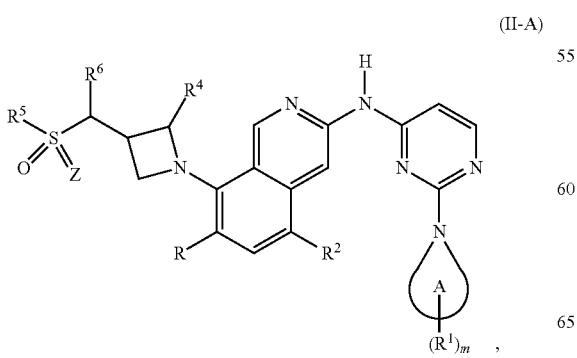

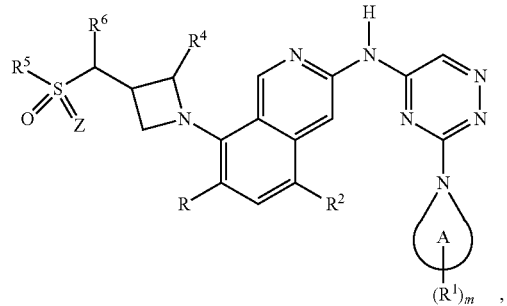

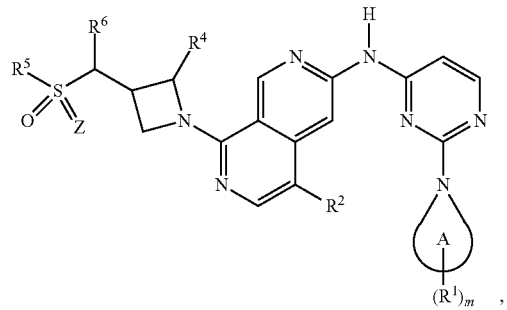

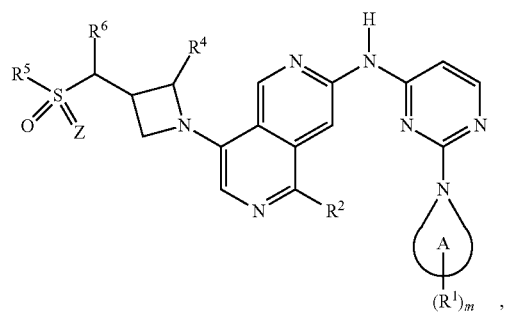

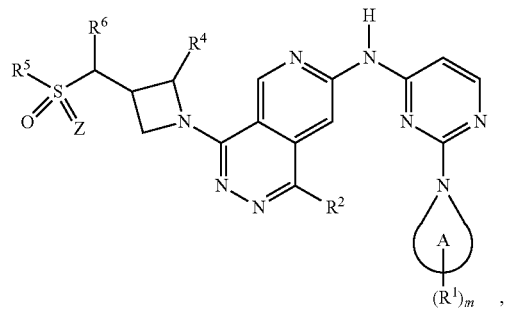

or a pharmaceutically acceptable salt thereof.

3. The compound of claim 1, wherein the compound is represented by structural formula (II-A):

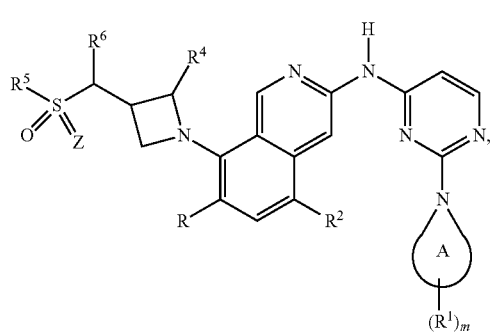

(II-A)

or a pharmaceutically acceptable salt thereof.

4. The compound of claim 3, or a pharmaceutically acceptable salt thereof, wherein Z is O.

5. The compound of claim 4, or a pharmaceutically acceptable salt thereof, wherein $R^2$ is H, fluorine, $C_1$-$C_4$ alkyl, $C_1$-$C_4$ alkoxy, or $C_3$-$C_6$ cycloalkyl, wherein the alkyl, alkoxy, or cycloalkyl represented by $R^2$ is optionally substituted with 1 to 3 groups selected from halogen and OH.

6. The compound of claim 5, or a pharmaceutically acceptable salt thereof, wherein $R^6$ is H, methyl, ethyl, $C_1$-$C_2$ haloalkyl, or $C_1$-$C_2$ aminoalkyl.

7. The compound of claim 6, or a pharmaceutically acceptable salt thereof, wherein $R^5$ is H; $C_1$-$C_4$ alkyl optionally substituted with 1 to 3 three groups selected from halogen, CN, and $NR_aR_b$; $C_3$-$C_6$ cycloalkyl; or 4-6 membered monocyclic heterocyclyl optionally substituted with $C_1$-$C_4$ alkyl; and wherein $R_a$ and $R_b$ are each independently selected from H, methyl and ethyl.

8. The compound of claim 7, or a pharmaceutically acceptable salt thereof, wherein Ring A is 4-7 membered monocyclic heterocyclyl optionally substituted with 1-6 $R^1$.

9. The compound of claim 7, or a pharmaceutically acceptable salt thereof, wherein Ring A is 7-12 membered bicyclic heterocyclyl optionally substituted with 1-6 $R^1$.

10. The compound of claim 8, or a pharmaceutically acceptable salt thereof, wherein m is 1, 2, 3, 4, or 5; and
each $R^1$ is independently halogen, CN, OH, $NR_aR_b$, $C_1$-$C_4$ alkyl, $C_1$-$C_4$ alkoxy, —O—$C_3$-$C_6$ cycloalkyl, wherein the alkyl, alkoxy, or cycloalkyl represented by $R^1$ or in the group represented by $R^1$ is optionally substituted with 1 to 3 groups selected from deuterium, halogen, OH, $NR_aR_b$, $C_1$-$C_2$ alkyl, and $C_1$-$C_2$ alkoxy.

11. The compound of claim 3, or a pharmaceutically acceptable salt thereof, wherein $R^2$ is H, F, methyl, ethyl, isopropyl, CH($CH_3$) $CH_2$F, CH($CH_3$) $CH_2$OH, $CF_3$, $OCH_3$, $OCH_2CH_3$, or cyclopropyl.

12. The compound of claim 11, or a pharmaceutically acceptable salt thereof, wherein $R^6$ is H, $CH_3$, or $CH_2NH_2$.

13. The compound of claim 12, or a pharmaceutically acceptable salt thereof, wherein Ring A is optionally substituted with 1-6 $R^1$, and Ring A is pyrrolidinyl, piperidinyl, morpholinyl, piperazinyl, azepanyl, 2-azabicyclo[2.2.1] heptanyl, 3-azabicyclo[3.2.1] octanyl, 6-oxa-2-azabicyclo [3.2.1] octanyl, 6-oxa-3-azabicyclo[3.2.1] octanyl, 8-oxa-3-azabicyclo[3.2.1] octanyl, hexahydro-1H-furo[3,4-b] pyrrolyl, hexahydro-1H-furo[3,4-c] pyrrolyl, 1-oxa-7-azaspiro [3.5] nonan-7-yl, 1,4-dioxa-8-azaspiro[4.5] decan-8-yl or 1,4-dioxa-9-azaspiro[5.5] undecan-9-yl.

14. The compound of claim 13, or a pharmaceutically acceptable salt thereof, wherein at least one $R^1$ is OH, $C_1$-$C_4$ alkoxy, or —O—$C_3$-$C_6$ cycloalkyl, wherein the alkoxy or cycloalkyl represented by $R^1$ or in the group represented by $R^1$ is optionally substituted with 1 to 3 groups selected from deuterium, halogen, OH, $NR_aR_b$, $C_1$-$C_2$ alkyl, and $C_1$-$C_2$ alkoxy.

15. The compound of claim 3, or a pharmaceutically acceptable salt thereof, wherein each $R^1$ is independently F, CN, OH, $NH_2$, $CH_3$, $CH_2CH_3$, $CHF_2$, CH (OH) $CH_3$, $CH_2OH$, $CH_2NH_2$, $CH_2CH_2NH_2$, $OCH_3$, $OCD_3$, $OCH_2CH_2OH$, $OCH_2CH$ (OH) $CH_3$, $OCH_2C$ (OH) ($CH_3$) 2, $OCH_2CH_2OCH_3$, $OCH_2CH_2NH_2$, $OCH_2CH_2NHCH_3$, $OCH_2CH_2N$ ($CH_3$)$_2$, —O-cyclopropyl, $NHCH_3$, or N ($CH_3$)$_2$.

16. The compound of claim 15, or a pharmaceutically acceptable salt thereof, wherein

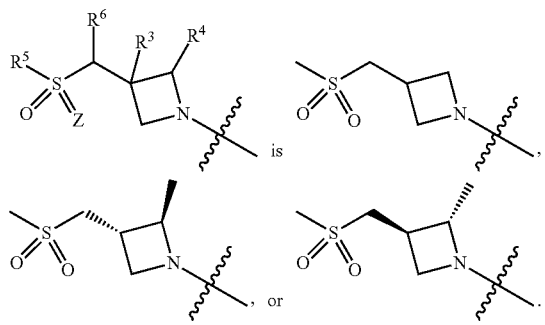

is , , , or .

17. The compound of claim 16, or a pharmaceutically acceptable salt thereof, wherein $R^2$ is H or isopropyl.

18. The compound of claim 17, or a pharmaceutically acceptable salt thereof, wherein Ring A is piperidinyl optionally substituted with 1-6 $R^1$.

19. A pharmaceutical composition comprising a pharmaceutically acceptable carrier and a compound of claim 1, or a pharmaceutically acceptable salt thereof.

20. A method of treating lung cancer, comprising administering a subject in need thereof an effective amount of a compound of claim 1, or a pharmaceutically acceptable salt thereof.

21. A method of inhibiting epidermal growth factor receptor (EGFR), comprising administering to a subject in need thereof an effective amount of a compound of claim 1, or a pharmaceutically acceptable salt thereof.

* * * * *

UNITED STATES PATENT AND TRADEMARK OFFICE
CERTIFICATE OF CORRECTION

PATENT NO. : 12,172,983 B2
APPLICATION NO. : 17/514457
DATED : December 24, 2024
INVENTOR(S) : John Emmerson Campbell et al.

It is certified that error appears in the above-identified patent and that said Letters Patent is hereby corrected as shown below:

In the Claims

At Column 466, Claim number 15, Line number 20, replace:
$OCH_2CH_2OH$, $OCH_2CH(OH)CH_3$, $OCH_2C(OH)(CH_3)2$,
With:
$OCH_2CH_2OH$, $OCH_2CH(OH)CH_3$, $OCH_2C(OH)(CH_3)_2$, Signed and Sealed this
Twenty-second Day of April, 2025

Coke Morgan Stewart
*Acting Director of the United States Patent and Trademark Office*